United States Patent
Carcache et al.

(10) Patent No.: US 12,404,261 B2
(45) Date of Patent: *Sep. 2, 2025

(54) COMPOUNDS AND COMPOSITIONS FOR TREATING CONDITIONS ASSOCIATED WITH cGAS

(71) Applicant: Novartis AG, Basel (CH)

(72) Inventors: David Carcache, Binningen (CH); Florian Gruber, Sissach (CH); Danilo Guerini, Reinach (CH); Martin Gunzenhauser, Gelterkinden (CH); Richard Heng, Hegenheim (FR); Francesca Perruccio, Basel (CH); Oliver Simic, Basel (CH); Carsten Spanka, Lorrach (DE)

(73) Assignee: NOVARTIS AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/645,071

(22) Filed: Dec. 20, 2021

(65) Prior Publication Data

US 2023/0085472 A1 Mar. 16, 2023

Related U.S. Application Data

(60) Provisional application No. 63/128,949, filed on Dec. 22, 2020.

(51) Int. Cl.
| | |
|---|---|
| *C07D 401/14* | (2006.01) |
| *A61K 31/4196* | (2006.01) |
| *A61K 31/454* | (2006.01) |
| *A61K 31/5377* | (2006.01) |
| *A61K 45/06* | (2006.01) |

(52) U.S. Cl.
CPC ........ *C07D 401/14* (2013.01); *A61K 31/4196* (2013.01); *A61K 31/454* (2013.01); *A61K 31/5377* (2013.01); *A61K 45/06* (2013.01)

(58) Field of Classification Search
CPC .. C07D 401/14; C07D 403/14; C07D 413/14; C07D 491/107; A61K 31/4196; A61K 31/454; A61K 31/5377; A61K 45/06; A61P 37/00
USPC ........................................................ 514/210
See application file for complete search history.

(56) References Cited

U.S. PATENT DOCUMENTS

| | | | | |
|---|---|---|---|---|
| 8,053,457 | B2 * | 11/2011 | Boettcher | C07D 403/04 548/312.1 |
| 2011/0118289 | A1 | 5/2011 | Giordani | |
| 2013/0281430 | A1 | 10/2013 | Dahmann | |
| 2019/0382377 | A1 | 12/2019 | Li et al. | |

FOREIGN PATENT DOCUMENTS

| | | | |
|---|---|---|---|
| WO | 2005/105213 A3 | 11/2005 | |
| WO | WO-2005105213 A2 * | 11/2005 | ............. A61K 31/00 |
| WO | 2019/055750 A1 | 3/2019 | |
| WO | 2019/153002 A1 | 8/2019 | |
| WO | 2020/123422 A1 | 6/2020 | |
| WO | 2020/142735 A1 | 7/2020 | |
| WO | 2020/186027 A1 | 9/2020 | |
| WO | 2021/209473 A1 | 10/2021 | |
| WO | 2021/209475 A1 | 10/2021 | |
| WO | 2021/209481 A1 | 10/2021 | |
| WO | 2021/209484 A1 | 10/2021 | |
| WO | 2021/209485 A1 | 10/2021 | |
| WO | 2022/051634 A1 | 3/2022 | |
| WO | 2022/066851 A1 | 3/2022 | |

OTHER PUBLICATIONS

Ablasser, Andrea et al., "cGAS in action: Expanding roles in immunity and inflammation," Science, Mar. 8, 2019, 363, 1055.
Decout, Alexiane et al., "The cGAS-STING pathway as a therapeutic target in inflammatory diseases" Nature Reviews Immunology, Sep. 2021, vol. 21, pp. 548-569.
Hall, Justin et al., "Discovery of PF-06928215 as a high affinity inhibitor of cGAS enabled by a novel fluorescence polarization assay." PLoS One, Sep. 21, 2017, 12(9): e0184843.
Lama, Lodoe et al.,"Development of human cGAS-specific small-molecule inhibitors for repression of dsDNA-triggered interferon expression," Nature Communications, May 21, 2019, 10, 2261.
Vincent, Jessica et al., "Small molecule inhibition of cGAS reduces interferon expression in primary macrophages from autoimmune mice," Nature Communications, Sep. 29, 2017, 8, 750.

* cited by examiner

Primary Examiner — Amy L Clark
Assistant Examiner — Liyuan Mou
(74) Attorney, Agent, or Firm — Elizabeth T. Karnas

(57) ABSTRACT

The present disclosure relates to a compound of Formula (I):

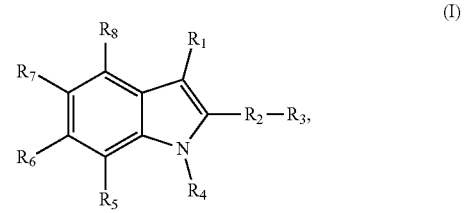

or a pharmaceutically acceptable salt, hydrate, solvate, stereoisomer, or tautomer thereof, wherein $R_1$ through $R_8$ are as defined herein, and methods of making and using the same.

4 Claims, No Drawings

COMPOUNDS AND COMPOSITIONS FOR TREATING CONDITIONS ASSOCIATED WITH cGAS

CROSS-REFERENCE TO RELATED APPLICATION

The present application claims priority to U.S. Provisional Application No. 63/128,949, filed on Dec. 22, 2020, the content of which is hereby incorporated by reference in its entirety.

FIELD OF THE INVENTION

The present invention relates to chemical entities (e.g., a compound that inhibits cyclic GMP-AMP synthase (cGAS) or cGAS pathway, or a pharmaceutically acceptable salt, and/or hydrate, and/or cocrystal, and/or drug combination of the compound) that are useful, e.g., for treating a condition, disease or disorder in which a decrease or increase in cGAS activity (e.g., an increase, e.g., a condition, disease or disorder associated with cGAS signaling) contributes to the pathology and/or symptoms and/or progression of the condition, disease or disorder in a subject (e.g., a human). The present invention relates to compositions as well as methods of using and making the same.

BACKGROUND

Nucleic acids are an important component of the cell. They store the genetic information and provide guidance to the cell on how to execute it. Nevertheless, when nucleic acids are found outside the cell or when large amounts are misplaced in the cytosol, which occurs as a consequence of damages of the cell (intrinsic cell death, viral infection, mitochondria damage), nucleic acids are recognized as harmful agents (as Pathogen Associated Molecular Patterns, "PAMPs") and trigger a strong immunological response. A similar response is also observed in many autoinflammatory and autoimmune diseases, where it was suggested that activation of nucleic acid sensors was a major molecular determinant (Barber, Nat Immunol, 12(10): 929-930, 2011).

Two novel gene products (cGAS and STING) have been recently recognized as the key members of an important pathway for the recognition of excess cytosolic dsDNA (Cai et al. Mol Cell, 54(2): 289-296, 2014). cGAS (the cyclic GMP/AMP synthase), upon binding of dsDNA, converts GTP and ATP to the cyclic nucleotide called cGAMP (Sun et al., Science 339(6121): 786-791, 2013) and STING (Stimulator of Interferon Genes) (Ishikawa et al., Nature 461(7265): 788-792, 2009), recognizes cGAMP and facilitates the phosphorylation of transcription factor IRF3, and finally leads to the expression of Type I IFN genes (Chen et al., Nat Immunol 17(10): 1142-1149, 2016). cGAMP, a cyclic nucleotide composed of one molecule of GMP and one AMP, couples the two phosphates via a very unusual 2'-,5' linkage and a classical 3',5' linkage (Ablasser et al., Nature 498(7454): 380-384, 2013) and represents a novel "2nd" messenger.

The mutation of the cytosolic DNase, Trex1, in Aicardi-Goutières-Syndrome patients has been shown to lead to an increase in cytosolic dsDNA sufficient to activate the cGAS/STING pathway resulting in a strong Type I IFN response (Crow & Manel, Nat Rev Immunol 15(7): 429-440, 2015). This results in a pathology similar to that generally observed in lupus patients, in addition to debilitating cognitive effects. A milder form of this defect is found in Familial Chilblain Lupus patients, who are carrying a heterozygous mutation in Trex1 (Fiehn, Curr Rheumatol Rep 19(10): 61, 2017). SAVI is a further disease that is the consequence of the activation of the cGAS/STING pathway. Identified as one of the interferonophaties, observed prevalently in young persons, this disease is the consequence of mutations hyperactivating STING, resulting in chronic production of Type I IFN cytokines. Manifestations of this pathology are evidenced as skin rashes, lung inflammation, chronic inflammation in the extremities, leading in extreme cases to amputation (Liu et al., N Engl J Med 371(6): 507-518, 2014).

Beside these rare genetic diseases, there are much evidence suggesting that the cGAS/STING pathway may play a role in chronic diseases, where programmed cell death is not sufficiently efficient to clear off all generated PAMPS/DAMPS (Motwani et al., Nat Rev Genet 20(11): 657-674, 2019). In particular, lupus patients, where chronic damages of different organs lead to the appearance of antiDNA antibodies, might benefit from tuning down the contribution of the cGAS/STING pathway to the production of inflammatory cytokines (Harley et al., Nat Rev Genet 10(5): 285-290, 2009).

An underlying driver of the diseases that ensues from hyper-activation of the cGAS pathway is the increased inflammatory cytokines (belonging to the so-called Type I interferons) in serum and in different organs. Type I interferon response is generally paralleled by an increase of the mRNA of ISG (interferon stimulated genes). These diseases are grouped in a family of pathologies defined as interferonopathies.

Aicardi-Goutières-Syndrome (Crow & Manel, Nat Rev Immunol 15(7): 429-440, 2015) is a genetically linked disease, which is homozygous for mutation in the DNA processing enzyme Trex1. Familial Chilblain Lupus groups patients carry a heterozygous mutation in Trex1 (Fiehn, Curr Rheumatol Rep 19(10): 61, 2017). Among the Mendelian diseases related to TREX1 loss-of-function mutation, a less severe form leads to a RVCL (autosomal dominant retinal vasculopathy with cerebral leukodystrophy), which is characterized by an adult-onset pf vasculopathy leading to retinopathy and juvenile ischemic stroke. This family of Trex1 dependent diseases is expected to respond strongly to cGAS inhibition, since TREX1 loss of function have been shown to lead to an increase of cytosolic dsDNA and consequently to uncontrolled activation of cGAS.

A specific damage to blood vessels in addition to a strong interferonopathy has been observed in STING-associated vasculopathy with an onset in infancy (SAVI) patients (Liu et al., N Engl J Med 371(6): 507-518, 2014). It is therefore predicted that cGAS/STING pathway will play an important role also in non-genetically linked vasculitis, in particular in the strong inflammation pathology observed in extremities.

Based on clinical manifestation similarities to those in AGS and SAVI, diseases including subtypes of systemic lupus erythematosus (SLE), lupus nephritis (LN) and dermatomyositis, which could be triggered by DNA viruses such as EBV, cytosolic dsDNA or mitochondrial dsDNA, are also predicted to be driven (at least in part) by aberrant activation of cGAS. Similarly it would be expected that activation of cGAS plays an important role in the development of Sjogren's Syndrome (SS), which shares some aspect of pathology with SLE.

Low molecular weight inhibitors of cGAS might also be effective in treating skin rushes/reddening associated with SLE, a pathology that is often observed when SLE patients are exposed to UV light (Skopelja-Gardner et al., Sci Rep 10(1): 7908, 2020). The possible involvement of the cGAS/

STING pathway in Rheumatoid Arthritis (RA) has been discussed, in particular since in TREX1 or other DNAses loss-of-function rodent models, joint inflammation has been observed. There has also been some evidence that accumulation of dsDNA in joints might be responsible for inflammation observed in RA patients (Wang et al., Int Immunopharmacol 76: 105791, 2019).

A model of age-related macular degeneration (AMD) has been shown to be strongly dependent from the cGAS/STING pathway, suggesting that cGAS inhibition might be a therapeutic option to treat this devastating eye disease (Kerur et al., Nat Med 24(1): 50-61, 2018; Wu et al., Clin Interv Aging 14: 1277-1283, 2019).

There is accumulating evidence that cGAS activation is involved in many neuroinflammatory diseases such as Parkinson's disease (or at least a subtype of them) (Sliter et al., Nature 561(7722): 258-262, 2018), Alzheimer's disease, Amyotrophic lateral sclerosis (ALS) (also called Lou Gehrig's disease), and Frontotemporal dementia (FTD) (McCauley et al., Nature 585(7823): 96-101, 2020).

Studies have linked cGAS/STING to the development of colitis and therefore suggest cGAS/STING modulation as the potential treatment of ulcerative colitis and inflammatory bowel disease (IBD) (Aden et al., J Exp Med 215(11): 2868-2886, 2018; Ahn et al., Cell Rep 21(13): 3873-3884, 2017; Canesso et al., Mucosal Immunol 11(3): 820-834, 2018; Martin et al., Sci Rep 9(1): 14281, 2019). Nevertheless, there are some data suggesting that blocking the cGAS/STING pathway may also under specific conditions worsen the outcome, as in the case of colorectal cancer in rodent, upon colitis induction (Zhu et al., J Immunol 193 (10): 4779-4782, 2014). It is worth mentioning in this context, that STING activation (likely via cGAS) have an important role in the development of inflammation driven by sepsis (Hu et al., EBioMedicine 41: 497-508, 2019).

A large body of evidence has indicated that cGAS plays an important role in lung inflammation. Damage to lung epithelial causes release of DNA, which can be detected in bronchoalveolar lavage (BAL). Intratracheal application of DNAse leads to improvement in a model of silicosis-driven lung inflammation, suggesting that cGAS plays a crucial role. The observation was confirmed using animals deficient in STING, strongly suggesting that activation of cGAS is the primary mechanism of inflammation in this and other similar models (Benmerzoug et al., Cell Rep 27(9): 2649-2664 e2645, 2019; Benmerzoug et al., Nat Commun 9(1): 5226, 2018; Benmerzoug et al., Trends Immunol 40(8): 719-734, 2019). While there is strong evidence of the involvement of cGAS in acute lung inflammation, its role in idiopathic pulmonary fibrosis is based on recent indirect evidence. It has been observed that the development of liver and renal fibrosis is strongly dependent on the activation of the cGAS/STING pathway. It is therefore predicted that therapeutic interference with the cGAS/STING pathway will be efficacious in diseases such as cirrhosis and endomyocardial fibrosis (Allison, Nat Rev Nephrol 15(11): 661, 2019; Bennion et al., J Virol 93(4), 2019; Iracheta-Vellve et al., J Biol Chem 291(52): 26794-26805, 2016; Sun et al., Biomed Pharmacother 127: 110119, 2020; Wang et al., Lab Invest 100(4): 542-552, 2020; Zhang et al., Biomed Pharmacother 125: 110022, 2020). Aberrant cGAS/STING activation, such as in the setting of mitochondrial dysfunction, also underlies more common diseases such as nonalcoholic steatohepatitis (NASH) and chronic obstructive pulmonary disease (COPD).

A partial protection by genetically or by pharmaceutically blocking the cGAS/STING pathway in a mouse model of acute pancreatitis has been recently reported (Zhao et al., Gastroenterology 154(6): 1822-1835 e1822, 2018), suggesting a potential protective effect by cGAS inhibitor in this devastating disease.

cGAS has been shown to play a role in cellular senescence, regulating the chronic inflammation driven by dying cells (Gluck et al., Nat Cell Biol 19(9): 1061-1070, 2017; Yang et al., Proc Natl Acad Sci USA 114(23): E4612-E4620, 2017). It is not clear if such finding will also translate in aging tissues and if blocking cGAS would help reducing chronic inflammation that is observed in aging people, but some indications in mice supporting this idea have recently been communicated. This observation is nevertheless relevant for many indications that are associated with elderly patient population, where a chronic activation of the cGAS/STING pathway might be a common co-morbidity. This might be particular true for many neurodegenerative diseases, where damage of mitochondria has been demonstrated, leading to release of mitochondrial DNA to the cytosol.

A recent observation in mice showed that inhibiting cGAS or STING promoted recovery of acute kidney injury induced by cisplatin (Maekawa et al., Cell Rep 29(5): 1261-1273 e1266, 2019). Since this agent is used in cancer therapy, blocking cGAS/STING might prevent organ damage in particular leading to kidney failure. Other recent publications showed a very robust therapeutic effect on blocking the cGAS/STING pathway in a mouse model for APOL1-associated podocytopathy (Davis et al. Sci Rep 9(1): 15485, 2019; Wu et al. J Clin Invest 131(20), 2021). These data suggest that cGAS inhibitors might be beneficial in treating kidney injury in general.

Although the cGAS/STING pathway activation is considered one of the first defense that the immune system deploys to fight against viral infection, once the acute phase is terminated, elevated type I interferon has been shown to propagate chronic inflammation that damages tissue and prevents tissue recovery (Teijaro et al., Science 340(6129): 207-211, 2013; Wilson et al., Science 340(6129): 202-207, 2013). It is therefore predicted that blocking cGAS at the late stage of this disease will greatly accelerate the recovery from chronic viral damage.

SUMMARY OF THE DISCLOSURE

The present disclosure relates to compounds and compositions that are capable of inhibiting cGAS pathway. The disclosure features methods of treating, preventing, or ameliorating a disease or disorder in which cGAS plays a role by administering to a patient in need thereof a therapeutically effective amount of a compound of Formula (I), or a pharmaceutically acceptable salt, hydrate, solvate, stereoisomer, or tautomer thereof. The methods of the present disclosure can be used in the treatment of a variety of cGAS-dependent diseases and disorders by inhibiting cGAS pathway. Inhibiting cGAS pathway provides a novel approach to the treatment, prevention, or amelioration of diseases including, but not limited to, immune diseases, inflammatory diseases, auto-immune diseases, or auto-inflammatory diseases, and other cGAS-dependent diseases or disorders.

In one aspect, the compounds of the disclosure have use as therapeutic agents, particularly for immune diseases, inflammatory diseases, auto-immune diseases, or auto-inflammatory diseases. In one aspect, the compounds of the disclosure have cGAS inhibition activity, preferably having such activity at or below the 30 μM level.

In a first aspect of the disclosure, the compounds of Formula (I) are described:

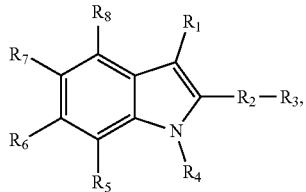

(I)

or a pharmaceutically acceptable salt, hydrate, solvate, stereoisomer, or tautomer thereof, wherein:

$R_1$ is a 5-membered heteroaryl ring comprising 1 to 4 heteroatoms selected from O, N and S, optionally substituted with at least one of $(C_1-C_4)$alkyl, OH, halogen, $-NR_aR_b$, and 5- or 6-membered heterocycloalkyl ring containing an oxygen;

$R_2$ is 5-membered heteroaryl ring comprising 3 nitrogen atoms at 1, 2 and 4-positions relative to each other, optionally substituted with $(C_1-C_4)$alkyl, $(C_1-C_4)$alkylene-OH, $-(C_1-C_4)$alkylene-$NR_9R_{10}$, $(C_1-C_4)$alkylene-C(O)OH, and wherein the 5-membered heteroaryl ring is further substituted with $R_3$ at a 5-membered heteroaryl ring carbon atom;

$R_3$ is H, halogen, $-OH$, $-NR_{11}R_{12}$, $-(C_1-C_4)$alkylene-$NR_{13}R_{14}$, $(C_1-C_4)$alkyl, halo$(C_1-C_4)$alkyl, $-(C_1-C_4)$alkylene-OH, $-(C_1-C_4)$alkylene-$(C_1-C_4)$alkoxy, $-C(O)(C_1-C_4)$alkyl, $-C(O)(C_1-C_4)$alkylene-O-$(C_1-C_4)$alkyl, $-C(O)(C_1-C_4)$alkylene-OH, $-C(O)NR_{15}R_{16}$, $(C_1-C_4)$alkoxy, $-(C_1-C_4)$alkylene-$S(O)C_1-C_4)$alkyl, $-C(O)(C_1-C_4)$alkoxy, $-CN$, $-O(C_1-C_4)$alkylene-OH, $-O(C_1-C_4)$alkylene-$(C_1-C_4)$alkoxy, $-(C_1-C_4)$alkylene-$C(O)(C_1-C_4)$alkyl, $-(C_1-C_4)$alkylene-$C(O)(C_1-C_4)$alkoxy, $-(C_1-C_4)$alkylene-$C(O)NR_{17}R_{18}$, 6-membered heterocycloalkyl ring Ri comprising 1 to 2 heteroatoms selected from O and N; or

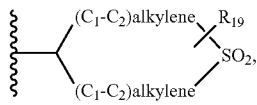

wherein the $(C_1-C_4)$alkyl is optionally substituted with at least one of CN, $=N-(C_1-C_4)$alkoxy, $=N-O-(C_1-C_4)$alkylene-$OR_{20}$, OH, $(C_1-C_4)$alkoxy, $-C(O)OH$, $-C(O)O(C_1-C_4)$alkyl, 4- to 6-membered heterocycloalkyl ring comprising 1 to 2 heteroatoms selected from O, N, and S, and 5 to 6-membered heteroaryl ring comprising 1 to 2 heteroatoms selected from O, N and S;

each $-(C_1-C_4)$alkylene-$NR_9R_{10}$ and $-(C_1-C_4)$alkylene-$NR_{13}R_{14}$ is optionally substituted at least one of the $(C_1-C_4)$alkylene carbons with OH, $(C_1-C_4)$alkoxy, $-(C_1-C_4)$alkylene-$O(C_1-C_4)$alkyl, $(C_1-C_4)$alkyl;

each halo$(C_1-C_4)$alkyl and $(C_1-C_4)$alkylene-OH is independently optionally substituted with at least one of OH, $(C_1-C_4)$alkoxy, $-O(C_1-C_4)$alkylene-OH, $-(C_1-C_4)$alkylene-OH, $-(C_1-C_4)$alkylene-$(C_1-C_4)$alkoxy;

Ri is optionally substituted with a $(C_1-C_4)$alkyl;

v is 0, 1 or 2;

$R_4$ is H, $(C_1-C_4)$alkyl, $-(C_1-C_4)$alkylene-OH, $-(C_1-C_4)$alkylene-$(C_1-C_4)$alkoxy, $-(C_1-C_4)$alkylene-C(O)OH, $-C(O)O(C_1-C_4)$alkyl or a 5 to 6-membered heteroaryl ring comprising 1 to 2 nitrogen atoms optionally substituted with one or more $(C_1-C_4)$alkoxy;

each $R_5$, $R_6$, $R_7$ and $R_8$ is independently H, halogen, OH, $(C_1-C_4)$alkyl, $(C_1-C_4)$alkoxy, halo$(C_1-C_4)$alkyl, halo$(C_1-C_4)$alkoxy, $(C_2-C_6)$alkenyl, $(C_2-C_6)$alkynyl, $-(C_1-C_4)$alkylene-OH, $-O(C_1-C_4)$alkylene-OH, CN, $-C(O)(C_1-C_4)$alkoxy, $-C(O)NR_{21}R_{22}$ or a 5-membered heteroaryl ring comprising 2 nitrogen heteroatoms, wherein each $(C_2-C_6)$alkenyl and $(C_2-C_6)$alkynyl is independently optionally substituted with one or more $(C_1-C_4)$alkoxy;

each $R_{20}$, $R_{21}$ and $R_{22}$ is independently H or $(C_1-C_4)$alkyl;

each $R_9$, $R_{10}$, $R_{11}$, $R_{12}$, $R_{13}$, $R_{14}$, $R_{15}$, $R_{16}$, $R_{17}$ and $R_{18}$ is independently H, $(C_1-C_4)$alkyl, $-(C_1-C_4)$alkylene-OH, $-(C_1-C_4)$alkylene-$O(C_1-C_4)$alkyl, $-C(O)(C_1-C_4)$alkylene-$(C_1-C_4)$alkoxy, or $-C(O)(C_1-C_4)$alkyl; or $R_9$ and $R_{10}$, together with the nitrogen atom to which they are attached, form a 5- or 6-membered heterocycloalkyl ring $R_{23}$ comprising 1 to 2 heteroatoms selected from O, N and S, wherein $R_{23}$ is optionally substituted with one or more $R_{24}$;

$R_{11}$ and $R_{12}$, together with the nitrogen atom to which they are attached, form a 5- or 6-membered heterocycloalkyl ring $R_{25}$ comprising 1 to 2 heteroatoms selected from O, N and S, wherein $R_{25}$ is optionally substituted with one or more $R_{26}$;

$R_{13}$ and $R_{14}$, together with the nitrogen atom to which they are attached, form a 5- or 6-membered heterocycloalkyl ring $R_{27}$ comprising 1 to 2 heteroatoms selected from O, N and S, wherein $R_{27}$ is optionally substituted with one or more $R_{28}$;

$R_{15}$ and $R_{16}$, together with the nitrogen atom to which they are attached, form a 5- or 6-membered heterocycloalkyl ring $R_{29}$ comprising 1 to 2 heteroatoms selected from O, N and S, wherein $R_{29}$ is optionally substituted with one or more $R_{30}$;

$R_{17}$ and $R_{18}$, together with the nitrogen atom to which they are attached, form a 5- or 6-membered heterocycloalkyl ring $R_{31}$ comprising 1 to 2 heteroatoms selected from O, N and S, wherein $R_{31}$ is optionally substituted with $R_{32}$;

each $R_{24}$, $R_{26}$, $R_{28}$, $R_{30}$ and $R_{32}$ is independently $(C_1-C_4)$alkyl, $(C_1-C_4)$alkoxy, $NR_cR_d$, OH or $=O$;

or two of each $R_{24}$, $R_{26}$, $R_{28}$, $R_{30}$ and $R_{32}$ together, when attached to the same atom, form a $(C_4-C_7)$ spirocycloalkyl or a 4- to 7-membered spiroheterocycloalkyl ring comprising 1 to 2 heteroatoms selected from O, N and S;

$R_{19}$ is H, OH or $(C_1-C_4)$alkyl; and each $R_a$, $R_b$, Re and Re is independently H, halogen, or $(C_1-C_4)$alkyl.

Another aspect of the present disclosure relates to a pharmaceutical composition comprising a therapeutically effective amount of a compound of Formula (I), or a pharmaceutically acceptable salt, hydrate, solvate, stereoisomer, or tautomer thereof, and a pharmaceutically acceptable carrier or excipient. The pharmaceutical composition is useful in the treatment of cGAS-dependent diseases or disorders.

In another aspect, the invention provides a combination, in particular a pharmaceutical combination, comprising a therapeutically effective amount of a compound according to the definition of a compound of formula (I), or a pharmaceutically acceptable salt thereof, and one or more therapeutic agents.

In another aspect, the invention provides a combination, in particular a pharmaceutical combination, as disclosed herein, for use as a medicament.

In another aspect, the present disclosure relates to a method of treating a disease or disorder that is affected by the inhibition of cGAS comprising the step of administering to a subject in need thereof a therapeutically effective amount of a compound of Formula (I), or a pharmaceutically acceptable salt, hydrate, solvate, stereoisomer, or tautomer thereof, wherein the disease or disorder is selected from cGAS-related diseases or disorders, for example, immune diseases, inflammatory diseases, auto-immune diseases, and auto-inflammatory diseases.

In another aspect, the cGAS-related diseases or disorders, are immune diseases, inflammatory diseases, auto-immune diseases, or auto-inflammatory diseases, including Aicardi-Goutières-Syndrome, Familial Chilblain Lupus, RVCL (autosomal dominant retinal vasculopathy with cerebral leukodystrophy), vasculitis, systemic lupus erythematosus (SLE), lupus nephritis (LN), dermatomyositis, Sjogren's Syndrome (SS), rheumatoid arthritis (RA), age-related macular degeneration (AMD), Parkinson's disease, Alzheimer, Amyotrophic lateral sclerosis (ALS), Frontotemporal dementia (FTD), lung inflammation, acute lung inflammation, idiopathic pulmonary fibrosis, liver and renal fibrosis, nonalcoholic steatohepatitis (NASH), cirrhosis, endomyocardial fibrosis, acute and chronic kidney injury, APOL1-associated podocytopathy, acute pancreatitis, ulcerative colitis, inflammatory bowel disease (IBD), chronic obstructive pulmonary disease (COPD), sepsis, senescence, and aging.

DETAILED DESCRIPTION OF THE INVENTION

The present disclosure relates to compounds and compositions that are capable of inhibiting cGAS. The disclosure features methods of treating, preventing, or ameliorating a disease or disorder in which cGAS plays a role by administering to a patient in need thereof a therapeutically effective amount of a compound of Formula (I), or a pharmaceutically acceptable salt, hydrate, solvate, stereoisomer, or tautomer thereof. The methods of the present disclosure can be used in the treatment of a variety of cGAS-dependent diseases and disorders by inhibiting cGAS or cGAS pathway. Inhibiting cGAS or cGAS pathway provides a novel approach to the treatment, prevention, or amelioration of diseases including, but not limited to, systemic lupus erythematosus (SLE), Familial Chilblain Lupus, vasculitis, Sjogren's Syndrome (SS), and other cGAS-dependent diseases or disorders.

In one aspect, the compounds of the disclosure have use as therapeutic agents, particularly for immune diseases, inflammatory diseases, auto-immune diseases, or auto-inflammatory diseases. In one aspect, the compounds of the disclosure have cGAS inhibition activity, preferably having such activity at or below the 30 μM level. The compounds of the disclosure have usefulness in treating immune diseases, inflammatory diseases, auto-immune diseases, auto-inflammatory diseases, and other diseases for which such cGAS inhibition activity would be beneficial for the patient. In summary, the present disclosure provides novel cGAS inhibitors useful for the treatment of auto-immune and auto-inflammatory diseases.

In a first aspect of the disclosure, the compounds of Formula (I) are described:

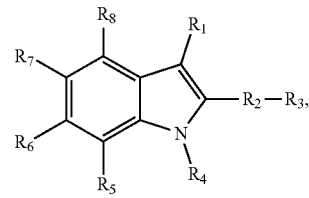

(I)

or pharmaceutically acceptable salts, hydrates, solvates, stereoisomers, and tautomers thereof, wherein $R_1$ through $R_8$ are as described herein above.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

DEFINITION OF TERMS AND CONVENTIONS USED

Terms not specifically defined herein should be given the meanings that would be given to them by one of skill in the art in light of the disclosure and the context. As used in the specification and appended claims, however, unless specified to the contrary, the following terms have the meaning indicated and the following conventions are adhered to.

A. Chemical Nomenclature, Terms, and Conventions

In the groups, radicals, or moieties defined below, the number of carbon atoms is often specified preceding the group, for example, $(C_1-C_{10})$alkyl means an alkyl group or radical having 1 to 10 carbon atoms. In general, for groups comprising two or more subgroups, the last named group is the radical attachment point, for example, "alkylaryl" means a monovalent radical of the formula alkyl-aryl-, while "arylalkyl" means a monovalent radical of the formula aryl-alkyl-. Furthermore, the use of a term designating a monovalent radical where a divalent radical is appropriate shall be construed to designate the respective divalent radical and vice versa. Unless otherwise specified, conventional definitions of terms control and conventional stable atom valences are presumed and achieved in all formulas and groups. The articles "a" and "an" refer to one or more than one (e.g., to at least one) of the grammatical object of the article. By way of example, "an element" means one element or more than one element.

The term "and/or" means either "and" or "or" unless indicated otherwise.

The term "optionally substituted" means that a given chemical moiety (e.g., an alkyl group) can (but is not required to) be bonded other substituents (e.g., heteroatoms). For instance, an alkyl group that is optionally substituted can be a fully saturated alkyl chain (e.g., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus, the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —CH$_2$CN, —O—($C_1$-$C_6$)alkyl, ($C_1$-$C_6$)alkyl, ($C_1$-$C_6$)alkoxy, ($C_1$-$C_6$)haloalkyl, ($C_1$-$C_6$)haloalkoxy, —O—($C_2$-$C_6$)alkenyl, —O—($C_2$-$C_6$)alkynyl, ($C_2$-$C_6$)alkenyl, ($C_2$-$C_6$)alkynyl, —OH, —OP(O)(OH)$_2$, —OC(O)($C_1$-$C_6$)alkyl, —C(O)($C_1$-$C_6$)alkyl, —OC(O)O($C_1$-$C_6$)alkyl, —NH$_2$, —NH(($C_1$-$C_6$)alkyl), —N(($C_1$-$C_6$)alkyl)$_2$, —NHC(O)($C_1$-$C_6$)alkyl, —C(O)NH($C_1$-$C_6$)alkyl, —S(O)$_2$($C_1$-$C_6$)alkyl, —S(O)NH($C_1$-$C_6$)alkyl, and —S(O)N(($C_1$-$C_6$)alkyl)$_2$. The substituents can themselves be optionally substituted. "Optionally substituted" as used herein also refers to substituted or unsubstituted whose meaning is described below.

The term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

The term "unsubstituted" means that the specified group bears no substituents.

Unless otherwise specifically defined, "aryl" means a cyclic, aromatic hydrocarbon group having 1 to 3 aromatic rings, including monocyclic or bicyclic groups such as phenyl, biphenyl, or naphthyl. When containing two aromatic rings (bicyclic, etc.), the aromatic rings of the aryl group are optionally joined at a single point (e.g., biphenyl), or fused (e.g., naphthyl). The aryl group is optionally substituted by one or more substituents, e.g., 1 to 5 substituents, at any point of attachment. Exemplary substituents include, but are not limited to, —H, -halogen, —CN, —O—($C_1$-$C_6$)alkyl, ($C_1$-$C_6$)alkyl, —O—($C_2$-$C_6$)alkenyl, —O—($C_2$-$C_6$)alkynyl, ($C_2$-$C_6$)alkenyl, ($C_2$-$C_6$)alkynyl, —OH, —OP(O)(OH)$_2$, —OC(O)($C_1$-$C_6$)alkyl, —C(O)($C_1$-$C_6$)alkyl, —OC(O)O($C_1$-$C_6$) alkyl, NH$_2$, NH(($C_1$-$C_6$)alkyl), N(($C_1$-$C_6$)alkyl)$_2$, —S(O)$_2$—($C_1$-$C_6$)alkyl, —S(O)NH($C_1$-$C_6$)alkyl, and —S(O)N(($C_1$-$C_6$)alkyl)$_2$. The substituents are themselves optionally substituted. Furthermore, when containing two fused rings, the aryl groups optionally have an unsaturated or partially saturated ring fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic aromatic radical of 5 to 24 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydropyrrolo[1,2-a]pyrimidinyl, 3,4-dihydro-2H-1Δ$^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo[1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4 d]thiazolyl, imidazo[2,1-b][1,3,4]thiadiazolyl, thieno[2,3-b]pyrrolyl, 3H-indolyl, and derivatives thereof. Furthermore, when containing two fused rings the aryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine,3,4-dihydro-1H-isoquinolinyl, 2,3-dihydrobenzofuran, indolinyl, indolyl, and dihydrobenzoxanyl.

Halogen or "halo" mean fluorine, chlorine, bromine, or iodine.

"Alkyl" means a straight or branched chain saturated hydrocarbon containing 1-12 carbon atoms. Examples of a ($C_1$-$C_6$)alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" means a straight or branched chain saturated hydrocarbon containing 1-12 carbon atoms containing a terminal "O" in the chain, e.g., —O(alkyl). Examples of alkoxy groups include, without limitation, methoxy, ethoxy, propoxy, butoxy, t-butoxy, or pentoxy groups.

"Alkenyl" means a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, iso-butenyl, pentenyl, or hexenyl. An alkenyl group can be unsubstituted or substituted and may be straight or branched.

"Alkynyl" means a straight or branched chain unsaturated hydrocarbon containing 2-12 carbon atoms. The "alkynyl" group contains at least one triple bond in the chain. Examples of alkenyl groups include ethynyl, propargyl, n-butynyl, iso-butynyl, pentynyl, or hexynyl. An alkynyl group can be unsubstituted or substituted.

"Alkylene" or "alkylenyl" means a divalent alkyl radical. Any of the above mentioned monovalent alkyl groups may be an alkylene by abstraction of a second hydrogen atom from the alkyl. As herein defined, alkylene may also be a ($C_1$-$C_6$)alkylene. An alkylene may further be a ($C_1$-$C_4$)

alkylene. Typical alkylene groups include, but are not limited to, —CH$_2$—, —CH(CH$_3$)—, —C(CH$_3$)$_2$—, —CH$_2$CH$_2$—, —CH$_2$CH(CH$_3$)—, —CH$_2$C(CH$_3$)$_2$—, —CH$_2$CH$_2$CH$_2$—, —CH$_2$CH$_2$CH$_2$CH—, and the like.

"Cycloalkyl" or "carbocyclyl" means a monocyclic or polycyclic saturated carbon ring containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl and derivatives thereof. A (C$_3$-C$_8$)cycloalkyl is a cycloalkyl group containing between 3 and 8 carbon atoms. A cycloalkyl group can be fused (e.g., decalin) or bridged (e.g., norbomane).

"Heterocyclyl" or "heterocycloalkyl" means a saturated or monocyclic or polycyclic ring containing carbon and at least one heteroatom selected from oxygen, nitrogen, or sulfur (O, N, or S) and wherein there is not delocalized π electrons (aromaticity) shared among the ring carbon or heteroatoms. The heterocycloalkyl ring structure may be substituted by one or more substituents. The substituents can themselves be optionally substituted. Examples of heterocyclyl rings include, but are not limited to, oxetanyl, azetadinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, 1,4-dioxanyl, dihydrofuranyl, 1,3-dioxolanyl, imidazolidinyl, imidazolinyl, dithiolanyl, and homotropanyl.

"Hydroxyalkyl" means an alkyl group substituted with one or more —OH groups. Examples of hydroxyalkyl groups include HO—CH$_2$—, HO—CH$_2$CH$_2$—, and CH$_3$—CH(OH)—.

"Haloalkyl" means an alkyl group substituted with one or more halogens. Examples of haloalkyl groups include, but are not limited to, trifluoromethyl, difluoromethyl, pentafluoroethyl, trichloromethyl, etc.

"Haloalkoxy" means an alkoxy group substituted with one or more halogens. Examples of haloalkyl groups include, but are not limited to, trifluoromethoxy, difluoromethoxy, pentafluoroethoxy, trichloromethoxy, etc.

"Cyano" means a substituent having a carbon atom joined to a nitrogen atom by a triple bond, e.g., C≡N.

"Amino" means a substituent containing at least one nitrogen atom (e.g., NH$_2$).

"Alkylamino" means an amino or NH$_2$ group where one of the hydrogens is replaced with an alkyl group, e.g., —NH(alkyl). Examples of alkylamino groups include, but are not limited to, methylamino (e.g., —NH(CH$_3$)), ethylamino, propylamino, iso-propylamino, n-butylamino, sec-butylamino, tert-butylamino, etc.

"Dialkylamino" means an amino or NH$_2$ group where both of the hydrogens are replaced with alkyl groups, e.g., —N(alkyl)$_2$. The alkyl groups on the amino group are the same or different alkyl groups. Examples of dialkylamino groups include, but are not limited to, dimethylamino (e.g., —N(CH$_3$)$_2$), diethylamino, dipropylamino, diiso-propylamino, di-n-butylamino, di-sec-butylamino, di-tert-butylamino, methyl(ethyl)amino, methyl(butylamino), etc.

"Spirocycloalkyl" or "spirocyclyl" means carbogenic bicyclic ring systems with both rings connected through a single atom. The rings can be different in size and nature, or identical in size and nature. Examples include spiropentane, spriohexane, spiroheptane, spirooctane, spirononane, or spirodecane. One or both of the rings in a spirocycle can be fused to another ring carbocyclic, heterocyclic, aromatic, or heteroaromatic ring. A (C$_3$-C$_{12}$)spirocycloalkyl is a spirocycle containing between 3 and 12 carbon atoms.

"Spiroheterocycloalkyl" or "spiroheterocyclyl" means a spirocycle wherein at least one of the rings is a heterocycle one or more of the carbon atoms can be substituted with a heteroatom (e.g., one or more of the carbon atoms can be substituted with a heteroatom in at least one of the rings). One or both of the rings in a spiroheterocycle can be fused to another ring carbocyclic, heterocyclic, aromatic, or heteroaromatic ring.

In the groups, radicals, or moieties defined below, the number of carbon atoms is often specified preceding the group, for example, (C$_1$-C$_{10}$)alkyl means an alkyl group or radical having 1 to 10 carbon atoms. In general, for groups comprising two or more subgroups, the last named group is the radical attachment point, for example, "alkylaryl" means a monovalent radical of the formula alkyl-aryl-, while "arylalkyl" means a monovalent radical of the formula aryl-alkyl-. Furthermore, the use of a term designating a monovalent radical where a divalent radical is appropriate shall be construed to designate the respective divalent radical and vice versa. Unless otherwise specified, conventional definitions of terms control and conventional stable atom valences are presumed and achieved in all formulas and groups. The articles "a" and "an" refer to one or more than one (e.g., to at least one) of the grammatical object of the article. By way of example, "an element" means one element or more than one element.

The term "and/or" means either "and" or "or" unless indicated otherwise.

The term "optionally substituted" means that a given chemical moiety (e.g., an alkyl group) can (but is not required to) be bonded other substituents (e.g., heteroatoms). For instance, an alkyl group that is optionally substituted can be a fully saturated alkyl chain (e.g., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus, the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —CH$_2$CN, —O—(C$_1$-C$_6$)alkyl, (C$_1$-C$_6$)alkyl, (C$_1$-C$_6$)alkoxy, (C$_1$-C$_6$)haloalkyl, (C$_1$-C$_6$)haloalkoxy, —O—(C$_2$-C$_6$)alkenyl, —O—(C$_2$-C$_6$)alkynyl, (C$_2$-C$_6$)alkenyl, (C$_2$-C$_6$)alkynyl, —OH, —OP(O)(OH)$_2$, —OC(O)(C$_1$-C$_6$)alkyl, —C(O)(C$_1$-C$_6$)alkyl, —OC(O)O(C$_1$-C$_6$)alkyl, —NH$_2$, —NH((C$_1$-C$_6$)alkyl), —N((C$_1$-C$_6$)alkyl)$_2$, —NHC(O)(C$_1$-C$_6$)alkyl, —C(O)NH(C$_1$-C$_6$)alkyl, —S(O)$_2$(C$_1$-C$_6$)alkyl, —S(O)NH(C$_1$-C$_6$)alkyl, and —S(O)N((C$_1$-C$_6$)alkyl)$_2$. The substituents can themselves be optionally substituted. "Optionally substituted" as used herein also refers to substituted or unsubstituted whose meaning is described below.

The term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

The term "unsubstituted" means that the specified group bears no substituents.

B. Salt, Derivative and Solvate Terms and Conventions

The terms "salt" or "salts" refers to an acid addition or base addition salt of a compound of the present invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto. When both a basic group and an acid group are present in the same molecule, the compounds of the present invention may also form internal salts, e.g., zwitterionic molecules.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of the present invention in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

"Solvate" means a complex of variable stoichiometry formed by a solute, for example, a compound of Formula (I)) and solvent, for example, water, ethanol, or acetic acid. This physical association may involve varying degrees of ionic and covalent bonding, including hydrogen bonding. In certain instances, the solvate will be capable of isolation, for example, when one or more solvent molecules are incorporated in the crystal lattice of the crystalline solid. In general, such solvents selected for the purpose of the disclosure do not interfere with the biological activity of the solute. Solvates encompasses both solution-phase and isolatable solvates. Representative solvates include hydrates, ethanolates, methanolates, and the like.

"Hydrate" means a solvate wherein the solvent molecule(s) is/are water.

The compounds of the present disclosure as discussed below include the free base or acid thereof, their salts, solvates, and may include oxidized sulfur atoms or quaternized nitrogen atoms in their structure, although not explicitly stated or shown, particularly the pharmaceutically acceptable forms thereof. Such forms, particularly the pharmaceutically acceptable forms, are intended to be embraced by the appended claims.

C. Isomer Terms and Conventions

"Isomers" means compounds having the same number and kind of atoms, and hence the same molecular weight, but differing with respect to the arrangement or configuration of the atoms in space. The term includes stereoisomers and geometric isomers.

"Stereoisomer" or "optical isomer" mean a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure exist in the compounds of the disclosure which may give rise to stereoisomerism, the disclosure contemplates stereoisomers and mixtures thereof. The compounds of the disclosure and their salts include asymmetric carbon atoms and may therefore exist as single stereoisomers, racemates, and as mixtures of enantiomers and diastereomers. Typically, such compounds will be prepared as a racemic mixture. If desired, however, such compounds can be prepared or isolated as pure stereoisomers, i.e., as individual enantiomers or diastereomers, or as stereoisomer-enriched mixtures. As discussed in more detail below, individual stereoisomers of compounds are prepared by synthesis from optically active starting materials containing the desired chiral centers or by preparation of mixtures of enantiomeric products followed by separation or resolution, such as conversion to a mixture of diastereomers followed by separation or recrystallization, chromatographic techniques, use of chiral resolving agents, or direct separation of the enantiomers on chiral chromatographic columns. Starting compounds of particular stereochemistry are either commercially available or are made by the methods described below and resolved by techniques well-known in the art.

"Enantiomers" means a pair of stereoisomers that are non-superimposable mirror images of each other.

"Diastereoisomers" or "diastereomers" mean optical isomers which are not mirror images of each other.

"Racemic mixture" or "racemate" mean a mixture containing equal parts of individual enantiomers.

"Non-racemic mixture" means a mixture containing unequal parts of individual enantiomers.

"Geometrical isomer" means a stable isomer which results from restricted freedom of rotation about double bonds (e.g., cis-2-butene and trans-2-butene) or in a cyclic structure (e.g., cis-1,3-dichlorocyclobutane and trans-1,3-dichlorocyclobutane). Because carbon-carbon double (olefinic) bonds, C=N double bonds, cyclic structures, and the like may be present in the compounds of the disclosure, the disclosure contemplates each of the various stable geometric isomers and mixtures thereof resulting from the arrangement of substituents around these double bonds and in these cyclic structures. The substituents and the isomers are designated using the cis/trans convention or using the E or Z system, wherein the term "E" means higher order substituents on opposite sides of the double bond, and the term "Z" means higher order substituents on the same side of the double bond. A thorough discussion of E and Z isomerism is provided in J. March, Advanced Organic Chemistry: Reactions, Mechanisms, and Structure, 4th ed., John Wiley & Sons, 1992, which is hereby incorporated by reference in its entirety. Several of the following examples represent single E isomers, single Z isomers, and mixtures of E/Z isomers. Determination of the E and Z isomers can be done by analytical methods such as x-ray crystallography, $^1$H NMR, and $^{13}$C NMR.

Some of the compounds of the disclosure can exist in more than one tautomeric form. As mentioned above, the compounds of the disclosure include all such tautomers.

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like.

Thus, although the racemic form of drug may be used, it is often less effective than administering an equal amount of enantiomerically pure drug; indeed, in some cases, one enantiomer may be pharmacologically inactive and would merely serve as a simple diluent. Furthermore, the pharmacological activities of enantiomers may have distinct biological activity. Indeed, some purified enantiomers have advantages over the racemates, as it has been reported that purified individual isomers have faster transdermal penetration rates compared to the racemic mixture.

Thus, if one enantiomer is pharmacologically more active, less toxic, or has a preferred disposition in the body than the other enantiomer, it would be therapeutically more beneficial to administer that enantiomer preferentially. In this way, the patient undergoing treatment would be exposed to a lower total dose of the drug and to a lower dose of an enantiomer that is possibly toxic or an inhibitor of the other enantiomer.

Preparation of pure enantiomers or mixtures of desired enantiomeric excess (ee) or enantiomeric purity are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, for example, GC, HPLC, CE, or NMR, and assignment of absolute configuration and conformation, for example, CD ORD, X-ray crystallography, or NMR.

In general, all tautomeric forms and isomeric forms and mixtures, whether individual geometric isomers or stereoisomers or racemic or non-racemic mixtures, of a chemical structure or compound is intended, unless the specific stereochemistry or isomeric form is specifically indicated in the compound name or structure.

D. Pharmaceutical Administration and Treatment Terms and Conventions

A "patient" or "subject" is a mammal, e.g., a human, mouse, rat, guinea pig, dog, cat, horse, cow, pig, or nonhuman primate, such as a monkey, chimpanzee, baboon or, rhesus. In certain embodiments, the subject is a primate. In yet other embodiments, the subject is a human.

An "effective amount" or "therapeutically effective amount" when used in connection with a compound means an amount of a compound of the present disclosure that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The terms "pharmaceutically effective amount" or "therapeutically effective amount" means an amount of a compound according to the disclosure which, when administered to a patient in need thereof, is sufficient to effect treatment for disease-states, conditions, or disorders for which the compounds have utility. Such an amount would be sufficient to elicit the biological or medical response of a tissue, system, or patient that is sought by a researcher or clinician. The amount of a compound of according to the disclosure which constitutes a therapeutically effective amount will vary depending on such factors as the compound and its biological activity, the composition used for administration, the time of administration, the route of administration, the rate of excretion of the compound, the duration of treatment, the type of disease-state or disorder being treated and its severity, drugs used in combination with or coincidentally with the compounds of the disclosure, and the age, body weight, general health, sex, and diet of the patient. Such a therapeutically effective amount can be determined routinely by one of ordinary skill in the art having regard to their own knowledge, the prior art, and this disclosure.

As used herein, the term "pharmaceutical composition" refers to a compound of the disclosure, or a pharmaceutically acceptable salt, hydrate, solvate, stereoisomer, or tautomer thereof, together with at least one pharmaceutically acceptable carrier, in a form suitable for oral or parenteral administration.

"Carrier" encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

A subject is "in need of" a treatment if such subject would benefit biologically, medically, or in quality of life from such treatment (preferably, a human).

As used herein, the term "inhibit", "inhibition", or "inhibiting" refers to the reduction or suppression of a given condition, symptom, or disorder, or disease, or a significant decrease in the baseline activity of a biological activity or process.

As used herein, the term "treat", "treating", or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing", or "prevention" of any disease or disorder refers to the prophylactic treatment of the disease or disorder; or delaying the onset or progression of the disease or disorder.

"Pharmaceutically acceptable" means that the substance or composition must be compatible chemically and/or toxicologically, with the other ingredients comprising a formulation, and/or the mammal being treated therewith.

"Disorder" means, and is used interchangeably with, the terms disease, condition, or illness, unless otherwise indicated.

"Administer", "administering", or "administration" means either directly administering a disclosed compound or pharmaceutically acceptable salt of the disclosed compound or a composition to a subject, or administering a pharmaceutically acceptable salt of the compound or composition to the subject, which can form an equivalent amount of active compound within the subject's body.

"Compounds of the present disclosure", "Compounds of Formula (I)", "compounds of the disclosure", "compounds of the invention" and equivalent expressions (unless specifically identified otherwise) refer to compounds of Formulae (I), and (Ia)-(Ih) as herein described including the tautomers, the salts particularly the pharmaceutically acceptable salts, and the solvates and hydrates thereof, where the context so permits thereof, as well as all stereoisomers (including diastereoisomers and enantiomers), rotamers, tautomers, and isotopically labelled compounds (including deuterium substitutions), as well as inherently formed moieties (e.g., polymorphs, solvates and/or hydrates). For purposes of this disclosure, solvates and hydrates are generally considered compositions. In general and preferably, the compounds of the disclosure and the formulas designating the compounds of the disclosure are understood to only include the stable compounds thereof and exclude unstable compounds, even if an unstable compound might be considered to be literally embraced by the compound formula. Similarly, reference to intermediates, whether or not they themselves are claimed, is meant to embrace their salts and solvates, where the context so permits. For the sake of clarity, particular instances when the context so permits are sometimes indicated in the text, but these instances are purely illustrative and it is not intended to exclude other instances when the context so permits.

"Stable compound" or "stable structure" means a compound that is sufficiently robust to survive isolation to a useful degree of purity from a reaction mixture, and formulation into an efficacious therapeutic or diagnostic agent. For example, a compound which would have a "dangling valency" or is a carbanion is not a compound contemplated by the disclosure.

In a specific embodiment, the term "about" or "approximately" means within 20%, preferably within 10%, and more preferably within 5% of a given value or range.

The yield of each of the reactions described herein is expressed as a percentage of the theoretical yield.

"cGAS-dependent disease or disorder" means any disease or disorder which is directly or indirectly affected by the modulation of cGAS protein levels.

E. Specific Embodiments and Methods for Testing Compounds of Formula (I)

The present disclosure relates to compounds or pharmaceutically acceptable salts, hydrates, solvates, stereoisomers, or tautomers thereof, capable of inhibiting cGAS or cGAS pathway, which are useful for the treatment of diseases and disorders associated with cGAS. The disclosure further relates to compounds, or pharmaceutically acceptable salts, hydrates, solvates, stereoisomers, or tautomers thereof, which are useful for inhibiting cGAS activity.

Embodiment 1. A compound of Formula (I):

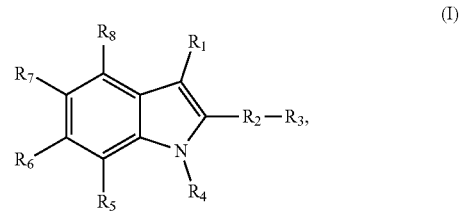

(I)

or a pharmaceutically acceptable salt, hydrate, solvate, stereoisomer, or tautomer thereof, wherein:

$R_1$ is a 5-membered heteroaryl ring comprising 1 to 4 heteroatoms selected from O, N, and S, optionally substituted with at least one of $(C_1-C_4)$alkyl, OH, halogen, —$NR_aR_b$, and 5- or 6-membered heterocycloalkyl ring containing an oxygen;

$R_2$ is 5-membered heteroaryl ring comprising 3 nitrogen atoms at 1, 2 and 4-positions relative to each other, optionally substituted with $(C_1-C_4)$alkyl, $(C_1-C_4)$alkylene-OH, —$(C_1-C_4)$alkylene-$NR_9R_{10}$, $(C_1-C_4)$alkylene-C(O)OH or benzyl at an available ring nitrogen atom, wherein the benzyl is optionally substituted with $(C_1-C_4)$alkoxy, and wherein the 5-membered heteroaryl ring is further substituted with $R_3$ at a 5-membered heteroaryl ring carbon atom;

$R_3$ is H, halogen, —OH, —$NR_{11}R_{12}$, —$(C_1-C_4)$alkylene-$NR_{13}R_{14}$, $(C_1-C_4)$alkyl, halo$(C_1-C_4)$alkyl, —$(C_1-C_4)$alkylene-OH, —$(C_1-C_4)$alkylene-$(C_1-C_4)$alkoxy, —$C(O)(C_1-C_4)$alkyl, —$C(O)(C_1-C_4)$alkylene-O—$(C_1-C_4)$alkyl, —$C(O)(C_1-C_4)$alkylene-OH, —$C(O)$$NR_{15}R_{16}$, $(C_1-C_4)$alkoxy, —$(C_1-C_4)$alkylene-S(O)$C_1$-$C_4)$alkyl, —$C(O)(C_1-C_4)$alkoxy, —CN, —$O(C_1-C_4)$alkylene-OH, —$O(C_1-C_4)$alkylene-$(C_1-C_4)$alkoxy, —$(C_1-C_4)$alkylene-C(O)$(C_1-C_4)$alkyl, —$(C_1-C_4)$alkylene-C(O)$(C_1-C_4)$alkoxy, —$(C_1-C_4)$alkylene-C(O)$NR_{17}R_{18}$, 6-membered heterocycloalkyl ring Ri comprising 1 to 2 heteroatoms selected from O and N, or

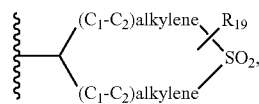

wherein
the $(C_1-C_4)$alkyl is optionally substituted with at least one of CN, =N—$(C_1-C_4)$alkoxy, =N—O—$(C_1-C_4)$alkylene-$OR_{20}$, OH, $(C_1-C_4)$alkoxy, —C(O)OH, —C(O)

O(C$_1$-C$_4$)alkyl, 4- to 6-membered heterocycloalkyl ring comprising 1 to 2 heteroatoms selected from O, N, and S, and 5 to 6-membered heteroaryl ring comprising 1 to 2 heteroatoms selected from O, N and S;

each —(C$_1$-C$_4$)alkylene-NR$_9$R$_{10}$ and —(C$_1$-C$_4$)alkylene-NR$_{13}$R$_{14}$ is optionally substituted at least one of the (C$_1$-C$_4$)alkylene carbons with OH, (C$_1$-C$_4$)alkoxy, —(C$_1$-C$_4$)alkylene-O(C$_1$-C$_4$)alkyl, (C$_1$-C$_4$)alkyl;

each halo(C$_1$-C$_4$)alkyl and (C$_1$-C$_4$)alkylene-OH is independently optionally substituted with at least one of OH, (C$_1$-C$_4$)alkoxy, —O(C$_1$-C$_4$)alkylene-OH, —(C$_1$-C$_4$)alkylene-OH, —(C$_1$-C$_4$)alkylene-(C$_1$-C$_4$)alkoxy;

Ri is optionally substituted with a (C$_1$-C$_4$)alkyl;

v is 0, 1 or 2;

R$_4$ is H, (C$_1$-C$_4$)alkyl, —(C$_1$-C$_4$)alkylene-OH, —(C$_1$-C$_4$)alkylene-(C$_1$-C$_4$)alkoxy, —(C$_1$-C$_4$)alkylene-C(O)OH, —C(O)O(C$_1$-C$_4$)alkyl or a 5 to 6-membered heteroaryl ring comprising 1 to 2 nitrogen atoms optionally substituted with one or more (C$_1$-C$_4$)alkoxy;

each R$_5$, R$_6$, R$_7$ and R$_8$ is independently H, halogen, OH, (C$_1$-C$_4$)alkyl, (C$_1$-C$_4$)cycloalkyl, (C$_1$-C$_4$)alkoxy, —O(C$_1$-C$_4$)cycloalkyl, halo(C$_1$-C$_4$)alkyl, halo(C$_1$-C$_4$)alkoxy, (C$_2$-C$_6$)alkenyl, (C$_2$-C$_6$)alkynyl, —(C$_1$-C$_4$)alkylene-OH, —O(C$_1$-C$_4$)alkylene-OH, CN, —C(O)(C$_1$-C$_4$)alkoxy, —C(O)NR$_{21}$R$_{22}$ or a 5-membered heteroaryl ring comprising 2 nitrogen heteroatoms, wherein each (C$_2$-C$_6$)alkenyl and (C$_2$-C$_6$)alkynyl is independently optionally substituted with one or more (C$_1$-C$_4$)alkoxy;

each R$_{20}$, R$_{21}$ and R$_{22}$ is independently H or (C$_1$-C$_4$)alkyl;

each R$_9$, R$_{10}$, R$_{11}$, R$_{12}$, R$_{13}$, R$_{14}$, R$_{15}$, R$_{16}$, R$_{17}$ and R$_{18}$ is independently, H, (C$_1$-C$_4$)alkyl, —(C$_1$-C$_4$)alkylene-OH, —(C$_1$-C$_4$)alkylene-O(C$_1$-C$_4$)alkyl, —C(O)(C$_1$-C$_4$)alkylene-(C$_1$-C$_4$)alkoxy, or —C(O)(C$_1$-C$_4$)alkyl; or R$_9$ and R$_{10}$, together with the nitrogen atom to which they are attached, form a 5- or 6-membered heterocycloalkyl ring R$_{23}$ comprising 1 to 2 heteroatoms selected from O, N, and S, wherein R$_{23}$ is optionally substituted with one or more R$_{24}$;

R$_{11}$ and R$_{12}$, together with the nitrogen atom to which they are attached, form a 5- or 6-membered heterocycloalkyl ring R$_{25}$ comprising 1 to 2 heteroatoms selected from O, N, and S, wherein R$_{25}$ is optionally substituted with one or more R$_{26}$;

R$_{13}$ and R$_{14}$, together with the nitrogen atom to which they are attached, form a 5- or 6-membered heterocycloalkyl ring R$_{27}$ comprising 1 to 2 heteroatoms selected from O, N, and S, wherein R$_{27}$ is optionally substituted with one or more R$_{28}$;

R$_{15}$ and R$_{16}$, together with the nitrogen atom to which they are attached, form a 5- or 6-membered heterocycloalkyl ring R$_{29}$ comprising 1 to 2 heteroatoms selected from O, N, and S, wherein R$_{29}$ is optionally substituted with one or more R$_{30}$;

R$_{17}$ and R$_{18}$, together with the nitrogen atom to which they are attached, form a 5- or 6-membered heterocycloalkyl ring R$_{31}$ comprising 1 to 2 heteroatoms selected from O, N, and S, wherein R$_{31}$ is optionally substituted with R$_{32}$;

each R$_{24}$, R$_{26}$, R$_{28}$, R$_{30}$ and R$_{32}$ is independently (C$_1$-C$_4$)alkyl, (C$_1$-C$_4$)alkoxy, NR$_c$R$_d$, OH or =O; or two of each R$_{24}$, R$_{26}$, R$_{28}$, R$_{30}$ and R$_{32}$ together, when attached to the same atom, form a (C$_4$-C$_7$) spirocycloalkyl or a 4- to 7-membered spiroheterocycloalkyl ring comprising 1 to 2 heteroatoms selected from O, N, and S;

R$_{19}$ is H, OH or (C$_1$-C$_4$)alkyl; and each R$_a$, R$_b$, Re and Re is independently H, halogen, or (C$_1$-C$_4$)alkyl.

Embodiment 2. The compound of Embodiment 1, wherein the 5-membered heteroaryl ring of R$_1$ is imidazolyl, optionally substituted with at least one of (C$_1$-C$_4$)alkyl, OH, and 5- or 6-membered heterocycloalkyl ring containing an oxygen.

Embodiment 3. The compound of Embodiment 1, wherein the 5-membered heteroaryl ring of R$_1$ is pyrazolyl, optionally substituted with at least one of (C$_1$-C$_4$)alkyl, OH, and 5- or 6-membered heterocycloalkyl ring containing an oxygen.

Embodiment 4. The compound of Embodiment 1, having the structure of Formula (Ia), Formula (Iaa):

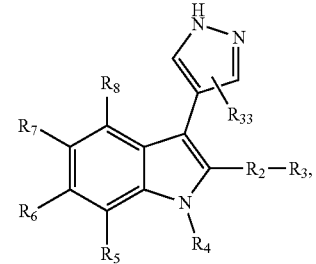

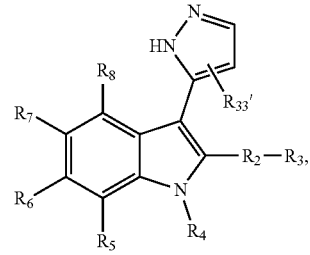

or pharmaceutically acceptable salts, hydrates, solvates, stereoisomers, and tautomers thereof, wherein R$_{33}$ or R$_{33}$' is at a ring carbon or nitrogen position H, (C$_1$-C$_4$)alkyl or 5- or 6-membered heterocycloalkyl ring containing an oxygen atom.

Embodiment 5. The compound of Embodiment 1, having the structure of Formula (Ib):

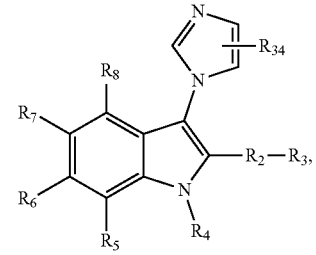

or pharmaceutically acceptable salts, hydrates, solvates, stereoisomers, and tautomers thereof, wherein R$_{34}$ is at a ring carbon or nitrogen position H, (C$_1$-C$_4$)alkyl or 5- or 6-membered heterocycloalkyl ring containing an oxygen atom.

Embodiment 6. The compound of Embodiment 1, having the structure of Formula (Ic), Formula (Icc), Formula (Iccc):

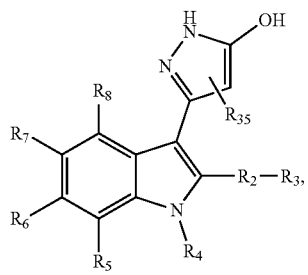

(Ic)

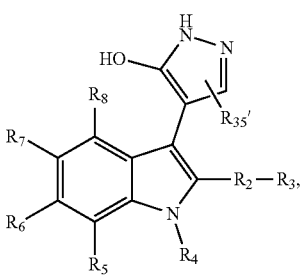

(Icc)

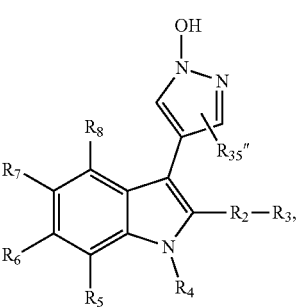

(Iccc)

or pharmaceutically acceptable salts, hydrates, solvates, stereoisomers, and tautomers thereof, wherein $R_{35}$, $R_{35}'$ or $R_{35}''$ is at a ring carbon or nitrogen position H, $(C_1\text{-}C_4)$alkyl or 5- or 6-membered heterocycloalkyl ring containing an oxygen atom.

Embodiment 7. The compound of Embodiment 1, having the structure of Formula (Id):

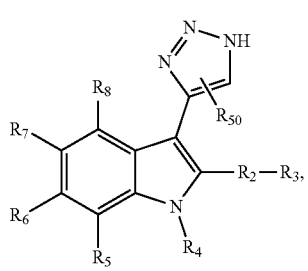

(Id)

or pharmaceutically acceptable salts, hydrates, solvates, stereoisomers, and tautomers thereof, wherein $R_{50}$ is at a ring carbon or nitrogen position H, $(C_1\text{-}C_4)$alkyl or 5- or 6-membered heterocycloalkyl ring containing an oxygen atom.

Embodiment 8. The compound of Embodiment 1, having the structure of Formula (Ie):

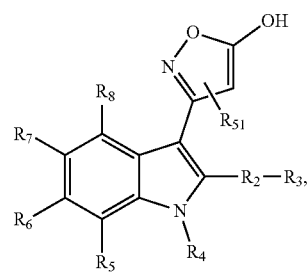

(Ie)

or pharmaceutically acceptable salts, hydrates, solvates, stereoisomers, and tautomers thereof, wherein $R_{51}$ is at a ring carbon or nitrogen position H, $(C_1\text{-}C_4)$alkyl or 5- or 6-membered heterocycloalkyl ring containing an oxygen atom.

Embodiment 9. The compound of Embodiment 1, having the structure of Formula (If):

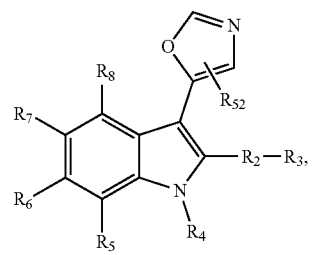

(If)

or pharmaceutically acceptable salts, hydrates, solvates, stereoisomers, and tautomers thereof, wherein $R_{52}$ is at a ring carbon or nitrogen position H, $(C_1\text{-}C_4)$alkyl or 5- or 6-membered heterocycloalkyl ring containing an oxygen atom.

Embodiment 10. The compound of Embodiment 1, having the structure of Formula (Ig):

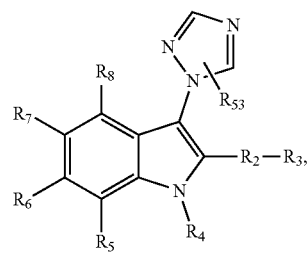

(Ig)

or pharmaceutically acceptable salts, hydrates, solvates, stereoisomers, and tautomers thereof, wherein $R_{53}$ is at a ring carbon or nitrogen position H, $(C_1\text{-}C_4)$alkyl or 5- or 6-membered heterocycloalkyl ring containing an oxygen atom.

Embodiment 11. The compound of Embodiment 1, having the structure of Formula (Ih):

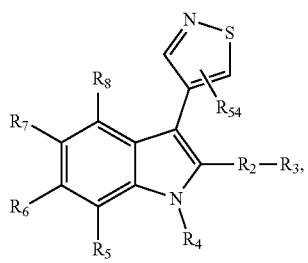

(Ih)

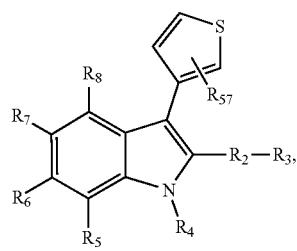

(Ik)

or pharmaceutically acceptable salts, hydrates, solvates, stereoisomers, and tautomers thereof, wherein $R_{54}$ is at a ring carbon or nitrogen position H, $(C_1-C_4)$alkyl or 5- or 6-membered heterocycloalkyl ring containing an oxygen atom.

Embodiment 12. The compound of Embodiment 1, having the structure of Formula (Ii):

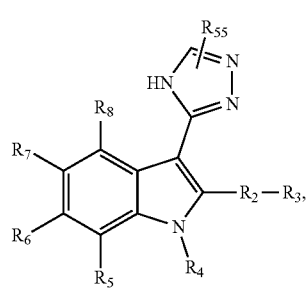

(Ii)

or pharmaceutically acceptable salts, hydrates, solvates, stereoisomers, and tautomers thereof, wherein $R_{55}$ is at a ring carbon or nitrogen position H, $(C_1-C_4)$alkyl or 5- or 6-membered heterocycloalkyl ring containing an oxygen atom.

Embodiment 13. The compound of Embodiment 1, having the structure of Formula (Ij):

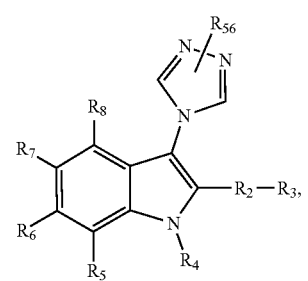

(Ij)

or pharmaceutically acceptable salts, hydrates, solvates, stereoisomers, and tautomers thereof, wherein $R_{56}$ is at a ring carbon or nitrogen position H, $(C_1-C_4)$alkyl or 5- or 6-membered heterocycloalkyl ring containing an oxygen atom.

Embodiment 14. The compound of Embodiment 1, having the structure of Formula (Ik):

or pharmaceutically acceptable salts, hydrates, solvates, stereoisomers, and tautomers thereof, wherein $R_{57}$ is at a ring carbon or nitrogen position H, $(C_1-C_4)$alkyl or 5- or 6-membered heterocycloalkyl ring containing an oxygen atom.

Embodiment 15. The compound of Embodiment 1, having the structure of Formula (Il):

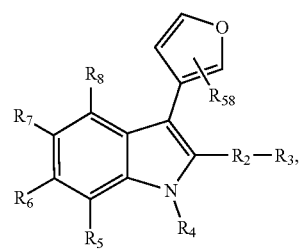

(Il)

or pharmaceutically acceptable salts, hydrates, solvates, stereoisomers, and tautomers thereof, wherein $R_{58}$ is at a ring carbon or nitrogen position H, $(C_1-C_4)$alkyl or 5- or 6-membered heterocycloalkyl ring containing an oxygen atom.

Embodiment 16. The compound of Embodiment 1, having the structure of Formula (Im):

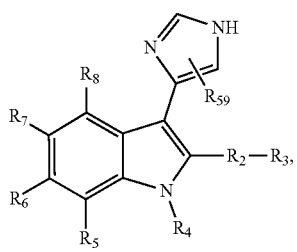

(Im)

or pharmaceutically acceptable salts, hydrates, solvates, stereoisomers, and tautomers thereof, wherein $R_{59}$ is at a ring carbon or nitrogen position H, $(C_1-C_4)$alkyl or 5- or 6-membered heterocycloalkyl ring containing an oxygen atom.

Embodiment 17. The compound of Embodiment 1, having the structure of Formula (In):

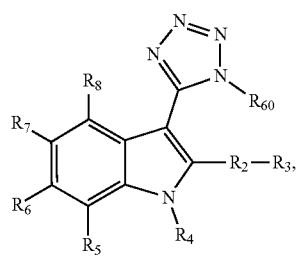

(In)

or pharmaceutically acceptable salts, hydrates, solvates, stereoisomers, and tautomers thereof, wherein $R_{60}$ is at a ring carbon or nitrogen position H, $(C_1-C_4)$alkyl or 5- or 6-membered heterocycloalkyl ring containing an oxygen atom.

Embodiment 18. The compound of Embodiment 1, having the structure of Formula (Io):

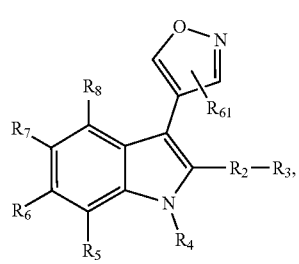

(Io)

or pharmaceutically acceptable salts, hydrates, solvates, stereoisomers, and tautomers thereof, wherein $R_{61}$ is at a ring carbon or nitrogen position H, $(C_1-C_4)$alkyl or 5- or 6-membered heterocycloalkyl ring containing an oxygen atom.

Embodiment 19. The compound of Embodiment 1, having the structure of Formula (Ip):

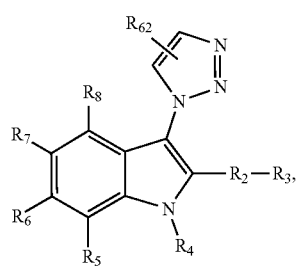

(Ip)

or pharmaceutically acceptable salts, hydrates, solvates, stereoisomers, and tautomers thereof, wherein $R_{62}$ is at a ring carbon or nitrogen position H, $(C_1-C_4)$alkyl or 5- or 6-membered heterocycloalkyl ring containing an oxygen atom.

Embodiment 20. The compound of Embodiment 1, having the structure of Formula (Iq):

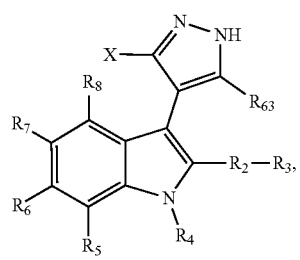

(Iq)

or pharmaceutically acceptable salts, hydrates, solvates, stereoisomers, and tautomers thereof, wherein X is a H, halogen or $NH_2$, $R_{63}$ is at a ring carbon or nitrogen position H, $(C_1-C_4)$alkyl or 5- or 6-membered heterocycloalkyl ring containing an oxygen atom.

Embodiment 21. The compound of Embodiment 1, having the structure of Formula (Ia1):

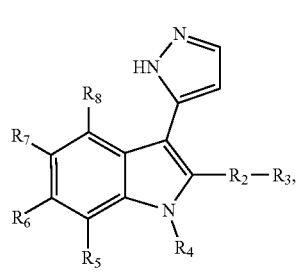

(Ia1)

or pharmaceutically acceptable salts, hydrates, solvates, stereoisomers, and tautomers thereof.

Embodiment 22. The compound of Embodiment 1, having the structure of Formula (Iaa1):

(Iaa1)

or pharmaceutically acceptable salts, hydrates, solvates, stereoisomers, and tautomers thereof.

Embodiment 22. The compound of Embodiment 1, having the structure of Formula (Ib1):

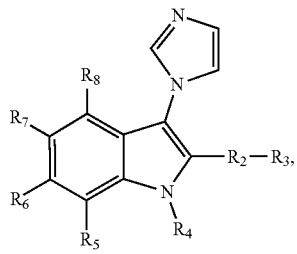

or pharmaceutically acceptable salts, hydrates, solvates, stereoisomers, and tautomers thereof.

Embodiment 23. The compound of Embodiment 1, having the structure of Formula (Ib2):

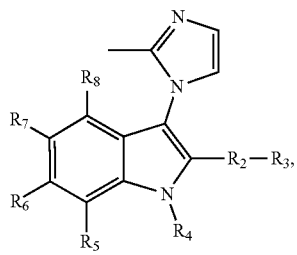

or pharmaceutically acceptable salts, hydrates, solvates, stereoisomers, and tautomers thereof.

Embodiment 24. The compound of Embodiment 1, having the structure of Formula (Ib2):

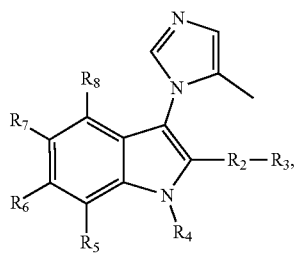

or pharmaceutically acceptable salts, hydrates, solvates, stereoisomers, and tautomers thereof.

Embodiment 25. The compound of Embodiment 1, having the structure of Formula (Ic1):

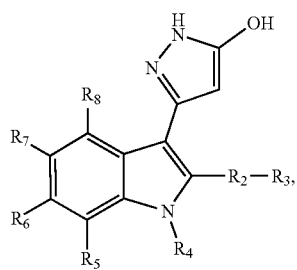

or pharmaceutically acceptable salts, hydrates, solvates, stereoisomers, and tautomers thereof.

Embodiment 26. The compound of Embodiment 1, having the structure of Formula (Icc1):

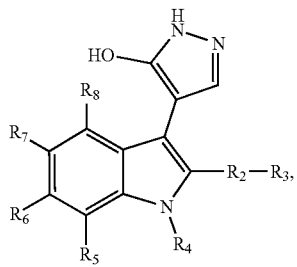

or pharmaceutically acceptable salts, hydrates, solvates, stereoisomers, and tautomers thereof.

Embodiment 27. The compound of Embodiment 1, having the structure of Formula (Iccc1):

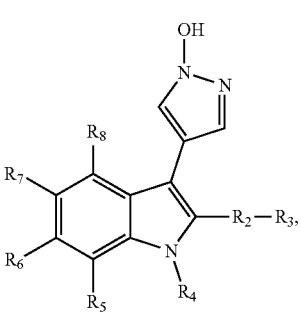

or pharmaceutically acceptable salts, hydrates, solvates, stereoisomers, and tautomers thereof.

Embodiment 28. The compound of Embodiment 1, having the structure of Formula (Id1):

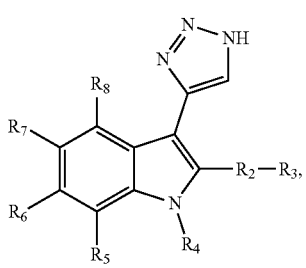

or pharmaceutically acceptable salts, hydrates, solvates, stereoisomers, and tautomers thereof.

Embodiment 29. The compound of Embodiment 1, having the structure of Formula (Ie1):

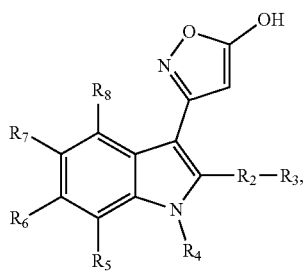

(Ie1)

or pharmaceutically acceptable salts, hydrates, solvates, stereoisomers, and tautomers thereof.

Embodiment 30. The compound of Embodiment 1, having the structure of Formula (If1):

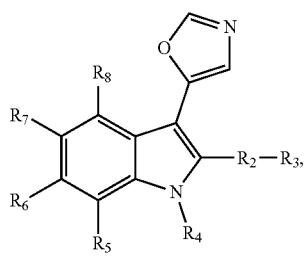

(If1)

or pharmaceutically acceptable salts, hydrates, solvates, stereoisomers, and tautomers thereof.

Embodiment 31. The compound of Embodiment 1, having the structure of Formula (Ig1):

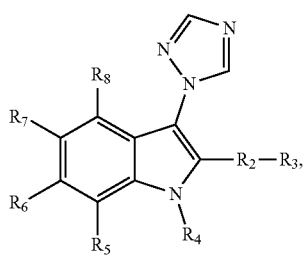

(Ig1)

or pharmaceutically acceptable salts, hydrates, solvates, stereoisomers, and tautomers thereof.

Embodiment 32. The compound of Embodiment 1, having the structure of Formula (Ih1):

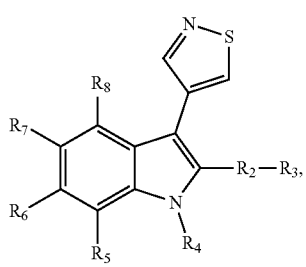

(Ih1)

or pharmaceutically acceptable salts, hydrates, solvates, stereoisomers, and tautomers thereof.

Embodiment 33. The compound of Embodiment 1, having the structure of Formula (Ii1):

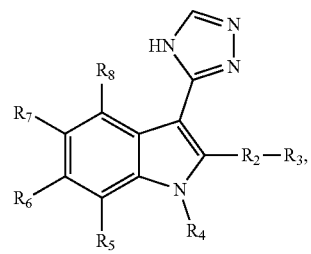

(Ii1)

or pharmaceutically acceptable salts, hydrates, solvates, stereoisomers, and tautomers thereof.

Embodiment 34. The compound of Embodiment 1, having the structure of Formula (Ij1):

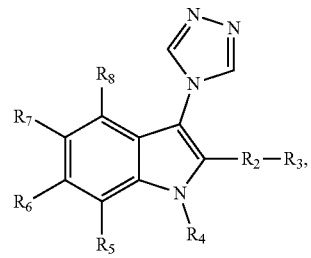

(Ij1)

or pharmaceutically acceptable salts, hydrates, solvates, stereoisomers, and tautomers thereof.

Embodiment 35. The compound of Embodiment 1, having the structure of Formula (Ik1):

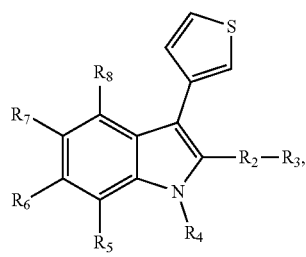

(Ik1)

or pharmaceutically acceptable salts, hydrates, solvates, stereoisomers, and tautomers thereof.

Embodiment 36. The compound of Embodiment 1, having the structure of Formula (Il1):

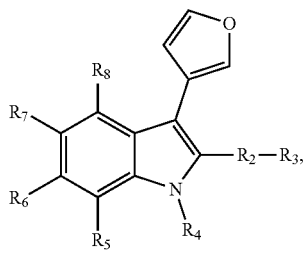

(Il1)

or pharmaceutically acceptable salts, hydrates, solvates, stereoisomers, and tautomers thereof.

Embodiment 37. The compound of Embodiment 1, having the structure of Formula (Im1):

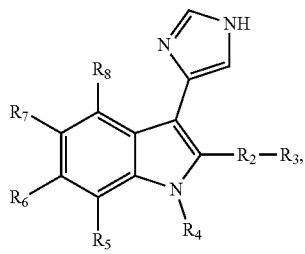

(Im1)

or pharmaceutically acceptable salts, hydrates, solvates, stereoisomers, and tautomers thereof.

Embodiment 38. The compound of Embodiment 1, having the structure of Formula (In1):

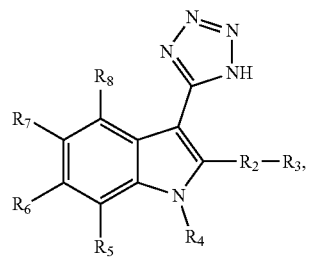

(In1)

or pharmaceutically acceptable salts, hydrates, solvates, stereoisomers, and tautomers thereof.

Embodiment 39. The compound of Embodiment 1, having the structure of Formula (Io1):

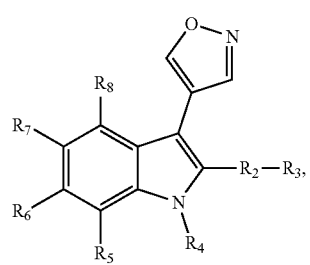

(Io1)

or pharmaceutically acceptable salts, hydrates, solvates, stereoisomers, and tautomers thereof.

Embodiment 40. The compound of Embodiment 1, having the structure of Formula (Ip1):

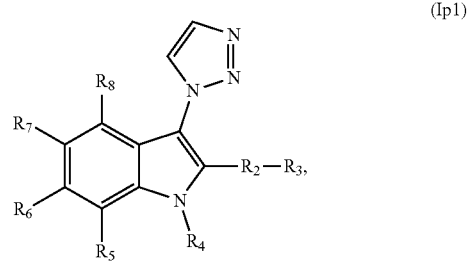

(Ip1)

or pharmaceutically acceptable salts, hydrates, solvates, stereoisomers, and tautomers thereof.

Embodiment 41. The compound of Embodiment 1, having the structure of Formula (Iq1):

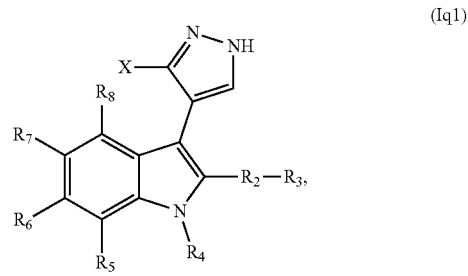

(Iq1)

or pharmaceutically acceptable salts, hydrates, solvates, stereoisomers, and tautomers thereof, wherein X is a H, halogen or $NH_2$, $R_{63}$ is at a ring carbon or nitrogen position H, $(C_1-C_4)$alkyl or 5- or 6-membered heterocycloalkyl ring containing an oxygen atom.

Embodiment 42. The compound of any of Embodiments 1 to 41, having the structure of Formula (IIa):

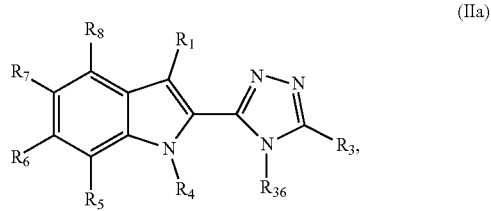

(IIa)

or pharmaceutically acceptable salts, hydrates, solvates, stereoisomers, and tautomers thereof, wherein $R_{36}$ is H, $(C_1-C_4)$alkyl, or —$(C_1-C_4)$alkylene-OH.

Embodiment 43. The compound of any of Embodiments 1 to 42, having the structure of Formula (Ib):

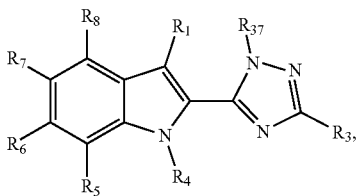

(IIb)

or pharmaceutically acceptable salts, hydrates, solvates, stereoisomers, and tautomers thereof, wherein $R_{37}$ is H, $(C_1-C_4)$alkyl, or —$(C_1-C_4)$alkylene-OH.

Embodiment 44. The compound of any of Embodiments 1 to 43, having the structure of Formula (IIc):

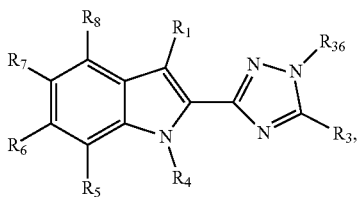

(IIc)

or pharmaceutically acceptable salts, hydrates, solvates, stereoisomers, and tautomers thereof, wherein $R_{38}$ is H, $(C_1-C_4)$alkyl, or —$(C_1-C_4)$alkylene-OH.

Embodiment 45. The compound of any of Embodiments 1 to 44, wherein $R_4$ is H, $(C_1-C_4)$alkyl, —$(C_1-C_4)$alkylene-$(C_1-C_4)$alkoxy, —$(C_1-C_4)$alkylene-OH, pyridyl, pyrazolyl or imidazolyl.

Embodiment 46. The compound of any of Embodiments 1 to 44, wherein $R_4$ is H.

Embodiment 47. The compound of any of Embodiments 1 to 44, wherein $R_4$ is methyl.

Embodiment 48. The compound of any of Embodiments 1 to 47, wherein $R_5$ is H, halogen CN, OH, $(C_1-C_4)$alkyl, $(C_2-C_6)$alkenyl, $(C_2-C_6)$alkynyl, $(C_1-C_4)$alkoxy or imidazolyl. Embodiment 49. The compound of any of Embodiments 1 to 47, wherein $R_5$ is H or methoxy.

Embodiment 50. The compound of any of Embodiments 1 to 47, wherein $R_5$ is halogen, preferably F or Cl.

Embodiment 51. The compound of any of Embodiments 1 to 47, wherein $R_5$ is OH.

Embodiment 52. The compound of any of Embodiments 1 to 47, wherein $R_5$ is CN.

Embodiment 53. The compound of any of Embodiments 1 to 52, wherein $R_6$ is H, halogen, CN, OH, $(C_1-C_4)$alkyl, —$(C_1-C_4)$alkoxy, $(C_2-C_6)$alkenyl, or $(C_2-C_6)$alkynyl.

Embodiment 54. The compound of any of Embodiments 1 to 52, wherein $R_6$ is H or methoxy.

Embodiment 55. The compound of any of Embodiments 1 to 52, wherein $R_6$ is halogen, preferably F or Cl.

Embodiment 56. The compound of any of Embodiments 1 to 55, wherein $R_7$ is H, halogen, CN, OH, $(C_1-C_4)$alkyl, $(C_1-C_4)$alkoxy, —O$(C_1-C_4)$cycloalkyl, halo$(C_1-C_4)$alkoxy, —C(O)NR$_{21}$R$_{22}$, wherein $R_{21}$ and $R_{22}$ is independently H or $(C_1-C_4)$alkyl.

Embodiment 57. The compound of any of Embodiments 1 to 55, wherein $R_7$ is H.

Embodiment 58. The compound of any of Embodiments 1 to 55, wherein $R_7$ is $(C_1-C_4)$alkoxy, preferably methoxy or ethoxy.

Embodiment 59. The compound of any of Embodiments 1 to 55, wherein $R_7$ is OH.

Embodiment 60. The compound of any of Embodiments 1 to 55, wherein $R_7$ is halogen, preferably F or Cl.

Embodiment 61. The compound of any of Embodiments 1 to 55, wherein $R_7$ is CN.

Embodiment 62. The compound of any of Embodiments 1 to 55, wherein $R_7$ is —O$(C_1-C_4)$cycloalkyl, preferably —O-cyclopropyl.

Embodiment 63. The compound of any of Embodiments 1 to 62, wherein $R_8$ is H, F, Cl, CN, OH, $(C_1-C_4)$alkyl, $(C_1-C_4)$alkoxy, preferably H or methyl.

Embodiment 64. The compound of any of Embodiments 1 to 62, wherein $R_8$ is H.

Embodiment 65. The compound of any of Embodiments 1 to 64, wherein $R_3$ is H.

Embodiment 66. The compound of any of Embodiments 1 to 64, wherein $R_3$ is halogen.

Embodiment 67. The compound of any of Embodiments 1 to 64, wherein $R_3$ is F, Cl or Br.

Embodiment 68. The compound of any of Embodiments 1 to 64, wherein $R_3$ is —OH.

Embodiment 69. The compound of any of Embodiments 1 to 64, wherein $R_3$ is halo$(C_1-C_4)$alkyl.

Embodiment 70. The compound of any of Embodiments 1 to 64, wherein $R_3$ is halo$(C_1-C_4)$alkyl, substituted with methoxy.

Embodiment 71. The compound of any of Embodiments 1 to 64, wherein $R_3$ is fluoro$(C_1-C_4)$alkyl.

Embodiment 72. The compound of any of Embodiments 1 to 64, wherein $R_3$ is monofluoromethyl, monofluoroethyl, or monofluoropropyl.

Embodiment 73. The compound of any of Embodiments 1 to 64, wherein $R_3$ is difluoromethyl or difluoroethyl.

Embodiment 74. The compound of any of Embodiments 1 to 64, wherein $R_3$ is trifluoromethyl or trifluoroethyl.

Embodiment 75. The compound of any of Embodiments 1 to 64, wherein $R_3$ is halo$(C_1-C_4)$alkyl substituted with at least one of OH, $(C_1-C_4)$alkoxy, —O$(C_1-C_4)$alkylene-OH, —$(C_1-C_4)$alkylene-OH, —$(C_1-C_4)$alkylene-$(C_1-C_4)$alkoxy.

Embodiment 76. The compound of any of Embodiments 1 to 64, wherein $R_3$ is halo$(C_1-C_4)$alkyl substituted with at least one of $(C_1-C_4)$alkoxy and OH.

Embodiment 77. The compound of any of Embodiments 1 to 64, wherein $R_3$ is monofluoroethyl substituted with one methoxy.

Embodiment 78. The compound of any of Embodiments 1 to 64, wherein $R_3$ is difluoroethyl substituted with one methoxy.

Embodiment 79. The compound of any of Embodiments 1 to 64, wherein $R_3$ is difluoroethyl substituted with OH, or a trifluoroethyl substituted with OH.

Embodiment 80. The compound of any of Embodiments 1 to 64, wherein $R_3$ is —C(O)NR$_{15}$R$_{16}$.

Embodiment 81. The compound of Embodiment 80, wherein each $R_{15}$ and $R_{16}$ is independently H, $(C_1-C_4)$alkyl, —$(C_1-C_4)$alkylene-OH, —$(C_1-C_4)$alkylene-O$(C_1-C_4)$alkyl, —C(O)$(C_1-C_4)$alkylene-$(C_1-C_4)$alkoxy, or —C(O)$(C_1-C_4)$alkyl.

Embodiment 82. The compound of any of Embodiments 1 to 64, wherein $R_3$ is —C(O)NR$_{15}$R$_{16}$, wherein each $R_{15}$ and $R_{16}$ is independently H, methyl, ethyl, -ethylene-OH, -methylene-OH, -ethylene-O-methyl, or -ethylene-O-ethyl.

Embodiment 83. The compound of Embodiment 82, wherein $R_{15}$ and $R_{16}$, together with the nitrogen atom to which they are attached, form a 4- to 6-membered heterocycloalkyl ring $R_{29}$ comprising 1 to 2 heteroatoms selected from O and N, preferably $R_{29}$ is substituted with one $R_{30}$, wherein $R_{30}$ is $(C_1-C_4)$alkyl or OH.

Embodiment 84. The compound of any of Embodiments 1 to 64, wherein $R_3$ is —C(O)($C_1$-$C_4$)alkylene-O—($C_1$-$C_4$)alkyl.

Embodiment 85. The compound of any of Embodiments 1 to 64, wherein $R_3$ is —C(O)methylene-O-methyl, —C(O)ethylene-O-methyl, —C(O)methylene-O-ethyl, or —C(O)ethylene-O-methyl.

Embodiment 86. The compound of any of Embodiments 1 to 64, wherein $R_3$ is —($C_1$-$C_4$)alkylene-OH.

Embodiment 87. The compound of any of Embodiments 1 to 64, wherein $R_3$ is -methylene-OH, -ethylene-OH, -propylene-OH.

Embodiment 88. The compound of any of Embodiments 1 to 64, wherein $R_3$ is —($C_1$-$C_4$)alkylene-OH substituted with ($C_1$-$C_4$)alkoxy.

Embodiment 89. The compound of any of Embodiments 1 to 64, wherein $R_3$ is -methylene-OH or -ethylene-OH, substituted at a methylene or ethylene carbon with ($C_1$-$C_4$)alkoxy.

Embodiment 90. The compound of any of Embodiments 1 to 64, wherein $R_3$ is -methylene-OH or -ethylene-OH, substituted at a methylene or ethylene carbon with methoxy or ethoxy.

Embodiment 91. The compound of any of Embodiments 1 to 64, wherein $R_3$ is —C(O)($C_1$-$C_4$)alkoxy.

Embodiment 92. The compound of any of Embodiments 1 to 64, wherein $R_3$ is —C(O)methoxy, —C(O)ethoxy, —C(O)propoxy.

Embodiment 93. The compound of any of Embodiments 1 to 64, wherein $R_3$ is —($C_1$-$C_4$)alkylene-C(O)($C_1$-$C_4$)alkoxy.

Embodiment 94. The compound of any of Embodiments 1 to 64, wherein $R_3$ is -methylene-C(O)methoxy, -methylene-C(O)ethoxy, -ethylene-C(O)methoxy, -ethylene-C(O)ethoxy, Embodiment 95. The compound of any of Embodiments 1 to 64, wherein $R_3$ is —CN.

Embodiment 96. The compound of any of Embodiments 1 to 64, wherein $R_3$ is —($C_1$-$C_4$)alkylene-($C_1$-$C_4$)alkoxy.

Embodiment 97. The compound of any of Embodiments 1 to 64, wherein $R_3$ is -methylene-methoxy, methylene-ethoxy, ethylene-methoxy, or ethylene-ethoxy.

Embodiment 98. The compound of any of Embodiments 1 to 64, wherein $R_3$ is —($C_1$-$C_4$)alkylene-S(O)$_v$($C_1$-$C_4$)alkyl, wherein v is 0, 1 or 2.

Embodiment 99. The compound of any of Embodiments 1 to 64, wherein $R_3$ is -methylene-S(O)$_v$-methyl, -methylene-S(O)$_v$-ethyl, -ethylene-S(O)$_v$-methyl, or -ethylene-S(O)$_v$-ethyl, wherein v is 0, 1 or 2; preferably $R_3$ is -methylene-S-methyl, -methylene-S-ethyl, -ethylene-S-methyl, or -ethylene-S-ethyl.

Embodiment 100. The compound of any of Embodiments 1 to 64, wherein $R_3$ is -methylene-S(O)-methyl, -methylene-S(O)-ethyl, -ethylene-S(O)-methyl, -ethylene-S(O)-ethyl.

Embodiment 101. The compound of any of Embodiments 1 to 64, wherein $R_3$ is -methylene-S(O)$_2$-methyl, -methylene-S(O)$_2$-ethyl, -ethylene-S(O)$_2$-methyl, or -ethylene-S(O)$_2$-ethyl.

Embodiment 102. The compound of any of Embodiments 1 to 64, wherein $R_3$ is —NR$_{11}$R$_{12}$, wherein R$_{11}$ and R$_{12}$, together with the nitrogen atom to which they are attached, form a 4- to 6-membered heterocycloalkyl ring R$_{25}$ comprising 1 to 2 heteroatoms selected from O, N, and S.

Embodiment 103. The compound of any of Embodiments 1 to 64, wherein $R_3$ is —NR$_{11}$R$_{12}$, wherein R$_{11}$ and R$_{12}$, together with the nitrogen atom to which they are attached, form a 4- to 6-membered heterocycloalkyl ring R$_{25}$ comprising 1 to 2 heteroatoms selected from 0 and N.

Embodiment 104. The compound of any of Embodiments 1 to 64, wherein $R_3$ is —NR$_{11}$R$_{12}$, wherein R$_{11}$ and R$_{12}$, together with the nitrogen atom to which they are attached, form a 4- to 6-membered heterocycloalkyl ring R$_{25}$ comprising 1 to 2 heteroatoms selected from 0 and N, preferably a 5- or 6-membered hetorocycloalkyl ring; wherein R$_{25}$ is substituted with one or more R$_{26}$, wherein R$_{26}$ is ($C_1$-$C_4$)alkyl, ($C_1$-$C_4$)alkoxy, OH or =O, preferably R$_{25}$ is substituted with one R$_{26}$, wherein R$_{26}$ is OH, methyl, or =O.

Embodiment 105. The compound of any of Embodiments 1 to 64, wherein $R_3$ is —NR$_{11}$R$_{12}$, wherein R$_{11}$ and R$_{12}$, together with the nitrogen atom to which they are attached, form a 6-membered heterocycloalkyl ring R$_{25}$ comprising 2 heteroatoms selected from O and N.

Embodiment 106. The compound of any of Embodiments 1 to 64, wherein $R_3$ is —NR$_{11}$R$_{12}$, wherein each R$_{11}$ and R$_{12}$ is independently H, ($C_1$-$C_4$)alkyl, —($C_1$-$C_4$)alkylene-OH, —($C_1$-$C_4$)alkylene-O($C_1$-$C_4$)alkyl, —C(O)($C_1$-$C_4$)alkylene-($C_1$-$C_4$)alkoxy, or —C(O)($C_1$-$C_4$)alkyl.

Embodiment 107. The compound of any of Embodiments 1 to 64, wherein $R_3$ is —NR$_{11}$R$_{12}$, wherein each R$_{11}$ and R$_{12}$ is independently H, methyl, ethyl, -methylene-OH, -ethylene-OH, -propylene-OH, -methylene-O-methyl, -methylene-O-ethyl, -ethylene-O-methyl, -ethylene-O-ethyl, —C(O)methylene-methoxy, —C(O)methylene-ethoxy, —C(O)ethylene-methoxy, —C(O)ethylene-ethoxy, —C(O)methyl, —C(O)ethyl, —C(O)propyl.

Embodiment 108. The compound of any of Embodiments 1 to 64, wherein $R_3$ is —C(O)($C_1$-$C_4$)alkyl.

Embodiment 109. The compound of any of Embodiments 1 to 64, wherein $R_3$ is —C(O)— methyl, or —C(O)-ethyl.

Embodiment 110. The compound of any of Embodiments 1 to 64, wherein $R_3$ is —($C_1$-$C_4$)alkylene-NR$_{13}$R$_{14}$, wherein each R$_{13}$ and R$_{14}$ is independently H, ($C_1$-$C_4$)alkyl, —($C_1$-$C_4$)alkylene-OH, —($C_1$-$C_4$)alkylene-O($C_1$-$C_4$)alkyl, —C(O)($C_1$-$C_4$)alkylene-($C_1$-$C_4$)alkoxy, or —C(O)($C_1$-$C_4$)alkyl.

Embodiment 111. The compound of any of Embodiments 1 to 64, wherein $R_3$ is —($C_1$-$C_4$)alkylene-NR$_{13}$R$_{14}$, wherein each R$_{13}$ and R$_{14}$ is independently H, ($C_1$-$C_4$)alkyl.

Embodiment 112. The compound of any of Embodiments 1 to 64, wherein $R_3$ is —($C_1$-$C_4$)alkylene-NR$_{13}$R$_{14}$, R$_{13}$ and R$_{14}$, together with the nitrogen atom to which they are attached, form a 4- to 6-membered heterocycloalkyl ring R$_{27}$ comprising 1 to 2 heteroatoms selected from O, N, and S.

Embodiment 113. The compound of any of Embodiments 1 to 64, wherein $R_3$ is —($C_1$-$C_4$)alkylene-NR$_{13}$R$_{14}$, R$_{13}$ and R$_{14}$, together with the nitrogen atom to which they are attached, form a 4- to 6-membered heterocycloalkyl ring R$_{27}$ comprising 1 to 2 heteroatoms selected from O and N.

Embodiment 114. The compound of any of Embodiments 1 to 64, wherein $R_3$ is —($C_1$-$C_4$)alkylene-NR$_{13}$R$_{14}$, R$_{13}$ and R$_{14}$, together with the nitrogen atom to which they are attached, form a 4- to 6-membered heterocycloalkyl ring R$_{27}$ comprising 1 to 2 heteroatoms selected from O, N, and S, wherein R$_{27}$ is substituted with one or more R$_{28}$, wherein R$_{28}$ is ($C_1$-$C_4$)alkyl, ($C_1$-$C_4$)alkoxy, OH or =O.

Embodiment 115. The compound of any of Embodiments 1 to 64, wherein $R_3$ is —($C_1$-$C_4$)alkylene-NR$_{13}$R$_{14}$, R$_{13}$ and R$_{14}$, together with the nitrogen atom to which they are attached, form a 4- to 6-membered heterocycloalkyl ring R$_{27}$ comprising 1 to 2 heteroatoms selected from O, N, and S, wherein R$_{27}$ is substituted with one or more R$_{28}$, wherein two of $R_{28}$ together, when attached to the same atom, form a $(C_4-C_7)$ spirocycloalkyl or a 4- to 7-membered spiroheterocycloalkyl ring comprising 1 to 2 heteroatoms selected from O, N, and S.

Embodiment 116. The compound of any of Embodiments 1 to 64, wherein $R_3$ is —$(C_1-C_4)$alkylene-$NR_{13}R_{14}$, wherein $R_{13}$ and $R_{14}$, together with the nitrogen atom to which they are attached, form a 4- to 6-membered heterocycloalkyl ring $R_{27}$ comprising 1 to 2 heteroatoms selected from O and N, wherein $R_{27}$ is substituted with one or more $R_{28}$, wherein two of $R_{28}$ together, when attached to the same atom, form a $(C_4-C_7)$ spirocycloalkyl or a 4- to 7-membered spiroheterocycloalkyl ring comprising 1 to 2 heteroatoms selected from O, N, and S.

Embodiment 117. The compound of any of Embodiments 1 to 64, wherein $R_3$ is —$(C_1-C_4)$alkylene-$NR_{13}R_{14}$, wherein $R_{13}$ and $R_{14}$, together with the nitrogen atom to which they are attached, form a 4- to 6-membered heterocycloalkyl ring $R_{27}$ comprising 1 to 2 heteroatoms selected from O and N, wherein $R_{27}$ is substituted with one or more $R_{28}$, wherein two of $R_{28}$ together, when attached to the same atom, form a $(C_4-C_7)$ spirocycloalkyl or a 4- to 7-membered spiroheterocycloalkyl ring comprising one oxygen atom.

Embodiment 118. The compound of any of Embodiments 1 to 64, wherein $R_3$ is —$(C_1-C_4)$alkylene-$NR_{13}R_{14}$ substituted at at least one of the $(C_1-C_4)$alkylene carbons with OH, $(C_1-C_4)$alkoxy, —$(C_1-C_4)$alkylene-O$(C_1-C_4)$alkyl, $(C_1-C_4)$alkyl, wherein each $R_{13}$ and $R_{14}$ is independently H, $(C_1-C_4)$alkyl, —$(C_1-C_4)$alkylene-OH, —$(C_1-C_4)$alkylene-O$(C_1-C_4)$alkyl, —C(O)$(C_1-C_4)$alkylene-$(C_1-C_4)$alkoxy, or —C(O)$(C_1-C_4)$alkyl.

Embodiment 119. The compound of any of Embodiments 1 to 64, wherein $R_3$ is —$(C_1-C_4)$alkylene-$NR_{13}R_{14}$ substituted at at least one (e.g. one) of the $(C_1-C_4)$alkylene carbons with OH, $(C_1-C_4)$alkoxy, —$(C_1-C_4)$alkylene-O$(C_1-C_4)$alkyl, $(C_1-C_4)$alkyl, wherein each $R_{13}$ and $R_{14}$ is independently H or $(C_1-C_4)$alkyl.

Embodiment 120. The compound of any of Embodiments 1 to 64, wherein $R_3$ is $(C_1-C_4)$alkyl.

Embodiment 121. The compound of any of Embodiments 1 to 64, wherein $R_3$ is $(C_1-C_4)$alkyl substituted with CN.

Embodiment 122. The compound of any of Embodiments 1 to 64, wherein $R_3$ is $(C_1-C_4)$alkyl substituted with at least one of CN, =N—$(C_1-C_4)$alkoxy, =N—O—$(C_1-C_4)$alkylene-$OR_{20}$, OH, $(C_1-C_4)$alkoxy, —C(O)OH, —C(O)O$(C_1-C_4)$alkyl, 4- to 6-membered heterocycloalkyl ring comprising 1 to 2 heteroatoms selected from O, N, and S, and 5 to 6-membered heteroaryl ring comprising 1 to 2 heteroatoms selected from O, N, and S.

Embodiment 123. The compound of any of Embodiments 1 to 64, wherein $R_3$ is $(C_1-C_4)$alkyl substituted with two groups selected from $(C_1-C_4)$alkoxy, 4- to 6-membered heterocycloalkyl ring comprising 1 to 2 heteroatoms selected from O and N, and 5 to 6-membered heteroaryl ring comprising 1 to 2 heteroatoms selected from O, N, and S.

Embodiment 124. The compound of any of Embodiments 1 to 64, wherein $R_3$ is $(C_1-C_4)$alkyl substituted with at least one of $(C_1-C_4)$alkoxy, and 5 to 6-membered heteroaryl ring comprising 1 to 2 heteroatoms selected from O and N.

Embodiment 125. The compound of any of Embodiments 1 to 64, wherein $R_3$ is $(C_1-C_4)$alkyl substituted with at least one of $(C_1-C_4)$alkoxy, 5-membered heteroaryl ring comprising 1 to 2 nitrogen atoms, and 6-membered heteroaryl ring comprising one nitrogen atom.

Embodiment 126. The compound of any of Embodiments 1 to 64, wherein $R_3$ is $(C_1-C_4)$alkoxy.

Embodiment 127. The compound of any of Embodiments 1 to 64 wherein $R_3$ is methoxy, ethoxy, propoxy, isopropoxy, butoxy, sec-butoxy, iso-butoxy, Embodiment 128. The compound of any of Embodiments 1 to 64, wherein $R_3$ is —O$(C_1-C_4)$alkylene-OH.

Embodiment 129. The compound of any of Embodiments 1 to 64, wherein $R_3$ is —C(O)$NR_{15}R_{16}$, wherein each $R_{15}$ and $R_{16}$ is independently H, $(C_1-C_4)$alkyl, —$(C_1-C_4)$alkylene-OH, —$(C_1-C_4)$alkylene-O$(C_1-C_4)$alkyl, —C(O)$(C_1-C_4)$alkylene-$(C_1-C_4)$alkoxy, or —C(O)$(C_1-C_4)$alkyl.

Embodiment 130. The compound of any of Embodiments 1 to 64, wherein $R_3$ is —C(O)$NR_{15}R_{16}$, wherein each $R_{15}$ and $R_{16}$ is independently H or $(C_1-C_4)$alkyl. Embodiment 131. The compound of any of Embodiments 1 to 64, wherein $R_3$ is —C(O)$NR_{15}R_{16}$, wherein each $R_{15}$ and $R_{16}$ is H.

Embodiment 132. The compound of any of Embodiments 1 to 64, wherein $R_3$ is —C(O)$NR_{15}R_{16}$, wherein each $R_{15}$ and $R_{16}$ is methyl.

Embodiment 133. The compound of any of Embodiments 1 to 64, wherein $R_3$ is C(O)$(C_1-C_4)$alkylene-OH.

Embodiment 134. The compound of any of Embodiments 1 to 64, wherein $R_3$ is —O$(C_1-C_4)$alkylene-$(C_1-C_4)$alkoxy.

Embodiment 135. The compound of any of Embodiments 1 to 64, wherein $R_3$ is —$(C_1-C_4)$alkylene-C(O)$(C_1-C_4)$alkyl.

Embodiment 136. The compound of any of Embodiments 1 to 64, wherein $R_3$ is —$(C_1-C_4)$alkylene-C(O)$(C_1-C_4)$alkoxy.

Embodiment 137. The compound of any of Embodiments 1 to 64, wherein $R_3$ is —$(C_1-C_4)$alkylene-C(O)$NR_{17}R_{18}$.

Embodiment 138. The compound of any of Embodiments 1 to 64, wherein $R_3$ is 6-membered heterocycloalkyl ring $R_1$ comprising 1 to 2 heteroatoms selected from O and N, wherein Ri is optionally substituted with a $(C_1-C_4)$alkyl.

Embodiment 139. The compound of any of Embodiments 1 to 64, wherein $R_3$ is 6-membered heterocycloalkyl ring $R_1$ comprising 1 to 2 heteroatoms selected from O and N, wherein Ri is optionally substituted with a $(C_1-C_4)$alkyl, further wherein $R_3$ is bonded to $R_2$ at a ring carbon position of $R_3$.

Embodiment 140. The compound of any of Embodiments 1 to 64, wherein $R_3$ is 6-membered heterocycloalkyl ring $R_1$ comprising 2 heteroatoms selected from O and N, wherein Ri is optionally substituted with a $(C_1-C_4)$alkyl.

Embodiment 141. The compound of any of Embodiments 1 to 64, wherein $R_3$ is 6-membered heterocycloalkyl ring $R_1$ comprising 2 heteroatoms selected from O and N, wherein Ri is substituted with a $(C_1-C_4)$alkyl.

Embodiment 142. The compound of any of Embodiments 1 to 64, wherein $R_3$ is 6-membered heterocycloalkyl ring $R_1$ comprising one O and one N, wherein $R_1$ is substituted with a $(C_1-C_4)$alkyl.

Embodiment 143. The compound of any of Embodiments 1 to 64, wherein $R_3$ is 6-membered heterocycloalkyl ring $R_1$ comprising one O and one N, wherein $R_1$ is substituted with a $(C_1-C_4)$alkyl at the N.

Embodiment 144. The compound of any of Embodiments 1 to 64, wherein $R_3$ is

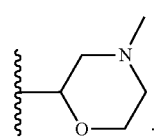

Embodiment 145. The compound of any of Embodiments 1 to 64, wherein $R_3$ is

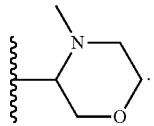 [SMILES: *C1COCCN1C]

Embodiment 146. The compound of any of Embodiments 1 to 64, wherein $R_3$ is

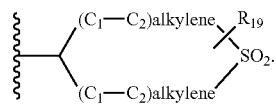

Embodiment 147. The compound of any of Embodiments 1 to 64, wherein $R_3$ is $(C_1-C_4)$alkyl substituted with $(C_1-C_4)$alkoxy and 5 to 6-membered heteroaryl ring comprising 1 to 2 heteroatoms selected from O and N.

Embodiment 148. The compound of any of Embodiments 1 to 64, wherein $R_3$ is $(C_1-C_4)$alkyl substituted with $(C_1-C_4)$alkoxy and 5-membered heteroaryl ring comprising 2 nitrogen heteroatoms.

Embodiment 149. The compound of any of Embodiments 1 to 64, wherein $R_3$ is $(C_1-C_4)$alkyl substituted with $(C_1-C_4)$alkoxy and 6-membered heteroaryl ring comprising 2 nitrogen heteroatoms.

Embodiment 150. The compound of any of Embodiments 1 to 64, wherein $R_3$ is $(C_1-C_4)$alkyl substituted with $(C_1-C_4)$alkoxy and 6-membered heterocycloalkyl ring comprising 2 heteroatoms selected from O and N.

Embodiment 151. The compound of any of Embodiments 1 to 64, wherein $R_3$ is $(C_1-C_4)$alkyl substituted with $(C_1-C_4)$alkoxy and 4-membered heterocycloalkyl ring comprising N.

Embodiment 152. The compound of any of Embodiments 1 to 151, selected from:

6-chloro-7-fluoro-5-methoxy-1-methyl-3-(1H-pyrazol-4-yl)-2-(5-(trifluoromethyl)-4H-1,2,4-triazol-3-yl)-1H-indole;
6-chloro-7-fluoro-5-methoxy-1-methyl-3-(1H-pyrazol-4-yl)-2-(3-(trifluoromethyl)-1H-1,2,4-triazol-5-yl)-1H-indole;
6-chloro-7-fluoro-5-methoxy-1-methyl-3-(1H-pyrazol-4-yl)-2-(5-(trifluoromethyl)-1H-1,2,4-triazol-3-yl)-1H-indole;
5-(6-chloro-7-fluoro-5-methoxy-1-methyl-3-(1H-pyrazol-4-yl)-1H-indol-2-yl)-N,N-dimethyl-4H-1,2,4-triazole-3-carboxamide;
5-(6-chloro-7-fluoro-5-methoxy-1-methyl-3-(1H-pyrazol-4-yl)-1H-indol-2-yl)-N,N-dimethyl-1H-1,2,4-triazole-3-carboxamide;
3-(6-chloro-7-fluoro-5-methoxy-1-methyl-3-(1H-pyrazol-4-yl)-1H-indol-2-yl)-N,N-dimethyl-1H-1,2,4-triazole-5-carboxamide;
6-chloro-7-fluoro-2-(5-fluoro-4H-1,2,4-triazol-3-yl)-5-methoxy-3-(1H-pyrazol-4-yl)-1H-indole;
6-chloro-7-fluoro-2-(3-fluoro-1H-1,2,4-triazol-5-yl)-5-methoxy-3-(1H-pyrazol-4-yl)-1H-indole;
6-chloro-7-fluoro-2-(5-fluoro-1H-1,2,4-triazol-3-yl)-5-methoxy-3-(1H-pyrazol-4-yl)-1H-indole;
6-chloro-7-fluoro-5-methoxy-3-(1H-pyrazol-4-yl)-2-(5-(trifluoromethyl)-4H-1,2,4-triazol-3-yl)-1H-indole;
6-chloro-7-fluoro-5-methoxy-3-(1H-pyrazol-4-yl)-2-(3-(trifluoromethyl)-1H-1,2,4-triazol-5-yl)-1H-indole;
6-chloro-7-fluoro-5-methoxy-3-(1H-pyrazol-4-yl)-2-(5-(trifluoromethyl)-1H-1,2,4-triazol-3-yl)-1H-indole;
2-(5-bromo-4H-1,2,4-triazol-3-yl)-6,7-dichloro-3-(1H-pyrazol-4-yl)-1H-indole;
2-(3-bromo-1H-1,2,4-triazol-5-yl)-6,7-dichloro-3-(1H-pyrazol-4-yl)-1H-indole;
2-(5-bromo-1H-1,2,4-triazol-3-yl)-6,7-dichloro-3-(1H-pyrazol-4-yl)-1H-indole;
6-chloro-7-fluoro-3-(1H-pyrazol-4-yl)-2-(5-(trifluoromethyl)-4H-1,2,4-triazol-3-yl)-1H-indole-5-carbonitrile;
6-chloro-7-fluoro-3-(1H-pyrazol-4-yl)-2-(3-(trifluoromethyl)-1H-1,2,4-triazol-5-yl)-1H-indole-5-carbonitrile;
6-chloro-7-fluoro-3-(1H-pyrazol-4-yl)-2-(5-(trifluoromethyl)-1H-1,2,4-triazol-3-yl)-1H-indole-5-carbonitrile;
1-(5-(6,7-dichloro-3-(1H-pyrazol-4-yl)-1H-indol-2-yl)-4H-1,2,4-triazol-3-yl)-2-methoxyethan-1-one;
1-(5-(6,7-dichloro-3-(1H-pyrazol-4-yl)-1H-indol-2-yl)-1H-1,2,4-triazol-3-yl)-2-methoxyethan-1-one;
1-(3-(6,7-dichloro-3-(1H-pyrazol-4-yl)-1H-indol-2-yl)-1H-1,2,4-triazol-5-yl)-2-methoxyethan-1-one;
6-chloro-7-fluoro-1-methyl-3-(1H-pyrazol-4-yl)-2-(5-(trifluoromethyl)-4H-1,2,4-triazol-3-yl)-1H-indole-5-carbonitrile;
6-chloro-7-fluoro-1-methyl-3-(1H-pyrazol-4-yl)-2-(3-(trifluoromethyl)-1H-1,2,4-triazol-5-yl)-1H-indole-5-carbonitrile;
6-chloro-7-fluoro-1-methyl-3-(1H-pyrazol-4-yl)-2-(5-(trifluoromethyl)-1H-1,2,4-triazol-3-yl)-1H-indole-5-carbonitrile;
6,7-dichloro-2-(5-(1,1-difluoro-2-methoxyethyl)-4H-1,2,4-triazol-3-yl)-3-(1H-pyrazol-4-yl)-1H-indole;
6,7-dichloro-2-(3-(1,1-difluoro-2-methoxyethyl)-1H-1,2,4-triazol-5-yl)-3-(1H-pyrazol-4-yl)-1H-indole;
6,7-dichloro-2-(5-(1,1-difluoro-2-methoxyethyl)-1H-1,2,4-triazol-3-yl)-3-(1H-pyrazol-4-yl)-1H-indole;
6,7-dichloro-2-(5-(1-fluoro-2-methoxyethyl)-4H-1,2,4-triazol-3-yl)-3-(1H-pyrazol-4-yl)-1H-indole;
6,7-dichloro-2-(3-(1-fluoro-2-methoxyethyl)-1H-1,2,4-triazol-5-yl)-3-(1H-pyrazol-4-yl)-1H-indole;
6,7-dichloro-2-(5-(1-fluoro-2-methoxyethyl)-1H-1,2,4-triazol-3-yl)-3-(1H-pyrazol-4-yl)-1H-indole;
(S)-6,7-dichloro-2-(5-(1-fluoro-2-methoxyethyl)-4H-1,2,4-triazol-3-yl)-3-(1H-pyrazol-4-yl)-1H-indole;
(S)-6,7-dichloro-2-(3-(1-fluoro-2-methoxyethyl)-1H-1,2,4-triazol-5-yl)-3-(1H-pyrazol-4-yl)-1H-indole;
(S)-6,7-dichloro-2-(5-(1-fluoro-2-methoxyethyl)-1H-1,2,4-triazol-3-yl)-3-(1H-pyrazol-4-yl)-1H-indole;
(R)-6,7-dichloro-2-(5-(1-fluoro-2-methoxyethyl)-4H-1,2,4-triazol-3-yl)-3-(1H-pyrazol-4-yl)-1H-indole;
(R)-6,7-dichloro-2-(3-(1-fluoro-2-methoxyethyl)-1H-1,2,4-triazol-5-yl)-3-(1H-pyrazol-4-yl)-1H-indole;
(R)-6,7-dichloro-2-(5-(1-fluoro-2-methoxyethyl)-1H-1,2,4-triazol-3-yl)-3-(1H-pyrazol-4-yl)-1H-indole;
6,7-dichloro-3-(1H-pyrazol-4-yl)-2-(5-(trifluoromethyl)-4H-1,2,4-triazol-3-yl)-1H-indole;
6,7-dichloro-3-(1H-pyrazol-4-yl)-2-(3-(trifluoromethyl)-1H-1,2,4-triazol-5-yl)-1H-indole;
6,7-dichloro-3-(1H-pyrazol-4-yl)-2-(5-(trifluoromethyl)-1H-1,2,4-triazol-3-yl)-1H-indole;
6,7-dichloro-1-methyl-3-(1H-pyrazol-4-yl)-2-(5-(trifluoromethyl)-4H-1,2,4-triazol-3-yl)-1H-indole;
6,7-dichloro-1-methyl-3-(1H-pyrazol-4-yl)-2-(3-(trifluoromethyl)-1H-1,2,4-triazol-5-yl)-1H-indole;

6,7-dichloro-1-methyl-3-(1H-pyrazol-4-yl)-2-(5-(trifluoromethyl)-1H-1,2,4-triazol-3-yl)-1H-indole;
6,7-dichloro-3-(1H-pyrazol-4-yl)-2-(5-(2,2,2-trifluoroethyl)-4H-1,2,4-triazol-3-yl)-1H-indole;
6,7-dichloro-3-(1H-pyrazol-4-yl)-2-(3-(2,2,2-trifluoroethyl)-1H-1,2,4-triazol-5-yl)-1H-indole;
6,7-dichloro-3-(1H-pyrazol-4-yl)-2-(5-(2,2,2-trifluoroethyl)-1H-1,2,4-triazol-3-yl)-1H-indole;
6,7-difluoro-3-(1H-pyrazol-4-yl)-2-(5-(trifluoromethyl)-4H-1,2,4-triazol-3-yl)-1H-indole;
6,7-difluoro-3-(1H-pyrazol-4-yl)-2-(3-(trifluoromethyl)-1H-1,2,4-triazol-5-yl)-1H-indole;
6,7-difluoro-3-(1H-pyrazol-4-yl)-2-(5-(trifluoromethyl)-1H-1,2,4-triazol-3-yl)-1H-indole;
2-(5-(6,7-dichloro-3-(1H-pyrazol-4-yl)-1H-indol-2-yl)-4H-1,2,4-triazol-3-yl)ethan-1-ol;
2-(5-(6,7-dichloro-3-(1H-pyrazol-4-yl)-1H-indol-2-yl)-1H-1,2,4-triazol-3-yl)ethan-1-ol;
2-(3-(6,7-dichloro-3-(1H-pyrazol-4-yl)-1H-indol-2-yl)-1H-1,2,4-triazol-5-yl)ethan-1-ol;
6-chloro-7-fluoro-3-(1H-pyrazol-4-yl)-2-(5-(trifluoromethyl)-4H-1,2,4-triazol-3-yl)-1H-indole;
6-chloro-7-fluoro-3-(1H-pyrazol-4-yl)-2-(3-(trifluoromethyl)-1H-1,2,4-triazol-5-yl)-1H-indole;
6-chloro-7-fluoro-3-(1H-pyrazol-4-yl)-2-(5-(trifluoromethyl)-1H-1,2,4-triazol-3-yl)-1H-indole;
6-chloro-7-methoxy-3-(1H-pyrazol-4-yl)-2-(5-(trifluoromethyl)-4H-1,2,4-triazol-3-yl)-1H-indole;
6-chloro-7-methoxy-3-(1H-pyrazol-4-yl)-2-(3-(trifluoromethyl)-1H-1,2,4-triazol-5-yl)-1H-indole;
6-chloro-7-methoxy-3-(1H-pyrazol-4-yl)-2-(5-(trifluoromethyl)-1H-1,2,4-triazol-3-yl)-1H-indole;
5,6-dichloro-3-(1H-pyrazol-4-yl)-2-(5-(trifluoromethyl)-4H-1,2,4-triazol-3-yl)-1H-indole;
5,6-dichloro-3-(1H-pyrazol-4-yl)-2-(3-(trifluoromethyl)-1H-1,2,4-triazol-5-yl)-1H-indole;
5,6-dichloro-3-(1H-pyrazol-4-yl)-2-(5-(trifluoromethyl)-1H-1,2,4-triazol-3-yl)-1H-indole;
6-chloro-3-(1H-pyrazol-4-yl)-2-(5-(trifluoromethyl)-4H-1,2,4-triazol-3-yl)-1H-indole-7-carbonitrile;
6-chloro-3-(1H-pyrazol-4-yl)-2-(3-(trifluoromethyl)-1H-1,2,4-triazol-5-yl)-1H-indole-7-carbonitrile;
6-chloro-3-(1H-pyrazol-4-yl)-2-(5-(trifluoromethyl)-1H-1,2,4-triazol-3-yl)-1H-indole-7-carbonitrile;
6-chloro-5-methoxy-1-methyl-3-(1H-pyrazol-4-yl)-2-(5-(trifluoromethyl)-4H-1,2,4-triazol-3-yl)-1H-indole;
6-chloro-5-methoxy-1-methyl-3-(1H-pyrazol-4-yl)-2-(3-(trifluoromethyl)-1H-1,2,4-triazol-5-yl)-1H-indole;
6-chloro-5-methoxy-1-methyl-3-(1H-pyrazol-4-yl)-2-(5-(trifluoromethyl)-1H-1,2,4-triazol-3-yl)-1H-indole;
ethyl 5-(6,7-dichloro-3-(1H-pyrazol-4-yl)-1H-indol-2-yl)-4H-1,2,4-triazole-3-carboxylate;
ethyl 5-(6,7-dichloro-3-(1H-pyrazol-4-yl)-1H-indol-2-yl)-1H-1,2,4-triazole-3-carboxylate;
ethyl 3-(6,7-dichloro-3-(1H-pyrazol-4-yl)-1H-indol-2-yl)-1H-1,2,4-triazole-5-carboxylate;
5-(6,7-dichloro-3-(1H-pyrazol-4-yl)-1H-indol-2-yl)-4H-1,2,4-triazole-3-carboxamide;
5-(6,7-dichloro-3-(1H-pyrazol-4-yl)-1H-indol-2-yl)-1H-1,2,4-triazole-3-carboxamide;
3-(6,7-dichloro-3-(1H-pyrazol-4-yl)-1H-indol-2-yl)-1H-1,2,4-triazole-5-carboxamide;
5,6-dichloro-1-methyl-3-(1H-pyrazol-4-yl)-2-(5-(trifluoromethyl)-4H-1,2,4-triazol-3-yl)-1H-indole;
5,6-dichloro-1-methyl-3-(1H-pyrazol-4-yl)-2-(3-(trifluoromethyl)-1H-1,2,4-triazol-5-yl)-1H-indole;
5,6-dichloro-1-methyl-3-(1H-pyrazol-4-yl)-2-(5-(trifluoromethyl)-1H-1,2,4-triazol-3-yl)-1H-indole;
6-chloro-5-methoxy-3-(1H-pyrazol-4-yl)-2-(5-(trifluoromethyl)-4H-1,2,4-triazol-3-yl)-1H-indole;
6-chloro-5-methoxy-3-(1H-pyrazol-4-yl)-2-(3-(trifluoromethyl)-1H-1,2,4-triazol-5-yl)-1H-indole;
6-chloro-5-methoxy-3-(1H-pyrazol-4-yl)-2-(5-(trifluoromethyl)-1H-1,2,4-triazol-3-yl)-1H-indole;
2-(6-chloro-5-methoxy-3-(1H-pyrazol-4-yl)-2-(5-(trifluoromethyl)-4H-1,2,4-triazol-3-yl)-1H-indol-1-yl)ethan-1-ol;
2-(6-chloro-5-methoxy-3-(1H-pyrazol-4-yl)-2-(3-(trifluoromethyl)-1H-1,2,4-triazol-5-yl)-1H-indol-1-yl)ethan-1-ol;
2-(6-chloro-5-methoxy-3-(1H-pyrazol-4-yl)-2-(5-(trifluoromethyl)-1H-1,2,4-triazol-3-yl)-1H-indol-1-yl)ethan-1-ol;
6-chloro-5-methoxy-1-(2-methoxyethyl)-3-(1H-pyrazol-4-yl)-2-(5-(trifluoromethyl)-4H-1,2,4-triazol-3-yl)-1H-indole;
6-chloro-5-methoxy-1-(2-methoxyethyl)-3-(1H-pyrazol-4-yl)-2-(3-(trifluoromethyl)-1H-1,2,4-triazol-5-yl)-1H-indole;
6-chloro-5-methoxy-1-(2-methoxyethyl)-3-(1H-pyrazol-4-yl)-2-(5-(trifluoromethyl)-1H-1,2,4-triazol-3-yl)-1H-indole;
6-chloro-1-methyl-3-(1H-pyrazol-4-yl)-2-(5-(trifluoromethyl)-4H-1,2,4-triazol-3-yl)-1H-indole-7-carbonitrile;
6-chloro-1-methyl-3-(1H-pyrazol-4-yl)-2-(3-(trifluoromethyl)-1H-1,2,4-triazol-5-yl)-1H-indole-7-carbonitrile;
6-chloro-1-methyl-3-(1H-pyrazol-4-yl)-2-(5-(trifluoromethyl)-1H-1,2,4-triazol-3-yl)-1H-indole-7-carbonitrile;
ethyl 5-(6-chloro-5-methoxy-3-(1H-pyrazol-4-yl)-1H-indol-2-yl)-4H-1,2,4-triazole-3-carboxylate;
ethyl 5-(6-chloro-5-methoxy-3-(1H-pyrazol-4-yl)-1H-indol-2-yl)-1H-1,2,4-triazole-3-carboxylate;
ethyl 3-(6-chloro-5-methoxy-3-(1H-pyrazol-4-yl)-1H-indol-2-yl)-1H-1,2,4-triazole-5-carboxylate;
methyl 2-(5-(6,7-dichloro-3-(1H-pyrazol-4-yl)-1H-indol-2-yl)-4H-1,2,4-triazol-3-yl)acetate;
methyl 2-(5-(6,7-dichloro-3-(1H-pyrazol-4-yl)-1H-indol-2-yl)-1H-1,2,4-triazol-3-yl)acetate;
methyl 2-(3-(6,7-dichloro-3-(1H-pyrazol-4-yl)-1H-indol-2-yl)-1H-1,2,4-triazol-5-yl)acetate;
7-chloro-3-(1H-pyrazol-4-yl)-2-(5-(trifluoromethyl)-4H-1,2,4-triazol-3-yl)-1H-indole-5-carboxamide;
7-chloro-3-(1H-pyrazol-4-yl)-2-(3-(trifluoromethyl)-1H-1,2,4-triazol-5-yl)-1H-indole-5-carboxamide;
7-chloro-3-(1H-pyrazol-4-yl)-2-(5-(trifluoromethyl)-1H-1,2,4-triazol-3-yl)-1H-indole-5-carboxamide;
5-(6-chloro-5-methoxy-3-(1H-pyrazol-4-yl)-1H-indol-2-yl)-4H-1,2,4-triazole-3-carboxamide;
5-(6-chloro-5-methoxy-3-(1H-pyrazol-4-yl)-1H-indol-2-yl)-1H-1,2,4-triazole-3-carboxamide;
3-(6-chloro-5-methoxy-3-(1H-pyrazol-4-yl)-1H-indol-2-yl)-1H-1,2,4-triazole-5-carboxamide;
4,5-dichloro-1-(1H-pyrazol-4-yl)-2-(5-(trifluoromethyl)-4H-1,2,4-triazol-3-yl)-1H-indole;
4,5-dichloro-1-(1H-pyrazol-4-yl)-2-(3-(trifluoromethyl)-1H-1,2,4-triazol-5-yl)-1H-indole;
4,5-dichloro-1-(1H-pyrazol-4-yl)-2-(5-(trifluoromethyl)-1H-1,2,4-triazol-3-yl)-1H-indole;
6-chloro-3-(1H-pyrazol-4-yl)-2-(5-(trifluoromethyl)-4H-1,2,4-triazol-3-yl)-1H-indol-5-ol;
6-chloro-3-(1H-pyrazol-4-yl)-2-(3-(trifluoromethyl)-1H-1,2,4-triazol-5-yl)-1H-indol-5-ol;

6-chloro-3-(1H-pyrazol-4-yl)-2-(5-(trifluoromethyl)-1H-1,2,4-triazol-3-yl)-1H-indol-5-ol;
6-chloro-3-(1H-pyrazol-4-yl)-2-(5-(trifluoromethyl)-4H-1,2,4-triazol-3-yl)-1H-indol-7-ol;
6-chloro-3-(1H-pyrazol-4-yl)-2-(3-(trifluoromethyl)-1H-1,2,4-triazol-5-yl)-1H-indol-7-ol;
6-chloro-3-(1H-pyrazol-4-yl)-2-(5-(trifluoromethyl)-1H-1,2,4-triazol-3-yl)-1H-indol-7-ol;
5-(6,7-dichloro-3-(1H-pyrazol-4-yl)-1H-indol-2-yl)-4H-1,2,4-triazole-3-carbonitrile;
5-(6,7-dichloro-3-(1H-pyrazol-4-yl)-1H-indol-2-yl)-1H-1,2,4-triazole-3-carbonitrile;
3-(6,7-dichloro-3-(1H-pyrazol-4-yl)-1H-indol-2-yl)-1H-1,2,4-triazole-5-carbonitrile;
(5-(6,7-dichloro-3-(1H-pyrazol-4-yl)-1H-indol-2-yl)-4H-1,2,4-triazol-3-yl)methanol;
(5-(6,7-dichloro-3-(1H-pyrazol-4-yl)-1H-indol-2-yl)-1H-1,2,4-triazol-3-yl)methanol;
(3-(6,7-dichloro-3-(1H-pyrazol-4-yl)-1H-indol-2-yl)-1H-1,2,4-triazol-5-yl)methanol;
2-(3-(6,7-dichloro-3-(1H-pyrazol-4-yl)-1H-indol-2-yl)-1H-1,2,4-triazol-1-yl)ethan-1-ol;
6,7-dichloro-3-(1H-pyrazol-4-yl)-2-(4H-1,2,4-triazol-3-yl)-1H-indole;
6,7-dichloro-3-(1H-pyrazol-4-yl)-2-(1H-1,2,4-triazol-5-yl)-1H-indole;
6,7-dichloro-3-(1H-pyrazol-4-yl)-2-(1H-1,2,4-triazol-3-yl)-1H-indole;
5-(6-chloro-7-fluoro-3-(1H-imidazol-1-yl)-5-methoxy-1-methyl-1H-indol-2-yl)-N,N-dimethyl-4H-1,2,4-triazole-3-carboxamide;
5-(6-chloro-7-fluoro-3-(1H-imidazol-1-yl)-5-methoxy-1-methyl-1H-indol-2-yl)-N,N-dimethyl-1H-1,2,4-triazole-3-carboxamide;
3-(6-chloro-7-fluoro-3-(1H-imidazol-1-yl)-5-methoxy-1-methyl-1H-indol-2-yl)-N,N-dimethyl-1H-1,2,4-triazole-5-carboxamide;
5-(6-chloro-7-fluoro-3-(1H-imidazol-1-yl)-5-methoxy-1-methyl-1H-indol-2-yl)-N-(2-methoxyethyl)-N-methyl-4H-1,2,4-triazole-3-carboxamide;
5-(6-chloro-7-fluoro-3-(1H-imidazol-1-yl)-5-methoxy-1-methyl-1H-indol-2-yl)-N-(2-methoxyethyl)-N-methyl-1H-1,2,4-triazole-3-carboxamide;
3-(6-chloro-7-fluoro-3-(1H-imidazol-1-yl)-5-methoxy-1-methyl-1H-indol-2-yl)-N-(2-methoxyethyl)-N-methyl-1H-1,2,4-triazole-5-carboxamide;
5-(6-chloro-7-fluoro-3-(1H-imidazol-1-yl)-5-methoxy-1-methyl-1H-indol-2-yl)-N-(2-hydroxyethyl)-N-methyl-4H-1,2,4-triazole-3-carboxamide;
5-(6-chloro-7-fluoro-3-(1H-imidazol-1-yl)-5-methoxy-1-methyl-1H-indol-2-yl)-N-(2-hydroxyethyl)-N-methyl-1H-1,2,4-triazole-3-carboxamide;
3-(6-chloro-7-fluoro-3-(1H-imidazol-1-yl)-5-methoxy-1-methyl-1H-indol-2-yl)-N-(2-hydroxyethyl)-N-methyl-1H-1,2,4-triazole-5-carboxamide;
(5-(6-chloro-7-fluoro-3-(1H-imidazol-1-yl)-5-methoxy-1-methyl-1H-indol-2-yl)-4H-1,2,4-triazol-3-yl)(morpholino)methanone;
(5-(6-chloro-7-fluoro-3-(1H-imidazol-1-yl)-5-methoxy-1-methyl-1H-indol-2-yl)-1H-1,2,4-triazol-3-yl)(morpholino)methanone;
(3-(6-chloro-7-fluoro-3-(1H-imidazol-1-yl)-5-methoxy-1-methyl-1H-indol-2-yl)-1H-1,2,4-triazol-5-yl)(morpholino)methanone;
(5-(6-chloro-7-fluoro-3-(1H-imidazol-1-yl)-5-methoxy-1-methyl-1H-indol-2-yl)-4H-1,2,4-triazol-3-yl)(3-hydroxypyrrolidin-1-yl)methanone;
(5-(6-chloro-7-fluoro-3-(1H-imidazol-1-yl)-5-methoxy-1-methyl-1H-indol-2-yl)-1H-1,2,4-triazol-3-yl)(3-hydroxypyrrolidin-1-yl)methanone;
(3-(6-chloro-7-fluoro-3-(1H-imidazol-1-yl)-5-methoxy-1-methyl-1H-indol-2-yl)-1H-1,2,4-triazol-5-yl)(3-hydroxypyrrolidin-1-yl)methanone;
(S)-(5-(6-chloro-7-fluoro-3-(1H-imidazol-1-yl)-5-methoxy-1-methyl-1H-indol-2-yl)-4H-1,2,4-triazol-3-yl)(3-hydroxypyrrolidin-1-yl)methanone;
(S)-(5-(6-chloro-7-fluoro-3-(1H-imidazol-1-yl)-5-methoxy-1-methyl-1H-indol-2-yl)-1H-1,2,4-triazol-3-yl)(3-hydroxypyrrolidin-1-yl)methanone;
(S)-(3-(6-chloro-7-fluoro-3-(1H-imidazol-1-yl)-5-methoxy-1-methyl-1H-indol-2-yl)-1H-1,2,4-triazol-5-yl)(3-hydroxypyrrolidin-1-yl)methanone;
(R)-(5-(6-chloro-7-fluoro-3-(1H-imidazol-1-yl)-5-methoxy-1-methyl-1H-indol-2-yl)-4H-1,2,4-triazol-3-yl)(3-hydroxypyrrolidin-1-yl)methanone;
(R)-(5-(6-chloro-7-fluoro-3-(1H-imidazol-1-yl)-5-methoxy-1-methyl-1H-indol-2-yl)-1H-1,2,4-triazol-3-yl)(3-hydroxypyrrolidin-1-yl)methanone;
(R)-(3-(6-chloro-7-fluoro-3-(1H-imidazol-1-yl)-5-methoxy-1-methyl-1H-indol-2-yl)-1H-1,2,4-triazol-5-yl)(3-hydroxypyrrolidin-1-yl)methanone;
(5-(6-chloro-7-fluoro-3-(1H-imidazol-1-yl)-5-methoxy-1-methyl-1H-indol-2-yl)-4H-1,2,4-triazol-3-yl)(4-hydroxypiperidin-1-yl)methanone;
(5-(6-chloro-7-fluoro-3-(1H-imidazol-1-yl)-5-methoxy-1-methyl-1H-indol-2-yl)-1H-1,2,4-triazol-3-yl)(4-hydroxypiperidin-1-yl)methanone;
(3-(6-chloro-7-fluoro-3-(1H-imidazol-1-yl)-5-methoxy-1-methyl-1H-indol-2-yl)-1H-1,2,4-triazol-5-yl)(4-hydroxypiperidin-1-yl)methanone;
(5-(6-chloro-7-fluoro-3-(1H-imidazol-1-yl)-5-methoxy-1-methyl-1H-indol-2-yl)-4H-1,2,4-triazol-3-yl)(3-hydroxypiperidin-1-yl)methanone;
(5-(6-chloro-7-fluoro-3-(1H-imidazol-1-yl)-5-methoxy-1-methyl-1H-indol-2-yl)-1H-1,2,4-triazol-3-yl)(3-hydroxypiperidin-1-yl)methanone;
(3-(6-chloro-7-fluoro-3-(1H-imidazol-1-yl)-5-methoxy-1-methyl-1H-indol-2-yl)-1H-1,2,4-triazol-5-yl)(3-hydroxypiperidin-1-yl)methanone;
(S)-(5-(6-chloro-7-fluoro-3-(1H-imidazol-1-yl)-5-methoxy-1-methyl-1H-indol-2-yl)-4H-1,2,4-triazol-3-yl)(3-hydroxypiperidin-1-yl)methanone;
(S)-(5-(6-chloro-7-fluoro-3-(1H-imidazol-1-yl)-5-methoxy-1-methyl-1H-indol-2-yl)-1H-1,2,4-triazol-3-yl)(3-hydroxypiperidin-1-yl)methanone;
(S)-(3-(6-chloro-7-fluoro-3-(1H-imidazol-1-yl)-5-methoxy-1-methyl-1H-indol-2-yl)-1H-1,2,4-triazol-5-yl)(3-hydroxypiperidin-1-yl)methanone;
(R)-(5-(6-chloro-7-fluoro-3-(1H-imidazol-1-yl)-5-methoxy-1-methyl-1H-indol-2-yl)-4H-1,2,4-triazol-3-yl)(3-hydroxypiperidin-1-yl)methanone;
(R)-(5-(6-chloro-7-fluoro-3-(1H-imidazol-1-yl)-5-methoxy-1-methyl-1H-indol-2-yl)-1H-1,2,4-triazol-3-yl)(3-hydroxypiperidin-1-yl)methanone;
(R)-(3-(6-chloro-7-fluoro-3-(1H-imidazol-1-yl)-5-methoxy-1-methyl-1H-indol-2-yl)-1H-1,2,4-triazol-5-yl)(3-hydroxypiperidin-1-yl)methanone;
(5-(6-chloro-7-fluoro-3-(1H-imidazol-1-yl)-5-methoxy-1-methyl-1H-indol-2-yl)-4H-1,2,4-triazol-3-yl)(4-methylpiperazin-1-yl)methanone;
(5-(6-chloro-7-fluoro-3-(1H-imidazol-1-yl)-5-methoxy-1-methyl-1H-indol-2-yl)-1H-1,2,4-triazol-3-yl)(4-methylpiperazin-1-yl)methanone;

(3-(6-chloro-7-fluoro-3-(1H-imidazol-1-yl)-5-methoxy-1-methyl-1H-indol-2-yl)-1H-1,2,4-triazol-5-yl)(4-methylpiperazin-1-yl)methanone;

6-chloro-7-fluoro-3-(1H-imidazol-1-yl)-5-methoxy-1-methyl-2-(5-(trifluoromethyl)-4H-1,2,4-triazol-3-yl)-1H-indole;

6-chloro-7-fluoro-3-(1H-imidazol-1-yl)-5-methoxy-1-methyl-2-(3-(trifluoromethyl)-1H-1,2,4-triazol-5-yl)-1H-indole;

6-chloro-7-fluoro-3-(1H-imidazol-1-yl)-5-methoxy-1-methyl-2-(5-(trifluoromethyl)-1H-1,2,4-triazol-3-yl)-1H-indole;

6-chloro-7-fluoro-3-(1H-imidazol-1-yl)-5-methoxy-2-(5-(trifluoromethyl)-4H-1,2,4-triazol-3-yl)-1H-indole;

6-chloro-7-fluoro-3-(1H-imidazol-1-yl)-5-methoxy-2-(3-(trifluoromethyl)-1H-1,2,4-triazol-5-yl)-1H-indole;

6-chloro-7-fluoro-3-(1H-imidazol-1-yl)-5-methoxy-2-(5-(trifluoromethyl)-1H-1,2,4-triazol-3-yl)-1H-indole;

6-chloro-7-fluoro-3-(1H-imidazol-1-yl)-5-methoxy-2-(5-(methoxymethyl)-4H-1,2,4-triazol-3-yl)-1-methyl-1H-indole;

6-chloro-7-fluoro-3-(1H-imidazol-1-yl)-5-methoxy-2-(3-(methoxymethyl)-1H-1,2,4-triazol-5-yl)-1-methyl-1H-indole;

6-chloro-7-fluoro-3-(1H-imidazol-1-yl)-5-methoxy-2-(5-(methoxymethyl)-1H-1,2,4-triazol-3-yl)-1-methyl-1H-indole;

6-chloro-7-fluoro-3-(1H-imidazol-1-yl)-5-methoxy-1-methyl-2-(5-((methylthio)methyl)-4H-1,2,4-triazol-3-yl)-1H-indole;

6-chloro-7-fluoro-3-(1H-imidazol-1-yl)-5-methoxy-1-methyl-2-(3-((methylthio)methyl)-1H-1,2,4-triazol-5-yl)-1H-indole;

6-chloro-7-fluoro-3-(1H-imidazol-1-yl)-5-methoxy-1-methyl-2-(5-((methylthio)methyl)-1H-1,2,4-triazol-3-yl)-1H-indole;

2-(5-(6-chloro-7-fluoro-3-(1H-imidazol-1-yl)-5-methoxy-1-methyl-1H-indol-2-yl)-4H-1,2,4-triazol-3-yl)ethan-1-ol;

2-(5-(6-chloro-7-fluoro-3-(1H-imidazol-1-yl)-5-methoxy-1-methyl-1H-indol-2-yl)-1H-1,2,4-triazol-3-yl)ethan-1-ol;

2-(3-(6-chloro-7-fluoro-3-(1H-imidazol-1-yl)-5-methoxy-1-methyl-1H-indol-2-yl)-1H-1,2,4-triazol-5-yl)ethan-1-ol;

6-chloro-7-fluoro-3-(1H-imidazol-1-yl)-5-methoxy-2-(5-(2-methoxyethyl)-4H-1,2,4-triazol-3-yl)-1-methyl-1H-indole;

6-chloro-7-fluoro-3-(1H-imidazol-1-yl)-5-methoxy-2-(3-(2-methoxyethyl)-1H-1,2,4-triazol-5-yl)-1-methyl-1H-indole;

6-chloro-7-fluoro-3-(1H-imidazol-1-yl)-5-methoxy-2-(5-(2-methoxyethyl)-1H-1,2,4-triazol-3-yl)-1-methyl-1H-indole;

6-chloro-2-(5-(1-hydroxy-2-methoxyethyl)-4H-1,2,4-triazol-3-yl)-3-(1H-imidazol-1-yl)-5-methoxy-1-methyl-1H-indole-7-carbonitrile;

6-chloro-2-(3-(1-hydroxy-2-methoxyethyl)-1H-1,2,4-triazol-5-yl)-3-(1H-imidazol-1-yl)-5-methoxy-1-methyl-1H-indole-7-carbonitrile;

6-chloro-2-(5-(1-hydroxy-2-methoxyethyl)-1H-1,2,4-triazol-3-yl)-3-(1H-imidazol-1-yl)-5-methoxy-1-methyl-1H-indole-7-carbonitrile;

(S)-6-chloro-2-(5-(1-hydroxy-2-methoxyethyl)-4H-1,2,4-triazol-3-yl)-3-(1H-imidazol-1-yl)-5-methoxy-1-methyl-1H-indole-7-carbonitrile;

(S)-6-chloro-2-(3-(1-hydroxy-2-methoxyethyl)-1H-1,2,4-triazol-5-yl)-3-(1H-imidazol-1-yl)-5-methoxy-1-methyl-1H-indole-7-carbonitrile;

(S)-6-chloro-2-(5-(1-hydroxy-2-methoxyethyl)-1H-1,2,4-triazol-3-yl)-3-(1H-imidazol-1-yl)-5-methoxy-1-methyl-1H-indole-7-carbonitrile;

(R)-6-chloro-2-(5-(1-hydroxy-2-methoxyethyl)-4H-1,2,4-triazol-3-yl)-3-(1H-imidazol-1-yl)-5-methoxy-1-methyl-1H-indole-7-carbonitrile;

(R)-6-chloro-2-(3-(1-hydroxy-2-methoxyethyl)-1H-1,2,4-triazol-5-yl)-3-(1H-imidazol-1-yl)-5-methoxy-1-methyl-1H-indole-7-carbonitrile;

(R)-6-chloro-2-(5-(1-hydroxy-2-methoxyethyl)-1H-1,2,4-triazol-3-yl)-3-(1H-imidazol-1-yl)-5-methoxy-1-methyl-1H-indole-7-carbonitrile;

6-chloro-3-(1H-imidazol-1-yl)-5-methoxy-2-(5-(methoxymethyl)-4H-1,2,4-triazol-3-yl)-1-methyl-1H-indole-7-carbonitrile;

6-chloro-3-(1H-imidazol-1-yl)-5-methoxy-2-(3-(methoxymethyl)-1H-1,2,4-triazol-5-yl)-1-methyl-1H-indole-7-carbonitrile;

6-chloro-3-(1H-imidazol-1-yl)-5-methoxy-2-(5-(methoxymethyl)-1H-1,2,4-triazol-3-yl)-1-methyl-1H-indole-7-carbonitrile;

6-chloro-2-(5-(1,1-difluoro-2-methoxyethyl)-4H-1,2,4-triazol-3-yl)-3-(1H-imidazol-1-yl)-5-methoxy-1-methyl-1H-indole-7-carbonitrile;

6-chloro-2-(3-(1,1-difluoro-2-methoxyethyl)-1H-1,2,4-triazol-5-yl)-3-(1H-imidazol-1-yl)-5-methoxy-1-methyl-1H-indole-7-carbonitrile;

6-chloro-2-(5-(1,1-difluoro-2-methoxyethyl)-1H-1,2,4-triazol-3-yl)-3-(1H-imidazol-1-yl)-5-methoxy-1-methyl-1H-indole-7-carbonitrile;

6-chloro-7-fluoro-3-(1H-imidazol-1-yl)-5-methoxy-1-methyl-2-(5-((methylsulfonyl)methyl)-4H-1,2,4-triazol-3-yl)-1H-indole;

6-chloro-7-fluoro-3-(1H-imidazol-1-yl)-5-methoxy-1-methyl-2-(3-((methylsulfonyl)methyl)-1H-1,2,4-triazol-5-yl)-1H-indole;

6-chloro-7-fluoro-3-(1H-imidazol-1-yl)-5-methoxy-1-methyl-2-(5-((methylsulfonyl)methyl)-1H-1,2,4-triazol-3-yl)-1H-indole;

1-(5-(6-chloro-7-fluoro-5-methoxy-3-(1H-pyrazol-4-yl)-1H-indol-2-yl)-4H-1,2,4-triazol-3-yl)-2-methoxyethan-1-one;

1-(5-(6-chloro-7-fluoro-5-methoxy-3-(1H-pyrazol-4-yl)-1H-indol-2-yl)-1H-1,2,4-triazol-3-yl)-2-methoxyethan-1-one;

1-(3-(6-chloro-7-fluoro-5-methoxy-1-methyl-3-(1H-pyrazol-4-yl)-1H-indol-2-yl)-1H-1,2,4-triazol-5-yl)-2-methoxyethan-1-one;

6-chloro-7-fluoro-2-(5-fluoro-4H-1,2,4-triazol-3-yl)-5-methoxy-1-methyl-3-(1H-pyrazol-4-yl)-1H-indole;

6-chloro-7-fluoro-2-(3-fluoro-1H-1,2,4-triazol-5-yl)-5-methoxy-1-methyl-3-(1H-pyrazol-4-yl)-1H-indole;

6-chloro-7-fluoro-2-(5-fluoro-1H-1,2,4-triazol-3-yl)-5-methoxy-1-methyl-3-(1H-pyrazol-4-yl)-1H-indole;

4-(5-(6-chloro-7-fluoro-5-methoxy-1-methyl-3-(1H-pyrazol-4-yl)-1H-indol-2-yl)-4H-1,2,4-triazol-3-yl)morpholine;

4-(5-(6-chloro-7-fluoro-5-methoxy-1-methyl-3-(1H-pyrazol-4-yl)-1H-indol-2-yl)-1H-1,2,4-triazol-3-yl)morpholine;

4-(3-(6-chloro-7-fluoro-5-methoxy-1-methyl-3-(1H-pyrazol-4-yl)-1H-indol-2-yl)-1H-1,2,4-triazol-5-yl)morpholine;

1-(5-(6-chloro-7-fluoro-5-methoxy-1-methyl-3-(1H-pyrazol-4-yl)-1H-indol-2-yl)-4H-1,2,4-triazol-3-yl)ethan-1-one;

1-(5-(6-chloro-7-fluoro-5-methoxy-1-methyl-3-(1H-pyrazol-4-yl)-1H-indol-2-yl)-1H-1,2,4-triazol-3-yl)ethan-1-one;

1-(3-(6-chloro-7-fluoro-5-methoxy-1-methyl-3-(1H-pyrazol-4-yl)-1H-indol-2-yl)-1H-1,2,4-triazol-5-yl)ethan-1-one;

N-(5-(6-chloro-7-fluoro-5-methoxy-1-methyl-3-(1H-pyrazol-4-yl)-1H-indol-2-yl)-4H-1,2,4-triazol-3-yl)-N-methylacetamide;

N-(5-(6-chloro-7-fluoro-5-methoxy-1-methyl-3-(1H-pyrazol-4-yl)-1H-indol-2-yl)-1H-1,2,4-triazol-3-yl)-N-methylacetamide;

N-(3-(6-chloro-7-fluoro-5-methoxy-1-methyl-3-(1H-pyrazol-4-yl)-1H-indol-2-yl)-1H-1,2,4-triazol-5-yl)-N-methylacetamide;

N-(5-(6-chloro-7-fluoro-5-methoxy-1-methyl-3-(1H-pyrazol-4-yl)-1H-indol-2-yl)-4H-1,2,4-triazol-3-yl)-2-methoxy-N-methylacetamide;

N-(5-(6-chloro-7-fluoro-5-methoxy-1-methyl-3-(1H-pyrazol-4-yl)-1H-indol-2-yl)-1H-1,2,4-triazol-3-yl)-2-methoxy-N-methylacetamide;

N-(3-(6-chloro-7-fluoro-5-methoxy-1-methyl-3-(1H-pyrazol-4-yl)-1H-indol-2-yl)-1H-1,2,4-triazol-5-yl)-2-methoxy-N-methylacetamide;

2-((5-(6-chloro-7-fluoro-5-methoxy-1-methyl-3-(1H-pyrazol-4-yl)-1H-indol-2-yl)-4H-1,2,4-triazol-3-yl)(methyl)amino)ethan-1-ol;

2-((5-(6-chloro-7-fluoro-5-methoxy-1-methyl-3-(1H-pyrazol-4-yl)-1H-indol-2-yl)-1H-1,2,4-triazol-3-yl)(methyl)amino)ethan-1-ol;

2-((3-(6-chloro-7-fluoro-5-methoxy-1-methyl-3-(1H-pyrazol-4-yl)-1H-indol-2-yl)-1H-1,2,4-triazol-5-yl)(methyl)amino)ethan-1-ol;

1-(5-(6-chloro-7-fluoro-5-methoxy-1-methyl-3-(1H-pyrazol-4-yl)-1H-indol-2-yl)-4H-1,2,4-triazol-3-yl)-2-methoxyethan-1-ol;

1-(5-(6-chloro-7-fluoro-5-methoxy-1-methyl-3-(1H-pyrazol-4-yl)-1H-indol-2-yl)-1H-1,2,4-triazol-3-yl)-2-methoxyethan-1-ol;

1-(3-(6-chloro-7-fluoro-5-methoxy-1-methyl-3-(1H-pyrazol-4-yl)-1H-indol-2-yl)-1H-1,2,4-triazol-5-yl)-2-methoxyethan-1-ol;

(R)-1-(5-(6-chloro-7-fluoro-5-methoxy-1-methyl-3-(1H-pyrazol-4-yl)-1H-indol-2-yl)-4H-1,2,4-triazol-3-yl)-2-methoxyethan-1-ol;

(R)-1-(5-(6-chloro-7-fluoro-5-methoxy-1-methyl-3-(1H-pyrazol-4-yl)-1H-indol-2-yl)-1H-1,2,4-triazol-3-yl)-2-methoxyethan-1-ol;

(R)-1-(3-(6-chloro-7-fluoro-5-methoxy-1-methyl-3-(1H-pyrazol-4-yl)-1H-indol-2-yl)-1H-1,2,4-triazol-5-yl)-2-methoxyethan-1-ol;

(S)-1-(5-(6-chloro-7-fluoro-5-methoxy-1-methyl-3-(1H-pyrazol-4-yl)-1H-indol-2-yl)-4H-1,2,4-triazol-3-yl)-2-methoxyethan-1-ol;

(S)-1-(5-(6-chloro-7-fluoro-5-methoxy-1-methyl-3-(1H-pyrazol-4-yl)-1H-indol-2-yl)-1H-1,2,4-triazol-3-yl)-2-methoxyethan-1-ol;

(S)-1-(3-(6-chloro-7-fluoro-5-methoxy-1-methyl-3-(1H-pyrazol-4-yl)-1H-indol-2-yl)-1H-1,2,4-triazol-5-yl)-2-methoxyethan-1-ol;

6-chloro-2-(5-(1,1-difluoro-2-methoxyethyl)-4H-1,2,4-triazol-3-yl)-7-fluoro-5-methoxy-3-(1H-pyrazol-4-yl)-1H-indole;

6-chloro-2-(3-(1,1-difluoro-2-methoxyethyl)-1H-1,2,4-triazol-5-yl)-7-fluoro-5-methoxy-3-(1H-pyrazol-4-yl)-1H-indole;

6-chloro-2-(5-(1,1-difluoro-2-methoxyethyl)-1H-1,2,4-triazol-3-yl)-7-fluoro-5-methoxy-3-(1H-pyrazol-4-yl)-1H-indole;

6-chloro-2-(5-(1,1-difluoro-2-methoxyethyl)-4H-1,2,4-triazol-3-yl)-7-fluoro-5-methoxy-1-methyl-3-(1H-pyrazol-4-yl)-1H-indole;

6-chloro-2-(3-(1,1-difluoro-2-methoxyethyl)-1H-1,2,4-triazol-5-yl)-7-fluoro-5-methoxy-1-methyl-3-(1H-pyrazol-4-yl)-1H-indole;

6-chloro-2-(5-(1,1-difluoro-2-methoxyethyl)-1H-1,2,4-triazol-3-yl)-7-fluoro-5-methoxy-1-methyl-3-(1H-pyrazol-4-yl)-1H-indole;

6-chloro-2-(5-(1,1-difluoroethyl)-4H-1,2,4-triazol-3-yl)-7-fluoro-5-methoxy-3-(1H-pyrazol-4-yl)-1H-indole;

6-chloro-2-(3-(1,1-difluoroethyl)-1H-1,2,4-triazol-5-yl)-7-fluoro-5-methoxy-3-(1H-pyrazol-4-yl)-1H-indole;

6-chloro-2-(5-(1,1-difluoroethyl)-1H-1,2,4-triazol-3-yl)-7-fluoro-5-methoxy-3-(1H-pyrazol-4-yl)-1H-indole;

6-chloro-2-(5-(1,1-difluoroethyl)-4H-1,2,4-triazol-3-yl)-7-fluoro-5-methoxy-1-methyl-3-(1H-pyrazol-4-yl)-1H-indole;

6-chloro-2-(3-(1,1-difluoroethyl)-1H-1,2,4-triazol-5-yl)-7-fluoro-5-methoxy-1-methyl-3-(1H-pyrazol-4-yl)-1H-indole;

6-chloro-2-(5-(1,1-difluoroethyl)-1H-1,2,4-triazol-3-yl)-7-fluoro-5-methoxy-1-methyl-3-(1H-pyrazol-4-yl)-1H-indole;

2-(5-(6-chloro-7-fluoro-5-methoxy-1-methyl-3-(1H-pyrazol-4-yl)-1H-indol-2-yl)-4H-1,2,4-triazol-3-yl)-2,2-difluoroethan-1-ol;

2-(5-(6-chloro-7-fluoro-5-methoxy-1-methyl-3-(1H-pyrazol-4-yl)-1H-indol-2-yl)-1H-1,2,4-triazol-3-yl)-2,2-difluoroethan-1-ol;

2-(3-(6-chloro-7-fluoro-5-methoxy-1-methyl-3-(1H-pyrazol-4-yl)-1H-indol-2-yl)-1H-1,2,4-triazol-5-yl)-2,2-difluoroethan-1-ol;

6-chloro-7-fluoro-2-(5-(1-fluoro-2-methoxyethyl)-4H-1,2,4-triazol-3-yl)-5-methoxy-1-methyl-3-(1H-pyrazol-4-yl)-1H-indole;

6-chloro-7-fluoro-2-(3-(1-fluoro-2-methoxyethyl)-1H-1,2,4-triazol-5-yl)-5-methoxy-1-methyl-3-(1H-pyrazol-4-yl)-1H-indole;

6-chloro-7-fluoro-2-(5-(1-fluoro-2-methoxyethyl)-1H-1,2,4-triazol-3-yl)-5-methoxy-1-methyl-3-(1H-pyrazol-4-yl)-1H-indole;

(S)-6-chloro-7-fluoro-2-(5-(1-fluoro-2-methoxyethyl)-4H-1,2,4-triazol-3-yl)-5-methoxy-1-methyl-3-(1H-pyrazol-4-yl)-1H-indole;

(S)-6-chloro-7-fluoro-2-(3-(1-fluoro-2-methoxyethyl)-1H-1,2,4-triazol-5-yl)-5-methoxy-1-methyl-3-(1H-pyrazol-4-yl)-1H-indole;

(S)-6-chloro-7-fluoro-2-(5-(1-fluoro-2-methoxyethyl)-1H-1,2,4-triazol-3-yl)-5-methoxy-1-methyl-3-(1H-pyrazol-4-yl)-1H-indole;

(R)-6-chloro-7-fluoro-2-(5-(1-fluoro-2-methoxyethyl)-4H-1,2,4-triazol-3-yl)-5-methoxy-1-methyl-3-(1H-pyrazol-4-yl)-1H-indole;

(R)-6-chloro-7-fluoro-2-(3-(1-fluoro-2-methoxyethyl)-1H-1,2,4-triazol-5-yl)-5-methoxy-1-methyl-3-(1H-pyrazol-4-yl)-1H-indole;

(R)-6-chloro-7-fluoro-2-(5-(1-fluoro-2-methoxyethyl)-1H-1,2,4-triazol-3-yl)-5-methoxy-1-methyl-3-(1H-pyrazol-4-yl)-1H-indole;

6-chloro-7-fluoro-2-(5-(1-fluoroethyl)-4H-1,2,4-triazol-3-yl)-5-methoxy-3-(1H-pyrazol-4-yl)-1H-indole;

6-chloro-7-fluoro-2-(3-(1-fluoroethyl)-1H-1,2,4-triazol-5-yl)-5-methoxy-3-(1H-pyrazol-4-yl)-1H-indole;

6-chloro-7-fluoro-2-(5-(1-fluoroethyl)-1H-1,2,4-triazol-3-yl)-5-methoxy-3-(1H-pyrazol-4-yl)-1H-indole;
(R)-6-chloro-7-fluoro-2-(5-(1-fluoroethyl)-4H-1,2,4-triazol-3-yl)-5-methoxy-3-(1H-pyrazol-4-yl)-1H-indole;
(R)-6-chloro-7-fluoro-2-(3-(1-fluoroethyl)-1H-1,2,4-triazol-5-yl)-5-methoxy-3-(1H-pyrazol-4-yl)-1H-indole;
(R)-6-chloro-7-fluoro-2-(5-(1-fluoroethyl)-1H-1,2,4-triazol-3-yl)-5-methoxy-3-(1H-pyrazol-4-yl)-1H-indole;
(S)-6-chloro-7-fluoro-2-(5-(1-fluoroethyl)-4H-1,2,4-triazol-3-yl)-5-methoxy-3-(1H-pyrazol-4-yl)-1H-indole;
(S)-6-chloro-7-fluoro-2-(3-(1-fluoroethyl)-1H-1,2,4-triazol-5-yl)-5-methoxy-3-(1H-pyrazol-4-yl)-1H-indole;
(S)-6-chloro-7-fluoro-2-(5-(1-fluoroethyl)-1H-1,2,4-triazol-3-yl)-5-methoxy-3-(1H-pyrazol-4-yl)-1H-indole;
6-chloro-7-fluoro-2-(5-(1-fluoroethyl)-4H-1,2,4-triazol-3-yl)-5-methoxy-1-methyl-3-(1H-pyrazol-4-yl)-1H-indole;
6-chloro-7-fluoro-2-(3-(1-fluoroethyl)-1H-1,2,4-triazol-5-yl)-5-methoxy-1-methyl-3-(1H-pyrazol-4-yl)-1H-indole;
6-chloro-7-fluoro-2-(5-(1-fluoroethyl)-1H-1,2,4-triazol-3-yl)-5-methoxy-1-methyl-3-(1H-pyrazol-4-yl)-1H-indole;
(R)-6-chloro-7-fluoro-2-(5-(1-fluoroethyl)-4H-1,2,4-triazol-3-yl)-5-methoxy-1-methyl-3-(1H-pyrazol-4-yl)-1H-indole;
(R)-6-chloro-7-fluoro-2-(3-(1-fluoroethyl)-1H-1,2,4-triazol-5-yl)-5-methoxy-1-methyl-3-(1H-pyrazol-4-yl)-1H-indole;
(R)-6-chloro-7-fluoro-2-(5-(1-fluoroethyl)-1H-1,2,4-triazol-3-yl)-5-methoxy-1-methyl-3-(1H-pyrazol-4-yl)-1H-indole;
(S)-6-chloro-7-fluoro-2-(5-(1-fluoroethyl)-4H-1,2,4-triazol-3-yl)-5-methoxy-1-methyl-3-(1H-pyrazol-4-yl)-1H-indole;
(S)-6-chloro-7-fluoro-2-(3-(1-fluoroethyl)-1H-1,2,4-triazol-5-yl)-5-methoxy-1-methyl-3-(1H-pyrazol-4-yl)-1H-indole;
(S)-6-chloro-7-fluoro-2-(5-(1-fluoroethyl)-1H-1,2,4-triazol-3-yl)-5-methoxy-1-methyl-3-(1H-pyrazol-4-yl)-1H-indole;
6-chloro-2-(5-(1,1-difluoro-2-methoxyethyl)-4H-1,2,4-triazol-3-yl)-5-methoxy-1-methyl-3-(1H-pyrazol-4-yl)-1H-indole-7-carbonitrile;
6-chloro-2-(3-(1,1-difluoro-2-methoxyethyl)-1H-1,2,4-triazol-5-yl)-5-methoxy-1-methyl-3-(1H-pyrazol-4-yl)-1H-indole-7-carbonitrile;
6-chloro-2-(5-(1,1-difluoro-2-methoxyethyl)-1H-1,2,4-triazol-3-yl)-5-methoxy-1-methyl-3-(1H-pyrazol-4-yl)-1H-indole-7-carbonitrile;
1-(5-(6-chloro-5-ethoxy-7-fluoro-1-methyl-3-(1H-pyrazol-4-yl)-1H-indol-2-yl)-4H-1,2,4-triazol-3-yl)ethan-1-one;
1-(5-(6-chloro-5-ethoxy-7-fluoro-1-methyl-3-(1H-pyrazol-4-yl)-1H-indol-2-yl)-1H-1,2,4-triazol-3-yl)ethan-1-one;
1-(3-(6-chloro-5-ethoxy-7-fluoro-1-methyl-3-(1H-pyrazol-4-yl)-1H-indol-2-yl)-1H-1,2,4-triazol-5-yl)ethan-1-one;
2-(5-(6-chloro-7-fluoro-5-methoxy-1-methyl-3-(1H-pyrazol-4-yl)-1H-indol-2-yl)-4H-1,2,4-triazol-3-yl)-2-methoxy-N,N-dimethylethan-1-amine;
2-(5-(6-chloro-7-fluoro-5-methoxy-1-methyl-3-(1H-pyrazol-4-yl)-1H-indol-2-yl)-1H-1,2,4-triazol-3-yl)-2-methoxy-N,N-dimethylethan-1-amine;
2-(3-(6-chloro-7-fluoro-5-methoxy-1-methyl-3-(1H-pyrazol-4-yl)-1H-indol-2-yl)-1H-1,2,4-triazol-5-yl)-2-methoxy-N,N-dimethylethan-1-amine;
(R)-2-(5-(6-chloro-7-fluoro-5-methoxy-1-methyl-3-(1H-pyrazol-4-yl)-1H-indol-2-yl)-4H-1,2,4-triazol-3-yl)-2-methoxy-N,N-dimethylethan-1-amine;
(R)-2-(5-(6-chloro-7-fluoro-5-methoxy-1-methyl-3-(1H-pyrazol-4-yl)-1H-indol-2-yl)-1H-1,2,4-triazol-3-yl)-2-methoxy-N,N-dimethylethan-1-amine;
(R)-2-(3-(6-chloro-7-fluoro-5-methoxy-1-methyl-3-(1H-pyrazol-4-yl)-1H-indol-2-yl)-1H-1,2,4-triazol-5-yl)-2-methoxy-N,N-dimethylethan-1-amine;
(S)-2-(5-(6-chloro-7-fluoro-5-methoxy-1-methyl-3-(1H-pyrazol-4-yl)-1H-indol-2-yl)-4H-1,2,4-triazol-3-yl)-2-methoxy-N,N-dimethylethan-1-amine;
(S)-2-(3-(6-chloro-7-fluoro-5-methoxy-1-methyl-3-(1H-pyrazol-4-yl)-1H-indol-2-yl)-1H-1,2,4-triazol-5-yl)-2-methoxy-N,N-dimethylethan-1-amine;
(S)-2-(3-(6-chloro-7-fluoro-5-methoxy-1-methyl-3-(1H-pyrazol-4-yl)-1H-indol-2-yl)-1H-1,2,4-triazol-5-yl)-2-methoxy-N,N-dimethylethan-1-amine;
3-(6,7-dichloro-2-(5-(trifluoromethyl)-4H-1,2,4-triazol-3-yl)-1H-indol-3-yl)-1H-pyrazol-5-ol;
3-(6,7-dichloro-2-(3-(trifluoromethyl)-1H-1,2,4-triazol-5-yl)-1H-indol-3-yl)-1H-pyrazol-5-ol;
3-(6,7-dichloro-2-(5-(trifluoromethyl)-1H-1,2,4-triazol-3-yl)-1H-indol-3-yl)-1H-pyrazol-5-ol;
3-(6,7-dichloro-2-(5-(trifluoromethyl)-4H-1,2,4-triazol-3-yl)-1H-indol-3-yl)isoxazol-5-ol;
3-(6,7-dichloro-2-(3-(trifluoromethyl)-1H-1,2,4-triazol-5-yl)-1H-indol-3-yl)isoxazol-5-ol;
3-(6,7-dichloro-2-(5-(trifluoromethyl)-1H-1,2,4-triazol-3-yl)-1H-indol-3-yl)isoxazol-5-ol;
6,7-dichloro-3-(1H-pyrazol-3-yl)-2-(5-(trifluoromethyl)-4H-1,2,4-triazol-3-yl)-1H-indole;
6,7-dichloro-3-(1H-pyrazol-3-yl)-2-(3-(trifluoromethyl)-1H-1,2,4-triazol-5-yl)-1H-indole;
6,7-dichloro-3-(1H-pyrazol-3-yl)-2-(5-(trifluoromethyl)-1H-1,2,4-triazol-3-yl)-1H-indole;
1-(5-(6-chloro-7-fluoro-5-methoxy-3-(1H-pyrazol-4-yl)-1H-indol-2-yl)-4H-1,2,4-triazol-3-yl)-N,N-dimethylethan-1-amine;
1-(5-(6-chloro-7-fluoro-5-methoxy-3-(1H-pyrazol-4-yl)-1H-indol-2-yl)-1H-1,2,4-triazol-3-yl)-N,N-dimethylethan-1-amine;
1-(3-(6-chloro-7-fluoro-5-methoxy-3-(1H-pyrazol-4-yl)-1H-indol-2-yl)-1H-1,2,4-triazol-5-yl)-N,N-dimethylethan-1-amine;
(S)-1-(5-(6-chloro-7-fluoro-5-methoxy-3-(1H-pyrazol-4-yl)-1H-indol-2-yl)-4H-1,2,4-triazol-3-yl)-N,N-dimethylethan-1-amine;
(S)-1-(5-(6-chloro-7-fluoro-5-methoxy-3-(1H-pyrazol-4-yl)-1H-indol-2-yl)-1H-1,2,4-triazol-3-yl)-N,N-dimethylethan-1-amine;
(S)-1-(3-(6-chloro-7-fluoro-5-methoxy-3-(1H-pyrazol-4-yl)-1H-indol-2-yl)-1H-1,2,4-triazol-5-yl)-N,N-dimethylethan-1-amine;
(R)-1-(5-(6-chloro-7-fluoro-5-methoxy-3-(1H-pyrazol-4-yl)-1H-indol-2-yl)-4H-1,2,4-triazol-3-yl)-N,N-dimethylethan-1-amine;
(R)-1-(5-(6-chloro-7-fluoro-5-methoxy-3-(1H-pyrazol-4-yl)-1H-indol-2-yl)-1H-1,2,4-triazol-3-yl)-N,N-dimethylethan-1-amine;
(R)-1-(3-(6-chloro-7-fluoro-5-methoxy-3-(1H-pyrazol-4-yl)-1H-indol-2-yl)-1H-1,2,4-triazol-5-yl)-N,N-dimethylethan-1-amine;
1-(5-(6-chloro-7-fluoro-5-methoxy-1-methyl-3-(1H-pyrazol-4-yl)-1H-indol-2-yl)-4H-1,2,4-triazol-3-yl)-N,N-dimethylethan-1-amine;
1-(5-(6-chloro-7-fluoro-5-methoxy-1-methyl-3-(1H-pyrazol-4-yl)-1H-indol-2-yl)-1H-1,2,4-triazol-3-yl)-N,N-dimethylethan-1-amine;

1-(3-(6-chloro-7-fluoro-5-methoxy-1-methyl-3-(1H-pyrazol-4-yl)-1H-indol-2-yl)-1H-1,2,4-triazol-5-yl)-N,N-dimethylethan-1-amine;

(S)-1-(5-(6-chloro-7-fluoro-5-methoxy-1-methyl-3-(1H-pyrazol-4-yl)-1H-indol-2-yl)-4H-1,2,4-triazol-3-yl)-N,N-dimethylethan-1-amine;

(S)-1-(5-(6-chloro-7-fluoro-5-methoxy-1-methyl-3-(1H-pyrazol-4-yl)-1H-indol-2-yl)-1H-1,2,4-triazol-3-yl)-N,N-dimethylethan-1-amine;

(S)-1-(3-(6-chloro-7-fluoro-5-methoxy-1-methyl-3-(1H-pyrazol-4-yl)-1H-indol-2-yl)-1H-1,2,4-triazol-5-yl)-N,N-dimethylethan-1-amine;

(R)-1-(5-(6-chloro-7-fluoro-5-methoxy-1-methyl-3-(1H-pyrazol-4-yl)-1H-indol-2-yl)-4H-1,2,4-triazol-3-yl)-N,N-dimethylethan-1-amine;

(R)-1-(5-(6-chloro-7-fluoro-5-methoxy-1-methyl-3-(1H-pyrazol-4-yl)-1H-indol-2-yl)-1H-1,2,4-triazol-3-yl)-N,N-dimethylethan-1-amine;

(R)-1-(3-(6-chloro-7-fluoro-5-methoxy-1-methyl-3-(1H-pyrazol-4-yl)-1H-indol-2-yl)-1H-1,2,4-triazol-5-yl)-N,N-dimethylethan-1-amine;

1-(5-(6-chloro-7-fluoro-5-methoxy-1-methyl-3-(1H-pyrazol-4-yl)-1H-indol-2-yl)-4H-1,2,4-triazol-3-yl)-2-methoxy-N,N-dimethylethan-1-amine;

1-(5-(6-chloro-7-fluoro-5-methoxy-1-methyl-3-(1H-pyrazol-4-yl)-1H-indol-2-yl)-1H-1,2,4-triazol-3-yl)-2-methoxy-N,N-dimethylethan-1-amine;

1-(3-(6-chloro-7-fluoro-5-methoxy-1-methyl-3-(1H-pyrazol-4-yl)-1H-indol-2-yl)-1H-1,2,4-triazol-5-yl)-2-methoxy-N,N-dimethylethan-1-amine;

(R)-1-(5-(6-chloro-7-fluoro-5-methoxy-1-methyl-3-(1H-pyrazol-4-yl)-1H-indol-2-yl)-4H-1,2,4-triazol-3-yl)-2-methoxy-N,N-dimethylethan-1-amine;

(R)-1-(5-(6-chloro-7-fluoro-5-methoxy-1-methyl-3-(1H-pyrazol-4-yl)-1H-indol-2-yl)-1H-1,2,4-triazol-3-yl)-2-methoxy-N,N-dimethylethan-1-amine;

(R)-1-(3-(6-chloro-7-fluoro-5-methoxy-1-methyl-3-(1H-pyrazol-4-yl)-1H-indol-2-yl)-1H-1,2,4-triazol-5-yl)-2-methoxy-N,N-dimethylethan-1-amine;

(S)-1-(5-(6-chloro-7-fluoro-5-methoxy-1-methyl-3-(1H-pyrazol-4-yl)-1H-indol-2-yl)-4H-1,2,4-triazol-3-yl)-2-methoxy-N,N-dimethylethan-1-amine;

(S)-1-(5-(6-chloro-7-fluoro-5-methoxy-1-methyl-3-(1H-pyrazol-4-yl)-1H-indol-2-yl)-1H-1,2,4-triazol-3-yl)-2-methoxy-N,N-dimethylethan-1-amine;

(S)-1-(3-(6-chloro-7-fluoro-5-methoxy-1-methyl-3-(1H-pyrazol-4-yl)-1H-indol-2-yl)-1H-1,2,4-triazol-5-yl)-2-methoxy-N,N-dimethylethan-1-amine;

2-(5-(6-chloro-7-fluoro-5-methoxy-1-methyl-3-(1H-pyrazol-4-yl)-1H-indol-2-yl)-4H-1,2,4-triazol-3-yl)propanenitrile;

2-(5-(6-chloro-7-fluoro-5-methoxy-1-methyl-3-(1H-pyrazol-4-yl)-1H-indol-2-yl)-1H-1,2,4-triazol-3-yl)propanenitrile;

2-(3-(6-chloro-7-fluoro-5-methoxy-1-methyl-3-(1H-pyrazol-4-yl)-1H-indol-2-yl)-1H-1,2,4-triazol-5-yl)propanenitrile;

(R)-2-(5-(6-chloro-7-fluoro-5-methoxy-1-methyl-3-(1H-pyrazol-4-yl)-1H-indol-2-yl)-4H-1,2,4-triazol-3-yl)propanenitrile;

(R)-2-(5-(6-chloro-7-fluoro-5-methoxy-1-methyl-3-(1H-pyrazol-4-yl)-1H-indol-2-yl)-1H-1,2,4-triazol-3-yl)propanenitrile;

(R)-2-(3-(6-chloro-7-fluoro-5-methoxy-1-methyl-3-(1H-pyrazol-4-yl)-1H-indol-2-yl)-1H-1,2,4-triazol-5-yl)propanenitrile;

(S)-2-(5-(6-chloro-7-fluoro-5-methoxy-1-methyl-3-(1H-pyrazol-4-yl)-1H-indol-2-yl)-4H-1,2,4-triazol-3-yl)propanenitrile;

(S)-2-(5-(6-chloro-7-fluoro-5-methoxy-1-methyl-3-(1H-pyrazol-4-yl)-1H-indol-2-yl)-1H-1,2,4-triazol-3-yl)propanenitrile;

(S)-2-(3-(6-chloro-7-fluoro-5-methoxy-1-methyl-3-(1H-pyrazol-4-yl)-1H-indol-2-yl)-1H-1,2,4-triazol-5-yl)propanenitrile;

1-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-ol;

1-(5-(6-chloro-7-fluoro-3-(1H-imidazol-1-yl)-5-methoxy-1-methyl-1H-indol-2-yl)-1H-1,2,4-triazol-3-yl)-2-methoxyethan-1-ol;

1-(3-(6-chloro-7-fluoro-3-(1H-imidazol-1-yl)-5-methoxy-1-methyl-1H-indol-2-yl)-1H-1,2,4-triazol-5-yl)-2-methoxyethan-1-ol;

(S)-1-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-ol;

(S)-1-(5-(6-chloro-7-fluoro-3-(1H-imidazol-1-yl)-5-methoxy-1-methyl-1H-indol-2-yl)-1H-1,2,4-triazol-3-yl)-2-methoxyethan-1-ol;

(S)-1-(3-(6-chloro-7-fluoro-3-(1H-imidazol-1-yl)-5-methoxy-1-methyl-1H-indol-2-yl)-1H-1,2,4-triazol-5-yl)-2-methoxyethan-1-ol;

(R)-1-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-ol;

(R)-1-(5-(6-chloro-7-fluoro-3-(1H-imidazol-1-yl)-5-methoxy-1-methyl-1H-indol-2-yl)-1H-1,2,4-triazol-3-yl)-2-methoxyethan-1-ol;

(R)-1-(3-(6-chloro-7-fluoro-3-(1H-imidazol-1-yl)-5-methoxy-1-methyl-1H-indol-2-yl)-1H-1,2,4-triazol-5-yl)-2-methoxyethan-1-ol;

6-chloro-7-fluoro-3-(1H-imidazol-1-yl)-2-(5-isopropoxy-4H-1,2,4-triazol-3-yl)-5-methoxy-1-methyl-1H-indole;

6-chloro-7-fluoro-3-(1H-imidazol-1-yl)-2-(3-isopropoxy-1H-1,2,4-triazol-5-yl)-5-methoxy-1-methyl-1H-indole;

6-chloro-7-fluoro-3-(1H-imidazol-1-yl)-2-(5-isopropoxy-1H-1,2,4-triazol-3-yl)-5-methoxy-1-methyl-1H-indole;

6-chloro-7-fluoro-2-(5-fluoro-4H-1,2,4-triazol-3-yl)-3-(1H-imidazol-1-yl)-5-methoxy-1-methyl-1H-indole;

6-chloro-7-fluoro-2-(3-fluoro-1H-1,2,4-triazol-5-yl)-3-(1H-imidazol-1-yl)-5-methoxy-1-methyl-1H-indole;

6-chloro-7-fluoro-2-(5-fluoro-1H-1,2,4-triazol-3-yl)-3-(1H-imidazol-1-yl)-5-methoxy-1-methyl-1H-indole;

6-chloro-7-fluoro-2-(5-fluoro-4H-1,2,4-triazol-3-yl)-3-(1H-imidazol-1-yl)-5-methoxy-1H-indole;

6-chloro-7-fluoro-2-(3-fluoro-1H-1,2,4-triazol-5-yl)-3-(1H-imidazol-1-yl)-5-methoxy-1H-indole;

6-chloro-7-fluoro-2-(5-fluoro-1H-1,2,4-triazol-3-yl)-3-(1H-imidazol-1-yl)-5-methoxy-1H-indole;

1-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-one;

1-(5-(6-chloro-7-fluoro-3-(1H-imidazol-1-yl)-5-methoxy-1-methyl-1H-indol-2-yl)-1H-1,2,4-triazol-3-yl)-2-methoxyethan-1-one;

1-(3-(6-chloro-7-fluoro-3-(1H-imidazol-1-yl)-5-methoxy-1-methyl-1H-indol-2-yl)-1H-1,2,4-triazol-5-yl)-2-methoxyethan-1-one;

6-chloro-2-(5-(1,1-difluoro-2-methoxyethyl)-4H-1,2,4-triazol-3-yl)-7-fluoro-3-(1H-imidazol-1-yl)-5-methoxy-1-methyl-1H-indole;

6-chloro-2-(3-(1,1-difluoro-2-methoxyethyl)-1H-1,2,4-triazol-5-yl)-7-fluoro-3-(1H-imidazol-1-yl)-5-methoxy-1-methyl-1H-indole;

6-chloro-2-(5-(1,1-difluoro-2-methoxyethyl)-1H-1,2,4-triazol-3-yl)-7-fluoro-3-(1H-imidazol-1-yl)-5-methoxy-1-methyl-1H-indole;

2-((5-(6-chloro-7-fluoro-3-(1H-imidazol-1-yl)-5-methoxy-1-methyl-1H-indol-2-yl)-4H-1,2,4-triazol-3-yl)(methyl)amino)ethan-1-ol;

2-((5-(6-chloro-7-fluoro-3-(1H-imidazol-1-yl)-5-methoxy-1-methyl-1H-indol-2-yl)-1H-1,2,4-triazol-3-yl)(methyl)amino)ethan-1-ol;

2-((3-(6-chloro-7-fluoro-3-(1H-imidazol-1-yl)-5-methoxy-1-methyl-1H-indol-2-yl)-1H-1,2,4-triazol-5-yl)(methyl)amino)ethan-1-ol;

1-(5-(6-chloro-7-fluoro-3-(1H-imidazol-1-yl)-5-methoxy-1-methyl-1H-indol-2-yl)-4H-1,2,4-triazol-3-yl)pyrrolidin-3-ol;

1-(5-(6-chloro-7-fluoro-3-(1H-imidazol-1-yl)-5-methoxy-1-methyl-1H-indol-2-yl)-1H-1,2,4-triazol-3-yl)pyrrolidin-3-ol;

1-(3-(6-chloro-7-fluoro-3-(1H-imidazol-1-yl)-5-methoxy-1-methyl-1H-indol-2-yl)-1H-1,2,4-triazol-5-yl)pyrrolidin-3-ol;

(R)-1-(5-(6-chloro-7-fluoro-3-(1H-imidazol-1-yl)-5-methoxy-1-methyl-1H-indol-2-yl)-4H-1,2,4-triazol-3-yl)pyrrolidin-3-ol;

(R)-1-(5-(6-chloro-7-fluoro-3-(1H-imidazol-1-yl)-5-methoxy-1-methyl-1H-indol-2-yl)-1H-1,2,4-triazol-3-yl)pyrrolidin-3-ol;

(R)-1-(3-(6-chloro-7-fluoro-3-(1H-imidazol-1-yl)-5-methoxy-1-methyl-1H-indol-2-yl)-1H-1,2,4-triazol-5-yl)pyrrolidin-3-ol;

(S)-1-(5-(6-chloro-7-fluoro-3-(1H-imidazol-1-yl)-5-methoxy-1-methyl-1H-indol-2-yl)-4H-1,2,4-triazol-3-yl)pyrrolidin-3-ol;

(S)-1-(5-(6-chloro-7-fluoro-3-(1H-imidazol-1-yl)-5-methoxy-1-methyl-1H-indol-2-yl)-1H-1,2,4-triazol-3-yl)pyrrolidin-3-ol;

(S)-1-(3-(6-chloro-7-fluoro-3-(1H-imidazol-1-yl)-5-methoxy-1-methyl-1H-indol-2-yl)-1H-1,2,4-triazol-5-yl)pyrrolidin-3-ol;

2-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-ol;

2-(5-(6-chloro-7-fluoro-3-(1H-imidazol-1-yl)-5-methoxy-1-methyl-1H-indol-2-yl)-1H-1,2,4-triazol-3-yl)-2-methoxyethan-1-ol;

2-(3-(6-chloro-7-fluoro-3-(1H-imidazol-1-yl)-5-methoxy-1-methyl-1H-indol-2-yl)-1H-1,2,4-triazol-5-yl)-2-methoxyethan-1-ol;

(S)-2-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-ol;

(S)-2-(5-(6-chloro-7-fluoro-3-(1H-imidazol-1-yl)-5-methoxy-1-methyl-1H-indol-2-yl)-1H-1,2,4-triazol-3-yl)-2-methoxyethan-1-ol;

(S)-2-(3-(6-chloro-7-fluoro-3-(1H-imidazol-1-yl)-5-methoxy-1-methyl-1H-indol-2-yl)-1H-1,2,4-triazol-5-yl)-2-methoxyethan-1-ol;

(R)-2-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-ol;

(R)-2-(5-(6-chloro-7-fluoro-3-(1H-imidazol-1-yl)-5-methoxy-1-methyl-1H-indol-2-yl)-1H-1,2,4-triazol-3-yl)-2-methoxyethan-1-ol;

(R)-2-(3-(6-chloro-7-fluoro-3-(1H-imidazol-1-yl)-5-methoxy-1-methyl-1H-indol-2-yl)-1H-1,2,4-triazol-5-yl)-2-methoxyethan-1-ol;

2-((5-(6-chloro-7-fluoro-3-(1H-imidazol-1-yl)-5-methoxy-1-methyl-1H-indol-2-yl)-4H-1,2,4-triazol-3-yl)oxy)ethan-1-ol;

2-((5-(6-chloro-7-fluoro-3-(1H-imidazol-1-yl)-5-methoxy-1-methyl-1H-indol-2-yl)-1H-1,2,4-triazol-3-yl)oxy)ethan-1-ol;

2-((3-(6-chloro-7-fluoro-3-(1H-imidazol-1-yl)-5-methoxy-1-methyl-1H-indol-2-yl)-1H-1,2,4-triazol-5-yl)oxy)ethan-1-ol;

2-(5-(6-chloro-7-fluoro-3-(1H-imidazol-1-yl)-5-methoxy-1-methyl-1H-indol-2-yl)-4H-1,2,4-triazol-3-yl)-2,2-difluoroethan-1-ol;

2-(5-(6-chloro-7-fluoro-3-(1H-imidazol-1-yl)-5-methoxy-1-methyl-1H-indol-2-yl)-1H-1,2,4-triazol-3-yl)-2,2-difluoroethan-1-ol;

2-(3-(6-chloro-7-fluoro-3-(1H-imidazol-1-yl)-5-methoxy-1-methyl-1H-indol-2-yl)-1H-1,2,4-triazol-5-yl)-2,2-difluoroethan-1-ol;

1-(5-(6-chloro-7-fluoro-3-(1H-imidazol-1-yl)-5-methoxy-1-methyl-1H-indol-2-yl)-4H-1,2,4-triazol-3-yl)-2,2-difluoroethan-1-ol;

1-(5-(6-chloro-7-fluoro-3-(1H-imidazol-1-yl)-5-methoxy-1-methyl-1H-indol-2-yl)-1H-1,2,4-triazol-3-yl)-2,2-difluoroethan-1-ol;

1-(3-(6-chloro-7-fluoro-3-(1H-imidazol-1-yl)-5-methoxy-1-methyl-1H-indol-2-yl)-1H-1,2,4-triazol-5-yl)-2,2-difluoroethan-1-ol;

(S)-1-(5-(6-chloro-7-fluoro-3-(1H-imidazol-1-yl)-5-methoxy-1-methyl-1H-indol-2-yl)-4H-1,2,4-triazol-3-yl)-2,2-difluoroethan-1-ol;

(S)-1-(5-(6-chloro-7-fluoro-3-(1H-imidazol-1-yl)-5-methoxy-1-methyl-1H-indol-2-yl)-1H-1,2,4-triazol-3-yl)-2,2-difluoroethan-1-ol;

(S)-1-(3-(6-chloro-7-fluoro-3-(1H-imidazol-1-yl)-5-methoxy-1-methyl-1H-indol-2-yl)-1H-1,2,4-triazol-5-yl)-2,2-difluoroethan-1-ol;

(R)-1-(5-(6-chloro-7-fluoro-3-(1H-imidazol-1-yl)-5-methoxy-1-methyl-1H-indol-2-yl)-4H-1,2,4-triazol-3-yl)-2,2-difluoroethan-1-ol;

(R)-1-(5-(6-chloro-7-fluoro-3-(1H-imidazol-1-yl)-5-methoxy-1-methyl-1H-indol-2-yl)-1H-1,2,4-triazol-3-yl)-2,2-difluoroethan-1-ol;

(R)-1-(3-(6-chloro-7-fluoro-3-(1H-imidazol-1-yl)-5-methoxy-1-methyl-1H-indol-2-yl)-1H-1,2,4-triazol-5-yl)-2,2-difluoroethan-1-ol;

2-(5-(6-chloro-7-fluoro-3-(1H-imidazol-1-yl)-5-methoxy-1-methyl-1H-indol-2-yl)-4H-1,2,4-triazol-3-yl)-2-methoxy-N,N-dimethylethan-1-amine;

2-(5-(6-chloro-7-fluoro-3-(1H-imidazol-1-yl)-5-methoxy-1-methyl-1H-indol-2-yl)-1H-1,2,4-triazol-3-yl)-2-methoxy-N,N-dimethylethan-1-amine;

2-(3-(6-chloro-7-fluoro-3-(1H-imidazol-1-yl)-5-methoxy-1-methyl-1H-indol-2-yl)-1H-1,2,4-triazol-5-yl)-2-methoxy-N,N-dimethylethan-1-amine;

(R)-2-(5-(6-chloro-7-fluoro-3-(1H-imidazol-1-yl)-5-methoxy-1-methyl-1H-indol-2-yl)-4H-1,2,4-triazol-3-yl)-2-methoxy-N,N-dimethylethan-1-amine;

(R)-2-(5-(6-chloro-7-fluoro-3-(1H-imidazol-1-yl)-5-methoxy-1-methyl-1H-indol-2-yl)-1H-1,2,4-triazol-3-yl)-2-methoxy-N,N-dimethylethan-1-amine;

(R)-2-(3-(6-chloro-7-fluoro-3-(1H-imidazol-1-yl)-5-methoxy-1-methyl-1H-indol-2-yl)-1H-1,2,4-triazol-5-yl)-2-methoxy-N,N-dimethylethan-1-amine;

(S)-2-(5-(6-chloro-7-fluoro-3-(1H-imidazol-1-yl)-5-methoxy-1-methyl-1H-indol-2-yl)-4H-1,2,4-triazol-3-yl)-2-methoxy-N,N-dimethylethan-1-amine;
(S)-2-(5-(6-chloro-7-fluoro-3-(1H-imidazol-1-yl)-5-methoxy-1-methyl-1H-indol-2-yl)-1H-1,2,4-triazol-3-yl)-2-methoxy-N,N-dimethylethan-1-amine;
(S)-2-(3-(6-chloro-7-fluoro-3-(1H-imidazol-1-yl)-5-methoxy-1-methyl-1H-indol-2-yl)-1H-1,2,4-triazol-5-yl)-2-methoxy-N,N-dimethylethan-1-amine;
1-(5-(6-chloro-7-fluoro-3-(1H-imidazol-1-yl)-5-methoxy-1-methyl-1H-indol-2-yl)-4H-1,2,4-triazol-3-yl)-2,2,2-trifluoroethan-1-ol;
1-(5-(6-chloro-7-fluoro-3-(1H-imidazol-1-yl)-5-methoxy-1-methyl-1H-indol-2-yl)-1H-1,2,4-triazol-3-yl)-2,2,2-trifluoroethan-1-ol;
1-(3-(6-chloro-7-fluoro-3-(1H-imidazol-1-yl)-5-methoxy-1-methyl-1H-indol-2-yl)-1H-1,2,4-triazol-5-yl)-2,2,2-trifluoroethan-1-ol;
(S)-1-(5-(6-chloro-7-fluoro-3-(1H-imidazol-1-yl)-5-methoxy-1-methyl-1H-indol-2-yl)-4H-1,2,4-triazol-3-yl)-2,2,2-trifluoroethan-1-ol;
(S)-1-(5-(6-chloro-7-fluoro-3-(1H-imidazol-1-yl)-5-methoxy-1-methyl-1H-indol-2-yl)-1H-1,2,4-triazol-3-yl)-2,2,2-trifluoroethan-1-ol;
(S)-1-(3-(6-chloro-7-fluoro-3-(1H-imidazol-1-yl)-5-methoxy-1-methyl-1H-indol-2-yl)-1H-1,2,4-triazol-5-yl)-2,2,2-trifluoroethan-1-ol;
(R)-1-(5-(6-chloro-7-fluoro-3-(1H-imidazol-1-yl)-5-methoxy-1-methyl-1H-indol-2-yl)-4H-1,2,4-triazol-3-yl)-2,2,2-trifluoroethan-1-ol;
(R)-1-(5-(6-chloro-7-fluoro-3-(1H-imidazol-1-yl)-5-methoxy-1-methyl-1H-indol-2-yl)-1H-1,2,4-triazol-3-yl)-2,2,2-trifluoroethan-1-ol;
(R)-1-(3-(6-chloro-7-fluoro-3-(1H-imidazol-1-yl)-5-methoxy-1-methyl-1H-indol-2-yl)-1H-1,2,4-triazol-5-yl)-2,2,2-trifluoroethan-1-ol;
6-chloro-2-(5-(2,2-difluoro-1-methoxyethyl)-4H-1,2,4-triazol-3-yl)-7-fluoro-3-(1H-imidazol-1-yl)-5-methoxy-1-methyl-1H-indole;
6-chloro-2-(3-(2,2-difluoro-1-methoxyethyl)-1H-1,2,4-triazol-5-yl)-7-fluoro-3-(1H-imidazol-1-yl)-5-methoxy-1-methyl-1H-indole;
6-chloro-2-(5-(2,2-difluoro-1-methoxyethyl)-1H-1,2,4-triazol-3-yl)-7-fluoro-3-(1H-imidazol-1-yl)-5-methoxy-1-methyl-1H-indole;
(S)-6-chloro-2-(5-(2,2-difluoro-1-methoxyethyl)-4H-1,2,4-triazol-3-yl)-7-fluoro-3-(1H-imidazol-1-yl)-5-methoxy-1-methyl-1H-indole;
(S)-6-chloro-2-(3-(2,2-difluoro-1-methoxyethyl)-1H-1,2,4-triazol-5-yl)-7-fluoro-3-(1H-imidazol-1-yl)-5-methoxy-1-methyl-1H-indole;
(S)-6-chloro-2-(5-(2,2-difluoro-1-methoxyethyl)-1H-1,2,4-triazol-3-yl)-7-fluoro-3-(1H-imidazol-1-yl)-5-methoxy-1-methyl-1H-indole;
(R)-6-chloro-2-(5-(2,2-difluoro-1-methoxyethyl)-4H-1,2,4-triazol-3-yl)-7-fluoro-3-(1H-imidazol-1-yl)-5-methoxy-1-methyl-1H-indole;
(R)-6-chloro-2-(3-(2,2-difluoro-1-methoxyethyl)-1H-1,2,4-triazol-5-yl)-7-fluoro-3-(1H-imidazol-1-yl)-5-methoxy-1-methyl-1H-indole;
(R)-6-chloro-2-(5-(2,2-difluoro-1-methoxyethyl)-1H-1,2,4-triazol-3-yl)-7-fluoro-3-(1H-imidazol-1-yl)-5-methoxy-1-methyl-1H-indole;
2-(5-(1-(1H-imidazol-1-yl)-2-methoxyethyl)-4H-1,2,4-triazol-3-yl)-6-chloro-7-fluoro-3-(1H-imidazol-1-yl)-5-methoxy-1-methyl-1H-indole;
2-(3-(1-(1H-imidazol-1-yl)-2-methoxyethyl)-1H-1,2,4-triazol-5-yl)-6-chloro-7-fluoro-3-(1H-imidazol-1-yl)-5-methoxy-1-methyl-1H-indole;
2-(5-(1-(1H-imidazol-1-yl)-2-methoxyethyl)-1H-1,2,4-triazol-3-yl)-6-chloro-7-fluoro-3-(1H-imidazol-1-yl)-5-methoxy-1-methyl-1H-indole;
(S)-2-(5-(1-(1H-imidazol-1-yl)-2-methoxyethyl)-4H-1,2,4-triazol-3-yl)-6-chloro-7-fluoro-3-(1H-imidazol-1-yl)-5-methoxy-1-methyl-1H-indole;
(S)-2-(3-(1-(1H-imidazol-1-yl)-2-methoxyethyl)-1H-1,2,4-triazol-5-yl)-6-chloro-7-fluoro-3-(1H-imidazol-1-yl)-5-methoxy-1-methyl-1H-indole;
(S)-2-(5-(1-(1H-imidazol-1-yl)-2-methoxyethyl)-1H-1,2,4-triazol-3-yl)-6-chloro-7-fluoro-3-(1H-imidazol-1-yl)-5-methoxy-1-methyl-1H-indole;
(R)-2-(5-(1-(1H-imidazol-1-yl)-2-methoxyethyl)-4H-1,2,4-triazol-3-yl)-6-chloro-7-fluoro-3-(1H-imidazol-1-yl)-5-methoxy-1-methyl-1H-indole;
(R)-2-(3-(1-(1H-imidazol-1-yl)-2-methoxyethyl)-1H-1,2,4-triazol-5-yl)-6-chloro-7-fluoro-3-(1H-imidazol-1-yl)-5-methoxy-1-methyl-1H-indole;
(R)-2-(5-(1-(1H-imidazol-1-yl)-2-methoxyethyl)-1H-1,2,4-triazol-3-yl)-6-chloro-7-fluoro-3-(1H-imidazol-1-yl)-5-methoxy-1-methyl-1H-indole;
1-(5-(6-chloro-5-ethoxy-7-fluoro-3-(1H-imidazol-1-yl)-1-methyl-1H-indol-2-yl)-4H-1,2,4-triazol-3-yl)ethan-1-one;
1-(5-(6-chloro-5-ethoxy-7-fluoro-3-(1H-imidazol-1-yl)-1-methyl-1H-indol-2-yl)-1H-1,2,4-triazol-3-yl)ethan-1-one;
1-(3-(6-chloro-5-ethoxy-7-fluoro-3-(1H-imidazol-1-yl)-1-methyl-1H-indol-2-yl)-1H-1,2,4-triazol-5-yl)ethan-1-one;
1-(5-(6-chloro-7-fluoro-3-(1H-imidazol-1-yl)-5-methoxy-1-methyl-1H-indol-2-yl)-4H-1,2,4-triazol-3-yl)ethan-1-one;
1-(5-(6-chloro-7-fluoro-3-(1H-imidazol-1-yl)-5-methoxy-1-methyl-1H-indol-2-yl)-1H-1,2,4-triazol-3-yl)ethan-1-one;
1-(3-(6-chloro-7-fluoro-3-(1H-imidazol-1-yl)-5-methoxy-1-methyl-1H-indol-2-yl)-1H-1,2,4-triazol-5-yl)ethan-1-one;
5-(6-chloro-7-cyano-3-(1H-imidazol-1-yl)-5-methoxy-1-methyl-1H-indol-2-yl)-N,N-dimethyl-4H-1,2,4-triazole-3-carboxamide;
5-(6-chloro-7-cyano-3-(1H-imidazol-1-yl)-5-methoxy-1-methyl-1H-indol-2-yl)-N,N-dimethyl-1H-1,2,4-triazole-3-carboxamide;
3-(6-chloro-7-cyano-3-(1H-imidazol-1-yl)-5-methoxy-1-methyl-1H-indol-2-yl)-N,N-dimethyl-1H-1,2,4-triazole-5-carboxamide;
5-(6,7-difluoro-3-(1H-imidazol-1-yl)-5-methoxy-1-methyl-1H-indol-2-yl)-N,N-dimethyl-4H-1,2,4-triazole-3-carboxamide;
5-(6,7-difluoro-3-(1H-imidazol-1-yl)-5-methoxy-1-methyl-1H-indol-2-yl)-N,N-dimethyl-1H-1,2,4-triazole-3-carboxamide;
3-(6,7-difluoro-3-(1H-imidazol-1-yl)-5-methoxy-1-methyl-1H-indol-2-yl)-N,N-dimethyl-1H-1,2,4-triazole-5-carboxamide;
5,6-dichloro-3-(1H-imidazol-1-yl)-2-(5-(trifluoromethyl)-4H-1,2,4-triazol-3-yl)-1H-indole;
5,6-dichloro-3-(1H-imidazol-1-yl)-2-(3-(trifluoromethyl)-1H-1,2,4-triazol-5-yl)-1H-indole;
5,6-dichloro-3-(1H-imidazol-1-yl)-2-(5-(trifluoromethyl)-1H-1,2,4-triazol-3-yl)-1H-indole;

6,7-dichloro-3-(1H-imidazol-1-yl)-2-(5-(trifluoromethyl)-4H-1,2,4-triazol-3-yl)-1H-indole;
6,7-dichloro-3-(1H-imidazol-1-yl)-2-(3-(trifluoromethyl)-1H-1,2,4-triazol-5-yl)-1H-indole;
6,7-dichloro-3-(1H-imidazol-1-yl)-2-(5-(trifluoromethyl)-1H-1,2,4-triazol-3-yl)-1H-indole;
6-chloro-3-(1H-imidazol-1-yl)-5-methoxy-2-(5-(trifluoromethyl)-4H-1,2,4-triazol-3-yl)-1H-indole;
6-chloro-3-(1H-imidazol-1-yl)-5-methoxy-2-(3-(trifluoromethyl)-1H-1,2,4-triazol-5-yl)-1H-indole;
6-chloro-3-(1H-imidazol-1-yl)-5-methoxy-2-(5-(trifluoromethyl)-1H-1,2,4-triazol-3-yl)-1H-indole;
5,6-dichloro-3-(1H-imidazol-1-yl)-1-methyl-2-(5-(trifluoromethyl)-4H-1,2,4-triazol-3-yl)-1H-indole;
5,6-dichloro-3-(1H-imidazol-1-yl)-1-methyl-2-(3-(trifluoromethyl)-1H-1,2,4-triazol-5-yl)-1H-indole;
5,6-dichloro-3-(1H-imidazol-1-yl)-1-methyl-2-(5-(trifluoromethyl)-1H-1,2,4-triazol-3-yl)-1H-indole;
6,7-dichloro-3-(1H-imidazol-1-yl)-1-methyl-2-(5-(trifluoromethyl)-4H-1,2,4-triazol-3-yl)-1H-indole;
6,7-dichloro-3-(1H-imidazol-1-yl)-1-methyl-2-(3-(trifluoromethyl)-1H-1,2,4-triazol-5-yl)-1H-indole;
6,7-dichloro-3-(1H-imidazol-1-yl)-1-methyl-2-(5-(trifluoromethyl)-1H-1,2,4-triazol-3-yl)-1H-indole;
6-chloro-3-(1H-imidazol-1-yl)-2-(5-(trifluoromethyl)-4H-1,2,4-triazol-3-yl)-1H-indole-7-carbonitrile;
6-chloro-3-(1H-imidazol-1-yl)-2-(3-(trifluoromethyl)-1H-1,2,4-triazol-5-yl)-1H-indole-7-carbonitrile;
6-chloro-3-(1H-imidazol-1-yl)-2-(5-(trifluoromethyl)-1H-1,2,4-triazol-3-yl)-1H-indole-7-carbonitrile;
6-chloro-3-(1H-imidazol-1-yl)-1-methyl-2-(5-(trifluoromethyl)-4H-1,2,4-triazol-3-yl)-1H-indole-7-carbonitrile;
6-chloro-3-(1H-imidazol-1-yl)-1-methyl-2-(3-(trifluoromethyl)-1H-1,2,4-triazol-5-yl)-1H-indole-7-carbonitrile;
6-chloro-3-(1H-imidazol-1-yl)-1-methyl-2-(5-(trifluoromethyl)-1H-1,2,4-triazol-3-yl)-1H-indole-7-carbonitrile;
6-chloro-5-(difluoromethoxy)-3-(1H-imidazol-1-yl)-2-(5-(trifluoromethyl)-4H-1,2,4-triazol-3-yl)-1H-indole;
6-chloro-5-(difluoromethoxy)-3-(1H-imidazol-1-yl)-2-(3-(trifluoromethyl)-1H-1,2,4-triazol-5-yl)-1H-indole;
6-chloro-5-(difluoromethoxy)-3-(1H-imidazol-1-yl)-2-(5-(trifluoromethyl)-1H-1,2,4-triazol-3-yl)-1H-indole;
6-chloro-5-cyclopropoxy-3-(1H-imidazol-1-yl)-2-(5-(trifluoromethyl)-4H-1,2,4-triazol-3-yl)-1H-indole;
6-chloro-5-cyclopropoxy-3-(1H-imidazol-1-yl)-2-(3-(trifluoromethyl)-1H-1,2,4-triazol-5-yl)-1H-indole;
6-chloro-5-cyclopropoxy-3-(1H-imidazol-1-yl)-2-(5-(trifluoromethyl)-1H-1,2,4-triazol-3-yl)-1H-indole;
6-chloro-3-(1H-imidazol-1-yl)-5-methoxy-1-methyl-2-(5-(trifluoromethyl)-4H-1,2,4-triazol-3-yl)-1H-indole;
6-chloro-3-(1H-imidazol-1-yl)-5-methoxy-1-methyl-2-(3-(trifluoromethyl)-1H-1,2,4-triazol-5-yl)-1H-indole;
6-chloro-3-(1H-imidazol-1-yl)-5-methoxy-1-methyl-2-(5-(trifluoromethyl)-1H-1,2,4-triazol-3-yl)-1H-indole;
6-chloro-3-(1H-imidazol-1-yl)-1-methyl-2-(5-(trifluoromethyl)-4H-1,2,4-triazol-3-yl)-1H-indol-5-ol;
6-chloro-3-(1H-imidazol-1-yl)-1-methyl-2-(3-(trifluoromethyl)-1H-1,2,4-triazol-5-yl)-1H-indol-5-ol;
6-chloro-3-(1H-imidazol-1-yl)-1-methyl-2-(5-(trifluoromethyl)-1H-1,2,4-triazol-3-yl)-1H-indol-5-ol;
5-(6-chloro-3-(1H-imidazol-1-yl)-5-methoxy-1-methyl-1H-indol-2-yl)-N,N-dimethyl-4H-1,2,4-triazole-3-carboxamide;
5-(6-chloro-3-(1H-imidazol-1-yl)-5-methoxy-1-methyl-1H-indol-2-yl)-N,N-dimethyl-1H-1,2,4-triazole-3-carboxamide;
3-(6-chloro-3-(1H-imidazol-1-yl)-5-methoxy-1-methyl-1H-indol-2-yl)-N,N-dimethyl-1H-1,2,4-triazole-5-carboxamide;
6-chloro-5-hydroxy-2-(5-(2-hydroxyethyl)-4H-1,2,4-triazol-3-yl)-3-(1H-imidazol-1-yl)-1-methyl-1H-indole-7-carbonitrile;
6-chloro-5-hydroxy-2-(3-(2-hydroxyethyl)-1H-1,2,4-triazol-5-yl)-3-(1H-imidazol-1-yl)-1-methyl-1H-indole-7-carbonitrile;
6-chloro-5-hydroxy-2-(5-(2-hydroxyethyl)-1H-1,2,4-triazol-3-yl)-3-(1H-imidazol-1-yl)-1-methyl-1H-indole-7-carbonitrile;
6-chloro-2-(5-(2-hydroxyethyl)-4H-1,2,4-triazol-3-yl)-3-(1H-imidazol-1-yl)-5-methoxy-1-methyl-1H-indole-7-carbonitrile;
6-chloro-2-(3-(2-hydroxyethyl)-1H-1,2,4-triazol-5-yl)-3-(1H-imidazol-1-yl)-5-methoxy-1-methyl-1H-indole-7-carbonitrile;
6-chloro-2-(5-(2-hydroxyethyl)-1H-1,2,4-triazol-3-yl)-3-(1H-imidazol-1-yl)-5-methoxy-1-methyl-1H-indole-7-carbonitrile;
2-(5-(6-chloro-3-(1H-imidazol-1-yl)-5-methoxy-1-methyl-1H-indol-2-yl)-4H-1,2,4-triazol-3-yl)ethan-1-ol;
2-(5-(6-chloro-3-(1H-imidazol-1-yl)-5-methoxy-1-methyl-1H-indol-2-yl)-1H-1,2,4-triazol-3-yl)ethan-1-ol;
2-(3-(6-chloro-3-(1H-imidazol-1-yl)-5-methoxy-1-methyl-1H-indol-2-yl)-1H-1,2,4-triazol-5-yl)ethan-1-ol;
5-(6,7-dicyano-3-(1H-imidazol-1-yl)-5-methoxy-1-methyl-1H-indol-2-yl)-N,N-dimethyl-4H-1,2,4-triazole-3-carboxamide;
5-(6,7-dicyano-3-(1H-imidazol-1-yl)-5-methoxy-1-methyl-1H-indol-2-yl)-N,N-dimethyl-1H-1,2,4-triazole-3-carboxamide;
3-(6,7-dicyano-3-(1H-imidazol-1-yl)-5-methoxy-1-methyl-1H-indol-2-yl)-N,N-dimethyl-1H-1,2,4-triazole-5-carboxamide;
4-(1-(5-(6-chloro-7-fluoro-3-(1H-imidazol-1-yl)-5-methoxy-1-methyl-1H-indol-2-yl)-4H-1,2,4-triazol-3-yl)ethyl)morpholine;
4-(1-(5-(6-chloro-7-fluoro-3-(1H-imidazol-1-yl)-5-methoxy-1-methyl-1H-indol-2-yl)-1H-1,2,4-triazol-3-yl)ethyl)morpholine;
4-(1-(3-(6-chloro-7-fluoro-3-(1H-imidazol-1-yl)-5-methoxy-1-methyl-1H-indol-2-yl)-1H-1,2,4-triazol-5-yl)ethyl)morpholine;
(S)-4-(1-(5-(6-chloro-7-fluoro-3-(1H-imidazol-1-yl)-5-methoxy-1-methyl-1H-indol-2-yl)-4H-1,2,4-triazol-3-yl)ethyl)morpholine;
(S)-4-(1-(5-(6-chloro-7-fluoro-3-(1H-imidazol-1-yl)-5-methoxy-1-methyl-1H-indol-2-yl)-1H-1,2,4-triazol-3-yl)ethyl)morpholine;
(S)-4-(1-(3-(6-chloro-7-fluoro-3-(1H-imidazol-1-yl)-5-methoxy-1-methyl-1H-indol-2-yl)-1H-1,2,4-triazol-5-yl)ethyl)morpholine;
(R)-4-(1-(5-(6-chloro-7-fluoro-3-(1H-imidazol-1-yl)-5-methoxy-1-methyl-1H-indol-2-yl)-4H-1,2,4-triazol-3-yl)ethyl)morpholine;
(R)-4-(1-(5-(6-chloro-7-fluoro-3-(1H-imidazol-1-yl)-5-methoxy-1-methyl-1H-indol-2-yl)-1H-1,2,4-triazol-3-yl)ethyl)morpholine;
(R)-4-(1-(3-(6-chloro-7-fluoro-3-(1H-imidazol-1-yl)-5-methoxy-1-methyl-1H-indol-2-yl)-1H-1,2,4-triazol-5-yl)ethyl)morpholine;
1-(5-(6-chloro-7-fluoro-3-(1H-imidazol-1-yl)-5-methoxy-1-methyl-1H-indol-2-yl)-4H-1,2,4-triazol-3-yl)-N,N-dimethylethan-1-amine;

1-(5-(6-chloro-7-fluoro-3-(1H-imidazol-1-yl)-5-methoxy-1-methyl-1H-indol-2-yl)-1H-1,2,4-triazol-3-yl)-N,N-dimethylethan-1-amine;
1-(3-(6-chloro-7-fluoro-3-(1H-imidazol-1-yl)-5-methoxy-1-methyl-1H-indol-2-yl)-1H-1,2,4-triazol-5-yl)-N,N-dimethylethan-1-amine;
(S)-1-(5-(6-chloro-7-fluoro-3-(1H-imidazol-1-yl)-5-methoxy-1-methyl-1H-indol-2-yl)-4H-1,2,4-triazol-3-yl)-N,N-dimethylethan-1-amine;
(S)-1-(5-(6-chloro-7-fluoro-3-(1H-imidazol-1-yl)-5-methoxy-1-methyl-1H-indol-2-yl)-1H-1,2,4-triazol-3-yl)-N,N-dimethylethan-1-amine;
(S)-1-(3-(6-chloro-7-fluoro-3-(1H-imidazol-1-yl)-5-methoxy-1-methyl-1H-indol-2-yl)-1H-1,2,4-triazol-5-yl)-N,N-dimethylethan-1-amine;
(R)-1-(5-(6-chloro-7-fluoro-3-(1H-imidazol-1-yl)-5-methoxy-1-methyl-1H-indol-2-yl)-4H-1,2,4-triazol-3-yl)-N,N-dimethylethan-1-amine;
(R)-1-(5-(6-chloro-7-fluoro-3-(1H-imidazol-1-yl)-5-methoxy-1-methyl-1H-indol-2-yl)-1H-1,2,4-triazol-3-yl)-N,N-dimethylethan-1-amine;
(R)-1-(3-(6-chloro-7-fluoro-3-(1H-imidazol-1-yl)-5-methoxy-1-methyl-1H-indol-2-yl)-1H-1,2,4-triazol-5-yl)-N,N-dimethylethan-1-amine;
1-(5-(6-chloro-7-fluoro-3-(1H-imidazol-1-yl)-5-methoxy-1-methyl-1H-indol-2-yl)-4H-1,2,4-triazol-3-yl)-N-methylethan-1-amine;
1-(5-(6-chloro-7-fluoro-3-(1H-imidazol-1-yl)-5-methoxy-1-methyl-1H-indol-2-yl)-1H-1,2,4-triazol-3-yl)-N-methylethan-1-amine;
1-(3-(6-chloro-7-fluoro-3-(1H-imidazol-1-yl)-5-methoxy-1-methyl-1H-indol-2-yl)-1H-1,2,4-triazol-5-yl)-N-methylethan-1-amine;
(S)-1-(5-(6-chloro-7-fluoro-3-(1H-imidazol-1-yl)-5-methoxy-1-methyl-1H-indol-2-yl)-4H-1,2,4-triazol-3-yl)-N-methylethan-1-amine;
(S)-1-(5-(6-chloro-7-fluoro-3-(1H-imidazol-1-yl)-5-methoxy-1-methyl-1H-indol-2-yl)-1H-1,2,4-triazol-3-yl)-N-methylethan-1-amine;
(S)-1-(3-(6-chloro-7-fluoro-3-(1H-imidazol-1-yl)-5-methoxy-1-methyl-1H-indol-2-yl)-1H-1,2,4-triazol-5-yl)-N-methylethan-1-amine;
(R)-1-(5-(6-chloro-7-fluoro-3-(1H-imidazol-1-yl)-5-methoxy-1-methyl-1H-indol-2-yl)-4H-1,2,4-triazol-3-yl)-N-methylethan-1-amine;
(R)-1-(5-(6-chloro-7-fluoro-3-(1H-imidazol-1-yl)-5-methoxy-1-methyl-1H-indol-2-yl)-1H-1,2,4-triazol-3-yl)-N-methylethan-1-amine;
(R)-1-(3-(6-chloro-7-fluoro-3-(1H-imidazol-1-yl)-5-methoxy-1-methyl-1H-indol-2-yl)-1H-1,2,4-triazol-5-yl)-N-methylethan-1-amine;
1-(5-(6-chloro-7-fluoro-3-(1H-imidazol-1-yl)-5-methoxy-1-methyl-1H-indol-2-yl)-4H-1,2,4-triazol-3-yl)-2-methoxy-N,N-dimethylethan-1-amine;
1-(5-(6-chloro-7-fluoro-3-(1H-imidazol-1-yl)-5-methoxy-1-methyl-1H-indol-2-yl)-1H-1,2,4-triazol-3-yl)-2-methoxy-N,N-dimethylethan-1-amine;
1-(3-(6-chloro-7-fluoro-3-(1H-imidazol-1-yl)-5-methoxy-1-methyl-1H-indol-2-yl)-1H-1,2,4-triazol-5-yl)-2-methoxy-N,N-dimethylethan-1-amine;
(R)-1-(5-(6-chloro-7-fluoro-3-(1H-imidazol-1-yl)-5-methoxy-1-methyl-1H-indol-2-yl)-4H-1,2,4-triazol-3-yl)-2-methoxy-N,N-dimethylethan-1-amine;
(R)-1-(5-(6-chloro-7-fluoro-3-(1H-imidazol-1-yl)-5-methoxy-1-methyl-1H-indol-2-yl)-1H-1,2,4-triazol-3-yl)-2-methoxy-N,N-dimethylethan-1-amine;
(R)-1-(3-(6-chloro-7-fluoro-3-(1H-imidazol-1-yl)-5-methoxy-1-methyl-1H-indol-2-yl)-1H-1,2,4-triazol-5-yl)-2-methoxy-N,N-dimethylethan-1-amine;
(S)-1-(5-(6-chloro-7-fluoro-3-(1H-imidazol-1-yl)-5-methoxy-1-methyl-1H-indol-2-yl)-4H-1,2,4-triazol-3-yl)-2-methoxy-N,N-dimethylethan-1-amine;
(S)-1-(5-(6-chloro-7-fluoro-3-(1H-imidazol-1-yl)-5-methoxy-1-methyl-1H-indol-2-yl)-1H-1,2,4-triazol-3-yl)-2-methoxy-N,N-dimethylethan-1-amine;
(S)-1-(3-(6-chloro-7-fluoro-3-(1H-imidazol-1-yl)-5-methoxy-1-methyl-1H-indol-2-yl)-1H-1,2,4-triazol-5-yl)-2-methoxy-N,N-dimethylethan-1-amine;
1-(5-(6-chloro-7-fluoro-3-(1H-imidazol-1-yl)-5-methoxy-1-methyl-1H-indol-2-yl)-4H-1,2,4-triazol-3-yl)-2-methoxy-N-methylethan-1-amine;
1-(5-(6-chloro-7-fluoro-3-(1H-imidazol-1-yl)-5-methoxy-1-methyl-1H-indol-2-yl)-1H-1,2,4-triazol-3-yl)-2-methoxy-N-methylethan-1-amine;
1-(3-(6-chloro-7-fluoro-3-(1H-imidazol-1-yl)-5-methoxy-1-methyl-1H-indol-2-yl)-1H-1,2,4-triazol-5-yl)-2-methoxy-N-methylethan-1-amine;
(R)-1-(5-(6-chloro-7-fluoro-3-(1H-imidazol-1-yl)-5-methoxy-1-methyl-1H-indol-2-yl)-4H-1,2,4-triazol-3-yl)-2-methoxy-N-methylethan-1-amine;
(R)-1-(5-(6-chloro-7-fluoro-3-(1H-imidazol-1-yl)-5-methoxy-1-methyl-1H-indol-2-yl)-1H-1,2,4-triazol-3-yl)-2-methoxy-N-methylethan-1-amine;
(R)-1-(3-(6-chloro-7-fluoro-3-(1H-imidazol-1-yl)-5-methoxy-1-methyl-1H-indol-2-yl)-1H-1,2,4-triazol-5-yl)-2-methoxy-N-methylethan-1-amine;
(S)-1-(5-(6-chloro-7-fluoro-3-(1H-imidazol-1-yl)-5-methoxy-1-methyl-1H-indol-2-yl)-4H-1,2,4-triazol-3-yl)-2-methoxy-N-methylethan-1-amine;
(S)-1-(5-(6-chloro-7-fluoro-3-(1H-imidazol-1-yl)-5-methoxy-1-methyl-1H-indol-2-yl)-1H-1,2,4-triazol-3-yl)-2-methoxy-N-methylethan-1-amine;
(S)-1-(3-(6-chloro-7-fluoro-3-(1H-imidazol-1-yl)-5-methoxy-1-methyl-1H-indol-2-yl)-1H-1,2,4-triazol-5-yl)-2-methoxy-N-methylethan-1-amine;
4-(1-(5-(6-chloro-7-fluoro-3-(1H-imidazol-1-yl)-5-methoxy-1-methyl-1H-indol-2-yl)-4H-1,2,4-triazol-3-yl)-2-methoxyethyl)morpholine;
4-(1-(5-(6-chloro-7-fluoro-3-(1H-imidazol-1-yl)-5-methoxy-1-methyl-1H-indol-2-yl)-1H-1,2,4-triazol-3-yl)-2-methoxyethyl)morpholine;
4-(1-(3-(6-chloro-7-fluoro-3-(1H-imidazol-1-yl)-5-methoxy-1-methyl-1H-indol-2-yl)-1H-1,2,4-triazol-5-yl)-2-methoxyethyl)morpholine;
(R)-4-(1-(5-(6-chloro-7-fluoro-3-(1H-imidazol-1-yl)-5-methoxy-1-methyl-1H-indol-2-yl)-4H-1,2,4-triazol-3-yl)-2-methoxyethyl)morpholine;
(R)-4-(1-(5-(6-chloro-7-fluoro-3-(1H-imidazol-1-yl)-5-methoxy-1-methyl-1H-indol-2-yl)-1H-1,2,4-triazol-3-yl)-2-methoxyethyl)morpholine;
(R)-4-(1-(3-(6-chloro-7-fluoro-3-(1H-imidazol-1-yl)-5-methoxy-1-methyl-1H-indol-2-yl)-1H-1,2,4-triazol-5-yl)-2-methoxyethyl)morpholine;
(S)-4-(1-(5-(6-chloro-7-fluoro-3-(1H-imidazol-1-yl)-5-methoxy-1-methyl-1H-indol-2-yl)-4H-1,2,4-triazol-3-yl)-2-methoxyethyl)morpholine;
(S)-4-(1-(5-(6-chloro-7-fluoro-3-(1H-imidazol-1-yl)-5-methoxy-1-methyl-1H-indol-2-yl)-1H-1,2,4-triazol-3-yl)-2-methoxyethyl)morpholine;
(S)-4-(1-(3-(6-chloro-7-fluoro-3-(1H-imidazol-1-yl)-5-methoxy-1-methyl-1H-indol-2-yl)-1H-1,2,4-triazol-5-yl)-2-methoxyethyl)morpholine;

2-(5-(1-(azetidin-1-yl)-2-methoxyethyl)-4H-1,2,4-triazol-3-yl)-6-chloro-7-fluoro-3-(1H-imidazol-1-yl)-5-methoxy-1-methyl-1H-indole;
2-(3-(1-(azetidin-1-yl)-2-methoxyethyl)-1H-1,2,4-triazol-5-yl)-6-chloro-7-fluoro-3-(1H-imidazol-1-yl)-5-methoxy-1-methyl-1H-indole;
2-(5-(1-(azetidin-1-yl)-2-methoxyethyl)-1H-1,2,4-triazol-3-yl)-6-chloro-7-fluoro-3-(1H-imidazol-1-yl)-5-methoxy-1-methyl-1H-indole;
(R)-2-(5-(1-(azetidin-1-yl)-2-methoxyethyl)-4H-1,2,4-triazol-3-yl)-6-chloro-7-fluoro-3-(1H-imidazol-1-yl)-5-methoxy-1-methyl-1H-indole;
(R)-2-(3-(1-(azetidin-1-yl)-2-methoxyethyl)-1H-1,2,4-triazol-5-yl)-6-chloro-7-fluoro-3-(1H-imidazol-1-yl)-5-methoxy-1-methyl-1H-indole;
(R)-2-(5-(1-(azetidin-1-yl)-2-methoxyethyl)-1H-1,2,4-triazol-3-yl)-6-chloro-7-fluoro-3-(1H-imidazol-1-yl)-5-methoxy-1-methyl-1H-indole;
(S)-2-(5-(1-(azetidin-1-yl)-2-methoxyethyl)-4H-1,2,4-triazol-3-yl)-6-chloro-7-fluoro-3-(1H-imidazol-1-yl)-5-methoxy-1-methyl-1H-indole;
(S)-2-(3-(1-(azetidin-1-yl)-2-methoxyethyl)-1H-1,2,4-triazol-5-yl)-6-chloro-7-fluoro-3-(1H-imidazol-1-yl)-5-methoxy-1-methyl-1H-indole;
(S)-2-(5-(1-(azetidin-1-yl)-2-methoxyethyl)-1H-1,2,4-triazol-3-yl)-6-chloro-7-fluoro-3-(1H-imidazol-1-yl)-5-methoxy-1-methyl-1H-indole;
1-(5-(6-chloro-7-fluoro-3-(1H-imidazol-1-yl)-5-methoxy-1-methyl-1H-indol-2-yl)-4H-1,2,4-triazol-3-yl)-N-(2-methoxyethyl)-N-methylethan-1-amine;
1-(5-(6-chloro-7-fluoro-3-(1H-imidazol-1-yl)-5-methoxy-1-methyl-1H-indol-2-yl)-1H-1,2,4-triazol-3-yl)-N-(2-methoxyethyl)-N-methylethan-1-amine;
1-(3-(6-chloro-7-fluoro-3-(1H-imidazol-1-yl)-5-methoxy-1-methyl-1H-indol-2-yl)-1H-1,2,4-triazol-5-yl)-N-(2-methoxyethyl)-N-methylethan-1-amine;
(S)-1-(5-(6-chloro-7-fluoro-3-(1H-imidazol-1-yl)-5-methoxy-1-methyl-1H-indol-2-yl)-4H-1,2,4-triazol-3-yl)-N-(2-methoxyethyl)-N-methylethan-1-amine;
(S)-1-(5-(6-chloro-7-fluoro-3-(1H-imidazol-1-yl)-5-methoxy-1-methyl-1H-indol-2-yl)-1H-1,2,4-triazol-3-yl)-N-(2-methoxyethyl)-N-methylethan-1-amine;
(S)-1-(3-(6-chloro-7-fluoro-3-(1H-imidazol-1-yl)-5-methoxy-1-methyl-1H-indol-2-yl)-1H-1,2,4-triazol-5-yl)-N-(2-methoxyethyl)-N-methylethan-1-amine;
(R)-1-(5-(6-chloro-7-fluoro-3-(1H-imidazol-1-yl)-5-methoxy-1-methyl-1H-indol-2-yl)-4H-1,2,4-triazol-3-yl)-N-(2-methoxyethyl)-N-methylethan-1-amine;
(R)-1-(5-(6-chloro-7-fluoro-3-(1H-imidazol-1-yl)-5-methoxy-1-methyl-1H-indol-2-yl)-1H-1,2,4-triazol-3-yl)-N-(2-methoxyethyl)-N-methylethan-1-amine;
(R)-1-(3-(6-chloro-7-fluoro-3-(1H-imidazol-1-yl)-5-methoxy-1-methyl-1H-indol-2-yl)-1H-1,2,4-triazol-5-yl)-N-(2-methoxyethyl)-N-methylethan-1-amine;
1-(5-(6-chloro-7-fluoro-3-(1H-imidazol-1-yl)-5-methoxy-1-methyl-1H-indol-2-yl)-4H-1,2,4-triazol-3-yl)-N-(2-methoxyethyl)ethan-1-amine;
1-(5-(6-chloro-7-fluoro-3-(1H-imidazol-1-yl)-5-methoxy-1-methyl-1H-indol-2-yl)-1H-1,2,4-triazol-3-yl)-N-(2-methoxyethyl)ethan-1-amine;
1-(3-(6-chloro-7-fluoro-3-(1H-imidazol-1-yl)-5-methoxy-1-methyl-1H-indol-2-yl)-1H-1,2,4-triazol-5-yl)-N-(2-methoxyethyl)ethan-1-amine;
(S)-1-(5-(6-chloro-7-fluoro-3-(1H-imidazol-1-yl)-5-methoxy-1-methyl-1H-indol-2-yl)-4H-1,2,4-triazol-3-yl)-N-(2-methoxyethyl)ethan-1-amine;
(S)-1-(5-(6-chloro-7-fluoro-3-(1H-imidazol-1-yl)-5-methoxy-1-methyl-1H-indol-2-yl)-1H-1,2,4-triazol-3-yl)-N-(2-methoxyethyl)ethan-1-amine;
(S)-1-(3-(6-chloro-7-fluoro-3-(1H-imidazol-1-yl)-5-methoxy-1-methyl-1H-indol-2-yl)-1H-1,2,4-triazol-5-yl)-N-(2-methoxyethyl)ethan-1-amine;
(R)-1-(5-(6-chloro-7-fluoro-3-(1H-imidazol-1-yl)-5-methoxy-1-methyl-1H-indol-2-yl)-4H-1,2,4-triazol-3-yl)-N-(2-methoxyethyl)ethan-1-amine;
(R)-1-(5-(6-chloro-7-fluoro-3-(1H-imidazol-1-yl)-5-methoxy-1-methyl-1H-indol-2-yl)-1H-1,2,4-triazol-3-yl)-N-(2-methoxyethyl)ethan-1-amine;
(R)-1-(3-(6-chloro-7-fluoro-3-(1H-imidazol-1-yl)-5-methoxy-1-methyl-1H-indol-2-yl)-1H-1,2,4-triazol-5-yl)-N-(2-methoxyethyl)ethan-1-amine;
6-(1-(5-(6-chloro-7-fluoro-3-(1H-imidazol-1-yl)-5-methoxy-1-methyl-1H-indol-2-yl)-4H-1,2,4-triazol-3-yl)ethyl)-2-oxa-6-azaspiro[3.3]heptane;
6-(1-(5-(6-chloro-7-fluoro-3-(1H-imidazol-1-yl)-5-methoxy-1-methyl-1H-indol-2-yl)-1H-1,2,4-triazol-3-yl)ethyl)-2-oxa-6-azaspiro[3.3]heptane;
6-(1-(3-(6-chloro-7-fluoro-3-(1H-imidazol-1-yl)-5-methoxy-1-methyl-1H-indol-2-yl)-1H-1,2,4-triazol-5-yl)ethyl)-2-oxa-6-azaspiro[3.3]heptane;
(S)-6-(1-(5-(6-chloro-7-fluoro-3-(1H-imidazol-1-yl)-5-methoxy-1-methyl-1H-indol-2-yl)-4H-1,2,4-triazol-3-yl)ethyl)-2-oxa-6-azaspiro[3.3]heptane;
(S)-6-(1-(5-(6-chloro-7-fluoro-3-(1H-imidazol-1-yl)-5-methoxy-1-methyl-1H-indol-2-yl)-1H-1,2,4-triazol-3-yl)ethyl)-2-oxa-6-azaspiro[3.3]heptane;
(S)-6-(1-(3-(6-chloro-7-fluoro-3-(1H-imidazol-1-yl)-5-methoxy-1-methyl-1H-indol-2-yl)-1H-1,2,4-triazol-5-yl)ethyl)-2-oxa-6-azaspiro[3.3]heptane;
(R)-6-(1-(5-(6-chloro-7-fluoro-3-(1H-imidazol-1-yl)-5-methoxy-1-methyl-1H-indol-2-yl)-4H-1,2,4-triazol-3-yl)ethyl)-2-oxa-6-azaspiro[3.3]heptane;
(R)-6-(1-(5-(6-chloro-7-fluoro-3-(1H-imidazol-1-yl)-5-methoxy-1-methyl-1H-indol-2-yl)-1H-1,2,4-triazol-3-yl)ethyl)-2-oxa-6-azaspiro[3.3]heptane;
(R)-6-(1-(3-(6-chloro-7-fluoro-3-(1H-imidazol-1-yl)-5-methoxy-1-methyl-1H-indol-2-yl)-1H-1,2,4-triazol-5-yl)ethyl)-2-oxa-6-azaspiro[3.3]heptane;
or a pharmaceutically acceptable salt, hydrate, solvate, stereoisomer, or tautomer thereof.

Embodiment 153. A compound selected from:
1-(5-(6-chloro-7-fluoro-5-methoxy-1-methyl-3-(1H-pyrazol-4-yl)-1H-indol-2-yl)-4H-1,2,4-triazol-3-yl)-2-methoxyethan-1-ol;
1-(5-(6-chloro-7-fluoro-5-methoxy-1-methyl-3-(1H-pyrazol-4-yl)-1H-indol-2-yl)-1H-1,2,4-triazol-3-yl)-2-methoxyethan-1-ol;
1-(3-(6-chloro-7-fluoro-5-methoxy-1-methyl-3-(1H-pyrazol-4-yl)-1H-indol-2-yl)-1H-1,2,4-triazol-5-yl)-2-methoxyethan-1-ol;
(R)-1-(5-(6-chloro-7-fluoro-5-methoxy-1-methyl-3-(1H-pyrazol-4-yl)-1H-indol-2-yl)-4H-1,2,4-triazol-3-yl)-2-methoxyethan-1-ol;
(R)-1-(5-(6-chloro-7-fluoro-5-methoxy-1-methyl-3-(1H-pyrazol-4-yl)-1H-indol-2-yl)-1H-1,2,4-triazol-3-yl)-2-methoxyethan-1-ol;
(R)-1-(3-(6-chloro-7-fluoro-5-methoxy-1-methyl-3-(1H-pyrazol-4-yl)-1H-indol-2-yl)-1H-1,2,4-triazol-5-yl)-2-methoxyethan-1-ol;
(S)-1-(5-(6-chloro-7-fluoro-5-methoxy-1-methyl-3-(1H-pyrazol-4-yl)-1H-indol-2-yl)-4H-1,2,4-triazol-3-yl)-2-methoxyethan-1-ol;

(S)-1-(5-(6-chloro-7-fluoro-5-methoxy-1-methyl-3-(1H-pyrazol-4-yl)-1H-indol-2-yl)-1H-1,2,4-triazol-3-yl)-2-methoxyethan-1-ol; and
(S)-1-(3-(6-chloro-7-fluoro-5-methoxy-1-methyl-3-(1H-pyrazol-4-yl)-1H-indol-2-yl)-1H-1,2,4-triazol-5-yl)-2-methoxyethan-1-ol,
or a pharmaceutically acceptable salt thereof.

Embodiment 154. A compound selected from:
1-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-ol;
1-(5-(6-chloro-7-fluoro-3-(1H-imidazol-1-yl)-5-methoxy-1-methyl-1H-indol-2-yl)-1H-1,2,4-triazol-3-yl)-2-methoxyethan-1-ol;
1-(3-(6-chloro-7-fluoro-3-(1H-imidazol-1-yl)-5-methoxy-1-methyl-1H-indol-2-yl)-1H-1,2,4-triazol-5-yl)-2-methoxyethan-1-ol;
(S)-1-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-ol;
(S)-1-(5-(6-chloro-7-fluoro-3-(1H-imidazol-1-yl)-5-methoxy-1-methyl-1H-indol-2-yl)-1H-1,2,4-triazol-3-yl)-2-methoxyethan-1-ol;
(S)-1-(3-(6-chloro-7-fluoro-3-(1H-imidazol-1-yl)-5-methoxy-1-methyl-1H-indol-2-yl)-1H-1,2,4-triazol-5-yl)-2-methoxyethan-1-ol;
(R)-1-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-ol;
(R)-1-(5-(6-chloro-7-fluoro-3-(1H-imidazol-1-yl)-5-methoxy-1-methyl-1H-indol-2-yl)-1H-1,2,4-triazol-3-yl)-2-methoxyethan-1-ol; and
(R)-1-(3-(6-chloro-7-fluoro-3-(1H-imidazol-1-yl)-5-methoxy-1-methyl-1H-indol-2-yl)-1H-1,2,4-triazol-5-yl)-2-methoxyethan-1-ol,
or a pharmaceutically acceptable salt thereof.

Embodiment 155. A compound selected from:
1-(5-(6-chloro-7-fluoro-3-(1H-imidazol-1-yl)-5-methoxy-1-methyl-1H-indol-2-yl)-4H-1,2,4-triazol-3-yl)ethan-1-one;
1-(5-(6-chloro-7-fluoro-3-(1H-imidazol-1-yl)-5-methoxy-1-methyl-1H-indol-2-yl)-1H-1,2,4-triazol-3-yl)ethan-1-one; and
1-(3-(6-chloro-7-fluoro-3-(1H-imidazol-1-yl)-5-methoxy-1-methyl-1H-indol-2-yl)-1H-1,2,4-triazol-5-yl)ethan-1-one,
or a pharmaceutically acceptable salt thereof.

Embodiment 156. A compound selected from:
1-(5-(6-chloro-7-fluoro-3-(1H-imidazol-1-yl)-5-methoxy-1-methyl-1H-indol-2-yl)-4H-1,2,4-triazol-3-yl)-2-methoxy-N,N-dimethylethan-1-amine;
1-(5-(6-chloro-7-fluoro-3-(1H-imidazol-1-yl)-5-methoxy-1-methyl-1H-indol-2-yl)-1H-1,2,4-triazol-3-yl)-2-methoxy-N,N-dimethylethan-1-amine;
1-(3-(6-chloro-7-fluoro-3-(1H-imidazol-1-yl)-5-methoxy-1-methyl-1H-indol-2-yl)-1H-1,2,4-triazol-5-yl)-2-methoxy-N,N-dimethylethan-1-amine;
(R)-1-(5-(6-chloro-7-fluoro-3-(1H-imidazol-1-yl)-5-methoxy-1-methyl-1H-indol-2-yl)-4H-1,2,4-triazol-3-yl)-2-methoxy-N,N-dimethylethan-1-amine;
(R)-1-(5-(6-chloro-7-fluoro-3-(1H-imidazol-1-yl)-5-methoxy-1-methyl-1H-indol-2-yl)-1H-1,2,4-triazol-3-yl)-2-methoxy-N,N-dimethylethan-1-amine;
(R)-1-(3-(6-chloro-7-fluoro-3-(1H-imidazol-1-yl)-5-methoxy-1-methyl-1H-indol-2-yl)-1H-1,2,4-triazol-5-yl)-2-methoxy-N,N-dimethylethan-1-amine;
(S)-1-(5-(6-chloro-7-fluoro-3-(1H-imidazol-1-yl)-5-methoxy-1-methyl-1H-indol-2-yl)-4H-1,2,4-triazol-3-yl)-2-methoxy-N,N-dimethylethan-1-amine;
(S)-1-(5-(6-chloro-7-fluoro-3-(1H-imidazol-1-yl)-5-methoxy-1-methyl-1H-indol-2-yl)-1H-1,2,4-triazol-3-yl)-2-methoxy-N,N-dimethylethan-1-amine; and
(S)-1-(3-(6-chloro-7-fluoro-3-(1H-imidazol-1-yl)-5-methoxy-1-methyl-1H-indol-2-yl)-1H-1,2,4-triazol-5-yl)-2-methoxy-N,N-dimethylethan-1-amine,
or a pharmaceutically acceptable salt thereof.

Embodiment 157. A compound selected from:
1-(5-(6-chloro-7-fluoro-3-(1H-imidazol-1-yl)-5-methoxy-1-methyl-1H-indol-2-yl)-4H-1,2,4-triazol-3-yl)-2-methoxy-N-methylethan-1-amine;
1-(5-(6-chloro-7-fluoro-3-(1H-imidazol-1-yl)-5-methoxy-1-methyl-1H-indol-2-yl)-1H-1,2,4-triazol-3-yl)-2-methoxy-N-methylethan-1-amine;
1-(3-(6-chloro-7-fluoro-3-(1H-imidazol-1-yl)-5-methoxy-1-methyl-1H-indol-2-yl)-1H-1,2,4-triazol-5-yl)-2-methoxy-N-methylethan-1-amine;
(R)-1-(5-(6-chloro-7-fluoro-3-(1H-imidazol-1-yl)-5-methoxy-1-methyl-1H-indol-2-yl)-4H-1,2,4-triazol-3-yl)-2-methoxy-N-methylethan-1-amine;
(R)-1-(5-(6-chloro-7-fluoro-3-(1H-imidazol-1-yl)-5-methoxy-1-methyl-1H-indol-2-yl)-1H-1,2,4-triazol-3-yl)-2-methoxy-N-methylethan-1-amine;
(R)-1-(3-(6-chloro-7-fluoro-3-(1H-imidazol-1-yl)-5-methoxy-1-methyl-1H-indol-2-yl)-1H-1,2,4-triazol-5-yl)-2-methoxy-N-methylethan-1-amine;
(S)-1-(5-(6-chloro-7-fluoro-3-(1H-imidazol-1-yl)-5-methoxy-1-methyl-1H-indol-2-yl)-4H-1,2,4-triazol-3-yl)-2-methoxy-N-methylethan-1-amine;
(S)-1-(5-(6-chloro-7-fluoro-3-(1H-imidazol-1-yl)-5-methoxy-1-methyl-1H-indol-2-yl)-1H-1,2,4-triazol-3-yl)-2-methoxy-N-methylethan-1-amine; and
(S)-1-(3-(6-chloro-7-fluoro-3-(1H-imidazol-1-yl)-5-methoxy-1-methyl-1H-indol-2-yl)-1H-1,2,4-triazol-5-yl)-2-methoxy-N-methylethan-1-amine,
or a pharmaceutically acceptable salt thereof.

The non-limiting illustrative compounds of the disclosure include the compounds in Table 1 below. As discussed below, each of the exemplified compounds is illustrated by one tautomeric form about the structural features where tautomerization is possible. For convenience, Tautomers A, B and C refer to the tautomers about the triazole motif in the compounds of the invention. Unless otherwise specified, the $IC_{50}$ is reported for the potential mixture in solution of the co-existing tautomers and/or racemates without regard to the specific tautomeric form.

TABLE 1

Illustrative compounds of the disclosure and cGAS inhibition activity

| Example No. | Tautomer | Structure | Name | cGAS IC$_{50}$ [μM] |
|---|---|---|---|---|
| 1 | A | 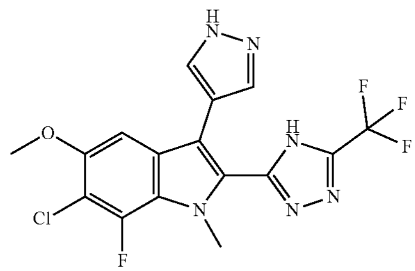 [SMILES: COc1cc2c(-c3cn[nH]c3)c(-c3nnc(C(F)(F)F)[nH]3)n(C)c2c(F)c1Cl] | 6-chloro-7-fluoro-5-methoxy-1-methyl-3-(1H-pyrazol-4-yl)-2-(5-(trifluoromethyl)-4H-1,2,4-triazol-3-yl)-1H-indole | 0.074 |
|  | B | | 6-chloro-7-fluoro-5-methoxy-1-methyl-3-(1H-pyrazol-4-yl)-2-(3-(trifluoromethyl)-1H-1,2,4-triazol-5-yl)-1H-indole | |
|  | C | | 6-chloro-7-fluoro-5-methoxy-1-methyl-3-(1H-pyrazol-4-yl)-2-(5-(trifluoromethyl)-1H-1,2,4-triazol-3-yl)-1H-indole | |
| 2 | A | 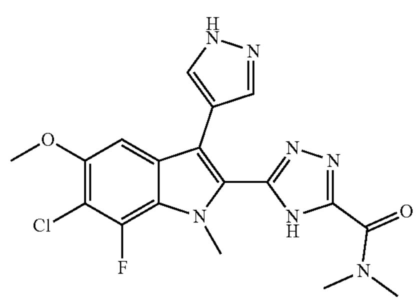 [SMILES: COc1cc2c(-c3cn[nH]c3)c(-c3nnc(C(=O)N(C)C)[nH]3)n(C)c2c(F)c1Cl] | 5-(6-chloro-7-fluoro-5-methoxy-1-methyl-3-(1H-pyrazol-4-yl)-1H-indol-2-yl)-N,N-dimethyl-4H-1,2,4-triazole-3-carboxamide | 0.046 |
|  | B | | 5-(6-chloro-7-fluoro-5-methoxy-1-methyl-3-(1H-pyrazol-4-yl)-1H-indol-2-yl)-N,N-dimethyl-1H-1,2,4-triazole-3-carboxamide | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | 3-(6-chloro-7-fluoro-5-methoxy-1-methyl-3-(1H-pyrazol-4-yl)-1H-indol-2-yl)-N,N-dimethyl-1H-1,2,4-triazole-5-carboxamide | |
| 3 | A | 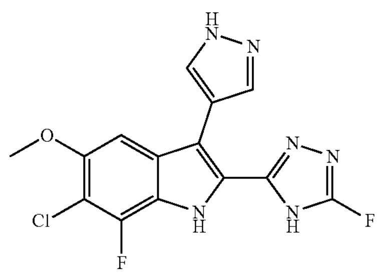 [SMILES: COc1cc2c(-c3cn[nH]c3)c(-c3nnc(F)[nH]3)[nH]c2c(F)c1Cl] | 6-chloro-7-fluoro-2-(5-fluoro-4H-1,2,4-triazol-3-yl)-5-methoxy-3-(1H-pyrazol-4-yl)-1H-indole | 0.030 |
| | B | | 6-chloro-7-fluoro-2-(3-fluoro-1H-1,2,4-triazol-5-yl)-5-methoxy-3-(1H-pyrazol-4-yl)-1H-indole | |
| | C | | 6-chloro-7-fluoro-2-(5-fluoro-1H-1,2,4-triazol-3-yl)-5-methoxy-3-(1H-pyrazol-4-yl)-1H-indole | |
| 4 | A | 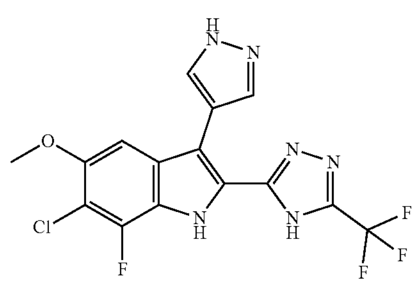 [SMILES: COc1cc2c(-c3cn[nH]c3)c(-c3nnc(C(F)(F)F)[nH]3)[nH]c2c(F)c1Cl] | 6-chloro-7-fluoro-5-methoxy-3-(1H-pyrazol-4-yl)-2-(5-(trifluoromethyl)-4H-1,2,4-triazol-3-yl)-1H-indole | 0.033 |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | 6-chloro-7-fluoro-5-methoxy-3-(1H-pyrazol-4-yl)-2-(3-(trifluoromethyl)-1H-1,2,4-triazol-5-yl)-1H-indole | |
| | C | | 6-chloro-7-fluoro-5-methoxy-3-(1H-pyrazol-4-yl)-2-(5-(trifluoromethyl)-1H-1,2,4-triazol-3-yl)-1H-indole | |
| 5 | A | 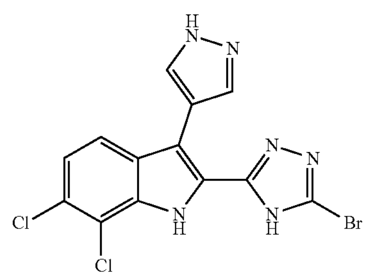 [SMILES: Clc1ccc2c(-c3cn[nH]c3)c(-c3nnc(Br)[nH]3)[nH]c2c1Cl] | 2-(5-bromo-4H-1,2,4-triazol-3-yl)-6,7-dichloro-3-(1H-pyrazol-4-yl)-1H-indole | 0.093 |
| | B | | 2-(3-bromo-1H-1,2,4-triazol-5-yl)-6,7-dichloro-3-(1H-pyrazol-4-yl)-1H-indole | |
| | C | | 2-(5-bromo-1H-1,2,4-triazol-3-yl)-6,7-dichloro-3-(1H-pyrazol-4-yl)-1H-indole | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 6 | A | 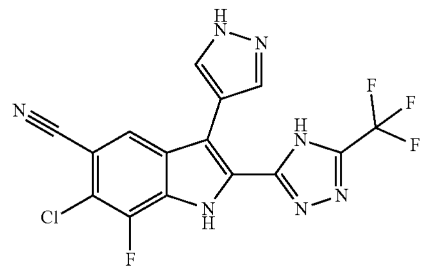 [SMILES: N#Cc1cc2c(-c3cn[nH]c3)c(-c3nnc(C(F)(F)F)[nH]3)[nH]c2c(F)c1Cl] | 6-chloro-7-fluoro-3-(1H-pyrazol-4-yl)-2-(5-(trifluoromethyl)-4H-1,2,4-triazol-3-yl)-1H-indole-5-carbonitrile | 0.152 |
| | B | | 6-chloro-7-fluoro-3-(1H-pyrazol-4-yl)-2-(3-(trifluoromethyl)-1H-1,2,4-triazol-5-yl)-1H-indole-5-carbonitrile | |
| | C | | 6-chloro-7-fluoro-3-(1H-pyrazol-4-yl)-2-(5-(trifluoromethyl)-1H-1,2,4-triazol-3-yl)-1H-indole-5-carbonitrile | |
| 7 | A | 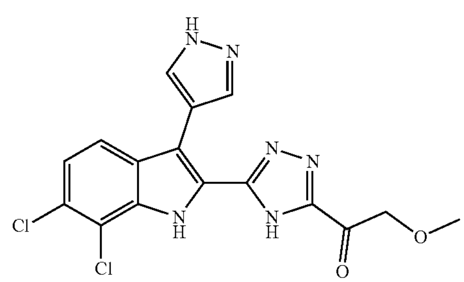 [SMILES: COCC(=O)c1nnc(-c2[nH]c3c(Cl)c(Cl)ccc3c2-c2cn[nH]c2)[nH]1] | 1-(5-(6,7-dichloro-3-(1H-pyrazol-4-yl)-1H-indol-2-yl)-4H-1,2,4-triazol-3-yl)-2-methoxyethan-1-one | 0.030 |
| | B | | 1-(5-(6,7-dichloro-3-(1H-pyrazol-4-yl)-1H-indol-2-yl)-1H-1,2,4-triazol-3-yl)-2-methoxyethan-1-one | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | 1-(3-(6,7-dichloro-3-(1H-pyrazol-4-yl)-1H-indol-2-yl)-1H-1,2,4-triazol-5-yl)-2-methoxyethan-1-one | |
| 8 | A | 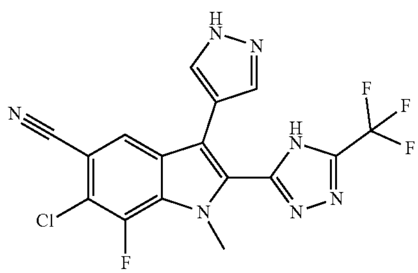 [SMILES: Cn1c(-c2nnc(C(F)(F)F)[nH]2)c(-c2cn[nH]c2)c2cc(C#N)c(Cl)c(F)c21] | 6-chloro-7-fluoro-1-methyl-3-(1H-pyrazol-4-yl)-2-(5-(trifluoromethyl)-4H-1,2,4-triazol-3-yl)-1H-indole-5-carbonitrile | 0.134 |
| | B | | 6-chloro-7-fluoro-1-methyl-3-(1H-pyrazol-4-yl)-2-(3-(trifluoromethyl)-1H-1,2,4-triazol-5-yl)-1H-indole-5-carbonitrile | |
| | C | | 6-chloro-7-fluoro-1-methyl-3-(1H-pyrazol-4-yl)-2-(5-(trifluoromethyl)-1H-1,2,4-triazol-3-yl)-1H-indole-5-carbonitrile | |
| 9 | A | 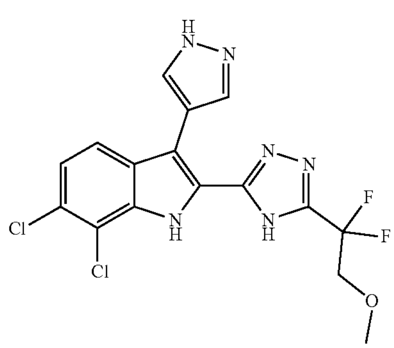 [SMILES: COCC(F)(F)c1nnc(-c2[nH]c3c(Cl)c(Cl)ccc3c2-c2cn[nH]c2)[nH]1] | 6,7-dichloro-2-(5-(1,1-difluoro-2-methoxyethyl)-4H-1,2,4-triazol-3-yl)-3-(1H-pyrazol-4-yl)-1H-indole | 0.030 |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | 6,7-dichloro-2-(3-(1,1-difluoro-2-methoxyethyl)-1H-1,2,4-triazol-5-yl)-3-(1H-pyrazol-4-yl)-1H-indole | |
| | C | | 6,7-dichloro-2-(5-(1,1-difluoro-2-methoxyethyl)-1H-1,2,4-triazol-3-yl)-3-(1H-pyrazol-4-yl)-1H-indole | |
| 10 | A | 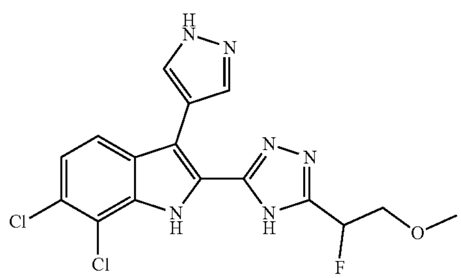 [SMILES: COCC(F)c1nnc(-c2[nH]c3c(Cl)c(Cl)ccc3c2-c2cn[nH]c2)[nH]1] | 6,7-dichloro-2-(5-(1-fluoro-2-methoxyethyl)-4H-1,2,4-triazol-3-yl)-3-(1H-pyrazol-4-yl)-1H-indole | 0.074 |
| | B | | 6,7-dichloro-2-(3-(1-fluoro-2-methoxyethyl)-1H-1,2,4-triazol-5-yl)-3-(1H-pyrazol-4-yl)-1H-indole | |
| | C | | 6,7-dichloro-2-(5-(1-fluoro-2-methoxyethyl)-1H-1,2,4-triazol-3-yl)-3-(1H-pyrazol-4-yl)-1H-indole | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 10a | A | 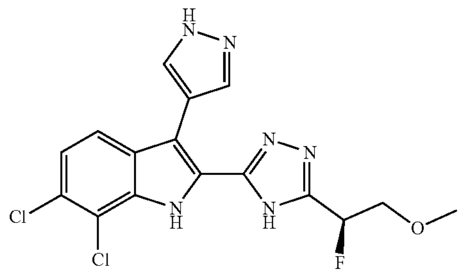 [SMILES: COC[C@@H](F)c1nnc(-c2[nH]c3c(Cl)c(Cl)ccc3c2-c2cn[nH]c2)[nH]1] | (S)-6,7-dichloro-2-(5-(1-fluoro-2-methoxyethyl)-4H-1,2,4-triazol-3-yl)-3-(1H-pyrazol-4-yl)-1H-indole | NA |
|  | B | | (S)-6,7-dichloro-2-(3-(1-fluoro-2-methoxyethyl)-1H-1,2,4-triazol-5-yl)-3-(1H-pyrazol-4-yl)-1H-indole | |
|  | C | | (S)-6,7-dichloro-2-(5-(1-fluoro-2-methoxyethyl)-1H-1,2,4-triazol-3-yl)-3-(1H-pyrazol-4-yl)-1H-indole | |
| 10b | A | 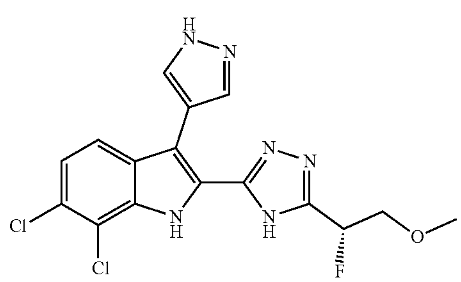 [SMILES: COC[C@H](F)c1nnc(-c2[nH]c3c(Cl)c(Cl)ccc3c2-c2cn[nH]c2)[nH]1] | (R)-6,7-dichloro-2-(5-(1-fluoro-2-methoxyethyl)-4H-1,2,4-triazol-3-yl)-3-(1H-pyrazol-4-yl)-1H-indole | NA |
|  | B | | (R)-6,7-dichloro-2-(3-(1-fluoro-2-methoxyethyl)-1H-1,2,4-triazol-5-yl)-3-(1H-pyrazol-4-yl)-1H-indole | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | (R)-6,7-dichloro-2-(5-(1-fluoro-2-methoxyethyl)-1H-1,2,4-triazol-3-yl)-3-(1H-pyrazol-4-yl)-1H-indole | |
| 11 | A | 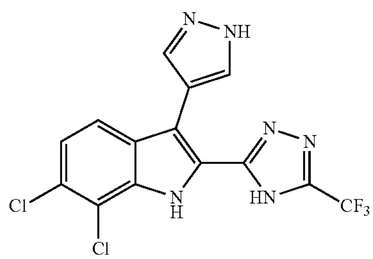 [SMILES: FC(F)(F)c1nnc(-c2[nH]c3c(Cl)c(Cl)ccc3c2-c2cn[nH]c2)[nH]1] | 6,7-dichloro-3-(1H-pyrazol-4-yl)-2-(5-(trifluoromethyl)-4H-1,2,4-triazol-3-yl)-1H-indole | 0.030 |
| | B | | 6,7-dichloro-3-(1H-pyrazol-4-yl)-2-(3-(trifluoromethyl)-1H-1,2,4-triazol-5-yl)-1H-indole | |
| | C | | 6,7-dichloro-3-(1H-pyrazol-4-yl)-2-(5-(trifluoromethyl)-1H-1,2,4-triazol-3-yl)-1H-indole | |
| 12 | A | 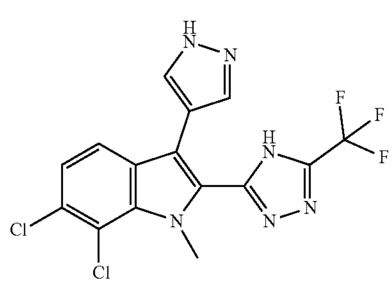 [SMILES: Cn1c(-c2nnc(C(F)(F)F)[nH]2)c(-c2cn[nH]c2)c2ccc(Cl)c(Cl)c21] | 6,7-dichloro-1-methyl-3-(1H-pyrazol-4-yl)-2-(5-(trifluoromethyl)-4H-1,2,4-triazol-3-yl)-1H-indole | 0.048 |

TABLE 1-continued

Illustrative compounds of the disclosure and cGAS inhibition activity

| Example No. | Tautomer | Structure | Name | cGAS IC$_{50}$ [µM] |
|---|---|---|---|---|
| | B | | 6,7-dichloro-1-methyl-3-(1H-pyrazol-4-yl)-2-(3-(trifluoromethyl)-1H-1,2,4-triazol-5-yl)-1H-indole | |
| | C | | 6,7-dichloro-1-methyl-3-(1H-pyrazol-4-yl)-2-(5-(trifluoromethyl)-1H-1,2,4-triazol-3-yl)-1H-indole | |
| 13 | A | 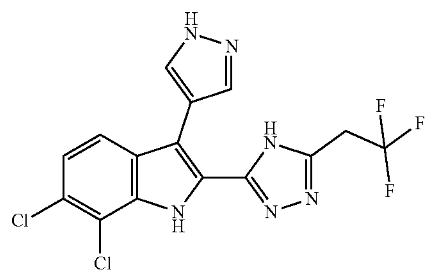 [SMILES: FC(F)(F)Cc1nnc(-c2[nH]c3c(Cl)c(Cl)ccc3c2-c2cn[nH]c2)[nH]1] | 6,7-dichloro-3-(1H-pyrazol-4-yl)-2-(5-(2,trifluoroethyl)-4H-1,2,4-triazol-3-yl)-1H-indole | 0.178 |
| | B | | 6,7-dichloro-3-(1H-pyrazol-4-yl)-2-(3-(2,2,2-trifluoroethyl)-1H-1,2,4-triazol-5-yl)-1H-indole | |
| | C | | 6,7-dichloro-3-(1H-pyrazol-4-yl)-2-(5-(2,2,2-trifluoroethyl)-1H-1,2,4-triazol-3-yl)-1H-indole | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 14 | A | 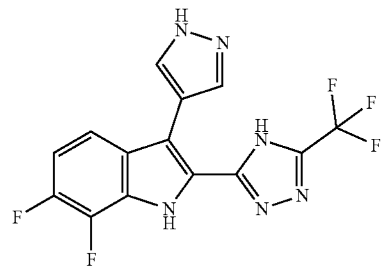 [SMILES: Fc1ccc2c(-c3cn[nH]c3)c(-c3nnc(C(F)(F)F)[nH]3)[nH]c2c1F] | 6,7-difluoro-3-(1H-pyrazol-4-yl)-2-(5-(trifluoromethyl)-4H-1,2,4-triazol-3-yl)-1H-indole | 0.196 |
| | B | | 6,7-difluoro-3-(1H-pyrazol-4-yl)-2-(3-(trifluoromethyl)-1H-1,2,4-triazol-5-yl)-1H-indole | |
| | C | | 6,7-difluoro-3-(1H-pyrazol-4-yl)-2-(5-(trifluoromethyl)-1H-1,2,4-triazol-3-yl)-1H-indole | |
| 15 | A | 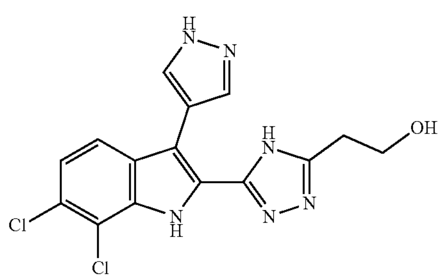 [SMILES: OCCc1nnc(-c2[nH]c3c(Cl)c(Cl)ccc3c2-c2cn[nH]c2)[nH]1] | 2-(5-(6,7-dichloro-3-(1H-pyrazol-4-yl)-1H-indol-2-yl)-4H-1,2,4-triazol-3-yl)ethan-1-ol | 0.188 |
| | B | | 2-(5-(6,7-dichloro-3-(1H-pyrazol-4-yl)-1H-indol-2-yl)-1H-1,2,4-triazol-3-yl)ethan-1-ol | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | 2-(3-(6,7-dichloro-3-(1H-pyrazol-4-yl)-1H-indol-2-yl)-1H-1,2,4-triazol-5-yl)ethan-1-ol | |
| 16 | A | 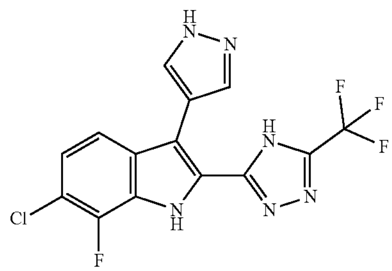 [SMILES: Fc1c(Cl)ccc2c(-c3cn[nH]c3)c(-c3nnc(C(F)(F)F)[nH]3)[nH]c12] | 6-chloro-7-fluoro-3-(1H-pyrazol-4-yl)-2-(5-(trifluoromethyl)-4H-1,2,4-triazol-3-yl)-1H-indole | 0.044 |
| | B | | 6-chloro-7-fluoro-3-(1H-pyrazol-4-yl)-2-(3-(trifluoromethyl)-1H-1,2,4-triazol-5-yl)-1H-indole | |
| | C | | 6-chloro-7-fluoro-3-(1H-pyrazol-4-yl)-2-(5-(trifluoromethyl)-1H-1,2,4-triazol-3-yl)-1H-indole | |
| 17 | A | 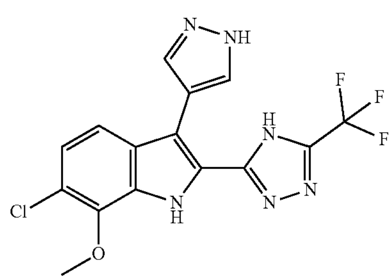 [SMILES: COc1c(Cl)ccc2c(-c3cn[nH]c3)c(-c3nnc(C(F)(F)F)[nH]3)[nH]c12] | 6-chloro-7-methoxy-3-(1H-pyrazol-4-yl)-2-(5-(trifluoromethyl)-4H-1,2,4-triazol-3-yl)-1H-indole | 1.49 |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | 6-chloro-7-methoxy-3-(1H-pyrazol-4-yl)-2-(3-(trifluoromethyl)-1H-1,2,4-triazol-5-yl)-1H-indole | |
| | C | | 6-chloro-7-methoxy-3-(1H-pyrazol-4-yl)-2-(5-(trifluoromethyl)-1H-1,2,4-triazol-3-yl)-1H-indole | |
| 18 | A | 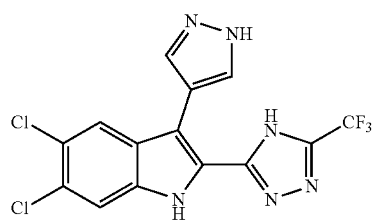 [SMILES: FC(F)(F)c1nnc(-c2[nH]c3cc(Cl)c(Cl)cc3c2-c2cn[nH]c2)[nH]1] | 5,6-dichloro-3-(1H-pyrazol-4-yl)-2-(5-(trifluoromethyl)-4H-1,2,4-triazol-3-yl)-1H-indole | 0.165 |
| | B | | 5,6-dichloro-3-(1H-pyrazol-4-yl)-2-(3-(trifluoromethyl)-1H-1,2,4-triazol-5-yl)-1H-indole | |
| | C | | 5,6-dichloro-3-(1H-pyrazol-4-yl)-2-(5-(trifluoromethyl)-1H-1,2,4-triazol-3-yl)-1H-indole | |
| 19 | A | 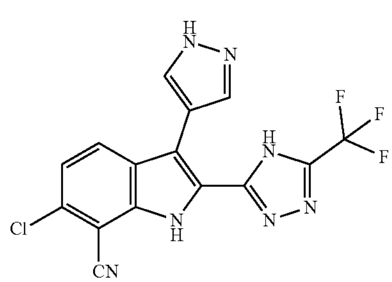 [SMILES: N#Cc1c(Cl)ccc2c(-c3cn[nH]c3)c(-c3nnc(C(F)(F)F)[nH]3)[nH]c12] | 6-chloro-3-(1H-pyrazol-4-yl)-2-(5-(trifluoromethyl)-4H-1,2,4-triazol-3-yl)-1H-indole-7-carbonitrile | 0.150 |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | 6-chloro-3-(1H-pyrazol-4-yl)-2-(3-(trifluoromethyl)-1H-1,2,4-triazol-5-yl)-1H-indole-7-carbonitrile | |
| | C | | 6-chloro-3-(1H-pyrazol-4-yl)-2-(5-(trifluoromethyl)-1H-1,2,4-triazol-3-yl)-1H-indole-7-carbonitrile | |
| 20 | A | 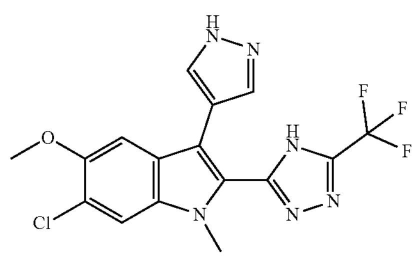 [SMILES: COc1cc2c(-c3cn[nH]c3)c(-c3nnc(C(F)(F)F)[nH]3)n(C)c2cc1Cl] | 6-chloro-5-methoxy-1-methyl-3-(1H-pyrazol-4-yl)-2-(5-(trifluoromethyl)-4H-1,2,4-triazol-3-yl)-1H-indole | 0.116 |
| | B | | 6-chloro-5-methoxy-1-methyl-3-(1H-pyrazol-4-yl)-2-(3-(trifluoromethyl)-1H-1,2,4-triazol-5-yl)-1H-indole | |
| | C | | 6-chloro-5-methoxy-1-methyl-3-(1H-pyrazol-4-yl)-2-(5-(trifluoromethyl)-1H-1,2,4-triazol-3-yl)-1H-indole | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 21 | A | 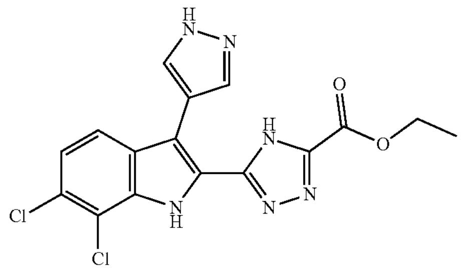 [SMILES: CCOC(=O)c1nnc(-c2[nH]c3c(Cl)c(Cl)ccc3c2-c2cn[nH]c2)[nH]1] | ethyl 5-(6,7-dichloro-3-(1H-pyrazol-4-yl)-1H-indol-2-yl)-4H-1,2,4-triazole-3-carboxylate | 0.030 |
| | B | | ethyl 5-(6,7-dichloro-3-(1H-pyrazol-4-yl)-1H-indol-2-yl)-1H-1,2,4-triazole-3-carboxylate | |
| | C | | ethyl 3-(6,7-dichloro-3-(1H-pyrazol-4-yl)-1H-indol-2-yl)-1H-1,2,4-triazole-5-carboxylate | |
| 22 | A | 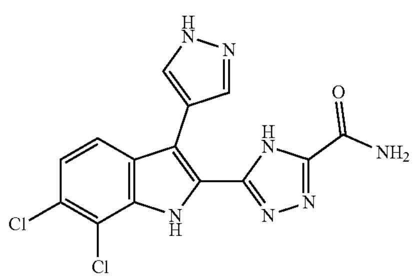 [SMILES: NC(=O)c1nnc(-c2[nH]c3c(Cl)c(Cl)ccc3c2-c2cn[nH]c2)[nH]1] | 5-(6,7-dichloro-3-(1H-pyrazol-4-yl)-1H-indol-2-yl)-4H-1,2,4-triazole-3-carboxamide | 0.030 |
| | B | | 5-(6,7-dichloro-3-(1H-pyrazol-4-yl)-1H-indol-2-yl)-1H-1,2,4-triazole-3-carboxamide | |

| Example No. | Tautomer | Structure | Name | cGAS IC$_{50}$ [μM] |
|---|---|---|---|---|
| | C | | 3-(6,7-dichloro-3-(1H-pyrazol-4-yl)-1H-indol-2-yl)-1H-1,2,4-triazole-5-carboxamide | |
| 23 | A | 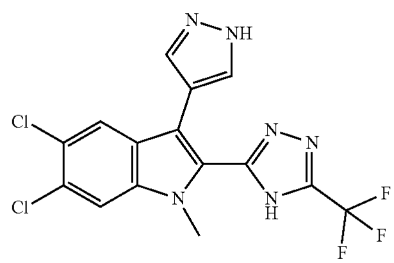 [SMILES: Cn1c(-c2nnc(C(F)(F)F)[nH]2)c(-c2cn[nH]c2)c2cc(Cl)c(Cl)cc21] | 5,6-dichloro-1-methyl-3-(1H-pyrazol-4-yl)-2-(5-(trifluoromethyl)-4H-1,2,4-triazol-3-yl)-1H-indole | 0.112 |
| | B | | 5,6-dichloro-1-methyl-3-(1H-pyrazol-4-yl)-2-(3-(trifluoromethyl)-1H-1,2,4-triazol-5-yl)-1H-indole | |
| | C | | 5,6-dichloro-1-methyl-3-(1H-pyrazol-4-yl)-2-(5-(trifluoromethyl)-1H-1,2,4-triazol-3-yl)-1H-indole | |
| 24 | A | 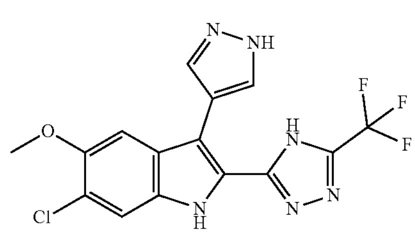 [SMILES: COc1cc2c(-c3cn[nH]c3)c(-c3nnc(C(F)(F)F)[nH]3)[nH]c2cc1Cl] | 6-chloro-5-methoxy-3-(1H-pyrazol-4-yl)-2-(5-(trifluoromethyl)-4H-1,2,4-triazol-3-yl)-1H-indole | 0.069 |
| | B | | 6-chloro-5-methoxy-3-(1H-pyrazol-4-yl)-2-(3-(trifluoromethyl)-1H-1,2,4-triazol-5-yl)-1H-indole | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | 6-chloro-5-methoxy-3-(1H-pyrazol-4-yl)-2-(5-(trifluoromethyl)-1H-1,2,4-triazol-3-yl)-1H-indole | |
| 25 | A | 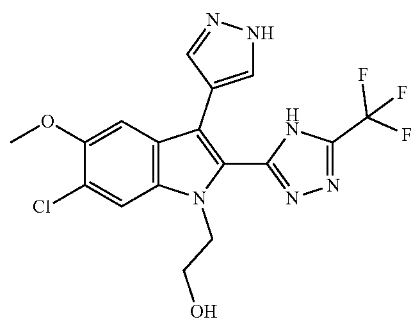 [SMILES: COc1cc2c(-c3cn[nH]c3)c(-c3nnc(C(F)(F)F)[nH]3)n(CCO)c2cc1Cl] | 2-(6-chloro-5-methoxy-3-(1H-pyrazol-4-yl)-2-(5-(trifluoromethyl)-4H-1,2,4-triazol-3-yl)-1H-indol-1-yl)ethan-1-ol | 1.43 |
| | B | | 2-(6-chloro-5-methoxy-3-(1H-pyrazol-4-yl)-2-(3-(trifluoromethyl)-1H-1,2,4-triazol-5-yl)-1H-indol-1-yl)ethan-1-ol | |
| | C | | 2-(6-chloro-5-methoxy-3-(1H-pyrazol-4-yl)-2-(5-(trifluoromethyl)-1H-1,2,4-triazol-3-yl)-1H-indol-1-yl)ethan-1-ol | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 26 | A | 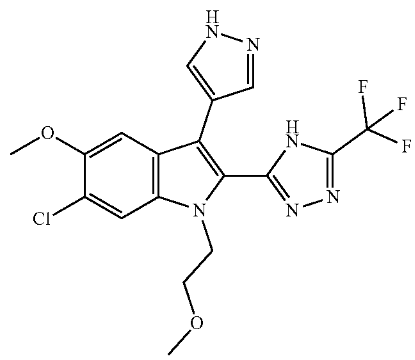 [SMILES: COCCn1c(-c2nnc(C(F)(F)F)[nH]2)c(-c2cn[nH]c2)c2cc(OC)c(Cl)cc21] | 6-chloro-5-methoxy-1-(2-methoxyethyl)-3-(1H-pyrazol-4-yl)-2-(5-(trifluoromethyl)-4H-1,2,4-triazol-3-yl)-1H-indole | 1.81 |
| | B | | 6-chloro-5-methoxy-1-(2-methoxyethyl)-3-(1H-pyrazol-4-yl)-2-(3-(trifluoromethyl)-1H-1,2,4-triazol-5-yl)-1H-indole | |
| | C | | 6-chloro-5-methoxy-1-(2-methoxyethyl)-3-(1H-pyrazol-4-yl)-2-(5-(trifluoromethyl)-1H-1,2,4-triazol-3-yl)-1H-indole | |
| 27 | A | 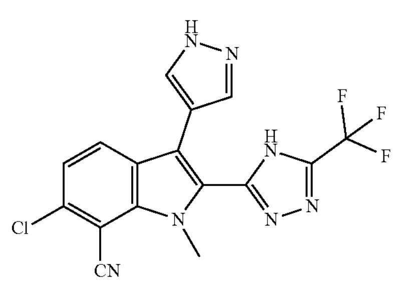 [SMILES: Cn1c(-c2nnc(C(F)(F)F)[nH]2)c(-c2cn[nH]c2)c2ccc(Cl)c(C#N)c21] | 6-chloro-1-methyl-3-(1H-pyrazol-4-yl)-2-(5-(trifluoromethyl)-4H-1,2,4-triazol-3-yl)-1H-indole-7-carbonitrile | 0.137 |

TABLE 1-continued

Illustrative compounds of the disclosure and cGAS inhibition activity

| Example No. | Tautomer | Structure | Name | cGAS IC$_{50}$ [µM] |
|---|---|---|---|---|
| | B | | 6-chloro-1-methyl-3-(1H-pyrazol-4-yl)-2-(3-(trifluoromethyl)-1H-1,2,4-triazol-5-yl)-1H-indole-7-carbonitrile | |
| | C | | 6-chloro-1-methyl-3-(1H-pyrazol-4-yl)-2-(5-(trifluoromethyl)-1H-1,2,4-triazol-3-yl)-1H-indole-7-carbonitrile | |
| 28 | A | 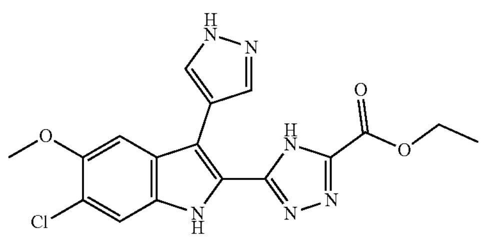 [SMILES: CCOC(=O)c1nnc(-c2[nH]c3cc(Cl)c(OC)cc3c2-c2cn[nH]c2)[nH]1] | ethyl 5-(6-chloro-5-methoxy-3-(1H-pyrazol-4-yl)-1H-indol-2-yl)-4H-1,2,4-triazole-3-carboxylate | 0.075 |
| | B | | ethyl 5-(6-chloro-5-methoxy-3-(1H-pyrazol-4-yl)-1H-indol-2-yl)-1H-1,2,4-triazole-3-carboxylate | |
| | C | | ethyl 3-(6-chloro-5-methoxy-3-(1H-pyrazol-4-yl)-1H-indol-2-yl)-1H-1,2,4-triazole-5-carboxylate | |
| 29 | A | 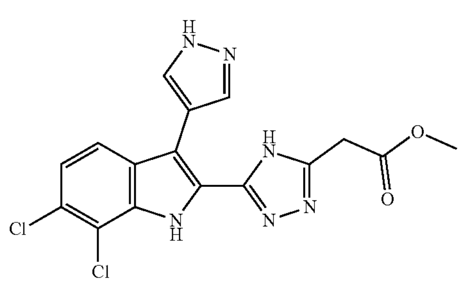 [SMILES: COC(=O)Cc1nnc(-c2[nH]c3c(Cl)c(Cl)ccc3c2-c2cn[nH]c2)[nH]1] | methyl 2-(5-(6,7-dichloro-3-(1H-pyrazol-4-yl)-1H-indol-2-yl)-4H-1,2,4-triazol-3-yl)acetate | 0.218 |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | methyl 2-(5-(6,7-dichloro-3-(1H-pyrazol-4-yl)-1H-indol-2-yl)-1H-1,2,4-triazol-3-yl)acetate | |
| | C | | methyl 2-(3-(6,7-dichloro-3-(1H-pyrazol-4-yl)-1H-indol-2-yl)-1H-1,2,4-triazol-5-yl)acetate | |
| 30 | A | 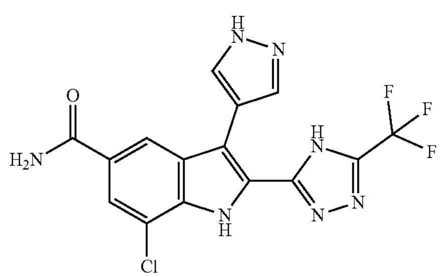 [SMILES: NC(=O)c1cc(Cl)c2[nH]c(-c3nnc(C(F)(F)F)[nH]3)c(-c3cn[nH]c3)c2c1] | 7-chloro-3-(1H-pyrazol-4-yl)-2-(5-(trifluoromethyl)-4H-1,2,4-triazol-3-yl)-1H-indole-5-carboxamide | |
| | B | | 7-chloro-3-(1H-pyrazol-4-yl)-2-(3-(trifluoromethyl)-1H-1,2,4-triazol-5-yl)-1H-indole-5-carboxamide | |
| | C | | 7-chloro-3-(1H-pyrazol-4-yl)-2-(5-(trifluoromethyl)-1H-1,2,4-triazol-3-yl)-1H-indole-5-carboxamide | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 31 | A | 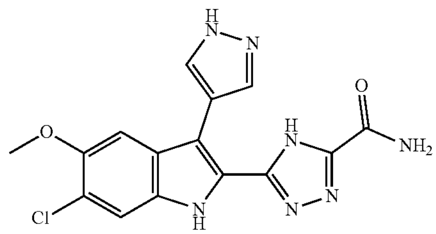 [SMILES: COc1cc2c(-c3cn[nH]c3)c(-c3nnc(C(N)=O)[nH]3)[nH]c2cc1Cl] | 5-(6-chloro-5-methoxy-3-(1H-pyrazol-4-yl)-1H-indol-2-yl)-4H-1,2,4-triazole-3-carboxamide | 0.049 |
| | B | | 5-(6-chloro-5-methoxy-3-(1H-pyrazol-4-yl)-1H-indol-2-yl)-1H-1,2,4-triazole-3-carboxamide | |
| | C | | 3-(6-chloro-5-methoxy-3-(1H-pyrazol-4-yl)-1H-indol-2-yl)-1H-1,2,4-triazole-5-carboxamide | |
| 32 | A | 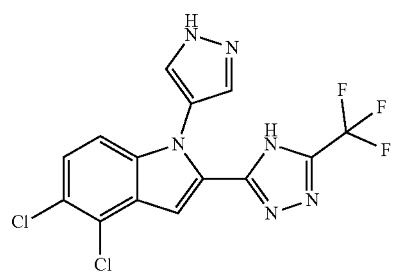 [SMILES: FC(F)(F)c1nnc(-c2cc3c(Cl)c(Cl)ccc3n2-c2cn[nH]c2)[nH]1] | 4,5-dichloro-1-(1H-pyrazol-4-yl)-2-(5-(trifluoromethyl)-4H-1,2,4-triazol-3-yl)-1H-indole | 0.496 |
| | B | | 4,5-dichloro-1-(1H-pyrazol-4-yl)-2-(3-(trifluoromethyl)-1H-1,2,4-triazol-5-yl)-1H-indole | |
| | C | | 4,5-dichloro-1-(1H-pyrazol-4-yl)-2-(5-(trifluoromethyl)-1H-1,2,4-triazol-3-yl)-1H-indole | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 33 | A | 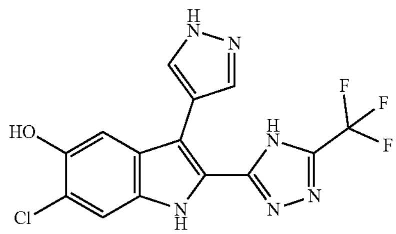 [SMILES: Oc1cc2c(-c3cn[nH]c3)c(-c3nnc(C(F)(F)F)[nH]3)[nH]c2cc1Cl] | 6-chloro-3-(1H-pyrazol-4-yl)-2-(5-(trifluoromethyl)-4H-1,2,4-triazol-3-yl)-1H-indol-5-ol | 0.038 |
| | B | | 6-chloro-3-(1H-pyrazol-4-yl)-2-(3-(trifluoromethyl)-1H-1,2,4-triazol-5-yl)-1H-indol-5-ol | |
| | C | | 6-chloro-3-(1H-pyrazol-4-yl)-2-(5-(trifluoromethyl)-1H-1,2,4-triazol-3-yl)-1H-indol-5-ol | |
| 34 | A | 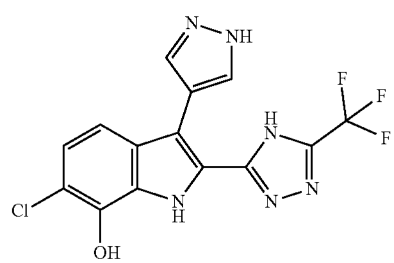 [SMILES: Oc1c(Cl)ccc2c(-c3cn[nH]c3)c(-c3nnc(C(F)(F)F)[nH]3)[nH]c12] | 6-chloro-3-(1H-pyrazol-4-yl)-2-(5-(trifluoromethyl)-4H-1,2,4-triazol-3-yl)-1H-indol-7-ol | 0.954 |
| | B | | 6-chloro-3-(1H-pyrazol-4-yl)-2-(3-(trifluoromethyl)-1H-1,2,4-triazol-5-yl)-1H-indol-7-ol | |
| | C | | 6-chloro-3-(1H-pyrazol-4-yl)-2-(5-(trifluoromethyl)-1H-1,2,4-triazol-3-yl)-1H-indol-7-ol | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 35 | A | 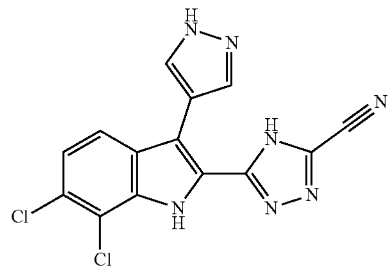 [SMILES: N#Cc1nnc(-c2[nH]c3c(Cl)c(Cl)ccc3c2-c2cn[nH]c2)[nH]1] | 5-(6,7-dichloro-3-(1H-pyrazol-4-yl)-1H-indol-2-yl)-4H-1,2,4-triazole-3-carbonitrile | 0.077 |
| | B | | 5-(6,7-dichloro-3-(1H-pyrazol-4-yl)-1H-indol-2-yl)-1H-1,2,4-triazole-3-carbonitrile | |
| | C | | 3-(6,7-dichloro-3-(1H-pyrazol-4-yl)-1H-indol-2-yl)-1H-1,2,4-triazole-5-carbonitrile | |
| 36 | A | 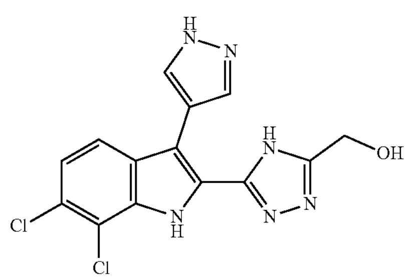 [SMILES: OCc1nnc(-c2[nH]c3c(Cl)c(Cl)ccc3c2-c2cn[nH]c2)[nH]1] | (5-(6,7-dichloro-3-(1H-pyrazol-4-yl)-1H-indol-2-yl)-4H-1,2,4-triazol-3-yl)methanol | 0.342 |
| | B | | (5-(6,7-dichloro-3-(1H-pyrazol-4-yl)-1H-indol-2-yl)-1H-1,2,4-triazol-3-yl)methanol | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | (3-(6,7-dichloro-3-(1H-pyrazol-4-yl)-1H-indol-2-yl)-1H-1,2,4-triazol-5-yl)methanol | |
| 37 | A | 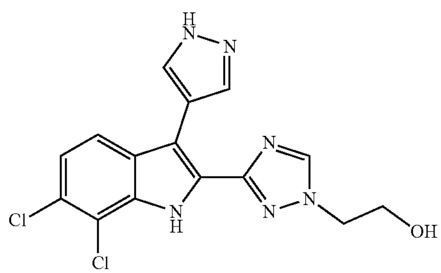 [SMILES: OCCn1cnc(-c2[nH]c3c(Cl)c(Cl)ccc3c2-c2cn[nH]c2)n1] | 2-(3-(6,7-dichloro-3-(1H-pyrazol-4-yl)-1H-indol-2-yl)-1H-1,2,4-triazol-1-yl)ethan-1-ol | 0.137 |
| 38 | A | 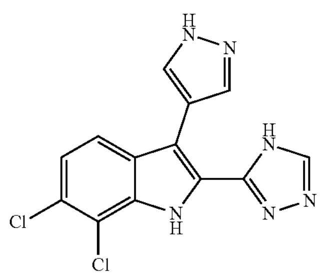 [SMILES: Clc1ccc2c(-c3cn[nH]c3)c(-c3nnc[nH]3)[nH]c2c1Cl] | 6,7-dichloro-3-(1H-pyrazol-4-yl)-2-(4H-1,2,4-triazol-3-yl)-1H-indole | 0.136 |
| | B | | 6,7-dichloro-3-(1H-pyrazol-4-yl)-2-(1H-1,2,4-triazol-5-yl)-1H-indole | |
| | C | | 6,7-dichloro-3-(1H-pyrazol-4-yl)-2-(1H-1,2,4-triazol-3-yl)-1H-indole | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 39 | A | 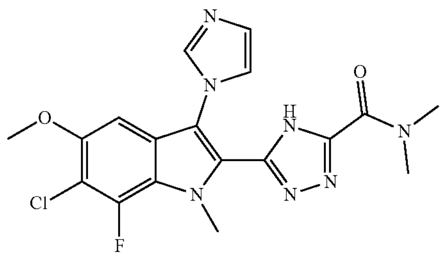 | 5-(6-chloro-7-fluoro-3-(1H-imidazol-1-yl)-5-methoxy-1-methyl-1H-indol-2-yl)-N,N-dimethyl-4H-1,2,4-triazole-3-carboxamide | 0.048 |
| | B | | 5-(6-chloro-7-fluoro-3-(1H-imidazol-1-yl)-5-methoxy-1-methyl-1H-indol-2-yl)-N,N-dimethyl-1H-1,2,4-triazole-3-carboxamide | |
| | C | | 3-(6-chloro-7-fluoro-3-(1H-imidazol-1-yl)-5-methoxy-1-methyl-1H-indol-2-yl)-N,N-dimethyl-1H-1,2,4-triazole-5-carboxamide | |
| 40 | A | 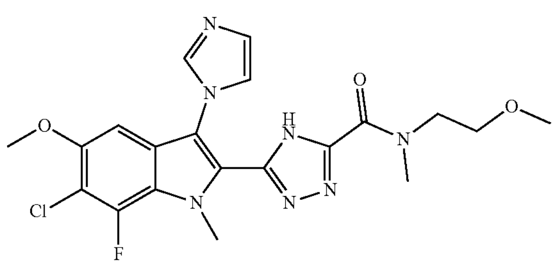 | 5-(6-chloro-7-fluoro-3-(1H-imidazol-1-yl)-5-methoxy-1-methyl-1H-indol-2-yl)-N-(2-methoxyethyl)-N-methyl-4H-1,2,4-triazole-3-carboxamide | 0.082 |
| | B | | 5-(6-chloro-7-fluoro-3-(1H-imidazol-1-yl)-5-methoxy-1-methyl-1H-indol-2-yl)-N-(2-methoxyethyl)-N-methyl-1H-1,2,4-triazole-3-carboxamide | |

TABLE 1-continued

Illustrative compounds of the disclosure and cGAS inhibition activity

| Example No. | Tautomer | Structure | Name | cGAS IC$_{50}$ [µM] |
|---|---|---|---|---|
| | C | | 3-(6-chloro-7-fluoro-3-(1H-imidazol-1-yl)-5-methoxy-1-methyl-1H-indol-2-yl)-N-(2-methoxyethyl)-N-methyl-1H-1,2,4-triazole-5-carboxamide | |
| 41 | A | 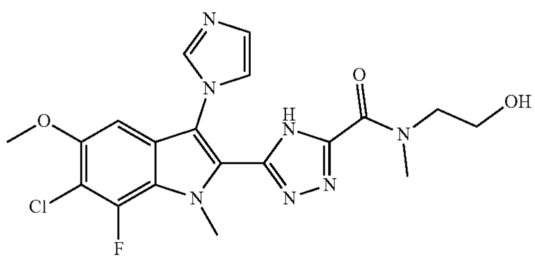 [SMILES: COc1cc2c(-n3ccnc3)c(-c3nnc(C(=O)N(C)CCO)[nH]3)n(C)c2c(F)c1Cl] | 5-(6-chloro-7-fluoro-3-(1H-imidazol-1-yl)-5-methoxy-1-methyl-1H-indol-2-yl)-N-(2-hydroxyethyl)-N-methyl-4H-1,2,4-triazole-3-carboxamide | 0.061 |
| | B | | 5-(6-chloro-7-fluoro-3-(1H-imidazol-1-yl)-5-methoxy-1-methyl-1H-indol-2-yl)-N-(2-hydroxyethyl)-N-methyl-1H-1,2,4-triazole-3-carboxamide | |
| | C | | 3-(6-chloro-7-fluoro-3-(1H-imidazol-1-yl)-5-methoxy-1-methyl-1H-indol-2-yl)-N-(2-hydroxyethyl)-N-methyl-1H-1,2,4-triazole-5-carboxamide | |
| 42 | A | 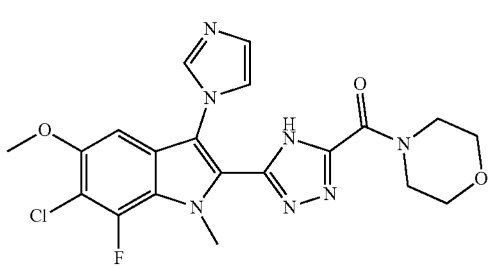 [SMILES: COc1cc2c(-n3ccnc3)c(-c3nnc(C(=O)N4CCOCC4)[nH]3)n(C)c2c(F)c1Cl] | (5-(6-chloro-7-fluoro-3-(1H-imidazol-1-yl)-5-methoxy-1-methyl-1H-indol-2-yl)-4H-1,2,4-triazol-3-yl)(morpholino)methanone | 0.063 |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | (5-(6-chloro-7-fluoro-3-(1H-imidazol-1-yl)-5-methoxy-1-methyl-1H-indol-2-yl)-1H-1,2,4-triazol-3-yl)(morpholino)methanone | |
| | C | | (3-(6-chloro-7-fluoro-3-(1H-imidazol-1-yl)-5-methoxy-1-methyl-1H-indol-2-yl)-1H-1,2,4-triazol-5-yl)(morpholino)methanone | |
| 43 | A | 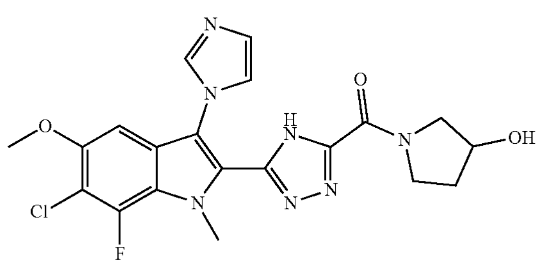 [SMILES: COc1cc2c(-n3ccnc3)c(-c3nnc(C(=O)N4CCC(O)C4)[nH]3)n(C)c2c(F)c1Cl] | (5-(6-chloro-7-fluoro-3-(1H-imidazol-1-yl)-5-methoxy-1-methyl-1H-indol-2-yl)-4H-1,2,4-triazol-3-yl)(3-hydroxypyrrolidin-1-yl)methanone | 0.061 |
| | B | | (5-(6-chloro-7-fluoro-3-(1H-imidazol-1-yl)-5-methoxy-1-methyl-1H-indol-2-yl)-1H-1,2,4-triazol-3-yl)(3-hydroxypyrrolidin-1-yl)methanone | |
| | C | | (3-(6-chloro-7-fluoro-3-(1H-imidazol-1-yl)-5-methoxy-1-methyl-1H-indol-2-yl)-1H-1,2,4-triazol-5-yl)(3-hydroxypyrrolidin-1-yl)methanone | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 43a | A | 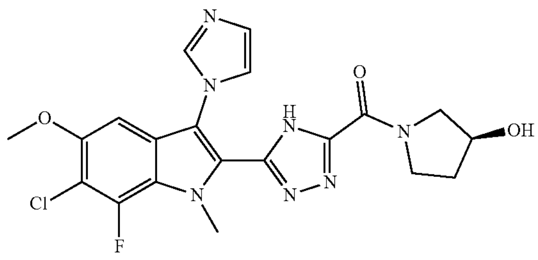 [SMILES: COc1cc2c(-n3ccnc3)c(-c3nnc(C(=O)N4CC[C@H](O)C4)[nH]3)n(C)c2c(F)c1Cl] | (S)-(5-(6-chloro-7-fluoro-3-(1H-imidazol-1-yl)-5-methoxy-1-methyl-1H-indol-2-yl)-4H-1,2,4-triazol-3-yl)(3-hydroxypyrrolidin-1-yl)methanone | NA |
| | B | | (S)-(5-(6-chloro-7-fluoro-3-(1H-imidazol-1-yl)-5-methoxy-1-methyl-1H-indol-2-yl)-1H-1,2,4-tnazol-3-yl)(3-hydroxypyrrolidin-1-yl)methanone | |
| | C | | (S)-(3-(6-chloro-7-fluoro-3-(1H-imidazol-1-yl)-5-methoxy-1-methyl-1H-indol-2-yl)-1H-1,2,4-triazol-5-yl)(3-hydroxypyrrolidin-1-yl)methanone | |
| 43b | A | 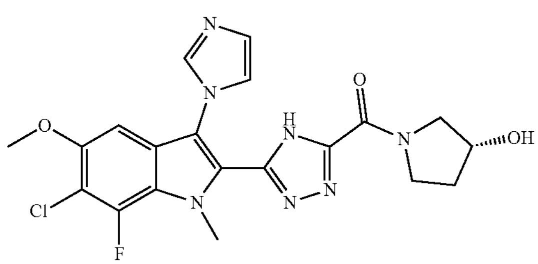 [SMILES: COc1cc2c(-n3ccnc3)c(-c3nnc(C(=O)N4CC[C@@H](O)C4)[nH]3)n(C)c2c(F)c1Cl] | (R)-(5-(6-chloro-7-fluoro-3-(1H-imidazol-1-yl)-5-methoxy-1-methyl-1H-indol-2-yl)-4H-1,2,4-triazol-3-yl)(3-hydroxypyrrolidin-1-yl)methanone | NA |
| | B | | (R)-(5-(6-chloro-7-fluoro-3-(1H-imidazol-1-yl)-5-methoxy-1-methyl-1H-indol-2-yl)-1H-1,2,4-triazol-3-yl)(3-hydroxypyrrolidin-1-yl)methanone | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | (R)-(3-(6-chloro-7-fluoro-3-(1H-imidazol-1-yl)-5-methoxy-1-methyl-1H-indol-2-yl)-1H-1,2,4-triazol-5-yl)(3-hydroxypyrrolidin-1-yl)methanone | |
| 44 | A | 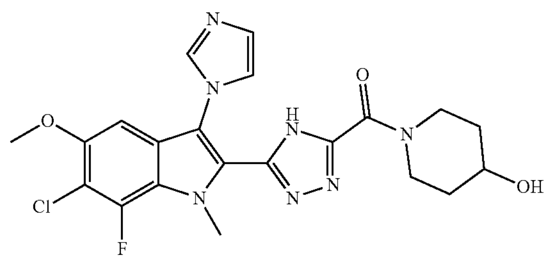 [SMILES: COc1cc2c(-n3ccnc3)c(-c3nnc(C(=O)N4CCC(O)CC4)[nH]3)n(C)c2c(F)c1Cl] | (5-(6-chloro-7-fluoro-3-(1H-imidazol-1-yl)-5-methoxy-1-methyl-1H-indol-2-yl)-4H-1,2,4-triazol-3-yl)(4-hydroxypiperidin-1-yl)methanone | 0.058 |
| | B | | (5-(6-chloro-7-fluoro-3-(1H-imidazol-1-yl)-5-methoxy-1-methyl-1H-indol-2-yl)-1H-1,2,4-triazol-3-yl)(4-hydroxypiperidin-1-yl)methanone | |
| | C | | (3-(6-chloro-7-fluoro-3-(1H-imidazol-1-yl)-5-methoxy-1-methyl-1H-indol-2-yl)-1H-1,2,4-triazol-5-yl)(4-hydroxypiperidin-1-yl)methanone | |
| 45 | A | 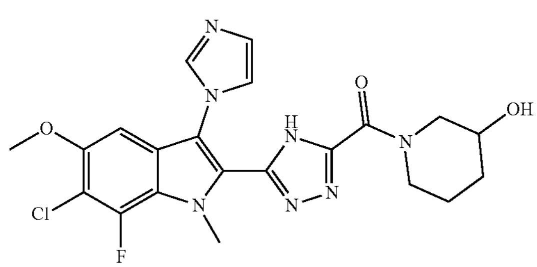 [SMILES: COc1cc2c(-n3ccnc3)c(-c3nnc(C(=O)N4CCCC(O)C4)[nH]3)n(C)c2c(F)c1Cl] | (5-(6-chloro-7-fluoro-3-(1H-imidazol-1-yl)-5-methoxy-1-methyl-1H-indol-2-yl)-4H-1,2,4-triazol-3-yl)(3-hydroxypiperidin-1-yl)methanone | 0.056 |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | (5-(6-chloro-7-fluoro-3-(1H-imidazol-1-yl)-5-methoxy-1-methyl-1H-indol-2-yl)-1H-1,2,4-triazol-3-yl)(3-hydroxypiperidin-1-yl)methanone | |
| | C | | (3-(6-chloro-7-fluoro-3-(1H-imidazol-1-yl)-5-methoxy-1-methyl-1H-indol-2-yl)-1H-1,2,4-triazol-5-yl)(3-hydroxypiperidin-1-yl)methanone | |
| 45a | A | 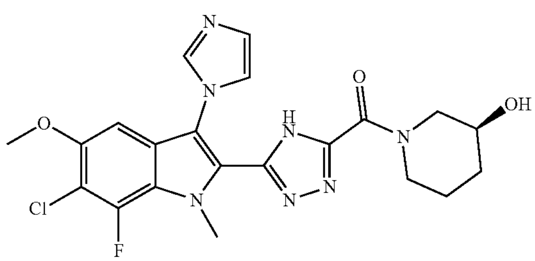 [SMILES: COc1cc2c(-n3ccnc3)c(-c3nnc(C(=O)N4CCC[C@H](O)C4)[nH]3)n(C)c2c(F)c1Cl] | (S)-(5-(6-chloro-7-fluoro-3-(1H-imidazol-1-yl)-5-methoxy-1-methyl-1H-indol-2-yl)-4H-1,2,4-triazol-3-yl)(3-hydroxypiperidin-1-yl)methanone | NA |
| | B | | (S)-(5-(6-chloro-7-fluoro-3-(1H-imidazol-1-yl)-5-methoxy-1-methyl-1H-indol-2-yl)-1H-1,2,4-triazol-3-yl)(3-hydroxypiperidin-1-yl)methanone | |
| | C | | (S)-(3-(6-chloro-7-fluoro-3-(1H-imidazol-1-yl)-5-methoxy-1-methyl-1H-indol-2-yl)-1H-1,2,4-triazol-5-yl)(3-hydroxypiperidin-1-yl)methanone | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 45b | A | 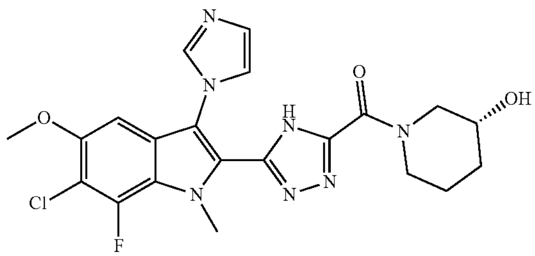 | (R)-(5-(6-chloro-7-fluoro-3-(1H-imidazol-1-yl)-5-methoxy-1-methyl-1H-indol-2-yl)-4H-1,2,4-triazol-3-yl)(3-hydroxypiperidin-1-yl)methanone | NA |
| | B | | (R)-(5-(6-chloro-7-fluoro-3-(1H-imidazol-1-yl)-5-methoxy-1-methyl-1H-indol-2-yl)-1H-1,2,4-triazol-3-yl)(3-hydroxypiperidin-1-yl)methanone | |
| | C | | (R)-(3-(6-chloro-7-fluoro-3-(1H-imidazol-1-yl)-5-methoxy-1-methyl-1H-indol-2-yl)-1H-1,2,4-triazol-5-yl)(3-hydroxypiperidin-1-yl)methanone | |
| 46 | A | 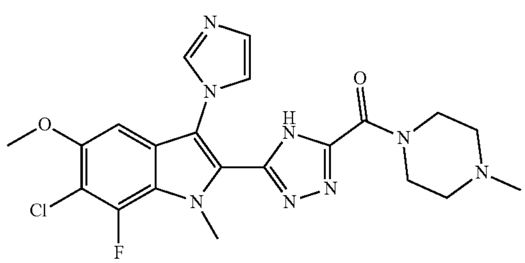 | (5-(6-chloro-7-fluoro-3-(1H-imidazol-1-yl)-5-methoxy-1-methyl-1H-indol-2-yl)-4H-1,2,4-triazol-3-yl)(4-methylpiperazin-1-yl)methanone | 0.138 |
| | B | | (5-(6-chloro-7-fluoro-3-(1H-imidazol-1-yl)-5-methoxy-1-methyl-1H-indol-2-yl)-1H-1,2,4-triazol-3-yl)(4-methylpiperazin-1-yl)methanone | |

TABLE 1-continued

Illustrative compounds of the disclosure and cGAS inhibition activity

| Example No. | Tautomer | Structure | Name | cGAS IC$_{50}$ [µM] |
|---|---|---|---|---|
| | C | | (3-(6-chloro-7-fluoro-3-(1H-imidazol-1-yl)-5-methoxy-1-methyl-1H-indol-2-yl)-1H-1,2,4-triazol-5-yl)(4-methylpiperazin-1-yl)methanone | |
| 47 | A | 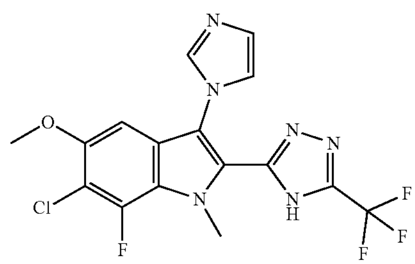 [SMILES: COc1cc2c(-n3ccnc3)c(-c3nnc(C(F)(F)F)[nH]3)n(C)c2c(F)c1Cl] | 6-chloro-7-fluoro-3-(1H-imidazol-1-yl)-5-methoxy-1-methyl-2-(5-(trifluoromethyl)-4H-1,2,4-triazol-3-yl)-1H-indole | 0.121 |
| | B | | 6-chloro-7-fluoro-3-(1H-imidazol-1-yl)-5-methoxy-1-methyl-2-(3-(trifluoromethyl)-1H-1,2,4-triazol-5-yl)-1H-indole | |
| | C | | 6-chloro-7-fluoro-3-(1H-imidazol-1-yl)-5-methoxy-1-methyl-2-(5-(trifluoromethyl)-1H-1,2,4-triazol-3-yl)-1H-indole | |
| 48 | A | 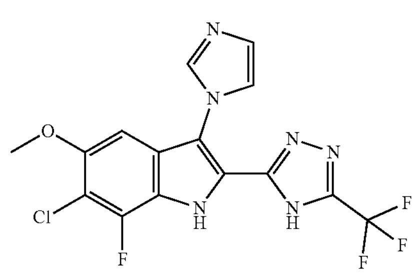 [SMILES: COc1cc2c(-n3ccnc3)c(-c3nnc(C(F)(F)F)[nH]3)[nH]c2c(F)c1Cl] | 6-chloro-7-fluoro-3-(1H-imidazol-1-yl)-5-methoxy-2-(5-(trifluoromethyl)-4H-1,2,4-triazol-3-yl)-1H-indole | 0.066 |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | 6-chloro-7-fluoro-3-(1H-imidazol-1-yl)-5-methoxy-2-(3-(trifluoromethyl)-1H-1,2,4-triazol-5-yl)-1H-indole | |
| | C | | 6-chloro-7-fluoro-3-(1H-imidazol-1-yl)-5-methoxy-2-(5-(trifluoromethyl)-1H-1,2,4-triazol-3-yl)-1H-indole | |
| 49 | A | 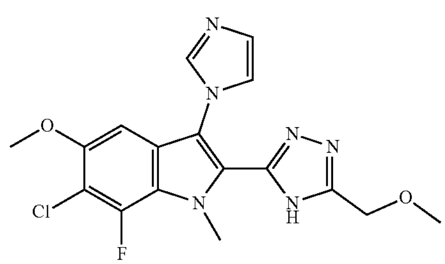 | 6-chloro-7-fluoro-3-(1H-imidazol-1-yl)-5-methoxy-2-(5-(methoxymethyl)-4H-1,2,4-triazol-3-yl)-1-methyl-1H-indole | 0.107 |
| | B | | 6-chloro-7-fluoro-3-(1H-imidazol-1-yl)-5-methoxy-2-(3-(methoxymethyl)-1H-1,2,4-triazol-5-yl)-1-methyl-1H-indole | |
| | C | | 6-chloro-7-fluoro-3-(1H-imidazol-1-yl)-5-methoxy-2-(5-(methoxymethyl)-1H-1,2,4-triazol-3-yl)-1-methyl-1H-indole | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 50 | A | 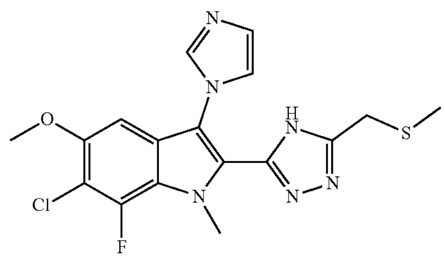 | 6-chloro-7-fluoro-3-(1H-imidazol-1-yl)-5-methoxy-1-methyl-2-(5-((methylthio)methyl)-4H-1,2,4-triazol-3-yl)-1H-indole | 0.057 |
|  | B | | 6-chloro-7-fluoro-3-(1H-imidazol-1-yl)-5-methoxy-1-methyl-2-(3-((methylthio)methyl)-1H-1,2,4-triazol-5-yl)-1H-indole | |
|  | C | | 6-chloro-7-fluoro-3-(1H-imidazol-1-yl)-5-methoxy-1-methyl-2-(5-((methylthio)methyl)-1H-1,2,4-triazol-3-yl)-1H-indole | |
| 51 | A | 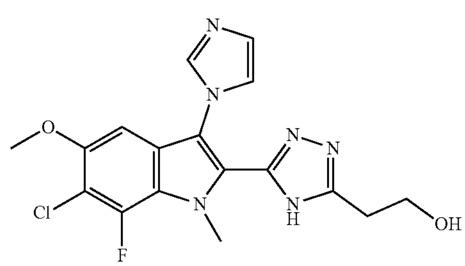 [SMILES: COc1cc2c(-n3ccnc3)c(-c3nnc(CCO)[nH]3)n(C)c2c(F)c1Cl] | 2-(5-(6-chloro-7-fluoro-3-(1H-imidazol-1-yl)-5-methoxy-1-methyl-1H-indol-2-yl)-4H-1,2,4-triazol-3-yl)ethan-1-ol | 0.169 |
|  | B | | 2-(5-(6-chloro-7-fluoro-3-(1H-imidazol-1-yl)-5-methoxy-1-methyl-1H-indol-2-yl)-1H-1,2,4-triazol-3-yl)ethan-1-ol | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | 2-(3-(6-chloro-7-fluoro-3-(1H-imidazol-1-yl)-5-methoxy-1-methyl-1H-indol-2-yl)-1H-1,2,4-triazol-5-yl)ethan-1-ol | |
| 52 | A | 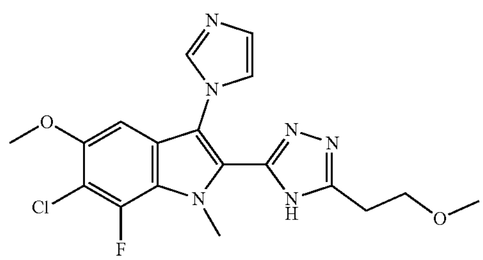 | 6-chloro-7-fluoro-3-(1H-imidazol-1-yl)-5-methoxy-2-(5-(2-methoxyethyl)-4H-1,2,4-triazol-3-yl)-1-methyl-1H-indole | 0.206 |
| | B | | 6-chloro-7-fluoro-3-(1H-imidazol-1-yl)-5-methoxy-2-(3-(2-methoxyethyl)-1H-1,2,4-triazol-5-yl)-1-methyl-1H-indole | |
| | C | | 6-chloro-7-fluoro-3-(1H-imidazol-1-yl)-5-methoxy-2-(5-(2-methoxyethyl)-1H-1,2,4-triazol-3-yl)-1-methyl-1H-indole | |
| 53 | A | 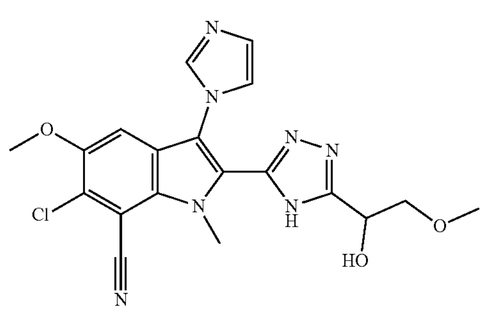 | 6-chloro-2-(5-(1-hydroxy-2-methoxyethyl)-4H-1,2,4-triazol-3-yl)-3-(1H-imidazol-1-yl)-5-methoxy-1-methyl-1H-indole-7-carbonitrile | 0.066 |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | 6-chloro-2-(3-(1-hydroxy-2-methoxyethyl)-1H-1,2,4-triazol-5-yl)-3-(1H-imidazol-1-yl)-5-methoxy-1-methyl-1H-indole-7-carbonitrile | |
| | C | | 6-chloro-2-(5-(1-hydroxy-2-methoxyethyl)-1H-1,2,4-triazol-3-yl)-3-(1H-imidazol-1-yl)-5-methoxy-1-methyl-1H-indole-7-carbonitrile | |
| 53a | A | 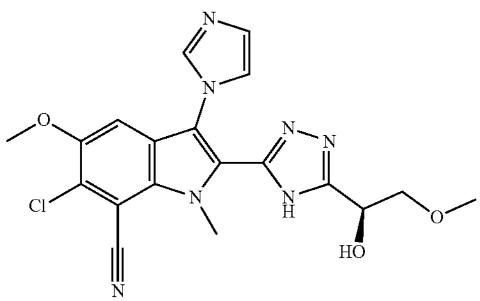 | (S)-6-chloro-2-(5-(1-hydroxy-2-methoxyethyl)-4H-1,2,4-triazol-3-yl)-3-(1H-imidazol-1-yl)-5-methoxy-1-methyl-1H-indole-7-carbonitrile | NA |
| | B | | (S)-6-chloro-2-(3-(1-hydroxy-2-methoxyethyl)-1H-1,2,4-triazol-5-yl)-3-(1H-imidazol-1-yl)-5-methoxy-1-methyl-1H-indole-7-carbonitrile | |
| | C | | (S)-6-chloro-2-(5-(1-hydroxy-2-methoxyethyl)-1H-1,2,4-triazol-3-yl)-3-(1H-imidazol-1-yl)-5-methoxy-1-methyl-1H-indole-7-carbonitrile | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 53b | A | 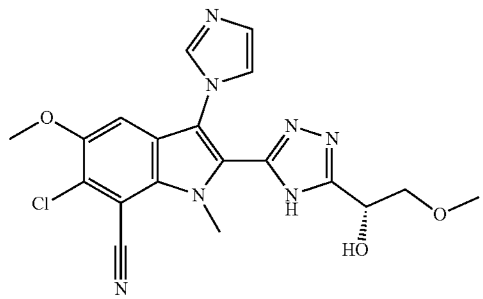 | (R)-6-chloro-2-(5-(1-hydroxy-2-methoxyethyl)-4H-1,2,4-triazol-3-yl)-3-(1H-imidazol-1-yl)-5-methoxy-1-methyl-1H-indole-7-carbonitrile | NA |
|  | B | | (R)-6-chloro-2-(3-(1-hydroxy-2-methoxyethyl)-1H-1,2,4-triazol-5-yl)-3-(1H-imidazol-1-yl)-5-methoxy-1-methyl-1H-indole-7-carbonitrile |  |
|  | C | | (R)-6-chloro-2-(5-(1-hydroxy-2-methoxyethyl)-1H-1,2,4-triazol-3-yl)-3-(1H-imidazol-1-yl)-5-methoxy-1-methyl-1H-indole-7-carbonitrile |  |
| 54 | A | 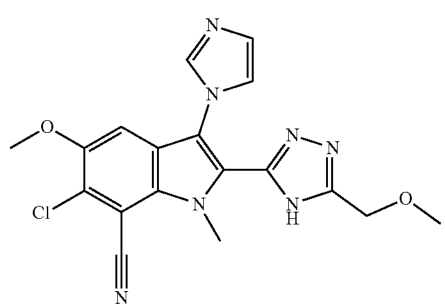 | 6-chloro-3-(1H-imidazol-1-yl)-5-methoxy-2-(5-(methoxymethyl)-4H-1,2,4-triazol-3-yl)-1-methyl-1H-indole-7-carbonitrile | 0.076 |
|  | B | | 6-chloro-3-(1H-imidazol-1-yl)-5-methoxy-2-(3-(methoxymethyl)-1H-1,2,4-triazol-5-yl)-1-methyl-1H-indole-7-carbonitrile |  |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | 6-chloro-3-(1H-imidazol-1-yl)-5-methoxy-2-(5-(methoxymethyl)-1H-1,2,4-triazol-3-yl)-1-methyl-1H-indole-7-carbonitrile | |
| 55 | A | 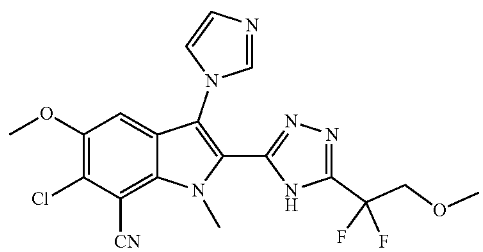 | 6-chloro-2-(5-(1,1-difluoro-2-methoxyethyl)-4H-1,2,4-triazol-3-yl)-3-(1H-imidazol-1-yl)-5-methoxy-1-methyl-1H-indole-7-carbonitrile | 0.055 |
| | B | | 6-chloro-2-(3-(1,1-difluoro-2-methoxyethyl)-1H-1,2,4-triazol-5-yl)-3-(1H-imidazol-1-yl)-5-methoxy-1-methyl-1H-indole-7-carbonitrile | |
| | C | | 6-chloro-2-(5-(1,1-difluoro-2-methoxyethyl)-1H-1,2,4-triazol-3-yl)-3-(1H-imidazol-1-yl)-5-methoxy-1-methyl-1H-indole-7-carbonitrile | |
| 56 | A | 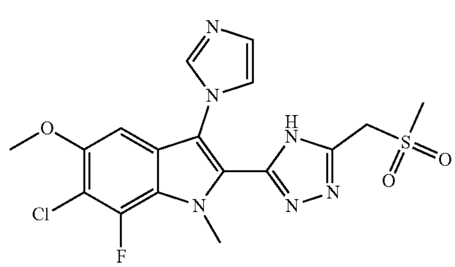 [SMILES: COc1cc2c(-n3ccnc3)c(-c3nnc(CS(C)(=O)=O)[nH]3)n(C)c2c(F)c1Cl] | 6-chloro-7-fluoro-3-(1H-imidazol-1-yl)-5-methoxy-1-methyl-2-(5-((methylsulfonyl)methyl)-4H-1,2,4-triazol-3-yl)-1H-indole | 0.056 |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | 6-chloro-7-fluoro-3-(1H-imidazol-1-yl)-5-methoxy-1-methyl-2-(3-((methylsulfonyl)methyl)-1H-1,2,4-triazol-5-yl)-1H-indole | |
| | C | | 6-chloro-7-fluoro-3-(1H-imidazol-1-yl)-5-methoxy-1-methyl-2-(5-((methylsulfonyl)methyl)-1H-1,2,4-triazol-3-yl)-1H-indole | |
| 57 | A | 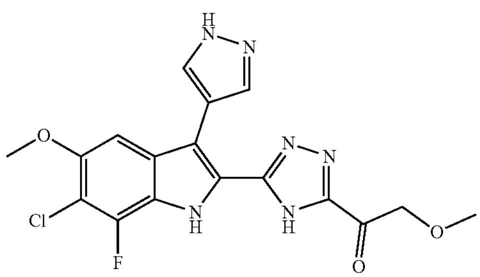 | 1-(5-(6-chloro-7-fluoro-5-methoxy-3-(1H-pyrazol-4-yl)-1H-indol-2-yl)-4H-1,2,4-triazol-3-yl)-2-methoxyethan-1-one | 0.030 |
| | B | | 1-(5-(6-chloro-7-fluoro-5-methoxy-3-(1H-pyrazol-4-yl)-1H-indol-2-yl)-1H-1,2,4-triazol-3-yl)-2-methoxyethan-1-one | |
| | C | | 1-(3-(6-chloro-7-fluoro-5-methoxy-1-methyl-3-(1H-pyrazol-4-yl)-1H-indol-2-yl)-1H-1,2,4-triazol-5-yl)-2-methoxyethan-1-one | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 58 | A | 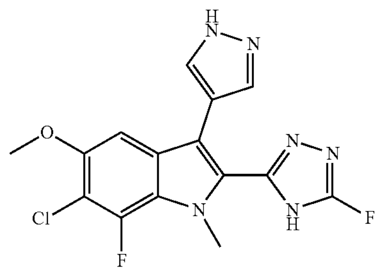 [SMILES: COc1cc2c(-c3cn[nH]c3)c(-c3nnc(F)[nH]3)n(C)c2c(F)c1Cl] | 6-chloro-7-fluoro-2-(5-fluoro-4H-1,2,4-triazol-3-yl)-5-methoxy-1-methyl-3-(1H-pyrazol-4-yl)-1H-indole | 0.030 |
| | B | | 6-chloro-7-fluoro-2-(3-fluoro-1H-1,2,4-triazol-5-yl)-5-methoxy-1-methyl-3-(1H-pyrazol-4-yl)-1H-indole | |
| | C | | 6-chloro-7-fluoro-2-(5-fluoro-1H-1,2,4-triazol-3-yl)-5-methoxy-1-methyl-3-(1H-pyrazol-4-yl)-1H-indole | |
| 59 | A | 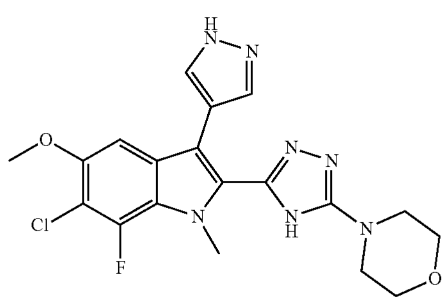 [SMILES: COc1cc2c(-c3cn[nH]c3)c(-c3nnc(N4CCOCC4)[nH]3)n(C)c2c(F)c1Cl] | 4-(5-(6-chloro-7-fluoro-5-methoxy-1-methyl-3-(1H-pyrazol-4-yl)-1H-indol-2-yl)-4H-1,2,4-triazol-3-yl)morpholine | 0.078 |
| | B | | 4-(5-(6-chloro-7-fluoro-5-methoxy-1-methyl-3-(1H-pyrazol-4-yl)-1H-indol-2-yl)-1H-1,2,4-triazol-3-yl)morpholine | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | 4-(3-(6-chloro-7-fluoro-5-methoxy-1-methyl-3-(1H-pyrazol-4-yl)-1H-indol-2-yl)-1H-1,2,4-triazol-5-yl)morpholine | |
| 60 | A | 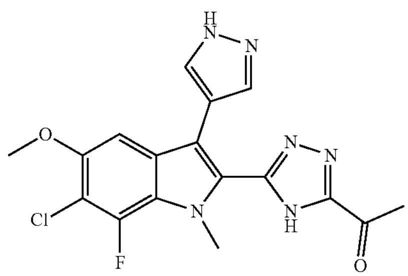 [SMILES: COc1cc2c(-c3cn[nH]c3)c(-c3nnc(C(C)=O)[nH]3)n(C)c2c(F)c1Cl] | 1-(5-(6-chloro-7-fluoro-5-methoxy-1-methyl-3-(1H-pyrazol-4-yl)-1H-indol-2-yl)-4H-1,2,4-triazol-3-yl)ethan-1-one | 0.032 |
| | B | | 1-(5-(6-chloro-7-fluoro-5-methoxy-1-methyl-3-(1H-pyrazol-4-yl)-1H-indol-2-yl)-1H-1,2,4-triazol-3-yl)ethan-1-one | |
| | C | | 1-(3-(6-chloro-7-fluoro-5-methoxy-1-methyl-3-(1H-pyrazol-4-yl)-1H-indol-2-yl)-1H-1,2,4-triazol-5-yl)ethan-1-one | |
| 61 | A | 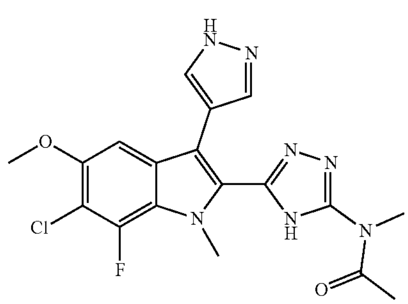 | N-(5-(6-chloro-7-fluoro-5-methoxy-1-methyl-3-(1H-pyrazol-4-yl)-1H-indol-2-yl)-4H-1,2,4-triazol-3-yl)-N-methylacetamide | 0.041 |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | N-(5-(6-chloro-7-fluoro-5-methoxy-1-methyl-3-(1H-pyrazol-4-yl)-1H-indol-2-yl)-1H-1,2,4-triazol-3-yl)-N-methylacetamide | |
| | C | | N-(3-(6-chloro-7-fluoro-5-methoxy-1-methyl-3-(1H-pyrazol-4-yl)-1H-indol-2-yl)-1H-1,2,4-triazol-5-yl)-N-methylacetamide | |
| 62 | A | 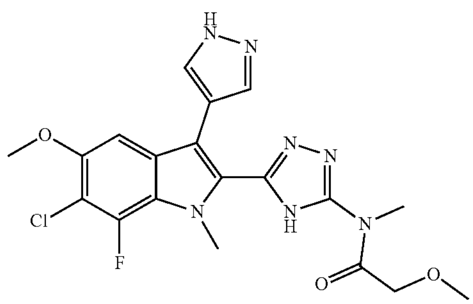 | N-(5-(6-chloro-7-fluoro-5-methoxy-1-methyl-3-(1H-pyrazol-4-yl)-1H-indol-2-yl)-4H-1,2,4-triazol-3-yl)-2-methoxy-N-methylacetamide | 0.060 |
| | B | | N-(5-(6-chloro-7-fluoro-5-methoxy-1-methyl-3-(1H-pyrazol-4-yl)-1H-indol-2-yl)-1H-1,2,4-triazol-3-yl)-2-methoxy-N-methylacetamide | |
| | C | | N-(3-(6-chloro-7-fluoro-5-methoxy-1-methyl-3-(1H-pyrazol-4-yl)-1H-indol-2-yl)-1H-1,2,4-triazol-5-yl)-2-methoxy-N-methylacetamide | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 63 | A | 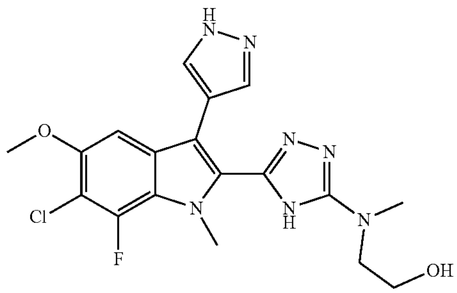 [SMILES: COc1cc2c(-c3cn[nH]c3)c(-c3nnc(N(C)CCO)[nH]3)n(C)c2c(F)c1Cl] | 2-((5-(6-chloro-7-fluoro-5-methoxy-1-methyl-3-(1H-pyrazol-4-yl)-1H-indol-2-yl)-4H-1,2,4-triazol-3-yl)(methyl)amino)ethan-1-ol | 0.054 |
|  | B | | 2-((5-(6-chloro-7-fluoro-5-methoxy-1-methyl-3-(1H-pyrazol-4-yl)-1H-indol-2-yl)-1H-1,2,4-triazol-3-yl)(methyl)amino)ethan-1-ol | |
|  | C | | 2-((3-(6-chloro-7-fluoro-5-methoxy-1-methyl-3-(1H-pyrazol-4-yl)-1H-indol-2-yl)-1H-1,2,4-triazol-5-yl)(methyl)amino)ethan-1-ol | |
| 64 | A | 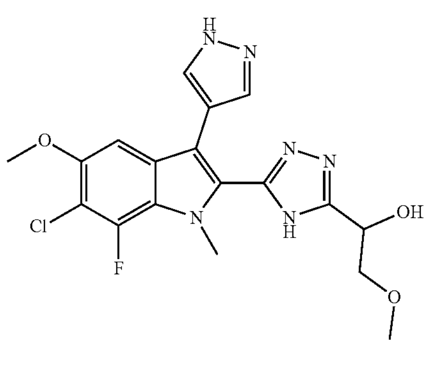 [SMILES: COCC(O)c1nnc(-c2c(-c3cn[nH]c3)c3cc(OC)c(Cl)c(F)c3n2C)[nH]1] | 1-(5-(6-chloro-7-fluoro-5-methoxy-1-methyl-3-(1H-pyrazol-4-yl)-1H-indol-2-yl)-4H-1,2,4-triazol-3-yl)-2-methoxyethan-1-ol | 0.052 |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | 1-(5-(6-chloro-7-fluoro-5-methoxy-1-methyl-3-(1H-pyrazol-4-yl)-1H-indol-2-yl)-1H-1,2,4-triazol-3-yl)-2-methoxyethan-1-ol | |
| | C | | 1-(3-(6-chloro-7-fluoro-5-methoxy-1-methyl-3-(1H-pyrazol-4-yl)-1H-indol-2-yl)-1H-1,2,4-triazol-5-yl)-2-methoxyethan-1-ol | |
| 64a | A | 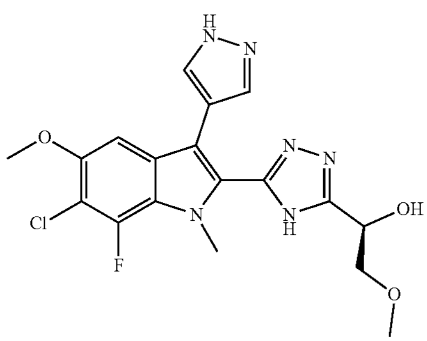 [SMILES: COC[C@H](O)c1nnc(-c2c(-c3cn[nH]c3)c3cc(OC)c(Cl)c(F)c3n2C)[nH]1] | (R)-1-(5-(6-chloro-7-fluoro-5-methoxy-1-methyl-3-(1H-pyrazol-4-yl)-1H-indol-2-yl)-4H-1,2,4-triazol-3-yl)-2-methoxyethan-1-ol | NA |
| | B | | (R)-1-(5-(6-chloro-7-fluoro-5-methoxy-1-methyl-3-(1H-pyrazol-4-yl)-1H-indol-2-yl)-1H-1,2,4-triazol-3-yl)-2-methoxyethan-1-ol | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | 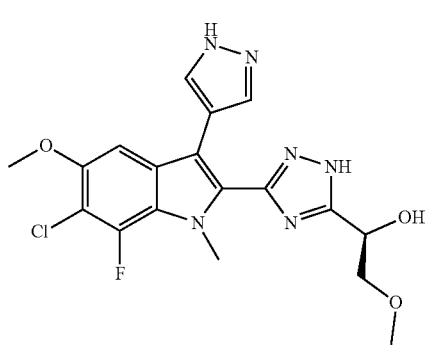 [SMILES: COC[C@H](O)c1nc(-c2c(-c3cn[nH]c3)c3cc(OC)c(Cl)c(F)c3n2C)n[nH]1] | (R)-1-(3-(6-chloro-7-fluoro-5-methoxy-1-methyl-3-(1H-pyrazol-4-yl)-1H-indol-2-yl)-1H-1,2,4-triazol-5-yl)-2-methoxyethan-1-ol | |
| 64b | A | 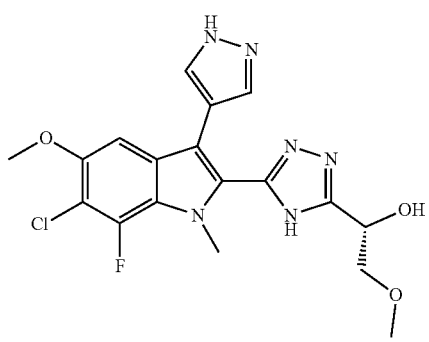 [SMILES: COC[C@@H](O)c1nnc(-c2c(-c3cn[nH]c3)c3cc(OC)c(Cl)c(F)c3n2C)[nH]1] | (S)-1-(5-(6-chloro-7-fluoro-5-methoxy-1-methyl-3-(1H-pyrazol-4-yl)-1H-indol-2-yl)-4H-1,2,4-triazol-3-yl)-2-methoxyethan-1-ol | NA |
| | B | 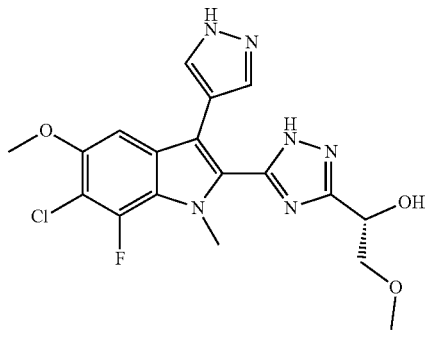 [SMILES: COC[C@@H](O)c1n[nH]c(-c2c(-c3cn[nH]c3)c3cc(OC)c(Cl)c(F)c3n2C)n1] | (S)-1-(5-(6-chloro-7-fluoro-5-methoxy-1-methyl-3-(1H-pyrazol-4-yl)-1H-indol-2-yl)-1H-1,2,4-triazol-3-yl)-2-methoxyethan-1-ol | |
| | C | 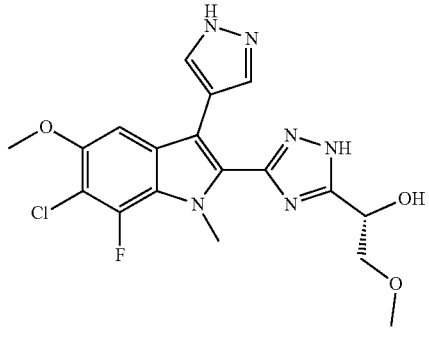 [SMILES: COC[C@@H](O)c1nc(-c2c(-c3cn[nH]c3)c3cc(OC)c(Cl)c(F)c3n2C)n[nH]1] | (S)-1-(3-(6-chloro-7-fluoro-5-methoxy-1-methyl-3-(1H-pyrazol-4-yl)-1H-indol-2-yl)-1H-1,2,4-triazol-5-yl)-2-methoxyethan-1-ol | |

TABLE 1-continued

Illustrative compounds of the disclosure and cGAS inhibition activity

| Example No. | Tautomer | Structure | Name | cGAS IC$_{50}$ [µM] |
|---|---|---|---|---|
| 65 | A | 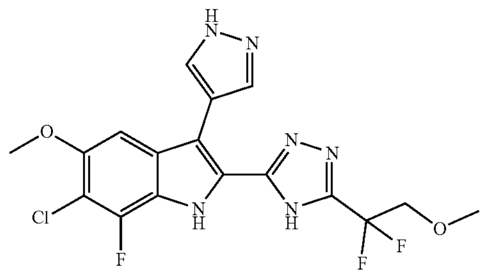 | 6-chloro-2-(5-(1,1-difluoro-2-methoxyethyl)-4H-1,2,4-triazol-3-yl)-7-fluoro-5-methoxy-3-(1H-pyrazol-4-yl)-1H-indole | 0.031 |
|  | B | | 6-chloro-2-(3-(1,1-difluoro-2-methoxyethyl)-1H-1,2,4-triazol-5-yl)-7-fluoro-5-methoxy-3-(1H-pyrazol-4-yl)-1H-indole |  |
|  | C | | 6-chloro-2-(5-(1,1-difluoro-2-methoxyethyl)-1H-1,2,4-triazol-3-yl)-7-fluoro-5-methoxy-3-(1H-pyrazol-4-yl)-1H-indole |  |
| 66 | A | 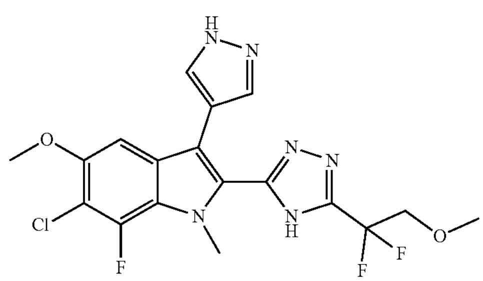 | 6-chloro-2-(5-(1,1-difluoro-2-methoxyethyl)-4H-1,2,4-triazol-3-yl)-7-fluoro-5-methoxy-1-methyl-3-(1H-pyrazol-4-yl)-1H-indole | 0.030 |
|  | B | | 6-chloro-2-(3-(1,1-difluoro-2-methoxyethyl)-1H-1,2,4-triazol-5-yl)-7-fluoro-5-methoxy-1-methyl-3-(1H-pyrazol-4-yl)-1H-indole |  |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | 6-chloro-2-(5-(1,1-difluoro-2-methoxyethyl)-1H-1,2,4-triazol-3-yl)-7-fluoro-5-methoxy-1-methyl-3-(1H-pyrazol-4-yl)-1H-indole | |
| 67 | A | 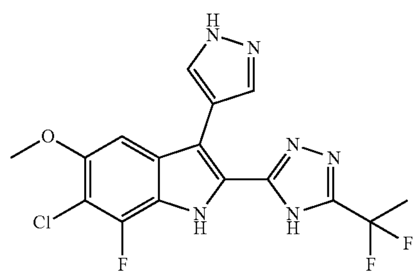 [SMILES: COc1cc2c(-c3cn[nH]c3)c(-c3nnc(C(C)(F)F)[nH]3)[nH]c2c(F)c1Cl] | 6-chloro-2-(5-(1,1-difluoroethyl)-4H-1,2,4-triazol-3-yl)-7-fluoro-5-methoxy-3-(1H-pyrazol-4-yl)-1H-indole | 0.030 |
| | B | | 6-chloro-2-(3-(1,1-difluoroethyl)-1H-1,2,4-triazol-5-yl)-7-fluoro-5-methoxy-3-(1H-pyrazol-4-yl)-1H-indole | |
| | C | | 6-chloro-2-(5-(1,1-difluoroethyl)-1H-1,2,4-triazol-3-yl)-7-fluoro-5-methoxy-3-(1H-pyrazol-4-yl)-1H-indole | |
| 68 | A | 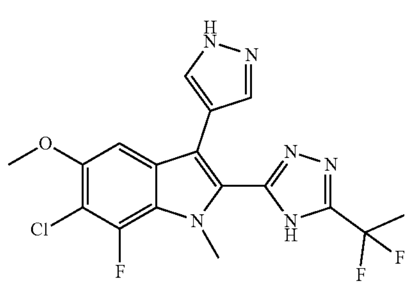 [SMILES: COc1cc2c(-c3cn[nH]c3)c(-c3nnc(C(C)(F)F)[nH]3)n(C)c2c(F)c1Cl] | 6-chloro-2-(5-(1,1-difluoroethyl)-4H-1,2,4-triazol-3-yl)-7-fluoro-5-methoxy-1-methyl-3-(1H-pyrazol-4-yl)-1H-indole | 0.033 |

TABLE 1-continued

Illustrative compounds of the disclosure and cGAS inhibition activity

| Example No. | Tautomer | Structure | Name | cGAS IC$_{50}$ [μM] |
|---|---|---|---|---|
|  | B |  | 6-chloro-2-(3-(1,1-difluoroethyl)-1H-1,2,4-triazol-5-yl)-7-fluoro-5-methoxy-1-methyl-3-(1H-pyrazol-4-yl)-1H-indole |  |
|  | C |  | 6-chloro-2-(5-(1,1-difluoroethyl)-1H-1,2,4-triazol-3-yl)-7-fluoro-5-methoxy-1-methyl-3-(1H-pyrazol-4-yl)-1H-indole |  |
| 69 | A | 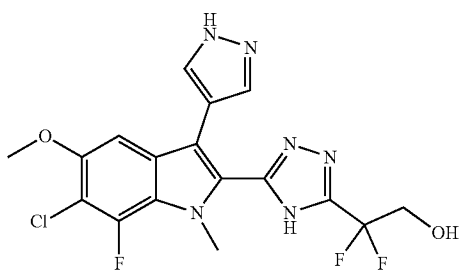 [SMILES: COc1cc2c(-c3cn[nH]c3)c(-c3nnc(C(F)(F)CO)[nH]3)n(C)c2c(F)c1Cl] | 2-(5-(6-chloro-7-fluoro-5-methoxy-1-methyl-3-(1H-pyrazol-4-yl)-1H-indol-2-yl)-4H-1,2,4-triazol-3-yl)-2,2-difluoroethan-1-ol | 0.038 |
|  | B |  | 2-(5-(6-chloro-7-fluoro-5-methoxy-1-methyl-3-(1H-pyrazol-4-yl)-1H-indol-2-yl)-1H-1,2,4-triazol-3-yl)-2,2-difluoroethan-1-ol |  |
|  | C |  | 2-(3-(6-chloro-7-fluoro-5-methoxy-1-methyl-3-(1H-pyrazol-4-yl)-1H-indol-2-yl)-1H-1,2,4-triazol-5-yl)-2,2-difluoroethan-1-ol |  |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 70 | A | 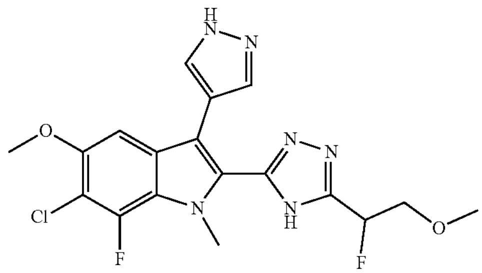 | 6-chloro-7-fluoro-2-(5-(1-fluoro-2-methoxyethyl)-4H-1,2,4-triazol-3-yl)-5-methoxy-1-methyl-3-(1H-pyrazol-4-yl)-1H-indole | 0.039 |
| | B | | 6-chloro-7-fluoro-2-(3-(1-fluoro-2-methoxyethyl)-1H-1,2,4-triazol-5-yl)-5-methoxy-1-methyl-3-(1H-pyrazol-4-yl)-1H-indole | |
| | C | | 6-chloro-7-fluoro-2-(5-(1-fluoro-2-methoxyethyl)-1H-1,2,4-triazol-3-yl)-5-methoxy-1-methyl-3-(1H-pyrazol-4-yl)-1H-indole | |
| 70a | A | 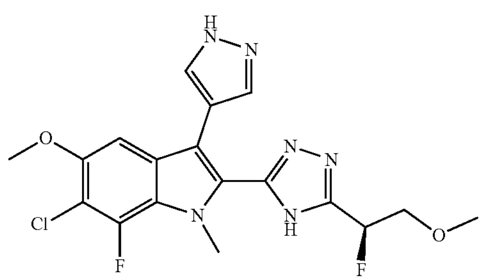 | (S)-6-chloro-7-fluoro-2-(5-(1-fluoro-2-methoxyethyl)-4H-1,2,4-triazol-3-yl)-5-methoxy-1-methyl-3-(1H-pyrazol-4-yl)-1H-indole | NA |
| | B | | (S)-6-chloro-7-fluoro-2-(3-(1-fluoro-2-methoxyethyl)-1H-1,2,4-triazol-5-yl)-5-methoxy-1-methyl-3-(1H-pyrazol-4-yl)-1H-indole | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | (S)-6-chloro-7-fluoro-2-(5-(1-fluoro-2-methoxyethyl)-1H-1,2,4-triazol-3-yl)-5-methoxy-1-methyl-3-(1H-pyrazol-4-yl)-1H-indole | |
| 70b | A | 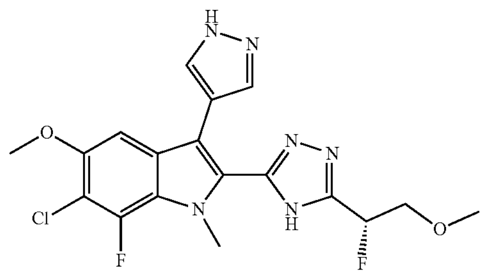 | (R)-6-chloro-7-fluoro-2-(5-(1-fluoro-2-methoxyethyl)-4H-1,2,4-triazol-3-yl)-5-methoxy-1-methyl-3-(1H-pyrazol-4-yl)-1H-indole | NA |
| | B | | (R)-6-chloro-7-fluoro-2-(3-(1-fluoro-2-methoxyethyl)-1H-1,2,4-triazol-5-yl)-5-methoxy-1-methyl-3-(1H-pyrazol-4-yl)-1H-indole | |
| | C | | (R)-6-chloro-7-fluoro-2-(5-(1-fluoro-2-methoxyethyl)-1H-1,2,4-triazol-3-yl)-5-methoxy-1-methyl-3-(1H-pyrazol-4-yl)-1H-indole | |
| 71 | A | 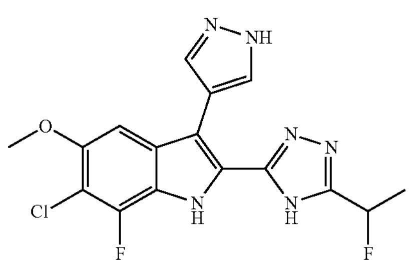 [SMILES: COc1cc2c(-c3cn[nH]c3)c(-c3nnc(C(C)F)[nH]3)[nH]c2c(F)c1Cl] | 6-chloro-7-fluoro-2-(5-(1-fluoroethyl)-4H-1,2,4-triazol-3-yl)-5-methoxy-3-(1H-pyrazol-4-yl)-1H-indole | 0.044 |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | 6-chloro-7-fluoro-2-(3-(1-fluoroethyl)-1H-1,2,4-triazol-5-yl)-5-methoxy-3-(1H-pyrazol-4-yl)-1H-indole | |
| | C | | 6-chloro-7-fluoro-2-(5-(1-fluoroethyl)-1H-1,2,4-triazol-3-yl)-5-methoxy-3-(1H-pyrazol-4-yl)-1H-indole | |
| 71a | A | 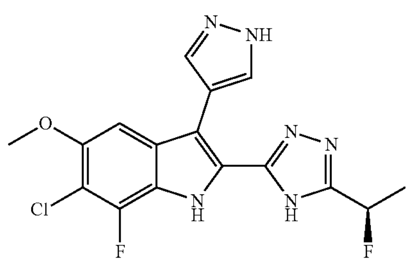 [SMILES: COc1cc2c(-c3cn[nH]c3)c(-c3nnc([C@@H](C)F)[nH]3)[nH]c2c(F)c1Cl] | (R)-6-chloro-7-fluoro-2-(5-(1-fluoroethyl)-4H-1,2,4-triazol-3-yl)-5-methoxy-3-(1H-pyrazol-4-yl)-1H-indole | NA |
| | B | | (R)-6-chloro-7-fluoro-2-(3-(1-fluoroethyl)-1H-1,2,4-triazol-5-yl)-5-methoxy-3-(1H-pyrazol-4-yl)-1H-indole | |
| | C | | (R)-6-chloro-7-fluoro-2-(5-(1-fluoroethyl)-1H-1,2,4-triazol-3-yl)-5-methoxy-3-(1H-pyrazol-4-yl)-1H-indole | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 71b | A | 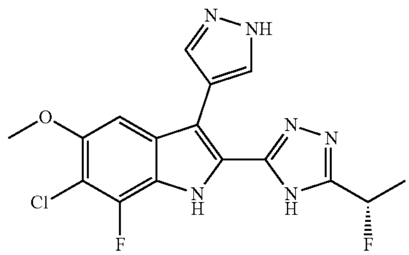 | (S)-6-chloro-7-fluoro-2-(5-(1-fluoroethyl)-4H-1,2,4-triazol-3-yl)-5-methoxy-3-(1H-pyrazol-4-yl)-1H-indole | NA |
| | B | | (S)-6-chloro-7-fluoro-2-(3-(1-fluoroethyl)-1H-1,2,4-triazol-5-yl)-5-methoxy-3-(1H-pyrazol-4-yl)-1H-indole | |
| | C | | (S)-6-chloro-7-fluoro-2-(5-(1-fluoroethyl)-1H-1,2,4-triazol-3-yl)-5-methoxy-3-(1H-pyrazol-4-yl)-1H-indole | |
| 72 | A | 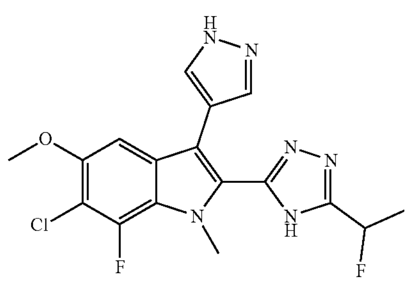 [SMILES: COc1cc2c(-c3cn[nH]c3)c(-c3nnc(C(C)F)[nH]3)n(C)c2c(F)c1Cl] | 6-chloro-7-fluoro-2-(5-(1-fluoroethyl)-4H-1,2,4-triazol-3-yl)-5-methoxy-1-methyl-3-(1H-pyrazol-4-yl)-1H-indole | 0.061 |
| | B | | 6-chloro-7-fluoro-2-(3-(1-fluoroethyl)-1H-1,2,4-triazol-5-yl)-5-methoxy-1-methyl-3-(1H-pyrazol-4-yl)-1H-indole | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | 6-chloro-7-fluoro-2-(5-(1-fluoroethyl)-1H-1,2,4-triazol-3-yl)-5-methoxy-1-methyl-3-(1H-pyrazol-4-yl)-1H-indole | |
| 72a | A | 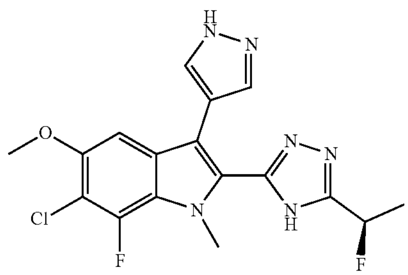 [SMILES: COc1cc2c(-c3cn[nH]c3)c(-c3nnc([C@@H](C)F)[nH]3)n(C)c2c(F)c1Cl] | (R)-6-chloro-7-fluoro-2-(5-(1-fluoroethyl)-4H-1,2,4-triazol-3-yl)-5-methoxy-1-methyl-3-(1H-pyrazol-4-yl)-1H-indole | NA |
| | B | | (R)-6-chloro-7-fluoro-2-(3-(1-fluoroethyl)-1H-1,2,4-triazol-5-yl)-5-methoxy-1-methyl-3-(1H-pyrazol-4-yl)-1H-indole | |
| | C | | (R)-6-chloro-7-fluoro-2-(5-(1-fluoroethyl)-1H-1,2,4-triazol-3-yl)-5-methoxy-1-methyl-3-(1H-pyrazol-4-yl)-1H-indole | |
| 72b | A | 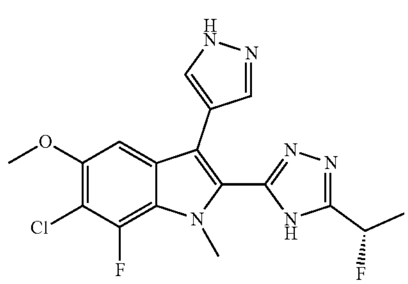 [SMILES: COc1cc2c(-c3cn[nH]c3)c(-c3nnc([C@H](C)F)[nH]3)n(C)c2c(F)c1Cl] | (S)-6-chloro-7-fluoro-2-(5-(1-fluoroethyl)-4H-1,2,4-triazol-3-yl)-5-methoxy-1-methyl-3-(1H-pyrazol-4-yl)-1H-indole | NA |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | (S)-6-chloro-7-fluoro-2-(3-(1-fluoroethyl)-1H-1,2,4-triazol-5-yl)-5-methoxy-1-methyl-3-(1H-pyrazol-4-yl)-1H-indole | |
| | C | | (S)-6-chloro-7-fluoro-2-(5-(1-fluoroethyl)-1H-1,2,4-triazol-3-yl)-5-methoxy-1-methyl-3-(1H-pyrazol-4-yl)-1H-indole | |
| 73 | A | 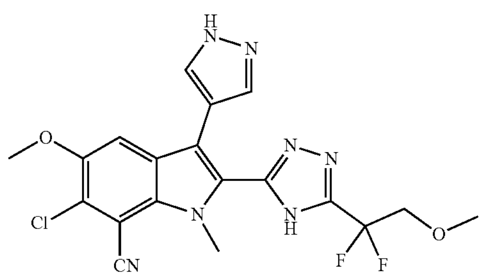 | 6-chloro-2-(5-(1,1-difluoro-2-methoxyethyl)-4H-1,2,4-triazol-3-yl)-5-methoxy-1-methyl-3-(1H-pyrazol-4-yl)-1H-indole-7-carbonitrile | 0.030 |
| | B | | 6-chloro-2-(3-(1,1-difluoro-2-methoxyethyl)-1H-1,2,4-triazol-5-yl)-5-methoxy-1-methyl-3-(1H-pyrazol-4-yl)-1H-indole-7-carbonitrile | |
| | C | | 6-chloro-2-(5-(1,1-difluoro-2-methoxyethyl)-1H-1,2,4-triazol-3-yl)-5-methoxy-1-methyl-3-(1H-pyrazol-4-yl)-1H-indole-7-carbonitrile | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 74 | A | 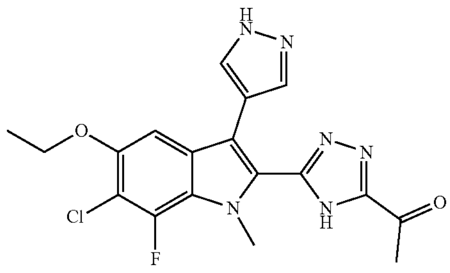 [SMILES: CCOc1cc2c(-c3cn[nH]c3)c(-c3nnc(C(C)=O)[nH]3)n(C)c2c(F)c1Cl] | 1-(5-(6-chloro-5-ethoxy-7-fluoro-1-methyl-3-(1H-pyrazol-4-yl)-1H-indol-2-yl)-4H-1,2,4-triazol-3-yl)ethan-1-one | 0.210 |
| | B | | 1-(5-(6-chloro-5-ethoxy-7-fluoro-1-methyl-3-(1H-pyrazol-4-yl)-1H-indol-2-yl)-1H-1,2,4-triazol-3-yl)ethan-1-one | |
| | C | | 1-(3-(6-chloro-5-ethoxy-7-fluoro-1-methyl-3-(1H-pyrazol-4-yl)-1H-indol-2-yl)-1H-1,2,4-triazol-5-yl)ethan-1-one | |
| 75 | A | 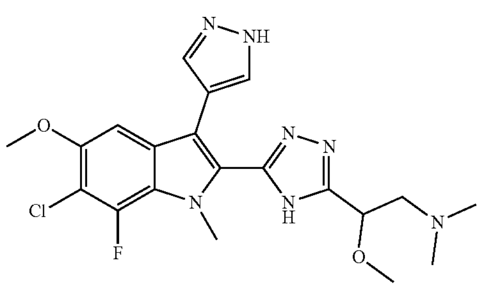 | 2-(5-(6-chloro-7-fluoro-5-methoxy-1-methyl-3-(1H-pyrazol-4-yl)-1H-indol-2-yl)-4H-1,2,4-triazol-3-yl)-2-methoxy-N,N-dimethylethan-1-amine | 0.070 |
| | B | | 2-(5-(6-chloro-7-fuoro-5-methoxy-1-methyl-3-(1H-pyrazol-4-yl)-1H-indol-2-yl)-1H-1,2,4-triazol-3-yl)-2-methoxy-N,N-dimethylethan-1-amine | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | 2-(3-(6-chloro-7-fluoro-5-methoxy-1-methyl-3-(1H-pyrazol-4-yl)-1H-indol-2-yl)-1H-1,2,4-triazol-5-yl)-2-methoxy-N,N-dimethylethan-1-amine | |
| 75a | A | 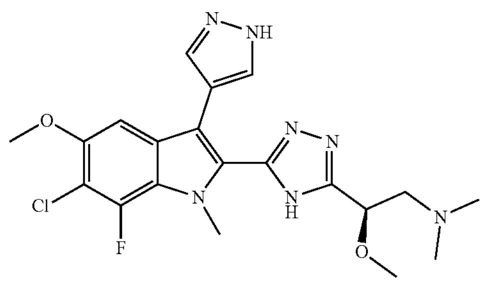 | (R)-2-(5-(6-chloro-7-fluoro-5-methoxy-1-methyl-3-(1H-pyrazol-4-yl)-1H-indol-2-yl)-4H-1,2,4-triazol-3-yl)-2-methoxy-N,N-dimethylethan-1-amine | NA |
| | B | | (R)-2-(5-(6-chloro-7-fluoro-5-methoxy-1-methyl-3-(1H-pyrazol-4-yl)-1H-indol-2-yl)-1H-1,2,4-triazol-3-yl)-2-methoxy-N,N-dimethylethan-1-amine | |
| | C | | (R)-2-(3-(6-chloro-7-fluoro-5-methoxy-1-methyl-3-(1H-pyrazol-4-yl)-1H-indol-2-yl)-1H-1,2,4-triazol-5-yl)-2-methoxy-N,N-dimethylethan-1-amine | |
| 75b | A | 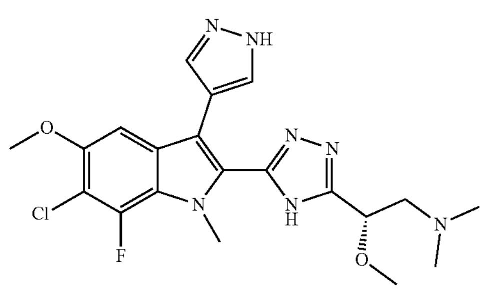 | (S)-2-(5-(6-chloro-7-fluoro-5-methoxy-1-methyl-3-(1H-pyrazol-4-yl)-1H-indol-2-yl)-4H-1,2,4-triazol-3-yl)-2-methoxy-N,N-dimethylethan-1-amine | NA |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | (S)-2-(3-(6-chloro-7-fluoro-5-methoxy-1-methyl-3-(1H-pyrazol-4-yl)-1H-indol-2-yl)-1H-1,2,4-triazol-5-yl)-2-methoxy-N,N-dimethylethan-1-amine | |
| | C | | (S)-2-(3-(6-chloro-7-fluoro-5-methoxy-1-methyl-3-(1H-pyrazol-4-yl)-1H-indol-2-yl)-1H-1,2,4-triazol-5-yl)-2-methoxy-N,N-dimethylethan-1-amine | |
| 76 | A | 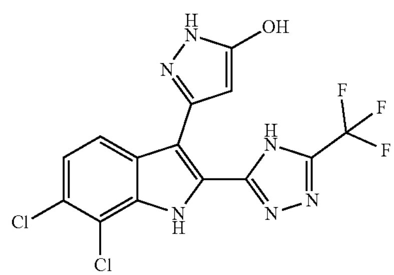 [SMILES: Oc1cc(-c2c(-c3nnc(C(F)(F)F)[nH]3)[nH]c3c(Cl)c(Cl)ccc23)n[nH]1] | 3-(6,7-dichloro-2-(5-(trifluoromethyl)-4H-1,2,4-triazol-3-yl)-1H-indol-3-yl)-1H-pyrazol-5-ol | 4.21 |
| | B | | 3-(6,7-dichloro-2-(3-(trifluoromethyl)-1H-1,2,4-triazol-5-yl)-1H-indol-3-yl)-1H-pyrazol-5-ol | |
| | C | | 3-(6,7-dichloro-2-(5-(trifluoromethyl)-1H-1,2,4-triazol-3-yl)-1H-indol-3-yl)-1H-pyrazol-5-ol | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 77 | A | 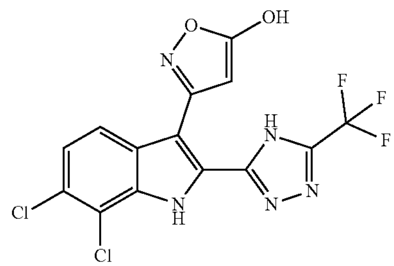 [SMILES: Oc1cc(-c2c(-c3nnc(C(F)(F)F)[nH]3)[nH]c3c(Cl)c(Cl)ccc23)no1] | 3-(6,7-dichloro-2-(5-(trifluoromethyl)-4H-1,2,4-triazol-3-yl)-1H-indol-3-yl)isoxazol-5-ol | 1.85 |
| | B | | 3-(6,7-dichloro-2-(3-(trifluoromethyl)-1H-1,2,4-triazol-5-yl)-1H-indol-3-yl)isoxazol-5-ol | |
| | C | | 3-(6,7-dichloro-2-(5-(trifluoromethyl)-1H-1,2,4-triazol-3-yl)-1H-indol-3-yl)isoxazol-5-ol | |
| 78 | A | 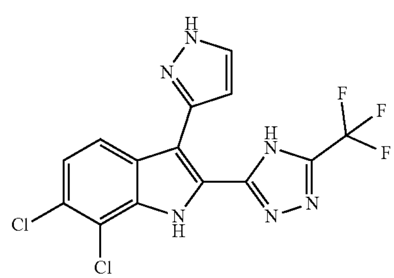 [SMILES: FC(F)(F)c1nnc(-c2[nH]c3c(Cl)c(Cl)ccc3c2-c2cc[nH]n2)[nH]1] | 6,7-dichloro-3-(1H-pyrazol-3-yl)-2-(5-(trifluoromethyl)-4H-1,2,4-triazol-3-yl)-1H-indole | 3.69 |
| | B | | 6,7-dichloro-3-(1H-pyrazol-3-yl)-2-(3-(trifluoromethyl)-1H-1,2,4-triazol-5-yl)-1H-indole | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | 6,7-dichloro-3-(1H-pyrazol-3-yl)-2-(5-(trifluoromethyl)-1H-1,2,4-triazol-3-yl)-1H-indole | |
| 79 | A | 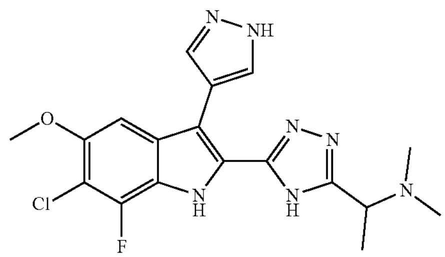 | 1-(5-(6-chloro-7-fluoro-5-methoxy-3-(1H-pyrazol-4-yl)-1H-indol-2-yl)-4H-1,2,4-triazol-3-yl)-N,N-dimethylethan-1-amine | 0.030 |
| | B | | 1-(5-(6-chloro-7-fluoro-5-methoxy-3-(1H-pyrazol-4-yl)-1H-indol-2-yl)-1H-1,2,4-triazol-3-yl)-N,N-dimethylethan-1-amine | |
| | C | | 1-(3-(6-chloro-7-fluoro-5-methoxy-3-(1H-pyrazol-4-yl)-1H-indol-2-yl)-1H-1,2,4-triazol-5-yl)-N,N-dimethylethan-1-amine | |
| 79a | A | 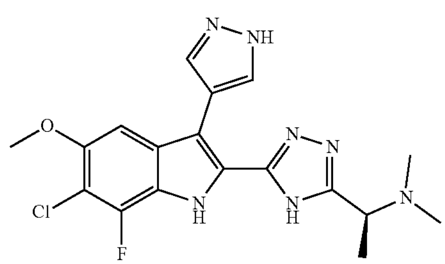 | (S)-1-(5-(6-chloro-7-fluoro-5-methoxy-3-(1H-pyrazol-4-yl)-1H-indol-2-yl)-4H-1,2,4-triazol-3-yl)-N,N-dimethylethan-1-amine | NA |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | (S)-1-(5-(6-chloro-7-fluoro-5-methoxy-3-(1H-pyrazol-4-yl)-1H-indol-2-yl)-1H-1,2,4-triazol-3-yl)-N,N-dimethylethan-1-amine | |
| | C | | (S)-1-(3-(6-chloro-7-fluoro-5-methoxy-3-(1H-pyrazol-4-yl)-1H-indol-2-yl)-1H-1,2,4-triazol-5-yl)-N,N-dimethylethan-1-amine | |
| 79b | A | 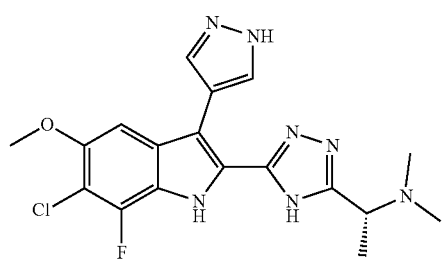 | (R)-1-(5-(6-chloro-7-fluoro-5-methoxy-3-(1H-pyrazol-4-yl)-1H-indol-2-yl)-4H-1,2,4-triazol-3-yl)-N,N-dimethylethan-1-amine | NA |
| | B | | (R)-1-(5-(6-chloro-7-fluoro-5-methoxy-3-(1H-pyrazol-4-yl)-1H-indol-2-yl)-1H-1,2,4-triazol-3-yl)-N,N-dimethylethan-1-amine | |
| | C | | (R)-1-(3-(6-chloro-7-fluoro-5-methoxy-3-(1H-pyrazol-4-yl)-1H-indol-2-yl)-1H-1,2,4-triazol-5-yl)-N,N-dimethylethan-1-amine | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 80 | A | 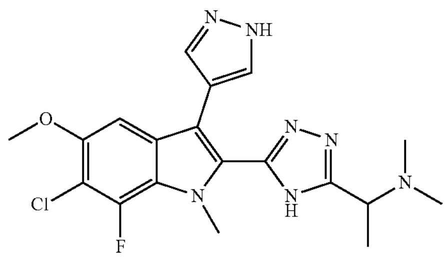 | 1-(5-(6-chloro-7-fluoro-5-methoxy-1-methyl-3-(1H-pyrazol-4-yl)-1H-indol-2-yl)-4H-1,2,4-triazol-3-yl)-N,N-dimethylethan-1-amine | 0.039 |
| | B | | 1-(5-(6-chloro-7-fluoro-5-methoxy-1-methyl-3-(1H-pyrazol-4-yl)-1H-indol-2-yl)-1H-1,2,4-triazol-3-yl)-N,N-dimethylethan-1-amine | |
| | C | | 1-(3-(6-chloro-7-fluoro-5-methoxy-1-methyl-3-(1H-pyrazol-4-yl)-1H-indol-2-yl)-1H-1,2,4-triazol-5-yl)-N,N-dimethylethan-1-amine | |
| 80a | A | 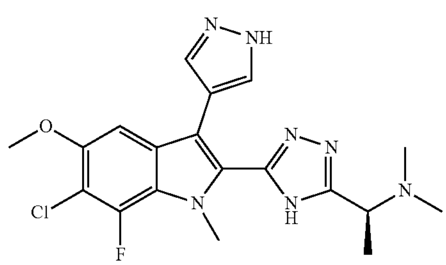 | (S)-1-(5-(6-chloro-7-fluoro-5-methoxy-1-methyl-3-(1H-pyrazol-4-yl)-1H-indol-2-yl)-4H-1,2,4-triazol-3-yl)-N,N-dimethylethan-1-amine | NA |
| | B | | (S)-1-(5-(6-chloro-7-fluoro-5-methoxy-1-methyl-3-(1H-pyrazol-4-yl)-1H-indol-2-yl)-1H-1,2,4-triazol-3-yl)-N,N-dimethylethan-1-amine | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | (S)-1-(3-(6-chloro-7-fluoro-5-methoxy-1-methyl-3-(1H-pyrazol-4-yl)-1H-indol-2-yl)-1H-1,2,4-triazol-5-yl)-N,N-dimethylethan-1-amine | |
| 80b | A | 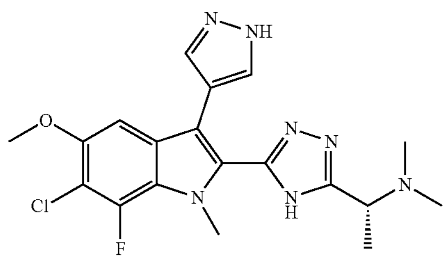 | (R)-1-(5-(6-chloro-7-fluoro-5-methoxy-1-methyl-3-(1H-pyrazol-4-yl)-1H-indol-2-yl)-4H-1,2,4-triazol-3-yl)-N,N-dimethylethan-1-amine | NA |
| | B | | (R)-1-(5-(6-chloro-7-fluoro-5-methoxy-1-methyl-3-(1H-pyrazol-4-yl)-1H-indol-2-yl)-1H-1,2,4-triazol-3-yl)-N,N-dimethylethan-1-amine | |
| | C | | (R)-1-(3-(6-chloro-7-fluoro-5-methoxy-1-methyl-3-(1H-pyrazol-4-yl)-1H-indol-2-yl)-1H-1,2,4-triazol-5-yl)-N,N-dimethylethan-1-amine | |
| 81 | A | | 1-(5-(6-chloro-7-fluoro-5-methoxy-1-methyl-3-(1H-pyrazol-4-yl)-1H-indol-2-yl)-4H-1,2,4-triazol-3-yl)-2-methoxy-N,N-dimethylethan-1-amine | 0.091 | ns

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | 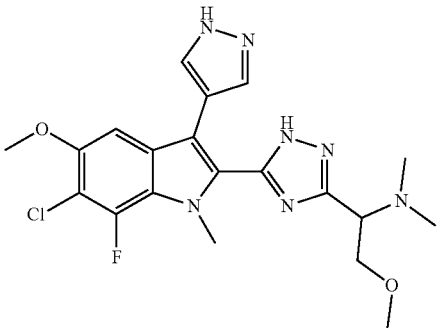 | 1-(5-(6-chloro-7-fluoro-5-methoxy-1-methyl-3-(1H-pyrazol-4-yl)-1H-indol-2-yl)-1H-1,2,4-triazol-3-yl)-2-methoxy-N,N-dimethylethan-1-amine | |
| | C | 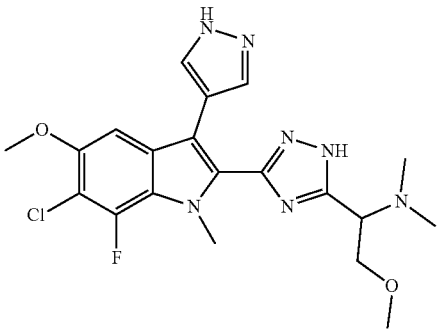 | 1-(3-(6-chloro-7-fluoro-5-methoxy-1-methyl-3-(1H-pyrazol-4-yl)-1H-indol-2-yl)-1H-1,2,4-triazol-5-yl)-2-methoxy-N,N-dimethylethan-1-amine | |
| 81a | A | 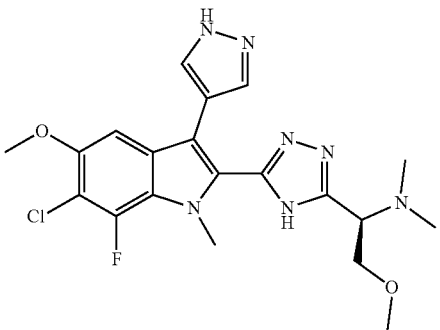 | (R)-1-(5-(6-chloro-7-fluoro-5-methoxy-1-methyl-3-(1H-pyrazol-4-yl)-1H-indol-2-yl)-4H-1,2,4-triazol-3-yl)-2-methoxy-N,N-dimethylethan-1-amine | NA |
| | B | 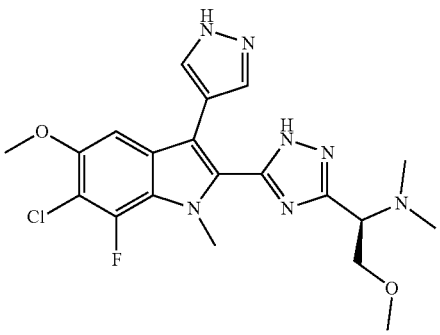 | (R)-1-(5-(6-chloro-7-fluoro-5-methoxy-1-methyl-3-(1H-pyrazol-4-yl)-1H-indol-2-yl)-1H-1,2,4-triazol-3-yl)-2-methoxy-N,N-dimethylethan-1-amine | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | (R)-1-(3-(6-chloro-7-fluoro-5-methoxy-1-methyl-3-(1H-pyrazol-4-yl)-1H-indol-2-yl)-1H-1,2,4-triazol-5-yl)-2-methoxy-N,N-dimethylethan-1-amine | |
| 81b | A | 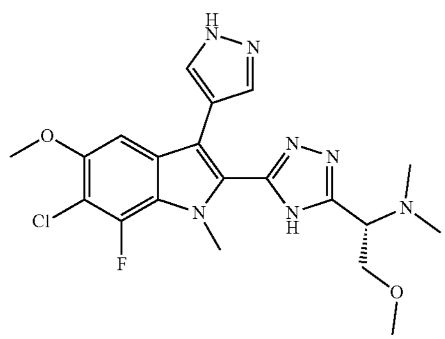 | (S)-1-(5-(6-chloro-7-fluoro-5-methoxy-1-methyl-3-(1H-pyrazol-4-yl)-1H-indol-2-yl)-4H-1,2,4-triazol-3-yl)-2-methoxy-N,N-dimethylethan-1-amine | NA |
| | B | | (S)-1-(5-(6-chloro-7-fluoro-5-methoxy-1-methyl-3-(1H-pyrazol-4-yl)-1H-indol-2-yl)-1H-1,2,4-triazol-3-yl)-2-methoxy-N,N-dimethylethan-1-amine | |
| | C | | (S)-1-(3-(6-chloro-7-fluoro-5-methoxy-1-methyl-3-(1H-pyrazol-4-yl)-1H-indol-2-yl)-1H-1,2,4-triazol-5-yl)-2-methoxy-N,N-dimethylethan-1-amine | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 82 | A | 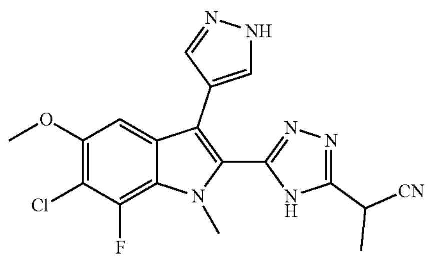 [SMILES: COc1cc2c(-c3cn[nH]c3)c(-c3nnc(C(C)C#N)[nH]3)n(C)c2c(F)c1Cl] | 2-(5-(6-chloro-7-fluoro-5-methoxy-1-methyl-3-(1H-pyrazol-4-yl)-1H-indol-2-yl)-4H-1,2,4-triazol-3-yl)propanenitrile | 0.030 |
| | B | | 2-(5-(6-chloro-7-fluoro-5-methoxy-1-methyl-3-(1H-pyrazol-4-yl)-1H-indol-2-yl)-1H-1,2,4-triazol-3-yl)propanenitrile | |
| | C | | 2-(3-(6-chloro-7-fluoro-5-methoxy-1-methyl-3-(1H-pyrazol-4-yl)-1H-indol-2-yl)-1H-1,2,4-triazol-5-yl)propanenitrile | |
| 82a | A | 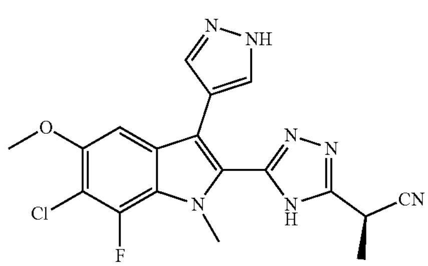 [SMILES: COc1cc2c(-c3cn[nH]c3)c(-c3nnc([C@H](C)C#N)[nH]3)n(C)c2c(F)c1Cl] | (R)-2-(5-(6-chloro-7-fluoro-5-methoxy-1-methyl-3-(1H-pyrazol-4-yl)-1H-indol-2-yl)-4H-1,2,4-triazol-3-yl)propanenitrile | NA |
| | B | | (R)-2-(5-(6-chloro-7-fluoro-5-methoxy-1-methyl-3-(1H-pyrazol-4-yl)-1H-indol-2-yl)-1H-1,2,4-triazol-3-yl)propanenitrile | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | (R)-2-(3-(6-chloro-7-fluoro-5-methoxy-1-methyl-3-(1H-pyrazol-4-yl)-1H-indol-2-yl)-1H-1,2,4-triazol-5-yl)propanenitrile | |
| 82b | A | 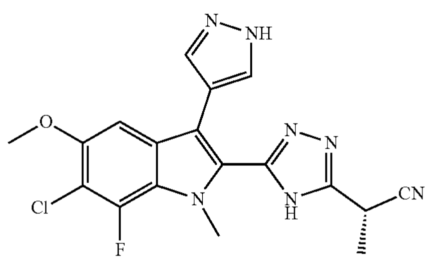 [SMILES: COc1cc2c(-c3cn[nH]c3)c(-c3nnc([C@@H](C)C#N)[nH]3)n(C)c2c(F)c1Cl] | (S)-2-(5-(6-chloro-7-fluoro-5-methoxy-1-methyl-3-(1H-pyrazol-4-yl)-1H-indol-2-yl)-4H-1,2,4-triazol-3-yl)propanenitrile | NA |
| | B | | (S)-2-(5-(6-chloro-7-fluoro-5-methoxy-1-methyl-3-(1H-pyrazol-4-yl)-1H-indol-2-yl)-1H-1,2,4-triazol-3-yl)propanenitrile | |
| | C | | (S)-2-(3-(6-chloro-7-fluoro-5-methoxy-1-methyl-3-(1H-pyrazol-4-yl)-1H-indol-2-yl)-1H-1,2,4-triazol-5-yl)propanenitrile | |
| 83a | A | 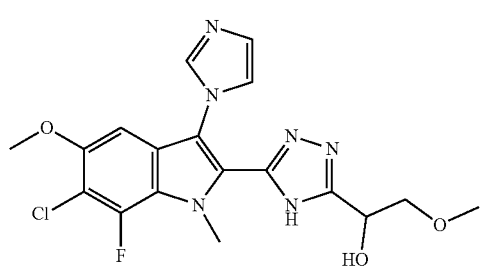 | 1-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-ol | 0.063 |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | 1-(5-(6-chloro-7-fluoro-3-(1H-imidazol-1-yl)-5-methoxy-1-methyl-1H-indol-2-yl)-1H-1,2,4-triazol-3-yl)-2-methoxyethan-1-ol | |
| | C | | 1-(3-(6-chloro-7-fluoro-3-(1H-imidazol-1-yl)-5-methoxy-1-methyl-1H-indol-2-yl)-1H-1,2,4-triazol-5-yl)-2-methoxyethan-1-ol | |
| 83 | A | 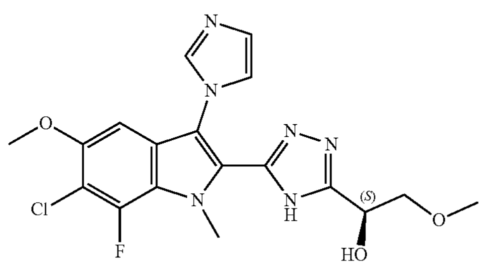 | (S)-1-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-ol | 0.078 |
| | B | | (S)-1-(5-(6-chloro-7-fluoro-3-(1H-imidazol-1-yl)-5-methoxy-1-methyl-1H-indol-2-yl)-1H-1,2,4-triazol-3-yl)-2-methoxyethan-1-ol | |
| | C | | (S)-1-(3-(6-chloro-7-fluoro-3-(1H-imidazol-1-yl)-5-methoxy-1-methyl-1H-indol-2-yl)-1H-1,2,4-triazol-5-yl)-2-methoxyethan-1-ol | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 84 | A | 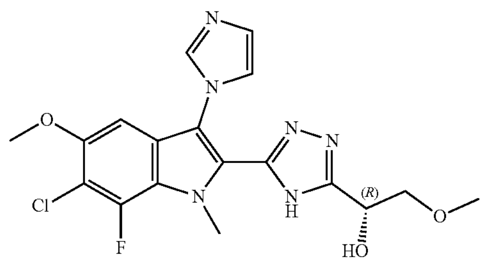 | (R)-1-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-ol | 0.063 |
| | B | | (R)-1-(5-(6-chloro-7-fluoro-3-(1H-imidazol-1-yl)-5-methoxy-1-methyl-1H-indol-2-yl)-1H-1,2,4-triazol-3-yl)-2-methoxyethan-1-ol | |
| | C | | (R)-1-(3-(6-chloro-7-fluoro-3-(1H-imidazol-1-yl)-5-methoxy-1-methyl-1H-indol-2-yl)-1H-1,2,4-triazol-5-yl)-2-methoxyethan-1-ol | |
| 85 | A | 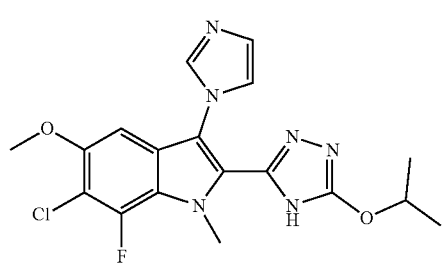 [SMILES: COc1cc2c(-n3ccnc3)c(-c3nnc(OC(C)C)[nH]3)n(C)c2c(F)c1Cl] | 6-chloro-7-fluoro-3-(1H-imidazol-1-yl)-2-(5-isopropoxy-4H-1,2,4-triazol-3-yl)-5-methoxy-1-methyl-1H-indole | 0.091 |
| | B | | 6-chloro-7-fluoro-3-(1H-imidazol-1-yl)-2-(3-isopropoxy-1H-1,2,4-triazol-5-yl)-5-methoxy-1-methyl-1H-indole | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | 6-chloro-7-fluoro-3-(1H-imidazol-1-yl)-2-(5-isopropoxy-1H-1,2,4-triazol-3-yl)-5-methoxy-1-methyl-1H-indole | |
| 86 | A | 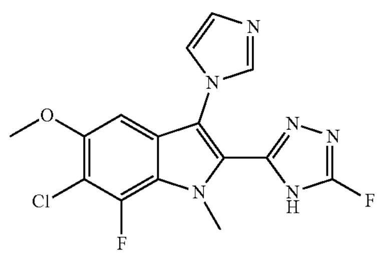 [SMILES: COc1cc2c(-n3ccnc3)c(-c3nnc(F)[nH]3)n(C)c2c(F)c1Cl] | 6-chloro-7-fluoro-2-(5-fluoro-4H-1,2,4-triazol-3-yl)-3-(1H-imidazol-1-yl)-5-methoxy-1-methyl-1H-indole | 0.264 |
| | B | | 6-chloro-7-fluoro-2-(3-fluoro-1H-1,2,4-triazol-5-yl)-3-(1H-imidazol-1-yl)-5-methoxy-1-methyl-1H-indole | |
| | C | | 6-chloro-7-fluoro-2-(5-fluoro-1H-1,2,4-triazol-3-yl)-3-(1H-imidazol-1-yl)-5-methoxy-1-methyl-1H-indole | |
| 87 | A | 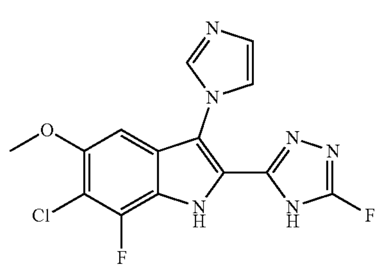 [SMILES: COc1cc2c(-n3ccnc3)c(-c3nnc(F)[nH]3)[nH]c2c(F)c1Cl] | 6-chloro-7-fluoro-2-(5-fluoro-4H-1,2,4-triazol-3-yl)-3-(1H-imidazol-1-yl)-5-methoxy-1H-indole | 0.043 |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | 6-chloro-7-fluoro-2-(3-fluoro-1H-1,2,4-triazol-5-yl)-3-(1H-imidazol-1-yl)-5-methoxy-1H-indole | |
| | C | | 6-chloro-7-fluoro-2-(5-fluoro-1H-1,2,4-triazol-3-yl)-3-(1H-imidazol-1-yl)-5-methoxy-1H-indole | |
| 88 | A | 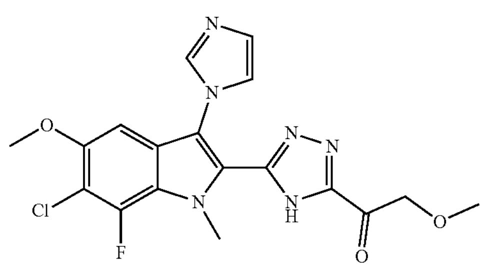 | 1-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-one | 0.075 |
| | B | | 1-(5-(6-chloro-7-fluoro-3-(1H-imidazol-1-yl)-5-methoxy-1-methyl-1H-indol-2-yl)-1H-1,2,4-triazol-3-yl)-2-methoxyethan-1-one | |
| | C | | 1-(3-(6-chloro-7-fluoro-3-(1H-imidazol-1-yl)-5-methoxy-1-methyl-1H-indol-2-yl)-1H-1,2,4-triazol-5-yl)-2-methoxyethan-1-one | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 89 | A | 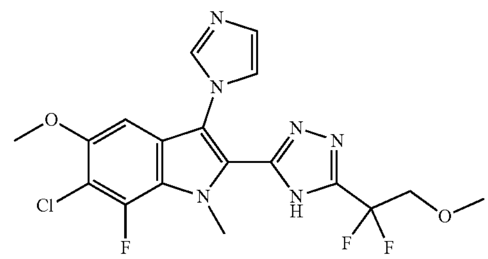 | 6-chloro-2-(5-(1,1-difluoro-2-methoxyethyl)-4H-1,2,4-triazol-3-yl)-7-fluoro-3-(1H-imidazol-1-yl)-5-methoxy-1-methyl-1H-indole | 0.040 |
| | B | | 6-chloro-2-(3-(1,1-difluoro-2-methoxyethyl)-1H-1,2,4-triazol-5-yl)-7-fluoro-3-(1H-imidazol-1-yl)-5-methoxy-1-methyl-1H-indole | |
| | C | | 6-chloro-2-(5-(1,1-difluoro-2-methoxyethyl)-1H-1,2,4-triazol-3-yl)-7-fluoro-3-(1H-imidazol-1-yl)-5-methoxy-1-methyl-1H-indole | |
| 90 | A | 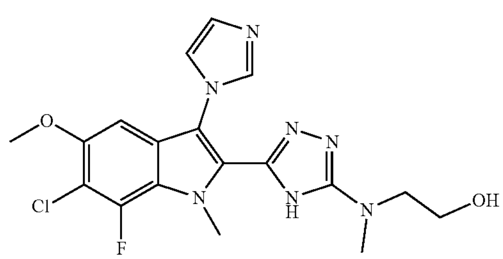 [SMILES: COc1cc2c(-n3ccnc3)c(-c3nnc(N(C)CCO)[nH]3)n(C)c2c(F)c1Cl] | 2-((5-(6-chloro-7-fluoro-3-(1H-imidazol-1-yl)-5-methoxy-1-methyl-1H-indol-2-yl)-4H-1,2,4-triazol-3-yl)(methyl)amino)ethan-1-ol | 0.093 |
| | B | | 2-((5-(6-chloro-7-fluoro-3-(1H-imidazol-1-yl)-5-methoxy-1-methyl-1H-indol-2-yl)-1H-1,2,4-triazol-3-yl)(methyl)amino)ethan-1-ol | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | 2-((3-(6-chloro-7-fluoro-3-(1H-imidazol-1-yl)-5-methoxy-1-methyl-1H-indol-2-yl)-1H-1,2,4-triazol-5-yl)(methyl)amino)ethan-1-ol | |
| 91a | A | 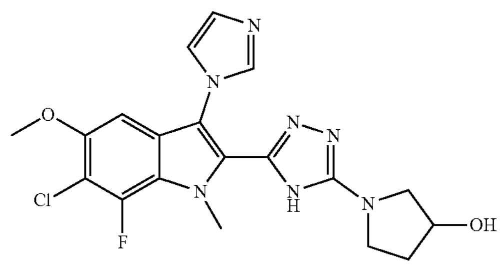 [SMILES: COc1cc2c(-n3ccnc3)c(-c3nnc(N4CCC(O)C4)[nH]3)n(C)c2c(F)c1Cl] | 1-(5-(6-chloro-7-fluoro-3-(1H-imidazol-1-yl)-5-methoxy-1-methyl-1H-indol-2-yl)-4H-1,2,4-triazol-3-yl)pyrrolidin-3-ol | NA |
| | B | | 1-(5-(6-chloro-7-fluoro-3-(1H-imidazol-1-yl)-5-methoxy-1-methyl-1H-indol-2-yl)-1H-1,2,4-triazol-3-yl)pyrrolidin-3-ol | |
| | C | | 1-(3-(6-chloro-7-fluoro-3-(1H-imidazol-1-yl)-5-methoxy-1-methyl-1H-indol-2-yl)-1H-1,2,4-triazol-5-yl)pyrrolidin-3-ol | |
| 91 | A | 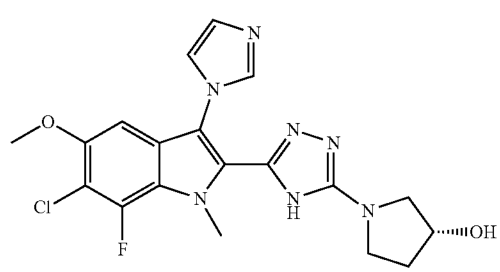 [SMILES: COc1cc2c(-n3ccnc3)c(-c3nnc(N4CC[C@@H](O)C4)[nH]3)n(C)c2c(F)c1Cl] | (R)-1-(5-(6-chloro-7-fluoro-3-(1H-imidazol-1-yl)-5-methoxy-1-methyl-1H-indol-2-yl)-4H-1,2,4-triazol-3-yl)pyrrolidin-3-ol | 0.109 |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | (R)-1-(5-(6-chloro-7-fluoro-3-(1H-imidazol-1-yl)-5-methoxy-1-methyl-1H-indol-2-yl)-1H-1,2,4-triazol-3-yl)pyrrolidin-3-ol | |
| | C | | (R)-1-(3-(6-chloro-7-fluoro-3-(1H-imidazol-1-yl)-5-methoxy-1-methyl-1H-indol-2-yl)-1H-1,2,4-triazol-5-yl)pyrrolidin-3-ol | |
| 92 | A | 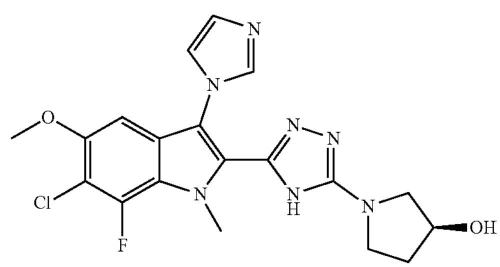 [SMILES: COc1cc2c(-n3ccnc3)c(-c3nnc(N4CC[C@H](O)C4)[nH]3)n(C)c2c(F)c1Cl] | (S)-1-(5-(6-chloro-7-fluoro-3-(1H-imidazol-1-yl)-5-methoxy-1-methyl-1H-indol-2-yl)-4H-1,2,4-triazol-3-yl)pyrrolidin-3-ol | 0.081 |
| | B | | (S)-1-(5-(6-chloro-7-fluoro-3-(1H-imidazol-1-yl)-5-methoxy-1-methyl-1H-indol-2-yl)-1H-1,2,4-triazol-3-yl)pyrrolidin-3-ol | |
| | C | | (S)-1-(3-(6-chloro-7-fluoro-3-(1H-imidazol-1-yl)-5-methoxy-1-methyl-1H-indol-2-yl)-1H-1,2,4-triazol-5-yl)pyrrolidin-3-ol | |

TABLE 1-continued

Illustrative compounds of the disclosure and cGAS inhibition activity

| Example No. | Tautomer | Structure | Name | cGAS IC$_{50}$ [µM] |
|---|---|---|---|---|
| 93 | A | 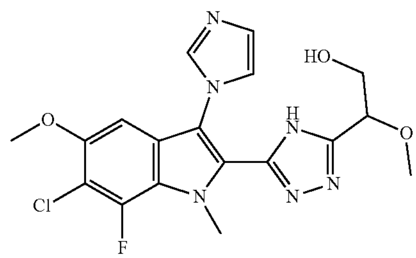 | 2-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-ol | 0.060 |
| | B | | 2-(5-(6-chloro-7-fluoro-3-(1H-imidazol-1-yl)-5-methoxy-1-methyl-1H-indol-2-yl)-1H-1,2,4-triazol-3-yl)-2-methoxyethan-1-ol | |
| | C | | 2-(3-(6-chloro-7-fluoro-3-(1H-imidazol-1-yl)-5-methoxy-1-methyl-1H-indol-2-yl)-1H-1,2,4-triazol-5-yl)-2-methoxyethan-1-ol | |
| 93a | A | 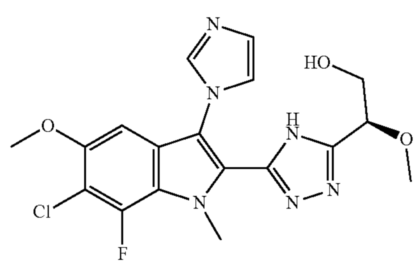 | (S)-2-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-ol | NA |
| | B | | (S)-2-(5-(6-chloro-7-fluoro-3-(1H-imidazol-1-yl)-5-methoxy-1-methyl-1H-indol-2-yl)-1H-1,2,4-triazol-3-yl)-2-methoxyethan-1-ol | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | (S)-2-(3-(6-chloro-7-fluoro-3-(1H-imidazol-1-yl)-5-methoxy-1-methyl-1H-indol-2-yl)-1H-1,2,4-triazol-5-yl)-2-methoxyethan-1-ol | |
| 93b | A | 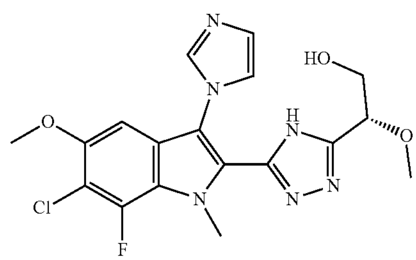 | (R)-2-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-ol | NA |
| | B | | (R)-2-(5-(6-chloro-7-fluoro-3-(1H-imidazol-1-yl)-5-methoxy-1-methyl-1H-indol-2-yl)-1H-1,2,4-triazol-3-yl)-2-methoxyethan-1-ol | |
| | C | | (R)-2-(3-(6-chloro-7-fluoro-3-(1H-imidazol-1-yl)-5-methoxy-1-methyl-1H-indol-2-yl)-1H-1,2,4-triazol-5-yl)-2-methoxyethan-1-ol | |
| 94 | A | 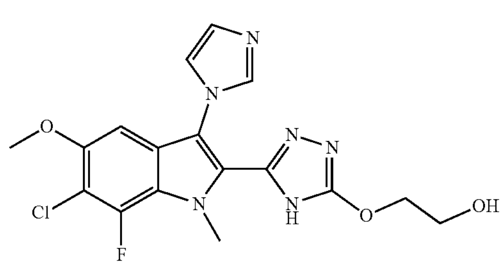 [SMILES: COc1cc2c(-n3ccnc3)c(-c3nnc(OCCO)[nH]3)n(C)c2c(F)c1Cl] | 2-((5-(6-chloro-7-fluoro-3-(1H-imidazol-1-yl)-5-methoxy-1-methyl-1H-indol-2-yl)-4H-1,2,4-triazol-3-yl)oxy)ethan-1-ol | 0.072 |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | 2-((5-(6-chloro-7-fluoro-3-(1H-imidazol-1-yl)-5-methoxy-1-methyl-1H-indol-2-yl)-1H-1,2,4-triazol-3-yl)oxy)ethan-1-ol | |
| | C | | 2-((3-(6-chloro-7-fluoro-3-(1H-imidazol-1-yl)-5-methoxy-1-methyl-1H-indol-2-yl)-1H-1,2,4-triazol-5-yl)oxy)ethan-1-ol | |
| 95 | A | 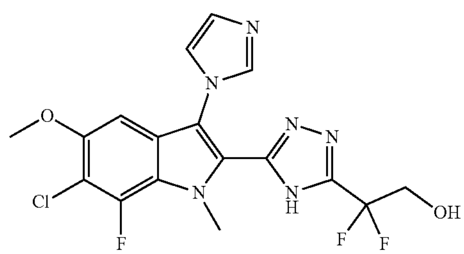 [SMILES: COc1cc2c(-n3ccnc3)c(-c3nnc(C(F)(F)CO)[nH]3)n(C)c2c(F)c1Cl] | 2-(5-(6-chloro-7-fluoro-3-(1H-imidazol-1-yl)-5-methoxy-1-methyl-1H-indol-2-yl)-4H-1,2,4-triazol-3-yl)-2,2-difluoroethan-1-ol | 0.056 |
| | B | | 2-(5-(6-chloro-7-fluoro-3-(1H-imidazol-1-yl)-5-methoxy-1-methyl-1H-indol-2-yl)-1H-1,2,4-triazol-3-yl)-2,2-difluoroethan-1-ol | |
| | C | | 2-(3-(6-chloro-7-fluoro-3-(1H-imidazol-1-yl)-5-methoxy-1-methyl-1H-indol-2-yl)-1H-1,2,4-triazol-5-yl)-2,2-difluoroethan-1-ol | |
| 96 | A | 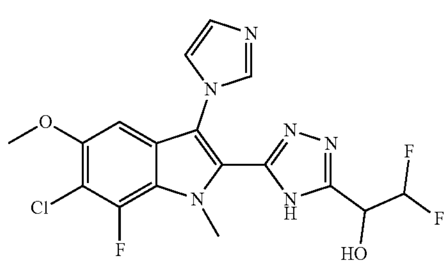 [SMILES: COc1cc2c(-n3ccnc3)c(-c3nnc(C(O)C(F)F)[nH]3)n(C)c2c(F)c1Cl] | 1-(5-(6-chloro-7-fluoro-3-(1H-imidazol-1-yl)-5-methoxy-1-methyl-1H-indol-2-yl)-4H-1,2,4-triazol-3-yl)-2,2-difluoroethan-1-ol | 0.030 |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | 1-(5-(6-chloro-7-fluoro-3-(1H-imidazol-1-yl)-5-methoxy-1-methyl-1H-indol-2-yl)-1H-1,2,4-triazol-3-yl)-2,2-difluoroethan-1-ol | |
| | C | | 1-(3-(6-chloro-7-fluoro-3-(1H-imidazol-1-yl)-5-methoxy-1-methyl-1H-indol-2-yl)-1H-1,2,4-triazol-5-yl)-2,2-difluoroethan-1-ol | |
| 96a | A | 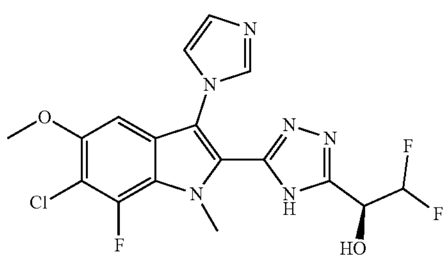 [SMILES: COc1cc2c(-n3ccnc3)c(-c3nnc([C@H](O)C(F)F)[nH]3)n(C)c2c(F)c1Cl] | (S)-1-(5-(6-chloro-7-fluoro-3-(1H-imidazol-1-yl)-5-methoxy-1-methyl-1H-indol-2-yl)-4H-1,2,4-triazol-3-yl)-2,2-difluoroethan-1-ol | NA |
| | B | | (S)-1-(5-(6-chloro-7-fluoro-3-(1H-imidazol-1-yl)-5-methoxy-1-methyl-1H-indol-2-yl)-1H-1,2,4-triazol-3-yl)-2,2-difluoroethan-1-ol | |
| | C | | (S)-1-(3-(6-chloro-7-fluoro-3-(1H-imidazol-1-yl)-5-methoxy-1-methyl-1H-indol-2-yl)-1H-1,2,4-triazol-5-yl)-2,2-difluoroethan-1-ol | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 96b | A | 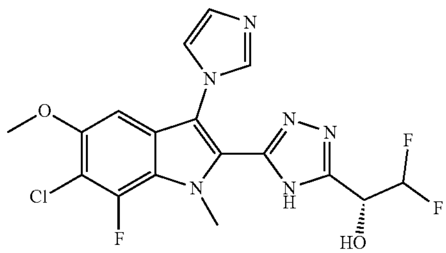 [SMILES: COc1cc2c(-n3ccnc3)c(-c3nnc([C@@H](O)C(F)F)[nH]3)n(C)c2c(F)c1Cl] | (R)-1-(5-(6-chloro-7-fluoro-3-(1H-imidazol-1-yl)-5-methoxy-1-methyl-1H-indol-2-yl)-4H-1,2,4-triazol-3-yl)-2,2-difluoroethan-1-ol | NA |
| | B | | (R)-1-(5-(6-chloro-7-fluoro-3-(1H-imidazol-1-yl)-5-methoxy-1-methyl-1H-indol-2-yl)-1H-1,2,4-triazol-3-yl)-2,2-difluoroethan-1-ol | |
| | C | | (R)-1-(3-(6-chloro-7-fluoro-3-(1H-imidazol-1-yl)-5-methoxy-1-methyl-1H-indol-2-yl)-1H-1,2,4-triazol-5-yl)-2,2-difluoroethan-1-ol | |
| 97 | A | 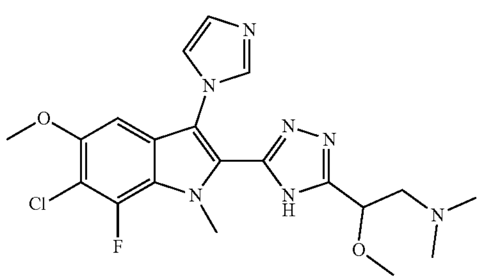 | 2-(5-(6-chloro-7-fluoro-3-(1H-imidazol-1-yl)-5-methoxy-1-methyl-1H-indol-2-yl)-4H-1,2,4-triazol-3-yl)-2-methoxy-N,N-dimethylethan-1-amine | 0.104 |
| | B | | 2-(5-(6-chloro-7-fluoro-3-(1H-imidazol-1-yl)-5-methoxy-1-methyl-1H-indol-2-yl)-1H-1,2,4-triazol-3-yl)-2-methoxy-N,N-dimethylethan-1-amine | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | 2-(3-(6-chloro-7-fluoro-3-(1H-imidazol-1-yl)-5-methoxy-1-methyl-1H-indol-2-yl)-1H-1,2,4-triazol-5-yl)-2-methoxy-N,N-dimethylethan-1-amine | |
| 97a | A | 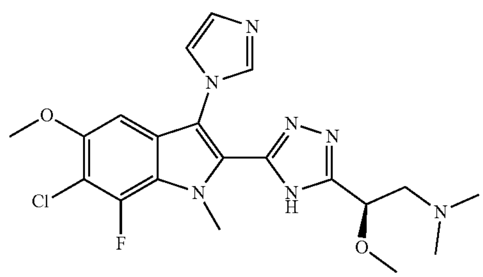 | (R)-2-(5-(6-chloro-7-fluoro-3-(1H-imidazol-1-yl)-5-methoxy-1-methyl-1H-indol-2-yl)-4H-1,2,4-triazol-3-yl)-2-methoxy-N,N-dimethylethan-1-amine | NA |
| | B | | (R)-2-(5-(6-chloro-7-fluoro-3-(1H-imidazol-1-yl)-5-methoxy-1-methyl-1H-indol-2-yl)-1H-1,2,4-triazol-3-yl)-2-methoxy-N,N-dimethylethan-1-amine | |
| | C | | (R)-2-(3-(6-chloro-7-fluoro-3-(1H-imidazol-1-yl)-5-methoxy-1-methyl-1H-indol-2-yl)-1H-1,2,4-triazol-5-yl)-2-methoxy-N,N-dimethylethan-1-amine | |
| 97b | A | 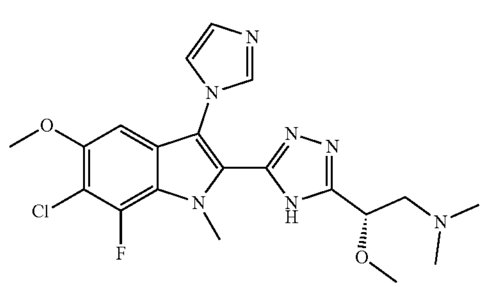 | (S)-2-(5-(6-chloro-7-fluoro-3-(1H-imidazol-1-yl)-5-methoxy-1-methyl-1H-indol-2-yl)-4H-1,2,4-triazol-3-yl)-2-methoxy-N,N-dimethylethan-1-amine | NA |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | (S)-2-(5-(6-chloro-7-fluoro-3-(1H-imidazol-1-yl)-5-methoxy-1-methyl-1H-indol-2-yl)-1H-1,2,4-triazol-3-yl)-2-methoxy-N,N-dimethylethan-1-amine | |
| | C | | (S)-2-(3-(6-chloro-7-fluoro-3-(1H-imidazol-1-yl)-5-methoxy-1-methyl-1H-indol-2-yl)-1H-1,2,4-triazol-5-yl)-2-methoxy-N,N-dimethylethan-1-amine | |
| 98 | A | 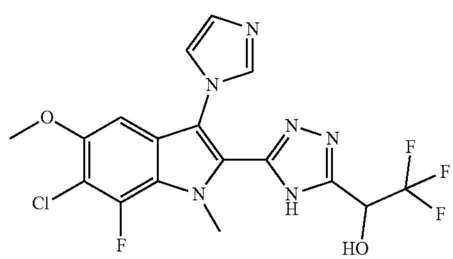 [SMILES: COc1cc2c(-n3ccnc3)c(-c3nnc(C(O)C(F)(F)F)[nH]3)n(C)c2c(F)c1Cl] | 1-(5-(6-chloro-7-fluoro-3-(1H-imidazol-1-yl)-5-methoxy-1-methyl-1H-indol-2-yl)-4H-1,2,4-triazol-3-yl)-2,2,2-trifluoroethan-1-ol | 0.037 |
| | B | | 1-(5-(6-chloro-7-fluoro-3-(1H-imidazol-1-yl)-5-methoxy-1-methyl-1H-indol-2-yl)-1H-1,2,4-triazol-3-yl)-2,2,2-trifluoroethan-1-ol | |
| | C | | 1-(3-(6-chloro-7-fluoro-3-(1H-imidazol-1-yl)-5-methoxy-1-methyl-1H-indol-2-yl)-1H-1,2,4-triazol-5-yl)-2,2,2-trifluoroethan-1-ol | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 98a | A | 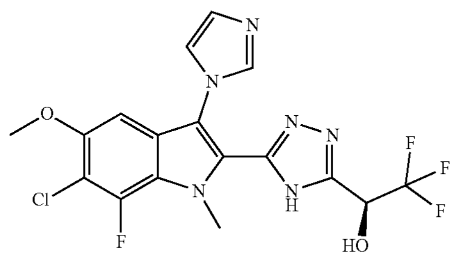 [SMILES: COc1cc2c(-n3ccnc3)c(-c3nnc([C@H](O)C(F)(F)F)[nH]3)n(C)c2c(F)c1Cl] | (S)-1-(5-(6-chloro-7-fluoro-3-(1H-imidazol-1-yl)-5-methoxy-1-methyl-1H-indol-2-yl)-4H-1,2,4-triazol-3-yl)-2,2,2-trifluoroethan-1-ol | NA |
| | B | | (S)-1-(5-(6-chloro-7-fluoro-3-(1H-imidazol-1-yl)-5-methoxy-1-methyl-1H-indol-2-yl)-1H-1,2,4-triazol-3-yl)-2,2,2-trifluoroethan-1-ol | |
| | C | | (S)-1-(3-(6-chloro-7-fluoro-3-(1H-imidazol-1-yl)-5-methoxy-1-methyl-1H-indol-2-yl)-1H-1,2,4-triazol-5-yl)-2,2,2-trifluoroethan-1-ol | |
| 98b | A | 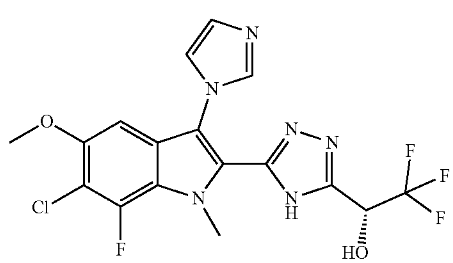 [SMILES: COc1cc2c(-n3ccnc3)c(-c3nnc([C@@H](O)C(F)(F)F)[nH]3)n(C)c2c(F)c1Cl] | (R)-1-(5-(6-chloro-7-fluoro-3-(1H-imidazol-1-yl)-5-methoxy-1-methyl-1H-indol-2-yl)-4H-1,2,4-triazol-3-yl)-2,2,2-trifluoroethan-1-ol | NA |
| | B | | (R)-1-(5-(6-chloro-7-fluoro-3-(1H-imidazol-1-yl)-5-methoxy-1-methyl-1H-indol-2-yl)-1H-1,2,4-triazol-3-yl)-2,2,2-trifluoroethan-1-ol | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | (R)-1-(3-(6-chloro-7-fluoro-3-(1H-imidazol-1-yl)-5-methoxy-1-methyl-1H-indol-2-yl)-1H-1,2,4-triazol-5-yl)-2,2,2-trifluoroethan-1-ol | |
| 99 | A | 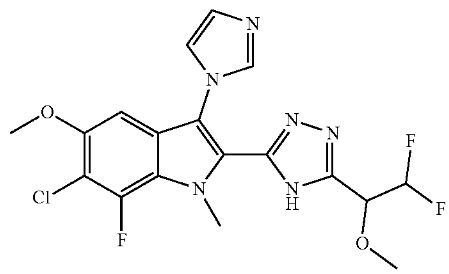 [SMILES: COc1cc2c(-n3ccnc3)c(-c3nnc(C(OC)C(F)F)[nH]3)n(C)c2c(F)c1Cl] | 6-chloro-2-(5-(2,2-difluoro-1-methoxyethyl)-4H-1,2,4-triazol-3-yl)-7-fluoro-3-(1H-imidazol-1-yl)-5-methoxy-1-methyl-1H-indole | 0.064 |
| | B | | 6-chloro-2-(3-(2,2-difluoro-1-methoxyethyl)-1H-1,2,4-triazol-5-yl)-7-fluoro-3-(1H-imidazol-1-yl)-5-methoxy-1-methyl-1H-indole | |
| | C | | 6-chloro-2-(5-(2,2-difluoro-1-methoxyethyl)-1H-1,2,4-triazol-3-yl)-7-fluoro-3-(1H-imidazol-1-yl)-5-methoxy-1-methyl-1H-indole | |
| 99a | A | 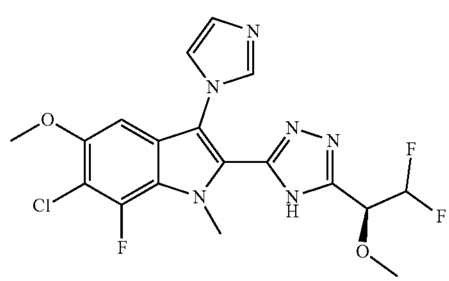 [SMILES: COc1cc2c(-n3ccnc3)c(-c3nnc([C@H](OC)C(F)F)[nH]3)n(C)c2c(F)c1Cl] | (S)-6-chloro-2-(5-(2,2-difluoro-1-methoxyethyl)-4H-1,2,4-triazol-3-yl)-7-fluoro-3-(1H-imidazol-1-yl)-5-methoxy-1-methyl-1H-indole | NA |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | (S)-6-chloro-2-(3-(2,2-difluoro-1-methoxyethyl)-1H-1,2,4-triazol-5-yl)-7-fluoro-3-(1H-imidazol-1-yl)-5-methoxy-1-methyl-1H-indole | |
| | C | | (S)-6-chloro-2-(5-(2,2-difluoro-1-methoxyethyl)-1H-1,2,4-triazol-3-yl)-7-fluoro-3-(1H-imidazol-1-yl)-5-methoxy-1-methyl-1H-indole | |
| 99b | A | 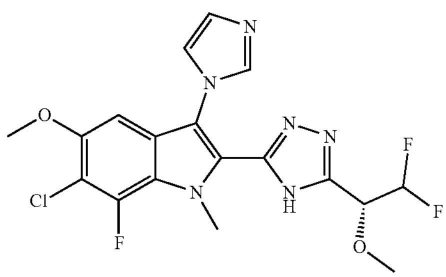 | (R)-6-chloro-2-(5-(2,2-difluoro-1-methoxyethyl)-4H-1,2,4-triazol-3-yl)-7-fluoro-3-(1H-imidazol-1-yl)-5-methoxy-1-methyl-1H-indole | NA |
| | B | | (R)-6-chloro-2-(3-(2,2-difluoro-1-methoxyethyl)-1H-1,2,4-triazol-5-yl)-7-fluoro-3-(1H-imidazol-1-yl)-5-methoxy-1-methyl-1H-indole | |
| | C | | (R)-6-chloro-2-(5-(2,2-difluoro-1-methoxyethyl)-1H-1,2,4-triazol-3-yl)-7-fluoro-3-(1H-imidazol-1-yl)-5-methoxy-1-methyl-1H-indole | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 100 | A | 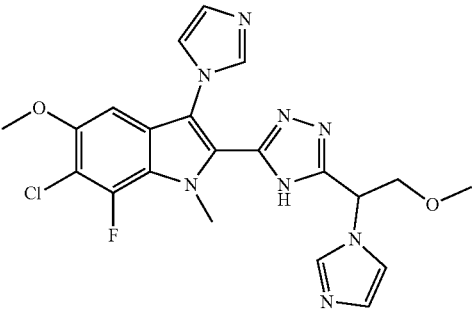 | 2-(5-(1-(1H-imidazol-1-yl)-2-methoxyethyl)-4H-1,2,4-triazol-3-yl)-6-chloro-7-fluoro-3-(1H-imidazol-1-yl)-5-methoxy-1-methyl-1H-indole | 0.065 |
|  | B | 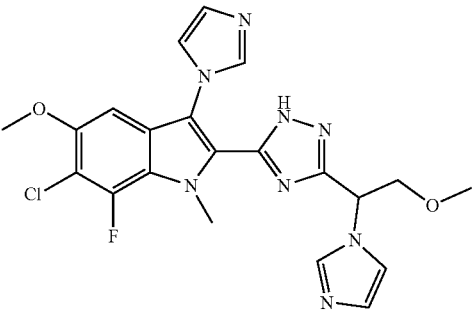 | 2-(3-(1-(1H-imidazol-1-yl)-2-methoxyethyl)-1H-1,2,4-triazol-5-yl)-6-chloro-7-fluoro-3-(1H-imidazol-1-yl)-5-methoxy-1-methyl-1H-indole |  |
|  | C | 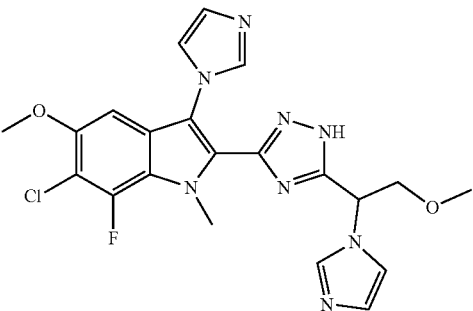 | 2-(5-(1-(1H-imidazol-1-yl)-2-methoxyethyl)-1H-1,2,4-triazol-3-yl)-6-chloro-7-fluoro-3-(1H-imidazol-1-yl)-5-methoxy-1-methyl-1H-indole |  |
| 100a | A | 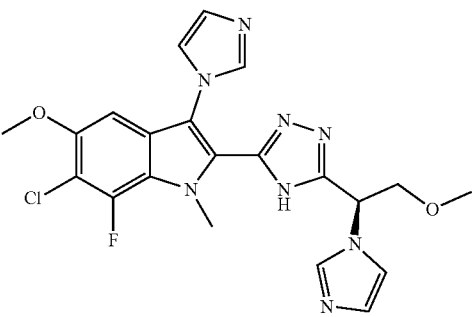 | (S)-2-(5-(1-(1H-imidazol-1-yl)-2-methoxyethyl)-4H-1,2,4-triazol-3-yl)-6-chloro-7-fluoro-3-(1H-imidazol-1-yl)-5-methoxy-1-methyl-1H-indole | NA |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | (S)-2-(3-(1-(1H-imidazol-1-yl)-2-methoxyethyl)-1H-1,2,4-triazol-5-yl)-6-chloro-7-fluoro-3-(1H-imidazol-1-yl)-5-methoxy-1-methyl-1H-indole | |
| | C | | (S)-2-(5-(1-(1H-imidazol-1-yl)-2-methoxyethyl)-1H-1,2,4-triazol-3-yl)-6-chloro-7-fluoro-3-(1H-imidazol-1-yl)-5-methoxy-1-methyl-1H-indole | |
| 100b | A | 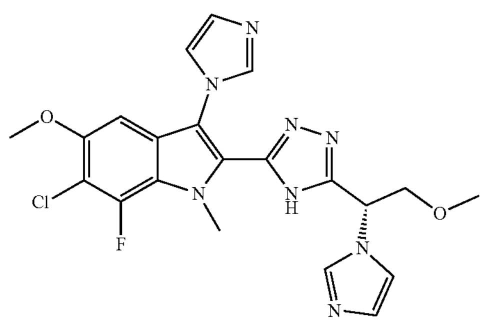 | (R)-2-(5-(1-(1H-imidazol-1-yl)-2-methoxyethyl)-4H-1,2,4-triazol-3-yl)-6-chloro-7-fluoro-3-(1H-imidazol-1-yl)-5-methoxy-1-methyl-1H-indole | NA |
| | B | | (R)-2-(3-(1-(1H-imidazol-1-yl)-2-methoxyethyl)-1H-1,2,4-triazol-5-yl)-6-chloro-7-fluoro-3-(1H-imidazol-1-yl)-5-methoxy-1-methyl-1H-indole | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | (R)-2-(5-(1-(1H-imidazol-1-yl)-2-methoxyethyl)-1H-1,2,4-triazol-3-yl)-6-chloro-7-fluoro-3-(1H-imidazol-1-yl)-5-methoxy-1-methyl-1H-indole | |
| 101 | A | 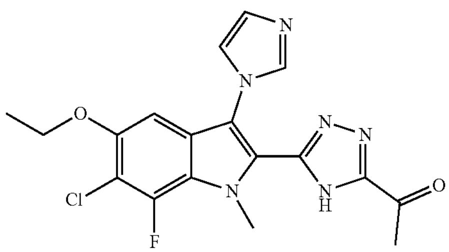 [SMILES: CCOc1cc2c(-n3ccnc3)c(-c3nnc(C(C)=O)[nH]3)n(C)c2c(F)c1Cl] | 1-(5-(6-chloro-5-ethoxy-7-fluoro-3-(1H-imidazol-1-yl)-1-methyl-1H-indol-2-yl)-4H-1,2,4-triazol-3-yl)ethan-1-one | 0.721 |
| | B | | 1-(5-(6-chloro-5-ethoxy-7-fluoro-3-(1H-imidazol-1-yl)-1-methyl-1H-indol-2-yl)-1H-1,2,4-triazol-3-yl)ethan-1-one | |
| | C | | 1-(3-(6-chloro-5-ethoxy-7-fluoro-3-(1H-imidazol-1-yl)-1-methyl-1H-indol-2-yl)-1H-1,2,4-triazol-5-yl)ethan-1-one | |
| 102 | A | 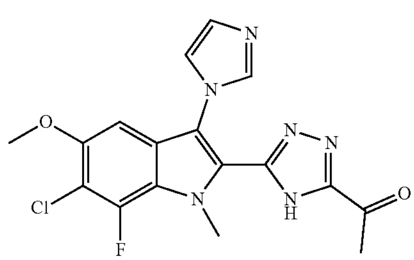 [SMILES: COc1cc2c(-n3ccnc3)c(-c3nnc(C(C)=O)[nH]3)n(C)c2c(F)c1Cl] | 1-(5-(6-chloro-7-fluoro-3-(1H-imidazol-1-yl)-5-methoxy-1-methyl-1H-indol-2-yl)-4H-1,2,4-triazol-3-yl)ethan-1-one | 0.108 |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | 1-(5-(6-chloro-7-fluoro-3-(1H-imidazol-1-yl)-5-methoxy-1-methyl-1H-indol-2-yl)-1H-1,2,4-triazol-3-yl)ethan-1-one | |
| | C | | 1-(3-(6-chloro-7-fluoro-3-(1H-imidazol-1-yl)-5-methoxy-1-methyl-1H-indol-2-yl)-1H-1,2,4-triazol-5-yl)ethan-1-one | |
| 103 | A | 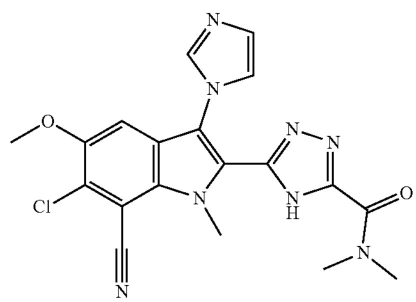 [SMILES: COc1cc2c(-n3ccnc3)c(-c3nnc(C(=O)N(C)C)[nH]3)n(C)c2c(C#N)c1Cl] | 5-(6-chloro-7-cyano-3-(1H-imidazol-1-yl)-5-methoxy-1-methyl-1H-indol-2-yl)-N,N-dimethyl-4H-1,2,4-triazole-3-carboxamide | 0.171 |
| | B | | 5-(6-chloro-7-cyano-3-(1H-imidazol-1-yl)-5-methoxy-1-methyl-1H-indol-2-yl)-N,N-dimethyl-1H-1,2,4-triazole-3-carboxamide | |
| | C | | 3-(6-chloro-7-cyano-3-(1H-imidazol-1-yl)-5-methoxy-1-methyl-1H-indol-2-yl)-N,N-dimethyl-1H-1,2,4-triazole-5-carboxamide | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 104 | A | 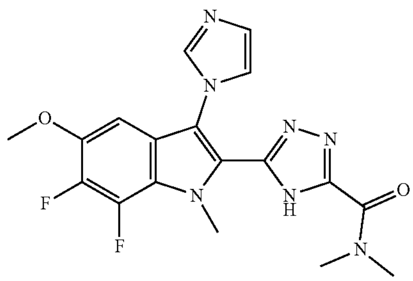 [SMILES: COc1cc2c(-n3ccnc3)c(-c3nnc(C(=O)N(C)C)[nH]3)n(C)c2c(F)c1F] | 5-(6,7-difluoro-3-(1H-imidazol-1-yl)-5-methoxy-1-methyl-1H-indol-2-yl)-N,N-dimethyl-4H-1,2,4-triazole-3-carboxamide | 0.318 |
| | B | | 5-(6,7-difluoro-3-(1H-imidazol-1-yl)-5-methoxy-1-methyl-1H-indol-2-yl)-N,N-dimethyl-1H-1,2,4-triazole-3-carboxamide | |
| | C | | 3-(6,7-difluoro-3-(1H-imidazol-1-yl)-5-methoxy-1-methyl-1H-indol-2-yl)-N,N-dimethyl-1H-1,2,4-triazole-5-carboxamide | |
| 105 | A | 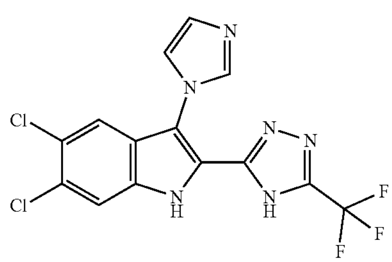 [SMILES: FC(F)(F)c1nnc(-c2[nH]c3cc(Cl)c(Cl)cc3c2-n2ccnc2)[nH]1] | 5,6-dichloro-3-(1H-imidazol-1-yl)-2-(5-(trifluoromethyl)-4H-1,2,4-triazol-3-yl)-1H-indole | 0.564 |
| | B | | 5,6-dichloro-3-(1H-imidazol-1-yl)-2-(3-(trifluoromethyl)-1H-1,2,4-triazol-5-yl)-1H-indole | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | 5,6-dichloro-3-(1H-imidazol-1-yl)-2-(5-(trifluoromethyl)-1H-1,2,4-triazol-3-yl)-1H-indole | |
| 106 | A | 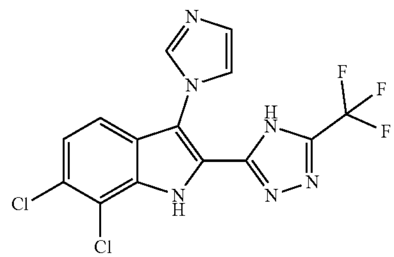 [SMILES: FC(F)(F)c1nnc(-c2[nH]c3c(Cl)c(Cl)ccc3c2-n2ccnc2)[nH]1] | 6,7-dichloro-3-(1H-imidazol-1-yl)-2-(5-(trifluoromethyl)-4H-1,2,4-triazol-3-yl)-1H-indole | 0.095 |
| | B | | 6,7-dichloro-3-(1H-imidazol-1-yl)-2-(3-(trifluoromethyl)-1H-1,2,4-triazol-5-yl)-1H-indole | |
| | C | | 6,7-dichloro-3-(1H-imidazol-1-yl)-2-(5-(trifluoromethyl)-1H-1,2,4-triazol-3-yl)-1H-indole | |
| 107 | A | 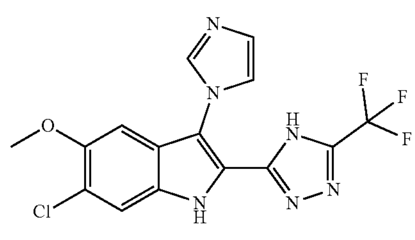 [SMILES: COc1cc2c(-n3ccnc3)c(-c3nnc(C(F)(F)F)[nH]3)[nH]c2cc1Cl] | 6-chloro-3-(1H-imidazol-1-yl)-5-methoxy-2-(5-(trifluoromethyl)-4H-1,2,4-triazol-3-yl)-1H-indole | 0.079 |
| | B | | 6-chloro-3-(1H-imidazol-1-yl)-5-methoxy-2-(3-(trifluoromethyl)-1H-1,2,4-triazol-5-yl)-1H-indole | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | 6-chloro-3-(1H-imidazol-1-yl)-5-methoxy-2-(5-(trifluoromethyl)-1H-1,2,4-triazol-3-yl)-1H-indole | |
| 108 | A | 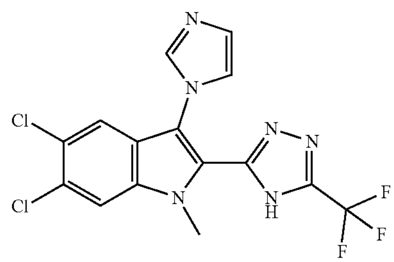 [SMILES: Cn1c(-c2nnc(C(F)(F)F)[nH]2)c(-n2ccnc2)c2cc(Cl)c(Cl)cc21] | 5,6-dichloro-3-(1H-imidazol-1-yl)-1-methyl-2-(5-(trifluoromethyl)-4H-1,2,4-triazol-3-yl)-1H-indole | 0.282 |
| | B | | 5,6-dichloro-3-(1H-imidazol-1-yl)-1-methyl-2-(3-(trifluoromethyl)-1H-1,2,4-triazol-5-yl)-1H-indole | |
| | C | | 5,6-dichloro-3-(1H-imidazol-1-yl)-1-methyl-2-(5-(trifluoromethyl)-1H-1,2,4-triazol-3-yl)-1H-indole | |
| 109 | A | 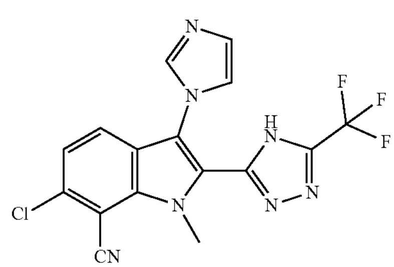 [SMILES: Cn1c(-c2nnc(C(F)(F)F)[nH]2)c(-n2ccnc2)c2ccc(Cl)c(C#N)c21] | 6,7-dichloro-3-(1H-imidazol-1-yl)-1-methyl-2-(5-(trifluoromethyl)-4H-1,2,4-triazol-3-yl)-1H-indole | 0.085 |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | 6,7-dichloro-3-(1H-imidazol-1-yl)-1-methyl-2-(3-(trifluoromethyl)-1H-1,2,4-triazol-5-yl)-1H-indole | |
| | C | | 6,7-dichloro-3-(1H-imidazol-1-yl)-1-methyl-2-(5-(trifluoromethyl)-1H-1,2,4-triazol-3-yl)-1H-indole | |
| 110 | A | 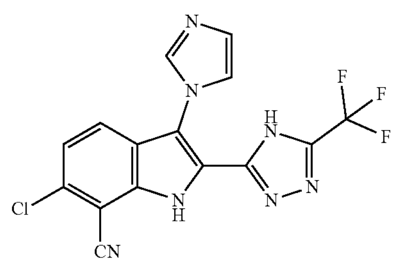 [SMILES: N#Cc1c(Cl)ccc2c(-n3ccnc3)c(-c3nnc(C(F)(F)F)[nH]3)[nH]c12] | 6-chloro-3-(1H-imidazol-1-yl)-2-(5-(trifluoromethyl)-4H-1,2,4-triazol-3-yl)-1H-indole-7-carbonitrile | 0.226 |
| | B | | 6-chloro-3-(1H-imidazol-1-yl)-2-(3-(trifluoromethyl)-1H-1,2,4-triazol-5-yl)-1H-indole-7-carbonitrile | |
| | C | | 6-chloro-3-(1H-imidazol-1-yl)-2-(5-(trifluoromethyl)-1H-1,2,4-triazol-3-yl)-1H-indole-7-carbonitrile | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 111 | A | 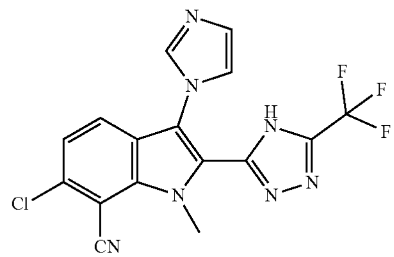 [SMILES: Cn1c(-c2nnc(C(F)(F)F)[nH]2)c(-n2ccnc2)c2ccc(Cl)c(C#N)c21] | 6-chloro-3-(1H-imidazol-1-yl)-1-methyl-2-(5-(trifluoromethyl)-4H-1,2,4-triazol-3-yl)-1H-indole-7-carbonitrile | 0.201 |
| | B | | 6-chloro-3-(1H-imidazol-1-yl)-1-methyl-2-(3-(trifluoromethyl)-1H-1,2,4-triazol-5-yl)-1H-indole-7-carbonitrile | |
| | C | | 6-chloro-3-(1H-imidazol-1-yl)-1-methyl-2-(5-(trifluoromethyl)-1H-1,2,4-triazol-3-yl)-1H-indole-7-carbonitrile | |
| 112 | A | 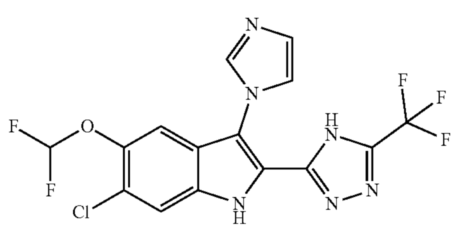 [SMILES: FC(F)Oc1cc2c(-n3ccnc3)c(-c3nnc(C(F)(F)F)[nH]3)[nH]c2cc1Cl] | 6-chloro-5-(difluoromethoxy)-3-(1H-imidazol-1-yl)-2-(5-(trifluoromethyl)-4H-1,2,4-triazol-3-yl)-1H-indole | 0.659 |
| | B | | 6-chloro-5-(difluoromethoxy)-3-(1H-imidazol-1-yl)-2-(3-(trifluoromethyl)-1H-1,2,4-triazol-5-yl)-1H-indole | |
| | C | | 6-chloro-5-(difluoromethoxy)-3-(1H-imidazol-1-yl)-2-(5-(trifluoromethyl)-1H-1,2,4-triazol-3-yl)-1H-indole | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 113 | A | 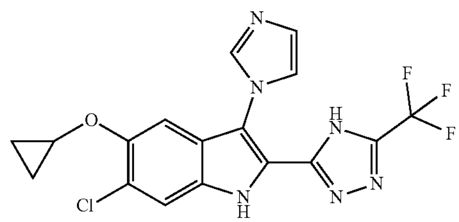 [SMILES: FC(F)(F)c1nnc(-c2[nH]c3cc(Cl)c(OC4CC4)cc3c2-n2ccnc2)[nH]1] | 6-chloro-5-cyclopropoxy-3-(1H-imidazol-1-yl)-2-(5-(trifluoromethyl)-4H-1,2,4-triazol-3-yl)-1H-indole | 0.861 |
| | B | | 6-chloro-5-cyclopropoxy-3-(1H-imidazol-1-yl)-2-(3-(trifluoromethyl)-1H-1,2,4-triazol-5-yl)-1H-indole | |
| | C | | 6-chloro-5-cyclopropoxy-3-(1H-imidazol-1-yl)-2-(5-(trifluoromethyl)-1H-1,2,4-triazol-3-yl)-1H-indole | |
| 114 | A | 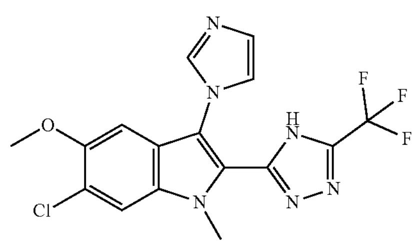 [SMILES: COc1cc2c(-n3ccnc3)c(-c3nnc(C(F)(F)F)[nH]3)n(C)c2cc1Cl] | 6-chloro-3-(1H-imidazol-1-yl)-5-methoxy-1-methyl-2-(5-(trifluoromethyl)-4H-1,2,4-triazol-3-yl)-1H-indole | 0.140 |
| | B | | 6-chloro-3-(1H-imidazol-1-yl)-5-methoxy-1-methyl-2-(3-(trifluoromethyl)-1H-1,2,4-triazol-5-yl)-1H-indole | |
| | C | | 6-chloro-3-(1H-imidazol-1-yl)-5-methoxy-1-methyl-2-(5-(trifluoromethyl)-1H-1,2,4-triazol-3-yl)-1H-indole | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 115 | A | 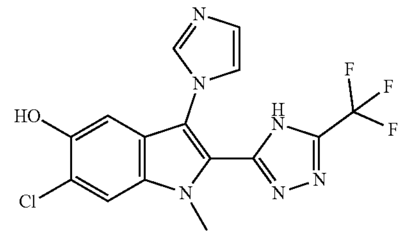 [SMILES: Cn1c(-c2nnc(C(F)(F)F)[nH]2)c(-n2ccnc2)c2cc(O)c(Cl)cc21] | 6-chloro-3-(1H-imidazol-1-yl)-1-methyl-2-(5-(trifluoromethyl)-4H-1,2,4-triazol-3-yl)-1H-indol-5-ol | 0.067 |
| | B | | 6-chloro-3-(1H-imidazol-1-yl)-1-methyl-2-(3-(trifluoromethyl)-1H-1,2,4-triazol-5-yl)-1H-indol-5-ol | |
| | C | | 6-chloro-3-(1H-imidazol-1-yl)-1-methyl-2-(5-(trifluoromethyl)-1H-1,2,4-triazol-3-yl)-1H-indol-5-ol | |
| 116 | A | 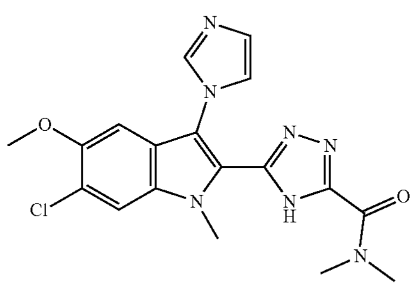 [SMILES: COc1cc2c(-n3ccnc3)c(-c3nnc(C(=O)N(C)C)[nH]3)n(C)c2cc1Cl] | 5-(6-chloro-3-(1H-imidazol-1-yl)-5-methoxy-1-methyl-1H-indol-2-yl)-N,N-dimethyl-4H-1,2,4-triazole-3-carboxamide | 0.103 |
| | B | | 5-(6-chloro-3-(1H-imidazol-1-yl)-5-methoxy-1-methyl-1H-indol-2-yl)-N,N-dimethyl-1H-1,2,4-triazole-3-carboxamide | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | 3-(6-chloro-3-(1H-imidazol-1-yl)-5-methoxy-1-methyl-1H-indol-2-yl)-N,N-dimethyl-1H-1,2,4-triazole-5-carboxamide | |
| 117 | A | 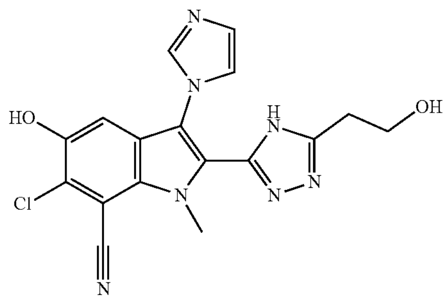 [SMILES: Cn1c(-c2nnc(CCO)[nH]2)c(-n2ccnc2)c2cc(O)c(Cl)c(C#N)c21] | 6-chloro-5-hydroxy-2-(5-(2-hydroxyethyl)-4H-1,2,4-triazol-3-yl)-3-(1H-imidazol-1-yl)-1-methyl-1H-indole-7-carbonitrile | 0.169 |
| | B | | 6-chloro-5-hydroxy-2-(3-(2-hydroxyethyl)-1H-1,2,4-triazol-5-yl)-3-(1H-imidazol-1-yl)-1-methyl-1H-indole-7-carbonitrile | |
| | C | | 6-chloro-5-hydroxy-2-(5-(2-hydroxyethyl)-1H-1,2,4-triazol-3-yl)-3-(1H-imidazol-1-yl)-1-methyl-1H-indole-7-carbonitrile | |
| 118 | A | 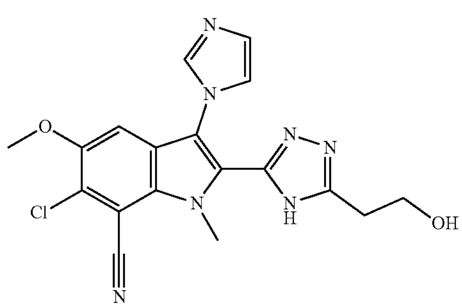 [SMILES: COc1cc2c(-n3ccnc3)c(-c3nnc(CCO)[nH]3)n(C)c2c(C#N)c1Cl] | 6-chloro-2-(5-(2-hydroxyethyl)-4H-1,2,4-triazol-3-yl)-3-(1H-imidazol-1-yl)-5-methoxy-1-methyl-1H-indole-7-carbonitrile | 0.291 |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | 6-chloro-2-(3-(2-hydroxyethyl)-1H-1,2,4-triazol-5-yl)-3-(1H-imidazol-1-yl)-5-methoxy-1-methyl-1H-indole-7-carbonitrile | |
| | C | | 6-chloro-2-(5-(2-hydroxyethyl)-1H-1,2,4-triazol-3-yl)-3-(1H-imidazol-1-yl)-5-methoxy-1-methyl-1H-indole-7-carbonitrile | |
| 119 | A | 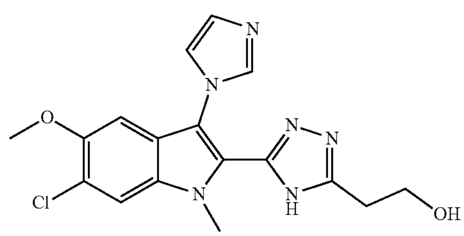 [SMILES: COc1cc2c(-n3ccnc3)c(-c3nnc(CCO)[nH]3)n(C)c2cc1Cl] | 2-(5-(6-chloro-3-(1H-imidazol-1-yl)-5-methoxy-1-methyl-1H-indol-2-yl)-4H-1,2,4-triazol-3-yl)ethan-1-ol | 0.990 |
| | B | | 2-(5-(6-chloro-3-(1H-imidazol-1-yl)-5-methoxy-1-methyl-1H-indol-2-yl)-1H-1,2,4-triazol-3-yl)ethan-1-ol | |
| | C | | 2-(3-(6-chloro-3-(1H-imidazol-1-yl)-5-methoxy-1-methyl-1H-indol-2-yl)-1H-1,2,4-triazol-5-yl)ethan-1-ol | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 120 | A | 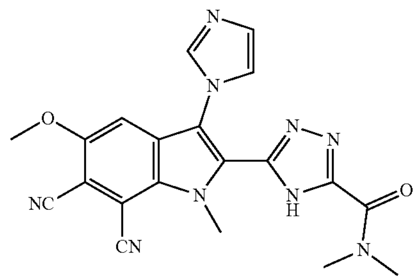 [SMILES: COc1cc2c(-n3ccnc3)c(-c3nnc(C(=O)N(C)C)[nH]3)n(C)c2c(C#N)c1C#N] | 5-(6,7-dicyano-3-(1H-imidazol-1-yl)-5-methoxy-1-methyl-1H-indol-2-yl)-N,N-dimethyl-4H-1,2,4-triazole-3-carboxamide | 0.172 |
| | B | | 5-(6,7-dicyano-3-(1H-imidazol-1-yl)-5-methoxy-1-methyl-1H-indol-2-yl)-N,N-dimethyl-1H-1,2,4-triazole-3-carboxamide | |
| | C | | 3-(6,7-dicyano-3-(1H-imidazol-1-yl)-5-methoxy-1-methyl-1H-indol-2-yl)-N,N-dimethyl-1H-1,2,4-triazole-5-carboxamide | |
| 121 | A | 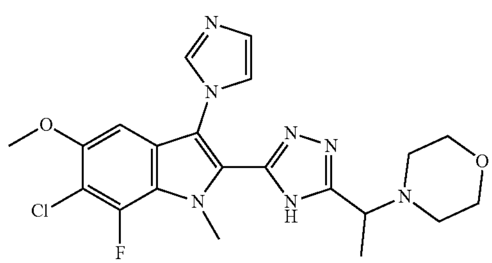 [SMILES: COc1cc2c(-n3ccnc3)c(-c3nnc(C(C)N4CCOCC4)[nH]3)n(C)c2c(F)c1Cl] | 4-(1-(5-(6-chloro-7-fluoro-3-(1H-imidazol-1-yl)-5-methoxy-1-methyl-1H-indol-2-yl)-4H-1,2,4-triazol-3-yl)ethyl)morpholine | 0.080 |
| | B | | 4-(1-(5-(6-chloro-7-fluoro-3-(1H-imidazol-1-yl)-5-methoxy-1-methyl-1H-indol-2-yl)-1H-1,2,4-triazol-3-yl)ethyl)morpholine | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | 4-(1-(3-(6-chloro-7-fluoro-3-(1H-imidazol-1-yl)-5-methoxy-1-methyl-1H-indol-2-yl)-1H-1,2,4-triazol-5-yl)ethyl)morpholine | |
| 121a | A | 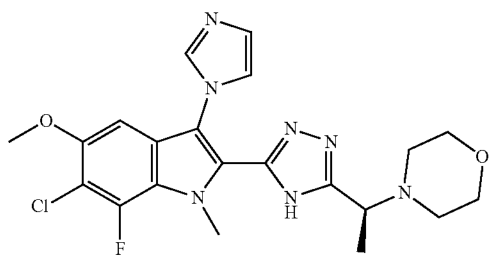 [SMILES: COc1cc2c(-n3ccnc3)c(-c3nnc([C@H](C)N4CCOCC4)[nH]3)n(C)c2c(F)c1Cl] | (S)-4-(1-(5-(6-chloro-7-fluoro-3-(1H-imidazol-1-yl)-5-methoxy-1-methyl-1H-indol-2-yl)-4H-1,2,4-triazol-3-yl)ethyl)morpholine | NA |
| | B | | (S)-4-(1-(5-(6-chloro-7-fluoro-3-(1H-imidazol-1-yl)-5-methoxy-1-methyl-1H-indol-2-yl)-1H-1,2,4-triazol-3-yl)ethyl)morpholine | |
| | C | | (S)-4-(1-(3-(6-chloro-7-fluoro-3-(1H-imidazol-1-yl)-5-methoxy-1-methyl-1H-indol-2-yl)-1H-1,2,4-triazol-5-yl)ethyl)morpholine | |
| 121b | A | 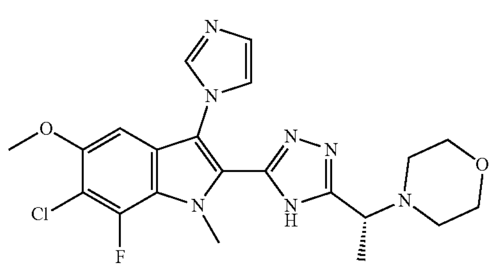 [SMILES: COc1cc2c(-n3ccnc3)c(-c3nnc([C@@H](C)N4CCOCC4)[nH]3)n(C)c2c(F)c1Cl] | (R)-4-(1-(5-(6-chloro-7-fluoro-3-(1H-imidazol-1-yl)-5-methoxy-1-methyl-1H-indol-2-yl)-4H-1,2,4-triazol-3-yl)ethyl)morpholine | NA |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | (R)-4-(1-(5-(6-chloro-7-fluoro-3-(1H-imidazol-1-yl)-5-methoxy-1-methyl-1H-indol-2-yl)-1H-1,2,4-triazol-3-yl)ethyl)morpholine | |
| | C | | (R)-4-(1-(3-(6-chloro-7-fluoro-3-(1H-imidazol-1-yl)-5-methoxy-1-methyl-1H-indol-2-yl)-1H-1,2,4-triazol-5-yl)ethyl)morpholine | |
| 122 | A | 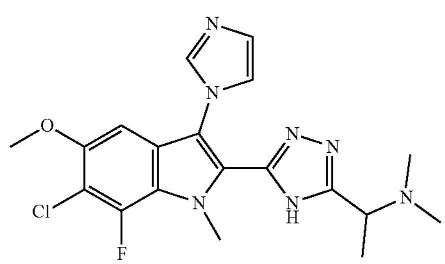 | 1-(5-(6-chloro-7-fluoro-3-(1H-imidazol-1-yl)-5-methoxy-1-methyl-1H-indol-2-yl)-4H-1,2,4-triazol-3-yl)-N,N-dimethylethan-1-amine | 0.177 |
| | B | | 1-(5-(6-chloro-7-fluoro-3-(1H-imidazol-1-yl)-5-methoxy-1-methyl-1H-indol-2-yl)-1H-1,2,4-triazol-3-yl)-N,N-dimethylethan-1-amine | |
| | C | | 1-(3-(6-chloro-7-fluoro-3-(1H-imidazol-1-yl)-5-methoxy-1-methyl-1H-indol-2-yl)-1H-1,2,4-triazol-5-yl)-N,N-dimethylethan-1-amine | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 122a | A | 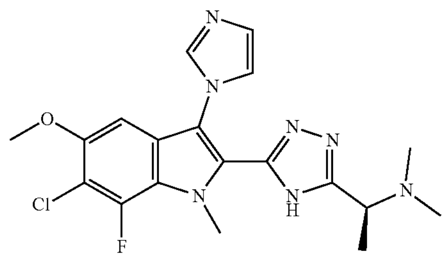 | (S)-1-(5-(6-chloro-7-fluoro-3-(1H-imidazol-1-yl)-5-methoxy-1-methyl-1H-indol-2-yl)-4H-1,2,4-triazol-3-yl)-N,N-dimethylethan-1-amine | NA |
| | B | | (S)-1-(5-(6-chloro-7-fluoro-3-(1H-imidazol-1-yl)-5-methoxy-1-methyl-1H-indol-2-yl)-1H-1,2,4-triazol-3-yl)-N,N-dimethylethan-1-amine | |
| | C | | (S)-1-(3-(6-chloro-7-fluoro-3-(1H-imidazol-1-yl)-5-methoxy-1-methyl-1H-indol-2-yl)-1H-1,2,4-triazol-5-yl)-N,N-dimethylethan-1-amine | |
| 122b | A | 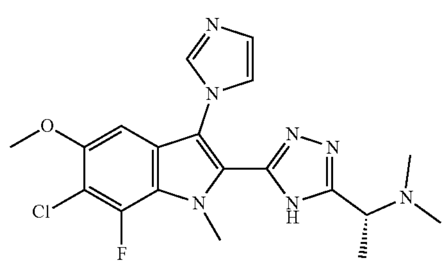 | (R)-1-(5-(6-chloro-7-fluoro-3-(1H-imidazol-1-yl)-5-methoxy-1-methyl-1H-indol-2-yl)-4H-1,2,4-triazol-3-yl)-N,N-dimethylethan-1-amine | NA |
| | B | | (R)-1-(5-(6-chloro-7-fluoro-3-(1H-imidazol-1-yl)-5-methoxy-1-methyl-1H-indol-2-yl)-1H-1,2,4-triazol-3-yl)-N,N-dimethylethan-1-amine | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | (R)-1-(3-(6-chloro-7-fluoro-3-(1H-imidazol-1-yl)-5-methoxy-1-methyl-1H-indol-2-yl)-1H-1,2,4-triazol-5-yl)-N,N-dimethylethan-1-amine | |
| 123 | A | 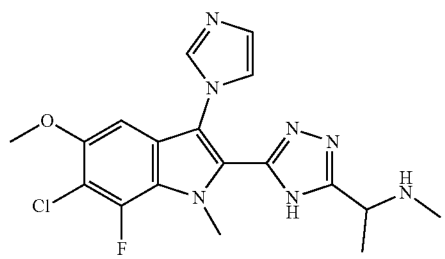 | 1-(5-(6-chloro-7-fluoro-3-(1H-imidazol-1-yl)-5-methoxy-1-methyl-1H-indol-2-yl)-4H-1,2,4-triazol-3-yl)-N-methylethan-1-amine | 0.121 |
| | B | | 1-(5-(6-chloro-7-fluoro-3-(1H-imidazol-1-yl)-5-methoxy-1-methyl-1H-indol-2-yl)-1H-1,2,4-triazol-3-yl)-N-methylethan-1-amine | |
| | C | | 1-(3-(6-chloro-7-fluoro-3-(1H-imidazol-1-yl)-5-methoxy-1-methyl-1H-indol-2-yl)-1H-1,2,4-triazol-5-yl)-N-methylethan-1-amine | |
| 123a | A | 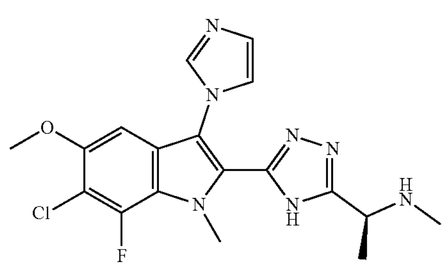 | (S)-1-(5-(6-chloro-7-fluoro-3-(1H-imidazol-1-yl)-5-methoxy-1-methyl-1H-indol-2-yl)-4H-1,2,4-triazol-3-yl)-N-methylethan-1-amine | NA |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | (S)-1-(5-(6-chloro-7-fluoro-3-(1H-imidazol-1-yl)-5-methoxy-1-methyl-1H-indol-2-yl)-1H-1,2,4-triazol-3-yl)-N-methylethan-1-amine | |
| | C | | (S)-1-(3-(6-chloro-7-fluoro-3-(1H-imidazol-1-yl)-5-methoxy-1-methyl-1H-indol-2-yl)-1H-1,2,4-triazol-5-yl)-N-methylethan-1-amine | |
| 123b | A | 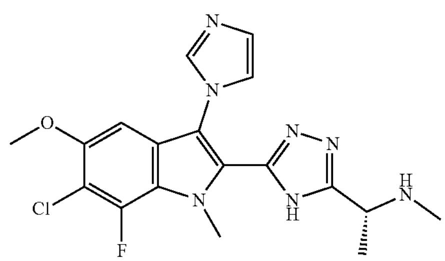 | (R)-1-(5-(6-chloro-7-fluoro-3-(1H-imidazol-1-yl)-5-methoxy-1-methyl-1H-indol-2-yl)-4H-1,2,4-triazol-3-yl)-N-methylethan-1-amine | NA |
| | B | | (R)-1-(5-(6-chloro-7-fluoro-3-(1H-imidazol-1-yl)-5-methoxy-1-methyl-1H-indol-2-yl)-1H-1,2,4-triazol-3-yl)-N-methylethan-1-amine | |
| | C | | (R)-1-(3-(6-chloro-7-fluoro-3-(1H-imidazol-1-yl)-5-methoxy-1-methyl-1H-indol-2-yl)-1H-1,2,4-triazol-5-yl)-N-methylethan-1-amine | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 124 | A | 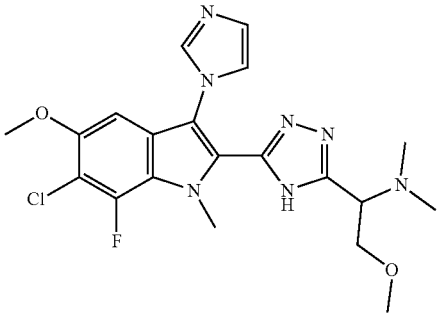 | 1-(5-(6-chloro-7-fluoro-3-(1H-imidazol-1-yl)-5-methoxy-1-methyl-1H-indol-2-yl)-4H-1,2,4-triazol-3-yl)-2-methoxy-N,N-dimethylethan-1-amine | 0.122 |
|  | B | 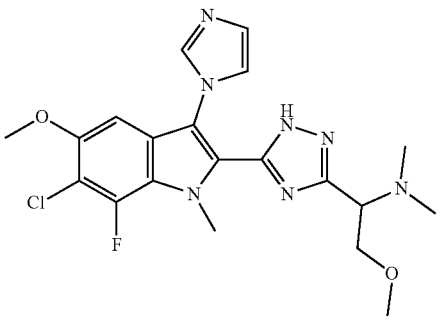 | 1-(5-(6-chloro-7-fluoro-3-(1H-imidazol-1-yl)-5-methoxy-1-methyl-1H-indol-2-yl)-1H-1,2,4-triazol-3-yl)-2-methoxy-N,N-dimethylethan-1-amine |  |
|  | C | 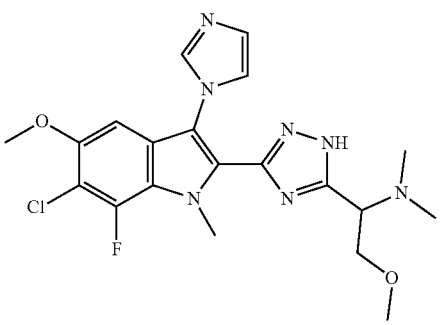 | 1-(3-(6-chloro-7-fluoro-3-(1H-imidazol-1-yl)-5-methoxy-1-methyl-1H-indol-2-yl)-1H-1,2,4-triazol-5-yl)-2-methoxy-N,N-dimethylethan-1-amine |  |
| 124a | A | 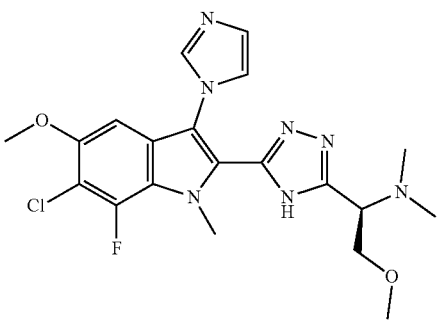 | (R)-1-(5-(6-chloro-7-fluoro-3-(1H-imidazol-1-yl)-5-methoxy-1-methyl-1H-indol-2-yl)-4H-1,2,4-triazol-3-yl)-2-methoxy-N,N-dimethylethan-1-amine | 0.12 |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | (R)-1-(5-(6-chloro-7-fluoro-3-(1H-imidazol-1-yl)-5-methoxy-1-methyl-1H-indol-2-yl)-1H-1,2,4-triazol-3-yl)-2-methoxy-N,N-dimethylethan-1-amine | |
| | C | | (R)-1-(3-(6-chloro-7-fluoro-3-(1H-imidazol-1-yl)-5-methoxy-1-methyl-1H-indol-2-yl)-1H-1,2,4-triazol-5-yl)-2-methoxy-N,N-dimethylethan-1-amine | |
| 124b | A | 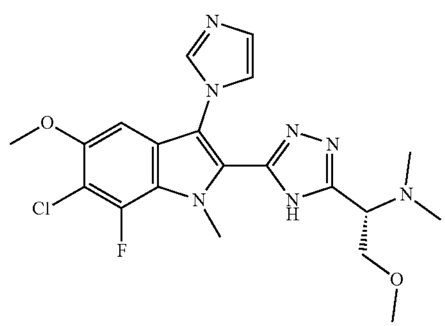 | (S)-1-(5-(6-chloro-7-fluoro-3-(1H-imidazol-1-yl)-5-methoxy-1-methyl-1H-indol-2-yl)-4H-1,2,4-triazol-3-yl)-2-methoxy-N,N-dimethylethan-1-amine | 0.14 |
| | B | | (S)-1-(5-(6-chloro-7-fluoro-3-(1H-imidazol-1-yl)-5-methoxy-1-methyl-1H-indol-2-yl)-1H-1,2,4-triazol-3-yl)-2-methoxy-N,N-dimethylethan-1-amine | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | (S)-1-(3-(6-chloro-7-fluoro-3-(1H-imidazol-1-yl)-5-methoxy-1-methyl-1H-indol-2-yl)-1H-1,2,4-triazol-5-yl)-2-methoxy-N,N-dimethylethan-1-amine | |
| 125 | A | 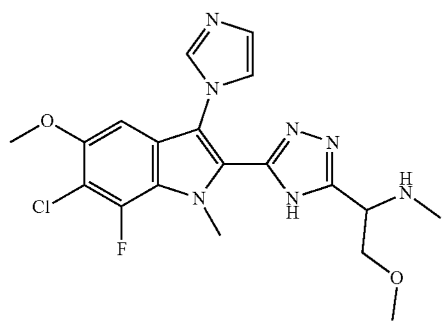 | 1-(5-(6-chloro-7-fluoro-3-(1H-imidazol-1-yl)-5-methoxy-1-methyl-1H-indol-2-yl)-4H-1,2,4-triazol-3-yl)-2-methoxy-N-methylethan-1-amine | 0.074 |
| | B | | 1-(5-(6-chloro-7-fluoro-3-(1H-imidazol-1-yl)-5-methoxy-1-methyl-1H-indol-2-yl)-1H-1,2,4-triazol-3-yl)-2-methoxy-N-methylethan-1-amine | |
| | C | | 1-(3-(6-chloro-7-fluoro-3-(1H-imidazol-1-yl)-5-methoxy-1-methyl-1H-indol-2-yl)-1H-1,2,4-triazol-5-yl)-2-methoxy-N-methylethan-1-amine | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 125a | A | 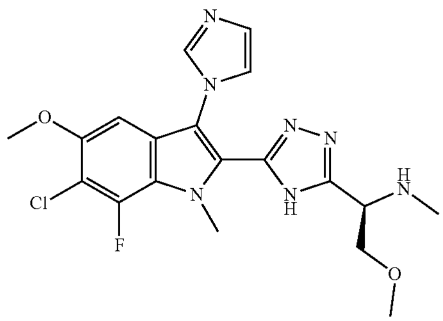 | (R)-1-(5-(6-chloro-7-fluoro-3-(1H-imidazol-1-yl)-5-methoxy-1-methyl-1H-indol-2-yl)-4H-1,2,4-triazol-3-yl)-2-methoxy-N-methylethan-1-amine | 0.18 |
| | B | | (R)-1-(5-(6-chloro-7-fluoro-3-(1H-imidazol-1-yl)-5-methoxy-1-methyl-1H-indol-2-yl)-1H-1,2,4-triazol-3-yl)-2-methoxy-N-methylethan-1-amine | |
| | C | | (R)-1-(3-(6-chloro-7-fluoro-3-(1H-imidazol-1-yl)-5-methoxy-1-methyl-1H-indol-2-yl)-1H-1,2,4-triazol-5-yl)-2-methoxy-N-methylethan-1-amine | |
| 125b | A | 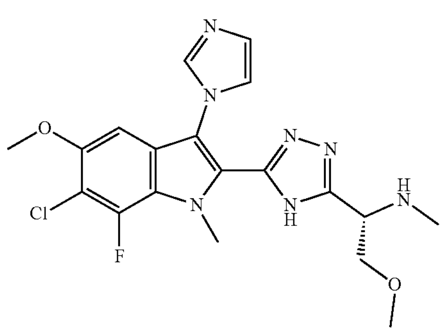 | (S)-1-(5-(6-chloro-7-fluoro-3-(1H-imidazol-1-yl)-5-methoxy-1-methyl-1H-indol-2-yl)-4H-1,2,4-triazol-3-yl)-2-methoxy-N-methylethan-1-amine | 0.18 |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | (S)-1-(5-(6-chloro-7-fluoro-3-(1H-imidazol-1-yl)-5-methoxy-1-methyl-1H-indol-2-yl)-1H-1,2,4-triazol-3-yl)-2-methoxy-N-methylethan-1-amine | |
| | C | | (S)-1-(3-(6-chloro-7-fluoro-3-(1H-imidazol-1-yl)-5-methoxy-1-methyl-1H-indol-2-yl)-1H-1,2,4-triazol-5-yl)-2-methoxy-N-methylethan-1-amine | |
| 126 | A | 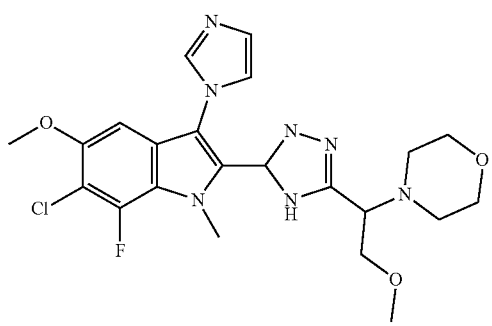 [SMILES: COCC(C1=NNC(c2c(-n3ccnc3)c3cc(OC)c(Cl)c(F)c3n2C)N1)N1CCOCC1] | 4-(1-(5-(6-chloro-7-fluoro-3-(1H-imidazol-1-yl)-5-methoxy-1-methyl-1H-indol-2-yl)-4H-1,2,4-triazol-3-yl)-2-methoxyethyl)morpholine | 0.411 |
| | B | | 4-(1-(5-(6-chloro-7-fluoro-3-(1H-imidazol-1-yl)-5-methoxy-1-methyl-1H-indol-2-yl)-1H-1,2,4-triazol-3-yl)-2-methoxyethyl)morpholine | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | 4-(1-(3-(6-chloro-7-fluoro-3-(1H-imidazol-1-yl)-5-methoxy-1-methyl-1H-indol-2-yl)-1H-1,2,4-triazol-5-yl)-2-methoxyethyl)morpholine | |
| 126a | A | 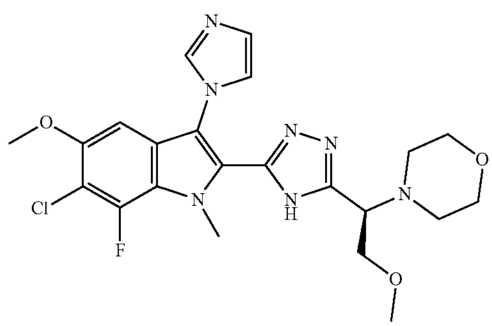 [SMILES: COC[C@@H](c1nnc(-c2c(-n3ccnc3)c3cc(OC)c(Cl)c(F)c3n2C)[nH]1)N1CCOCC1] | (R)-4-(1-(5-(6-chloro-7-fluoro-3-(1H-imidazol-1-yl)-5-methoxy-1-methyl-1H-indol-2-yl)-4H-1,2,4-triazol-3-yl)-2-methoxyethyl)morpholine | NA |
| | B | | (R)-4-(1-(5-(6-chloro-7-fluoro-3-(1H-imidazol-1-yl)-5-methoxy-1-methyl-1H-indol-2-yl)-1H-1,2,4-triazol-3-yl)-2-methoxyethyl)morpholine | |
| | C | | (R)-4-(1-(3-(6-chloro-7-fluoro-3-(1H-imidazol-1-yl)-5-methoxy-1-methyl-1H-indol-2-yl)-1H-1,2,4-triazol-5-yl)-2-methoxyethyl)morpholine | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 126b | A | 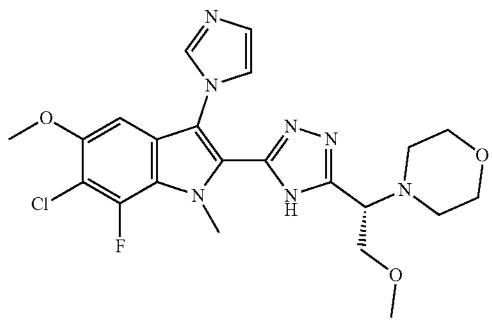 [SMILES: COC[C@H](c1nnc(-c2c(-n3ccnc3)c3cc(OC)c(Cl)c(F)c3n2C)[nH]1)N1CCOCC1] | (S)-4-(1-(5-(6-chloro-7-fluoro-3-(1H-imidazol-1-yl)-5-methoxy-1-methyl-1H-indol-2-yl)-4H-1,2,4-triazol-3-yl)-2-methoxyethyl)morpholine | NA |
| | B | | (S)-4-(1-(5-(6-chloro-7-fluoro-3-(1H-imidazol-1-yl)-5-methoxy-1-methyl-1H-indol-2-yl)-1H-1,2,4-triazol-3-yl)-2-methoxyethyl)morpholine | |
| | C | | (S)-4-(1-(3-(6-chloro-7-fluoro-3-(1H-imidazol-1-yl)-5-methoxy-1-methyl-1H-indol-2-yl)-1H-1,2,4-triazol-5-yl)-2-methoxyethyl)morpholine | |
| 127 | A | 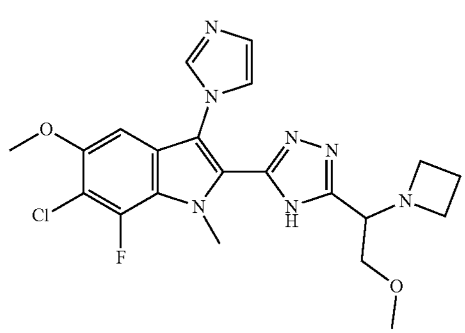 [SMILES: COCC(c1nnc(-c2c(-n3ccnc3)c3cc(OC)c(Cl)c(F)c3n2C)[nH]1)N1CCC1] | 2-(5-(1-(azetidin-1-yl)-2-methoxyethyl)-4H-1,2,4-triazol-3-yl)-6-chloro-7-fluoro-3-(1H-imidazol-1-yl)-5-methoxy-1-methyl-1H-indole | 0.487 |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | 2-(3-(1-(azetidin-1-yl)-2-methoxyethyl)-1H-1,2,4-triazol-5-yl)-6-chloro-7-fluoro-3-(1H-imidazol-1-yl)-5-methoxy-1-methyl-1H-indole | |
| | C | | 2-(5-(1-(azetidin-1-yl)-2-methoxyethyl)-1H-1,2,4-triazol-3-yl)-6-chloro-7-fluoro-3-(1H-imidazol-1-yl)-5-methoxy-1-methyl-1H-indole | |
| 127a | A | 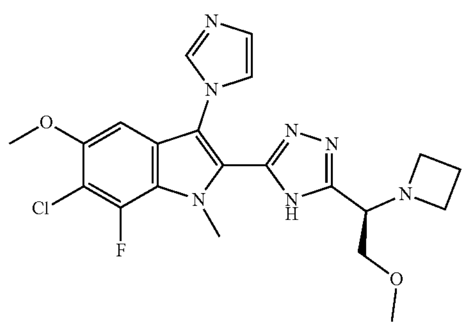 [SMILES: COC[C@@H](c1nnc(-c2c(-n3ccnc3)c3cc(OC)c(Cl)c(F)c3n2C)[nH]1)N1CCC1] | (R)-2-(5-(1-(azetidin-1-yl)-2-methoxyethyl)-4H-1,2,4-triazol-3-yl)-6-chloro-7-fluoro-3-(1H-imidazol-1-yl)-5-methoxy-1-methyl-1H-indole | NA |
| | B | | (R)-2-(3-(1-(azetidin-1-yl)-2-methoxyethyl)-1H-1,2,4-triazol-5-yl)-6-chloro-7-fluoro-3-(1H-imidazol-1-yl)-5-methoxy-1-methyl-1H-indole | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | (R)-2-(5-(1-(azetidin-1-yl)-2-methoxyethyl)-1H-1,2,4-triazol-3-yl)-6-chloro-7-fluoro-3-(1H-imidazol-1-yl)-5-methoxy-1-methyl-1H-indole | |
| 127b | A | 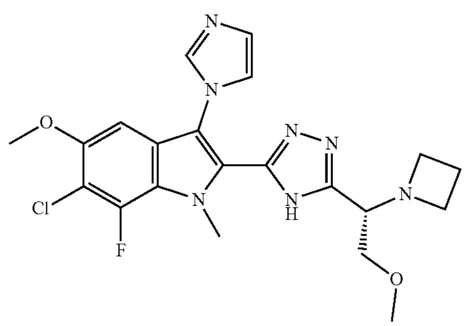 [SMILES: COC[C@H](c1nnc(-c2c(-n3ccnc3)c3cc(OC)c(Cl)c(F)c3n2C)[nH]1)N1CCC1] | (S)-2-(5-(1-(azetidin-1-yl)-2-methoxyethyl)-4H-1,2,4-triazol-3-yl)-6-chloro-7-fluoro-3-(1H-imidazol-1-yl)-5-methoxy-1-methyl-1H-indole | NA |
| | B | | (S)-2-(3-(1-(azetidin-1-yl)-2-methoxyethyl)-1H-1,2,4-triazol-5-yl)-6-chloro-7-fluoro-3-(1H-imidazol-1-yl)-5-methoxy-1-methyl-1H-indole | |
| | C | | (S)-2-(5-(1-(azetidin-1-yl)-2-methoxyethyl)-1H-1,2,4-triazol-3-yl)-6-chloro-7-fluoro-3-(1H-imidazol-1-yl)-5-methoxy-1-methyl-1H-indole | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 128 | A | 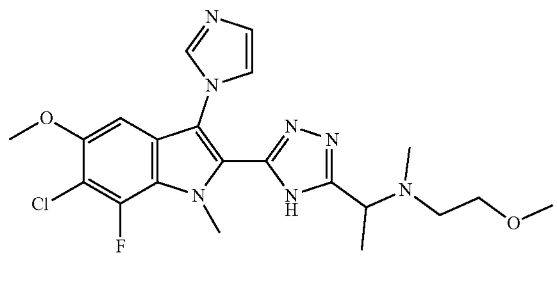 | 1-(5-(6-chloro-7-fluoro-3-(1H-imidazol-1-yl)-5-methoxy-1-methyl-1H-indol-2-yl)-4H-1,2,4-triazol-3-yl)-N-(2-methoxyethyl)-N-methylethan-1-amine | 0.454 |
| | B | | 1-(5-(6-chloro-7-fluoro-3-(1H-imidazol-1-yl)-5-methoxy-1-methyl-1H-indol-2-yl)-1H-1,2,4-triazol-3-yl)-N-(2-methoxyethyl)-N-methylethan-1-amine | |
| | C | | 1-(3-(6-chloro-7-fluoro-3-(1H-imidazol-1-yl)-5-methoxy-1-methyl-1H-indol-2-yl)-1H-1,2,4-triazol-5-yl)-N-(2-methoxyethyl)-N-methylethan-1-amine | |
| 128a | A | 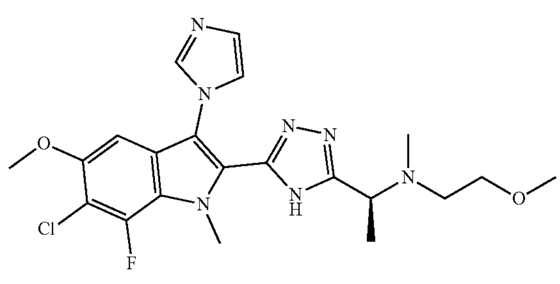 | (S)-1-(5-(6-chloro-7-fluoro-3-(1H-imidazol-1-yl)-5-methoxy-1-methyl-1H-indol-2-yl)-4H-1,2,4-triazol-3-yl)-N-(2-methoxyethyl)-N-methylethan-1-amine | NA |
| | B | | (S)-1-(5-(6-chloro-7-fluoro-3-(1H-imidazol-1-yl)-5-methoxy-1-methyl-1H-indol-2-yl)-1H-1,2,4-triazol-3-yl)-N-(2-methoxyethyl)-N-methylethan-1-amine | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | | (S)-1-(3-(6-chloro-7-fluoro-3-(1H-imidazol-1-yl)-5-methoxy-1-methyl-1H-indol-2-yl)-1H-1,2,4-triazol-5-yl)-N-(2-methoxyethyl)-N-methylethan-1-amine | |
| 128b | A | 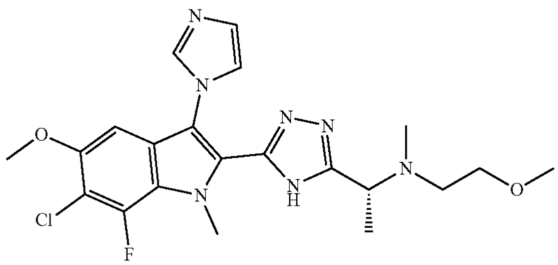 | (R)-1-(5-(6-chloro-7-fluoro-3-(1H-imidazol-1-yl)-5-methoxy-1-methyl-1H-indol-2-yl)-4H-1,2,4-triazol-3-yl)-N-(2-methoxyethyl)-N-methylethan-1-amine | NA |
| | B | | (R)-1-(5-(6-chloro-7-fluoro-3-(1H-imidazol-1-yl)-5-methoxy-1-methyl-1H-indol-2-yl)-1H-1,2,4-triazol-3-yl)-N-(2-methoxyethyl)-N-methylethan-1-amine | |
| | C | | (R)-1-(3-(6-chloro-7-fluoro-3-(1H-imidazol-1-yl)-5-methoxy-1-methyl-1H-indol-2-yl)-1H-1,2,4-triazol-5-yl)-N-(2-methoxyethyl)-N-methylethan-1-amine | |
| 129 | A | 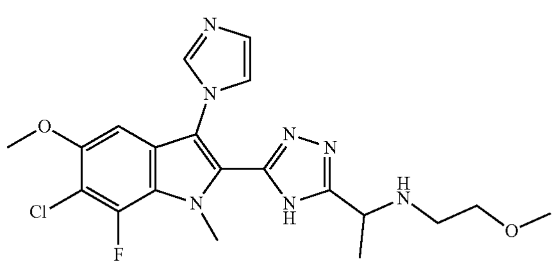 | 1-(5-(6-chloro-7-fluoro-3-(1H-imidazol-1-yl)-5-methoxy-1-methyl-1H-indol-2-yl)-4H-1,2,4-triazol-3-yl)-N-(2-methoxyethyl)ethan-1-amine | 0.757 |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | 1-(5-(6-chloro-7-fluoro-3-(1H-imidazol-1-yl)-5-methoxy-1-methyl-1H-indol-2-yl)-1H-1,2,4-triazol-3-yl)-N-(2-methoxyethyl)ethan-1-amine | |
| | C | | 1-(3-(6-chloro-7-fluoro-3-(1H-imidazol-1-yl)-5-methoxy-1-methyl-1H-indol-2-yl)-1H-1,2,4-triazol-5-yl)-N-(2-methoxyethyl)ethan-1-amine | |
| 129a | A | 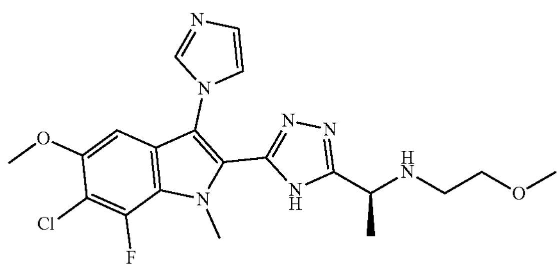 | (S)-1-(5-(6-chloro-7-fluoro-3-(1H-imidazol-1-yl)-5-methoxy-1-methyl-1H-indol-2-yl)-4H-1,2,4-triazol-3-yl)-N-(2-methoxyethyl)ethan-1-amine | NA |
| | B | | (S)-1-(5-(6-chloro-7-fluoro-3-(1H-imidazol-1-yl)-5-methoxy-1-methyl-1H-indol-2-yl)-1H-1,2,4-triazol-3-yl)-N-(2-methoxyethyl)ethan-1-amine | |
| | C | | (S)-1-(3-(6-chloro-7-fluoro-3-(1H-imidazol-1-yl)-5-methoxy-1-methyl-1H-indol-2-yl)-1H-1,2,4-triazol-5-yl)-N-(2-methoxyethyl)ethan-1-amine | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| 129b | A | 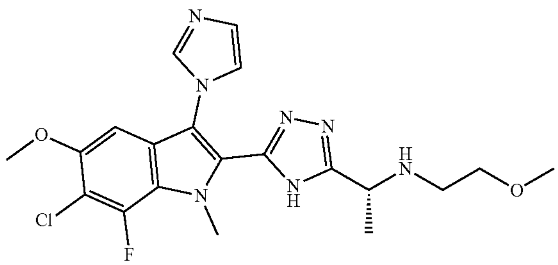 | (R)-1-(5-(6-chloro-7-fluoro-3-(1H-imidazol-1-yl)-5-methoxy-1-methyl-1H-indol-2-yl)-4H-1,2,4-triazol-3-yl)-N-(2-methoxyethyl)ethan-1-amine | NA |
| | B | | (R)-1-(5-(6-chloro-7-fluoro-3-(1H-imidazol-1-yl)-5-methoxy-1-methyl-1H-indol-2-yl)-1H-1,2,4-triazol-3-yl)-N-(2-methoxyethyl)ethan-1-amine | |
| | C | | (R)-1-(3-(6-chloro-7-fluoro-3-(1H-imidazol-1-yl)-5-methoxy-1-methyl-1H-indol-2-yl)-1H-1,2,4-triazol-5-yl)-N-(2-methoxyethyl)ethan-1-amine | |
| 130 | A | 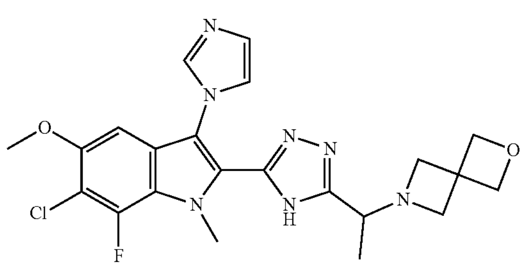 [SMILES: COc1cc2c(-n3ccnc3)c(-c3nnc(C(C)N4CC5(COC5)C4)[nH]3)n(C)c2c(F)c1Cl] | 6-(1-(5-(6-chloro-7-fluoro-3-(1H-imidazol-1-yl)-5-methoxy-1-methyl-1H-indol-2-yl)-4H-1,2,4-triazol-3-yl)ethyl)-2-oxa-6-azaspiro[3.3]heptane | 0.268 |
| | B | | 6-(1-(5-(6-chloro-7-fluoro-3-(1H-imidazol-1-yl)-5-methoxy-1-methyl-1H-indol-2-yl)-1H-1,2,4-triazol-3-yl)ethyl)-2-oxa-6-azaspiro[3.3]heptane | |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | C | 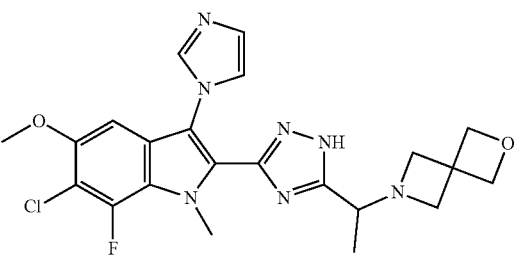 [SMILES: COc1cc2c(-n3ccnc3)c(-c3n[nH]c(C(C)N4CC5(COC5)C4)n3)n(C)c2c(F)c1Cl] | 6-(1-(3-(6-chloro-7-fluoro-3-(1H-imidazol-1-yl)-5-methoxy-1-methyl-1H-indol-2-yl)-1H-1,2,4-triazol-5-yl)ethyl)-2-oxa-6-azaspiro[3.3]heptane | |
| 130a | A | 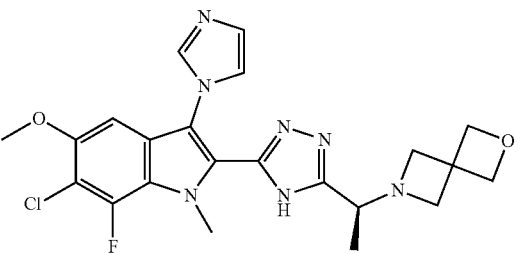 [SMILES: COc1cc2c(-n3ccnc3)c(-c3nnc([C@H](C)N4CC5(COC5)C4)[nH]3)n(C)c2c(F)c1Cl] | (S)-6-(1-(5-(6-chloro-7-fluoro-3-(1H-imidazol-1-yl)-5-methoxy-1-methyl-1H-indol-2-yl)-4H-1,2,4-triazol-3-yl)ethyl)-2-oxa-6-azaspiro[3.3]heptane | NA |
| | B | 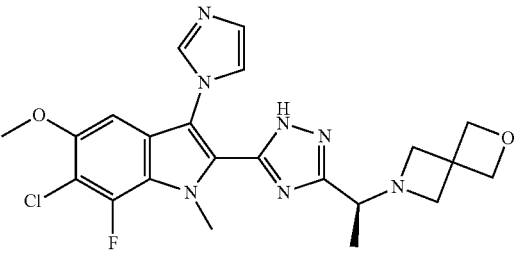 [SMILES: COc1cc2c(-n3ccnc3)c(-c3nc([C@H](C)N4CC5(COC5)C4)n[nH]3)n(C)c2c(F)c1Cl] | (S)-6-(1-(5-(6-chloro-7-fluoro-3-(1H-imidazol-1-yl)-5-methoxy-1-methyl-1H-indol-2-yl)-1H-1,2,4-triazol-3-yl)ethyl)-2-oxa-6-azaspiro[3.3]heptane | |
| | C | 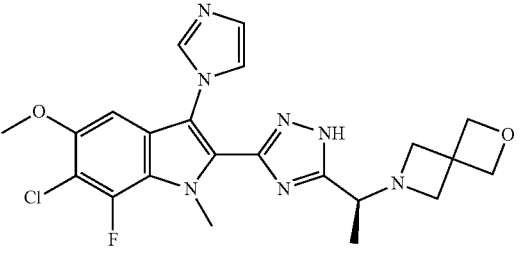 [SMILES: COc1cc2c(-n3ccnc3)c(-c3n[nH]c([C@H](C)N4CC5(COC5)C4)n3)n(C)c2c(F)c1Cl] | (S)-6-(1-(3-(6-chloro-7-fluoro-3-(1H-imidazol-1-yl)-5-methoxy-1-methyl-1H-indol-2-yl)-1H-1,2,4-triazol-5-yl)ethyl)-2-oxa-6-azaspiro[3.3]heptane | |
| 130b | A | 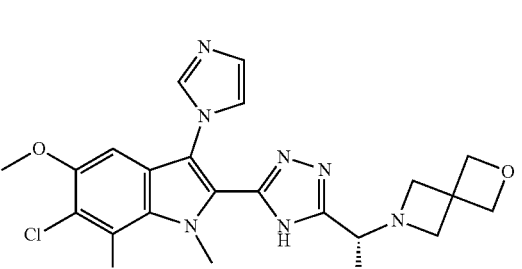 | (R)-6-(1-(5-(6-chloro-7-fluoro-3-(1H-imidazol-1-yl)-5-methoxy-1-methyl-1H-indol-2-yl)-4H-1,2,4-triazol-3-yl)ethyl)-2-oxa-6-azaspiro[3.3]heptane | NA |

TABLE 1-continued

Illustrative compounds of the disclosure and cGAS inhibition activity

| Example No. | Tautomer | Structure | Name | cGAS IC$_{50}$ [μM] |
|---|---|---|---|---|
| | B | | (R)-6-(1-(5-(6-chloro-7-fluoro-3-(1H-imidazol-1-yl)-5-methoxy-1-methyl-1H-indol-2-yl)-1H-1,2,4-triazol-3-yl)ethyl)-2-oxa-6-azaspiro[3.3]heptane | |
| | C | | (R)-6-(1-(3-(6-chloro-7-fluoro-3-(1H-imidazol-1-yl)-5-methoxy-1-methyl-1H-indol-2-yl)-1H-1,2,4-triazol-5-yl)ethyl)-2-oxa-6-azaspiro[3.3]heptane | |

In another embodiment of the disclosure, the compounds of the present disclosure are enantiomers. In some embodiments the compounds are the (S)-enantiomer. In other embodiments the compounds are the (R)-enantiomer. In yet other embodiments, the compounds of the present disclosure may be (+) or (−) enantiomers.

It should be understood that all isomeric forms are included within the present disclosure, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Compounds of the disclosure, and pharmaceutically acceptable salts, hydrates, solvates, and stereoisomers thereof may exist in their tautomeric form (for example, as an amide or imino ether). All such tautomeric forms are contemplated herein as part of the present disclosure.

The compounds of the disclosure may contain asymmetric or chiral centers and, therefore, exist in different stereoisomeric forms. It is intended that all stereoisomeric forms of the compounds of the disclosure as well as mixtures thereof, including racemic mixtures, form part of the present disclosure. In addition, the present disclosure embraces all geometric and positional isomers. For example, if a compound of the disclosure incorporates a double bond or a fused ring, both the cis- and trans-forms, as well as mixtures, are embraced within the scope of the disclosure.

Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the disclosure may be atropisomers (e.g., substituted biaryls) and are considered as part of this disclosure. Enantiomers can also be separated by use of a chiral HPLC column.

It is also possible that the compounds of the disclosure may exist in different tautomeric forms, and all such forms are embraced within the scope of the disclosure and chemical structures and names. Also, for example, all keto-enol and imine-enamine forms of the compounds are included in the disclosure.

All stereoisomers (for example, geometric isomers, optical isomers, and the like) of the present compounds (including those of the salts, solvates, and esters of the compounds), such as those which may exist due to asymmetric carbons on various substituents, including enantiomeric forms (which may exist even in the absence of asymmetric carbons), rotameric forms, atropisomers, and diastereomeric forms, are contemplated within the scope of this disclosure, as are positional isomers (such as, for example, 4-pyridyl and 3-pyridyl). Individual stereoisomers of the compounds of the disclosure may, for example, be substantially free of other isomers, or is admixed, for example, as racemates or with all other, or other selected, stereoisomers.

The chiral centers of the compounds of the disclosure can have the S or R configuration as defined by the IUPAC 1974 Recommendations. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

The use of the terms "salt", "solvate", "ester," and the like, is intended to equally apply to the salt, solvate, and ester of enantiomers, stereoisomers, rotamers, tautomers, positional isomers, or racemates of the inventive compounds.

The compounds of the disclosure may form salts which are also within the scope of this disclosure. Reference to a compound of any of the Formulae disclosed herein is generally understood to include reference to salts thereof, unless otherwise indicated.

The compounds and intermediates may be isolated and used as the compound per se. Any formula given herein is also intended to represent unlabeled forms as well as isotopically labeled forms of the compounds. Isotopically labeled compounds have structures depicted by the formulae given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine, and, such as $^2$H, $^3$H, $^{11}$C, $^{13}$C, $^{14}$C, $^{15}$N, $^{18}$F, $^{31}$P, $^{32}$P, respectively. The disclosure includes various isotopically labeled compounds as defined herein, for example those into which radioactive isotopes, such as $^3$H, $^{13}$C, and $^{14}$C, are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F, $^{11}$C or labeled compound may be particularly desirable for PET or SPECT studies.

Further, substitution with heavier isotopes, particularly deuterium (i.e., $^2$H or D) may afford certain therapeutic advantages resulting from greater metabolic stability, for example, increased in vivo half-life, reduced dosage requirements, reduced CYP450 inhibition (competitive or time dependent) or an improvement in therapeutic index. For example, substitution with deuterium may modulate undesirable side effects of the undeuterated compound, such as competitive CYP450 inhibition, time dependent CYP450 inactivation, etc. It is understood that deuterium in this context is regarded as a substituent in compounds of the present disclosure. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of the present disclosure can generally be prepared by conventional techniques known to those skilled in the art or by carrying out the procedures disclosed in the schemes or in the examples and preparations described below using an appropriate isotopically-labeled reagent in place of the non-isotopically labeled reagent.

Pharmaceutically acceptable solvates in accordance with the disclosure include those wherein the solvent of crystallization may be isotopically substituted, e.g., D20, d6-acetone, d6-DMSO.

The present disclosure relates to compounds which are modulators of cGAS activity. In one embodiment, the compounds of the present disclosure decrease cGAS activity. In yet one embodiment, the compounds of the present disclosure reduce cGAS activity. In another embodiment, the compounds of the present disclosure are inhibitors of cGAS activity.

In some embodiments, the compounds of the disclosure are selective over other proteins. As used herein "selective modulator", "selective inhibitor", or "selective compound" means, for example, a compound of the disclosure, that effectively modulates, decreases, or reduces the levels of a specific protein activity to a greater extent than any other protein. A "selective modulator", "selective inhibitor", or "selective compound" can be identified, for example, by comparing the ability of a compound to modulate, decrease, or reduce the levels of or to inhibit a specific protein to its ability to modulate, decrease, or reduce the levels of its activity. In some embodiments, the selectivity can be identified by measuring the $EC_{50}$ or $IC_{50}$ of the compounds.

In some embodiments, the compounds of the present application are selective cGAS modulators. As used herein "selective cGAS modulator", "selective cGAS inhibitor", or "selective cGAS compound" refers to a compound of the application, for example, that effectively modulates, decrease, or reduces the levels of cGAS activity to a greater extent than any other protein.

In some embodiments, the inhibition of cGAS is measured by $IC_{50}$.

Potency of can be determined by $IC_{50}$ value. A compound with a lower $IC_{50}$ value, as determined under substantially similar conditions, is a more potent inhibitor relative to a compound with a higher $IC_{50}$ value. In some embodiments, the substantially similar conditions comprise determining inhibition of protein levels in cells expressing the specific protein, or a fragment of any thereof.

The disclosure is directed to compounds as described herein and pharmaceutically acceptable salts, hydrates, solvates, stereoisomers, or tautomers thereof, and pharmaceutical compositions comprising one or more compounds as described herein, or pharmaceutically acceptable salts, hydrates, solvates, stereoisomers, or tautomers thereof.

F. Methods of Synthesizing Compounds of Formula (I)

The compounds of the present disclosure may be made by a variety of methods, including standard chemistry. Suitable synthetic routes are depicted in the Schemes given below.

The compounds of the present disclosure may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of Compounds of Formula (I).

Those skilled in the art will recognize if a stereocenter exists in the compounds of the present disclosure. Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

The compounds of the present disclosure can be prepared in a number of ways well known to those skilled in the art of organic synthesis. By way of example, compounds of the present disclosure can be synthesized using the methods described below, together with synthetic methods known in the art of synthetic organic chemistry, or variations thereon as appreciated by those skilled in the art. Preferred methods include but are not limited to those methods described below.

The general procedures for synthesis of intermediates and the compounds of general Formula M1-34 are described in the following reaction schemes, and are specifically illustrated in the preparations and Examples.

In the following reaction schemes, the general routes to the corresponding indole intermediates are described which were further transformed to the corresponding compounds of the invention.

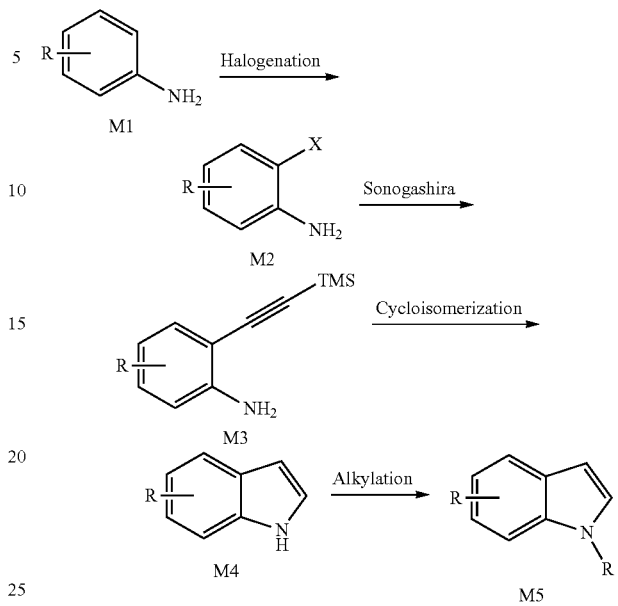

A compound of general structure (M2) was obtained following published procedures (e.g. WO2016/103037), by reacting an aniline (M1) with a halogenating agent such as bromine in a suitable solvent such as acetic acid. Subsequent transformation of (M2) in a Pd-catalysed cross-coupling reaction with a corresponding alkyne results in (M3) (e.g. Org. Process Res. Dev. 2015, 19, 1282-1285). Treatment of (M3) with bases such as sodium hydride or KOtBu results in cycloisomerization to the corresponding indole (M4). Alkylation of the indole NH to give (M5) can be achieved by using bases such as e.g. sodium hydride, KOtBu and suitable alkylating agents such as iodomethane, dimethylsulfate or other alkyl halides.

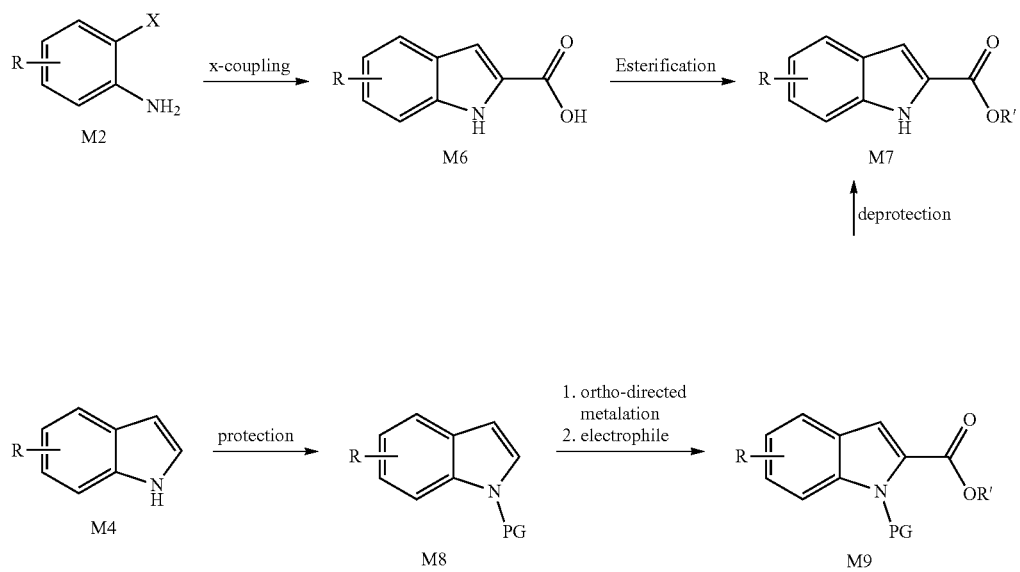

Intermediate (M2) can be converted to the corresponding indole in which initial enamine formation with pyruvic acid is followed by an intramolecular Heck-coupling to provide the indole 2-carboxylate (M6). Subsequent esterification by heating with a corresponding alcohol, e.g. MeOH and sulfuric acid or using TMS-diazomethane in MeOH affords the ester (M7). Alternatively, suitable ortho-directing groups like Boc or phenylsulfonamides can be utilized for selective deprotonation of (M8) in the indole-2-position with bases such as LDA and subsequent treatment with a corresponding chloro formate to furnish (M9). Removal of the protecting groups using appropriate conditions (Greene's Protective Groups in Organic Synthesis, 5$^{th}$ ed.) leads to (M7).

Scheme 3

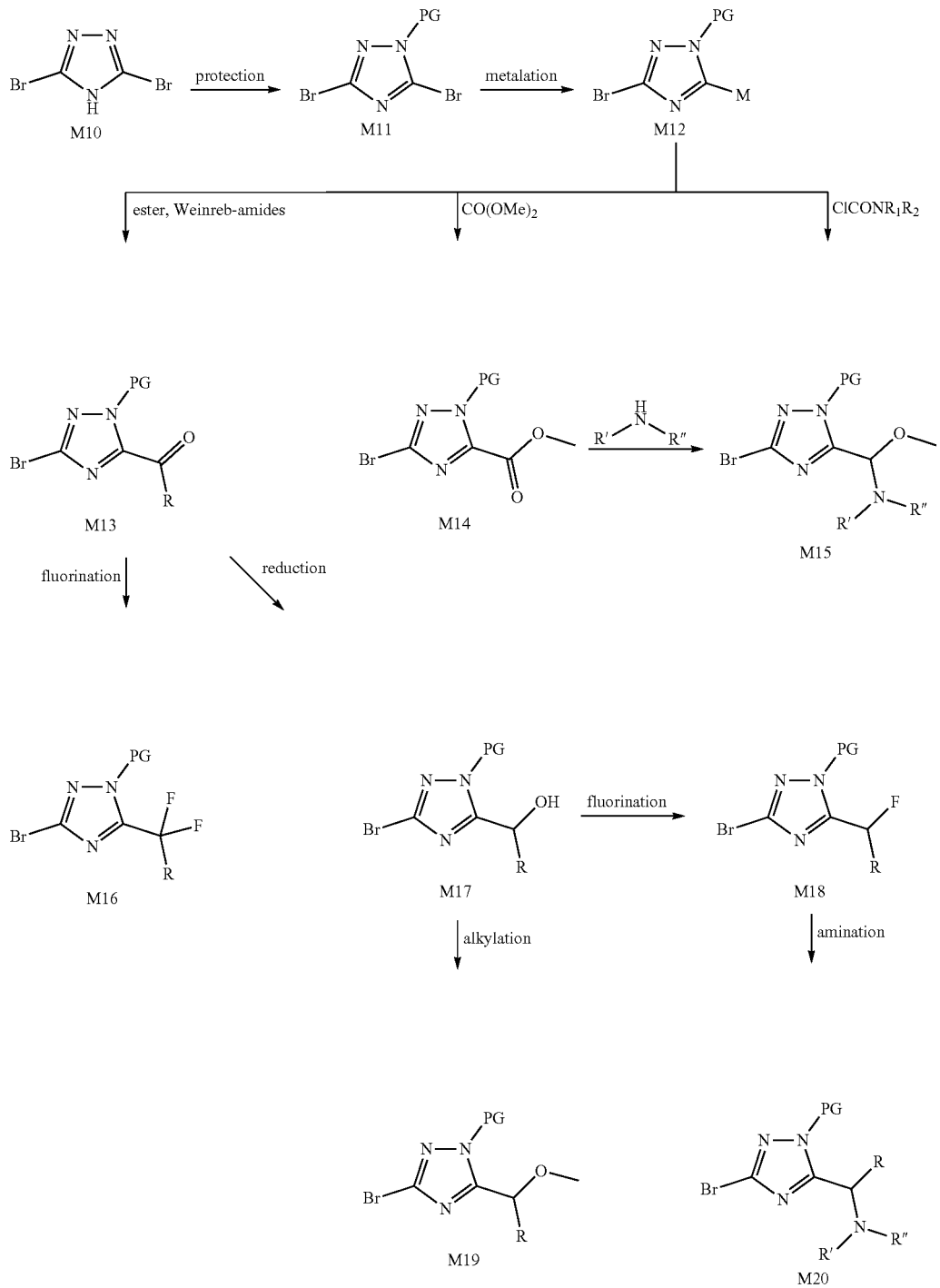

The syntheses of the triazole intermediates generally start with protection of 1,3-dibromo triazole (M10) with an appropriate protecting group, not limited to but preferably PMB- or SEM-protected. Dibromide (M11) can be subjected to a halogen-metal exchange using n-butyllithium, iPrMgCl or TurboGrignard at temperatures between −78° C. and 0° C. to give (M12). Utilization of the appropriate electrophiles affords access to the corresponding ketones (M13), esters (M14) and amides (M15). Latter can be obtained alternatively by direct amidolysis of the ester (M14) with an amine at elevated temperatures in solvents like THF, EtOH or iPrOH. Fluorination of the ketone (M13) with fluorinating agents like DAST gives access to the difluorinated compounds (M16) Reduction of ketone (M13), e.g. with NaBH₄ provides the desired alcohols (M17) which can be further functionalized by alkylation to (M19) or transformed to the mono-fluoro analogs (M18) with reagents like DAST. Intermediates (M18) can be utilized further to replace the fluorine with an appropriate amine, optionally requiring removal of the protecting group first, to give intermediate (M20).

Scheme 3 represents only one tautomeric or regioisomeric form about the triazole ring for each of intermediates M11 to M20. It is possible that each intermediate is a mixture of up to all three tautomers or regioisomers about the triazole ring as illustrated below using M13 as an example. Such mixtures are directly employed in subsequent steps without separation.

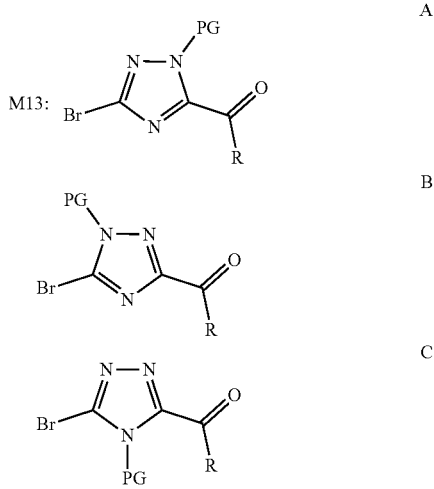

Scheme 4

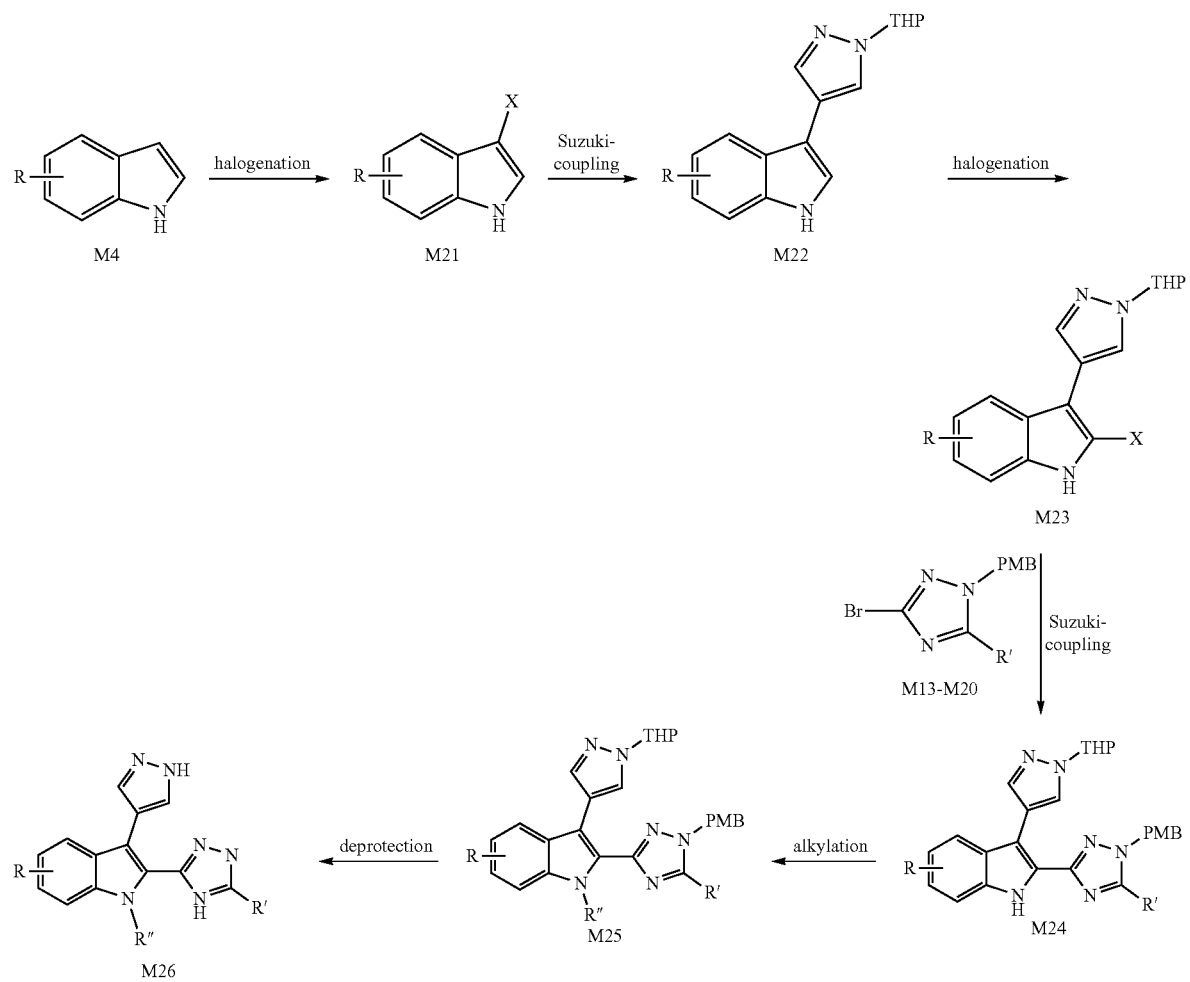

An appropriately substituted indole (M4) can be halogenated by using a suitable agent such as NBS in a suitable solvent such as DCM, ACN or THF to give (M21), which is subsequently treated with an appropriate boronic acid/ester to introduce appropriate 5-membered heterocycles, such as pyrazoles resulting in (M22). In a next step halogenation is performed in a similar way as at the beginning of the reaction sequence, e.g. by bromination with NBS. Intermediate (M23) and bromo-triazoles (M13-20) are coupled in a Pd-cross coupling reaction using e.g. PdCl$_2$(dppf) and bis(pinacolato)diboron, bases such as KOAc or K$_2$CO$_3$, solvents such as water, THF, dioxane or surfactants such a TPGS-750M at suitable temperatures, typically ranging from ambient temperature to 130° C. to give (M24). Intermediate (M24) can be subjected directly to deprotection, e.g. by treatment with triflic acid to get to the corresponding NH analogs (M26, R'=H), or optionally includes N-alkylation with iodomethane or dimethylsulfate prior to deprotection to (M26, R'=alkyl).

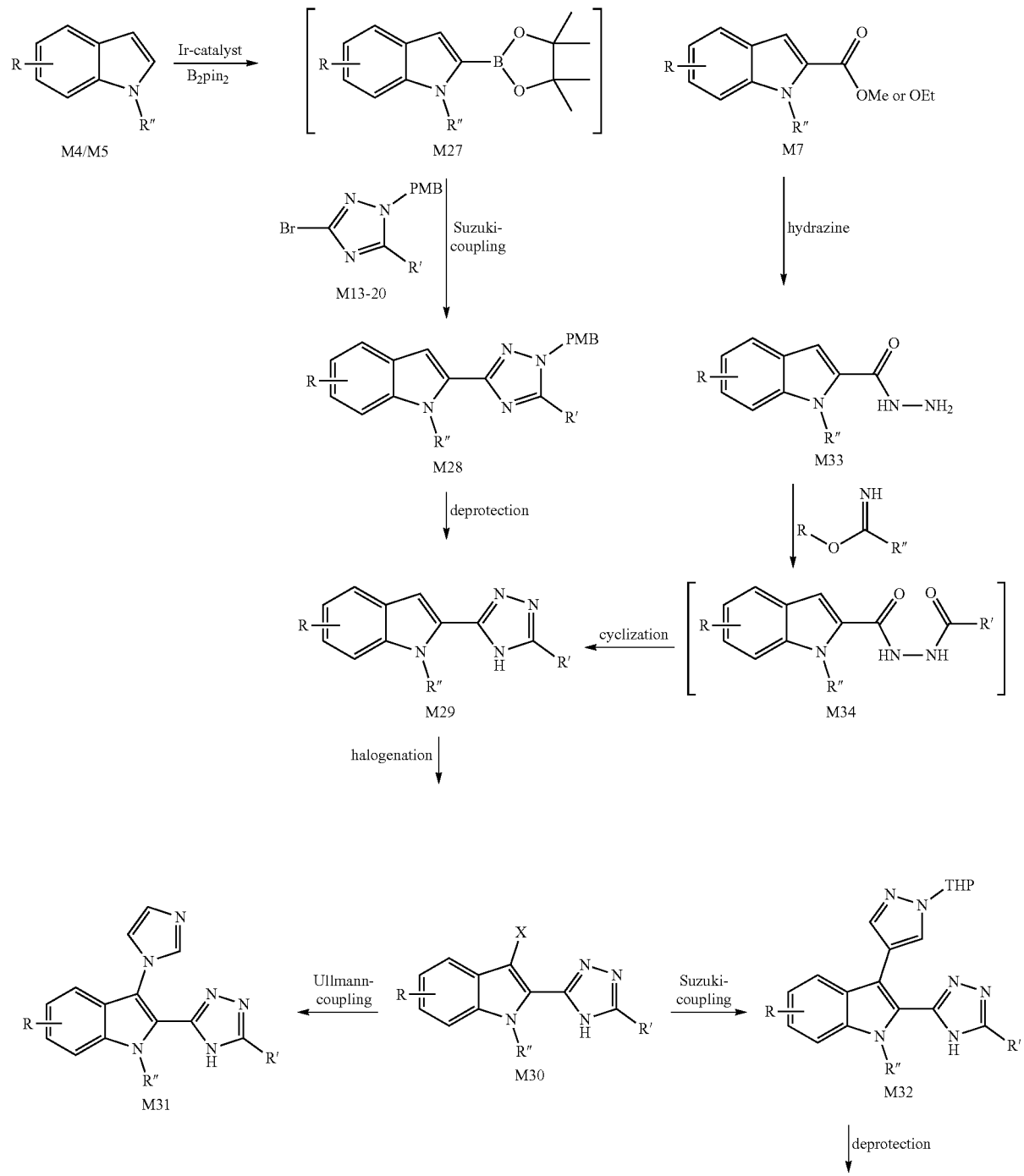

Scheme 5

-continued

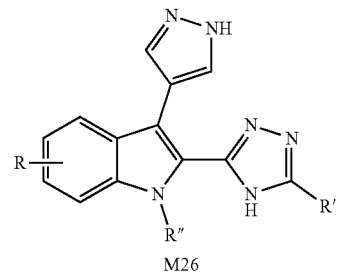

M26

Following a similar procedure described by Hartwig et al. (Org. Lett. 2012, 14(16), 4266-4269), indole (M4/M5), optionally substituted or unsubstituted at the indole NH, is converted to the corresponding organoboronate (M27) by iridium-catalysed CH-borylation and further transformed, usually without isolation/purification, in a subsequent Suzuki-coupling with the corresponding protected bromotriazole (M13-20). Deprotection of (M28) in the next is usually performed by using triflic acid or TFA or mixtures of both to give (M29) which can be halogenated to (M30) by using a suitable agent such as NBS in a suitable solvent such as DCM, ACN or THF. Introduction of 5-membered heterocycles, e.g. such as imidazole can be achieved in an Ullmann-coupling with suitable copper-salts, e.g. CuI and bases, e.g. $K_2CO_3$ or $Cs_2CO_3$ in polar solvents, e.g. DMSO, DMF or NMP in the presence of appropriate ligands, e.g. proline at temperatures ranging from 60–150° C. to give (M31). Alternatively, intermediate (M30) can be subjected to a Suzuki-reaction with appropriate 5-membered heterocycles, such as pyrazoles following a deprotection step which is usually performed using strong acids, e.g. hydrochloric acid in dioxane to give (M26).

Access to intermediate (M29) can be alternatively achieved starting from the corresponding ester (M7) by treatment with an aqueous solution of hydrazine hydrate in protic solvents, such as EtOH at temperatures up to 100° C. The resulting hydrazide (M33) can be treated with readily available iminoesters in solvents such as EtOH at temperatures up to 100° C. to give intermediate (M34), which is usually further subjected to condensation without isolation/purification by treatment with bases, e.g. sodium ethylate or DBU at temperatures up to 160° C. to give the desired triazole intermediate (M29).

A mixture of enantiomers, diastereomers, and cis/trans isomers resulting from the process described above can be separated into their single components by chiral salt technique, chromatography using normal phase, reverse phase or chiral column, depending on the nature of the separation.

Any resulting racemates of compounds of the present disclosure or of intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present disclosure into their optical antipodes, e.g., by fractional crystallization of a salt formed with an optically active acid, e.g., tartaric acid, dibenzoyl tartaric acid, diacetyl tartaric acid, di-0,0'-p-toluoyl tartaric acid, mandelic acid, malic acid, or camphor-10-sulfonic acid. Racemic compounds of the present disclosure or racemic intermediates can also be resolved by chiral chromatography, e.g., high pressure liquid chromatography (HPLC) using a chiral adsorbent.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

It should be understood that in the description and formula shown above, the various groups $R_1$, $R_2$, $R_3$, $R_4$, $R_5$, $R_6$, $R_7$ and $R_8$ are chosen consistent with the definition as defined above at each position of the Compounds of Formula (I), except where otherwise indicated. Furthermore, for synthetic purposes, the compounds of General Schemes 1 to 5 are merely representative with elected radicals to illustrate the general synthetic methodology of the Compounds of Formula (I) as defined herein.

G. Methods of Using Compounds of Formula (I)

The compounds of the present invention in free form or in pharmaceutically acceptable salt form, exhibit valuable pharmacological properties, e.g. cGAS modulating properties, e.g. as indicated in vitro and in vivo tests as provided in the next sections, and are therefore indicated for therapy or for use as research chemicals, e.g. as tool compounds.

Compounds of the present invention may be useful in the treatment of an indication selected from Aicardi-Goutières-Syndrome, Familial Chilblain Lupus, RVCL (autosomal dominant retinal vasculopathy with cerebral leukodystrophy), vasculitis, systemic lupus erythematosus (SLE), lupus nephritis (LN), dermatomyositis, Sjogren's Syndrome (SS), rheumatoid arthritis (RA), age-related macular degeneration (AMD), Parkinson's disease, Alzheimer, Amyotrophic lateral sclerosis (ALS), Frontotemporal dementia (FTD), lung inflammation, acute lung inflammation, idiopathic pulmonary fibrosis, liver and renal fibrosis, nonalcoholic steatohepatitis (NASH), cirrhosis, endomyocardial fibrosis, acute and chronic kidney injury, APOL1-associated podocytopathy, acute pancreatitis, ulcerative colitis, inflammatory bowel disease (IBD), chronic obstructive pulmonary disease (COPD), sepsis, senescence, and aging; preferably Aicardi-Goutières-Syndrome (AGS), vasculitis, systemic lupus erythematosus (SLE), Familial Chilblain Lupus, and Sjogren's syndrome.

Compounds of the present invention may also be useful in the treatment of an indication selected from Aicardi-Goutières-Syndrome, Familial Chilblain Lupus, RVCL (autosomal dominant retinal vasculopathy with cerebral leukodystrophy), vasculitis, systemic lupus erythematosus (SLE), lupus nephritis (LN), dermatomyositis, Sjogren's Syndrome (SS), rheumatoid arthritis (RA), age-related macular degeneration (AMD), Parkinson's disease, Alzheimer, Amyotrophic lateral sclerosis (ALS), lung inflammation, acute lung inflammation, idiopathic pulmonary fibrosis, liver and renal fibrosis, nonalcoholic steatohepatitis (NASH), cirrhosis, endomyocardial fibrosis, acute kidney injury, ulcerative colitis, inflammatory bowel disease (IBD), chronic obstructive pulmonary disease (COPD), sepsis, senescence, and aging; preferably Aicardi-Goutières-Syndrome (AGS), vasculitis, systemic lupus erythematosus (SLE), Familial Chilblain Lupus, and Sjogren's syndrome.

Thus, as a further aspect, the present invention provides the use of a compound of the present invention, or a pharmaceutically acceptable salt, hydrate, solvate, stereoisomer, or tautomer thereof, or a composition comprising a compound of the present invention, or a pharmaceutically acceptable salt, hydrate, solvate, stereoisomer, or tautomer thereof in therapy. In a further embodiment, the therapy is selected from a disease which may be treated by modulation of cGAS. In another embodiment, the disease is selected from the afore-mentioned list; preferably Aicardi-Goutières-Syndrome (AGS), vasculitis, systemic lupus erythematosus (SLE), Familial Chilblain Lupus, and Sjogren's syndrome.

Thus, as a further aspect, the present invention provides a compound of the present invention, or a pharmaceutically acceptable salt, hydrate, solvate, stereoisomer, or tautomer thereof, or a composition comprising a compound of the present invention, or a pharmaceutically acceptable salt, hydrate, solvate, stereoisomer, or tautomer thereof for use in therapy. In a further embodiment, the therapy is selected from a disease which may be treated by modulation of cGAS. In another embodiment, the disease is selected from the afore-mentioned list; preferably Aicardi-Goutières-Syndrome (AGS), vasculitis, systemic lupus erythematosus (SLE), Familial Chilblain Lupus, and Sjogren's syndrome.

In another aspect, the disclosure provides a method of treating a disease or disorder which is treated by modulation of cGAS comprising administration of a therapeutically acceptable amount of a compound of the present invention, or a pharmaceutically acceptable salt, hydrate, solvate, stereoisomer, or tautomer thereof, or a composition comprising a compound of the present invention, or a pharmaceutically acceptable salt, hydrate, solvate, stereoisomer, or tautomer thereof. In a further embodiment, the disease is selected from the afore-mentioned list; preferably Aicardi-Goutières-Syndrome (AGS), vasculitis, systemic lupus erythematosus (SLE), Familial Chilblain Lupus, and Sjogren's syndrome.

In another aspect, the invention provides a method of treating a disease which is treated by modulation of cGAS comprising administration of a therapeutically acceptable amount of a compound of the present invention, or a pharmaceutically acceptable salt, hydrate, solvate, stereoisomer, or tautomer thereof, or a composition comprising a compound of the present invention, or a pharmaceutically acceptable salt, hydrate, solvate, stereoisomer, or tautomer thereof. In a further embodiment, the disease is selected from the afore-mentioned list; preferably Aicardi-Goutières-Syndrome (AGS), vasculitis, systemic lupus erythematosus (SLE), Familial Chilblain Lupus, and Sjogren's syndrome.

Thus, as a further aspect, the present invention provides the use of a compound of the present invention, or a pharmaceutically acceptable salt, hydrate, solvate, stereoisomer, or tautomer thereof, or a composition comprising a compound of the present invention, or a pharmaceutically acceptable salt, hydrate, solvate, stereoisomer, or tautomer thereof, for the manufacture of a medicament. In a further embodiment, the medicament is for treatment of a disease which may be treated by modulation of cGAS. In another embodiment, the disease is selected from the afore-mentioned list; preferably Aicardi-Goutières-Syndrome (AGS), vasculitis, systemic lupus erythematosus (SLE), Familial Chilblain Lupus, and Sjogren's syndrome.

H. Administration and Pharmaceutical Compositions of Compounds of Formula (I)

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. The pharmaceutical composition can be formulated for particular routes of administration such as oral administration, parenteral administration (e.g. by injection, infusion, transdermal or topical administration), and rectal administration. Topical administration may also pertain to inhalation or intranasal application. The pharmaceutical compositions of the present invention can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art. Typically, the pharmaceutical compositions are tablets or gelatin capsules comprising the active ingredient together with one or more of:
  a) diluents, e.g., lactose, dextrose, sucrose, mannitol, sorbitol, cellulose and/or glycine;
  b) lubricants, e.g., silica, talcum, stearic acid, its magnesium or calcium salt and/or polyethyleneglycol; for tablets also
  c) binders, e.g., magnesium aluminum silicate, starch paste, gelatin, tragacanth, methylcellulose, sodium carboxymethylcellulose and/or polyvinylpyrrolidone; if desired
  d) disintegrants, e.g., starches, agar, alginic acid or its sodium salt, or effervescent mixtures; and
  e) absorbents, colorants, flavors and sweeteners.

The compound of the present invention may be administered either simultaneously with, or before or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the present invention.

In one embodiment, the invention provides a product comprising a compound of the present invention and at least one other therapeutic agent as a combined preparation for simultaneous, separate or sequential use in therapy. In one embodiment, the therapy is the treatment of a disease or condition mediated by cGAS. Products provided as a combined preparation include a composition comprising the compound of the present invention and the other therapeutic agent(s) together in the same pharmaceutical composition, or the compound of the present invention and the other therapeutic agent(s) in separate form, e.g. in the form of a kit.

In one embodiment, the invention provides a pharmaceutical composition comprising a compound of the present invention and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of the present invention. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the present invention and the other therapeutic agent may be manufactured and/or formulated by the same or different manufacturers. Moreover, the compound of the present invention and the other therapeutic may be brought together into a combination therapy: (i) prior to release of the combination product to physicians (e.g. in the case of a kit comprising the compound of the present invention and the other therapeutic agent); (ii) by the physician themselves (or under the guidance of the physician) shortly before administration; (iii) in the patient themselves, e.g. during sequential administration of the compound of the present invention and the other therapeutic agent.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Compounds of the present disclosure may be prepared by methods known in the art of organic synthesis. In all of the methods it is understood that protecting groups for sensitive or reactive groups may be employed where necessary in accordance with general principles of chemistry. Protecting groups are manipulated according to standard methods of organic synthesis (T. W. Green and P. G. M. Wuts (1999) Protective Groups in Organic Synthesis, 3rd edition, John Wiley & Sons). These groups are removed at a convenient stage of the compound synthesis using methods that are readily apparent to those skilled in the art.

Abbreviations used in the following examples and elsewhere herein are:
AIBN azobisisobutyronitrile
Bn benzyl
br broad
$Bu_4NI$ tetrabutylammonium iodide
d doublet
dd doublet of doublets
ddd doublet of doublet of doublets
ddq doublet of doublet of quartets
ddt doublet of doublet of triplets
dq doublet of quartets
dt doublet of triplets
dtd doublet of triplet of doublets
$CCl_4$ carbon tetrachloride
$Cs_2CO_3$ cesium carbonate
$Cu(OAc)_2$ copper (II) acetate
DAST diethylaminosulfur trifluoride
DBU 1,8-diazabicyclo[5.4.0]undec-7-en
DCM dichloromethane
di-tBu-bipy 4,4'-di-tert-butyl-2,2'-dipyridyl
DIBAL-H Diisobutylaluminium hydride
DMA N,N-dimethylacetamide
DMAP 4-dimethylaminopyridine
DME 1,2-Dimethoxyethane
DMF N,N-dimethylformamide
DMP Dess-Martin periodinane or 1,1,1-Tris(acetyloxy)-1,1-dihydro-1,2-benziodoxol-3-(1H)-one
DMSO dimethylsulfoxide
$EC_{50}$ half maximal effective concentration
e.e. enantiomeric excess
$Et_2O$ diethyl ether
EtOAc ethyl acetate
4-Et-Py 4-ethylpyridine
HATU 1-[Bis(dimethylamino)methylene]-1H-1,2,3-triazolo[4,5-b]pyridinium 3-oxid hexafluorophosphate
HCl hydrogen chloride
hept heptet
HPLC high performance liquid chromatography
h or hr hour
HRMS high resolution mass spectrometry
g gram
$IC_{50}$ half maximal inhibitory concentration
$K_2CO_3$ potassium carbonate
KI potassium iodide
$K_3PO_4$ tripotassium phosphate
KOAc potassium acetate
$LiAlH_4$ Lithium aluminum hydride
LCMS liquid chromatography mass spectrometry
LiHMDS Lithium bis(trimethylsilyl)amide
m multiplet
MeCN acetonitrile
MeOH methanol
mg milligram
$MgCl_2$ magnesium chloride
MHz megahertz
min minutes
mL milliliter
mmol millimole
M molar
MS mass spectrometry
$NaBH(OAc)_3$ sodium triacetoxyborohydride
$NaHCO_3$ sodium bicarbonate
$Na_2S_2O_3$ sodium thiosulfate
$Na_2SO_4$ sodium sulfate
NBS N-bromosuccinimide
$NEt_3$ triethylamine
$NH_4OAc$ ammonium acetate
$NH_4OH$ ammonium hydroxide
$NiBr_2(DME)$ nickel (II) bromide ethylene glycol dimethyl ether complex
$NiBr_2(glyme)$ nickel (II) bromide ethylene glycol dimethyl ether complex
$NiI_2$ nickel (II) iodide
NMR Nuclear magnetic resonance
PCC Pyridinium chlorochromate
$PdCl_2(dppf)_2$ [1,1'-Bis(diphenylphosphino)ferrocene]palladium(II) dichloride
$PdCl_2(dppf)\cdot DCM$ [1,1'-Bis(diphenylphosphino)ferrocene]dichloropalladium(II), complex with dichloromethane\Pd$(Ph_3P)_4$tetrakis(triphenylphosphine)palladium(0)
$PtO_2$ platinum (IV) oxide
q quartet
qd quartet of doublets quint quintet
quintd quintet of doublets
rt room temperature
Rt retention time
s singlet
SFC supercritical fluid chromatography
t triplet
TEA triethylamine
td triplet of doublets
tdd triplet of doublet of doublets
THF tetrahydrofuran
Ti(Oi-Pr)$_4$ titanium isopropoxide
TfOH triflic acid
Ts tosyl
TsCl 4-toluenesulfonyl chloride
tt triplet of triplets
ttd triplet of triplet of doublets
TLC thin-layer chromatography
UPLC ultra-Performance Liquid Chromatography
Xphos Pd G2 chloro(2-dicyclohexylphosphino-2',4',6'-triisopropyl-1,1'-biphenyl)[2-(2'-amino-1,1'-biphenyl)] palladium(II)
μW microwave Analytical Details
  NMR: Measurements were performed on a Bruker Ultrashield™ 400 (400 MHz) or Bruker Ascend™ (400 MHz) or Bruker cryo system (600 MHz) spectrometer using or not tetramethylsilane (TMS) as an internal standard. Chemical shifts (δ) are reported in ppm downfield from TMS, spectra splitting pattern are designated as singlet (s), doublet (d), triplet (t), quartet (q), quintet (quint), septet (sept), multiplet, unresolved or overlapping signals (m), broad signal (br). Deuterated solvents are given in parentheses and have a chemical shifts of dimethyl sulfoxide (δ 2.50 ppm), methanol (δ 3.31 ppm), chloroform (δ 7.26 ppm), or other solvent as indicated in NMR spectral data.
  LC-MS methods: Mass spectrometry results are reported as the ratio of mass over charge.
    Method A: Waters UPLC Acquity; column: Acquity CORTECS C18+, 2.7 μm, 2.1×50 mm at 80° C., Eluent A: H$_2$O+0.05% HCOOH+4.76% iPrOH+3.75 mM ammonium acetate, Eluent B: iPrOH+0.05% HCOOH, Gradient: initial 1% B; 1% to 50% B in 1.4 min, 50% to 98% B in 0.3 min; 0.1 min 98% B, flow: 1.0 mL/min.
    Method B: Waters UPLC Acquity; column: Acquity UPLC BEH C18, 1.7 μm, 2.1×50 mm at 80° C., Eluent A: H$_2$O+0.05% HCOOH+4.76% iPrOH+3.75 mM ammonium acetate, Eluent B: iPrOH+0.05% HCOOH, Gradient: 1-98% B in 1.7 min, flow: 0.6 mL/min.
    Method C: Waters UPLC Acquity; column: Ascentis® Express C18 2.7 μm, 2.1×50 mm at 80° C., Eluent A: water+4.76% iPrOH+0.05% FA+3.75 mM ammonium acetate Eluent B: iPrOH+0.05% HCOOH, Gradient: initial 1-50% B in 1.4 min; 50-98% B in 0.3 min Flow: 1.0 mL/min.

Preparative Methods
  Flash Column Chromatography System
    Method A: Samples were typically adsorbed on Isolute.
      System: Teledyne ISCO, CombiFlash Rf
      Columns: pre-packed RediSep Rf cartridges
    Method B: Samples were typically loaded as solutions in DCM.
      System: Biotage ISOLERA or SELEKT
      Columns: pre-packed KPSil cartridges or SFÄR cartridges
  Achiral reverse phase (RP) chromatography:
    System: Waters System
      XBridge-C18 or Sunfire-C18 (5 um, 30×100 mm or 50×250 mm column; as described in examples)
    Detection: Waters DAD 2998 Detector; Waters Acquity Qda Mass Spectrometer
    Column temperature: RT
    Eluent A: water+0.2% HCOOH or water 0.1% TFA (as described in examples)
    Eluent B: acetonitrile
    Flow: 49 mL/min or 100 mL/min
    Gradient: as described in examples All starting materials, building blocks, reagents, acids, bases, dehydrating agents, solvents, and catalysts utilized to synthesis the compounds of the present invention are either commercially available or can be produced by organic synthesis methods known to one of ordinary skill in the art.

Synthesis of Indole Intermediates

Example A:
6-Chloro-7-fluoro-5-methoxy-1-methyl-1H-indole

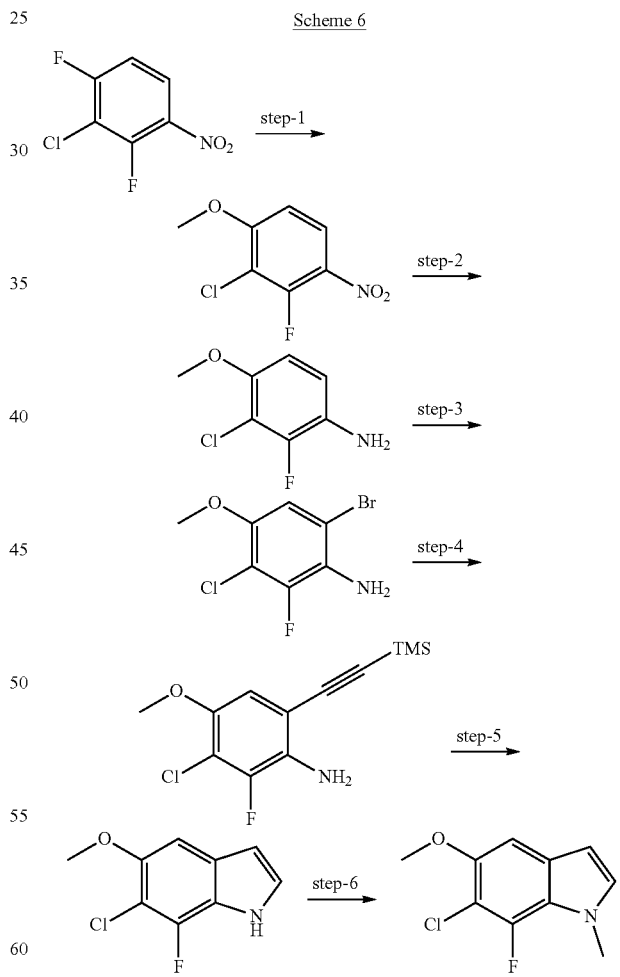

Scheme 6

Step 1: 2-chloro-3-fluoro-1-methoxy-4-nitrobenzene

A solution of sodium (3.71 g, 161 mmol) in MeOH (125 mL) was added dropwise via a dropping funnel to an ice-cooled solution of 3-chloro-2,4-difluoronitrobenzene (26 g, 134 mmol) in MeOH (500 mL). The ice-cooling was removed and the reaction mixture was stirred for 16 h at rt. The solvent was removed in vacuo. Water was added and the aq. phase was extracted with DCM. The combined organic extracts were dried over Na$_2$SO$_4$, filtered and the solvent was removed in vacuo. The crude product was purified by flash-chromatography on silica (Teledyne) using cyclohexane and EtOAc (from 0-40% EtOAc) to give the title compound (9.5 g). UPLC-MS (Method B): Rt=1.02 min; no mass detected; $^1$H NMR (400 MHz, DMSO-d6) δ 8.23 (dd, J=9.5, 8.7 Hz, 1H), 7.23 (dd, J=9.6, 1.8 Hz, 1H), 4.04 (s, 3H).

Step 2: 3-chloro-2-fluoro-4-methoxyaniline

A solution of 2-chloro-3-fluoro-1-methoxy-4-nitrobenzene (9.1 g, 44.1 mmol) in EtOH (250 mL) was warmed to 80° C. and treated with a solution of NH$_4$Cl (11.79 g, 220 mmol) in water (125 mL). Iron powder (12.31 g, 220 mmol) was added to this mixture and the reaction was stirred for 1 h at 80° C. The reaction mixture was filtered over Celite and washed with EtOAc. The filtrate was concentrated, the residue was diluted with water and extracted twice with EtOAc. The combined organic phase was dried over Na$_2$SO$_4$, filtered and the solvent was removed in vacuo to give the title compound (8.17 g) which was used without further purification. UPLC-MS (Method A): Rt=0.63 min; 255.1 [M+H]$^+$; $^1$H NMR (400 MHz, DMSO-d6) δ 6.78-6.66 (m, 2H), 4.91 (s, 2H), 3.74 (s, 3H).

Step 3: 6-bromo-3-chloro-2-fluoro-4-methoxyaniline

To an ice-cooled solution of 3-chloro-2-fluoro-4-methoxyaniline (2.01 g, 8.59 mmol) in THF (80 mL) was added NBS (1.60 g, 9.01 mmol). The reaction mixture was stirred at rt for 1 h at 0° C. warmed to rt and the solvent was removed in vacuo. The crude product was purified by flash chromatography on silica (Biotage) using heptane/EtOAc (from 0-20% EtOAc) to give the title compound (1.61 g). UPLC-MS (Method A): Rt=0.93 min; no mass detected; $^1$H NMR (400 MHz, DMSO-d6) δ 7.08 (d, J=2.2 Hz, 1H), 5.05 (s, 2H), 3.78 (s, 3H).

Step 4: 3-chloro-2-fluoro-4-methoxy-6-((trimethylsilyl)ethynyl)aniline

To a solution of 6-bromo-3-chloro-2-fluoro-4-methoxyaniline (17 g, 66.8 mmol) in THF (400 mL) was added under argon TEA (46.3 mL, 334 mmol), ethynyltrimethylsilane (11.11 mL, 80 mmol), CuI (1.02 g, 5.34 mmol) and PdCl$_2$(dppf) DCM adduct (6.55 g, 8.02 mmol). The reaction mixture was heated at 70° C. for 2 h. The reaction was cooled to rt, filtered over hyflo and washed with TBME. The filtrate was diluted with water and extracted with TBME. The combined organic phases were washed with brine, dried over Na$_2$SO$_4$, filtered and the solvent was removed in vacuo The crude product was purified by flash chromatography on silica (Teledyne) using cyclohexane and EtOAc (from 0-100% EtOAc) to give the title compound (12.5 g). UPLC-MS (Method B): Rt=1.46 min; 272.1 [M+H]$^+$; $^1$H NMR (400 MHz, DMSO-d6) δ 6.80 (d, J=1.9 Hz, 1H), 5.07 (s, 2H), 3.77 (s, 3H), 0.25 (s, 9H).

Step 5: 6-chloro-7-fluoro-5-methoxy-1H-indole

To a solution of 3-chloro-2-fluoro-4-methoxy-6-((trimethylsilyl)ethynyl)aniline (27.2 g, 83 mmol) in DMF (400 mL) was added in portions 60% NaH in mineral oil (8.0 g, 200 mmol) at rt and the reaction mixture was stirred for 1 h at 60° C. The reaction mixture was cooled to rt, slowly poured on ice-cold aq. citric acid (500 mL) and extracted with EtOAc (4×700 mL). The combined organic phase was dried over Na$_2$SO$_4$, filtered and the solvent was removed in vacuo The crude product was purified by flash-chromatography on silica (Biotage) using heptane and EtOAc (from 0-20% EtOAc) to give the title compound (12.5 g). UPLC-MS (Method B): Rt=0.92 min; 199.9 [M+H]$^+$; $^1$H NMR (400 MHz, DMSO-d6) δ 11.58 (s, 1H), 7.40 (d, J=3.0 Hz, 1H), 7.08 (d, J=1.1 Hz, 1H), 6.47 (t, J=3.2 Hz, 1H), 3.85 (s, 3H).

Step 6:
6-chloro-7-fluoro-5-methoxy-1-methyl-1H-indole

A suspension of 6-chloro-7-fluoro-5-methoxy-1H-indole (5 g, 25.1 mmol) in acetone (100 mL) was cooled to 0° C. Potassium tert-butoxide (3.37 g, 30.1 mmol) was added slowly followed by dimethyl sulfate (4.74 mL, 50.1 mmol). The ice-bath was removed and the reaction mixture was stirred at rt for 30 min. The reaction mixture was quenched with sat NH$_4$Cl under ice bath cooling and extracted twice with EtOAc. The combined organic phase was dried over Na$_2$SO$_4$, filtered and the solvent was removed in vacuo. The crude product was purified by flash chromatography on silica (Biotage) using heptane and EtOAc (from 0-30% EtOAc) to give the title compound (3.77 g). UPLC-MS (Method A): Rt=1.19 min; 214.1 [M+H]$^+$; $^1$H NMR (400 MHz, DMSO-d6) δ 7.34 (d, J=3.0 Hz, 1H), 7.06 (d, J=1.2 Hz, 1H), 6.41 (t, J=2.8 Hz, 1H), 3.91 (d, J=2.1 Hz, 3H), 3.85 (s, 3H).

Example B: 2-bromo-6-chloro-7-fluoro-5-methoxy-3-(1-(tetrahydro-2H-pyran-2-yl)-1H-pyrazol-4-yl)-1H-indole, 6-chloro-7-fluoro-5-methoxy-3-(1H-pyrazol-4-yl)-1H-indole

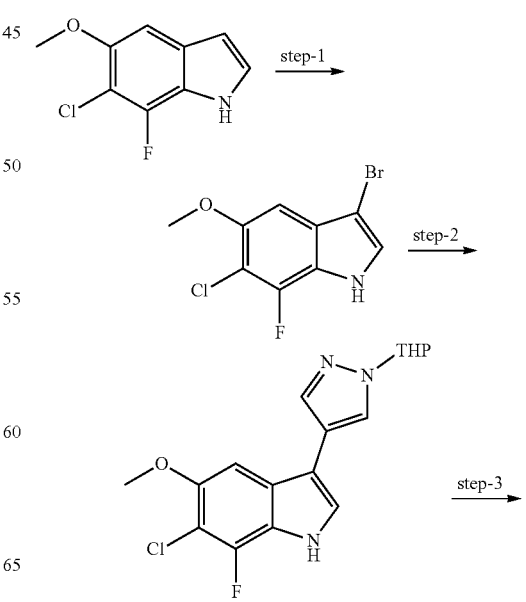

Scheme 7

-continued

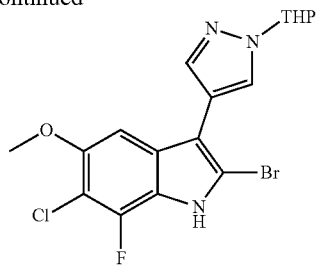

Step 1:
3-bromo-6-chloro-7-fluoro-5-methoxy-1H-indole

To a solution of 6-chloro-7-fluoro-5-methoxy-1H-indole (1 g, 5.01 mmol) in THF (50 mL) from Example A was added NBS (0.89 g, 5.01 mmol). The mixture was stirred for 30 min at rt. The solvent was removed in vacuo until dryness to give the title compound (1.9 g) which was used without further purification in the next step. UPLC-MS (Method A): Rt=1.16 min; 278.0 [M+H]+; $^1$H NMR (400 MHz, DMSO-d6) δ 12.07 (s, 1H), 7.65 (d, 1H), 6.84 (s, 1H), 3.91 (s, 3H).

Step 2: 6-chloro-7-fluoro-5-methoxy-3-(1-(tetrahydro-2H-pyran-2-yl)-1H-pyrazol-4-yl)-1H-indole To a mixture of TPGS-750M (76 ml, 2% in water) and THF (70 ml) was added under argon 3-bromo-6-chloro-7-fluoro-5-methoxy-1H-indole (1.94 g, 6.97 mmol), 1-(tetrahydro-2H-pyran-2-yl)-4-(4,4,5,5-tetramethyl-1,3,2-dioxaborolan-2-yl)-1H-pyrazole (2.91 g, 10.5 mmol), K₃PO₄ (4.44 g, 20.9 mmol) and PdCl₂(dtbpf) (1.36 g, 2.09 mmol). The reaction mixture was stirred at rt for 16 h and diluted with EtOAc. The organic phase was washed with water and brine, dried over Na₂SO₄, filtered and the solvent was removed in vacuo. The crude product was purified by flash chromatography on silica (Teledyne) using cyclohexane and EtOAc (from 0-60% EtOAc) to give the title compound (1.91 g) as a pale yellow solid. UPLC-MS (Method A): Rt=1.02 min; 350.1; $^1$H NMR (400 MHz, DMSO-d6) δ 11.69 (s, 1H), 8.27 (d, 1H), 7.99-7.89 (m, 1H), 7.67 (d, 1H), 7.17 (s, 1H), 5.44 (m, 1H), 3.98 (s, 1H), 3.95 (s, 3H), 3.74-3.55 (m, 1H), 2.31-2.10 (m, 1H), 2.02-1.92 (m, 2H), 1.76-1.47 (m, 3H).

Step 3: 2-bromo-6-chloro-7-fluoro-5-methoxy-3-(1-(tetrahydro-2H-pyran-2-yl)-1H-pyrazol-4-yl)-1H-indole, 6-chloro-7-fluoro-5-methoxy-3-(1H-pyrazol-4-yl)-1H-indole To a solution of 6-chloro-7-fluoro-5-methoxy-3-(1-(tetrahydro-2H-pyran-2-yl)-1H-pyrazol-4-yl)-1H-indole (200 mg, 0.57 mmol) in THF (15 mL) was added NBS (102 mg, 0.57 mmol). The mixture was stirred for 30 min at rt and the solvent was removed in vacuo to give the title compound (378 mg) which was used without further purification. UPLC-MS (Method A): Rt=1.16 min; 430.1 [M+H]+; $^1$H NMR (400 MHz, DMSO-d&) S 12.50 (s, 1H), 8.24 (d, 1H), 7.94 (d, 1H), 7.03 (d, 1H), 5.50 (m, 1H), 4.02-3.87 (m, 4H), 3.67 (m, 1H), 2.27-2.11 (m, 1H), 2.02-1.90 (m, 2H), 1.80-1.51 (m, 3H).

Example C: Ethyl 6-chloro-7-fluoro-5-methoxy-1-methyl-1H-indole-2-carboxylate

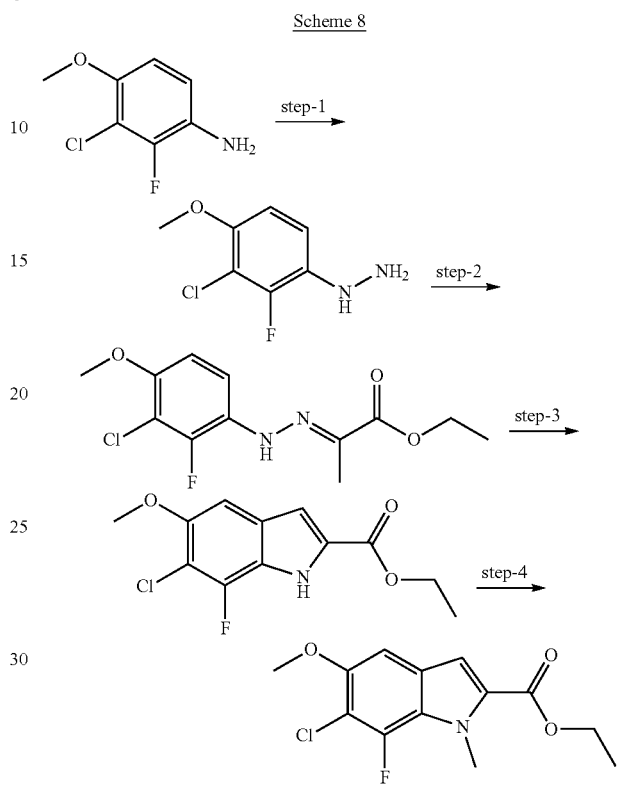

Step 1:
(3-Chloro-2-fluoro-4-methoxyphenyl)hydrazine

3-Chloro-2-fluoro-4-methoxyaniline (13.13 g, 74.8 mmol) was suspended under argon in a mixture of concentrated hydrochloric acid (350 mL) and water (175 mL). The suspension was cooled to 2° C. and a solution of sodium nitrite (6.45 g, 93 mmol) in water (25.8 mL) was added within 20 min while the temperature of the mixture was kept below 5° C. The resulting solution was stirred for a further 30 min. A solution of tin(II) chloride (56.7 g, 299 mmol) in a mixture of concentrated hydrochloric acid (63.5 mL) and water (15.9 mL) was added within 30 min at a temperature below 5° C. The resulting suspension was stirred for 90 min. Water was added and the resulting solution was adjusted to pH 7-8 by adding sodium hydroxide (222 g, 5.55 mol) while maintaining the temperature below 20° C. with ice bath cooling. Ethyl acetate (600 mL) was added and the mixture was stirred vigorously stirred for 15 min. The mixture was filtered over hyflo and rinsed thoroughly with ethyl acetate. The filtrate phase was separated and the aq. phase was extracted with ethyl acetate (500 mL). The combined organic extracts were washed once with brine (300 mL), dried over Na₂SO₄, filtered and the solvent was removed in vacuo to give the title compound (12 g) as a brown solid. UPLC-MS (Method A): Rt=0.36 min; no ionisation. $^1$H NMR (400 MHz, DMSO-d6) δ 7.07 (dd, 1H), 6.86 (dd, 1H), 6.44 (br s, 1H), 3.97 (br s, 2H), 3.77 (s, 3H).

Step 2: Ethyl (E)-2-(2-(3-chloro-2-fluoro-4-methoxyphenyl)hydrazineylidene)propanoate and Ethyl (Z)-2-(2-(3-chloro-2-fluoro-4-methoxyphenyl)hydrazineylidene)propanoate To a suspension of 3-chloro-2-fluoro-4-methoxyphenyl)hydrazine (1.5 g, 7.85 mmol) in EtOH (42 mL) were added AcOH (0.46 mL, 8 mmol) and ethyl 2-oxopropanoate (1.76 mL, 15.7 mmol) resulting in a clear solution. The mixture turned shortly after into a thick suspension which was stirred for 1 h at rt. The reaction mixture was concentrated and the crude product was purified by flash chromatography on silica (Biotage) using cyclohexane and EtOAc (from 0-25% EtOAc) to give the title compound (1.93 g) as mixture of E/Z-isomers. The crude product was purified by column chromatography on silica gel (Teledyne) using cyclohexane and EtOAc (from 3% to 25%) to give title compounds. (E)-Isomer: yellow solid (1.64 g). UPLC-MS (Method A): Rt=1.06 min; 289.10 [M+H]$^+$; $^1$H NMR (400 MHz, DMSO-d6) δ 9.24 (br s, 1H), 7.38 (dd, 1H), 7.02 (dd, 1H), 4.19 (q, 2H), 3.85 (s, 3H), 2.09 (s, 3H), 1.26 (t, 3H). (Z)-Isomer: yellow solid (0.29 g) UPLC-MS (Method A): Rt=1.47 min; 289.10 [M+H]$^+$; $^1$H NMR (400 MHz, DMSO-d6) δ 11.93 (br s, 1H), 7.43 (dd, 1H), 7.01 (dd, 1H), 4.26 (q, 2H), 3.84 (s, 3H), 2.12 (s, 3H), 1.29 (t, 3H).

Step 3: Ethyl 6-chloro-7-fluoro-5-methoxy-1H-indole-2-carboxylate

To a solution of ethyl (E)-2-(2-(3-chloro-2-fluoro-4-methoxyphenyl)hydrazineylidene)propanoate and ethyl (Z)-2-(2-(3-chloro-2-fluoro-4-methoxyphenyl)hydrazineylidene)propanoate (6.83 g, 23.66 mmol) in toluene (130 mL) was added anhydrous 4-methylbenzenesulfonic acid (6.11 g, 35.49 mmol). The dark solution was stirred for 30 min at rt and for 3 h at 50° C. The reaction mixture was cooled to rt, diluted with ethyl acetate (300 mL) and subsequently washed with water (3×100 mL) and with 20% aq. KHCO$_3$ solution (100 mL). The aqueous phase was re-extracted with ethyl acetate (2×100 mL). The combined organic phase was dried over Na$_2$SO$_4$, filtered and the solvent was removed in vacuo. The crude product was purified by flash chromatography on silica (Teledyne) using cyclohexane and EtOAc (from 0-25% EtOAc) to give the title compound (3.14 g) as a yellow solid. UPLC-MS (Method A): Rt=1.11 min; no ionisation; $^1$H NMR (400 MHz, DMSO-d6) δ 12.43 (s, 1H), 7.17 (dd, 2H), 4.34 (q, 2H), 3.88 (s, 3H), 1.34 (t, 3H).

Step 4: Ethyl 6-chloro-7-fluoro-5-methoxy-1-methyl-1H-indole-2-carboxylate

To a suspension of ethyl 6-chloro-7-fluoro-5-methoxy-1H-indole-2-carboxylate (1.28 g, 4.71 mmol) in acetone (70 mL) cooled to 0° C. was added potassium tert-butoxide (0.79 g, 7.1 mmol) followed by dimethyl sulfate (0.90 mL, 9.42 mmol). The ice-bath was removed and the mixture was stirred at rt for 20 min. An aqueous sat. NaHCO$_3$-solution was added and the mixture was extracted with CH$_2$Cl$_2$. The combined organic phase was dried over an IST cartridge phase separator and the solvent was removed in vacuo. The crude product was purified by flash chromatography on silica (Teledyne) using cyclohexane and EtOAc (from 0-100% EtOAc) to give the title compound (1.15 g) as a yellow solid. UPLC-MS (Method A): Rt=1.43 min; 286.0 [M+H]$^+$. $^1$H NMR (400 MHz, DMSO-d6) δ 7.22 (d, J=2.1 Hz, 1H), 7.18 (d, J=1.3 Hz, 1H), 4.33 (q, J=7.1 Hz, 2H), 4.16 (d, J=1.5 Hz, 3H), 3.88 (s, 3H), 1.33 (t, J=7.1 Hz, 3H).

Example D: Ethyl 5-(6-chloro-7-fluoro-5-methoxy-1-methyl-1H-indol-2-yl)-4H-1,2,4-triazole-3-carboxylate

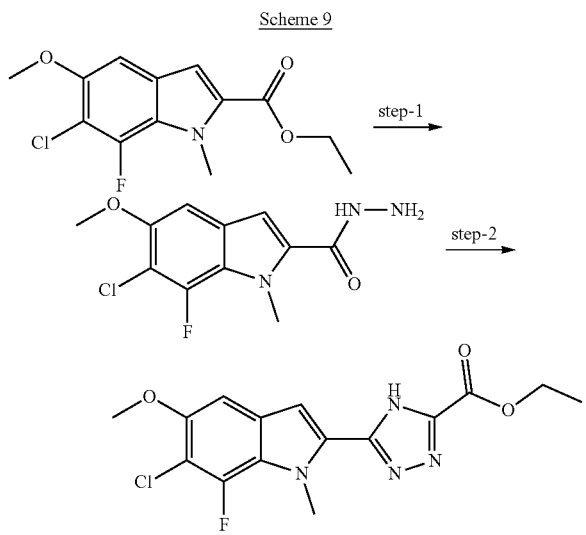

Scheme 9

Step 1: 6-chloro-7-fluoro-5-methoxy-1-methyl-1H-indole-2-carbohydrazide

To a suspension of ethyl 6-chloro-7-fluoro-5-methoxy-1-methyl-1H-indole-2-carboxylate (9.23 g, 32.3 mmol) in EtOH (350 mL) was added hydrazine monohydrate (39.2 mL, 808 mmol) and the mixture was refluxed for 10 h. The reaction mixture was cooled to rt. Water (350 mL) was added and the suspension was cooled with an ice-bath and stirred for 15 min. The solid was collected by filtration, washed with water/EtOH (1:1) and dried under high vacuum at 40° C. to give the title compound (8.4 g) as colorless solid. UPLC-MS (Method A): Rt=0.79 min; 271.1 [M+H]$^+$.
$^1$H NMR (400 MHz, DMSO-d6) δ 9.84 (s, 1H), 7.13 (d, J=1.2 Hz, 1H), 6.95 (d, J=2.2 Hz, 1H), 4.52 (s, 2H), 4.10 (d, J=1.9 Hz, 3H), 3.87 (s, 3H).

Step 2: ethyl 5-(6-chloro-7-fluoro-5-methoxy-1-methyl-1H-indol-2-yl)-4H-1,2,4-triazole-3-carboxylate To a suspension of 6-chloro-7-fluoro-5-methoxy-1-methyl-1H-indole-2-carbohydrazide (500 mg, 1.84 mmol) in EtOH (18 mL) was added ethyl 2-ethoxy-2-iminoacetate (0.41 mL, 2.76 mmol). The mixture was heated at 70° C. for 19 h in a sealed tube to form ethyl 2-(2-(6-chloro-7-fluoro-5-methoxy-1-methyl-1H-indole-2-carbonyl)hydrazineyl)-2-iminoacetate. DBU (0.83 mL, 5.5.2 mmol) was added and the mixture was heated in a sealed tube at 115° C. for 3 h. The reaction mixture was cooled to rt, diluted with EtOAc and 10% aq. citric acid was added. The aq. phase was extracted with EtOAc, and the combined organic phase was washed with brine, dried over Na$_2$SO$_4$, filtered and the solvent was removed in vacuo. The crude product was purified by flash-chromatography on silica (Teledyne) using cyclohexane and EtOAc/EtOH (95:5) (from 0-100% EtOAc/

EtOH (95:5)) to give the title compound (0.42 g) as a yellow solid. UPLC-MS (Method A): Rt=1.05 min; 352.1 [M+H]⁺. ¹H NMR (400 MHz, DMSO-d6) δ 15.43 (d, J=153.0 Hz, 1H), 7.36-6.93 (m, 2H), 4.38 (d, J=8.7 Hz, 2H), 4.26 (d, J=1.8 Hz, 3H), 3.90 (s, 3H), 1.45-1.26 (m, 3H).

Synthesis of 1,2,4-Triazole Intermediates

As discussed above in the context of Scheme 3, the triazole intermediates may each represent a mixture of up to three regioisomers. The regioisomers were not separated and were used directly. In each of the Examples below, only one regioisomer was illustrated as a representative.

Example E:
3,5-Dibromo-1-(4-methoxybenzyl)-1H-1,2,4-triazole

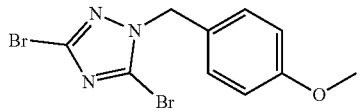 [SMILES: COc1ccc(Cn2nc(Br)nc2Br)cc1]

3,5-Dibromo-4H-1,2,4-triazole (119.5 g, 500 mmol) was dissolved in ACN (600 mL). 1-(Chloromethyl)-4-methoxybenzene (81 mL, 601 mmol) and K₂CO₃ (83 g, 601 mmol) were added and the reaction mixture was stirred for 3 h at 60° C. The reaction mixture was concentrated, diluted with water (700 mL) and extracted with EtOAc (2×1000 mL). The combined organic phase was dried over Na₂SO₄, filtered and the solvent was removed in vacuo. The brown oil was dissolved in DCM (150 mL) and heptane (1400 mL) was added slowly. The colorless precipitate was collected by filtration, washed with heptane and dried under vacuum to afford the title compound (109.1 g) UPLC/MS (Method A): Rt=0.94 min, 348.1[M+H]⁺.

Example F: 1-(3-bromo-1-(4-methoxybenzyl)-1H-1,2,4-triazol-5-yl)-2-methoxyethan-1-one and others

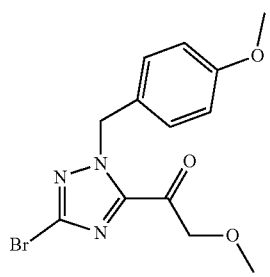 [SMILES: COCC(=O)c1nc(Br)nn1Cc1ccc(OC)cc1]

3,5-Dibromo-1-(4-methoxybenzyl)-1H-1,2,4-triazole (11.0 g, 31.7 mmol) from Example E was dissolved in THF (400 mL). Under inert and anhydrous atmosphere, n-butyllithium (22.78 mL, 36.5 mmol) was added dropwise over 5 min at −78° C. and the mixture was stirred for 45 min at −78° C. A solution of N,2-dimethoxy-N-methylacetamide (5.0 g, 35.7 mmol) in THF (10 mL) was added to the mixture. The reaction mixture was stirred at −78° C. for 45 min, quenched with aq. sat. NH₄Cl (400 mL) and extracted with EtOAc (2×300 mL). The combined organic phases were dried over Na₂SO₄, filtered and the solvent was removed in vacuo. The crude product was purified by flash chromatography on silica (Biotage) using heptane and EtOAc (from 0-20% EtOAc) to give the title compound (4.60 g). UPLC/MS (Method A): Rt=0.90 min, 340.1 and 342.1 [M+H]⁺.

The following intermediates were prepared analogous to the procedure described above for 1-(3-bromo-1-(4-methoxybenzyl)-1H-1,2,4-triazol-5-yl)-2-methoxyethan-1-one by halogen-metal exchange with n-butyllithium or iPrMgCl and subsequent reaction with the corresponding electrophile (Weinreb-amide, ester, carbamoylchloride).

| Structure and Name | LC-MS (min; m/z); Method |
|---|---|
| 1-(3-bromo-1-(4-methoxybenzyl)-1H-1,2,4-triazol-5-yl)-2-((tetrahydro-2H-pyran-2-yl)oxy)ethan-1-one | Rt = 1.19; 410.1 [M + H]⁺; Method A |
| 1-(3-bromo-1-(4-methoxybenzyl)-1H-1,2,4-triazol-5-yl)-2-((tert-butyldimethylsilyl)oxy)ethan-1-one | Rt = 1.65, 440.1, [M + H]⁺; Method A |
| 1-(3-bromo-1-(4-methoxybenzyl)-1H-1,2,4-triazol-5-yl)ethan-1-one | Rt = 1.01; 310.1, [M + H]⁺; Method A |
| 1-(3-bromo-1-(4-methoxybenzyl)-1H-1,2,4-triazol-5-yl)-2,2,2-trifluoroethan-1-one (hydrate form) | Rt = 0.84; 382.1, [M + H]⁺; Method A |
| 1-(3-bromo-1-(4-methoxybenzyl)-1H-1,2,4-triazol-5-yl)-2,2-difluoroethan-1-one (hydrate form) | Rt = 0.72; 364.1, [M + H]⁺; Method A |

| Structure and Name | LC-MS (min; m/z); Method |
|---|---|
| 3-bromo-1-(4-methoxybenzyl)-N,N-dimethyl-1H-1,2,4-triazole-5-carboxamide | Rt = 0.78; 341.1, [M + H]+; Method A |
| 3-bromo-5-(1-fluoroethyl)-1-(4-methoxybenzyl)-1H-1,2,4-triazole | Rt = 0.93; 314.0 [M + H]+; Method A |
| 3-bromo-5-(1-fluoro-2-methoxyethyl)-1-(4-methoxybenzyl)-1H-1,2,4-triazole | Rt = 0.88; 344.1 [M + H]+; Method A |

Example G: 3-bromo-5-(1,1-difluoro-2-((tetrahydro-2H-pyran-2-yl)oxy)ethyl)-1-(4-methoxybenzyl)-1H-1,2,4-triazole and others To a solution of 1-(3-bromo-1-(4-methoxybenzyl)-1H-1,2,4-triazol-5-yl)-2-((tetrahydro-2H-pyran-2-yl)oxy)ethan-1-one (6 g, 14.62 mmol) in DCM (120 mL) was added DAST (19.32 mL, 146 mmol) at rt and the reaction was heated at 40° C. for 5.5 h. The reaction mixture was cooled to ambient temperature and carefully added to an ice-cooled saturated NaHCO$_3$ solution. The aqueous phase was extracted twice with EtOAc. The combined organic phase was dried over Na$_2$SO$_4$, filtered and the solvent was evaporated. The crude product was purified by flash chromatography on silica (Teledyne) using cyclohexane/EtOAc (from 0-10% EtOAc) to give the title compound (3.82 g). UPLC/MS (Method A): Rt=1.24 min, 432.2 [M+H]+.

The following intermediates were prepared analogous to the procedure described above using the corresponding ketone or alcohol.

| Structure and Name | LC-MS (min; m/z); Method |
|---|---|
| 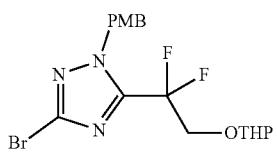 3-bromo-5-(1,1-difluoro-2-methoxyethyl)-1-(4-methoxybenzyl)-1H-1,2,4-triazole | Rt = 1.05; 362.2 [M + H]+; Method A |
| 3-bromo-5-(1,1-difluoroethyl)-1-(4-methoxybenzyl)-1H-1,2,4-triazole | Rt = 1.15; 332.2 [M + H]+; Method A |

Example H: 1-(3-bromo-1-(4-methoxybenzyl)-1H-1,2,4-triazol-5-yl)-2-methoxyethan-1-ol

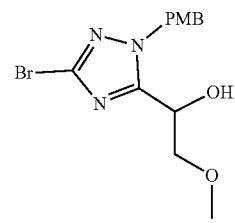

1-(3-Bromo-1-(4-methoxybenzyl)-1H-1,2,4-triazol-5-yl)-2-methoxyethan-1-one from Example F (2.76 g, 8.11 mmol) was dissolved in MeOH (50 mL) and THF (150 mL). NaBH$_4$ (0.376 g, 9.74 mmol) was added and the mixture was stirred for 20 min at 23° C. The reaction was quenched with aq. sat. NH$_4$Cl and the aq. phase was extracted twice with EtOAc. The combined organic phase was dried over Na$_2$SO$_4$, filtered and the solvent was evaporated. The crude product was purified by flash-chromatography on silica (Teledyne) using cyclohexane/EtOAc (from 0-40% EtOAc) to give the title compound (2.76 g). UPLC/MS (Method A): Rt=0.68 min, 342.1 [M+H]+.

The following intermediates were prepared analogous to the procedure described above using the corresponding ketone.

| Structure and Name | LC-MS (min; m/z); Method |
|---|---|
| 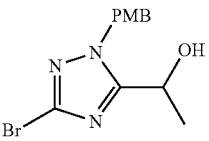<br>1-(3-bromo-1-(4-methoxybenzyl)-1H-1,2,4-triazol-5-yl)ethan-1-ol | Rt = 0.68; 312.1 [M + H]$^+$; Method A |
| 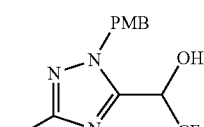<br>1-(3-bromo-1-(4-methoxybenzyl)-1H-1,2,4-triazol-5-yl)-2,2,2-trifluoroethan-1-ol | Rt = 0.92; 366.1 [M + H]$^+$; Method A |
| 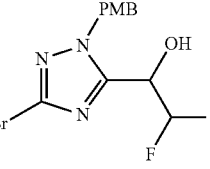<br>1-(3-bromo-1-(4-methoxybenzyl)-1H-1,2,4-triazol-5-yl)-2,2-difluoroethan-1-ol | Rt = 0.76; 348.3 [M + H]$^+$; Method A |

Example I: 3-Bromo-5-(1-(2-((tert-butyldimethylsilyl)oxy)ethoxy)-2,2,2-trifluoroethyl)-1-(4-methoxybenzyl)-1H-1,2,4-triazole

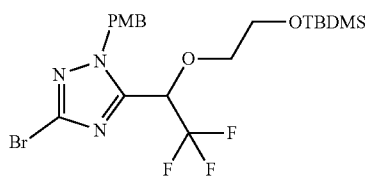

To a solution of 1-(3-bromo-1-(4-methoxybenzyl)-1H-1,2,4-triazol-5-yl)-2,2,2-trifluoroethan-1-ol (1.0 g, 2.73 mmol) and 2-(tert-butyldimethylsiloxy)ethanol (0.482 g, 2.73 mmol) in toluene (15 mL) was added 2-(tributylphosphoranylidene)acetonitrile (1.43 mL, 5.46 mmol). The reaction was stirred for 4 h at rt under argon. Additional 2-(tert-butyldimethylsiloxy)ethanol (0.250 g, 1.35 mmol) and 2-(tributylphosphoranylidene)acetonitrile (0.7 mL, 5.22 mmol) were added and the reaction was stirred overnight at rt. The mixture was concentrated, sat. aq. NaHCO$_3$ was added and the aq. phase was extracted twice with EtOAc. The combined organic phases were washed with brine, dried over Na$_2$SO$_4$, filtered and the solvent was evaporated. The crude product was purified by flash-chromatography on silica (Teledyne) using cyclohexane/EtOAc (from 0-10% EtOAc) to give the title compound (773 mg). UPLC-MS (Method A): Rt=1.62 min, 524.3 [M+H]$^+$.

Example J: 3-Bromo-1-(4-methoxybenzyl)-5-(2,2,2-trifluoro-1-methoxyethyl)-1H-1,2,4-triazole

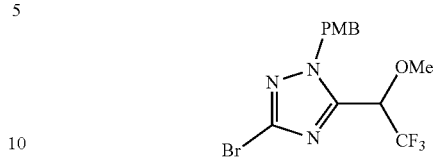

To a solution of 1-(3-bromo-1-(4-methoxybenzyl)-1H-1,2,4-triazol-5-yl)-2,2,2-trifluoroethan-1-ol (1 g, 2.73 mmol) in THF (20 mL) was added NaH (60% in mineral oil) (0.262 g, 6.55 mmol) and the reaction was stirred for 20 min at rt. Iodomethane (0.342 mL, 5.46 mmol) was added and the reaction was stirred for 2 h at rt. The mixture was quenched with aq. sat. NaHCO$_3$ and the aq. phase was extracted twice with EtOAc. The combined organic phase was washed with brine, dried over Na$_2$SO$_4$, filtered and the solvent was removed in vacuo. The crude product was purified by flash chromatography on silica (Teledyne) using cyclohexane/EtOAc (from 0-35% EtOAc) to give the title compound (587 mg). UPLC-MS (Method A): Rt=1.05 min, 380.1 [M+H]$^+$.

The following intermediates were prepared analogous to the procedure described above using the corresponding alcohol.

| Structure and Name | LC-MS (min; m/z); Method |
|---|---|
| 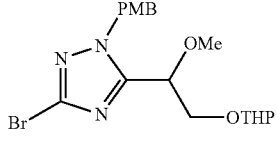<br>3-bromo-5-(1-methoxy-2-((tetrahydro-2H-pyran-2-yl)oxy)ethyl)-1-(4-methoxybenzyl)-1H-1,2,4-triazole | Rt = 1.04; 426.1 [M + H]$^+$; Method B |
| 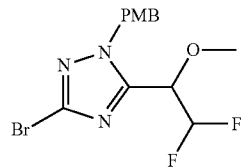<br>3-bromo-5-(2,2-difluoro-1-methoxyethyl)-1-(4-methoxybenzyl)-1H-1,2,4-triazole | Rt = 0.93; 364.2 [M + H]$^+$; Method A |

Example K: 3-bromo-1-(4-methoxybenzyl)-5-(((4-methoxybenzyl)oxy)methyl)-1H-1,2,4-triazole

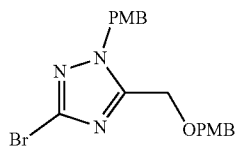

To a solution of (5-bromo-4H-1,2,4-triazol-3-yl)methanol (0.95 g, 5.34 mmol) in DMF (30 mL) was added NaH (60% in mineral oil) (0.534 g, 13.34 mmol) in portion and the mixture was stirred for 30 min at rt. 1-(chloromethyl)-4-methoxybenzene (1.67 mL, 12.28 mmol) was added and the reaction was stirred for 2 days at rt. The mixture was concentrated, diluted with water (150 mL) and the aq. phase was extracted with EtOAc (2×200 mL). The combined organic phase was dried over Na$_2$SO$_4$, filtered and the solvent was evaporated. The crude product was purified by flash-chromatography on silica (Biotage) using heptane/EtOAc (from 0-80% EtOAc) to give the title compound (1.02 g). UPLC/MS (Method A): Rt=1.11 min, 418.3 [M+H]$^+$.

The following intermediates were prepared analogous to the procedure described above using the corresponding commercial triazole building block.

| Structure and Name | LC-MS (min; m/z); Method |
|---|---|
| 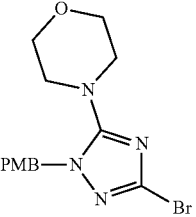<br>3-bromo-1-(4-methoxybenzyl)-5-(methoxymethyl)-1H-1,2,4-triazole | Rt = 0.79; 312.2 [M + H]$^+$; Method A |
| 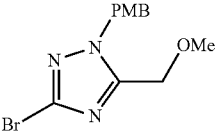<br>ethyl 3-bromo-1-(4-methoxybenzyl)-1H-1,2,4-triazole-5-carboxylate | Rt = 1.01; 340.0 [M + H]$^+$; Method A |
| 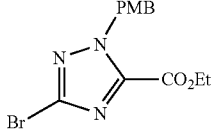<br>3-bromo-5-chloro-1-(4-methoxybenzyl)-1H-1,2,4-triazole (mixture of regioisomers) | Rt = 0.95; 302.0 [M + H]$^+$; Method A |
| 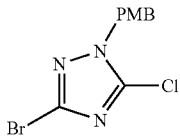<br>4-(5-bromo-1-(4-methoxybenzyl)-1H-1,2,4-triazol-3-yl)morpholine (mixture of regioisomers) | Rt = 0.79 and 0.86, 353.1 [M + H]$^+$ Method A |

Example L: 3-Bromo-5-fluoro-1-(4-methoxybenzyl)-1H-1,2,4-triazole

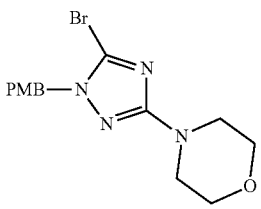

To a solution of 3,5-dibromo-1-(4-methoxybenzyl)-1H-1,2,4-triazole from Example E (16.5 g, 47.5 mmol) in DMSO (40 mL) was added CsF (14.45 g, 95.0 mmol) and the reaction was heated at 100° C. for 90 min. The reaction mixture was cooled to rt and poured on ice water. The aq. phase was extracted with EtOAc (2×300 mL). The combined organic phase was dried over Na$_2$SO$_4$, filtered and the solvent was evaporated. The crude product was purified by flash-chromatography on silica (Biotage) using heptane/EtOAc (from 0-20% EtOAc) to give the title compound (12.2 g) as a mixture of isomers. UPLC-MS (Method A): Rt=0.91 min, no ionisation. δ 7.35-7.21 (m, 2H), 7.00-6.86 (m, 2H), 5.20 (s, 2H), 3.75 (s, 3H).

Example M: (R)-1-(3-Bromo-1-(4-methoxybenzyl)-1H-1,2,4-triazol-5-yl)pyrrolidin-3-ol

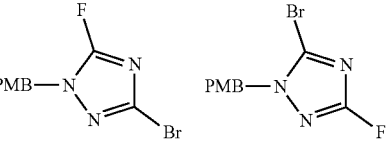

3,5-Dibromo-1-(4-methoxybenzyl)-1H-1,2,4-triazole (3 g, 8.65 mmol) from Example E, (R)-pyrrolidin-3-ol (0.753 g, 8.65 mmol) and K$_2$CO$_3$ (1.43 g, 10.4 mmol) were suspended in DMSO (20 mL) and heated for 6 days at 50° C. The reaction mixture was diluted with water and extracted twice with EtOAc. The combined organic phase was dried over Na$_2$SO$_4$, filtered and the solvent was evaporated. The crude product was purified by flash chromatography on silica (Biotage) using EtOAc/MeOH (from 0-30% MeOH) to give the title compound (2.51 g). UPLC-MS (Method A): Rt=0.63 min, 353.1 [M+H]$^+$.

The following intermediates were prepared analogous to the procedure described above using the corresponding amines.

| Structure and Name | LC-MS (min; m/z); Method |
|---|---|
| 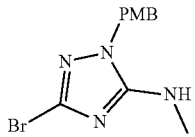<br>3-bromo-1-(4-methoxybenzyl)-N-methyl-1H-1,2,4-triazol-5-amine | Rt = 0.63; 297.1 [M + H]$^+$; Method A |
| 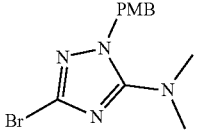<br>3-bromo-1-(4-methoxybenzyl)-N,N-dimethyl-1H-1,2,4-triazol-5-amine | Rt = 0.83; 311.1 M + H]$^+$; Method A |
| 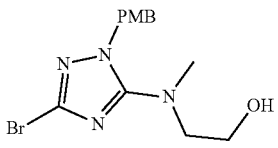<br>2-((3-bromo-1-(4-methoxybenzyl)-1H-1,2,4-triazol-5-yl)(methyl)amino)ethan-1-ol | Rt = 0.67; 341.1 M + H]$^+$; Method A |

Example N: N-(3-Bromo-1-(4-methoxybenzyl)-1H-1,2,4-triazol-5-yl)-N-methylacetamide

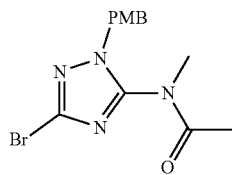

To a solution of 3-bromo-1-(4-methoxybenzyl)-N-methyl-1H-1,2,4-triazol-5-amine (1.8 g, 6.06 mmol) from Example M in dioxane (20 mL) was added Et$_3$N (1.26 mL, 9.09 mmol) and acetyl chloride (0.517 mL, 7.27 mmol). The reaction mixture was stirred for 1 h at rt and then at 80° C. for 1 h. Additional acetyl chloride (0.517 mL, 7.27 mmol) was added and heating was continued for 2 h. The mixture was cooled to rt, diluted with water and extracted twice with EtOAc. The combined organic phase was dried over Na$_2$SO$_4$, filtered and the solvent was evaporated. The crude product was purified by flash-chromatography on silica (Biotage) using heptane/EtOAc (from 0-100% EtOAc) to give the title compound (1.41 g). UPLC-MS (Method A): Rt=0.72 min, 339.1 [M+H]$^+$.

The following intermediate was prepared analogous to the procedure described above using 2-methoxyacetyl chloride.

| Structure and Name | LC-MS (min; m/z); Method |
|---|---|
| 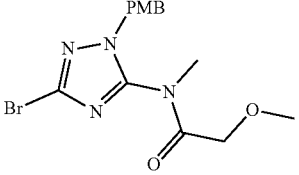<br>N-(3-bromo-1-(4-methoxybenzyl)-1H-1,2,4-triazol-5-yl)-2-methoxy-N-methylacetamide | Rt = 0.71; 369.1 [M + H]$^+$; Method A |

Example O: 1-(5-Bromo-1-(4-methoxybenzyl)-1H-1,2,4-triazol-3-yl)pyrrolidin-2-one

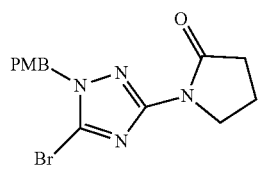

3,5-dibromo-1-(4-methoxybenzyl)-1H-1,2,4-triazole (3 g, 8.65 mmol) from Example E, pyrrolidin-2-one (0.736 g, 8.65 mmol), N1,N1-dimethylethane-1,2-diamine (0.152 g, 1.729 mmol), CuI (0.165 g, 0.865 mmol) and K$_2$CO$_3$ (2.63 g, 19.02 mmol) were suspended in toluene (100 mL) and stirred at 110° C. for 5 days. Additional pyrrolidin-2-one (0.736 g, 8.65 mmol), N1,N1-dimethylethane-1,2-diamine (0.152 g, 1.729 mmol), CuI (0.165 g, 0.865 mmol) and K$_2$CO$_3$ (2.63 g, 19.02 mmol) were added and heating was continued for 5 days. The reaction mixture was quenched with sat. aq. NH$_4$Cl and the aq. phase was extracted twice with EtOAc. The combined organic phase was washed with water and brine, dried with Na$_2$SO$_4$, filtered and the solvent was evaporated. The crude product was purified by flash-chromatography on silica (Biotage) using heptane/EtOAc (from 0-50% EtOAc) to give the title compound (884 mg). UPLC-MS (Method A): Rt=0.74 min, 351.2 [M+H]$^+$.

Example P: 3-bromo-1-(4-methoxybenzyl)-5-(2-((tetrahydro-2H-pyran-2-yl)oxy)ethoxy)-1H-1,2,4-triazole

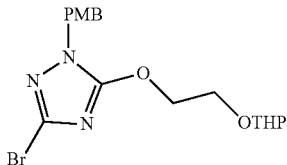

2-(Tetrahydro-2H-pyran-2-yloxy)ethanol (2.99 mL, 21.61 mmol) was dissolved in THF (100 mL) and NaH (0.864 g, 21.61 mmol) was added portionwise and the mixture was stirred at 23° C. for 45 min. 3,5-Dibromo-1-(4-methoxybenzyl)-1H-1,2,4-triazole from Example E was added (5 g, 14.41 mmol) and stirring was continued for 2.5 h at rt. The mixture was quenched with 10% citric acid and extracted with EtOAc. The organic layer was dried over an IST cartridge phase separator and the filtrate was concentrated. The crude product was purified by flash chromatography on silica (Teledyne) using cyclohexane/EtOAc (from 0-100% EtOAc) to give the title compound (4.35 g). UPLC-MS (Method A): Rt=1.06 min, 412.4 [M+H]+.

The following intermediate was prepared analogous to the procedure described above using sodium methylate in MeOH.

| Structure and Name | LC-MS (min; m/z); Method |
|---|---|
| 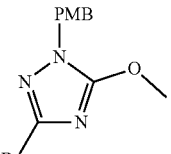 3-bromo-5-methoxy-1-(4-methoxybenzyl)-1H-1,2,4-triazole | Rt = 0.86; 298.1 [M + H]+; Method A |

Example Q: Methyl 5-bromo-2-(4-methoxybenzyl)-2H-1,2,3-triazole-4-carboxylate and methyl 4-bromo-1-(4-methoxybenzyl)-1H-1,2,3-triazole-5-carboxylate (1:1 mixture)

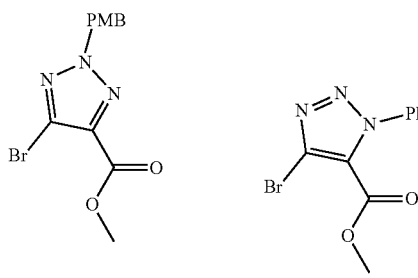

To a solution of methyl 4-bromo-1H-1,2,3-triazole-5-carboxylate (7.08 g, 32.7 mmol) in acetonitrile (300 mL) was added 1-(chloromethyl)-4-methoxybenzene (5.62 g, 35.9 mmol) followed by K$_2$CO$_3$ (5.41 g, 39.2 mmol) and the reaction was heated for 6 h at 60° C. The reaction mixture was concentrated, diluted with water (250 mL) and the aq. phase was extracted with EtOAc (2×400 mL). The crude product was purified by flash chromatography on silica (Biotage) using heptane/EtOAc (from 0-50% EtOAc) to give the title compound (8.55 g) of the title compound as a 1:1 mixture of regioisomers which was used without further separation. UPLC-MS (Method A): Rt=0.92 & 0.95 min, 326.1 [M+H]+.

Synthesis of Compounds of Invention

In the Examples below, where tautomerization or regioisomerization is possible for each compound, only one form is presented as illustration. Mixtures of regioisomers or tautomers were not separated. Each compound of the invention is represented below by only one tautomeric form. To avoid confusion, a list of compounds including the tautomers is in Table 1.

Example 1: 6-Chloro-7-fluoro-5-methoxy-1-methyl-3-(1H-pyrazol-4-yl)-2-(5-(trifluoromethyl)-4H-1,2,4-triazol-3-yl)-1H-indole The title compound was synthesized via the method illustrated in Scheme 10 below.

Scheme 10

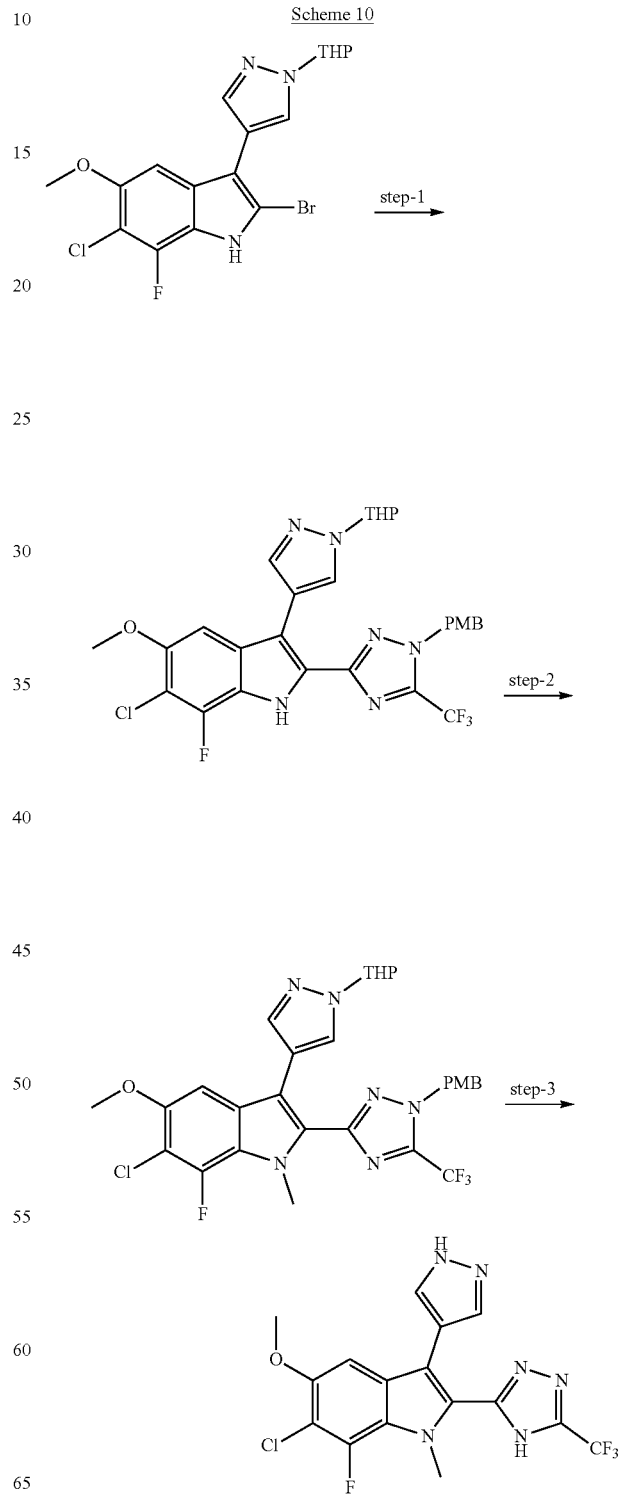

Step 1: 6-chloro-7-fluoro-5-methoxy-2-(1-(4-methoxybenzyl)-5-(trifluoromethyl)-1H-1,2,4-triazol-3-yl)-3-(1-(tetrahydro-2H-pyran-2-yl)-1H-pyrazol-4-yl)-1H-indole

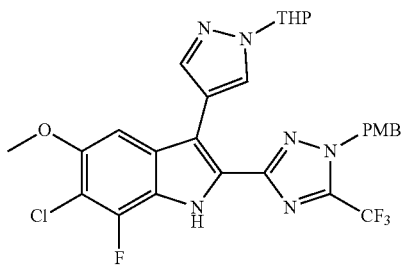

To a suspension of 2-bromo-6-chloro-7-fluoro-5-methoxy-3-(1-(tetrahydro-2H-pyran-2-yl)-1H-pyrazol-4-yl)-1H-indole (378 mg, 0.864 mmol) in dioxane (40 mL) was added under argon 4,4,4',4',5,5,5',5'-octamethyl-2,2'-bi(1,3,2-dioxaborolane) (1.8 g, 6.91 mmol), KOAc (848 mg, 8.64 mmol) and PdCl$_2$(dppf) DCM adduct (106 mg, 0.130 mmol) and the mixture was heated at 110° C. for 2 h. 3-Bromo-1-(4-methoxybenzyl)-5-(trifluoromethyl)-1H-1,2,4-triazole (349 mg, 1.04 mmol), K$_2$CO$_3$ (358 mg, 2.59 mmol), PdCl$_2$(dppf) DCM adduct (106 mg, 0.13 mmol) and water (3.6 mL) were added to the mixture and heating was continued at 11° C. for 60 min. The reaction mixture was cooled to rt, diluted with EtOAc, and the organic phase was washed with water and brine. The organic phase was dried over an IST cartridge phase separator and the solvent was removed in vacuo. The crude product was purified by flash chromatography on silica (Teledyne) using cyclohexane and EtOAc (from 0-50% EtOAc) to give the title compound (798 mg, 0.92 mmol) as a brown oil. UPLC-MS (Method A): Rt=1.47 min, 605.3 [M+H]$^+$.

Step 2: 6-chloro-7-fluoro-5-methoxy-2-(1-(4-methoxybenzyl)-5-(trifluoromethyl)-1H-1,2,4-triazol-3-yl)-1-methyl-3-(1-(tetrahydro-2H-pyran-2-yl)-1H-pyrazol-4-yl)-1H-indole

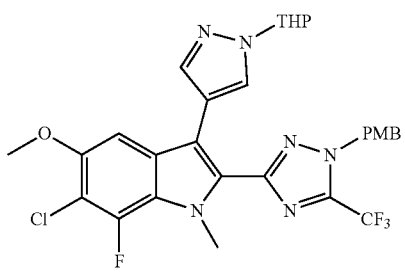

To a solution of 6-chloro-7-fluoro-5-methoxy-2-(1-(4-methoxybenzyl)-5-(trifluoromethyl)-1H-1,2,4-triazol-3-yl)-3-(1-(tetrahydro-2H-pyran-2-yl)-1H-pyrazol-4-yl)-1H-indole (798 mg, 0.92 mmol) in DMF (9.2 mL) was added at 0° C. sodium hydride (60% in mineral oil) (44.3 mg, 1.11 mmol). After 60 min at 0° C., iodomethane (69 µl, 1.11 mmol) was added and mixture was stirred for 6 h at rt. The reaction mixture was quenched by addition of water and the aq. phase was extracted with EtOAc. The combined organic phase was washed with brine, dried over an IST cartridge phase separator and the solvent was removed in vacuo. The crude product was purified by flash chromatography on silica (Teledyne) using cyclohexane and EtOAc (from 0-50% EtOAc) to give the title compound (214 mg, 0.31 mmol) as a pale yellow oil. UPLC-MS (Method A): Rt=1.57 min, 619.2 [M+H]$^+$.

Step 3: 6-Chloro-7-fluoro-5-methoxy-1-methyl-3-(1H-pyrazol-4-yl)-2-(5-(trifluoromethyl)-4H-1,2,4-triazol-3-yl)-1H-indole

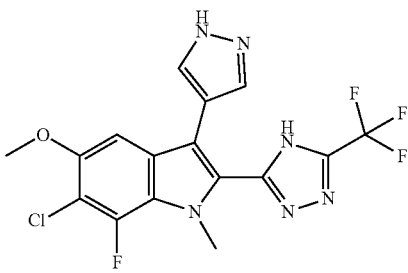 [SMILES: COc1cc2c(-c3cn[nH]c3)c(-c3nnc(C(F)(F)F)[nH]3)n(C)c2c(F)c1Cl]

To a solution of 6-chloro-7-fluoro-5-methoxy-2-(1-(4-methoxybenzyl)-5-(trifluoromethyl)-1H-1,2,4-triazol-3-yl)-1-methyl-3-(1-(tetrahydro-2H-pyran-2-yl)-1H-pyrazol-4-yl)-1H-indole (214 mg, 0.31 mmol) in 1,2-DCE (7.7 ml) was added triflic acid (276 µl, 3.11 mmol). The reaction mixture was stirred for 30 min at rt, quenched carefully by addition of sat. aq. NaHCO$_3$ and extracted twice with EtOAc. The organic layer was dried over an IST cartridge phase separator and the solvent was removed in vacuo. The crude product was purified by flash chromatography on silica (Teledyne) using cyclohexane and EtOAc (from 0-100% EtOAc) to give the title compound (35 mg, 0.08 mmol) as a colorless solid. UPLC-MS (Method A): Rt=1.18 min, 415.3 [M+H]$^+$. $^1$H NMR (400 MHz, DMSO-d6) δ 15.29 (s, 1H), 13.01 (s, 1H), 7.92 (s, 1H), 7.45 (s, 1H), 7.12 (d, 1H), 3.97-3.81 (m, 6H).

The following examples were synthesized analogous to the above procedures using the corresponding protected triazole building block, optionally including N-methylation:

| Ex No. | Structure and Name | ¹H NMR (400 MHz, DMSO-d₆) | LC-MS (min; m/z); Method |
|---|---|---|---|
| 2 | 5-(6-chloro-7-fluoro-5-methoxy-1-methyl-3-(1H-pyrazol-4-yl)-1H-indol-2-yl)-N,N-dimethyl-4H-1,2,4-triazole-3-carboxamide | δ 12.89 (s, 1H), 7.95 (s, 1H), 7.57 (s, 1H), 7.08 (s, 1H), 3.92 (s, 3H), 3.89 (d, J = 1.6 Hz, 3H), 3.36 (s, 3H), 3.06 (s, 3H). | Rt = 0.89; 418.2 [M + H]⁺; Method A |
| 3 | 6-chloro-7-fluoro-2-(5-fluoro-4H-1,2,4-triazol-3-yl)-5-methoxy-3-(1H-pyrazol-4-yl)-1H-indole | δ 14.06 (s, 1H), 13.01 (s, 1H), 12.18 (s, 1H), 8.12 (s, 1H), 7.79 (s, 1H), 7.10 (s, 1H), 3.93 (s, 3H). | Rt = 0.85; 351.0 [M + H]⁺; Method A |
| 4 | 6-chloro-7-fluoro-5-methoxy-3-(1H-pyrazol-4-yl)-2-(5-(trifluoromethyl)-4H-1,2,4-triazol-3-yl)-1H-indole | δ 15.04 (s, 1H), 13.03 (s, 1H), 12.28 (s, 1H), 8.13 (s, 1H), 7.78 (s, 1H), 7.12 (s, 1H), 3.94 (s, 3H). | Rt = 1.05; 401.2 [M + H]⁺; Method B |
| 5 | 2-(5-bromo-4H-1,2,4-triazol-3-yl)-6,7-dichloro-3-(1H-pyrazol-4-yl)-1H-indole | δ 15.04 (s, 1H), 14.75 (s, 1H), 12.98 (s, 1H), 12.04 (s, 1H), 7.72 (d, J = 8.6 Hz, 3H), 7.31 (d, J = 8.6 Hz, 1H). | Rt = 1.08; 399.0 [M + H]⁺; Method A |

| Ex No. | Structure and Name | ¹H NMR (400 MHz, DMSO-d₆) | LC-MS (min; m/z); Method |
|---|---|---|---|
| 6 | 6-chloro-7-fluoro-3-(1H-pyrazol-4-yl)-2-(5-(trifluoromethyl)-4H-1,2,4-triazol-3-yl)-1H-indole-5-carbonitrile | δ 15.31 (s, 1H), 13.13 (s, 2H), 8.28 (s, 1H), 8.25 (s, 1H), 7.80 (s, 1H). | Rt = 1.03; 396.1 [M + H]⁺; Method A |
| 7 | 1-(5-(6,7-dichloro-3-(1H-pyrazol-4-yl)-1H-indol-2-yl)-4H-1,2,4-triazol-3-yl)-2-methoxyethan-1-one | δ 15.23 (d, J = 249.6 Hz, 1H), 12.02 (d, J = 103.5 Hz, 1H), 8.01 (s, 2H), 7.75 (s, 1H), 7.32 (s, 1H), 4.87 (s, 2H), 3.42 (s, 3H). | Rt = 0.91; 391.2 [M + H]⁺; Method A |
| 8 | 6-chloro-7-fluoro-1-methyl-3-(1H-pyrazol-4-yl)-2-(5-(trifluoromethyl)-4H-1,2,4-triazol-3-yl)-1H-indole-5-carbonitrile | δ 15.51 (s, 1H), 13.11 (s, 1H), 8.30 (s, 1H), 8.06 (s, 1H), 7.42 (s, 1H), 3.93 (d, J = 1.8 Hz, 3H). | Rt = 1.11; 410.1 [M + H]⁺; Method A |
| 9 | 6,7-dichloro-2-(5-(1,1-difluoro-2-methoxyethyl)-4H-1,2,4-triazol-3-yl)-3-(1H-pyrazol-4-yl)-1H-indole | δ 14.78 (s, 1H), 12.94 (s, 1H), 12.10 (s, 1H), 8.37-7.49 (m, 3H), 7.33 (d, J = 8.6 Hz, 1H), 4.11 (t, J = 13.8 Hz, 2H), 3.40 (s, 3H). | Rt = 1.06; 413.1 [M + H]⁺; Method A |

| Ex No. | Structure and Name | $^1$H NMR (400 MHz, DMSO-$d_6$) | LC-MS (min; m/z); Method |
|---|---|---|---|
| 10 | 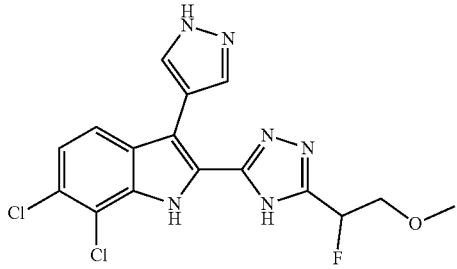 [SMILES: COCC(F)c1nnc(-c2[nH]c3c(Cl)c(Cl)ccc3c2-c2cn[nH]c2)[nH]1]

6,7-dichloro-2-(5-(1-fluoro-2-methoxyethyl)-4H-1,2,4-triazol-3-yl)-3-(1H-pyrazol-4-yl)-1H-indole | δ 11.94 (s, 1H), 8.00 (s, 2H), 7.73 (d, J = 8.6 Hz, 1H), 7.30 (d, J = 8.6 Hz, 1H), 5.88 (d, J = 49.1 Hz, 1H), 4.05-3.82 (m, 2H), 3.37 (s, 3H). | Rt = 0.99; 395.1 [M + H]$^+$; Method A |

Example 11: 6,7-dichloro-3-(1H-pyrazol-4-yl)-2-(5-(trifluoromethyl)-4H-1,2,4-triazol-3-yl)-1H-indole The title compound was synthesized via the method illustrated in Scheme 11 below.

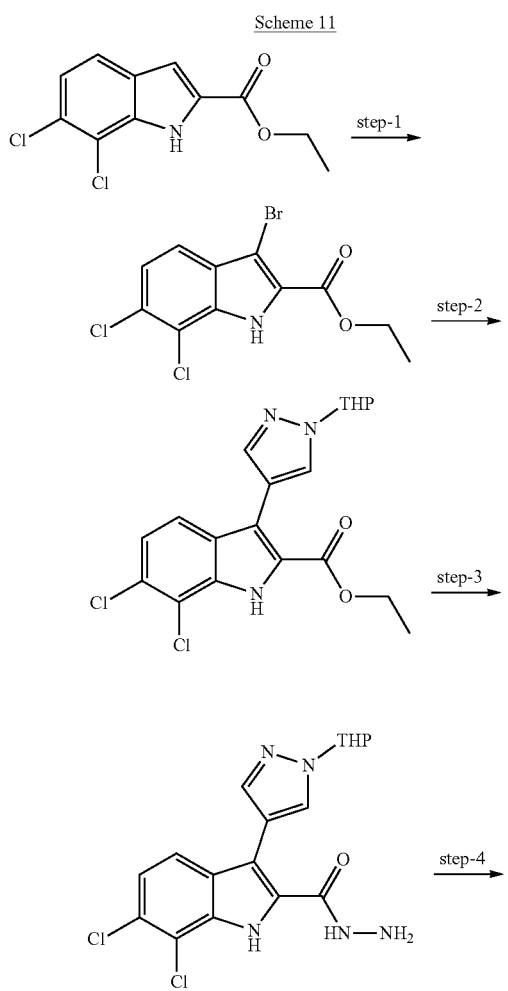

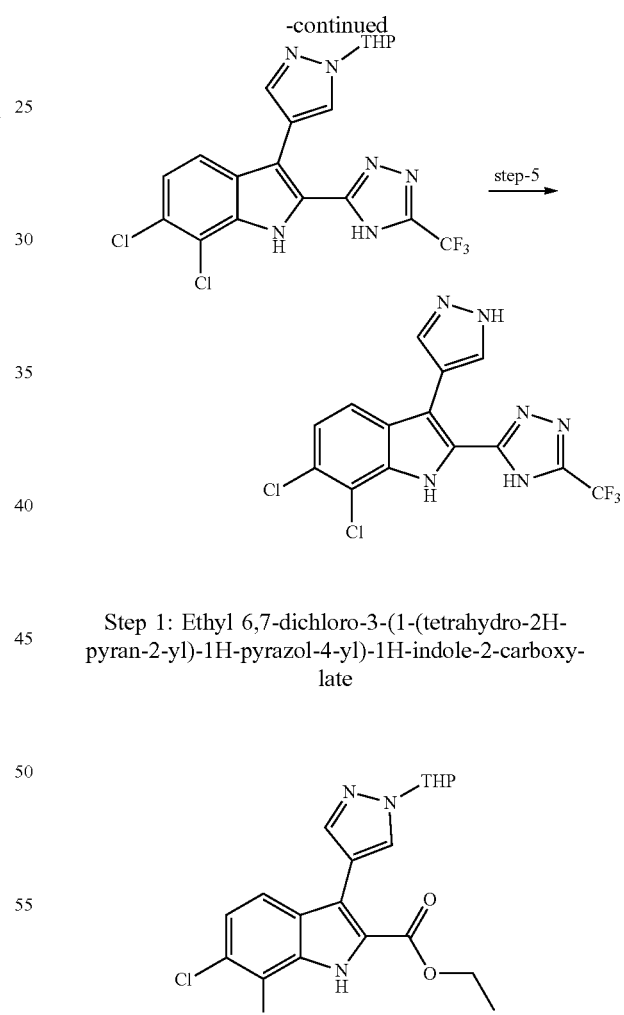

Step 1: Ethyl 6,7-dichloro-3-(1-(tetrahydro-2H-pyran-2-yl)-1H-pyrazol-4-yl)-1H-indole-2-carboxylate To a solution of ethyl 6,7-dichloro-1H-indole-2-carboxylate (10 g, 38.7 mmol) in DME (160 mL) was added NBS (7.59 g, 42.6 mmol) and the reaction was stirred for 60 min at rt. To the reaction mixture were added 1-(tetrahydro-2H-pyran-2-yl)-4-(4,4,5,5-tetramethyl-1,3,2-dioxaborolan-2-yl)-1H-pyrazole (12.71 g, 45.7 mmol), K$_2$CO$_3$ (26.8 g, 194 mmol), water (35 ml) and PdCl$_2$(dppf) DCM adduct (3.16 g, 3.87 mmol) and the reaction was heated at 100° C. for 2.5 h. The reaction mixture was cooled to rt, diluted with water and the aq. phase was extracted with EtOAc. The combined organic phase was dried over Na$_2$SO$_4$, filtered and the solvent was removed in vacuo. The crude product was purified by flash chromatography on silica (Biotage) using heptane and EtOAc (from 0-50% EtOAc) to give the title compound (10.7 g). UPLC-MS (Method C): Rt=1.28 min, 408.2 [M+H]$^+$. $^1$H NMR (600 MHz, DMSO-d6) δ 12.07 (s, 1H), 8.25 (s, 1H), 7.86 (s, 1H), 7.68 (d, J=8.6 Hz, 1H), 7.33 (d, J=8.6 Hz, 1H), 5.48 (dd, J=10.3, 2.1 Hz, 1H), 4.32 (q, J=7.1 Hz, 2H), 4.02-3.92 (m, 1H), 3.73-3.61 (m, 1H), 2.23-2.11 (m, 1H), 1.98 (d, J=11.4 Hz, 2H), 1.75-1.67 (m, 1H), 1.56 (dq, J=9.1, 4.5 Hz, 2H), 1.31 (t, J=7.1 Hz, 3H).

Step 2: 6,7-dichloro-3-(1-(tetrahydro-2H-pyran-2-yl)-1H-pyrazol-4-yl)-1H-indole-2-carbohydrazide

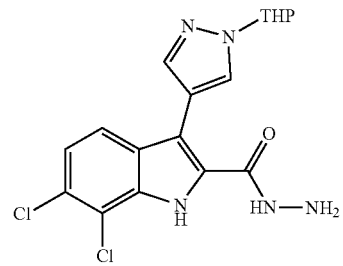

To a solution of ethyl 6,7-dichloro-3-(1-(tetrahydro-2H-pyran-2-yl)-1H-pyrazol-4-yl)-1H-indole-2-carboxylate (2.01 g, 4.92 mmol) in EtOH (10 mL) was added hydrazine hydrate (6.0 g, 120 mmol) and the reaction mixture was stirred for 20 h at 100° C. The reaction mixture was concentrated to dryness and the crude product was purified by flash-chromatography on silica (Biotage) using heptane, EtOAc and MeOH (from 0-100% EtOAc and EtOAc/MeOH 0-20%) to give the title compound (1.54 g). UPLC-MS (Method C): Rt=0.93 min, 394.1 [M+H]$^+$.

Step 3: 6,7-dichloro-3-(1-(tetrahydro-2H-pyran-2-yl)-1H-pyrazol-4-yl)-2-(5-(trifluoromethyl)-4H-1,2,4-triazol-3-yl)-1H-indole

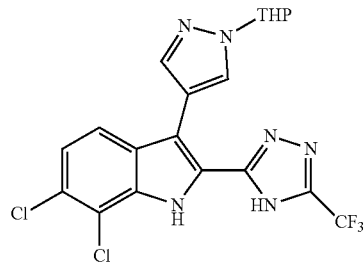

6,7-Dichloro-3-(1-(tetrahydro-2H-pyran-2-yl)-1H-pyrazol-4-yl)-1H-indole-2-carbohydrazide (800 mg, 2.03 mmol) and ethyl 2,2,2-trifluoroacetimidate (500 mg, 3.54 mmol) were suspended in EtOH (16 mL) and the reaction mixture was stirred for 3 d at 50° C. to form 6,7-dichloro-3-(1-(tetrahydro-2H-pyran-2-yl)-1H-pyrazol-4-yl)-N'-(2,2,2-trifluoro-1-iminoethyl)-1H-indole-2-carbohydrazide. Sodium methoxide in EtOH (3.18 mL, 8.12 mmol) was added and the reaction mixture was heated for 10 min at 160° C. in the microwave. The reaction mixture was concentrated, aq. 10% citric acid and EtOAc were added and the aq. phase was extracted with EtOAc. The combined organic phase was washed with brine, dried over Na$_2$SO$_4$, filtered and the solvent was removed in vacuo. The crude product was purified by flash chromatography on silica (Biotage) using heptane and EtOAc (from 0-100% EtOAc) to give the title compound (840 mg) as a pale yellow solid. UPLC-MS (Method C): Rt=1.21 min, 471.1 [M+H]$^+$.

Step 4: 6,7-Dichloro-3-(1H-pyrazol-4-yl)-2-(5-(trifluoromethyl)-4H-1,2,4-triazol-3-yl)-1H-indole

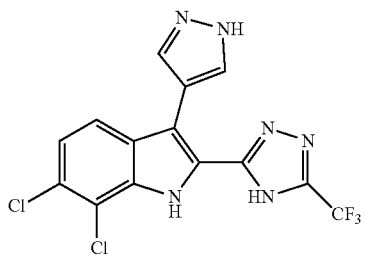 [SMILES: FC(F)(F)c1nnc(-c2[nH]c3c(Cl)c(Cl)ccc3c2-c2cn[nH]c2)[nH]1]

A suspension of 6,7-dichloro-3-(1-(tetrahydro-2H-pyran-2-yl)-1H-pyrazol-4-yl)-2-(5-(trifluoromethyl)-4H-1,2,4-triazol-3-yl)-1H-indole (833 mg, 1.59 mmol) in 4N HCl in dioxane (40 ml, 160 mmol) was stirred for 30 h at rt. The reaction mixture was poured carefully on aq. sat. NaHCO$_3$ (300 mL) and the aq. phase was extracted with EtOAc (2×400 mL). The combined organic phase was dried over Na$_2$SO$_4$, filtered and the solvent was removed in vacuo. The crude product was purified by flash chromatography on silica (Biotage) using heptane and EtOAc (from 0-100% EtOAc) to give the title compound (840 mg) as a pale yellow solid. UPLC-MS (Method C): Rt=1.06 min, 387.1 [M+H]$^+$. $^1$H NMR (600 MHz, DMSO-d6) δ 15.20 (s, 1H), 13.06 (s, 1H), 12.22 (s, 1H), 7.90 (s, 2H), 7.78 (d, J=8.5 Hz, 1H), 7.36 (d, J=8.5, 2.3 Hz, 1H).

The following examples were synthesized analogous to the above procedures, using the corresponding indole building block and commercial imino ester, respectively, optionally including indole N-alkylation.

| Ex No. | Structure and Name | ¹H NMR (400 MHz DMSO-d₆) | LC-MS (min; m/z); Method |
|---|---|---|---|
| 12 | 6,7-dichloro-1-methyl-3-(1H-pyrazol-4-yl)-2-(5-(trifluoromethyl)-4H-1,2,4-triazol-3-yl)-1H-indole | δ 15.40 (s, 1H), 13.06 (s, 1H), 7.89 (s, 1H), 7.75 (d, J = 8.7 Hz, 1H), 7.52-7.27 (m, 2H), 4.01 (d, J = 2.1 Hz, 3H). | Rt = 1.11; 401.1 [M + H]⁺; Method C |
| 13 | 6,7-dichloro-3-(1H-pyrazol-4-yl)-2-(5-(2,2,2-trifluoroethyl)-4H-1,2,4-triazol-3-yl)-1H-indole | δ 11.98 (s, 1H), 8.03 (s, 2H), 7.77 (d, J = 8.6 Hz, 1H), 7.33 (d, J = 8.6 Hz, 1H), 3.97 (m, 2H). | Rt = 1.01; 401.1 [M + H]⁺; Method C |
| 14 | 6,7-difluoro-3-(1H-pyrazol-4-yl)-2-(5-(trifluoromethyl)-4H-1,2,4-triazol-3-yl)-1H-indole | δ 15.09 (s, 1H), 13.05 (s, 1H), 12.46 (s, 1H), 8.13 (s, 1H), 7.75 (s, 1H), 7.63-7.53 (m, 1H), 7.24-7.11 (m, 1H). | Rt = 0.89; 355.1 [M + H]⁺; Method C |
| 15 | 2-(5-(6,7-dichloro-3-(1H-pyrazol-4-yl)-1H-indol-2-yl)-4H-1,2,4-triazol-3-yl)ethan-1-ol | δ 13.95 (s, 1H), 12.89 (s, 1H), 11.67 (s, 1H), 8.14 (s, 2H), 7.68 (d, J = 8.6 Hz, 1H), 7.26 (d, J = 8.5 Hz, 1H), 4.89 (s, 1H), 3.82-3.76 (m, 2H), 2.97-2.87 (m, 2H). | Rt = 0.77; 363.2 [M + H]⁺; Method C |

| Ex No. | Structure and Name | ¹H NMR (400 MHz DMSO-d₆) | LC-MS (min; m/z); Method |
|---|---|---|---|
| 16 | 6-chloro-7-fluoro-3-(1H-pyrazol-4-yl)-2-(5-(trifluoromethyl)-4H-1,2,4-triazol-3-yl)-1H-indole | δ 15.12 (s, 1H), 13.04 (s, 1H), 12.48 (s, 1H), 8.11 (s, 1H), 7.74 (s, 1H), 7.60 (d, J = 8.6 Hz, 1H), 7.31-7.17 (m, 1H). | Rt = 0.97; 371.1 [M + H]⁺; Method C |
| 17 | 6-chloro-7-methoxy-3-(1H-pyrazol-4-yl)-2-(5-(trifluoromethyl)-4H-1,2,4-triazol-3-yl)-1H-indole | δ 15.04 (s, 1H), 12.98 (s, 1H), 12.02 (s, 1H), 8.21-7.64 (m, 2H), 7.53 (d, J = 8.6 Hz, 1H), 7.16 (d, J = 8.6 Hz, 1H), 3.97 (s, 3H). | Rt = 1.08; 383.1 [M + H]⁺; Method C |
| 18 | 5,6-dichloro-3-(1H-pyrazol-4-yl)-2-(5-(trifluoromethyl)-4H-1,2,4-triazol-3-yl)-1H-indole | δ 14.98 (s, 1H), 13.04 (s, 1H), 12.16 (s, 1H), 8.13 (s, 1H), 7.87 (s, 1H), 7.71 (s, 2H). | Rt = 1.11 387.1 [M + H]⁺; Method B |
| 19 | 6-chloro-3-(1H-pyrazol-4-yl)-2-(5-(trifluoromethyl)-4H-1,2,4-triazol-3-yl)-1H-indole-7-carbonitrile | δ 15.21 (s, 1H), 13.06 (s, 2H), 8.35-7.57 (m, 3H), 7.43 (d, J = 8.6 Hz, 1H). | Rt = 1.02; 378.1 [M + H]⁺; Method C |

-continued

| Ex No. | Structure and Name | $^1$H NMR (400 MHz DMSO-$d_6$) | LC-MS (min; m/z); Method |
|---|---|---|---|
| 20 | 6-chloro-5-methoxy-1-methyl-3-(1H-pyrazol-4-yl)-2-(5-(trifluoromethyl)-4H-1,2,4-triazol-3-yl)-1H-indole | δ 15.17 (s, 1H), 12.97 (s, 1H), 7.92 (s, 1H), 7.82 (s, 1H), 7.47 (s, 1H), 7.29 (s, 1H), 3.91 (s, 3H), 3.72 (s, 3H). | Rt = 1.05; 397.2 [M + H]$^+$; Method B |
| 21 | ethyl 5-(6,7-dichloro-3-(1H-pyrazol-4-yl)-1H-indol-2-yl)-4H-1,2,4-triazole-3-carboxylate | δ 15.24 (d, J = 289.2 Hz, 1H), 12.07 (d, J = 77.0 Hz, 1H), 7.96 (s, 2H), 7.74 (s, 1H), 7.32 (d, J = 8.5 Hz, 1H), 4.40 (s, 2H), 1.35 (t, J = 7.1 Hz, 3H). | Rt = 1.07; 391.1 [M + H]$^+$; Method B |
| 22 | 5-(6,7-dichloro-3-(1H-pyrazol-4-yl)-1H-indol-2-yl)-4H-1,2,4-triazole-3-carboxamide | δ 15.25 (s, 1H), 11.78 (s, 1H), 8.03 (m, 4H), 7.73 (d, J = 8.5 Hz, 1H), 7.30 (d, J = 8.5 Hz, 1H). | Rt = 0.94; 362.0 [M + H]$^+$; Method B |
| 23 | 5,6-dichloro-1-methyl-3-(1H-pyrazol-4-yl)-2-(5-(trifluoromethyl)-4H-1,2,4-triazol-3-yl)-1H-indole | δ 15.32 (s, 1H), 13.03 (s, 1H), 8.05 (s, 1H), 7.95 (m, 3H), 3.76 (s, 3H). | Rt = 1.21.; 401.2 [M + H]$^+$; Method C |

| Ex No. | Structure and Name | ¹H NMR (400 MHz DMSO-d₆) | LC-MS (min; m/z); Method |
|---|---|---|---|
| 24 | 6-chloro-5-methoxy-3-(1H-pyrazol-4-yl)-2-(5-(trifluoromethyl)-4H-1,2,4-triazol-3-yl)-1H-indole | δ 14.83 (s, 1H), 13.01 (s, 1H), 11.78 (s, 1H), 8.10 (s, 1H), 7.76 (s, 1H), 7.53 (s, 1H), 7.24 (s, 1H), 3.89 (s, 3H). | Rt = 1.02; 383.1 [M + H]⁺; Method B |
| 25 | 2-(6-chloro-5-methoxy-3-(1H-pyrazol-4-yl)-2-(5-(trifluoromethyl)-4H-1,2,4-triazol-3-yl)-1H-indol-1-yl)ethan-1-ol | δ 15.08 (s, 1H), 7.83 (s, 1H), 7.65 (s, 2H), 7.27 (s, 1H), 4.26 (t, J = 5.5 Hz, 2H), 3.91 (s, 3H), 3.55 (t, J = 5.4 Hz, 2H). | Rt = 0.86; 427.3 [M + H]⁺; Method C |
| 26 | 6-chloro-5-methoxy-1-(2-methoxyethyl)-3-(1H-pyrazol-4-yl)-2-(5-(trifluoromethyl)-4H-1,2,4-triazol-3-yl)-1H-indole | δ 15.08 (s, 1H), 7.85 (s, 1H), 7.65 (s, 2H), 7.27 (s, 1H), 4.40 (t, J = 5.1 Hz, 2H), 3.91 (s, 3H), 3.45 (t, 2H), 2.99 (s, 3H). | Rt = 1.07; 441.1 [M + H]⁺; Method B |
| 27 | 6-chloro-1-methyl-3-(1H-pyrazol-4-yl)-2-(5-(trifluoromethyl)-4H-1,2,4-triazol-3-yl)-1H-indole-7-carbonitrile | δ 13.09 (s, 1H), 8.11 (d, J = 8.6 Hz, 1H), 7.94 (s, 1H), 7.48 (d, J = 8.6 Hz, 1H), 7.43 (s, 1H), 4.01 (s, 3H). | Rt = 1.08; 358.3 [M + H]⁺; Method B |

| Ex No. | Structure and Name | ¹H NMR (400 MHz DMSO-d₆) | LC-MS (min; m/z); Method |
|---|---|---|---|
| 28 | ethyl 5-(6-chloro-5-methoxy-3-(1H-pyrazol-4-yl)-1H-indol-2-yl)-4H-1,2,4-triazole-3-carboxylate | δ 11.68 (s, 1H), 8.09 (s, 2H), 7.50 (s, 1H), 7.23 (s, 1H), 4.40 (q, J = 7.1 Hz, 2H), 3.88 (s, 3H), 1.35 (t, J = 7.1 Hz, 3H). | Rt = 0.79; 387.3 [M + H]⁺; Method A |
| 29 | methyl 2-(5-(6,7-dichloro-3-(1H-pyrazol-4-yl)-1H-indol-2-yl)-4H-1,2,4-triazol-3-yl)acetate | δ 11.82 (s, 1H), 8.00 (s, 2H), 7.71 (d, J = 8.6 Hz, 1H), 7.28 (d, J = 8.6 Hz, 1H), 3.96 (s, 2H), 3.68 (s, 3H). | Rt = 0.94; 391.1 [M + H]⁺; Method A |
| 30 | 7-chloro-3-(1H-pyrazol-4-yl)-2-(5-(trifluoromethyl)-4H-1,2,4-triazol-3-yl)-1H-indole-5-carboxamide | δ 15.18 (s, 1H), 13.04 (s, 1H), 12.22 (s, 1H), 8.29 (d, J = 1.4 Hz, 1H), 8.26-8.08 (m, 2H), 7.90 (d, J = 1.3 Hz, 1H), 7.87-7.74 (m, 1H), 7.34 (s, 1H). | Rt = 0.87; 396.1 [M + H]⁺; Method B |
| 31 | 5-(6-chloro-5-methoxy-3-(1H-pyrazol-4-yl)-1H-indol-2-yl)-4H-1,2,4-triazole-3-carboxamide | δ 11.53 (s, 1H), 8.10 (s, 2H), 7.96 (s, 2H), 7.50 (s, 1H), 7.25 (s, 1H), 3.88 (s, 3H). | Rt = 0.63; 358.2 [M + H]⁺; Method A |

Example 32: 4,5-dichloro-1-(1H-pyrazol-4-yl)-2-(5-(trifluoromethyl)-4H-1,2,4-triazol-3-yl)-1H-indole

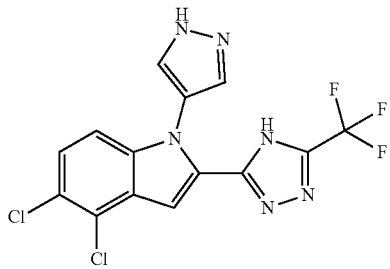 [SMILES: FC(F)(F)c1nnc(-c2cc3c(Cl)c(Cl)ccc3n2-c2cn[nH]c2)[nH]1]

Step 1: 4,5-dichloro-1-(1-(tetrahydro-2H-pyran-2-yl)-1H-pyrazol-4-yl)-1H-indole-2-carboxylic acid

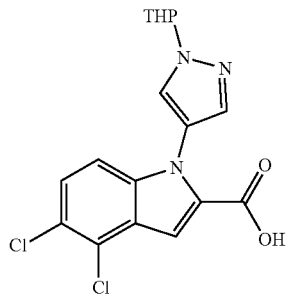

A mixture of ethyl 4,5-dichloro-1H-indole-2-carboxylate (1 g, 3.87 mmol), 4-iodo-1-(tetrahydro-2H-pyran-2-yl)-1H-pyrazole (1.62 g, 5.81 mmol), $Cs_2CO_3$ (1.26 g, 3.87 mmol) and CuBr (0.06 g, 0.39 mmol) in DMF (15 mL) was heated for 16 h at 180° C. The reaction mixture cooled to rt quenched with sat. aq. $NaHCO_3$ and the aq. phase was extracted with EtOAc. The aq. phase was acidified with 1N HCl to pH 1 and extracted three times with EtOAc. The combined organic phase was dried over $Na_2SO_4$, filtered and the solvent was removed in vacuo. The crude product was purified by flash chromatography on silica (Biotage) using heptane, EtOAc and MeOH (from 0-100% EtOAc and EtOAc/MeOH from 0-30%) to give the title compound (707 mg). UPLC-MS (Method B): Rt=1.09 min, 382.0 $[M+H]^+$.

Step 2: Methyl 4,5-dichloro-1-(1H-pyrazol-4-yl)-1H-indole-2-carboxylate

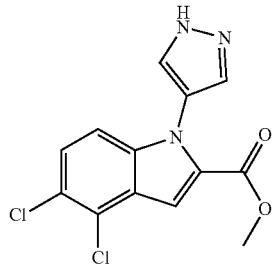 [SMILES: COC(=O)c1cc2c(Cl)c(Cl)ccc2n1-c1cn[nH]c1]

4,5-Dichloro-1-(1-(tetrahydro-2H-pyran-2-yl)-1H-pyrazol-4-yl)-1H-indole-2-carboxylic acid (700 mg, 1.841 mmol) was dissolved in HCl in MeOH (15 ml, 18.75 mmol) and the reaction mixture was heated at 50° C. for 16 h. The reaction mixture was cooled to rt and concentrated. 1M NaOH (20 mL) was added and the mixture was stirred for stirred for 5 min. The resulting precipitate was collected by filtration, washed with water and dried under high vacuum to give the title compound (256 mg) as a colorless solid. UPLC-MS (Method B): Rt=1.07 min, 312.1 $[M+H]^+$; $^1$H NMR (400 MHz, DMSO-d6) δ 13.17 (s, 1H), 8.03-7.80 (m, 2H), 7.49 (d, J=8.9 Hz, 1H), 7.38 (d, J=0.9 Hz, 1H), 7.15 (dd, J=8.9, 0.9 Hz, 1H), 3.77 (s, 3H).

Step 3: 4,5-dichloro-1-(1H-pyrazol-4-yl)-1H-indole-2-carbohydrazide

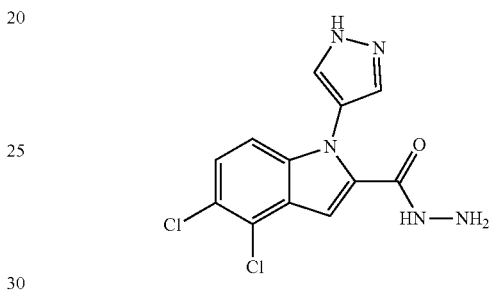

To a solution of methyl 4,5-dichloro-1-(1H-pyrazol-4-yl)-1H-indole-2-carboxylate (250 mg, 0.81 mmol) in EtOH (5 mL) was added hydrazine hydrate (500 mg, 9.99 mmol) and the reaction mixture was stirred for 16 h at 100° C. The reaction mixture cooled to rt and concentrated to dryness. The residue was triturated in DCM (5 mL) to give the title compound (223 mg) as a yellow solid and was used without further purification. UPLC-MS (Method B): Rt=0.85 min, 312.1 $[M+H]^+$; $^1$H NMR (400 MHz, DMSO-d6) δ 13.14 (s, 1H), 9.94-9.80 (m, 1H), 7.85 (s, 2H), 7.40 (d, J=8.8 Hz, 1H), 7.14 (d, J=8.8 Hz, 1H), 7.10 (s, 1H), 4.45 (s, 2H). UPLC-MS (Method B): Rt=1.07 min, 312.1 $[M+H]^+$; $^1$H NMR (400 MHz, DMSO-d6) δ 13.17 (s, 1H), 8.03-7.80 (m, 2H), 7.49 (d, J=8.9 Hz, 1H), 7.38 (d, J=0.9 Hz, 1H), 7.15 (dd, J=8.9, 0.9 Hz, 1H), 3.77 (s, 3H).

Step 4: 4,5-dichloro-1-(1H-pyrazol-4-yl)-2-(5-(trifluoromethyl)-4H-1,2,4-triazol-3-yl)-1H-indole

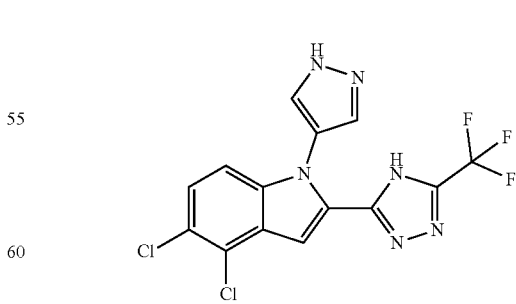

A mixture of 4,5-dichloro-1-(1H-pyrazol-4-yl)-1H-indole-2-carbohydrazide (220 mg, 0.709 mmol) and ethyl 2,2,2-trifluoroacetimidate (100 mg, 0.709 mmol) in EtOH (16 mL) was heated for 3 d at 50° C. to form 4,5-dichloro- 1-(1H-pyrazol-4-yl)-N'-(2,2,2-trifluoro-1-iminoethyl)-1H-indole-2-carbohydrazide. Sodium ethoxide in EtOH (1.11 mL, 2.84 mmol) was added and the reaction mixture was heated for 10 min at 160° C. in the microwave. The reaction mixture was cooled to rt and concentrated to dryness. Aq. 10% citric acid (150 mL) was added and the mixture was extracted with EtOAc (2×350 mL). The combined organic phase was dried over Na₂SO₄, filtered and the solvent was removed in vacuo. The crude product was purified by flash-chromatography on silica (Biotage) using heptane, EtOAc and MeOH (from 0-100% EtOAc and EtOAc/MeOH from 0-40%) to give the title compound (127 mg). UPLC-MS (Method B): Rt=1.13 min, 387.1 [M+H]⁺. ¹H NMR (400 MHz, DMSO-d6) δ 15.42 (s, 1H), 13.21 (s, 1H), 8.15-7.62 (m, 2H), 7.47 (d, J=8.8 Hz, 1H), 7.41 (s, 1H), 7.22 (d, J=8.8 Hz, 1H).

Example 33: 6-Chloro-3-(1H-pyrazol-4-yl)-2-(5-(trifluoromethyl)-4H-1,2,4-triazol-3-yl)-1H-indol-5-ol

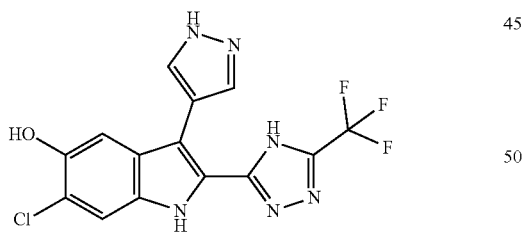

A suspension of 6-chloro-5-methoxy-3-(1-(tetrahydro-2H-pyran-2-yl)-1H-pyrazol-4-yl)-2-(5-(trifluoromethyl)-4H-1,2,4-triazol-3-yl)-1H-indole (283 mg, 0.61 mmol) in DCM (15 mL) was cooled to 0° C. A solution of 1M BBr₃ in DCM (6.06 mL, 6.06 mmol) was added slowly and the mixture was stirred for 5 h at 0° C. The mixture was carefully added to MeOH (120 mL) and concentrated to dryness. The residue was diluted in EtOAc and neutralized (pH 7) with sat. aq. NaHCO₃. The aq. phase was extracted with EtOAc, the combined organic phase was washed with brine, dried over an IST cartridge phase separator and the solvent was removed in vacuo. The crude product was purified by flash-chromatography on silica (Teledyne) using cyclohexane and EtOAc (from 0-100% EtOAc) to give the title compound (106 mg). UPLC-MS (Method B): Rt=0.92 min, 369.0 [M+H]⁺. ¹H NMR (400 MHz, DMSO-d6) δ 14.77 (s, 1H), 12.97 (s, 1H), 11.61 (s, 1H), 9.57 (s, 1H), 7.82 (d, J=110.1 Hz, 2H), 7.44 (s, 1H), 7.19 (s, 1H).

The following example was synthesized by an analogous method to the above procedure.

| Ex No. | Structure and Name | ¹H NMR (600 MHz, DMSO-d6) | LC-MS (min; m/z); Method |
|---|---|---|---|
| 34 | 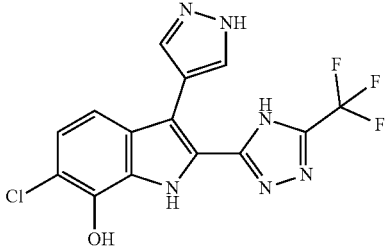 [SMILES: Oc1c(Cl)ccc2c(-c3cn[nH]c3)c(-c3nnc(C(F)(F)F)[nH]3)[nH]c12]<br>6-chloro-3-(1H-pyrazol-4-yl)-2-(5-(trifluoromethyl)-4H-1,2,4-triazol-3-yl)-1H-indol-7-ol | δ 14.84 (s, 1H), 12.97 (s, 1H), 11.54 (s, 1H), 9.87 (s, 1H), 7.91 (d, J = 99.4 Hz, 2H), 7.21 (d, J = 8.6 Hz, 1H), 7.05 (d, J = 8.6 Hz, 1H). | Rt = 0.96; 369.1 [M + H]⁺; Method B |

Example 35: 5-(6,7-Dichloro-3-(1H-pyrazol-4-yl)-1H-indol-2-yl)-4H-1,2,4-triazole-3-carbonitrile

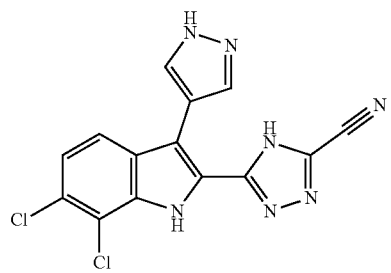 [SMILES: N#Cc1nnc(-c2[nH]c3c(Cl)c(Cl)ccc3c2-c2cn[nH]c2)[nH]1]

Step 1: 5-(6,7-Dichloro-3-(1-(tetrahydro-2H-pyran-2-yl)-1H-pyrazol-4-yl)-1H-indol-2-yl)-4H-1,2,4-triazole-3-carboxamide

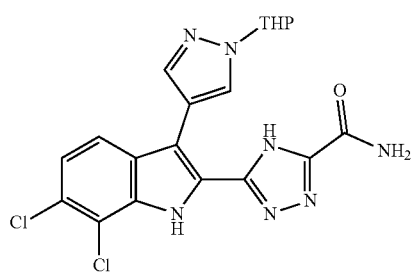

Ethyl 5-(6,7-dichloro-3-(1-(tetrahydro-2H-pyran-2-yl)-1H-pyrazol-4-yl)-1H-indol-2-yl)-4H-1,2,4-triazole-3-carboxylate (339 mg, 0.52 mmol) was suspended in a solution of 7M ammonia in MeOH (10 mL, 70.0 mmol) and the reaction mixture was stirred for 16 h at 60° C. in a sealed tube. The reaction mixture was concentrated to dryness to give the title compound (353 mg) which was used without further purification. UPLC-MS (Method B): Rt=1.08 min, 468.3 [M+H]+.

Step 2: 5-(6,7-Dichloro-3-(1H-pyrazol-4-yl)-1H-indol-2-yl)-4H-1,2,4-triazole-3-carbonitrile

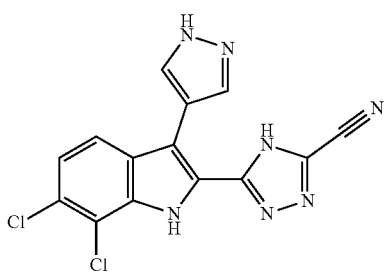 [SMILES: N#Cc1nnc(-c2[nH]c3c(Cl)c(Cl)ccc3c2-c2cn[nH]c2)[nH]1]

5-(6,7-Dichloro-3-(1-(tetrahydro-2H-pyran-2-yl)-1H-pyrazol-4-yl)-1H-indol-2-yl)-4H-1,2,4-triazole-3-carboxamide (253 mg, 0.380 mmol) was suspended in 1,2-DCE (10 mL), and POCl$_3$ (1 mL, 10.73 mmol) was added. The reaction mixture was stirred for 1 h at 100° C. cooled to rt and concentrated to dryness. Sat. aq. bicarbonate (100 mL) was added and the aq. phase was extracted with EtOAc (2×200 mL). The combined organic phase was dried over Na$_2$SO$_4$, filtered and the solvent was removed in vacuo. The compound was purified by preparative reverse phase chromatography (XBridge-C18 (5 um, 50×250 mm), Eluent A: H$_2$O+0.2% HCOOH, B: ACN, Gradient: initial 0.8% B; 0.8% to 28% B in 21 min, flow: 100 mL/min) to give the title compound (9 mg). UPLC-MS (Method B): Rt=1.04 min; 344.0 [M+H]+. $^1$H NMR (400 MHz, DMSO-d6) δ 15.46 (s, 1H), 12.18 (s, 1H), 7.93 (s, 2H), 7.76 (d, J=8.6 Hz, 1H), 7.35 (d, J=8.6 Hz, 1H). 1 proton hidden.

Example 36: (5-(6,7-Dichloro-3-(1H-pyrazol-4-yl)-1H-indol-2-yl)-4H-1,2,4-triazol-3-yl)methanol

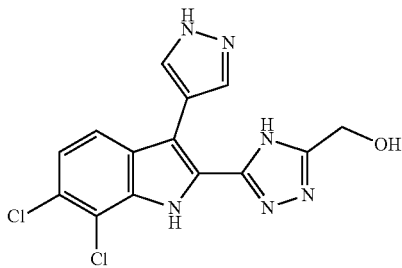 [SMILES: OCc1nnc(-c2[nH]c3c(Cl)c(Cl)ccc3c2-c2cn[nH]c2)[nH]1]

To a solution of ethyl 5-(6,7-dichloro-3-(1H-pyrazol-4-yl)-1H-indol-2-yl)-4H-1,2,4-triazole-3-carboxylate (72 mg, 0.144 mmol) in THF (20 mL) was added a 2 M solution of LiAlH$_4$ in THF (0.3 mL, 0.60 mmol) dropwise over 2 min at 0° C. and the mixture was stirred for 2 h at 0° C. Sodium sulfate decahydrate (925 mg, 2.87 mmol) was added in portions and the mixture was stirred for 20 min. The solid was removed by filtration, washed with THF and the filtrate was concentrated. The compound was purified by preparative reverse phase chromatography (XBridge-C18 (5 μm, 50×250 mm), Eluent A: H$_2$O+0.2% HCOOH, B: ACN, Gradient: initial 0.8% B; 0.8% to 28% B in 21 min, flow: 100 mL/min) to give the title compound (10 mg). UPLC-MS (Method B): Rt=0.93 min; 349.1 [M+H]+. $^1$H NMR (400 MHz, DMSO-d6) δ 11.75 (s, 1H), 8.03 (s, 2H), 7.68 (d, J=8.5 Hz, 1H), 7.26 (d, J=8.5 Hz, 1H), 4.67 (s, 2H). 2 protons hidden.

Example 37: 2-(3-(6,7-dichloro-3-(1H-pyrazol-4-yl)-1H-indol-2-yl)-1H-1,2,4-triazol-1-yl)ethan-1-ol

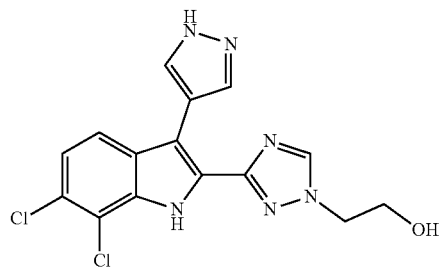 [SMILES: OCCn1cnc(-c2[nH]c3c(Cl)c(Cl)ccc3c2-c2cn[nH]c2)n1]

Step 1: 6,7-Dichloro-3-(1-(tetrahydro-2H-pyran-2-yl)-1H-pyrazol-4-yl)-1H-indole-2-carboxamide

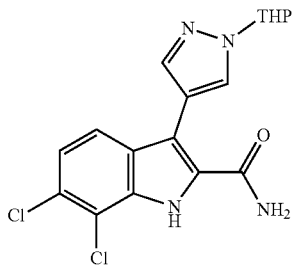

A suspension of ethyl 6,7-dichloro-3-(1-(tetrahydro-2H-pyran-2-yl)-1H-pyrazol-4-yl)-1H-indole-2-carboxylate (2.11 g, 4.66 mmol) ammonia (20 ml, 140 mmol, 7M solution in MeOH) was heated at 50° C. for 6 days. The reaction mixture was concentrated, water (100 mL) was added and the aq. phase was extracted with EtOAc. The combined organic phase was dried over sodium sulfate, filtered and the solvent was removed in vacuo to give the title compound (1.84 g) which was used without further purification. UPLC-MS (Method C): Rt=1.01 min, 381.1 [M+H]+.

Step 2: (E)-6,7-Dichloro-N-((dimethylamino)methylene)-3-(1-(tetrahydro-2H-pyran-2-yl)-1H-pyrazol-4-yl)-1H-indole-2-carboxamide

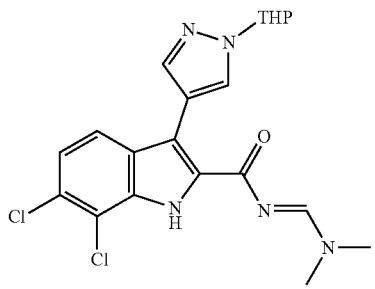

A suspension of 6,7-dichloro-3-(1-(tetrahydro-2H-pyran-2-yl)-1H-pyrazol-4-yl)-1H-indole-2-carboxamide (1.84 g, 4.37 mmol) in 1,1-dimethoxy-N,N-dimethylmethanamine (17 ml, 127 mmol) was heated at 120° C. for 30 min. The reaction mixture was cooled to rt and concentrated to dryness to give the title compound (1.97 g) which was used without further purification. UPLC-MS (Method C): Rt=1.19 min; 436.3 [M+H]$^+$.

Step 3: 6,7-dichloro-3-(1-(tetrahydro-2H-pyran-2-yl)-1H-pyrazol-4-yl)-2-(4H-1,2,4-triazol-3-yl)-1H-indole

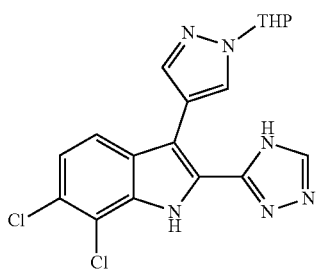

A mixture of (E)-6,7-dichloro-N-((dimethylamino)methylene)-3-(1-(tetrahydro-2H-pyran-2-yl)-1H-pyrazol-4-yl)-1H-indole-2-carboxamide (1.92 g, 3.98 mmol) and hydrazine monohydrate (0.215 mL, 4.38 mmol) in AcOH (19 mL) was heated for 15 min at 90° C. The reaction was cooled to rt, sat. aq. NaHCO$_3$ (100 mL) was added and the aq. phase was extracted with EtOAc (400 mL). The combined organic phase was dried over sodium sulfate, filtered and the solvent was removed in vacuo. The crude product was purified by flash-chromatography on silica (Biotage) using heptane, EtOAc and MeOH (from 0-100% EtOAc and EtOAc/MeOH from 0-20%) to give the title compound (1.10 g). UPLC-MS (Method C): Rt=1.03 min, 405.2 [M+H]$^+$.

$^1$H NMR (600 MHz, DMSO-d6) δ 14.39 (s, 1H), 11.85 (s, 1H), 8.77 (s, 1H), 8.30 (s, 1H), 7.86 (s, 1H), 7.67 (d, J=8.5 Hz, 1H), 7.28 (d, J=8.5 Hz, 1H), 5.44 (dd, J=10.0, 2.1 Hz, 1H), 3.70-3.56 (m, 1H), 3.31 (s, 1H), 2.16 (q, J=10.3 Hz, 1H), 2.03-1.87 (m, 3H), 1.68 (q, J=10.8, 9.0 Hz, 1H), 1.59-1.47 (m, 3H).

Step 4: 6,7-dichloro-3-(1-(tetrahydro-2H-pyran-2-yl)-1H-pyrazol-4-yl)-2-(1-(2-((tetrahydro-2H-pyran-2-yl)oxy)ethyl)-1H-1,2,4-triazol-3-yl)-1H-indole

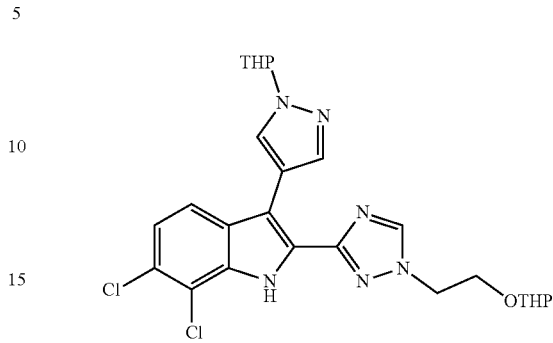

To a solution of 6,7-dichloro-3-(1-(tetrahydro-2H-pyran-2-yl)-1H-pyrazol-4-yl)-2-(1H-1,2,4-triazol-3-yl)-1H-indole (400 mg, 0.99 mmol) in DMF (5 mL) was added K$_2$CO$_3$ (548 mg, 3.97 mmol) and 2-(2-bromoethoxy)tetrahydro-2H-pyran (249 mg, 1.19 mmol) and the reaction was stirred for 1 h at 50° C. The reaction mixture was diluted with water (50 mL) and the aq. phase was extracted with EtOAc (2×150 mL). The combined organic phases were dried over sodium sulfate, filtered and the solvent was removed in vacuo. The crude product was purified by flash-chromatography on silica (Biotage) using heptane and EtOAc (from 0-100% EtOAc) to give the title compound (560 mg). UPLC-MS (Method C): Rt=1.28 min, 533.3 [M+H]$^+$.

Step 5: 2-(3-(6,7-dichloro-3-(1H-pyrazol-4-yl)-1H-indol-2-yl)-1H-1,2,4-triazol-1-yl)ethan-1-ol

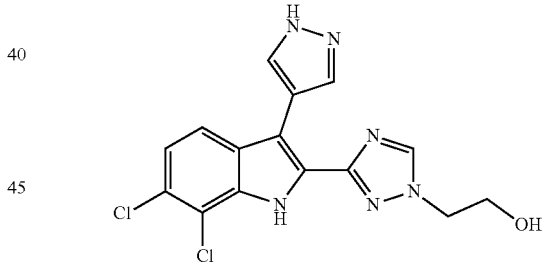

A solution of 6,7-dichloro-3-(1-(tetrahydro-2H-pyran-2-yl)-1H-pyrazol-4-yl)-2-(1-(2-((tetrahydro-2H-pyran-2-yl)oxy)ethyl)-1H-1,2,4-triazol-3-yl)-1H-indole (560 mg, 0.89 mmol) in 4N HCl in dioxane (5 mL, 20.00 mmol) was stirred for 30 min at rt. The reaction mixture was carefully poured on sat. aq. NaHCO$_3$ and the aq. phase was extracted with EtOAc. The combined organic phase was dried over Na$_2$SO$_4$, filtered and the solvent was removed in vacuo. The resulting solid was triturated in MeOH, filtered, washed with MeOH and dried under high vacuum to give the title compound as a colorless solid. UPLC-MS (Method C): Rt=0.81 min, 363.2 [M+H]$^+$. $^1$H NMR (600 MHz, DMSO-d6) δ 12.88 (s, 1H), 11.75 (s, 1H), 8.63 (s, 1H), 8.31-7.78 (m, 2H), 7.69 (d, J=8.5 Hz, 1H), 7.26 (d, J=8.5 Hz, 1H), 5.04 (d, J=5.6 Hz, 1H), 4.30 (t, J=5.4 Hz, 2H), 3.81 (q, J=4.8 Hz, 2H).

The following example was synthesized b an analogous method to the above procedure.

| Ex No. | Structure and Name | $^1$H NMR (600 MHz, DMSO-d6) | LC-MS (min; m/z); Method |
|---|---|---|---|
| 38 | ![structure] 6,7-dichloro-3-(1H-pyrazol-4-yl)-2-(4H-1,2,4-triazol-3-yl)-1H-indole | δ 11.92 (s, 1H), 8.69 (s, 1H), 8.12 (s, 2H), 7.69 (d, J = 8.5 Hz, 1H), 7.29 (d, J = 8.4 Hz, 1H). | Rt = 0.81; 319.1 [M + H]$^+$; Method C |

Example 39: 5-(6-chloro-7-fluoro-3-(1H-imidazol-1-yl)-5-methoxy-1-methyl-1H-indol-2-yl)-N,N-dimethyl-4H-1,2,4-triazole-3-carboxamide The title compound was synthesized via the method illustrated in Scheme 12 below.

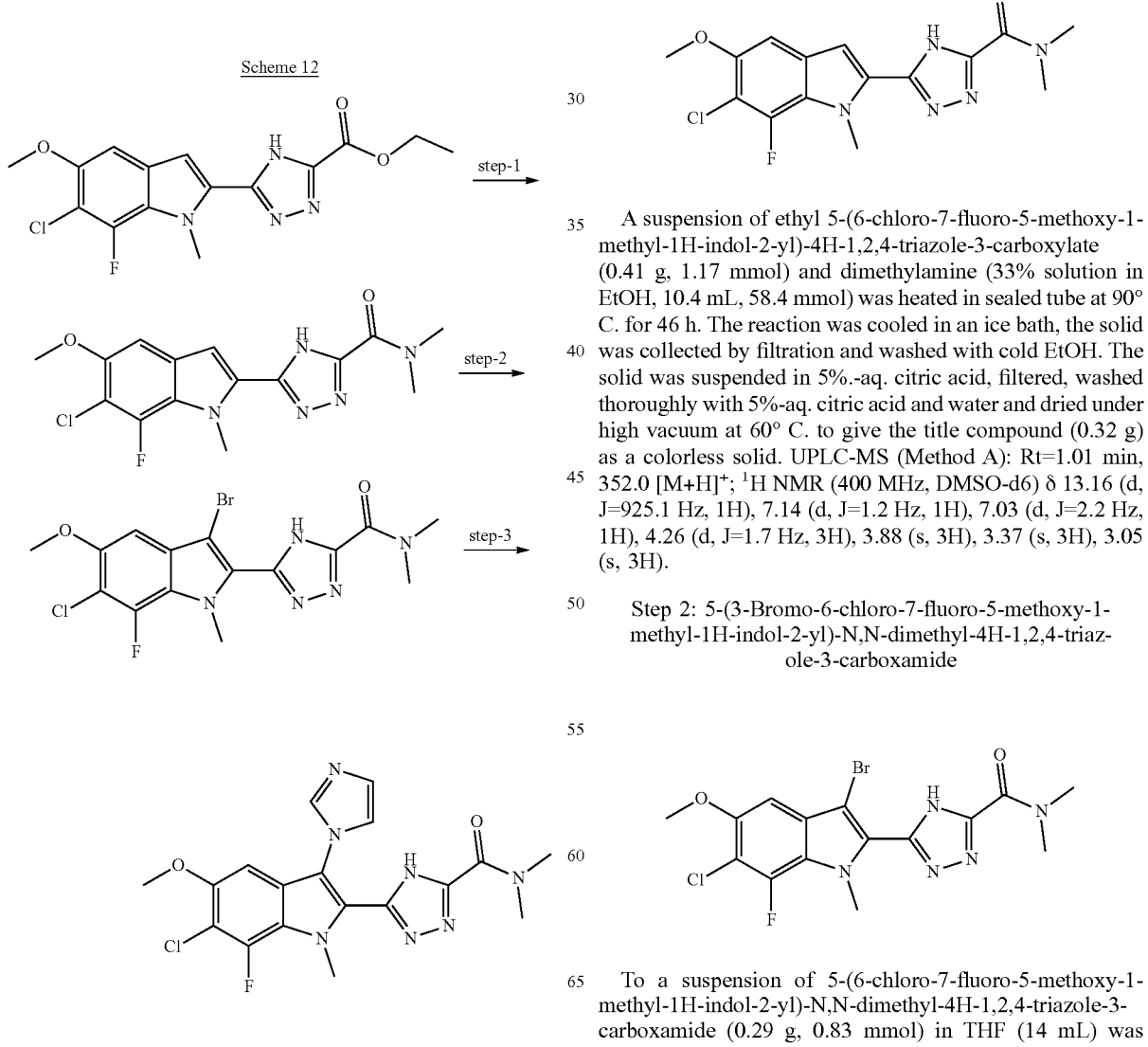

Step 1: 5-(6-Chloro-7-fluoro-5-methoxy-1-methyl-1H-indol-2-yl)-N,N-dimethyl-4H-1,2,4-triazole-3-carboxamide A suspension of ethyl 5-(6-chloro-7-fluoro-5-methoxy-1-methyl-1H-indol-2-yl)-4H-1,2,4-triazole-3-carboxylate (0.41 g, 1.17 mmol) and dimethylamine (33% solution in EtOH, 10.4 mL, 58.4 mmol) was heated in sealed tube at 90° C. for 46 h. The reaction was cooled in an ice bath, the solid was collected by filtration and washed with cold EtOH. The solid was suspended in 5%.-aq. citric acid, filtered, washed thoroughly with 5%-aq. citric acid and water and dried under high vacuum at 60° C. to give the title compound (0.32 g) as a colorless solid. UPLC-MS (Method A): Rt=1.01 min, 352.0 [M+H]$^+$; $^1$H NMR (400 MHz, DMSO-d6) δ 13.16 (d, J=925.1 Hz, 1H), 7.14 (d, J=1.2 Hz, 1H), 7.03 (d, J=2.2 Hz, 1H), 4.26 (d, J=1.7 Hz, 3H), 3.88 (s, 3H), 3.37 (s, 3H), 3.05 (s, 3H).

Step 2: 5-(3-Bromo-6-chloro-7-fluoro-5-methoxy-1-methyl-1H-indol-2-yl)-N,N-dimethyl-4H-1,2,4-triazole-3-carboxamide To a suspension of 5-(6-chloro-7-fluoro-5-methoxy-1-methyl-1H-indol-2-yl)-N,N-dimethyl-4H-1,2,4-triazole-3-carboxamide (0.29 g, 0.83 mmol) in THF (14 mL) was added NBS (0.16 g, 0.87 mmol) and the resulting suspension was stirred for 45 min at rt. The reaction mixture was diluted with water, cooled in an ice bath and citric acid (0.16 g, 0.83 mmol) was added to adjust pH 4-5. The resulting precipitate was collected by filtration, washed with ice-cold THF/water (1:2) and dried under high vacuum to give the title compound (0.32 g) as a colorless solid. UPLC-MS (Method A): Rt=1.13 min, 429.9 [M+H]$^+$; $^1$H NMR (400 MHz, DMSO-d6) δ 15.33 (s, 1H), 6.92 (d, J=1.2 Hz, 1H), 4.06 (d, J=1.7 Hz, 3H), 3.95 (s, 3H), 3.47 (s, 3H), 3.08 (s, 3H).

Step 3: 5-(6-chloro-7-fluoro-3-(1H-imidazol-1-yl)-5-methoxy-1-methyl-1H-indol-2-yl)-N,N-dimethyl-4H-1,2,4-triazole-3-carboxamide

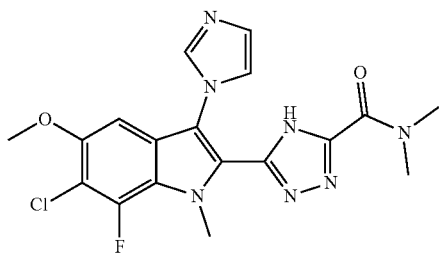

A mixture of 5-(3-bromo-6-chloro-7-fluoro-5-methoxy-1-methyl-1H-indol-2-yl)-N,N-dimethyl-4H-1,2,4-triazole-3-carboxamide (0.151 g, 0.35 mmol), 1H-imidazole (0.120 g, 1.76 mmol), copper(I) iodide (6.7 mg, 0.035 mmol), potassium carbonate (0.146 g, 1.05 mmol) and L-proline (8.1 mg, 0.07 mmol) in DMSO (3 mL) was heated under argon in sealed tube at 110° C. for 16 h. The reaction mixture was cooled to rt and diluted with ethyl acetate (40 mL) and water (20 mL). AcOH (0.21 mL) was added to adjust pH 4-5, phases were separated and the aq. phase was with ethyl acetate (2×25 mL). The combined organic phase was washed with brine, dried over Na$_2$SO$_4$, filtered and the solvent was removed in vacuo. The crude product was purified by SFC chromatography (column: 100×50 Reprospher PEI 100 A 3 μm, Gradient: 35-43% in 4 min in MeOH/DCM) to give the title compound (42 mg). UPLC-MS (Method A): Rt=0.78 min, 418.1 [M+H]$^+$; $^1$H NMR (400 MHz, DMSO-d6) δ 15.26 (s, 1H), 7.79 (d, J=1.1 Hz, 1H), 7.32 (t, J=1.3 Hz, 1H), 7.07 (d, J=1.1 Hz, 1H), 6.71 (d, J=1.2 Hz, 1H), 4.15 (d, J=1.7 Hz, 3H), 3.85 (s, 3H), 3.27 (s, 3H), 3.02 (s, 3H).

The following examples were synthesized by an analogous method to the above procedures, using ethyl 5-(6-chloro-7-fluoro-5-methoxy-1-methyl-1H-indol-2-yl)-4H-1,2,4-triazole-3-carboxylate and the corresponding amine, respectively.

| Ex No. | Structure and Name | $^1$H NMR (400 MHz, DMSO-d$_6$) | LC-MS (min; m/z); Method |
|---|---|---|---|
| 40 | 5-(6-chloro-7-fluoro-3-(1H-imidazol-1-yl)-5-methoxy-1-methyl-1H-indol-2-yl)-N-(2-methoxyethyl)-N-methyl-4H-1,2,4-triazole-3-carboxamide | δ 15.41 (d, J = 19.1 Hz, 1H), 9.19 (d, J = 15.6 Hz, 1H), 8.05-7.64 (m, 2H), 6.95 (dd, J = 4.6, 1.2 Hz, 1H) 4.28 (dd, J = 9.2, 1.5 Hz, 3H), 3.91 (t, J = 5.3 Hz, 1H), 3.87 (s, 3H), 3.65 (t, J = 5.5 Hz, 1H), 3.50 (dt, J = 36.3, 5.3 Hz, 2H), 3.31-3.00 (m, 6H). | Rt = 0.81; 462.4 [M + H]$^+$; Method A |
| 41 | 5-(6-chloro-7-fluoro-3-(1H-imidazol-1-yl)-5-methoxy-1-methyl-1H-indol-2-yl)-N-(2-hydroxyethyl)-N-methyl-4H-1,2,4-triazole-3-carboxamide | δ 15.26 (d, J = 20.9 Hz, 1H), 8.01 (s, 1H), 7.41 (s, 1H), 7.19 (s, 1H), 6.74 (s, 1H), 4.78 (s, 1H), 4.16 (dd, J = 3.1, 1.6 Hz, 3H), 3.86 (s, 3H), 3.83 (d, J = 4.9 Hz, 1H), 3.60 (t, J = 5.0 Hz, 1H), 3.53 (tt, J = 3.7, 1.8 Hz, 2H), 3.31 (d, J = 4.2 Hz, 3H) | Rt = 0.69 min; m/z [M + H]$^+$; 448.3; Method A |

| Ex No. | Structure and Name | $^1$H NMR (400 MHz, DMSO-$d_6$) | LC-MS (min; m/z); Method |
|---|---|---|---|
| 42 | 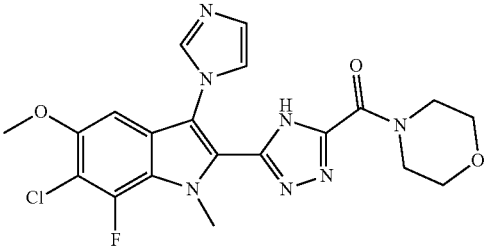 [SMILES: COc1cc2c(-n3ccnc3)c(-c3nnc(C(=O)N4CCOCC4)[nH]3)n(C)c2c(F)c1Cl]<br><br>(5-(6-chloro-7-fluoro-3-(1H-imidazol-1-yl)-5-methoxy-1-methyl-1H-indol-2-yl)-4H-1,2,4-triazol-3-yl)(morpholino)methanone | δ 15.37 (s, 1H), 7.76 (s, 1H), 7.30 (s, 1H), 7.08 (s, 1H), 6.69 (d, J = 1.2 Hz, 1H), 4.17 (d, J = 1.6 Hz, 3H), 3.96 (t, J = 4.7 Hz, 2H), 3.85 (s, 3H), 3.69-3.61 (m, 4H), 3.59 (t, J = 4.8 Hz, 2H). | Rt = 0.78 min; m/z [M + H]$^+$ 460.3; Method A |
| 43 | 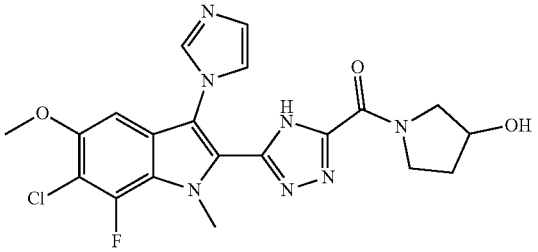 [SMILES: COc1cc2c(-n3ccnc3)c(-c3nnc(C(=O)N4CCC(O)C4)[nH]3)n(C)c2c(F)c1Cl]<br><br>(5-(6-chloro-7-fluoro-3-(1H-imidazol-1-yl)-5-methoxy-1-methyl-1H-indol-2-yl)-4H-1,2,4-triazol-3-yl)(3-hydroxypyrrolidin-1-yl)methanone | δ 15.33 (s, 1H), 7.78 (t, J = 1.1 Hz, 1H), 7.32 (t, J = 1.3 Hz, 1H), 7.07 (dt, J = 4.6, 1.1 Hz, 1H), 6.70 (dd, J = 4.4, 1.2 Hz, 1H), 4.99 (t, J = 3.9 Hz, 1H), 4.33 (d, J = 13.7 Hz, 1H), 4.16 (dd, J = 6.5, 1.6 Hz, 3H), 3.85 (d, J = 1.2 Hz, 7H), 2.00-1.78 (m, 2H). | Rt = 0.73 min; m/z [M + H]$^+$ 460.3; Method A |
| 44 | 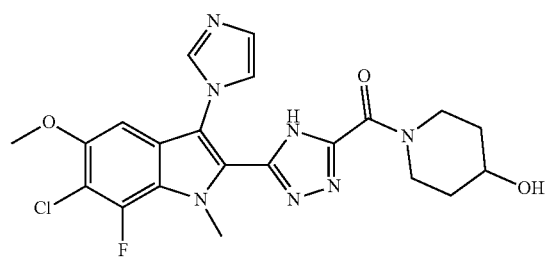 [SMILES: COc1cc2c(-n3ccnc3)c(-c3nnc(C(=O)N4CCC(O)CC4)[nH]3)n(C)c2c(F)c1Cl]<br><br>(5-(6-chloro-7-fluoro-3-(1H-imidazol-1-yl)-5-methoxy-1-methyl-1H-indol-2-yl)-4H-1,2,4-triazol-3-yl)(4-hydroxypiperidin-1-yl)methanone | δ 15.28 (s, 1H), 7.77 (s, 1H), 7.31 (d, J = 1.3 Hz, 1H), 7.06 (d, J = 1.3 Hz, 1H), 6.69 (s, 1H), 4.81 (d, J = 3.9 Hz, 1H), 4.24 (d, J = 13.1 Hz, 1H), 4.15 (d, J = 1.6 Hz, 3H), 3.98 (dt, J = 11.9, 4.9 Hz, 1H), 3.85 (s, 3H), 3.77 (dt, J = 8.4, 4.4 Hz, 1H), 3.52 (ddd, J = 13.2, 9.2, 3.2 Hz, 1H), 3.30-3.23 (m, 1H), 1.85-1.68 (m, 2H), 1.36 (qd, J = 12.2, 10.6, 4.0 Hz, 2H). | Rt = 0.72 min; m/z [M + H]$^+$ 474.2; Method A |

| Ex No. | Structure and Name | $^1$H NMR (400 MHz, DMSO-$d_6$) | LC-MS (min; m/z); Method |
|---|---|---|---|
| 45 | 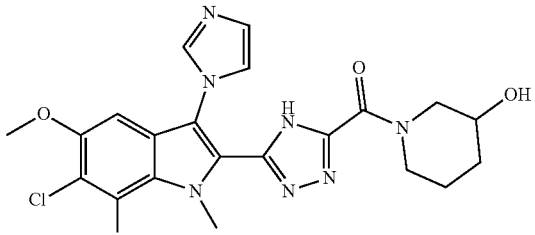<br>(5-(6-chloro-7-fluoro-3-(1H-imidazol-1-yl)-5-methoxy-1-methyl-1H-indol-2-yl)-4H-1,2,4-triazol-3-yl)(3-hydroxypiperidin-1-yl)methanone | Mixture of rotamers (A:B = 1.2:1)<br>Rotamer A:<br>δ (ppm) 15.28 (s, 1H), 7.89 (s, 1H), 7.36 (s, 1H), 7.10 (s, 1H), 6.74 (s, 1H), 5.23 (br s, 1H), 4.24 (m, 1H), 4.17 (s, 3H), 4.12 (m, 1H), 3.86 (s, 3H), 3.57 (cm, 1H), 3.39 (m, 1H), 2.94 (dd, 1H), 1.98-1.63 (m, 2H), 1.54-1.31 (m, 2H).<br>Rotamer B:<br>δ (ppm) 15.28 (s, 1H), 7.77 (s, 1H), 7.31 (s, 1H), 7.07 (s, 1H), 6.69 (s, 1H), 4.99 (d, 1H), 4.26 (m, 1H), 4.15 (s, 3H), 3.85 (s, 3H), 3.80 (m, 1H), 3.50 (m, 1H), 3.33 (cm, 1H), 3.28 (m, 1H), 1.98-1.63 (m, 2H), 1.54-1.31 (m, 2H). | Rt = 0.79 min; m/z [M + H]$^+$ 474.4; Method A |
| 46 | 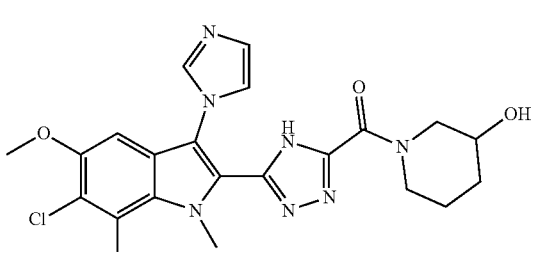<br>(5-(6-chloro-7-fluoro-3-(1H-imidazol-1-yl)-5-methoxy-1-methyl-1H-indol-2-yl)-4H-1,2,4-triazol-3-yl)(4-methylpiperazin-1-yl)methanone | δ (ppm) 15.65 (br s, 1H), 10.33 (br s, 1H), 9.10 (s, 1H), 7.82 (s, 1H), 7.77 (s, 1H), 6.95 (s, 1H), 4.29 (s, 3H), 3.87 (s, 3H), 2.85 (s, 3H), 5.39-2.38 (br m 9H, broad maxima at 5.00, 4.55, 3.49, and 3.15 ppm) | Rt = 0.65 min; m/z [M + H]$^+$ 473.5; Method A |

The following examples were synthesized by an analogous method to the above procedures, starting from ethyl 6-chloro-7-fluoro-5-methoxy-1H-indole-2-carboxylate or ethyl 6-chloro-7-fluoro-5-methoxy-1-methyl-1H-indole-2-carboxylate and using corresponding imino ester, respectively.

| Ex No. | Structure and Name | $^1$H NMR (400 MHz, DMSO-$d_6$) | LC-MS (min; m/z); Method |
|---|---|---|---|
| 47 | 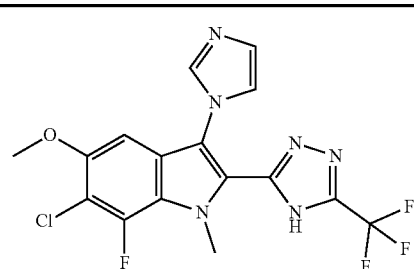<br>6-chloro-7-fluoro-3-(1H-imidazol-1-yl)-5-methoxy-1-methyl-2-(5-(trifluoromethyl)-4H-1,2,4-triazol-3-yl)-1H-indole | δ 8.14 (s, 1H), 7.41 (s, 1H), 7.23 (s, 1H), 6.83 (s, 1H), 4.03 (s, 3H), 3.88 (s, 3H). | Rt = 1.00; 415.1 [M + H]$^+$; Method A |

| Ex No. | Structure and Name | $^1$H NMR (400 MHz, DMSO-$d_6$) | LC-MS (min; m/z); Method |
|---|---|---|---|
| 48 | 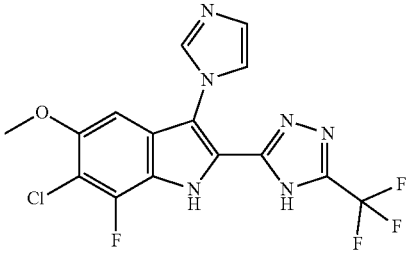 [SMILES: COc1cc2c(-n3ccnc3)c(-c3nnc(C(F)(F)F)[nH]3)[nH]c2c(F)c1Cl]<br>6-chloro-7-fluoro-3-(1H-imidazol-1-yl)-5-methoxy-2-(5-(trifluoromethyl)-4H-1,2,4-triazol-3-yl)-1H-indole | δ 15.19 (s, 1H), 12.74 (s, 1H), 8.16 (s, 1H), 7.51 (s, 1H), 7.24 (s, 1H), 6.81 (s, 1H), 3.88 (s, 3H). | Rt = 0.84; 401.1 [M + H]$^+$; Method A |
| 49 | 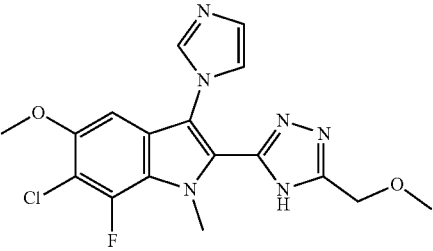<br>6-chloro-7-fluoro-3-(1H-imidazol-1-yl)-5-methoxy-2-(5-(methoxymethyl)-4H-1,2,4-triazol-3-yl)-1-methyl-1H-indole | δ 14.50 (s, 1H), 7.78 (s, 1H), 7.31 (s, 1H), 7.05 (s, 1H), 6.71 (s, 1H), 4.57 (s, 2H), 4.07 (d, J = 1.8 Hz, 3H), 3.85 (s, 3H), 3.34 (s, 3H). | Rt = 0.73; 391.2 [M + H]$^+$; Method A |
| 50 | 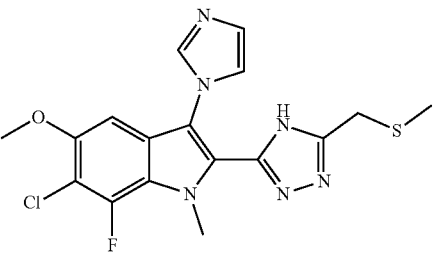<br>6-Chloro-7-fluoro-3-(1H-imidazol-1-yl)-5-methoxy-1-methyl-2-(5-((methylthio)methyl)-4H-1,2,4-triazol-3-yl)-1H-indole | δ 14.34 (s, 1H), 7.79 (s, 1H), 7.33 (s, 1H), 7.07 (s, 1H), 6.70 (s, 1H), 4.08 (s, 3H), 3.85 (s, 3H), 3.82 (s, 2H), 2.08 (s, 3H). | Rt = 0.83; 407.2 [M + H]$^+$; Method A |
| 51 | 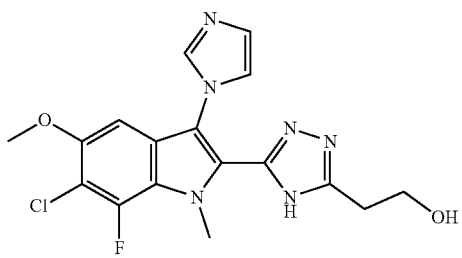 [SMILES: COc1cc2c(-n3ccnc3)c(-c3nnc(CCO)[nH]3)n(C)c2c(F)c1Cl]<br>2-(5-(6-chloro-7-fluoro-3-(1H-imidazol-1-yl)-5-methoxy-1-methyl-1H-indol-2-yl)-4H-1,2,4-triazol-3-yl)ethan-1-ol | δ 14.08 (s, 1H), 7.79 (s, 1H), 7.32 (s, 1H), 7.05 (s, 1H), 6.70 (d, J = 1.2 Hz, 1H), 4.82 (s, 1H), 4.09 (s, 3H), 3.85 (s, 3H), 3.77-3.69 (m, 2H), 2.88 (t, J = 6.6 Hz, 2H). | Rt = 0.64; 391.1 [M + H]$^+$; Method A |

| Ex No. | Structure and Name | $^1$H NMR (400 MHz, DMSO-$d_6$) | LC-MS (min; m/z); Method |
|---|---|---|---|
| 52 | 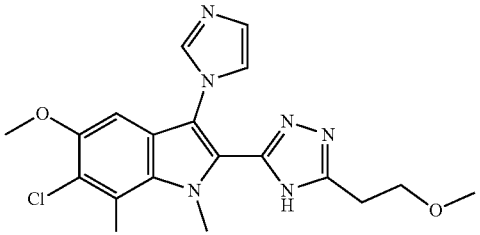<br>6-chloro-7-fluoro-3-(1H-imidazol-1-yl)-5-methoxy-2-(5-(2-methoxyethyl)-4H-1,2,4-triazol-3-yl)-1-methyl-1H-indole | δ 14.12 (s, 1H), 7.83 (s, 1H), 7.34 (s, 1H), 7.08 (s, 1H), 6.71 (s, 1H), 4.10 (s, 3H), 3.85 (s, 3H), 3.66 (t, J = 6.4 Hz, 2H), 3.23 (s, 3H), 2.98 (t, J = 6.4 Hz, 2H). | Rt = 0.76; 405.3 [M + H]$^+$; Method A |
| 53 | 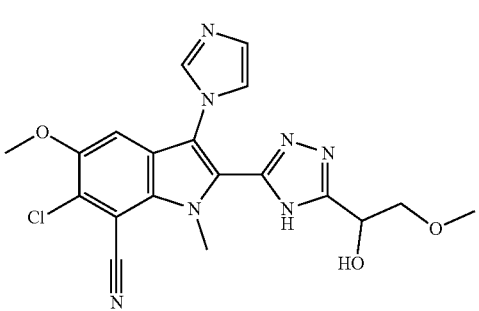<br>6-chloro-2-(5-(1-hydroxy-2-methoxyethyl)-4H-1,2,4-triazol-3-yl)-3-(1H-imidazol-1-yl)-5-methoxy-1-methyl-1H-indole-7-carbonitrile | δ 14.42 (s, 1H), 7.81 (s, 1H), 7.35 (s, 1H), 7.26 (s, 1H), 7.07 (s, 1H), 6.10 (d, J = 5.1 Hz, 1H), 4.96-4.87 (m, 1H), 4.20 (s, 3H), 3.91 (s, 3H), 3.70-3.52 (m, 2H), 3.27 (s, 3H). | Rt = 0.60; 428.3 [M + H]$^+$; Method A |
| 54 | 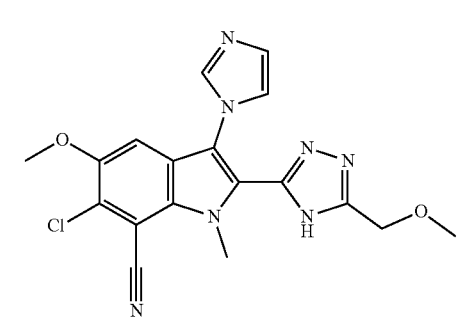<br>6-chloro-3-(1H-imidazol-1-yl)-5-methoxy-2-(5-(methoxymethyl)-4H-1,2,4-triazol-3-yl)-1-methyl-1H-indole-7-carbonitrile | δ 14.58 (s, 1H), 7.80 (s, 1H), 7.34 (s, 1H), 7.26 (s, 1H), 7.06 (s, 1H), 4.59 (s, 2H), 4.20 (s, 3H), 3.91 (s, 3H), 3.35 (s, 3H). | Rt = 0.60; 398.2 [M + H]$^+$; Method A |
| 55 | 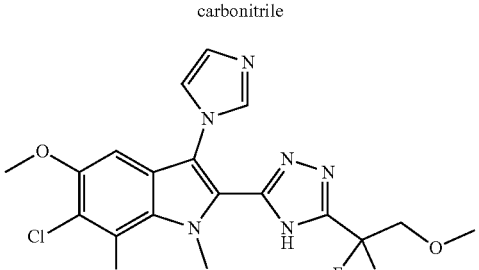<br>6-chloro-2-(5-(1,1-difluoro-2-methoxyethyl)-4H-1,2,4-triazol-3-yl)-3-(1H-imidazol-1-yl)-5-methoxy-1-methyl-1H-indole-7-carbonitrile | δ 15.36 (s, 1H), 7.86 (s, 1H), 7.32 (s, 2H), 7.11 (s, 1H), 4.16 (s, 3H), 4.06 (t, J = 13.8 Hz, 2H), 3.92 (s, 3H), 3.36 (s, 3H). | Rt = 0.76; 448.2 [M + H]$^+$; Method A |

Example 56: 6-Chloro-7-fluoro-3-(1H-imidazol-1-yl)-5-methoxy-1-methyl-2-(5-((methylsulfonyl)methyl)-4H-1,2,4-triazol-3-yl)-1H-indole

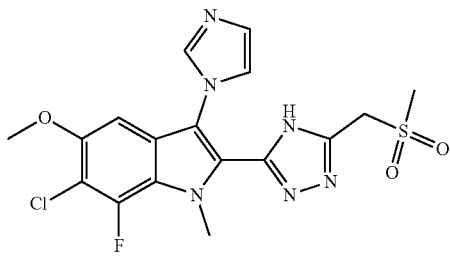 [SMILES: COc1cc2c(-n3ccnc3)c(-c3nnc(CS(C)(=O)=O)[nH]3)n(C)c2c(F)c1Cl]

To a suspension of 6-chloro-7-fluoro-3-(1H-imidazol-1-yl)-5-methoxy-1-methyl-2-(5-((methylthio)methyl)-4H-1,2,4-triazol-3-yl)-1H-indole (52 mg, 0.13 mmol) in DCM (2 mL) was added m-CPBA (75 mg, 0.28 mmol) and the mixture was stirred for 90 min at rt. The reaction mixture was diluted with DCM (3 mL) and stirred for 10 min. The solid was collected by filtration, washed with small amounts of DCM and dried under high vacuum to give the title compound (41 mg) as a beige solid. UPLC-MS: Rt=0.68 min; 439.3 [M+H]$^+$; $^1$H NMR (400 MHz, DMSO-d6) δ 14.71 (s, 1H), 7.79 (s, 1H), 7.31 (s, 1H), 7.06 (s, 1H), 6.72 (s, 1H), 4.76 (s, 2H), 4.09 (d, J=1.8 Hz, 3H), 3.86 (s, 3H), 3.06 (s, 3H).

Example 57: 1-(5-(6-chloro-7-fluoro-5-methoxy-3-(1H-pyrazol-4-yl)-1H-indol-2-yl)-4H-1,2,4-triazol-3-yl)-2-methoxyethan-1-one The title compound was synthesized via the method illustrated in Steps 1 and 2 in Scheme 13 below.

Scheme 13

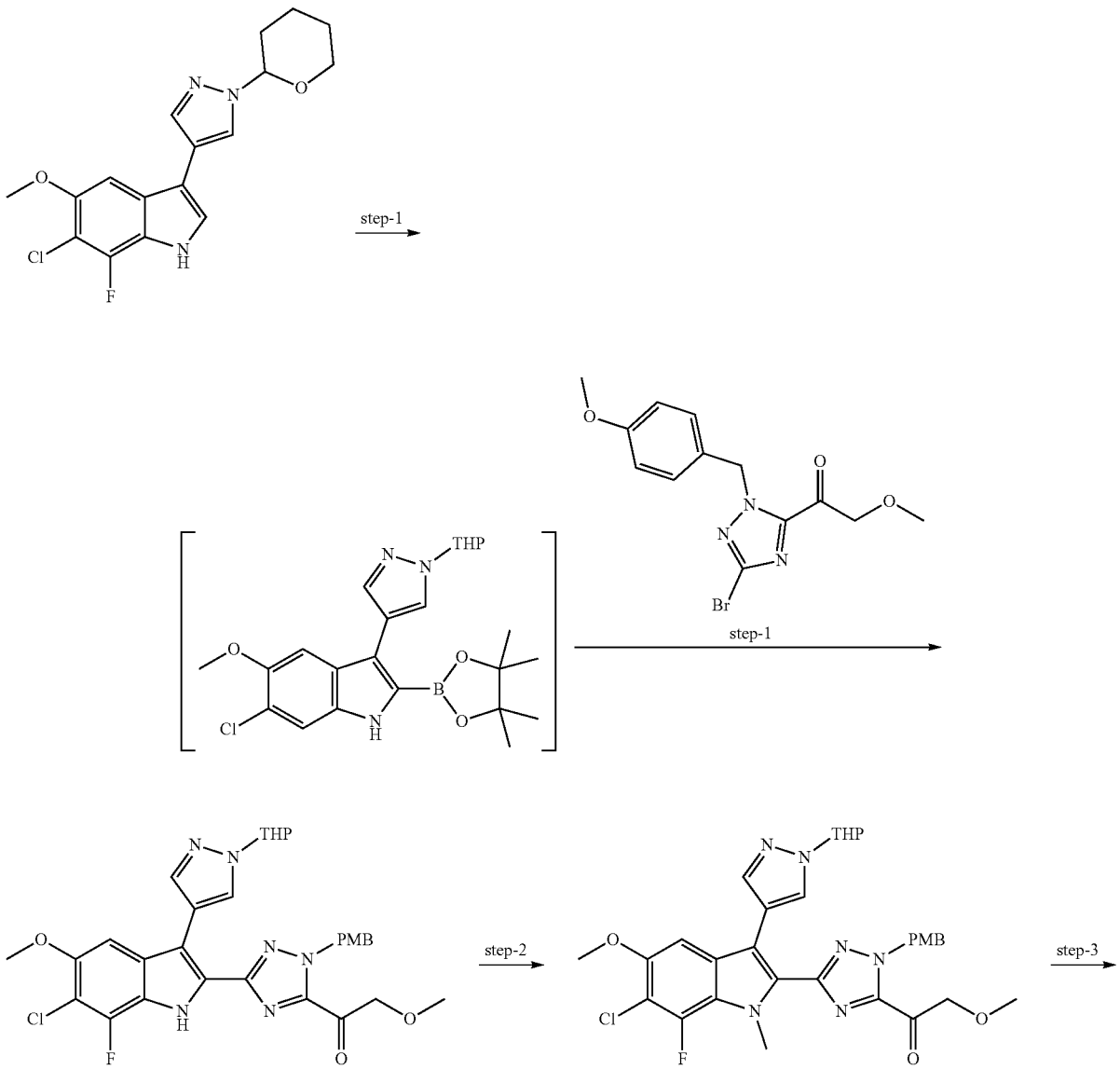

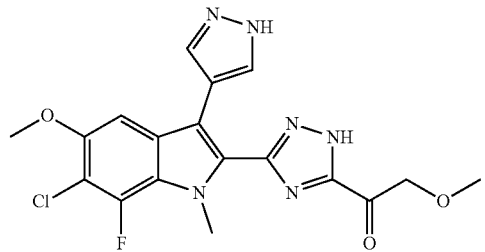

Step 1: 1-(3-(6-Chloro-7-fluoro-5-methoxy-3-(1-(tetrahydro-2H-pyran-2-yl)-1H-pyrazol-4-yl)-1H-indol-2-yl)-1-(4-methoxybenzyl)-1H-1,2,4-triazol-5-yl)-2-methoxyethan-1-one A mixture of 6-chloro-7-fluoro-5-methoxy-3-(1-(tetrahydro-2H-pyran-2-yl)-1H-pyrazol-4-yl)-1H-indole (1.5 g, 4.29 mmol), 4,4'-di-tert-butyl-2,2'-bipyridine (0.023 g, 0.09 mmol), (1,5-cyclooctadienexmethoxy)iridium(I) dimer (0.028 g, 0.043 mmol) and bis(pinacolato)diboron (1.31 g, 5.15 mmol) in THF (15 mL) was heated under argon for 15 min at 80° C. to form 6-chloro-5-methoxy-3-(1-(tetrahydro-2H-pyran-2-yl)-1H-pyrazol-4-yl)-2-(4,4,5,5-tetramethyl-1,3,2-dioxaborolan-2-yl)-1H-indole. This mixture was slowly added at rt to a solution of 1-(3-bromo-1-(4-methoxybenzyl)-1H-1,2,4-triazol-5-yl)-2-methoxyethan-1-one (1.46 g, 4.29 mmol), $K_3PO_4$ (2.73 g, 12.9 mmol) and $PdCl_2$(dtbpf) (0.838 g, 1.29 mmol) in THF (20 mL) and TPGS-750M (2% in water) (20 mL) and the mixture was stirred for 15 min at rt. The reaction mixture was diluted with brine (300 mL) and extracted with EtOAc (2×350 mL). The combined organic phases were dried over $Na_2SO_4$, filtered and the solvent was removed in vacuo. The crude product was purified by flash chromatography on silica (Biotage) using heptane and EtOAc (from 0-100% EtOAc) to give the title compound (697 mg). UPLC-MS (Method A): Rt=1.28 min, 609.2 [M+H]$^+$.

Step 2: 1-(5-(6-chloro-7-fluoro-5-methoxy-3-(1H-pyrazol-4-yl)-1H-indol-2-yl)-4H-1,2,4-triazol-3-yl)-2-methoxyethan-1-one To a solution of 1-(3-(6-chloro-7-fluoro-5-methoxy-3-(1-(tetrahydro-2H-pyran-2-yl)-1H-pyrazol-4-yl)-1H-indol-2-yl)-1-(4-methoxybenzyl)-1H-1,2,4-triazol-5-yl)-2-methoxyethan-1-one (146 mg, 0.24 mmol) in 1,2-DCE (20 mL) was added triflic acid (0.021 mL, 0.24 mmol) and the reaction was stirred for 30 min at rt. UPL-/MS (desired product was formed). The reaction mixture was quenched with aq. sat. $NaHCO_3$ (150 mL) and the aq. phase was extracted with EtOAc (2×300 mL). The combined organic phases were dried over $Na_2SO_4$, filtered and the solvent was removed in vacuo. The crude product was purified by flash chromatography on silica (Biotage) using heptane, EtOAc, MeOH (from 0-100% EtOAc and EtOAc to EtOAc/MeOH from 0-20%). The resulting solid was triturated in aq. bicarbonate (10 mL), filtered, washed with water and dried under high vacuum to give the title compound (35 mg). UPLC-MS (Method A): Rt=0.78 min, 407.0 [M+H]$^+$. $^1$H NMR (400 MHz, DMSO-d6) δ 12.94 (s, 1H), 12.14 (s, 1H), 8.22 (s, 1H), 7.90 (s, 1H), 7.11 (s, 1H), 4.86 (s, 2H), 3.93 (s, 3H), 3.41 (s, 3H).

The following examples were synthesized by an analogous method to the above procedure, using the corresponding triazole building block, optionally including indole NH-methylation (Step 3).

| Ex No. | Structure and Name | $^1$H NMR (400 MHz, DMSO-d$_6$) | LC-MS (min; m/z); Method |
|---|---|---|---|
| 58 | 6-chloro-7-fluoro-2-(5-fluoro-4H-1,2,4-triazol-3-yl)-5-methoxy-1-methyl-3-(1H-pyrazol-4-yl)-1H-indole | δ 14.33 (s, 1H), 13.01 (s, 1H), 7.94 (s, 1H), 7.50 (s, 1H), 7.10 (s, 1H), 3.93 (s, 3H), 3.85 (s, 3H). | Rt = 0.98; 365.0 [M + H]$^+$; Method A |

-continued

| Ex No. | Structure and Name | $^1$H NMR (400 MHz, DMSO-$d_6$) | LC-MS (min; m/z); Method |
|---|---|---|---|
| 59 | 4-(5-(6-chloro-7-fluoro-5-methoxy-1-methyl-3-(1H-pyrazol-4-yl)-1H-indol-2-yl)-4H-1,2,4-triazol-3-yl)morpholine | δ 7.89 (s, 2H), 7.08 (s, 1H), 3.92 (s, 3H), 3.88 (s, 3H), 3.76-3.71 (m, 4H), 3.40-3.34 (m, 4H). | Rt = 0.92; 432.2 [M + H]$^+$; Method D |
| 60 | 1-(5-(6-chloro-7-fluoro-5-methoxy-1-methyl-3-(1H-pyrazol-4-yl)-1H-indol-2-yl)-4H-1,2,4-triazol-3-yl)ethan-1-one | δ 7.78 (s, 2H), 7.11 (s, 1H), 3.93 (s, 3H), 3.88 (s, 3H), 2.65 (s, 3H). | Rt = 0.90; 389.1 [M + H]$^+$; Method A |
| 61 | N-(5-(6-chloro-7-fluoro-5-methoxy-1-methyl-3-(1H-pyrazol-4-yl)-1H-indol-2-yl)-4H-1,2,4-triazol-3-yl)-N-methylacetamide | δ 12.91 (s, 1H), 7.76 (d, J = 155.6 Hz, 2H), 7.10 (s, 1H), 3.93 (s, 3H), 3.87 (s, 3H), 3.31 (s, 3H), 2.25 (s, 3H). | Rt = 0.88; 418.3 [M + H]$^+$; Method A |
| 62 | N-(5-(6-chloro-7-fluoro-5-methoxy-1-methyl-3-(1H-pyrazol-4-yl)-1H-indol-2-yl)-4H-1,2,4-triazol-3-yl)-2-methoxy-N-methylacetamide | δ 14.23 (s, 1H), 12.94 (s, 1H), 7.95 (s, 1H), 7.56 (s, 1H), 7.10 (s, 1H), 4.37 (s, 2H), 3.93 (s, 3H), 3.88 (d, J = 1.7 Hz, 3H), 3.36 (s, 3H). | Rt = 0.87; 448.2 [M + H]$^+$; Method A |

-continued

| Ex No. | Structure and Name | $^1$H NMR (400 MHz, DMSO-$d_6$) | LC-MS (min; m/z); Method |
|---|---|---|---|
| 63 | 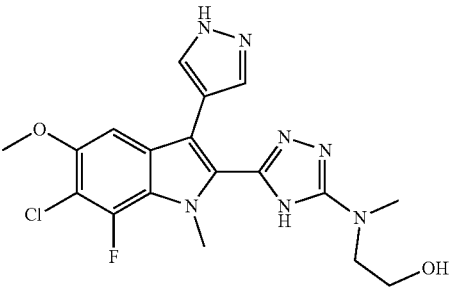 [SMILES: COc1cc2c(-c3cn[nH]c3)c(-c3nnc(N(C)CCO)[nH]3)n(C)c2c(F)c1Cl]<br>2-((5-(6-chloro-7-fluoro-5-methoxy-1-methyl-3-(1H-pyrazol-4-yl)-1H-indol-2-yl)-4H-1,2,4-triazol-3-yl)(methyl)amino)ethan-1-ol | δ 12.83 (s, 1H), 8.01 (s, 1H), 7.72 (s, 1H), 7.08 (d, J = 1.1 Hz, 1H), 3.92 (s, 3H), 3.87 (d, J = 1.8 Hz, 3H), 3.60 (t, J = 5.8 Hz, 2H), 3.44 (t, J = 5.8 Hz, 2H), 3.04 (s, 3H). | Rt = 0.82; 420.2 [M + H]$^+$; Method A |
| 64 | 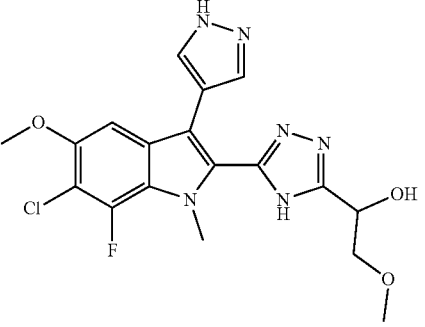 [SMILES: COCC(O)c1nnc(-c2c(-c3cn[nH]c3)c3cc(OC)c(Cl)c(F)c3n2C)[nH]1]<br>1-(5-(6-chloro-7-fluoro-5-methoxy-1-methyl-3-(1H-pyrazol-4-yl)-1H-indol-2-yl)-4H-1,2,4-triazol-3-yl)-2-methoxyethan-1-ol | δ 14.28 (s, 1H), 12.86 (s, 1H), 7.80 (d, J = 128.6 Hz, 2H), 7.10 (s, 1H), 6.08 (s, 1H), 4.95 (d, J = 6.6 Hz, 1H), 3.92 (s, 3H), 3.85 (s, 3H), 3.76-3.59 (m, 2H), 3.30 (s, 3H). | Rt = 0.80; 421.3 [M + H]$^+$; Method A |
| 65 | 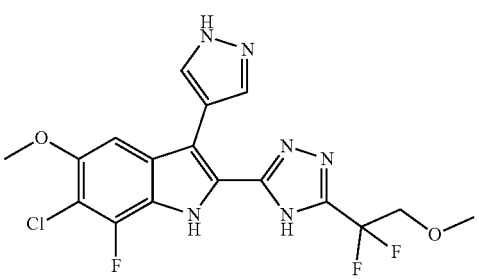<br>6-chloro-2-(5-(1,1-difluoro-2-methoxyethyl)-4H-1,2,4-triazol-3-yl)-7-fluoro-5-methoxy-3-(1H-pyrazol-4-yl)-1H-indole | δ 12.20 (s, 1H), 8.00 (s, 2H), 7.13 (s, 1H), 4.11 (t, J = 13.8 Hz, 2H), 3.93 (s, 3H), 3.40 (s, 3H). | Rt = 0.92; 427.1 [M + H]$^+$; Method A |

| Ex No. | Structure and Name | ¹H NMR (400 MHz, DMSO-d₆) | LC-MS (min; m/z); Method |
|---|---|---|---|
| 66 | 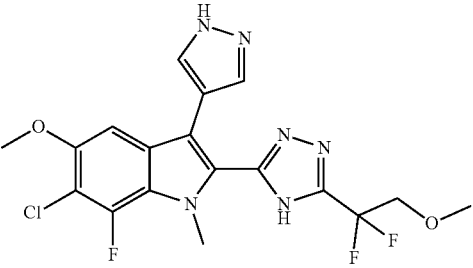<br>6-chloro-2-(5-(1,1-difluoro-2-methoxyethyl)-4H-1,2,4-triazol-3-yl)-7-fluoro-5-methoxy-1-methyl-3-(1H-pyrazol-4-yl)-1H-indole | δ 14.87 (s, 1H), 13.00 (s, 1H), 7.90 (s, 1H), 7.44 (s, 1H), 7.12 (s, 1H), 4.12 (t, J = 13.9 Hz, 2H), 3.94 (s, 3H), 3.83 (s, 3H), 3.40 (s, 3H). | Rt = 0.99; 441.1 [M + H]⁺; Method A |
| 67 | 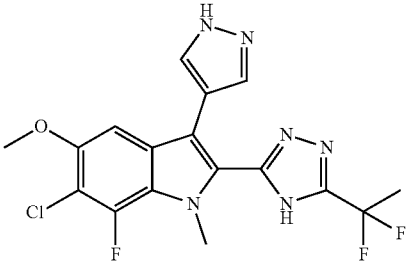<br>6-chloro-2-(5-(1,1-difluoroethyl)-4H-1,2,4-triazol-3-yl)-7-fluoro-5-methoxy-3-(1H-pyrazol-4-yl)-1H-indole | δ 12.97 (s, 1H), 12.18 (s, 1H), 8.17 (s, 1H), 7.82 (s, 1H), 7.12 (s, 1H), 3.93 (s, 3H), 2.11 (t, J = 19.0 Hz, 3H). | Rt = 0.91; 397.3 [M + H]⁺; Method A |
| 68 | 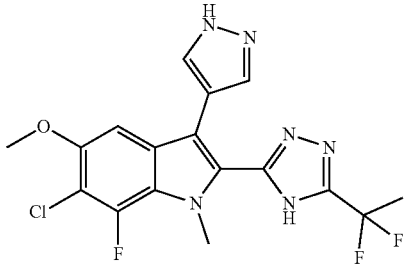 [SMILES: COc1cc2c(-c3cn[nH]c3)c(-c3nnc(C(C)(F)F)[nH]3)n(C)c2c(F)c1Cl]<br>6-chloro-2-(5-(1,1-difluoroethyl)-4H-1,2,4-triazol-3-yl)-7-fluoro-5-methoxy-1-methyl-3-(1H-pyrazol-4-yl)-1H-indole | δ 14.83 (s, 1H), 12.98 (s, 1H), 7.94 (s, 1H), 7.48 (s, 1H), 7.11 (s, 1H), 3.94 (s, 3H), 3.84 (s, 3H), 2.12 (t, J = 19.0 Hz, 3H). | Rt = 1.01; 411.2 [M + H]⁺; Method A |
| 69 | 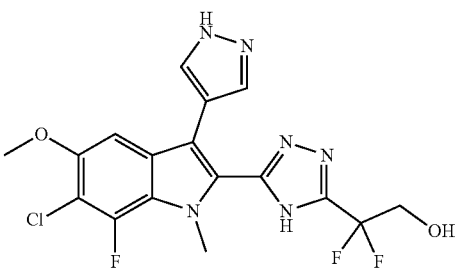 [SMILES: COc1cc2c(-c3cn[nH]c3)c(-c3nnc(C(F)(F)CO)[nH]3)n(C)c2c(F)c1Cl]<br>2-(5-(6-chloro-7-fluoro-5-methoxy-1-methyl-3-(1H-pyrazol-4-yl)-1H-indol-2-yl)-4H-1,2,4-triazol-3-yl)-2,2-difluoroethan-1-ol | δ 12.95 (s, 1H), 7.92 (s, 1H), 7.52 (s, 1H), 7.12 (s, 1H), 5.72 (s, 1H), 4.07 (t, J = 14.3 Hz, 2H), 3.94 (s, 3H), 3.84 (s, 3H). | Rt = 0.87; 427.1 [M + H]⁺; Method A |

| Ex No. | Structure and Name | $^1$H NMR (400 MHz, DMSO-$d_6$) | LC-MS (min; m/z); Method |
|---|---|---|---|
| 70 | 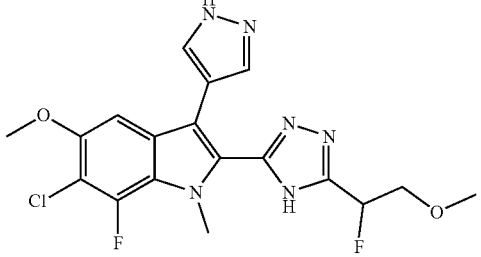<br>6-chloro-7-fluoro-2-(5-(1-fluoro-2-methoxyethyl)-4H-1,2,4-triazol-3-yl)-5-methoxy-1-methyl-3-(1H-pyrazol-4-yl)-1H-indole | δ 7.76 (s, 2H), 7.10 (s, 1H), 6.00-5.85 (m, 1H), 4.05-3.85 (m, 5H), 3.84 (s, 3H), 3.36 (s, 3H). | Rt = 0.92; 423.2 [M + H]$^+$; Method A |
| 71 | 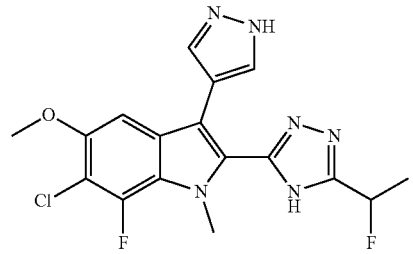<br>6-chloro-7-fluoro-2-(5-(1-fluoroethyl)-4H-1,2,4-triazol-3-yl)-5-methoxy-3-(1H-pyrazol-4-yl)-1H-indole | δ 14.44 (s, 1H), 12.92 (s, 1H), 12.07 (s, 1H), 8.18 (s, 1H), 7.88 (s, 1H), 7.09 (s, 1H), 5.89 (d, J = 47.9 Hz, 1H), 3.92 (s, 3H), 1.75 (dd, J = 24.2, 6.5 Hz, 3H). | Rt = 0.89; 379.1 [M + H]$^+$; Method A |
| 72 | 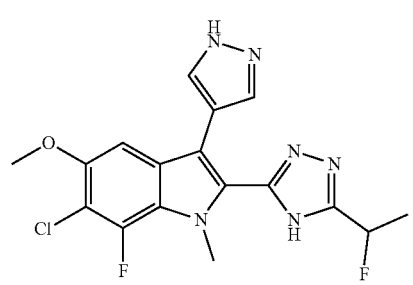 [SMILES: COc1cc2c(-c3cn[nH]c3)c(-c3nnc(C(C)F)[nH]3)n(C)c2c(F)c1Cl]<br>6-chloro-7-fluoro-2-(5-(1-fluoroethyl)-4H-1,2,4-triazol-3-yl)-5-methoxy-1-methyl-3-(1H-pyrazol-4-yl)-1H-indole | δ 14.63 (s, 1H), 12.92 (s, 1H), 7.95 (s, 1H), 7.55 (s, 1H), 7.10 (s, 1H), 5.91 (d, J = 47.9 Hz, 1H), 3.93 (s, 3H), 3.85 (s, 3H), 1.75 (dd, J = 24.3, 6.5 Hz, 3H). | Rt = 0.93; 393.2 [M + H]$^+$; Method A |
| 73 | 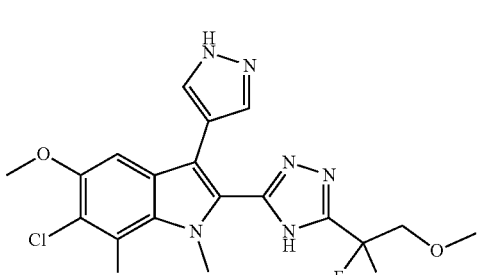<br>6-chloro-2-(5-(1,1-difluoro-2-methoxyethyl)-4H-1,2,4-triazol-3-yl)-5-methoxy-1-methyl-3-(1H-pyrazol-4-yl)-1H-indole-7-carbonitrile | δ 14.99 (s, 1H), 13.04 (s, 1H), 7.94 (s, 2H), 7.65 (s, 1H), 4.13 (t, J = 13.9 Hz, 2H), 3.99 (s, 3H), 3.96 (s, 3H), 3.40 (s, 3H). | Rt = 0.88; 448.2 [M + H]$^+$; Method A |

-continued

| Ex No. | Structure and Name | $^1$H NMR (400 MHz, DMSO-$d_6$) | LC-MS (min; m/z); Method |
|---|---|---|---|
| 74 | 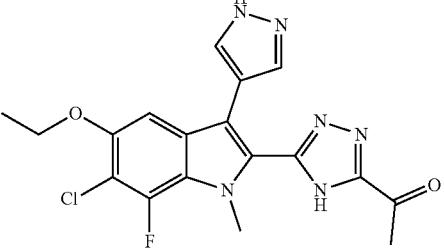<br>1-(5-(6-chloro-5-ethoxy-7-fluoro-1-methyl-3-(1H-pyrazol-4-yl)-1H-indol-2-yl)-4H-1,2,4-triazol-3-yl)ethan-1-one | δ 7.75 (s, 2H), 7.10 (d, J = 1.1 Hz, 1H), 4.27-4.09 (m, 2H), 3.87 (d, J = 1.7 Hz, 3H), 2.64 (s, 3H), 1.39 (t, J = 6.9 Hz, 3H). | Rt = 1.00; 403.2 [M + H]$^+$; Method A |
| 75 | 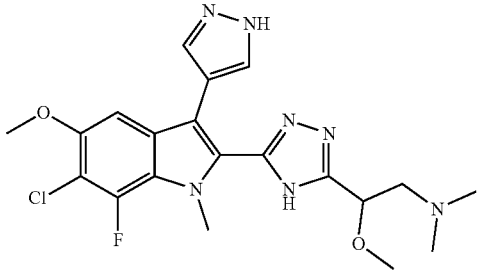<br>2-(5-(6-chloro-7-fluoro-5-methoxy-1-methyl-3-(1H-pyrazol-4-yl)-1H-indol-2-yl)-4H-1,2,4-triazol-3-yl)-2-methoxy-N,N-dimethylethan-1-amine | δ 14.34 (s, 1H), 12.85 (s, 1H), 7.76 (d, J = 130.0 Hz, 2H), 7.11 (d, J = 1.1 Hz, 1H), 4.61 (t, J = 6.4 Hz, 1H), 3.93 (s, 3H), 3.85 (d, J = 1.8 Hz, 3H), 3.27 (s, 3H), 2.75 (dd, J = 8.8, 6.4 Hz, 2H), 2.20 (s, 6H). | Rt = 0.66; 447.0 [M + H]$^+$; Method A |
| 76 | 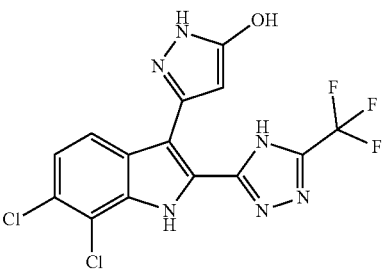 [SMILES: Oc1cc(-c2c(-c3nnc(C(F)(F)F)[nH]3)[nH]c3c(Cl)c(Cl)ccc23)n[nH]1]<br>3-(6,7-dichloro-2-(5-(trifluoromethyl)-4H-1,2,4-triazol-3-yl)-1H-indol-3-yl)-1H-pyrazol-5-ol | δ 12.48 (s, 1H), 7.92 (s, 1H), 7.39 (d, J = 8.6 Hz, 1H), 5.67 (s, 1H). | Rt = 1.25; 403.3 [M + H]$^+$; Method B |
| 77 | 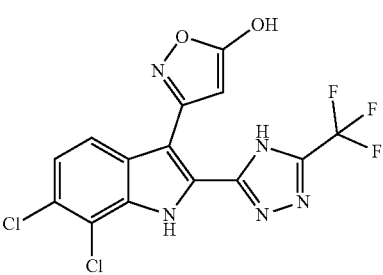 [SMILES: Oc1cc(-c2c(-c3nnc(C(F)(F)F)[nH]3)[nH]c3c(Cl)c(Cl)ccc23)no1]<br>3-(6,7-dichloro-2-(5-(trifluoromethyl)-4H-1,2,4-triazol-3-yl)-1H-indol-3-yl)isoxazol-5-ol | δ 15.69 (s, 1H), 13.03 (d, J = 62.7 Hz, 1H), 8.26-7.83 (m, 1H), 7.69-7.34 (m, 1H), 5.25 (s, 1H), 4.14 (s, 1H). | Rt = 1.13; 404.1 [M + H]$^+$; Method B |

| Ex No. | Structure and Name | $^1$H NMR (400 MHz, DMSO-d$_6$) | LC-MS (min; m/z); Method |
|---|---|---|---|
| 78 | 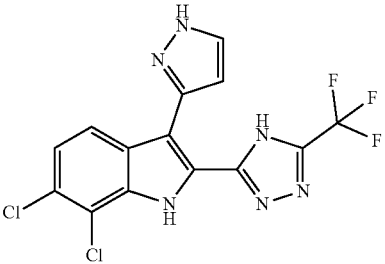 [SMILES: FC(F)(F)c1nnc(-c2[nH]c3c(Cl)c(Cl)ccc3c2-c2cc[nH]n2)[nH]1]  6,7-dichloro-3-(1H-pyrazol-3-yl)-2-(5-(trifluoromethyl)-4H-1,2,4-triazol-3-yl)-1H-indole | δ 15.74 (s, 1H), 13.35-13.06 (m, 1H), 12.46 (s, 1H), 8.15 (d, J = 8.6 Hz, 1H), 7.91 (s, 1H), 7.40 (d, J = 8.5 Hz, 1H), 6.58 (s, 1H). | Rt = 1.25; 389.0 [M + H]$^+$; Method B |

Example 79: 1-(5-(6-chloro-7-fluoro-5-methoxy-3-(1H-pyrazol-4-yl)-1H-indol-2-yl)-4H-1,2,4-triazol-3-yl)-N,N-dimethylethan-1-amine

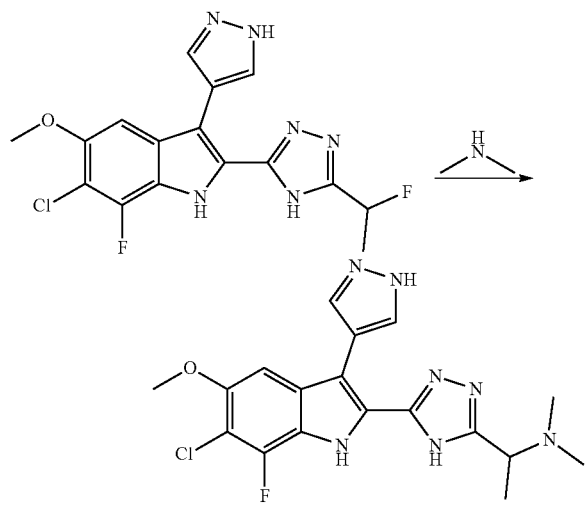

To a solution of 6-chloro-7-fluoro-2-(5-(1-fluoroethyl)-4H-1,2,4-triazol-3-yl)-5-methoxy-3-(1H-pyrazol-4-yl)-1H-indole (50 mg, 0.13 mmol) in MeOH (1 mL) was added dimethylamine (2 M in MeOH, 0.990 mL, 1.980 mmol) and the reaction mixture was stirred for 2 h at rt. The reaction mixture was concentrated and the crude product was purified by flash chromatography on silica (Teledyne) using cyclohexane, EtOAc and MeOH (from 0-100% EtOAc and EtOAc to EtOAc/MeOH from 0-20%) to give the title compound (20 mg). UPLC-MS (Method B): Rt=0.56 min, 404.1 [M+H]+. 1H NMR (400 MHz, DMSO-d6) δ 8.08 (s, 2H), 7.09 (s, 1H), 3.89 (d, J=16.8 Hz, 4H), 2.19 (s, 6H), 1.41 (d, J=6.9 Hz, 3H).

The following examples were synthesized by an analogous method to the above procedure, using the corresponding mono-fluorinated precursor.

| Ex No. | Structure and Name | $^1$H NMR (400 MHz, DMSO-d6) | LC-MS (min; m/z); Method |
|---|---|---|---|
| 80 | 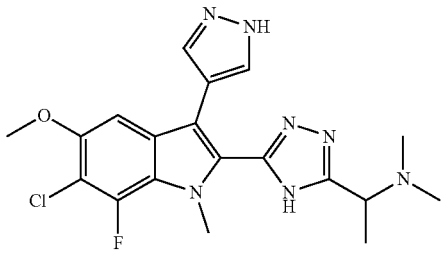  1-(5-(6-chloro-7-fluoro-5-methoxy-1-methyl-3-(1H-pyrazol-4-yl)-1H-indol-2-yl)-4H-1,2,4-triazol-3-yl)-N,N-dimethylethan-1-amine | δ 14.18 (s, 1H), 12.85 (s, 1H), 7.78 (d, J = 116.6 Hz, 2H), 7.10 (s, 1H), 3.98-3.88 (m, 4H), 3.84 (d, J = 1.8 Hz, 3H), 2.18 (s, 6H), 1.41 (d, J = 6.9 Hz, 3H). | Rt = 0.61; 418.3 [M + H]$^+$; Method A |

| Ex No. | Structure and Name | $^1$H NMR (400 MHz, DMSO-d6) | LC-MS (min; m/z); Method |
|---|---|---|---|
| 81 | 1-(5-(6-chloro-7-fluoro-5-methoxy-1-methyl-3-(1H-pyrazol-4-yl)-1H-indol-2-yl)-4H-1,2,4-triazol-3-yl)-2-methoxy-N,N-dimethylethan-1-amine | δ 14.26 (s, 1H), 12.87 (s, 1H), 7.95 (s, 1H), 7.60 (s, 1H), 7.11 (s, 1H), 4.02-3.96 (m, 1H), 3.93 (s, 3H), 3.85 (s, 5H), 3.26 (s, 3H), 2.22 (s, 6H). | Rt = 0.64; 448.3 [M + H]$^+$; Method A |

Example 82: 2-(5-(6-Chloro-7-fluoro-5-methoxy-1-methyl-3-(1H-pyrazol-4-yl)-1H-indol-2-yl)-4H-1,2,4-triazol-3-yl)propanenitrile To a solution of 6-chloro-7-fluoro-2-(5-(1-fluoroethyl)-4H-1,2,4-triazol-3-yl)-5-methoxy-1-methyl-3-(1H-pyrazol-4-yl)-1H-indole (200 mg, 0.51 mmol) in DMSO (4 mL) were added KCN (99 mg, 1.53 mmol) and K$_2$CO$_3$ (141 mg, 1.02 mmol) and the reaction was heated at 80° C. for 6 h. Additional KCN (99 mg, 1.53 mmol) and K$_2$CO$_3$ (141 mg, 1.02 mmol) were added and heating was continued for 2 h. The reaction mixture was cooled to rt, diluted with water and the aq. phase was extracted with EtOAc. The combined organic phase was dried over Na$_2$SO$_4$, filtered and the solvent was removed in vacuo. The crude product was purified by flash chromatography on silica (Teledyne) using cyclohexane and EtOAc (from 0-100% EtOAc) to give the title compound (61 mg) as a colorless solid. UPLC-MS (Method B3): Rt=0.89 min, 400.2 [M+H]+. $^1$H NMR (400 MHz, DMSO-d6) δ 14.51 (s, 1H), 12.95 (s, 1H), 7.95 (s, 1H), 7.51 (s, 1H), 7.11 (d, J=1.2 Hz, 1H), 4.63 (d, J=7.4 Hz, 1H), 3.93 (s, 3H), 3.84 (d, J=1.7 Hz, 3H), 1.68 (d, J=7.2 Hz, 3H).

Examples 83a, 83, and 84: 1-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-ol (Example 83a), (S)-1-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-ol (Example 83) and (R)-1-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-ol (Example 84)

Examples 83a, 83, and 84 were prepared according to Scheme 14 below.

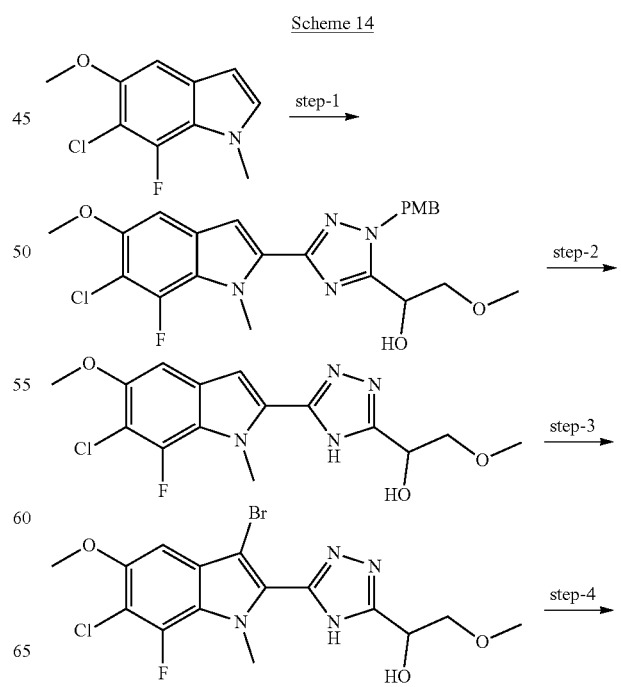

Scheme 14

-continued

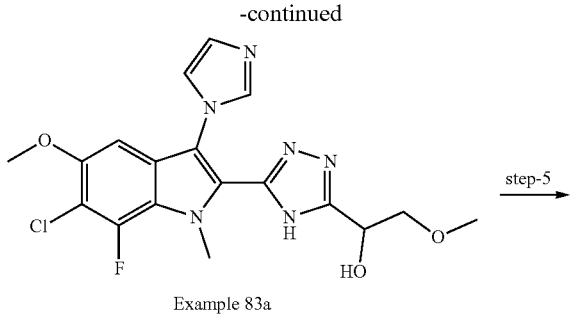

Example 83a step-5

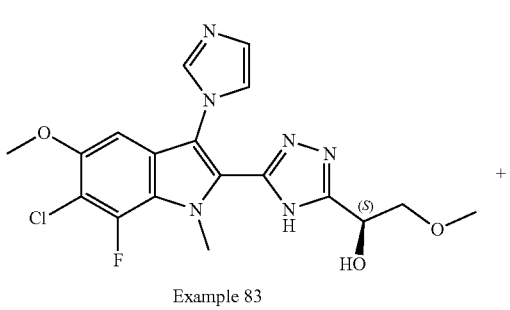

Example 83

+

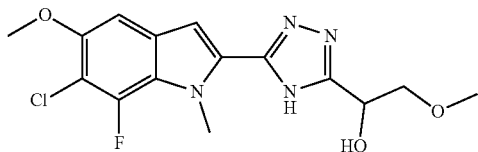

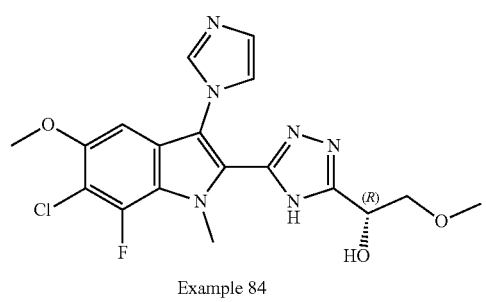

Example 84

Step 1: 1-(3-(6-chloro-7-fluoro-5-methoxy-1-methyl-1H-indol-2-yl)-1-(4-methoxybenzyl)-1H-1,2,4-triazol-5-yl)-2-methoxyethan-1-ol

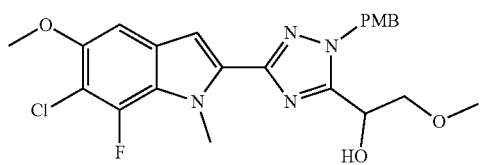

A mixture of 6-chloro-7-fluoro-5-methoxy-1-methyl-1H-indole (1.20 g, 5.62 mmol) 4,4'-di-tert-butyl-2,2'-bipyridine (0.03 g, 0.11 mmol), (1,5-cyclooctadienexmethoxy)iridium (I) dimer (0.04 g, 0.056 mmol) and bis(pinacolato)diboron (1.71 g, 6.74 mmol) in THF (7.5 mL) was stirred for 60 min at 80° C. to form 6-chloro-7-fluoro-5-methoxy-1-methyl-2-(4,4,5,5-tetramethyl-1,3,2-dioxaborolan-2-yl)-1H-indole. The reaction mixture was cooled to rt and added slowly to a solution of 1-(3-bromo-1-(4-methoxybenzyl)-1H-1,2,4-triazol-5-yl)-2-methoxyethan-1-ol (2.02 g, 5.90 mmol), $Cs_2CO_3$ (5.49 g, 16.9 mmol) and $PdCl_2$(dtbpf) (0.37 g, 0.56 mmol) in THF (7.5 mL) and water (16 mL) at 70° C. The reaction mixture was stirred for 60 min at 70° C., cooled to rt and diluted with water (100 mL). The aq. phase was extracted with EtOAc (2×250 mL), the combined organic phase was washed with brine, dried over $Na_2SO_4$, filtered and the solvent was removed in vacuo. The crude product was purified by flash chromatography on silica (Biotage) using heptane and EtOAc (from 0-100% EtOAc) to give the title compound (2.20 g). UPLC-MS (Method A): Rt=1.22 min, 475.4 $[M+H]^+$.

Step 2: 1-(5-(6-chloro-7-fluoro-5-methoxy-1-methyl-1H-indol-2-yl)-4H-1,2,4-triazol-3-yl)-2-methoxyethan-1-ol To a mixture of 1-(3-(6-chloro-7-fluoro-5-methoxy-1-methyl-1H-indol-2-yl)-1-(4-methoxybenzyl)-1H-1,2,4-triazol-5-yl)-2-methoxyethan-1-ol (2.20 g, 4.45 mmol) in DCM (200 mL) was added triflic acid (1.98 mL, 22.2 mmol) and the reaction was stirred for 2 h at rt. The reaction mixture was quenched with aq. sat. $NaHCO_3$ (300 mL) and the aq. phase was extracted with EtOAc (2×300 mL). The combined organic phase was dried over $Na_2SO_4$, filtered and the solvent was removed in vacuo. The crude product was purified by flash chromatography on silica (Biotage) using heptane, EtOAc and MeOH (from 0-100% EtOAc and from 0-20% EtOAc to MeOH) to give the title compound (0.92 g). UPLC-MS (Method A): Rt=0.90 min, 355.2 $[M+H]^+$.

Step 3: 1-(5-(6-chloro-7-fluoro-5-methoxy-1-methyl-1H-indol-2-yl)-4H-1,2,4-triazol-3-yl)-2-methoxyethan-1-ol

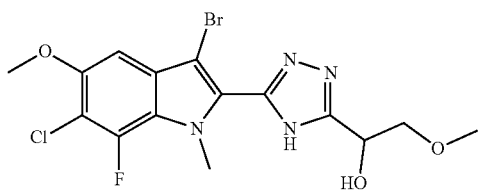

To a solution of 1-(5-(6-chloro-7-fluoro-5-methoxy-1-methyl-1H-indol-2-yl)-4H-1,2,4-triazol-3-yl)-2-methoxyethan-1-ol (0.89 g, 2.43 mmol) in THF (15 mL) was added NBS (0.48 g, 2.68 mmol) and the reaction was stirred for 30 min at rt. The reaction mixture was concentrated to give the title compound (1.39 g) which was used without further purification. UPLC-MS (Method A): Rt=0.99 min, 435.2 [M+H]+.

Step 4: 1-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-ol (Example 83a)

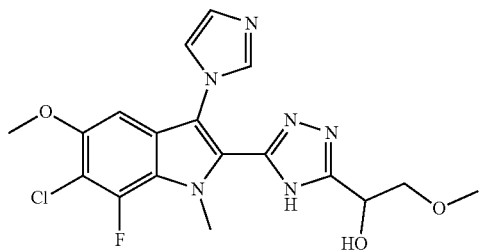

A mixture of 1-(5-(3-bromo-6-chloro-7-fluoro-5-methoxy-1-methyl-1H-indol-2-yl)-4H-1,2,4-triazol-3-yl)-2-methoxyethan-1-ol (1.38 g, 2.39 mmol), imidazole (0.65 g, 9.55 mmol), $K_2CO_3$ (0.99 g, 7.16 mmol), CuI (0.045 g, 0.24 mmol) and L-proline (0.055 g, 0.48 mmol) in DMSO (8.0 mL) was stirred for 18 h at 100° C. The reaction mixture was cooled to rt and carefully quenched with 10% citric acid (30 mL). Water (300 mL) was added, saturated with solid NaCl and the aq. phase was extracted with EtOAc. The combined organic phase was dried over $Na_2SO_4$, filtered and the solvent was removed in vacuo. The crude product was purified by flash-chromatography on silica (Biotage) using DCM and MeOH (from 0-10% MeOH) to give the title compound (0.62 g). UPLC-MS (Method A): Rt=0.62 min, 421.4 [M+H]+.

Step 5: Examples 83 and 84

Separation of a small sample of enantiomers was performed by preparative chiral SFC chromatography on a Sepiatec 100 Preparative SFC instrument (column: ChiralPak AD 250×30 mm, 5 μm; mobile phase: 22% MeOH+ 0.1% of 25% aq. $NH_4OH$ in $CO_2$, flow rate: 90 mL/min; column temperature: 40° C., back pressure 120 bar) to give the enantiomerically pure title compounds.

Example 84: (R)-1-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-ol UPLC/MS (Method A): Rt=0.67 min, 421.4 [M+H]+. Analytical chiral SFC: $R_t$=2.1 min; e.e. 99.6 (Waters $UPC^2$ analytical SFC instrument; column: ChiralPak AD, 100×4.6 mm, 5 μm; 22% methanol+ 0.1% of 25% aq. $NH_4OH$ in $CO_2$; flow rate: 3 mL/min; column temperature: 40° C., back pressure 1800 psi). $^1H$ NMR (400 MHz, DMSO-d6) δ 7.78 (s, 1H), 7.32 (s, 1H), 7.05 (s, 1H), 6.70 (s, 1H), 6.05 (d, J=5.0 Hz, 1H), 4.89 (m, 1H), 4.08 (s, 3H), 3.85 (s, 3H), 3.74-3.50 (m, 2H), 3.26 (s, 3H). Absolute stereochemistry (R) was assigned by x-ray crystallography.

Example 83: (S)-1-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-ol UPLC/MS (Method A): Rt=0.67 min, 421.4 [M+H]+. Analytical chiral SFC: $R_t$=2.9 min; e.e. 98.1 (Waters $UPC^2$ analytical SFC instrument; column: ChiralPak AD, 100×4.6 mm, 5 μm; 22% methanol+0.1% of 25% aq. $NH_4OH$ in $CO_2$; flow rate: 3 mL/min; column temperature: 40° C., back pressure 1800 psi). 1H NMR (400 MHz, DMSO-d6) δ 7.78 (s, 1H), 7.32 (d, J=1.4 Hz, 1H), 7.05 (s, 1H), 6.70 (s, 1H), 6.05 (s, 1H), 4.89 (m, 1H), 4.08 (s, 3H), 3.85 (s, 3H), 3.67 (m, 2H), 3.26 (s, 3H). The following examples were synthesized by an analogous method to the above procedure, using the corresponding indole intermediate and triazole building block.

| Ex No. | Structure and Name | $^1H$ NMR (400 MHz, DMSO-d6) | LC-MS (min; m/z); Method |
|---|---|---|---|
| 85 | 6-chloro-7-fluoro-3-(1H-imidazol-1-yl)-2-(5-isopropoxy-4H-1,2,4-triazol-3-yl)-5-methoxy-1-methyl-1H-indole | δ 13.58 (s, 1H), 7.78 (s, 1H), 7.32 (s, 1H), 7.05 (s, 1H), 6.70 (s, 1H), 4.97-4.79 (m, 1H), 4.10 (s, 3H), 3.85 (s, 3H), 1.31 (d, J = 6.2 Hz, 6H). | Rt = 0.99; 405.2 [M + H]+; Method A |

-continued

| Ex No. | Structure and Name | $^1$H NMR (400 MHz, DMSO-d6) | LC-MS (min; m/z); Method |
|---|---|---|---|
| 86 | 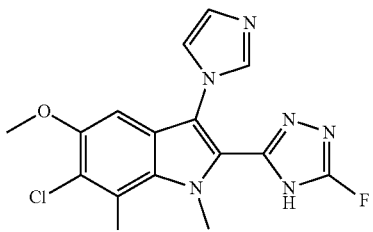<br>6-chloro-7-fluoro-2-(5-fluoro-4H-1,2,4-triazol-3-yl)-3-(1H-imidazol-1-yl)-5-methoxy-1-methyl-1H-indole | δ 9.47 (s, 1H), 7.91 (s, 1H), 7.86 (s, 1H), 7.06 (s, 1H), 4.12 (s, 3H), 3.89 (s, 3H). | Rt = 0.85; 365.1 [M + H]$^+$; Method A |
| 87 | 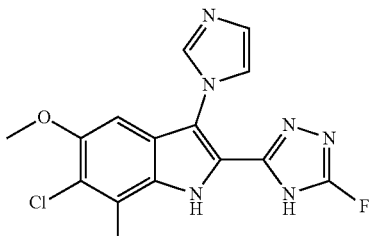<br>6-chloro-7-fluoro-2-(5-fluoro-4H-1,2,4-triazol-3-yl)-3-(1H-imidazol-1-yl)-5-methoxy-1H-indole | δ 7.91 (s, 1H), 7.42 (s, 1H), 7.10 (s, 1H), 6.72 (s, 1H), 3.85 (s, 3H). | Rt = 0.60; 351.2 [M + H]$^+$; Method A |
| 88 | 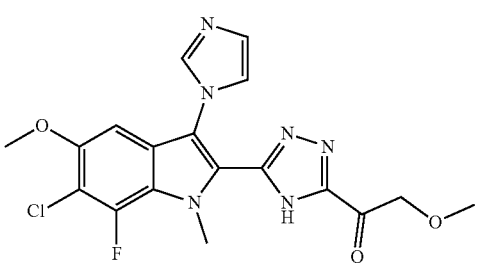<br>1-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-one | δ 8.82 (s, 1H), 7.66 (s, 2H), 6.93 (s, 1H), 4.72 (s, 2H), 4.22 (s, 3H), 3.87 (s, 3H), 3.36 (s, 3H). | Rt = 0.73; 419.1 [M + H]$^+$; Method A |
| 89 | 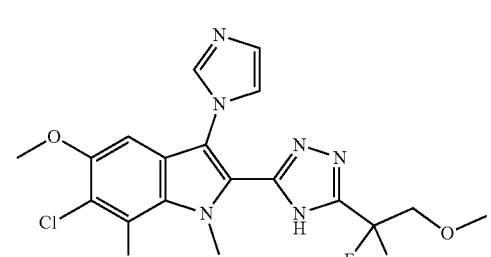<br>6-chloro-2-(5-(1,1-difluoro-2-methoxyethyl)-4H-1,2,4-triazol-3-yl)-7-fluoro-3-(1H-imidazol-1-yl)-5-methoxy-1-methyl-1H-indole | δ 15.29 (s, 1H), 7.83 (s, 1H), 7.30 (s, 1H), 7.09 (s, 1H), 6.77 (s, 1H), 4.11-4.00 (m, 5H), 3.87 (s, 3H), 3.36 (s, 3H). | Rt = 0.88; 441.2 [M + H]$^+$; Method A |

| Ex No. | Structure and Name | $^1$H NMR (400 MHz, DMSO-d6) | LC-MS (min; m/z); Method |
|---|---|---|---|
| 90 | 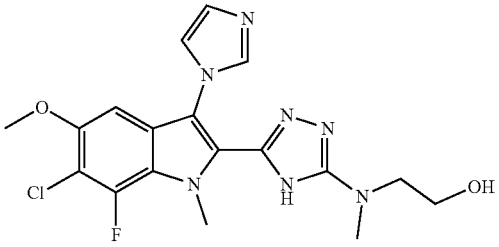 [SMILES: COc1cc2c(-n3ccnc3)c(-c3nnc(N(C)CCO)[nH]3)n(C)c2c(F)c1Cl]<br>2-((5-(6-chloro-7-fluoro-3-(1H-imidazol-1-yl)-5-methoxy-1-methyl-1H-indol-2-yl)-4H-1,2,4-triazol-3-yl)(methyl)amino)ethan-1-ol | δ 12.74 (s, 1H), 7.81 (s, 1H), 7.34 (s, 1H), 7.05 (s, 1H), 6.68 (s, 1H), 4.70 (s, 1H), 4.11 (s, 3H), 3.84 (s, 3H), 3.60-3.50 (m, 2H), 3.37 (t, J = 6.1 Hz, 2H), 2.99 (s, 3H). | Rt = 0.71; 420.2 [M + H]$^+$; Method A |
| 91 | 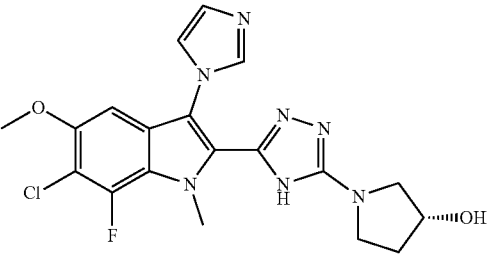 [SMILES: COc1cc2c(-n3ccnc3)c(-c3nnc(N4CC[C@@H](O)C4)[nH]3)n(C)c2c(F)c1Cl]<br>(R)-1-(5-(6-chloro-7-fluoro-3-(1H-imidazol-1-yl)-5-methoxy-1-methyl-1H-indol-2-yl)-4H-1,2,4-triazol-3-yl)pyrrolidin-3-ol | δ 12.78 (s, 1H), 7.81 (s, 1H), 7.34 (s, 1H), 7.04 (s, 1H), 6.68 (s, 1H), 5.01 (s, 1H), 4.41-4.32 (m, 1H), 4.09 (s, 3H), 3.84 (s, 3H), 3.48-3.19 (m, 4H), 2.08-1.93 (m, 1H), 1.93-1.81 (m, 1H). | Rt = 0.66; 432.2 [M + H]$^+$; Method A |
| 92 | 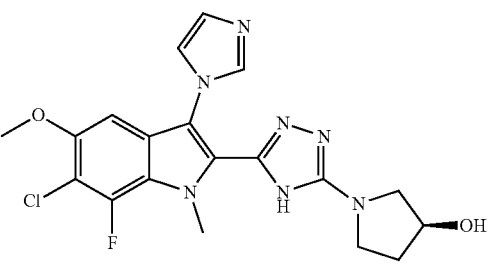 [SMILES: COc1cc2c(-n3ccnc3)c(-c3nnc(N4CC[C@H](O)C4)[nH]3)n(C)c2c(F)c1Cl]<br>(S)-1-(5-(6-chloro-7-fluoro-3-(1H-imidazol-1-yl)-5-methoxy-1-methyl-1H-indol-2-yl)-4H-1,2,4-triazol-3-yl)pyrrolidin-3-ol | δ 12.78 (s, 1H), 7.81 (s, 1H), 7.34 (s, 1H), 7.05 (s, 1H), 6.69 (s, 1H), 5.01 (d, J = 3.7 Hz, 1H), 4.36 (s, 1H), 4.09 (s, 3H), 3.84 (s, 3H), 3.49-3.13 (m, 4H), 2.08-1.78 (m, 2H). | Rt = 0.67; 432.2 [M + H]$^+$; Method A |
| 93 | 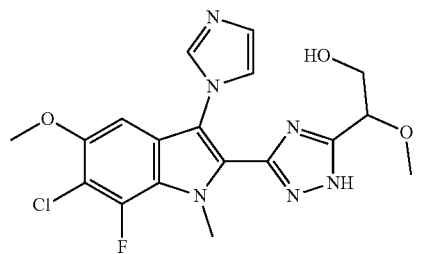<br>2-(3-(6-chloro-7-fluoro-3-(1H-imidazol-1-yl)-5-methoxy-1-methyl-1H-indol-2-yl)-1H-1,2,4-triazol-5-yl)-2-methoxyethan-1-ol | δ 9.45 (s, 1H), 7.91 (d, J = 6.4 Hz, 1H), 7.69 (s, 1H), 6.99 (s, 1H), 4.42 (t, J = 6.0, 4.9 Hz, 1H), 4.31 (s, 3H), 3.87 (s, 3H), 3.74-3.60 (m, 2H), 3.29 (s, 3H). | Rt = 0.65; 421.2 [M + H]$^+$; Method A |

| Ex No. | Structure and Name | ¹H NMR (400 MHz, DMSO-d6) | LC-MS (min; m/z); Method |
|---|---|---|---|
| 94 | 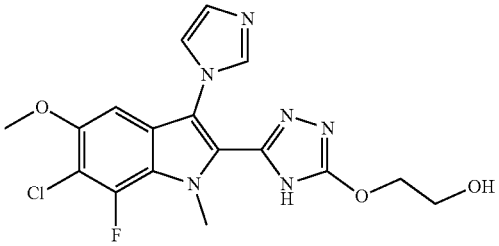 [SMILES: COc1cc2c(-n3ccnc3)c(-c3nnc(OCCO)[nH]3)n(C)c2c(F)c1Cl]<br>2-((5-(6-chloro-7-fluoro-3-(1H-imidazol-1-yl)-5-methoxy-1-methyl-1H-indol-2-yl)-4H-1,2,4-triazol-3-yl)oxy)ethan-1-ol | δ 7.79 (s, 1H), 7.32 (s, 1H), 7.06 (s, 1H), 6.71 (s, 1H), 4.29 (t, J = 4.7 Hz, 2H), 4.08 (s, 3H), 3.85 (s, 3H), 3.69 (t, J = 4.8 Hz, 2H). 2 protons hidden | Rt = 0.67; 407.2 [M + H]⁺; Method A |
| 95 | 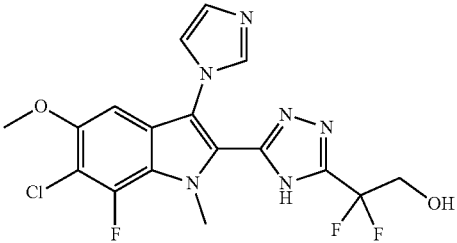 [SMILES: COc1cc2c(-n3ccnc3)c(-c3nnc(C(F)(F)CO)[nH]3)n(C)c2c(F)c1Cl]<br>2-(5-(6-chloro-7-fluoro-3-(1H-imidazol-1-yl)-5-methoxy-1-methyl-1H-indol-2-yl)-4H-1,2,4-triazol-3-yl)-2,2-difluoroethan-1-ol | δ 7.82 (s, 1H), 7.31 (s, 1H), 7.08 (s, 1H), 6.76 (s, 1H), 5.76 (t, 1H), 4.05 (d, J = 1.8 Hz, 3H), 4.03-3.95 (m, 2H), 3.87 (s, 3H). 1 proton hidden | Rt = 0.75; 427.2 [M + H]⁺; Method A |
| 96 | 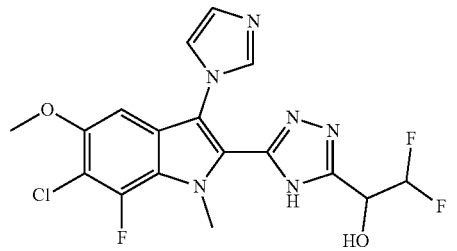 [SMILES: COc1cc2c(-n3ccnc3)c(-c3nnc(C(O)C(F)F)[nH]3)n(C)c2c(F)c1Cl]<br>1-(5-(6-chloro-7-fluoro-3-(1H-imidazol-1-yl)-5-methoxy-1-methyl-1H-indol-2-yl)-4H-1,2,4-triazol-3-yl)-2,2-difluoroethan-1-ol | δ 7.79 (s, 1H), 7.32 (s, 1H), 7.05 (s, 1H), 6.86 (s, 1H), 6.72 (s, 1H), 6.42-6.05 (m, 1H), 5.06 (s, 1H), 4.07 (s, 3H), 3.86 (s, 3H). 1 proton hidden | Rt = 0.68; 427.3 [M + H]⁺; Method A |
| 97 | 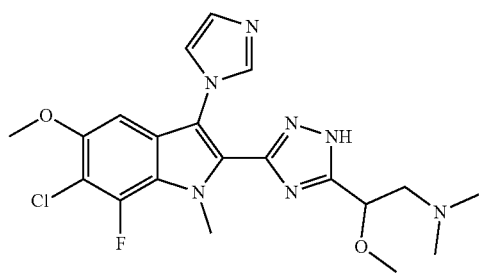<br>2-(3-(6-chloro-7-fluoro-3-(1H-imidazol-1-yl)-5-methoxy-1-methyl-1H-indol-2-yl)-1H-1,2,4-triazol-5-yl)-2-methoxy-N,N-dimethylethan-1-amine | δ 14.42 (s, 1H), 7.78 (s, 1H), 7.32 (s, 1H), 7.05 (s, 1H), 6.78-6.66 (m, 1H), 4.57 (t, J = 6.4 Hz, 1H), 4.09 (d, J = 1.8 Hz, 3H), 3.86 (s, 3H), 3.24 (s, 3H), 2.78-2.64 (m, 2H), 2.17 (s, 6H) | Rt = 0.64; 447.0 [M + H]⁺; Method A |

| Ex No. | Structure and Name | ¹H NMR (400 MHz, DMSO-d6) | LC-MS (min; m/z); Method |
|---|---|---|---|
| 98 | 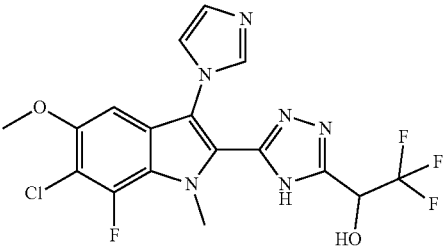 [SMILES: COc1cc2c(-n3ccnc3)c(-c3nnc(C(O)C(F)(F)F)[nH]3)n(C)c2c(F)c1Cl]<br>1-(5-(6-chloro-7-fluoro-3-(1H-imidazol-1-yl)-5-methoxy-1-methyl-1H-indol-2-yl)-4H-1,2,4-triazol-3-yl)-2,2,2-trifluoroethan-1-ol | δ 14.85 (s, 1H), 7.81 (s, 1H), 7.57 (s, 1H), 7.33 (s, 1H), 7.08 (s, 1H), 6.73 (s, 1H), 5.50 (t, J = 6.5 Hz, 1H), 4.05 (s, 3H), 3.86 (s, 3H). | Rt = 0.83; 445.3 [M + H]⁺; Method A |
| 99 | 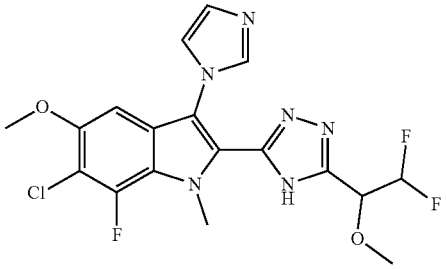 [SMILES: COc1cc2c(-n3ccnc3)c(-c3nnc(C(OC)C(F)F)[nH]3)n(C)c2c(F)c1Cl]<br>6-chloro-2-(5-(2,2-difluoro-1-methoxyethyl)-4H-1,2,4-triazol-3-yl)-7-fluoro-3-(1H-imidazol-1-yl)-5-methoxy-1-methyl-1H-indole | δ 14.79 (s, 1H), 8.21-6.92 (m, 3H), 6.74 (s, 1H), 6.34 (td, J = 54.4, 3.6 Hz, 1H), 4.93 (td, J = 11.1, 3.4 Hz, 1H), 4.07 (s, 3H), 3.86 (s, 3H), 3.41 (s, 3H). | Rt = 0.80; 441.3 [M + H]⁺; Method A |
| 100 | 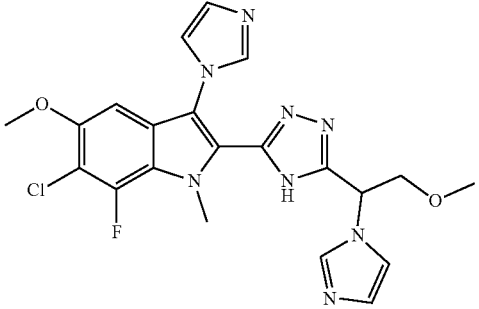<br>2-(5-(1-(1H-imidazol-1-yl)-2-methoxyethyl)-4H-1,2,4-triazol-3-yl)-6-chloro-7-fluoro-3-(1H-imidazol-1-yl)-5-methoxy-1-methyl-1H-indole | δ 9.34 (d, J = 55.0 Hz, 2H), 7.82 (d, J = 42.3 Hz, 4H), 7.01 (s, 1H), 6.26 (s, 1H), 4.25 (s, 3H), 4.13-3.95 (m, 2H), 3.87 (s, 3H), 3.31 (s, 3H). | Rt = 0.68; 471.3 [M + H]⁺; Method A |
| 101 | 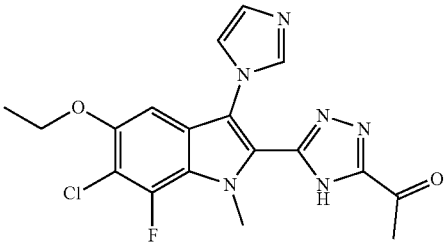 [SMILES: CCOc1cc2c(-n3ccnc3)c(-c3nnc(C(C)=O)[nH]3)n(C)c2c(F)c1Cl]<br>1-(5-(6-chloro-5-ethoxy-7-fluoro-3-(1H-imidazol-1-yl)-1-methyl-1H-indol-2-yl)-4H-1,2,4-triazol-3-yl)ethan-1-one | δ 7.82 (s, 1H), 7.30 (d, J = 24.3 Hz, 1H), 7.08 (s, 1H), 6.73 (s, 1H), 4.14-4.04 (m, 5H), 2.58 (s, 3H), 1.36 (t, J = 6.9 Hz, 3H). | Rt = 0.90; 403.3 [M + H]⁺; Method A |

-continued

| Ex No. | Structure and Name | ¹H NMR (400 MHz, DMSO-d6) | LC-MS (min; m/z); Method |
|---|---|---|---|
| 102 | 1-(5-(6-chloro-7-fluoro-3-(1H-imidazol-1-yl)-5-methoxy-1-methyl-1H-indol-2-yl)-4H-1,2,4-triazol-3-yl)ethan-1-one | δ 7.83 (s, 1H), 7.34 (s, 1H), 7.08 (s, 1H), 6.74 (s, 1H), 4.11 (d, J = 1.7 Hz, 3H), 3.86 (s, 3H), 2.58 (s, 3H). | Rt = 0.74; 389.2 [M + H]⁺; Method A |
| 103 | 5-(6-chloro-7-cyano-3-(1H-imidazol-1-yl)-5-methoxy-1-methyl-1H-indol-2-yl)-N,N-dimethyl-4H-1,2,4-triazole-3-carboxamide | δ 15.33 (s, 1H), 7.80 (s, 1H), 7.34 (s, 1H), 7.26 (s, 1H), 7.08 (s, 1H), 4.27 (s, 3H), 3.91 (s, 3H), 3.28 (s, 3H), 3.03 (s, 3H). | Rt = 0.70; 425.2 [M + H]⁺; Method A |
| 104 | 5-(6,7-difluoro-3-(1H-imidazol-1-yl)-5-methoxy-1-methyl-1H-indol-2-yl)-N,N-dimethyl-4H-1,2,4-triazole-3-carboxamide | δ 15.22 (s, 1H), 7.77 (s, 1H), 7.31 (s, 1H), 7.06 (s, 1H), 6.70 (d, J = 7.1, 1.5 Hz, 1H)., 4.13 (d, J = 1.4 Hz, 3H), 3.85 (s, 3H), 3.27 (s, 3H), 3.02 (s, 3H). | Rt = 0.69; 402.3 [M + H]⁺; Method A |
| 105 | 5,6-dichloro-3-(1H-imidazol-1-yl)-2-(5-(trifluoromethyl)-4H-1,2,4-triazol-3-yl)-1H-indole | δ 12.55 (s, 1H), 8.55 (s, 1H), 7.74 (s, 1H), 7.68 (s, 1H), 7.62 (d, J = 3.2 Hz, 1H), 7.43 (s, 1H). 1 proton hidden | Rt = 1.08; 385.1 [M + H]⁺; Method B |

-continued

| Ex No. | Structure and Name | ¹H NMR (400 MHz, DMSO-d6) | LC-MS (min; m/z); Method |
|---|---|---|---|
| 106 | 6,7-dichloro-3-(1H-imidazol-1-yl)-2-(5-(trifluoromethyl)-4H-1,2,4-triazol-3-yl)-1H-indole | δ 8.08 (s, 1H), 7.50 (s, 1H), 7.46-7.38 (m, 2H), 7.20 (s, 1H). 2 protons hidden | Rt = 1.03; 387.1 [M + H]⁺; Method B |
| 107 | 6-chloro-3-(1H-imidazol-1-yl)-5-methoxy-2-(5-(trifluoromethyl)-4H-1,2,4-triazol-3-yl)-1H-indole | δ 15.08 (s, 1H), 12.13 (s, 1H), 8.23 (s, 1H), 7.60 (s, 1H), 7.54 (s, 1H), 7.28 (s, 1H), 6.95 (s, 1H), 3.84 (s, 3H). | Rt = 0.85; 383.1 [M + H]⁺; Method B |
| 108 | 5,6-dichloro-3-(1H-imidazol-1-yl)-1-methyl-2-(5-(trifluoromethyl)-4H-1,2,4-triazol-3-yl)-1H-indole | δ 8.25 (s, 1H), 8.17 (s, 1H), 7.69 (s, 1H), 7.47 (s, 1H), 7.28 (s, 1H), 3.97 (s, 3H). | Rt = 1.05; 401.1 [M + H]⁺; Method C |
| 109 | 6,7-dichloro-3-(1H-imidazol-1-yl)-1-methyl-2-(5-(trifluoromethyl)-4H-1,2,4-triazol-3-yl)-1H-indole | δ 9.15-8.93 (m, 1H), 7.78-7.67 (m, 2H), 7.61-7.48 (m, 2H), 4.26 (s, 3H). | Rt = 1.09; 401.2 [M + H]⁺; Method B |

-continued

| Ex No. | Structure and Name | ¹H NMR (400 MHz, DMSO-d6) | LC-MS (min; m/z); Method |
|---|---|---|---|
| 110 | 6-chloro-3-(1H-imidazol-1-yl)-2-(5-(trifluoromethyl)-4H-1,2,4-triazol-3-yl)-1H-indole-7-carbonitrile | δ 8.16 (s, 1H), 7.76 (d, J = 8.6 Hz, 1H), 7.53 (s, 1H), 7.46 (d, J = 8.6 Hz, 1H), 7.23 (s, 1H). | Rt = 0.89; 378.0 [M + H]⁺; Method B |
| 111 | 6-chloro-3-(1H-imidazol-1-yl)-1-methyl-2-(5-(trifluoromethyl)-4H-1,2,4-triazol-3-yl)-1H-indole-7-carbonitrile | δ 8.18 (s, 1H), 7.81 (d, J = 8.6 Hz, 1H), 7.54 (d, J = 8.6 Hz, 1H), 7.46 (s, 1H), 7.29 (s, 1H), 4.23 (s, 3H). | Rt = 0.86; 392.2 [M + H]⁺; Method A |
| 112 | 6-chloro-5-(difluoromethoxy)-3-(1H-imidazol-1-yl)-2-(5-(trifluoromethyl)-4H-1,2,4-triazol-3-yl)-1H-indole | δ 12.65-12.36 (m, 1H), 8.41 (s, 1H), 7.72 (s, 1H), 7.61 (s, 1H), 7.43-6.96 (m, 3H). | Rt = 0.87; 419.1 [M + H]⁺; Method A |
| 113 | 6-chloro-5-cyclopropoxy-3-(1H-imidazol-1-yl)-2-(5-(trifluoromethyl)-4H-1,2,4-triazol-3-yl)-1H-indole | δ 12.21 (s, 1H), 8.30 (s, 1H), 7.60 (s, 1H), 7.57 (d, J = 1.4 Hz, 1H), 7.33 (s, 1H), 7.26 (s, 1H), 4.06-3.88 (m, 1H), 0.87-0.73 (m, 2H), 0.73-0.66 (m, 2H). | Rt = 0.87; 419.1 [M + H]⁺; Method A |

| Ex No. | Structure and Name | ¹H NMR (400 MHz, DMSO-d6) | LC-MS (min; m/z); Method |
|---|---|---|---|
| 114 | 6-chloro-3-(1H-imidazol-1-yl)-5-methoxy-1-methyl-2-(5-(trifluoromethyl)-4H-1,2,4-triazol-3-yl)-1H-indole | δ 8.07 (s, 1H), 7.96 (s, 1H), 7.37 (s, 1H), 7.19 (s, 1H), 7.01 (s, 1H), 3.89 (s, 3H), 3.86 (s, 3H). | Rt = 0.85; 397.2 [M + H]⁺; Method A |
| 115 | 6-chloro-3-(1H-imidazol-1-yl)-1-methyl-2-(5-(trifluoromethyl)-4H-1,2,4-triazol-3-yl)-1H-indol-5-ol | δ 8.07 (s, 1H), 7.96 (s, 1H), 7.37 (s, 1H), 7.19 (s, 1H), 7.01 (s, 1H), 3.89 (s, 3H), 3.86 (s, 3H). | Rt = 0.85; 397.2 [M + H]⁺; Method A |
| 116 | 5-(6-chloro-3-(1H-imidazol-1-yl)-5-methoxy-1-methyl-1H-indol-2-yl)-N,N-dimethyl-4H-1,2,4-triazole-3-carboxamide-dimethyl-4H-1,2,4-triazole-3-carboxamide | δ 15.17 (s, 1H), 7.91 (s, 1H), 7.78 (s, 1H), 7.32 (s, 1H), 7.06 (s, 1H), 6.88 (s, 1H), 4.01 (s, 3H), 3.83 (s, 3H), 3.28 (s, 3H), 3.02 (s, 3H). | Rt = 0.63; 400.3 [M + H]⁺; Method A |
| 117 | 6-chloro-5-hydroxy-2-(5-(2-hydroxyethyl)-4H-1,2,4-triazol-3-yl)-3-(1H-imidazol-1-yl)-1-methyl-1H-indole-7-carbonitrile | δ 14.13 (s, 1H), 10.48 (s, 1H), 7.78 (s, 1H), 7.32 (s, 1H), 7.13 (s, 1H), 7.05 (s, 1H), 4.82 (t, J = 5.3 Hz, 1H), 4.21 (s, 3H), 3.76-3.68 (m, 2H), 2.89 (t, J = 6.6 Hz, 2H). | Rt = 0.41; 384.3 [M + H]⁺; Method A |

| Ex No. | Structure and Name | $^1$H NMR (400 MHz, DMSO-d6) | LC-MS (min; m/z); Method |
|---|---|---|---|
| 118 | 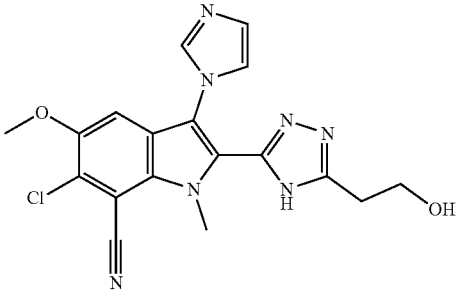 [SMILES: COc1cc2c(-n3ccnc3)c(-c3nnc(CCO)[nH]3)n(C)c2c(C#N)c1Cl]<br>6-chloro-2-(5-(2-hydroxyethyl)-4H-1,2,4-triazol-3-yl)-3-(1H-imidazol-1-yl)-5-methoxy-1-methyl-1H-indole-7-carbonitrile | δ 14.12 (s, 1H), 7.81 (s, 1H), 7.34 (s, 1H), 7.25 (s, 1H), 7.06 (s, 1H), 4.83 (s, 1H), 4.22 (s, 3H), 3.90 (s, 3H), 3.73 (t, J = 6.6 Hz, 2H), 2.89 (t, J = 6.6 Hz, 2H). | Rt = 0.52; 398.2 [M + H]$^+$; Method A |
| 119 | 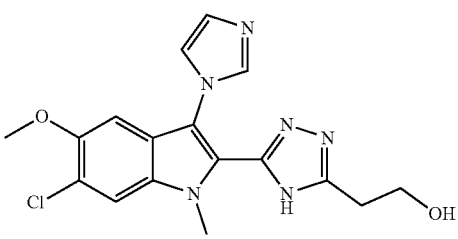 [SMILES: COc1cc2c(-n3ccnc3)c(-c3nnc(CCO)[nH]3)n(C)c2cc1Cl]<br>2-(5-(6-chloro-3-(1H-imidazol-1-yl)-5-methoxy-1-methyl-1H-indol-2-yl)-4H-1,2,4-triazol-3-yl)ethan-1-ol | δ 14.00 (s, 1H), 7.85 (s, 1H), 7.81 (s, 1H), 7.34 (s, 1H), 7.06 (s, 1H), 6.88 (s, 1H), 4.80 (t, J = 5.4 Hz, 1H), 3.96 (s, 3H), 3.83 (s, 3H), 3.77-3.70 (m, 2H), 2.88 (t, J = 6.6 Hz, 2H). | Rt = 0.52; 373.3 [M + H]$^+$; Method A |

Example 120: 5-(6,7-dicyano-3-(1H-imidazol-1-yl)-5-methoxy-1-methyl-1H-indol-2-yl)-N,N-dimethyl-4H-1,2,4-triazole-3-carboxamide

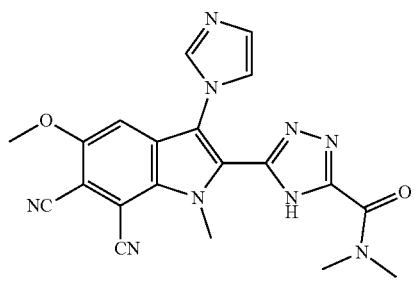 [SMILES: COc1cc2c(-n3ccnc3)c(-c3nnc(C(=O)N(C)C)[nH]3)n(C)c2c(C#N)c1C#N]

A mixture of 5-(6,7-difluoro-3-(1H-imidazol-1-yl)-5-methoxy-1-methyl-1H-indol-2-yl)-N,N-dimethyl-4H-1,2,4-triazole-3-carboxamide (65 mg, 0.154 mmol), $K_2CO_3$ (85 mg, 0.62 mmol) and KCN (100 mg, 1.54 mmol) in DMSO (1 mL) was heated for 4 h at 130° C. The reaction mixture was cooled to rt, filtered through a pad of celite and the filtrate was concentrated. The compound was purified by preparative reverse phase chromatography (XBridge-C18 (5 um, 50×250 mm), Eluent A: $H_2O$+0.2% HCOOH, B: ACN, Gradient: initial 0.8% B; 0.8% to 28% B in 21 min, flow: 100 mL/min) to give the title compound (25 mg) as a white solid. UPLC-MS (Method A): Rt=0.47 min; 402.3 [M+H]$^+$.

$^1$H NMR (400 MHz, DMSO-d6) δ 7.78 (s, 1H), 7.32 (s, 1H), 7.08 (d, J=14.5 Hz, 2H), 4.31 (s, 3H), 3.23 (s, 3H), 3.01 (s, 3H).

Example 121: 4-(1-(5-(6-chloro-7-fluoro-3-(1H-imidazol-1-yl)-5-methoxy-1-methyl-1H-indol-2-yl)-4H-1,2,4-triazol-3-yl)ethyl)morpholine

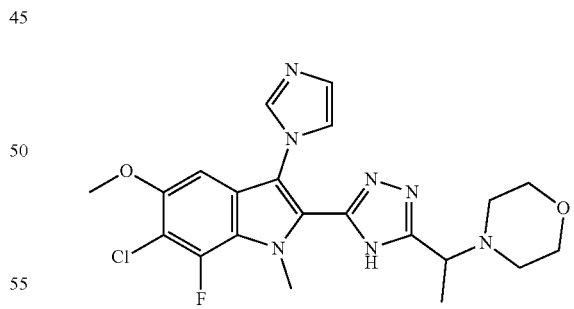

To a solution of 1-(5-(6-chloro-7-fluoro-3-(1H-imidazol-1-yl)-5-methoxy-1-methyl-1H-indol-2-yl)-4H-1,2,4-triazol-3-yl)ethan-1-ol (121 mg, 0.28 mmol) in DCM (40 mL) was added morpholine (0.36 mL, 4.13 mmol) followed by DAST (0.26 mL, 1.93 mmol) and the reaction was stirred at rt for 10 min. The reaction mixture was concentrated to dryness and the crude product was purified by flash-chromatography on silica (Biotage) using EtOAc and MeOH (from 0-30% MeOH) to give the title compound (94 mg). UPLC-MS (Method A): Rt=0.64 min, 460.4 [M+H]$^+$. $^1$H NMR (400

MHz, DMSO-d6) δ 7.78 (s, 1H), 7.31 (s, 1H), 7.04 (s, 1H), 6.71 (s, 1H), 4.10 (s, 3H), 3.94-3.81 (m, 4H), 3.58-3.53 (m, 4H), 2.40-2.32 (m, 4H), 1.37 (d, J=7.0 Hz, 3H).

The following examples were synthesized by an analogous method to the above procedure, using the corresponding alcohol intermediate and commercial amine.

To a suspension of 1-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-ol (see, e.g., Example 83a) (504 mg, 1.174 mmol) in CH$_2$Cl$_2$ (30 mL) was added dimethylamine 2M in THF (5.87 mL, 11.74 mmol). DAST (0.93 mL, 7.04 mmol) was added dropwise over a period of

| Ex No. | Structure and Name | $^1$H NMR (400 MHz, DMSO-d6) | LC-MS (min; m/z); Method |
|---|---|---|---|
| 122 | 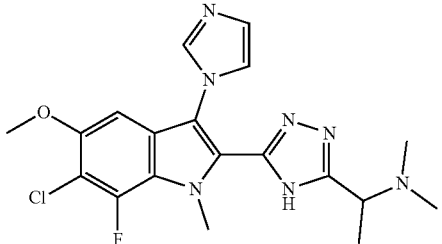<br>1-(5-(6-chloro-7-fluoro-3-(1H-imidazol-1-yl)-5-methoxy-1-methyl-1H-indol-2-yl)-4H-1,2,4-triazol-3-yl)-N,N-dimethylethan-1-amine | δ 7.79 (s, 1H), 7.32 (s, 1H), 7.05 (s, 1H), 6.72 (s, 1H), 4.09 (d, J = 1.8 Hz, 3H), 3.94-3.88 (m, 1H), 3.85 (s, 3H), 2.14 (s, 6H), 1.35 (d, J = 6.9 Hz, 3H). | Rt = 0.52; 418.3 [M + H]$^+$; Method A |
| 123 | 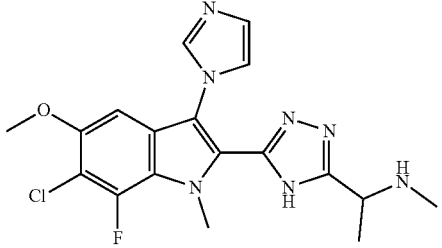<br>1-(5-(6-chloro-7-fluoro-3-(1H-imidazol-1-yl)-5-methoxy-1-methyl-1H-indol-2-yl)-4H-1,2,4-triazol-3-yl)-N-methylethan-1-amine | δ 7.79 (s, 1H), 7.32 (s, 1H), 7.05 (s, 1H), 6.72 (s, 1H), 4.08 (d, J = 1.9 Hz, 3H), 3.96-3.90 (m, 1H), 3.85 (s, 3H), 2.24 (s, 3H), 1.37 (d, J = 6.8 Hz, 3H). | Rt = 0.59; 404.4 [M + H]+; Method A |

Examples 124, 124a, and 124b: 1-(5-(6-chloro-7-fluoro-3-(1H-imidazol-1-yl)-5-methoxy-1-methyl-1H-indol-2-yl)-4H-1,2,4-triazol-3-yl)-2-methoxy-N,N-dimethylethan-1-amine (Example 124), (R)-1-(5-(6-chloro-7-fluoro-3-(1H-imidazol-1-yl)-5-methoxy-1-methyl-1H-indol-2-yl)-4H-1,2,4-triazol-3-yl)-2-methoxy-N,N-dimethylethan-1-amine (Example 124a), and (S)-1-(5-(6-chloro-7-fluoro-3-(1H-imidazol-1-yl)-5-methoxy-1-methyl-1H-indol-2-yl)-4H-1,2,4-triazol-3-yl)-2-methoxy-N,N-dimethylethan-1-amine (Example 124b);

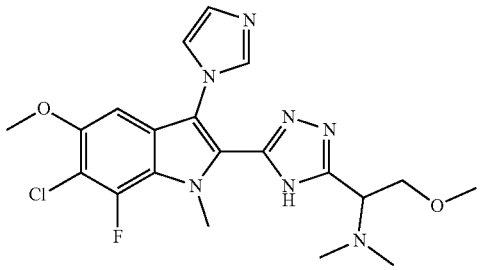

2 min at 0° C. and the reaction mixture was stirred at 0° C. for 10 min. The solvent was removed in vacuo and the crude product was purified by flash-chromatography on silica (Biotage) using EtOAc and MeOH (from 0-50% MeOH) to give the title compound (0.53 mg). UPLC-MS (Method A): Rt=0.57 min, 448.4 [M+H]$^+$. $^1$H NMR (400 MHz, DMSO-d6) δ 14.30 (s, 1H), 7.77 (s, 1H), 7.31 (s, 1H), 7.05 (s, 1H), 6.71 (s, 1H), 4.10 (s, 3H), 3.99-3.89 (m, 1H), 3.85 (s, 3H), 3.81-3.67 (m, 2H), 3.22 (s, 3H), 2.14 (s, 6H).

Separation of 3.89 g racemic 1-(5-(6-chloro-7-fluoro-3-(1H-imidazol-1-yl)-5-methoxy-1-methyl-1H-indol-2-yl)-4H-1,2,4-triazol-3-yl)-2-methoxy-N,N-dimethylethan-1-amine was performed by preparative chiral SFC chromatography on a Sepiatec 100 Preparative SFC instrument (column: ChiralPak IB-N 250×30 mm, 5 µm; mobile phase: 20% MeOH+0.1% of 25% aq. NH$_4$OH in CO$_2$, flow rate: 80 m/min; column temperature: 40° C., back pressure 130 bar) to give the enantiomerically pure title compounds.

Example 124a: (R)-1-(5-(6-chloro-7-fluoro-3-(1H-imidazol-1-yl)-5-methoxy-1-methyl-1H-indol-2-yl)-4H-1,2,4-triazol-3-yl)-2-methoxy-N,N-dimethylethan-1-amine, Peak 1 (1.80 g), UPLC/MS (Method A): Rt=0.54 min, 448.2 [M+H]+. Analytical chiral SFC: R$_t$=1.17 min; e.e. 99.5%

(Waters UPC² analytical SFC instrument; column: Chiral-Pak IB-N, 100×4.6 mm, 3 μm; A for CO₂ and B for MeOH (+0.05% NH₄OH), gradient B 20%, flow rate: 3.0 mL/min, column temperature: 40° C., back pressure: 1800 psi). ¹H NMR (400 MHz, DMSO-d6) δ 14.30 (s, 1H), 7.77 (s, 1H), 7.31 (s, 1H), 7.05 (s, 1H), 6.71 (s, 1H), 4.10 (s, 3H), 3.99-3.89 (m, 1H), 3.85 (s, 3H), 3.81-3.67 (m, 2H), 3.22 (s, 3H), 2.14 (s, 6H). Absolute stereochemistry (R-configuration) was assigned by x-ray crystallography.

Example 124b: (S)-1-(5-(6-chloro-7-fluoro-3-(1H-imidazol-1-yl)-5-methoxy-1-methyl-1H-indol-2-yl)-4H-1,2,4-triazol-3-yl)-2-methoxy-N,N-dimethylethan-1-amine, Peak 2 (1.81 g), UPLC/MS (Method A): Rt=0.54 min, 448.2 [M+H]+. Analytical chiral SFC: R$_t$=1.1.84 min; e.e. 99.5% (Waters UPC² analytical SFC instrument; column: Chiral-Pak IB-N, 100×4.6 mm, 3 μm; A for CO₂ and B for MeOH (+0.05% NH₄OH), gradient B 20%, flow rate: 3.0 mL/min, column temperature: 40° C., back pressure: 1800 psi). 1H NMR (400 MHz, DMSO-d6) δ 14.30 (s, 1H), 7.77 (s, 1H), 7.31 (s, 1H), 7.05 (s, 1H), 6.71 (s, 1H), 4.10 (s, 3H), 3.92 (t, J=7.5, 6.0 Hz, 1H), 3.85 (s, 3H), 3.82-3.67 (m, 2H), 3.22 (s, 3H), 2.14 (s, 6H).

Examples 125, 125a and 125b: 1-(5-(6-chloro-7-fluoro-3-(1H-imidazol-1-yl)-5-methoxy-1-methyl-1H-indol-2-yl)-4H-1,2,4-triazol-3-yl)-2-methoxy-N-methylethan-1-amine (Example 125), (R)-1-(5-(6-chloro-7-fluoro-3-(1H-imidazol-1-yl)-5-methoxy-1-methyl-1H-indol-2-yl)-4H-1,2,4-triazol-3-yl)-2-methoxy-N-methylethan-1-amine (Example 125a) and (S)-1-(5-(6-chloro-7-fluoro-3-(1H-imidazol-1-yl)-5-methoxy-1-methyl-1H-indol-2-yl)-4H-1,2,4-triazol-3-yl)-2-methoxy-N-methylethan-1-amine (Example 125b)

Examples 125, 125a, and 125b were prepared according to Scheme 15 below.

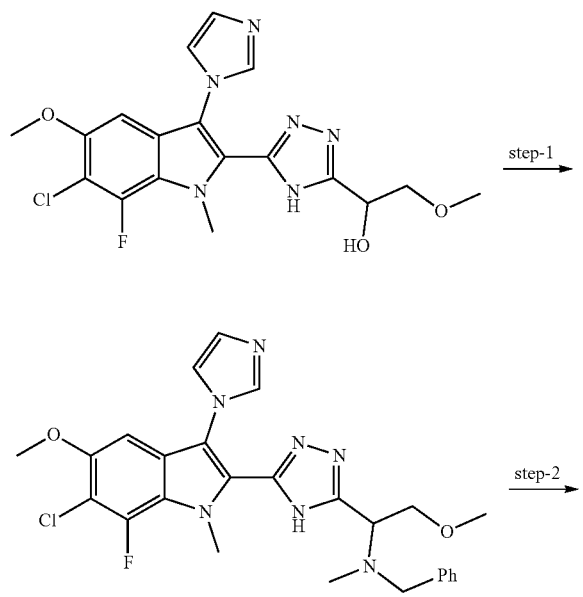

Scheme 15

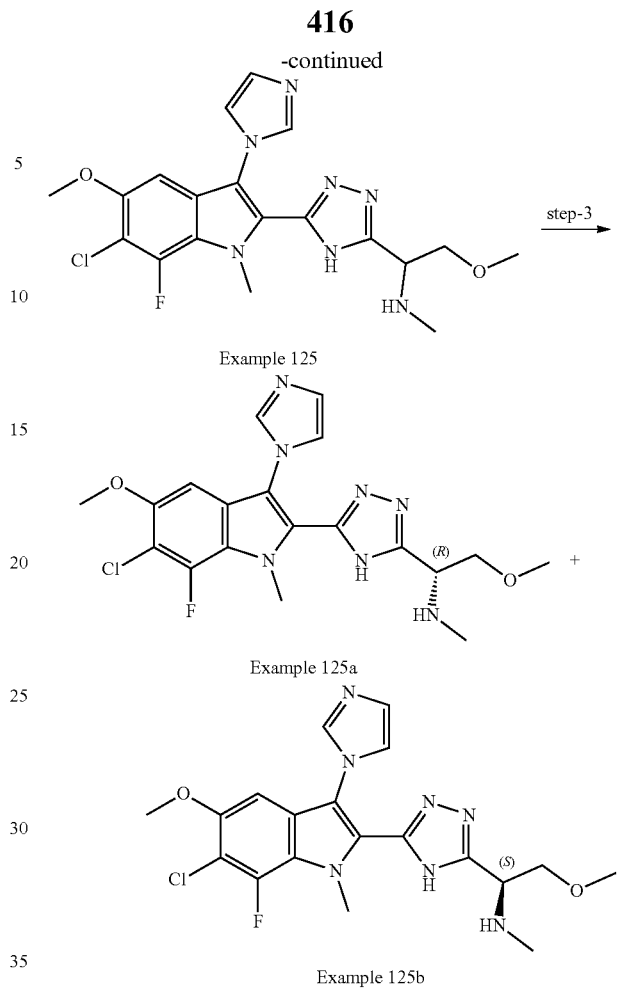

Step 1: N-benzyl-1-(5-(6-chloro-7-fluoro-3-(1H-imidazol-1-yl)-5-methoxy-1-methyl-1H-indol-2-yl)-4H-1,2,4-triazol-3-yl)-2-methoxy-N-methylethan-1-amine 1-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-ol (see, e.g., Example 83a) (3 g, 7.13 mmol) was suspended in CH₂Cl₂ (285 mL) and N-benzylmethylamine was added. The suspension was cooled to 0° C. and DAST (2.83 mL, 21.4 mmol) was added. The ice-bath was removed and the yellow solution was stirred at rt for 5 min. The reaction mixture was washed with sat. aq. bicarbonate and the organic phase was dried over Na₂SO₄, filtered and the solvent was removed in vacuo. The crude product was purified by flash chromatography on silica (Biotage) using DCM and DCM/MeOH (4:1)(from 0-70% DCM/MeOH 4:1) to give the title compound (3.71 g). UPLC-MS (Method A): Rt=0.99 min, 524.4 [M+H]+.

Step 2: 1-(5-(6-chloro-7-fluoro-3-(1H-imidazol-1-yl)-5-methoxy-1-methyl-1H-indol-2-yl)-4H-1,2,4-triazol-3-yl)-2-methoxy-N-methylethan-1-amine (Example 125)

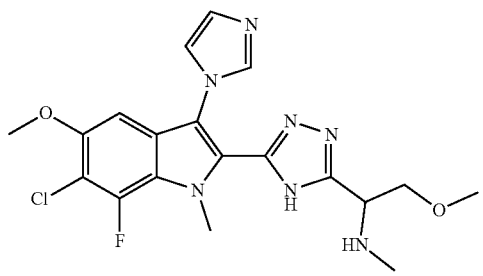

To a cooled solution of N-benzyl-1-(5-(6-chloro-7-fluoro-3-(1H-imidazol-1-yl)-5-methoxy-1-methyl-1H-indol-2-yl)-4H-1,2,4-triazol-3-yl)-2-methoxy-N-methylethan-1-amine (3.6 g, 6.87 mmol) in AcOH (69 mL) was added Pd/C 10% (0.37 g, 0.34 mmol) at 0° C. The flask was evacuated, equipped with a hydrogen balloon and purged with hydrogen gas. The mixture was stirred for 2 h at rt, diluted with EtOAc, filtered through a pad of hyflo and the filtrate was concentrated in vacuo. The crude product was purified by flash-chromatography on silica (Biotage) using DCM and DCM/MeOH (7:3) (from 0-100% DCM/MeOH 7:3) to give the title compound (2.63 g). UPLC-MS (Method A): Rt=0.51 min, 434.1 [M+H]+. $^1$H NMR (400 MHz, DMSO-d6) δ 7.78 (t, J=1.1 Hz, 1H), 7.32 (t, J=1.3 Hz, 1H), 7.05 (t, J=1.1 Hz, 1H), 6.71 (d, J=1.1 Hz, 1H), 4.09 (d, J=1.9 Hz, 3H), 3.94 (t, J=6.0 Hz, 1H), 3.85 (s, 3H), 3.59 (dd, J=6.0, 2.1 Hz, 2H), 3.23 (s, 3H), 2.23 (s, 3H).

Step 3: Examples 125a and 125b

Separation of 13.75 g racemic 1-(5-(6-chloro-7-fluoro-3-(1H-imidazol-1-yl)-5-methoxy-1-methyl-1H-indol-2-yl)-4H-1,2,4-triazol-3-yl)-2-methoxy-N-methylethan-1-amine was performed by preparative chiral SFC chromatography on a MG II Preparative SFC instrument (column: ChiralCel OD 250×30 mm, 10 μm, mobile phase A for CO$_2$ and B for EtOH (+0.1% aq. NH$_4$OH), gradient B 30%, flow rate: 70 mL/min, column temperature: 38° C., back pressure: 100 bar, wavelength: 260 nm) to give the enantiomerically pure title compounds.

Example 125a: (R)-1-(5-(6-chloro-7-fluoro-3-(1H-imidazol-1-yl)-5-methoxy-1-methyl-1H-indol-2-yl)-4H-1,2,4-triazol-3-yl)-2-methoxy-N-methylethan-1-amine Peak 1 (6.62 g), UPLC/MS (Method A): Rt=0.49 min, 434.3 [M+H]+. Analytical chiral SFC: R=2.1 min; e.e. 100% (Waters UPC$^2$ analytical SFC instrument; column: ChiralCel OD, 150×4.6 mm, 3 μm; A for CO$_2$ and B for MeOH (+0.05% diethylamine), gradient B 30%, flow rate: 2.5 mL/min, column temperature: 35° C., back pressure: 100 bar, wavelength: 220 nm). $^1$H NMR (400 MHz, DMSO-d6) δ 7.78 (t, J=1.1 Hz, 1H), 7.32 (t, J=1.3 Hz, 1H), 7.05 (t, J=1.1 Hz, 1H), 6.71 (d, J=1.1 Hz, 1H), 4.09 (d, J=1.9 Hz, 3H), 3.94 (t, J=6.0 Hz, 1H), 3.85 (s, 3H), 3.59 (dd, J=6.0, 2.1 Hz, 2H), 3.23 (s, 3H), 2.23 (s, 3H). Absolute stereochemistry (R-configuration) was assigned by x-ray crystallography.

Example 125b: (S)-1-(5-(6-chloro-7-fluoro-3-(1H-imidazol-1-yl)-5-methoxy-1-methyl-1H-indol-2-yl)-4H-1,2,4-triazol-3-yl)-2-methoxy-N-methylethan-1-amine Peak 2 (5.94 g), UPLC/MS (Method A): Rt=0.46 min, 434.4 [M+H]+. Analytical chiral SFC: R=2.9 min; e.e. 99.2% (Waters UPC$^2$ analytical SFC instrument; column: ChiralCel OD, 150×4.6 mm, 3 μm; A for CO$_2$ and B for MeOH (+0.05% diethylamine), gradient B 30%, flow rate: 2.5 mL/min, column temperature: 35° C., back pressure: 100 bar, wavelength: 220 nm). 1H NMR (400 MHz, DMSO-d6) δ 7.78 (t, J=1.1 Hz, 1H), 7.32 (t, J=1.3 Hz, 1H), 7.05 (t, J=1.1 Hz, 1H), 6.71 (d, J=1.1 Hz, 1H), 4.08 (d, J=1.9 Hz, 3H), 3.94 (t, J=6.0 Hz, 1H), 3.85 (s, 3H), 3.60 (dd, 2H), 3.23 (s, 3H), 2.23 (s, 3H).

| Ex No. | Structure and Name | $^1$H NMR (400 MHz, DMSO-d6) | LC-MS (min; m/z); Method |
|---|---|---|---|
| 126 | 4-(1-(5-(6-chloro-7-fluoro-3-(1H-imidazol-1-yl)-5-methoxy-1-methyl-1H-indol-2-yl)-4H-1,2,4-triazol-3-yl)-2-methoxyethyl)morpholine | δ 14.28 (s, 1H), 7.78 (s, 1H), 7.31 (s, 1H), 7.05 (s, 1H), 6.71 (s, 1H), 4.11 (s, 3H), 3.97 (t, J = 6.6 Hz, 1H), 3.85 (s, 3H), 3.82-3.69 (m, 2H), 3.57-3.51 (m, 4H), 3.23 (s, 3H), 2.47-2.35 (m, 4H). | Rt = 0.68; 490.4 [M + H]+; Method A |

| Ex No. | Structure and Name | ¹H NMR (400 MHz, DMSO-d6) | LC-MS (min; m/z); Method |
|---|---|---|---|
| 127 | 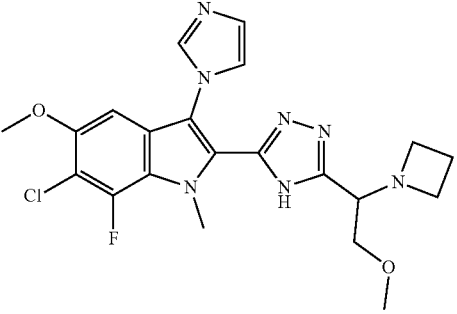 [SMILES: COCC(c1nnc(-c2c(-n3ccnc3)c3cc(OC)c(Cl)c(F)c3n2C)[nH]1)N1CCC1]<br>2-(5-(1-(azetidin-1-yl)-2-methoxyethyl)-4H-1,2,4-triazol-3-yl)-6-chloro-7-fluoro-3-(1H-imidazol-1-yl)-5-methoxy-1-methyl-1H-indole | δ 7.77 (s, 1H), 7.31 (s, 1H), 7.05 (s, 1H), 6.71 (s, 1H), 4.09 (d, J = 1.8 Hz, 3H), 3.85 (s, 3H), 3.74 (t, J = 6.0 Hz, 1H), 3.54-3.49 (m, 2H), 3.20-3.15 (m, 5H), 3.13-3.06 (m, 2H), 1.95 (td, J = 14.3, 13.7, 6.7 Hz, 2H). | Rt = 0.51; 460.4 [M + H]⁺; Method A |
| 128 | 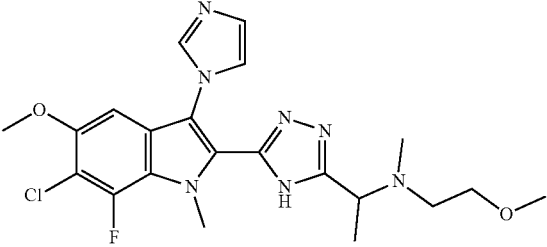<br>1-(5-(6-chloro-7-fluoro-3-(1H-imidazol-1-yl)-5-methoxy-1-methyl-1H-indol-2-yl)-4H-1,2,4-triazol-3-yl)-N-(2-methoxyethyl)-N-methylethan-1-amine | δ 14.19 (s, 1H), 7.77 (s, 1H), 7.31 (s, 1H), 7.04 (s, 1H), 6.71 (s, 1H), 4.10 (s, 3H), 4.07-3.97 (m, 1H), 3.85 (s, 3H), 3.38 (t, J = 6.0 Hz, 2H), 3.21 (s, 3H), 2.58-2.39 (m, 2H), 2.15 (s, 3H), 1.35 (d, J = 6.9 Hz, 3H). | Rt = 0.60; 462.3 [M + H]⁺; Method A |
| 129 | 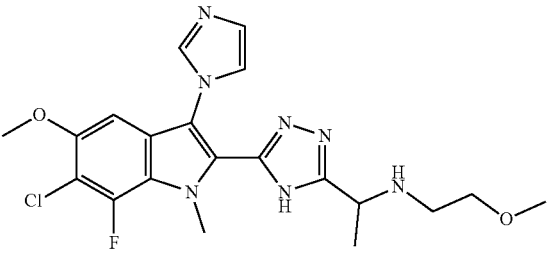<br>1-(5-(6-chloro-7-fluoro-3-(1H-imidazol-1-yl)-5-methoxy-1-methyl-1H-indol-2-yl)-4H-1,2,4-triazol-3-yl)-N-(2-methoxyethyl)ethan-1-amine | δ 7.78 (s, 1H), 7.31 (s, 1H), 7.04 (s, 1H), 6.71 (s, 1H), 4.08 (s, 3H), 3.96 (s, 1H), 3.85 (s, 3H), 3.35 (s, 2H), 3.20 (s, 3H), 2.61-2.49 (m, 2H), 1.35 (d, J = 6.7 Hz, 3H). | Rt = 0.59; 448.4 [M + H]⁺; Method A |

| Ex No. | Structure and Name | $^1$H NMR (400 MHz, DMSO-d6) | LC-MS (min; m/z); Method |
|---|---|---|---|
| 130 | 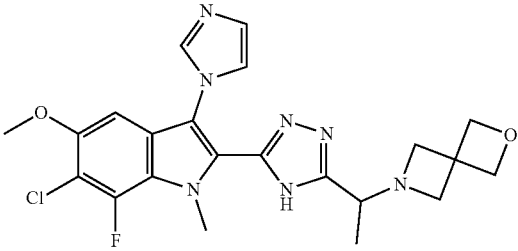 [SMILES: COc1cc2c(-n3ccnc3)c(-c3nnc(C(C)N4CC5(COC5)C4)[nH]3)n(C)c2c(F)c1Cl]<br>6-(1-(5-(6-chloro-7-fluoro-3-(1H-imidazol-1-yl)-5-methoxy-1-methyl-1H-indol-2-yl)-4H-1,2,4-triazol-3-yl)ethyl)-2-oxa-6-azaspiro[3.3]heptane | δ 7.77 (s, 1H), 7.31 (s, 1H), 7.06 (s, 1H), 6.70 (s, 1H), 4.57 (s, 4H), 4.08 (s, 3H), 3.85 (s, 3H), 3.57 (s, 1H), 3.38-3.21 (m, 4H), 1.18 (s, 3H). | Rt = 0.57; 472.4 [M + H]$^+$; Method A |

Biochemical Assays and Data

The activity of a compound according to the present disclosure can be assessed by the following method.

Example 131: Quantification of cGAS Protein Inhibition

A reagent buffer was prepared in filtered and autoclaved water according to the following:
- 50 mM Tris-buffer pH 7.5 (1 M Tris-buffer pH 7.5, Invitrogen, Cat. No. 15567-027);
- 50 mM NaCl (5 M NaCl, Sodium Chloride Solution, Sigma, 59222C-);
- 5 mM MgCl$_2$ (1 M MgCl$_2$, Sigma, M1028);
- 0.1 mM ZnCl$_2$ (Zinc Chloride [7646-85-7], powder, Cell Culture Tested, Sigma, Z-0152); and
- 0.001% Tween 20 (TWEEN 20, Sigma Aldrich, P1379-).

A buffer for the cGAS enzyme was prepared in filtered and autoclaved water according to the following:
- 50 mM Tris-buffer pH 7.5;
- 5 mM MgCl$_2$; and
- 0.001% Tween 20.

Compounds were dispensed to a 386 well plate. The human truncated cGAS enzyme (4.2 mg/mL 147-522 human cGAS, MW 43,909 g/mol) was stored in 50 mM Tris, 500 mM NaCl, 5% (v/v) glycerol at pH 8 and diluted in the cGAS buffer enzyme shortly before use. The enzyme solution was transferred into the reagent buffer to give a final concentration of 30 nM. The reaction was started by mixing the enzyme with ISD (a 45 bp double stranded DNA, MW 27,670 g/mol, 5 mM), GTP and ATP to a final concentration of 5 µM, 0.5 mM and 0.5 mM respectively in a final volume of 10 µl. The reaction plates were then centrifuged at 1000 rpm for 1 minute and incubated at room temperature for 1 h. After 1 h of incubation, [$^5$Ns]-2'3'-cGAMP to a final concentration of 200 nM and 30 µL of 100% acetonitrile/0.175% of TFA were added to the reaction mixture. The plates were centrifuged at 1000 rpm for 1 minute before being sealed for 3 seconds at 170° C. using a ThermoScientific sealer (ALPS™ 50V) and an aluminum sealing cover (Pierce Seal, 4titude, Product Code: 4TI-0531).

The concentration of cGAMP was measured on a LC-MS/MS system consisting of a THERMO Dionex Ultimate LC system with a high pressure pump, an autosampler, a column heating compartment (Reinach, Switzerland) and a SCIEX Triple Quad 5500 (Framingham, MA, USA) mass spectrometer for detection. The sample plates were centrifuged for 10 minutes at 2000 rpm. Up to three plates were placed in the autosampler for injection. An aliquot of 10 µL of each sample was injected on an XBridge BEH Amide 3.5 µm, 2.1×50 mm column (P/N 186004859) with an XBridge BEH Amide 5 µm 2.1×5 mm VanGuard Cartridge (P/N 186007760) pre-column (both WATERS, MA, USA) held at 40° C. An isocratic flow of 1.0 mL/min solvent (60% ACN, 8 mM ammonium acetate, 5 mM ammonium hydroxide, 0.04% acetic acid) was applied and sprayed into the ion source of the mass spectrometers. The MS parameters were optimized based on the properties of the compounds to be detected and run in positive multi-reaction mode (MRM) based on the mass transitions. LC and MS parameters were also optimized to allow for a sample-to-sample measuring time of approximately 75 sec and a run time of 8 hours per 384-well plate. All data were analyzed with Excel; and the dose response curves were generated using the auto fitting function of XLfit. The IC$_{50}$ was determined by plotting the cGAMP concentration ratio (cGAMP divided by the internal standard [$^{15}$Ns]-2'3'-cGAMP) versus the concentration of compound.

The activities of the representative compounds of the present disclosure are reported in Table 1 above. Unless otherwise specified, the IC$_{50}$ is reported for the potential mixture of the co-existing tautomers and/or racemates without regard to the specific tautomeric form. The compounds of the present invention provide IC$_{50}$ ranging from nanomolar to sub-mM against cGAS.

What is claimed is:
1. A compound selected from:
   6-chloro-7-fluoro-5-methoxy-1-methyl-3-(1H-pyrazol-4-yl)-2-(5-(trifluoromethyl)-4H-1,2,4-triazol-3-yl)-1H-indole;
   6-chloro-7-fluoro-5-methoxy-1-methyl-3-(1H-pyrazol-4-yl)-2-(3-(trifluoromethyl)-1H-1,2,4-triazol-5-yl)-1H-indole;
   6-chloro-7-fluoro-5-methoxy-1-methyl-3-(1H-pyrazol-4-yl)-2-(5-(trifluoromethyl)-1H-1,2,4-triazol-3-yl)-1H-indole;

5-(6-chloro-7-fluoro-5-methoxy-1-methyl-3-(1H-pyrazol-4-yl)-1H-indol-2-yl)-N,N-dimethyl-4H-1,2,4-triazole-3-carboxamide;
5-(6-chloro-7-fluoro-5-methoxy-1-methyl-3-(1H-pyrazol-4-yl)-1H-indol-2-yl)-N,N-dimethyl-1H-1,2,4-triazole-3-carboxamide;
3-(6-chloro-7-fluoro-5-methoxy-1-methyl-3-(1H-pyrazol-4-yl)-1H-indol-2-yl)-N,N-dimethyl-1H-1,2,4-triazole-5-carboxamide;
6-chloro-7-fluoro-2-(5-fluoro-4H-1,2,4-triazol-3-yl)-5-methoxy-3-(1H-pyrazol-4-yl)-1H-indole;
6-chloro-7-fluoro-2-(3-fluoro-1H-1,2,4-triazol-5-yl)-5-methoxy-3-(1H-pyrazol-4-yl)-1H-indole;
6-chloro-7-fluoro-2-(5-fluoro-1H-1,2,4-triazol-3-yl)-5-methoxy-3-(1H-pyrazol-4-yl)-1H-indole;
6-chloro-7-fluoro-5-methoxy-3-(1H-pyrazol-4-yl)-2-(5-(trifluoromethyl)-4H-1,2,4-triazol-3-yl)-1H-indole;
6-chloro-7-fluoro-5-methoxy-3-(1H-pyrazol-4-yl)-2-(3-(trifluoromethyl)-1H-1,2,4-triazol-5-yl)-1H-indole;
6-chloro-7-fluoro-5-methoxy-3-(1H-pyrazol-4-yl)-2-(5-(trifluoromethyl)-1H-1,2,4-triazol-3-yl)-1H-indole;
2-(5-bromo-4H-1,2,4-triazol-3-yl)-6,7-dichloro-3-(1H-pyrazol-4-yl)-1H-indole;
2-(3-bromo-1H-1,2,4-triazol-5-yl)-6,7-dichloro-3-(1H-pyrazol-4-yl)-1H-indole;
2-(5-bromo-1H-1,2,4-triazol-3-yl)-6,7-dichloro-3-(1H-pyrazol-4-yl)-1H-indole;
6-chloro-7-fluoro-3-(1H-pyrazol-4-yl)-2-(5-(trifluoromethyl)-4H-1,2,4-triazol-3-yl)-1H-indole-5-carbonitrile;
6-chloro-7-fluoro-3-(1H-pyrazol-4-yl)-2-(3-(trifluoromethyl)-1H-1,2,4-triazol-5-yl)-1H-indole-5-carbonitrile;
6-chloro-7-fluoro-3-(1H-pyrazol-4-yl)-2-(5-(trifluoromethyl)-1H-1,2,4-triazol-3-yl)-1H-indole-5-carbonitrile;
1-(5-(6,7-dichloro-3-(1H-pyrazol-4-yl)-1H-indol-2-yl)-4H-1,2,4-triazol-3-yl)-2-methoxyethan-1-one;
1-(5-(6,7-dichloro-3-(1H-pyrazol-4-yl)-1H-indol-2-yl)-1H-1,2,4-triazol-3-yl)-2-methoxyethan-1-one;
1-(3-(6,7-dichloro-3-(1H-pyrazol-4-yl)-1H-indol-2-yl)-1H-1,2,4-triazol-5-yl)-2-methoxyethan-1-one;
6-chloro-7-fluoro-1-methyl-3-(1H-pyrazol-4-yl)-2-(5-(trifluoromethyl)-4H-1,2,4-triazol-3-yl)-1H-indole-5-carbonitrile;
6-chloro-7-fluoro-1-methyl-3-(1H-pyrazol-4-yl)-2-(3-(trifluoromethyl)-1H-1,2,4-triazol-5-yl)-1H-indole-5-carbonitrile;
6-chloro-7-fluoro-1-methyl-3-(1H-pyrazol-4-yl)-2-(5-(trifluoromethyl)-1H-1,2,4-triazol-3-yl)-1H-indole-5-carbonitrile;
6,7-dichloro-2-(5-(1,1-difluoro-2-methoxyethyl)-4H-1,2,4-triazol-3-yl)-3-(1H-pyrazol-4-yl)-1H-indole;
6,7-dichloro-2-(3-(1,1-difluoro-2-methoxyethyl)-1H-1,2,4-triazol-5-yl)-3-(1H-pyrazol-4-yl)-1H-indole;
6,7-dichloro-2-(5-(1,1-difluoro-2-methoxyethyl)-1H-1,2,4-triazol-3-yl)-3-(1H-pyrazol-4-yl)-1H-indole;
6,7-dichloro-2-(5-(1-fluoro-2-methoxyethyl)-4H-1,2,4-triazol-3-yl)-3-(1H-pyrazol-4-yl)-1H-indole;
6,7-dichloro-2-(3-(1-fluoro-2-methoxyethyl)-1H-1,2,4-triazol-5-yl)-3-(1H-pyrazol-4-yl)-1H-indole;
6,7-dichloro-2-(5-(1-fluoro-2-methoxyethyl)-1H-1,2,4-triazol-3-yl)-3-(1H-pyrazol-4-yl)-1H-indole;
6,7-dichloro-3-(1H-pyrazol-4-yl)-2-(5-(trifluoromethyl)-4H-1,2,4-triazol-3-yl)-1H-indole;
6,7-dichloro-3-(1H-pyrazol-4-yl)-2-(3-(trifluoromethyl)-1H-1,2,4-triazol-5-yl)-1H-indole;
6,7-dichloro-3-(1H-pyrazol-4-yl)-2-(5-(trifluoromethyl)-1H-1,2,4-triazol-3-yl)-1H-indole;
6,7-dichloro-1-methyl-3-(1H-pyrazol-4-yl)-2-(5-(trifluoromethyl)-4H-1,2,4-triazol-3-yl)-1H-indole;
6,7-dichloro-1-methyl-3-(1H-pyrazol-4-yl)-2-(3-(trifluoromethyl)-1H-1,2,4-triazol-5-yl)-1H-indole;
6,7-dichloro-1-methyl-3-(1H-pyrazol-4-yl)-2-(5-(trifluoromethyl)-1H-1,2,4-triazol-3-yl)-1H-indole;
6,7-dichloro-3-(1H-pyrazol-4-yl)-2-(5-(2,2,2-trifluoroethyl)-4H-1,2,4-triazol-3-yl)-1H-indole;
6,7-dichloro-3-(1H-pyrazol-4-yl)-2-(3-(2,2,2-trifluoroethyl)-1H-1,2,4-triazol-5-yl)-1H-indole;
6,7-dichloro-3-(1H-pyrazol-4-yl)-2-(5-(2,2,2-trifluoroethyl)-1H-1,2,4-triazol-3-yl)-1H-indole;
6,7-difluoro-3-(1H-pyrazol-4-yl)-2-(5-(trifluoromethyl)-4H-1,2,4-triazol-3-yl)-1H-indole;
6,7-difluoro-3-(1H-pyrazol-4-yl)-2-(3-(trifluoromethyl)-1H-1,2,4-triazol-5-yl)-1H-indole;
6,7-difluoro-3-(1H-pyrazol-4-yl)-2-(5-(trifluoromethyl)-1H-1,2,4-triazol-3-yl)-1H-indole;
2-(5-(6,7-dichloro-3-(1H-pyrazol-4-yl)-1H-indol-2-yl)-4H-1,2,4-triazol-3-yl) ethan-1-ol;
2-(5-(6,7-dichloro-3-(1H-pyrazol-4-yl)-1H-indol-2-yl)-1H-1,2,4-triazol-3-yl) ethan-1-ol;
2-(3-(6,7-dichloro-3-(1H-pyrazol-4-yl)-1H-indol-2-yl)-1H-1,2,4-triazol-5-yl) ethan-1-ol;
6-chloro-7-fluoro-3-(1H-pyrazol-4-yl)-2-(5-(trifluoromethyl)-4H-1,2,4-triazol-3-yl)-1H-indole;
6-chloro-7-fluoro-3-(1H-pyrazol-4-yl)-2-(3-(trifluoromethyl)-1H-1,2,4-triazol-5-yl)-1H-indole;
6-chloro-7-fluoro-3-(1H-pyrazol-4-yl)-2-(5-(trifluoromethyl)-1H-1,2,4-triazol-3-yl)-1H-indole;
6-chloro-7-methoxy-3-(1H-pyrazol-4-yl)-2-(5-(trifluoromethyl)-4H-1,2,4-triazol-3-yl)-1H-indole;
6-chloro-7-methoxy-3-(1H-pyrazol-4-yl)-2-(3-(trifluoromethyl)-1H-1,2,4-triazol-5-yl)-1H-indole;
6-chloro-7-methoxy-3-(1H-pyrazol-4-yl)-2-(5-(trifluoromethyl)-1H-1,2,4-triazol-3-yl)-1H-indole; 5,6-dichloro-3-(1H-pyrazol-4-yl)-2-(5-(trifluoromethyl)-4H-1,2,4-triazol-3-yl)-1H-indole;
5,6-dichloro-3-(1H-pyrazol-4-yl)-2-(3-(trifluoromethyl)-1H-1,2,4-triazol-5-yl)-1H-indole;
5,6-dichloro-3-(1H-pyrazol-4-yl)-2-(5-(trifluoromethyl)-1H-1,2,4-triazol-3-yl)-1H-indole;
6-chloro-3-(1H-pyrazol-4-yl)-2-(5-(trifluoromethyl)-4H-1,2,4-triazol-3-yl)-1H-indole-7-carbonitrile;
6-chloro-3-(1H-pyrazol-4-yl)-2-(3-(trifluoromethyl)-1H-1,2,4-triazol-5-yl)-1H-indole-7-carbonitrile;
6-chloro-3-(1H-pyrazol-4-yl)-2-(5-(trifluoromethyl)-1H-1,2,4-triazol-3-yl)-1H-indole-7-carbonitrile;
6-chloro-5-methoxy-1-methyl-3-(1H-pyrazol-4-yl)-2-(5-(trifluoromethyl)-4H-1,2,4-triazol-3-yl)-1H-indole;
6-chloro-5-methoxy-1-methyl-3-(1H-pyrazol-4-yl)-2-(3-(trifluoromethyl)-1H-1,2,4-triazol-5-yl)-1H-indole;
6-chloro-5-methoxy-1-methyl-3-(1H-pyrazol-4-yl)-2-(5-(trifluoromethyl)-1H-1,2,4-triazol-3-yl)-1H-indole;
ethyl 5-(6,7-dichloro-3-(1H-pyrazol-4-yl)-1H-indol-2-yl)-4H-1,2,4-triazole-3-carboxylate;
ethyl 5-(6,7-dichloro-3-(1H-pyrazol-4-yl)-1H-indol-2-yl)-1H-1,2,4-triazole-3-carboxylate;
ethyl 3-(6,7-dichloro-3-(1H-pyrazol-4-yl)-1H-indol-2-yl)-1H-1,2,4-triazole-5-carboxylate;
5-(6,7-dichloro-3-(1H-pyrazol-4-yl)-1H-indol-2-yl)-4H-1,2,4-triazole-3-carboxamide;
5-(6,7-dichloro-3-(1H-pyrazol-4-yl)-1H-indol-2-yl)-1H-1,2,4-triazole-3-carboxamide;
3-(6,7-dichloro-3-(1H-pyrazol-4-yl)-1H-indol-2-yl)-1H-1,2,4-triazole-5-carboxamide;

5,6-dichloro-1-methyl-3-(1H-pyrazol-4-yl)-2-(5-(trifluoromethyl)-4H-1,2,4-triazol-3-yl)-1H-indole;
5,6-dichloro-1-methyl-3-(1H-pyrazol-4-yl)-2-(3-(trifluoromethyl)-1H-1,2,4-triazol-5-yl)-1H-indole;
5,6-dichloro-1-methyl-3-(1H-pyrazol-4-yl)-2-(5-(trifluoromethyl)-1H-1,2,4-triazol-3-yl)-1H-indole;
6-chloro-5-methoxy-3-(1H-pyrazol-4-yl)-2-(5-(trifluoromethyl)-4H-1,2,4-triazol-3-yl)-1H-indole;
6-chloro-5-methoxy-3-(1H-pyrazol-4-yl)-2-(3-(trifluoromethyl)-1H-1,2,4-triazol-5-yl)-1H-indole;
6-chloro-5-methoxy-3-(1H-pyrazol-4-yl)-2-(5-(trifluoromethyl)-1H-1,2,4-triazol-3-yl)-1H-indole;
2-(6-chloro-5-methoxy-3-(1H-pyrazol-4-yl)-2-(5-(trifluoromethyl)-4H-1,2,4-triazol-3-yl)-1H-indol-1-yl) ethan-1-ol;
2-(6-chloro-5-methoxy-3-(1H-pyrazol-4-yl)-2-(3-(trifluoromethyl)-1H-1,2,4-triazol-5-yl)-1H-indol-1-yl) ethan-1-ol;
2-(6-chloro-5-methoxy-3-(1H-pyrazol-4-yl)-2-(5-(trifluoromethyl)-1H-1,2,4-triazol-3-yl)-1H-indol-1-yl) ethan-1-ol;
6-chloro-5-methoxy-1-(2-methoxyethyl)-3-(1H-pyrazol-4-yl)-2-(5-(trifluoromethyl)-4H-1,2,4-triazol-3-yl)-1H-indole;
6-chloro-5-methoxy-1-(2-methoxyethyl)-3-(1H-pyrazol-4-yl)-2-(3-(trifluoromethyl)-1H-1,2,4-triazol-5-yl)-1H-indole;
6-chloro-5-methoxy-1-(2-methoxyethyl)-3-(1H-pyrazol-4-yl)-2-(5-(trifluoromethyl)-1H-1,2,4-triazol-3-yl)-1H-indole;
6-chloro-1-methyl-3-(1H-pyrazol-4-yl)-2-(5-(trifluoromethyl)-4H-1,2,4-triazol-3-yl)-1H-indole-7-carbonitrile;
6-chloro-1-methyl-3-(1H-pyrazol-4-yl)-2-(3-(trifluoromethyl)-1H-1,2,4-triazol-5-yl)-1H-indole-7-carbonitrile;
6-chloro-1-methyl-3-(1H-pyrazol-4-yl)-2-(5-(trifluoromethyl)-1H-1,2,4-triazol-3-yl)-1H-indole-7-carbonitrile;
ethyl 5-(6-chloro-5-methoxy-3-(1H-pyrazol-4-yl)-1H-indol-2-yl)-4H-1,2,4-triazole-3-carboxylate;
ethyl 5-(6-chloro-5-methoxy-3-(1H-pyrazol-4-yl)-1H-indol-2-yl)-1H-1,2,4-triazole-3-carboxylate;
ethyl 3-(6-chloro-5-methoxy-3-(1H-pyrazol-4-yl)-1H-indol-2-yl)-1H-1,2,4-triazole-5-carboxylate;
methyl 2-(5-(6,7-dichloro-3-(1H-pyrazol-4-yl)-1H-indol-2-yl)-4H-1,2,4-triazol-3-yl)acetate;
methyl 2-(5-(6,7-dichloro-3-(1H-pyrazol-4-yl)-1H-indol-2-yl)-1H-1,2,4-triazol-3-yl)acetate;
methyl 2-(3-(6,7-dichloro-3-(1H-pyrazol-4-yl)-1H-indol-2-yl)-1H-1,2,4-triazol-5-yl)acetate;
7-chloro-3-(1H-pyrazol-4-yl)-2-(5-(trifluoromethyl)-4H-1,2,4-triazol-3-yl)-1H-indole-5-carboxamide;
7-chloro-3-(1H-pyrazol-4-yl)-2-(3-(trifluoromethyl)-1H-1,2,4-triazol-5-yl)-1H-indole-5-carboxamide;
7-chloro-3-(1H-pyrazol-4-yl)-2-(5-(trifluoromethyl)-1H-1,2,4-triazol-3-yl)-1H-indole-5-carboxamide;
5-(6-chloro-5-methoxy-3-(1H-pyrazol-4-yl)-1H-indol-2-yl)-4H-1,2,4-triazole-3-carboxamide;
5-(6-chloro-5-methoxy-3-(1H-pyrazol-4-yl)-1H-indol-2-yl)-1H-1,2,4-triazole-3-carboxamide;
3-(6-chloro-5-methoxy-3-(1H-pyrazol-4-yl)-1H-indol-2-yl)-1H-1,2,4-triazole-5-carboxamide;
4,5-dichloro-1-(1H-pyrazol-4-yl)-2-(5-(trifluoromethyl)-4H-1,2,4-triazol-3-yl)-1H-indole;
4,5-dichloro-1-(1H-pyrazol-4-yl)-2-(3-(trifluoromethyl)-1H-1,2,4-triazol-5-yl)-1H-indole;
4,5-dichloro-1-(1H-pyrazol-4-yl)-2-(5-(trifluoromethyl)-1H-1,2,4-triazol-3-yl)-1H-indole;
6-chloro-3-(1H-pyrazol-4-yl)-2-(5-(trifluoromethyl)-4H-1,2,4-triazol-3-yl)-1H-indol-5-ol;
6-chloro-3-(1H-pyrazol-4-yl)-2-(3-(trifluoromethyl)-1H-1,2,4-triazol-5-yl)-1H-indol-5-ol;
6-chloro-3-(1H-pyrazol-4-yl)-2-(5-(trifluoromethyl)-1H-1,2,4-triazol-3-yl)-1H-indol-5-ol;
6-chloro-3-(1H-pyrazol-4-yl)-2-(5-(trifluoromethyl)-4H-1,2,4-triazol-3-yl)-1H-indol-7-ol;
6-chloro-3-(1H-pyrazol-4-yl)-2-(3-(trifluoromethyl)-1H-1,2,4-triazol-5-yl)-1H-indol-7-ol;
6-chloro-3-(1H-pyrazol-4-yl)-2-(5-(trifluoromethyl)-1H-1,2,4-triazol-3-yl)-1H-indol-7-ol;
5-(6,7-dichloro-3-(1H-pyrazol-4-yl)-1H-indol-2-yl)-4H-1,2,4-triazole-3-carbonitrile;
5-(6,7-dichloro-3-(1H-pyrazol-4-yl)-1H-indol-2-yl)-1H-1,2,4-triazole-3-carbonitrile;
3-(6,7-dichloro-3-(1H-pyrazol-4-yl)-1H-indol-2-yl)-1H-1,2,4-triazole-5-carbonitrile;
(5-(6,7-dichloro-3-(1H-pyrazol-4-yl)-1H-indol-2-yl)-4H-1,2,4-triazol-3-yl)methanol;
(5-(6,7-dichloro-3-(1H-pyrazol-4-yl)-1H-indol-2-yl)-1H-1,2,4-triazol-3-yl)methanol;
(3-(6,7-dichloro-3-(1H-pyrazol-4-yl)-1H-indol-2-yl)-1H-1,2,4-triazol-5-yl)methanol;
2-(3-(6,7-dichloro-3-(1H-pyrazol-4-yl)-1H-indol-2-yl)-1H-1,2,4-triazol-1-yl) ethan-1-ol;
6,7-dichloro-3-(1H-pyrazol-4-yl)-2-(4H-1,2,4-triazol-3-yl)-1H-indole;
6,7-dichloro-3-(1H-pyrazol-4-yl)-2-(1H-1,2,4-triazol-5-yl)-1H-indole;
6,7-dichloro-3-(1H-pyrazol-4-yl)-2-(1H-1,2,4-triazol-3-yl)-1H-indole;
5-(6-chloro-7-fluoro-3-(1H-imidazol-1-yl)-5-methoxy-1-methyl-1H-indol-2-yl)-N,N-dimethyl-4H-1,2,4-triazole-3-carboxamide;
5-(6-chloro-7-fluoro-3-(1H-imidazol-1-yl)-5-methoxy-1-methyl-1H-indol-2-yl)-N,N-dimethyl-1H-1,2,4-triazole-3-carboxamide;
3-(6-chloro-7-fluoro-3-(1H-imidazol-1-yl)-5-methoxy-1-methyl-1H-indol-2-yl)-N,N-dimethyl-1H-1,2,4-triazole-5-carboxamide;
5-(6-chloro-7-fluoro-3-(1H-imidazol-1-yl)-5-methoxy-1-methyl-1H-indol-2-yl)-N-(2-methoxyethyl)-N-methyl-4H-1,2,4-triazole-3-carboxamide;
5-(6-chloro-7-fluoro-3-(1H-imidazol-1-yl)-5-methoxy-1-methyl-1H-indol-2-yl)-N-(2-methoxyethyl)-N-methyl-1H-1,2,4-triazole-3-carboxamide;
3-(6-chloro-7-fluoro-3-(1H-imidazol-1-yl)-5-methoxy-1-methyl-1H-indol-2-yl)-N-(2-methoxyethyl)-N-methyl-1H-1,2,4-triazole-5-carboxamide;
5-(6-chloro-7-fluoro-3-(1H-imidazol-1-yl)-5-methoxy-1-methyl-1H-indol-2-yl)-N-(2-hydroxyethyl)-N-methyl-4H-1,2,4-triazole-3-carboxamide;
5-(6-chloro-7-fluoro-3-(1H-imidazol-1-yl)-5-methoxy-1-methyl-1H-indol-2-yl)-N-(2-hydroxyethyl)-N-methyl-1H-1,2,4-triazole-3-carboxamide;
3-(6-chloro-7-fluoro-3-(1H-imidazol-1-yl)-5-methoxy-1-methyl-1H-indol-2-yl)-N-(2-hydroxyethyl)-N-methyl-1H-1,2,4-triazole-5-carboxamide;
(5-(6-chloro-7-fluoro-3-(1H-imidazol-1-yl)-5-methoxy-1-methyl-1H-indol-2-yl)-4H-1,2,4-triazol-3-yl) (morpholino) methanone;
(5-(6-chloro-7-fluoro-3-(1H-imidazol-1-yl)-5-methoxy-1-methyl-1H-indol-2-yl)-1H-1,2,4-triazol-3-yl) (morpholino) methanone;

(3-(6-chloro-7-fluoro-3-(1H-imidazol-1-yl)-5-methoxy-1-methyl-1H-indol-2-yl)-1H-1,2,4-triazol-5-yl) (morpholino) methanone;
(5-(6-chloro-7-fluoro-3-(1H-imidazol-1-yl)-5-methoxy-1-methyl-1H-indol-2-yl)-4H-1,2,4-triazol-3-yl) (3-hydroxypyrrolidin-1-yl) methanone;
(5-(6-chloro-7-fluoro-3-(1H-imidazol-1-yl)-5-methoxy-1-methyl-1H-indol-2-yl)-1H-1,2,4-triazol-3-yl) (3-hydroxypyrrolidin-1-yl) methanone;
(3-(6-chloro-7-fluoro-3-(1H-imidazol-1-yl)-5-methoxy-1-methyl-1H-indol-2-yl)-1H-1,2,4-triazol-5-yl) (3-hydroxypyrrolidin-1-yl) methanone;
(5-(6-chloro-7-fluoro-3-(1H-imidazol-1-yl)-5-methoxy-1-methyl-1H-indol-2-yl)-4H-1,2,4-triazol-3-yl) (4-hydroxypiperidin-1-yl) methanone;
(5-(6-chloro-7-fluoro-3-(1H-imidazol-1-yl)-5-methoxy-1-methyl-1H-indol-2-yl)-1H-1,2,4-triazol-3-yl) (4-hydroxypiperidin-1-yl) methanone;
(3-(6-chloro-7-fluoro-3-(1H-imidazol-1-yl)-5-methoxy-1-methyl-1H-indol-2-yl)-1H-1,2,4-triazol-5-yl) (4-hydroxypiperidin-1-yl) methanone;
(5-(6-chloro-7-fluoro-3-(1H-imidazol-1-yl)-5-methoxy-1-methyl-1H-indol-2-yl)-4H-1,2,4-triazol-3-yl) (3-hydroxypiperidin-1-yl) methanone;
(5-(6-chloro-7-fluoro-3-(1H-imidazol-1-yl)-5-methoxy-1-methyl-1H-indol-2-yl)-1H-1,2,4-triazol-3-yl) (3-hydroxypiperidin-1-yl) methanone;
(3-(6-chloro-7-fluoro-3-(1H-imidazol-1-yl)-5-methoxy-1-methyl-1H-indol-2-yl)-1H-1,2,4-triazol-5-yl) (3-hydroxypiperidin-1-yl) methanone;
(5-(6-chloro-7-fluoro-3-(1H-imidazol-1-yl)-5-methoxy-1-methyl-1H-indol-2-yl)-4H-1,2,4-triazol-3-yl) (4-methylpiperazin-1-yl) methanone;
(5-(6-chloro-7-fluoro-3-(1H-imidazol-1-yl)-5-methoxy-1-methyl-1H-indol-2-yl)-1H-1,2,4-triazol-3-yl) (4-methylpiperazin-1-yl) methanone;
(3-(6-chloro-7-fluoro-3-(1H-imidazol-1-yl)-5-methoxy-1-methyl-1H-indol-2-yl)-1H-1,2,4-triazol-5-yl) (4-methylpiperazin-1-yl) methanone;
6-chloro-7-fluoro-3-(1H-imidazol-1-yl)-5-methoxy-1-methyl-2-(5-(trifluoromethyl)-4H-1,2,4-triazol-3-yl)-1H-indole;
6-chloro-7-fluoro-3-(1H-imidazol-1-yl)-5-methoxy-1-methyl-2-(3-(trifluoromethyl)-1H-1,2,4-triazol-5-yl)-1H-indole;
6-chloro-7-fluoro-3-(1H-imidazol-1-yl)-5-methoxy-1-methyl-2-(5-(trifluoromethyl)-1H-1,2,4-triazol-3-yl)-1H-indole;
6-chloro-7-fluoro-3-(1H-imidazol-1-yl)-5-methoxy-2-(5-(trifluoromethyl)-4H-1,2,4-triazol-3-yl)-1H-indole;
6-chloro-7-fluoro-3-(1H-imidazol-1-yl)-5-methoxy-2-(3-(trifluoromethyl)-1H-1,2,4-triazol-5-yl)-1H-indole;
6-chloro-7-fluoro-3-(1H-imidazol-1-yl)-5-methoxy-2-(5-(trifluoromethyl)-1H-1,2,4-triazol-3-yl)-1H-indole;
6-chloro-7-fluoro-3-(1H-imidazol-1-yl)-5-methoxy-2-(5-(methoxymethyl)-4H-1,2,4-triazol-3-yl)-1-methyl-1H-indole;
6-chloro-7-fluoro-3-(1H-imidazol-1-yl)-5-methoxy-2-(3-(methoxymethyl)-1H-1,2,4-triazol-5-yl)-1-methyl-1H-indole;
6-chloro-7-fluoro-3-(1H-imidazol-1-yl)-5-methoxy-2-(5-(methoxymethyl)-1H-1,2,4-triazol-3-yl)-1-methyl-1H-indole;
6-chloro-7-fluoro-3-(1H-imidazol-1-yl)-5-methoxy-1-methyl-2-(5-((methylthio)methyl)-4H-1,2,4-triazol-3-yl)-1H-indole;
6-chloro-7-fluoro-3-(1H-imidazol-1-yl)-5-methoxy-1-methyl-2-(3-((methylthio)methyl)-1H-1,2,4-triazol-5-yl)-1H-indole;
6-chloro-7-fluoro-3-(1H-imidazol-1-yl)-5-methoxy-1-methyl-2-(5-((methylthio)methyl)-1H-1,2,4-triazol-3-yl)-1H-indole;
2-(5-(6-chloro-7-fluoro-3-(1H-imidazol-1-yl)-5-methoxy-1-methyl-1H-indol-2-yl)-4H-1,2,4-triazol-3-yl) ethan-1-ol;
2-(5-(6-chloro-7-fluoro-3-(1H-imidazol-1-yl)-5-methoxy-1-methyl-1H-indol-2-yl)-1H-1,2,4-triazol-3-yl) ethan-1-ol;
2-(3-(6-chloro-7-fluoro-3-(1H-imidazol-1-yl)-5-methoxy-1-methyl-1H-indol-2-yl)-1H-1,2,4-triazol-5-yl) ethan-1-ol;
6-chloro-7-fluoro-3-(1H-imidazol-1-yl)-5-methoxy-2-(5-(2-methoxyethyl)-4H-1,2,4-triazol-3-yl)-1-methyl-1H-indole;
6-chloro-7-fluoro-3-(1H-imidazol-1-yl)-5-methoxy-2-(3-(2-methoxyethyl)-1H-1,2,4-triazol-5-yl)-1-methyl-1H-indole;
6-chloro-7-fluoro-3-(1H-imidazol-1-yl)-5-methoxy-2-(5-(2-methoxyethyl)-1H-1,2,4-triazol-3-yl)-1-methyl-1H-indole;
6-chloro-2-(5-(1-hydroxy-2-methoxyethyl)-4H-1,2,4-triazol-3-yl)-3-(1H-imidazol-1-yl)-5-methoxy-1-methyl-1H-indole-7-carbonitrile;
6-chloro-2-(3-(1-hydroxy-2-methoxyethyl)-1H-1,2,4-triazol-5-yl)-3-(1H-imidazol-1-yl)-5-methoxy-1-methyl-1H-indole-7-carbonitrile;
6-chloro-2-(5-(1-hydroxy-2-methoxyethyl)-1H-1,2,4-triazol-3-yl)-3-(1H-imidazol-1-yl)-5-methoxy-1-methyl-1H-indole-7-carbonitrile;
6-chloro-3-(1H-imidazol-1-yl)-5-methoxy-2-(5-(methoxymethyl)-4H-1,2,4-triazol-3-yl)-1-methyl-1H-indole-7-carbonitrile;
6-chloro-3-(1H-imidazol-1-yl)-5-methoxy-2-(3-(methoxymethyl)-1H-1,2,4-triazol-5-yl)-1-methyl-1H-indole-7-carbonitrile;
6-chloro-3-(1H-imidazol-1-yl)-5-methoxy-2-(5-(methoxymethyl)-1H-1,2,4-triazol-3-yl)-1-methyl-1H-indole-7-carbonitrile;
6-chloro-2-(5-(1,1-difluoro-2-methoxyethyl)-4H-1,2,4-triazol-3-yl)-3-(1H-imidazol-1-yl)-5-methoxy-1-methyl-1H-indole-7-carbonitrile;
6-chloro-2-(3-(1,1-difluoro-2-methoxyethyl)-1H-1,2,4-triazol-5-yl)-3-(1H-imidazol-1-yl)-5-methoxy-1-methyl-1H-indole-7-carbonitrile;
6-chloro-2-(5-(1,1-difluoro-2-methoxyethyl)-1H-1,2,4-triazol-3-yl)-3-(1H-imidazol-1-yl)-5-methoxy-1-methyl-1H-indole-7-carbonitrile;
6-chloro-7-fluoro-3-(1H-imidazol-1-yl)-5-methoxy-1-methyl-2-(5-((methylsulfonyl)methyl)-4H-1,2,4-triazol-3-yl)-1H-indole;
6-chloro-7-fluoro-3-(1H-imidazol-1-yl)-5-methoxy-1-methyl-2-(3-((methylsulfonyl)methyl)-1H-1,2,4-triazol-5-yl)-1H-indole;
6-chloro-7-fluoro-3-(1H-imidazol-1-yl)-5-methoxy-1-methyl-2-(5-((methylsulfonyl)methyl)-1H-1,2,4-triazol-3-yl)-1H-indole;
1-(5-(6-chloro-7-fluoro-5-methoxy-3-(1H-pyrazol-4-yl)-1H-indol-2-yl)-4H-1,2,4-triazol-3-yl)-2-methoxyethan-1-one;
1-(5-(6-chloro-7-fluoro-5-methoxy-3-(1H-pyrazol-4-yl)-1H-indol-2-yl)-1H-1,2,4-triazol-3-yl)-2-methoxyethan-1-one;

1-(3-(6-chloro-7-fluoro-5-methoxy-1-methyl-3-(1H-pyrazol-4-yl)-1H-indol-2-yl)-1H-1,2,4-triazol-5-yl)-2-methoxyethan-1-one;

6-chloro-7-fluoro-2-(5-fluoro-4H-1,2,4-triazol-3-yl)-5-methoxy-1-methyl-3-(1H-pyrazol-4-yl)-1H-indole;

6-chloro-7-fluoro-2-(3-fluoro-1H-1,2,4-triazol-5-yl)-5-methoxy-1-methyl-3-(1H-pyrazol-4-yl)-1H-indole;

6-chloro-7-fluoro-2-(5-fluoro-1H-1,2,4-triazol-3-yl)-5-methoxy-1-methyl-3-(1H-pyrazol-4-yl)-1H-indole;

4-(5-(6-chloro-7-fluoro-5-methoxy-1-methyl-3-(1H-pyrazol-4-yl)-1H-indol-2-yl)-4H-1,2,4-triazol-3-yl)morpholine;

4-(5-(6-chloro-7-fluoro-5-methoxy-1-methyl-3-(1H-pyrazol-4-yl)-1H-indol-2-yl)-1H-1,2,4-triazol-3-yl)morpholine;

4-(3-(6-chloro-7-fluoro-5-methoxy-1-methyl-3-(1H-pyrazol-4-yl)-1H-indol-2-yl)-1H-1,2,4-triazol-5-yl)morpholine;

1-(5-(6-chloro-7-fluoro-5-methoxy-1-methyl-3-(1H-pyrazol-4-yl)-1H-indol-2-yl)-4H-1,2,4-triazol-3-yl)ethan-1-one;

1-(5-(6-chloro-7-fluoro-5-methoxy-1-methyl-3-(1H-pyrazol-4-yl)-1H-indol-2-yl)-1H-1,2,4-triazol-3-yl)ethan-1-one;

1-(3-(6-chloro-7-fluoro-5-methoxy-1-methyl-3-(1H-pyrazol-4-yl)-1H-indol-2-yl)-1H-1,2,4-triazol-5-yl)ethan-1-one;

N-(5-(6-chloro-7-fluoro-5-methoxy-1-methyl-3-(1H-pyrazol-4-yl)-1H-indol-2-yl)-4H-1,2,4-triazol-3-yl)-N-methylacetamide;

N-(5-(6-chloro-7-fluoro-5-methoxy-1-methyl-3-(1H-pyrazol-4-yl)-1H-indol-2-yl)-1H-1,2,4-triazol-3-yl)-N-methylacetamide;

N-(3-(6-chloro-7-fluoro-5-methoxy-1-methyl-3-(1H-pyrazol-4-yl)-1H-indol-2-yl)-1H-1,2,4-triazol-5-yl)-N-methylacetamide;

N-(5-(6-chloro-7-fluoro-5-methoxy-1-methyl-3-(1H-pyrazol-4-yl)-1H-indol-2-yl)-4H-1,2,4-triazol-3-yl)-2-methoxy-N-methylacetamide;

N-(5-(6-chloro-7-fluoro-5-methoxy-1-methyl-3-(1H-pyrazol-4-yl)-1H-indol-2-yl)-1H-1,2,4-triazol-3-yl)-2-methoxy-N-methylacetamide;

N-(3-(6-chloro-7-fluoro-5-methoxy-1-methyl-3-(1H-pyrazol-4-yl)-1H-indol-2-yl)-1H-1,2,4-triazol-5-yl)-2-methoxy-N-methylacetamide;

2-((5-(6-chloro-7-fluoro-5-methoxy-1-methyl-3-(1H-pyrazol-4-yl)-1H-indol-2-yl)-4H-1,2,4-triazol-3-yl)(methyl)amino)ethan-1-ol;

2-((5-(6-chloro-7-fluoro-5-methoxy-1-methyl-3-(1H-pyrazol-4-yl)-1H-indol-2-yl)-1H-1,2,4-triazol-3-yl)(methyl)amino)ethan-1-ol;

2-((3-(6-chloro-7-fluoro-5-methoxy-1-methyl-3-(1H-pyrazol-4-yl)-1H-indol-2-yl)-1H-1,2,4-triazol-5-yl)(methyl)amino)ethan-1-ol;

1-(5-(6-chloro-7-fluoro-5-methoxy-1-methyl-3-(1H-pyrazol-4-yl)-1H-indol-2-yl)-4H-1,2,4-triazol-3-yl)-2-methoxyethan-1-ol;

1-(5-(6-chloro-7-fluoro-5-methoxy-1-methyl-3-(1H-pyrazol-4-yl)-1H-indol-2-yl)-1H-1,2,4-triazol-3-yl)-2-methoxyethan-1-ol;

1-(3-(6-chloro-7-fluoro-5-methoxy-1-methyl-3-(1H-pyrazol-4-yl)-1H-indol-2-yl)-1H-1,2,4-triazol-5-yl)-2-methoxyethan-1-ol;

6-chloro-2-(5-(1,1-difluoro-2-methoxyethyl)-4H-1,2,4-triazol-3-yl)-7-fluoro-5-methoxy-3-(1H-pyrazol-4-yl)-1H-indole;

6-chloro-2-(3-(1,1-difluoro-2-methoxyethyl)-1H-1,2,4-triazol-5-yl)-7-fluoro-5-methoxy-3-(1H-pyrazol-4-yl)-1H-indole;

6-chloro-2-(5-(1,1-difluoro-2-methoxyethyl)-1H-1,2,4-triazol-3-yl)-7-fluoro-5-methoxy-3-(1H-pyrazol-4-yl)-1H-indole;

6-chloro-2-(5-(1,1-difluoro-2-methoxyethyl)-4H-1,2,4-triazol-3-yl)-7-fluoro-5-methoxy-1-methyl-3-(1H-pyrazol-4-yl)-1H-indole;

6-chloro-2-(3-(1,1-difluoro-2-methoxyethyl)-1H-1,2,4-triazol-5-yl)-7-fluoro-5-methoxy-1-methyl-3-(1H-pyrazol-4-yl)-1H-indole;

6-chloro-2-(5-(1,1-difluoro-2-methoxyethyl)-1H-1,2,4-triazol-3-yl)-7-fluoro-5-methoxy-1-methyl-3-(1H-pyrazol-4-yl)-1H-indole;

6-chloro-2-(5-(1,1-difluoroethyl)-4H-1,2,4-triazol-3-yl)-7-fluoro-5-methoxy-3-(1H-pyrazol-4-yl)-1H-indole;

6-chloro-2-(3-(1,1-difluoroethyl)-1H-1,2,4-triazol-5-yl)-7-fluoro-5-methoxy-3-(1H-pyrazol-4-yl)-1H-indole;

6-chloro-2-(5-(1,1-difluoroethyl)-1H-1,2,4-triazol-3-yl)-7-fluoro-5-methoxy-3-(1H-pyrazol-4-yl)-1H-indole;

6-chloro-2-(5-(1,1-difluoroethyl)-4H-1,2,4-triazol-3-yl)-7-fluoro-5-methoxy-1-methyl-3-(1H-pyrazol-4-yl)-1H-indole;

6-chloro-2-(3-(1,1-difluoroethyl)-1H-1,2,4-triazol-5-yl)-7-fluoro-5-methoxy-1-methyl-3-(1H-pyrazol-4-yl)-1H-indole;

6-chloro-2-(5-(1,1-difluoroethyl)-1H-1,2,4-triazol-3-yl)-7-fluoro-5-methoxy-1-methyl-3-(1H-pyrazol-4-yl)-1H-indole;

2-(5-(6-chloro-7-fluoro-5-methoxy-1-methyl-3-(1H-pyrazol-4-yl)-1H-indol-2-yl)-4H-1,2,4-triazol-3-yl)-2,2-difluoroethan-1-ol;

2-(5-(6-chloro-7-fluoro-5-methoxy-1-methyl-3-(1H-pyrazol-4-yl)-1H-indol-2-yl)-1H-1,2,4-triazol-3-yl)-2,2-difluoroethan-1-ol;

2-(3-(6-chloro-7-fluoro-5-methoxy-1-methyl-3-(1H-pyrazol-4-yl)-1H-indol-2-yl)-1H-1,2,4-triazol-5-yl)-2,2-difluoroethan-1-ol;

6-chloro-7-fluoro-2-(5-(1-fluoro-2-methoxyethyl)-4H-1,2,4-triazol-3-yl)-5-methoxy-1-methyl-3-(1H-pyrazol-4-yl)-1H-indole;

6-chloro-7-fluoro-2-(3-(1-fluoro-2-methoxyethyl)-1H-1,2,4-triazol-5-yl)-5-methoxy-1-methyl-3-(1H-pyrazol-4-yl)-1H-indole;

6-chloro-7-fluoro-2-(5-(1-fluoro-2-methoxyethyl)-1H-1,2,4-triazol-3-yl)-5-methoxy-1-methyl-3-(1H-pyrazol-4-yl)-1H-indole;

6-chloro-7-fluoro-2-(5-(1-fluoroethyl)-4H-1,2,4-triazol-3-yl)-5-methoxy-3-(1H-pyrazol-4-yl)-1H-indole;

6-chloro-7-fluoro-2-(3-(1-fluoroethyl)-1H-1,2,4-triazol-5-yl)-5-methoxy-3-(1H-pyrazol-4-yl)-1H-indole;

6-chloro-7-fluoro-2-(5-(1-fluoroethyl)-1H-1,2,4-triazol-3-yl)-5-methoxy-3-(1H-pyrazol-4-yl)-1H-indole;

6-chloro-7-fluoro-2-(5-(1-fluoroethyl)-4H-1,2,4-triazol-3-yl)-5-methoxy-1-methyl-3-(1H-pyrazol-4-yl)-1H-indole;

6-chloro-7-fluoro-2-(3-(1-fluoroethyl)-1H-1,2,4-triazol-5-yl)-5-methoxy-1-methyl-3-(1H-pyrazol-4-yl)-1H-indole;

6-chloro-7-fluoro-2-(5-(1-fluoroethyl)-1H-1,2,4-triazol-3-yl)-5-methoxy-1-methyl-3-(1H-pyrazol-4-yl)-1H-indole;

6-chloro-2-(5-(1,1-difluoro-2-methoxyethyl)-4H-1,2,4-triazol-3-yl)-5-methoxy-1-methyl-3-(1H-pyrazol-4-yl)-1H-indole-7-carbonitrile;

6-chloro-2-(3-(1,1-difluoro-2-methoxyethyl)-1H-1,2,4-triazol-5-yl)-5-methoxy-1-methyl-3-(1H-pyrazol-4-yl)-1H-indole-7-carbonitrile;
6-chloro-2-(5-(1,1-difluoro-2-methoxyethyl)-1H-1,2,4-triazol-3-yl)-5-methoxy-1-methyl-3-(1H-pyrazol-4-yl)-1H-indole-7-carbonitrile;
1-(5-(6-chloro-5-ethoxy-7-fluoro-1-methyl-3-(1H-pyrazol-4-yl)-1H-indol-2-yl)-4H-1,2,4-triazol-3-yl) ethan-1-one;
1-(5-(6-chloro-5-ethoxy-7-fluoro-1-methyl-3-(1H-pyrazol-4-yl)-1H-indol-2-yl)-1H-1,2,4-triazol-3-yl) ethan-1-one;
1-(3-(6-chloro-5-ethoxy-7-fluoro-1-methyl-3-(1H-pyrazol-4-yl)-1H-indol-2-yl)-1H-1,2,4-triazol-5-yl) ethan-1-one;
2-(5-(6-chloro-7-fluoro-5-methoxy-1-methyl-3-(1H-pyrazol-4-yl)-1H-indol-2-yl)-4H-1,2,4-triazol-3-yl)-2-methoxy-N,N-dimethylethan-1-amine;
2-(5-(6-chloro-7-fluoro-5-methoxy-1-methyl-3-(1H-pyrazol-4-yl)-1H-indol-2-yl)-1H-1,2,4-triazol-3-yl)-2-methoxy-N,N-dimethylethan-1-amine;
2-(3-(6-chloro-7-fluoro-5-methoxy-1-methyl-3-(1H-pyrazol-4-yl)-1H-indol-2-yl)-1H-1,2,4-triazol-5-yl)-2-methoxy-N,N-dimethylethan-1-amine;
3-(6,7-dichloro-2-(5-(trifluoromethyl)-4H-1,2,4-triazol-3-yl)-1H-indol-3-yl)-1H-pyrazol-5-ol;
3-(6,7-dichloro-2-(3-(trifluoromethyl)-1H-1,2,4-triazol-5-yl)-1H-indol-3-yl)-1H-pyrazol-5-ol;
3-(6,7-dichloro-2-(5-(trifluoromethyl)-1H-1,2,4-triazol-3-yl)-1H-indol-3-yl)-1H-pyrazol-5-ol;
3-(6,7-dichloro-2-(5-(trifluoromethyl)-4H-1,2,4-triazol-3-yl)-1H-indol-3-yl) isoxazol-5-ol;
3-(6,7-dichloro-2-(3-(trifluoromethyl)-1H-1,2,4-triazol-5-yl)-1H-indol-3-yl) isoxazol-5-ol;
3-(6,7-dichloro-2-(5-(trifluoromethyl)-1H-1,2,4-triazol-3-yl)-1H-indol-3-yl) isoxazol-5-ol;
6,7-dichloro-3-(1H-pyrazol-3-yl)-2-(5-(trifluoromethyl)-4H-1,2,4-triazol-3-yl)-1H-indole;
6,7-dichloro-3-(1H-pyrazol-3-yl)-2-(3-(trifluoromethyl)-1H-1,2,4-triazol-5-yl)-1H-indole;
6,7-dichloro-3-(1H-pyrazol-3-yl)-2-(5-(trifluoromethyl)-1H-1,2,4-triazol-3-yl)-1H-indole;
1-(5-(6-chloro-7-fluoro-5-methoxy-3-(1H-pyrazol-4-yl)-1H-indol-2-yl)-4H-1,2,4-triazol-3-yl)-N,N-dimethylethan-1-amine;
1-(5-(6-chloro-7-fluoro-5-methoxy-3-(1H-pyrazol-4-yl)-1H-indol-2-yl)-1H-1,2,4-triazol-3-yl)-N,N-dimethylethan-1-amine;
1-(3-(6-chloro-7-fluoro-5-methoxy-3-(1H-pyrazol-4-yl)-1H-indol-2-yl)-1H-1,2,4-triazol-5-yl)-N,N-dimethylethan-1-amine;
1-(5-(6-chloro-7-fluoro-5-methoxy-1-methyl-3-(1H-pyrazol-4-yl)-1H-indol-2-yl)-4H-1,2,4-triazol-3-yl)-N,N-dimethylethan-1-amine;
1-(5-(6-chloro-7-fluoro-5-methoxy-1-methyl-3-(1H-pyrazol-4-yl)-1H-indol-2-yl)-1H-1,2,4-triazol-3-yl)-N,N-dimethylethan-1-amine;
1-(3-(6-chloro-7-fluoro-5-methoxy-1-methyl-3-(1H-pyrazol-4-yl)-1H-indol-2-yl)-1H-1,2,4-triazol-5-yl)-N,N-dimethylethan-1-amine;
1-(5-(6-chloro-7-fluoro-5-methoxy-1-methyl-3-(1H-pyrazol-4-yl)-1H-indol-2-yl)-4H-1,2,4-triazol-3-yl)-2-methoxy-N,N-dimethylethan-1-amine;
1-(5-(6-chloro-7-fluoro-5-methoxy-1-methyl-3-(1H-pyrazol-4-yl)-1H-indol-2-yl)-1H-1,2,4-triazol-3-yl)-2-methoxy-N,N-dimethylethan-1-amine;
1-(3-(6-chloro-7-fluoro-5-methoxy-1-methyl-3-(1H-pyrazol-4-yl)-1H-indol-2-yl)-1H-1,2,4-triazol-5-yl)-2-methoxy-N,N-dimethylethan-1-amine;
2-(5-(6-chloro-7-fluoro-5-methoxy-1-methyl-3-(1H-pyrazol-4-yl)-1H-indol-2-yl)-4H-1,2,4-triazol-3-yl) propanenitrile;
2-(5-(6-chloro-7-fluoro-5-methoxy-1-methyl-3-(1H-pyrazol-4-yl)-1H-indol-2-yl)-1H-1,2,4-triazol-3-yl) propanenitrile;
2-(3-(6-chloro-7-fluoro-5-methoxy-1-methyl-3-(1H-pyrazol-4-yl)-1H-indol-2-yl)-1H-1,2,4-triazol-5-yl) propanenitrile;
1-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-ol;
1-(5-(6-chloro-7-fluoro-3-(1H-imidazol-1-yl)-5-methoxy-1-methyl-1H-indol-2-yl)-1H-1,2,4-triazol-3-yl)-2-methoxyethan-1-ol;
1-(3-(6-chloro-7-fluoro-3-(1H-imidazol-1-yl)-5-methoxy-1-methyl-1H-indol-2-yl)-1H-1,2,4-triazol-5-yl)-2-methoxyethan-1-ol;
6-chloro-7-fluoro-3-(1H-imidazol-1-yl)-2-(5-isopropoxy-4H-1,2,4-triazol-3-yl)-5-methoxy-1-methyl-1H-indole;
6-chloro-7-fluoro-3-(1H-imidazol-1-yl)-2-(3-isopropoxy-1H-1,2,4-triazol-5-yl)-5-methoxy-1-methyl-1H-indole;
6-chloro-7-fluoro-3-(1H-imidazol-1-yl)-2-(5-isopropoxy-1H-1,2,4-triazol-3-yl)-5-methoxy-1-methyl-1H-indole;
6-chloro-7-fluoro-2-(5-fluoro-4H-1,2,4-triazol-3-yl)-3-(1H-imidazol-1-yl)-5-methoxy-1-methyl-1H-indole;
6-chloro-7-fluoro-2-(3-fluoro-1H-1,2,4-triazol-5-yl)-3-(1H-imidazol-1-yl)-5-methoxy-1-methyl-1H-indole;
6-chloro-7-fluoro-2-(5-fluoro-1H-1,2,4-triazol-3-yl)-3-(1H-imidazol-1-yl)-5-methoxy-1-methyl-1H-indole;
6-chloro-7-fluoro-2-(5-fluoro-4H-1,2,4-triazol-3-yl)-3-(1H-imidazol-1-yl)-5-methoxy-1H-indole;
6-chloro-7-fluoro-2-(3-fluoro-1H-1,2,4-triazol-5-yl)-3-(1H-imidazol-1-yl)-5-methoxy-1H-indole;
6-chloro-7-fluoro-2-(5-fluoro-1H-1,2,4-triazol-3-yl)-3-(1H-imidazol-1-yl)-5-methoxy-1H-indole;
1-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-one;
1-(5-(6-chloro-7-fluoro-3-(1H-imidazol-1-yl)-5-methoxy-1-methyl-1H-indol-2-yl)-1H-1,2,4-triazol-3-yl)-2-methoxyethan-1-one;
1-(3-(6-chloro-7-fluoro-3-(1H-imidazol-1-yl)-5-methoxy-1-methyl-1H-indol-2-yl)-1H-1,2,4-triazol-5-yl)-2-methoxyethan-1-one;
6-chloro-2-(5-(1,1-difluoro-2-methoxyethyl)-4H-1,2,4-triazol-3-yl)-7-fluoro-3-(1H-imidazol-1-yl)-5-methoxy-1-methyl-1H-indole;
6-chloro-2-(3-(1,1-difluoro-2-methoxyethyl)-1H-1,2,4-triazol-5-yl)-7-fluoro-3-(1H-imidazol-1-yl)-5-methoxy-1-methyl-1H-indole;
6-chloro-2-(5-(1,1-difluoro-2-methoxyethyl)-1H-1,2,4-triazol-3-yl)-7-fluoro-3-(1H-imidazol-1-yl)-5-methoxy-1-methyl-1H-indole;
2-((5-(6-chloro-7-fluoro-3-(1H-imidazol-1-yl)-5-methoxy-1-methyl-1H-indol-2-yl)-4H-1,2,4-triazol-3-yl)(methyl)amino) ethan-1-ol;
2-((5-(6-chloro-7-fluoro-3-(1H-imidazol-1-yl)-5-methoxy-1-methyl-1H-indol-2-yl)-1H-1,2,4-triazol-3-yl)(methyl)amino) ethan-1-ol;
2-((3-(6-chloro-7-fluoro-3-(1H-imidazol-1-yl)-5-methoxy-1-methyl-1H-indol-2-yl)-1H-1,2,4-triazol-5-yl)(methyl)amino) ethan-1-ol;

1-(5-(6-chloro-7-fluoro-3-(1H-imidazol-1-yl)-5-methoxy-1-methyl-1H-indol-2-yl)-4H-1,2,4-triazol-3-yl) pyrrolidin-3-ol;

1-(5-(6-chloro-7-fluoro-3-(1H-imidazol-1-yl)-5-methoxy-1-methyl-1H-indol-2-yl)-1H-1,2,4-triazol-3-yl) pyrrolidin-3-ol;

1-(3-(6-chloro-7-fluoro-3-(1H-imidazol-1-yl)-5-methoxy-1-methyl-1H-indol-2-yl)-1H-1,2,4-triazol-5-yl) pyrrolidin-3-ol;

2-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-ol;

2-(5-(6-chloro-7-fluoro-3-(1H-imidazol-1-yl)-5-methoxy-1-methyl-1H-indol-2-yl)-1H-1,2,4-triazol-3-yl)-2-methoxyethan-1-ol;

2-(3-(6-chloro-7-fluoro-3-(1H-imidazol-1-yl)-5-methoxy-1-methyl-1H-indol-2-yl)-1H-1,2,4-triazol-5-yl)-2-methoxyethan-1-ol;

2-((5-(6-chloro-7-fluoro-3-(1H-imidazol-1-yl)-5-methoxy-1-methyl-1H-indol-2-yl)-4H-1,2,4-triazol-3-yl)oxy) ethan-1-ol;

2-((5-(6-chloro-7-fluoro-3-(1H-imidazol-1-yl)-5-methoxy-1-methyl-1H-indol-2-yl)-1H-1,2,4-triazol-3-yl)oxy) ethan-1-ol;

2-((3-(6-chloro-7-fluoro-3-(1H-imidazol-1-yl)-5-methoxy-1-methyl-1H-indol-2-yl)-1H-1,2,4-triazol-5-yl)oxy) ethan-1-ol;

2-(5-(6-chloro-7-fluoro-3-(1H-imidazol-1-yl)-5-methoxy-1-methyl-1H-indol-2-yl)-4H-1,2,4-triazol-3-yl)-2,2-difluoroethan-1-ol;

2-(5-(6-chloro-7-fluoro-3-(1H-imidazol-1-yl)-5-methoxy-1-methyl-1H-indol-2-yl)-1H-1,2,4-triazol-3-yl)-2,2-difluoroethan-1-ol;

2-(3-(6-chloro-7-fluoro-3-(1H-imidazol-1-yl)-5-methoxy-1-methyl-1H-indol-2-yl)-1H-1,2,4-triazol-5-yl)-2,2-difluoroethan-1-ol;

1-(5-(6-chloro-7-fluoro-3-(1H-imidazol-1-yl)-5-methoxy-1-methyl-1H-indol-2-yl)-4H-1,2,4-triazol-3-yl)-2,2-difluoroethan-1-ol;

1-(5-(6-chloro-7-fluoro-3-(1H-imidazol-1-yl)-5-methoxy-1-methyl-1H-indol-2-yl)-1H-1,2,4-triazol-3-yl)-2,2-difluoroethan-1-ol;

1-(3-(6-chloro-7-fluoro-3-(1H-imidazol-1-yl)-5-methoxy-1-methyl-1H-indol-2-yl)-1H-1,2,4-triazol-5-yl)-2,2-difluoroethan-1-ol;

2-(5-(6-chloro-7-fluoro-3-(1H-imidazol-1-yl)-5-methoxy-1-methyl-1H-indol-2-yl)-4H-1,2,4-triazol-3-yl)-2-methoxy-N,N-dimethylethan-1-amine;

2-(5-(6-chloro-7-fluoro-3-(1H-imidazol-1-yl)-5-methoxy-1-methyl-1H-indol-2-yl)-1H-1,2,4-triazol-3-yl)-2-methoxy-N,N-dimethylethan-1-amine;

2-(3-(6-chloro-7-fluoro-3-(1H-imidazol-1-yl)-5-methoxy-1-methyl-1H-indol-2-yl)-1H-1,2,4-triazol-5-yl)-2-methoxy-N,N-dimethylethan-1-amine;

1-(5-(6-chloro-7-fluoro-3-(1H-imidazol-1-yl)-5-methoxy-1-methyl-1H-indol-2-yl)-4H-1,2,4-triazol-3-yl)-2,2,2-trifluoroethan-1-ol;

1-(5-(6-chloro-7-fluoro-3-(1H-imidazol-1-yl)-5-methoxy-1-methyl-1H-indol-2-yl)-1H-1,2,4-triazol-3-yl)-2,2,2-trifluoroethan-1-ol;

1-(3-(6-chloro-7-fluoro-3-(1H-imidazol-1-yl)-5-methoxy-1-methyl-1H-indol-2-yl)-1H-1,2,4-triazol-5-yl)-2,2,2-trifluoroethan-1-ol;

6-chloro-2-(5-(2,2-difluoro-1-methoxyethyl)-4H-1,2,4-triazol-3-yl)-7-fluoro-3-(1H-imidazol-1-yl)-5-methoxy-1-methyl-1H-indole;

6-chloro-2-(3-(2,2-difluoro-1-methoxyethyl)-1H-1,2,4-triazol-5-yl)-7-fluoro-3-(1H-imidazol-1-yl)-5-methoxy-1-methyl-1H-indole;

6-chloro-2-(5-(2,2-difluoro-1-methoxyethyl)-1H-1,2,4-triazol-3-yl)-7-fluoro-3-(1H-imidazol-1-yl)-5-methoxy-1-methyl-1H-indole;

2-(5-(1-(1H-imidazol-1-yl)-2-methoxyethyl)-4H-1,2,4-triazol-3-yl)-6-chloro-7-fluoro-3-(1H-imidazol-1-yl)-5-methoxy-1-methyl-1H-indole;

2-(3-(1-(1H-imidazol-1-yl)-2-methoxyethyl)-1H-1,2,4-triazol-5-yl)-6-chloro-7-fluoro-3-(1H-imidazol-1-yl)-5-methoxy-1-methyl-1H-indole;

2-(5-(1-(1H-imidazol-1-yl)-2-methoxyethyl)-1H-1,2,4-triazol-3-yl)-6-chloro-7-fluoro-3-(1H-imidazol-1-yl)-5-methoxy-1-methyl-1H-indole;

1-(5-(6-chloro-5-ethoxy-7-fluoro-3-(1H-imidazol-1-yl)-1-methyl-1H-indol-2-yl)-4H-1,2,4-triazol-3-yl) ethan-1-one;

1-(5-(6-chloro-5-ethoxy-7-fluoro-3-(1H-imidazol-1-yl)-1-methyl-1H-indol-2-yl)-1H-1,2,4-triazol-3-yl) ethan-1-one;

1-(3-(6-chloro-5-ethoxy-7-fluoro-3-(1H-imidazol-1-yl)-1-methyl-1H-indol-2-yl)-1H-1,2,4-triazol-5-yl) ethan-1-one;

1-(5-(6-chloro-7-fluoro-3-(1H-imidazol-1-yl)-5-methoxy-1-methyl-1H-indol-2-yl)-4H-1,2,4-triazol-3-yl) ethan-1-one;

1-(5-(6-chloro-7-fluoro-3-(1H-imidazol-1-yl)-5-methoxy-1-methyl-1H-indol-2-yl)-1H-1,2,4-triazol-3-yl) ethan-1-one;

1-(3-(6-chloro-7-fluoro-3-(1H-imidazol-1-yl)-5-methoxy-1-methyl-1H-indol-2-yl)-1H-1,2,4-triazol-5-yl) ethan-1-one;

5-(6-chloro-7-cyano-3-(1H-imidazol-1-yl)-5-methoxy-1-methyl-1H-indol-2-yl)-N,N-dimethyl-4H-1,2,4-triazole-3-carboxamide;

5-(6-chloro-7-cyano-3-(1H-imidazol-1-yl)-5-methoxy-1-methyl-1H-indol-2-yl)-N,N-dimethyl-1H-1,2,4-triazole-3-carboxamide;

3-(6-chloro-7-cyano-3-(1H-imidazol-1-yl)-5-methoxy-1-methyl-1H-indol-2-yl)-N,N-dimethyl-1H-1,2,4-triazole-5-carboxamide;

5-(6,7-difluoro-3-(1H-imidazol-1-yl)-5-methoxy-1-methyl-1H-indol-2-yl)-N,N-dimethyl-4H-1,2,4-triazole-3-carboxamide;

5-(6,7-difluoro-3-(1H-imidazol-1-yl)-5-methoxy-1-methyl-1H-indol-2-yl)-N,N-dimethyl-1H-1,2,4-triazole-3-carboxamide;

3-(6,7-difluoro-3-(1H-imidazol-1-yl)-5-methoxy-1-methyl-1H-indol-2-yl)-N,N-dimethyl-1H-1,2,4-triazole-5-carboxamide;

5,6-dichloro-3-(1H-imidazol-1-yl)-2-(5-(trifluoromethyl)-4H-1,2,4-triazol-3-yl)-1H-indole;

5,6-dichloro-3-(1H-imidazol-1-yl)-2-(3-(trifluoromethyl)-1H-1,2,4-triazol-5-yl)-1H-indole;

5,6-dichloro-3-(1H-imidazol-1-yl)-2-(5-(trifluoromethyl)-1H-1,2,4-triazol-3-yl)-1H-indole;

6,7-dichloro-3-(1H-imidazol-1-yl)-2-(5-(trifluoromethyl)-4H-1,2,4-triazol-3-yl)-1H-indole;

6,7-dichloro-3-(1H-imidazol-1-yl)-2-(3-(trifluoromethyl)-1H-1,2,4-triazol-5-yl)-1H-indole;

6,7-dichloro-3-(1H-imidazol-1-yl)-2-(5-(trifluoromethyl)-1H-1,2,4-triazol-3-yl)-1H-indole;

6-chloro-3-(1H-imidazol-1-yl)-5-methoxy-2-(5-(trifluoromethyl)-4H-1,2,4-triazol-3-yl)-1H-indole;

6-chloro-3-(1H-imidazol-1-yl)-5-methoxy-2-(3-(trifluoromethyl)-1H-1,2,4-triazol-5-yl)-1H-indole;

6-chloro-3-(1H-imidazol-1-yl)-5-methoxy-2-(5-(trifluoromethyl)-1H-1,2,4-triazol-3-yl)-1H-indole;
5,6-dichloro-3-(1H-imidazol-1-yl)-1-methyl-2-(5-(trifluoromethyl)-4H-1,2,4-triazol-3-yl)-1H-indole;
5,6-dichloro-3-(1H-imidazol-1-yl)-1-methyl-2-(3-(trifluoromethyl)-1H-1,2,4-triazol-5-yl)-1H-indole;
5,6-dichloro-3-(1H-imidazol-1-yl)-1-methyl-2-(5-(trifluoromethyl)-1H-1,2,4-triazol-3-yl)-1H-indole;
6,7-dichloro-3-(1H-imidazol-1-yl)-1-methyl-2-(5-(trifluoromethyl)-4H-1,2,4-triazol-3-yl)-1H-indole;
6,7-dichloro-3-(1H-imidazol-1-yl)-1-methyl-2-(3-(trifluoromethyl)-1H-1,2,4-triazol-5-yl)-1H-indole;
6,7-dichloro-3-(1H-imidazol-1-yl)-1-methyl-2-(5-(trifluoromethyl)-1H-1,2,4-triazol-3-yl)-1H-indole;
6-chloro-3-(1H-imidazol-1-yl)-2-(5-(trifluoromethyl)-4H-1,2,4-triazol-3-yl)-1H-indole-7-carbonitrile;
6-chloro-3-(1H-imidazol-1-yl)-2-(3-(trifluoromethyl)-1H-1,2,4-triazol-5-yl)-1H-indole-7-carbonitrile;
6-chloro-3-(1H-imidazol-1-yl)-2-(5-(trifluoromethyl)-1H-1,2,4-triazol-3-yl)-1H-indole-7-carbonitrile;
6-chloro-3-(1H-imidazol-1-yl)-1-methyl-2-(5-(trifluoromethyl)-4H-1,2,4-triazol-3-yl)-1H-indole-7-carbonitrile;
6-chloro-3-(1H-imidazol-1-yl)-1-methyl-2-(3-(trifluoromethyl)-1H-1,2,4-triazol-5-yl)-1H-indole-7-carbonitrile;
6-chloro-3-(1H-imidazol-1-yl)-1-methyl-2-(5-(trifluoromethyl)-1H-1,2,4-triazol-3-yl)-1H-indole-7-carbonitrile;
6-chloro-5-(difluoromethoxy)-3-(1H-imidazol-1-yl)-2-(5-(trifluoromethyl)-4H-1,2,4-triazol-3-yl)-1H-indole;
6-chloro-5-(difluoromethoxy)-3-(1H-imidazol-1-yl)-2-(3-(trifluoromethyl)-1H-1,2,4-triazol-5-yl)-1H-indole;
6-chloro-5-(difluoromethoxy)-3-(1H-imidazol-1-yl)-2-(5-(trifluoromethyl)-1H-1,2,4-triazol-3-yl)-1H-indole;
6-chloro-5-cyclopropoxy-3-(1H-imidazol-1-yl)-2-(5-(trifluoromethyl)-4H-1,2,4-triazol-3-yl)-1H-indole;
6-chloro-5-cyclopropoxy-3-(1H-imidazol-1-yl)-2-(3-(trifluoromethyl)-1H-1,2,4-triazol-5-yl)-1H-indole;
6-chloro-5-cyclopropoxy-3-(1H-imidazol-1-yl)-2-(5-(trifluoromethyl)-1H-1,2,4-triazol-3-yl)-1H-indole;
6-chloro-3-(1H-imidazol-1-yl)-5-methoxy-1-methyl-2-(5-(trifluoromethyl)-4H-1,2,4-triazol-3-yl)-1H-indole;
6-chloro-3-(1H-imidazol-1-yl)-5-methoxy-1-methyl-2-(3-(trifluoromethyl)-1H-1,2,4-triazol-5-yl)-1H-indole;
6-chloro-3-(1H-imidazol-1-yl)-5-methoxy-1-methyl-2-(5-(trifluoromethyl)-1H-1,2,4-triazol-3-yl)-1H-indole;
6-chloro-3-(1H-imidazol-1-yl)-1-methyl-2-(5-(trifluoromethyl)-4H-1,2,4-triazol-3-yl)-1H-indol-5-ol;
6-chloro-3-(1H-imidazol-1-yl)-1-methyl-2-(3-(trifluoromethyl)-1H-1,2,4-triazol-5-yl)-1H-indol-5-ol;
6-chloro-3-(1H-imidazol-1-yl)-1-methyl-2-(5-(trifluoromethyl)-1H-1,2,4-triazol-3-yl)-1H-indol-5-ol;
5-(6-chloro-3-(1H-imidazol-1-yl)-5-methoxy-1-methyl-1H-indol-2-yl)-N,N-dimethyl-4H-1,2,4-triazole-3-carboxamide;
5-(6-chloro-3-(1H-imidazol-1-yl)-5-methoxy-1-methyl-1H-indol-2-yl)-N,N-dimethyl-1H-1,2,4-triazole-3-carboxamide;
3-(6-chloro-3-(1H-imidazol-1-yl)-5-methoxy-1-methyl-1H-indol-2-yl)-N,N-dimethyl-1H-1,2,4-triazole-5-carboxamide;
6-chloro-5-hydroxy-2-(5-(2-hydroxyethyl)-4H-1,2,4-triazol-3-yl)-3-(1H-imidazol-1-yl)-1-methyl-1H-indole-7-carbonitrile;
6-chloro-5-hydroxy-2-(3-(2-hydroxyethyl)-1H-1,2,4-triazol-5-yl)-3-(1H-imidazol-1-yl)-1-methyl-1H-indole-7-carbonitrile;
6-chloro-5-hydroxy-2-(5-(2-hydroxyethyl)-1H-1,2,4-triazol-3-yl)-3-(1H-imidazol-1-yl)-1-methyl-1H-indole-7-carbonitrile;
6-chloro-2-(5-(2-hydroxyethyl)-4H-1,2,4-triazol-3-yl)-3-(1H-imidazol-1-yl)-5-methoxy-1-methyl-1H-indole-7-carbonitrile;
6-chloro-2-(3-(2-hydroxyethyl)-1H-1,2,4-triazol-5-yl)-3-(1H-imidazol-1-yl)-5-methoxy-1-methyl-1H-indole-7-carbonitrile;
6-chloro-2-(5-(2-hydroxyethyl)-1H-1,2,4-triazol-3-yl)-3-(1H-imidazol-1-yl)-5-methoxy-1-methyl-1H-indole-7-carbonitrile;
2-(5-(6-chloro-3-(1H-imidazol-1-yl)-5-methoxy-1-methyl-1H-indol-2-yl)-4H-1,2,4-triazol-3-yl) ethan-1-ol;
2-(5-(6-chloro-3-(1H-imidazol-1-yl)-5-methoxy-1-methyl-1H-indol-2-yl)-1H-1,2,4-triazol-3-yl) ethan-1-ol;
2-(3-(6-chloro-3-(1H-imidazol-1-yl)-5-methoxy-1-methyl-1H-indol-2-yl)-1H-1,2,4-triazol-5-yl) ethan-1-ol;
5-(6,7-dicyano-3-(1H-imidazol-1-yl)-5-methoxy-1-methyl-1H-indol-2-yl)-N,N-dimethyl-4H-1,2,4-triazole-3-carboxamide;
5-(6,7-dicyano-3-(1H-imidazol-1-yl)-5-methoxy-1-methyl-1H-indol-2-yl)-N,N-dimethyl-1H-1,2,4-triazole-3-carboxamide;
3-(6,7-dicyano-3-(1H-imidazol-1-yl)-5-methoxy-1-methyl-1H-indol-2-yl)-N,N-dimethyl-1H-1,2,4-triazole-5-carboxamide;
4-(1-(5-(6-chloro-7-fluoro-3-(1H-imidazol-1-yl)-5-methoxy-1-methyl-1H-indol-2-yl)-4H-1,2,4-triazol-3-yl)ethyl) morpholine;
4-(1-(5-(6-chloro-7-fluoro-3-(1H-imidazol-1-yl)-5-methoxy-1-methyl-1H-indol-2-yl)-1H-1,2,4-triazol-3-yl)ethyl) morpholine;
4-(1-(3-(6-chloro-7-fluoro-3-(1H-imidazol-1-yl)-5-methoxy-1-methyl-1H-indol-2-yl)-1H-1,2,4-triazol-5-yl)ethyl) morpholine;
1-(5-(6-chloro-7-fluoro-3-(1H-imidazol-1-yl)-5-methoxy-1-methyl-1H-indol-2-yl)-4H-1,2,4-triazol-3-yl)-N,N-dimethylethan-1-amine;
1-(5-(6-chloro-7-fluoro-3-(1H-imidazol-1-yl)-5-methoxy-1-methyl-1H-indol-2-yl)-1H-1,2,4-triazol-3-yl)-N,N-dimethylethan-1-amine;
1-(3-(6-chloro-7-fluoro-3-(1H-imidazol-1-yl)-5-methoxy-1-methyl-1H-indol-2-yl)-1H-1,2,4-triazol-5-yl)-N,N-dimethylethan-1-amine;
1-(5-(6-chloro-7-fluoro-3-(1H-imidazol-1-yl)-5-methoxy-1-methyl-1H-indol-2-yl)-4H-1,2,4-triazol-3-yl)-N-methylethan-1-amine;
1-(5-(6-chloro-7-fluoro-3-(1H-imidazol-1-yl)-5-methoxy-1-methyl-1H-indol-2-yl)-1H-1,2,4-triazol-3-yl)-N-methylethan-1-amine;
1-(3-(6-chloro-7-fluoro-3-(1H-imidazol-1-yl)-5-methoxy-1-methyl-1H-indol-2-yl)-1H-1,2,4-triazol-5-yl)-N-methylethan-1-amine;
1-(5-(6-chloro-7-fluoro-3-(1H-imidazol-1-yl)-5-methoxy-1-methyl-1H-indol-2-yl)-4H-1,2,4-triazol-3-yl)-2-methoxy-N,N-dimethylethan-1-amine;
1-(5-(6-chloro-7-fluoro-3-(1H-imidazol-1-yl)-5-methoxy-1-methyl-1H-indol-2-yl)-1H-1,2,4-triazol-3-yl)-2-methoxy-N,N-dimethylethan-1-amine;

1-(3-(6-chloro-7-fluoro-3-(1H-imidazol-1-yl)-5-methoxy-1-methyl-1H-indol-2-yl)-1H-1,2,4-triazol-5-yl)-2-methoxy-N,N-dimethylethan-1-amine;
1-(5-(6-chloro-7-fluoro-3-(1H-imidazol-1-yl)-5-methoxy-1-methyl-1H-indol-2-yl)-4H-1,2,4-triazol-3-yl)-2-methoxy-N-methylethan-1-amine;
1-(5-(6-chloro-7-fluoro-3-(1H-imidazol-1-yl)-5-methoxy-1-methyl-1H-indol-2-yl)-1H-1,2,4-triazol-3-yl)-2-methoxy-N-methylethan-1-amine;
1-(3-(6-chloro-7-fluoro-3-(1H-imidazol-1-yl)-5-methoxy-1-methyl-1H-indol-2-yl)-1H-1,2,4-triazol-5-yl)-2-methoxy-N-methylethan-1-amine;
4-(1-(5-(6-chloro-7-fluoro-3-(1H-imidazol-1-yl)-5-methoxy-1-methyl-1H-indol-2-yl)-4H-1,2,4-triazol-3-yl)-2-methoxyethyl) morpholine;
4-(1-(5-(6-chloro-7-fluoro-3-(1H-imidazol-1-yl)-5-methoxy-1-methyl-1H-indol-2-yl)-1H-1,2,4-triazol-3-yl)-2-methoxyethyl) morpholine;
4-(1-(3-(6-chloro-7-fluoro-3-(1H-imidazol-1-yl)-5-methoxy-1-methyl-1H-indol-2-yl)-1H-1,2,4-triazol-5-yl)-2-methoxyethyl) morpholine;
2-(5-(1-(azetidin-1-yl)-2-methoxyethyl)-4H-1,2,4-triazol-3-yl)-6-chloro-7-fluoro-3-(1H-imidazol-1-yl)-5-methoxy-1-methyl-1H-indole;
2-(3-(1-(azetidin-1-yl)-2-methoxyethyl)-1H-1,2,4-triazol-5-yl)-6-chloro-7-fluoro-3-(1H-imidazol-1-yl)-5-methoxy-1-methyl-1H-indole;
2-(5-(1-(azetidin-1-yl)-2-methoxyethyl)-1H-1,2,4-triazol-3-yl)-6-chloro-7-fluoro-3-(1H-imidazol-1-yl)-5-methoxy-1-methyl-1H-indole;
1-(5-(6-chloro-7-fluoro-3-(1H-imidazol-1-yl)-5-methoxy-1-methyl-1H-indol-2-yl)-4H-1,2,4-triazol-3-yl)-N-(2-methoxyethyl)-N-methylethan-1-amine;
1-(5-(6-chloro-7-fluoro-3-(1H-imidazol-1-yl)-5-methoxy-1-methyl-1H-indol-2-yl)-1H-1,2,4-triazol-3-yl)-N-(2-methoxyethyl)-N-methylethan-1-amine;
1-(3-(6-chloro-7-fluoro-3-(1H-imidazol-1-yl)-5-methoxy-1-methyl-1H-indol-2-yl)-1H-1,2,4-triazol-5-yl)-N-(2-methoxyethyl)-N-methylethan-1-amine;
1-(5-(6-chloro-7-fluoro-3-(1H-imidazol-1-yl)-5-methoxy-1-methyl-1H-indol-2-yl)-4H-1,2,4-triazol-3-yl)-N-(2-methoxyethyl) ethan-1-amine;
1-(5-(6-chloro-7-fluoro-3-(1H-imidazol-1-yl)-5-methoxy-1-methyl-1H-indol-2-yl)-1H-1,2,4-triazol-3-yl)-N-(2-methoxyethyl) ethan-1-amine;
1-(3-(6-chloro-7-fluoro-3-(1H-imidazol-1-yl)-5-methoxy-1-methyl-1H-indol-2-yl)-1H-1,2,4-triazol-5-yl)-N-(2-methoxyethyl) ethan-1-amine;
6-(1-(5-(6-chloro-7-fluoro-3-(1H-imidazol-1-yl)-5-methoxy-1-methyl-1H-indol-2-yl)-4H-1,2,4-triazol-3-yl)ethyl)-2-oxa-6-azaspiro[3.3]heptane;
6-(1-(5-(6-chloro-7-fluoro-3-(1H-imidazol-1-yl)-5-methoxy-1-methyl-1H-indol-2-yl)-1H-1,2,4-triazol-3-yl)ethyl)-2-oxa-6-azaspiro[3.3]heptane; and
6-(1-(3-(6-chloro-7-fluoro-3-(1H-imidazol-1-yl)-5-methoxy-1-methyl-1H-indol-2-yl)-1H-1,2,4-triazol-5-yl)ethyl)-2-oxa-6-azaspiro[3.3]heptane;
or a pharmaceutically acceptable salt, hydrate, solvate, stereoisomer, or tautomer thereof.

2. A pharmaceutical composition comprising a compound according to claim 1, or a pharmaceutically acceptable salt, hydrate, solvate, stereoisomer, or tautomer thereof, and a pharmaceutically acceptable carrier or excipient.

3. The compound of claim 1 selected from:
(S)-6,7-dichloro-2-(5-(1-fluoro-2-methoxyethyl)-4H-1,2,4-triazol-3-yl)-3-(1H-pyrazol-4-yl)-1H-indole;
(S)-6,7-dichloro-2-(3-(1-fluoro-2-methoxyethyl)-1H-1,2,4-triazol-5-yl)-3-(1H-pyrazol-4-yl)-1H-indole;
(S)-6,7-dichloro-2-(5-(1-fluoro-2-methoxyethyl)-1H-1,2,4-triazol-3-yl)-3-(1H-pyrazol-4-yl)-1H-indole;
(R)-6,7-dichloro-2-(5-(1-fluoro-2-methoxyethyl)-4H-1,2,4-triazol-3-yl)-3-(1H-pyrazol-4-yl)-1H-indole;
(R)-6,7-dichloro-2-(3-(1-fluoro-2-methoxyethyl)-1H-1,2,4-triazol-5-yl)-3-(1H-pyrazol-4-yl)-1H-indole;
(R)-6,7-dichloro-2-(5-(1-fluoro-2-methoxyethyl)-1H-1,2,4-triazol-3-yl)-3-(1H-pyrazol-4-yl)-1H-indole;
(S)-(5-(6-chloro-7-fluoro-3-(1H-imidazol-1-yl)-5-methoxy-1-methyl-1H-indol-2-yl)-4H-1,2,4-triazol-3-yl) (3-hydroxypyrrolidin-1-yl) methanone;
(S)-(5-(6-chloro-7-fluoro-3-(1H-imidazol-1-yl)-5-methoxy-1-methyl-1H-indol-2-yl)-1H-1,2,4-triazol-3-yl) (3-hydroxypyrrolidin-1-yl) methanone;
(S)-(3-(6-chloro-7-fluoro-3-(1H-imidazol-1-yl)-5-methoxy-1-methyl-1H-indol-2-yl)-1H-1,2,4-triazol-5-yl) (3-hydroxypyrrolidin-1-yl) methanone;
(R)-(5-(6-chloro-7-fluoro-3-(1H-imidazol-1-yl)-5-methoxy-1-methyl-1H-indol-2-yl)-4H-1,2,4-triazol-3-yl) (3-hydroxypyrrolidin-1-yl) methanone;
(R)-(5-(6-chloro-7-fluoro-3-(1H-imidazol-1-yl)-5-methoxy-1-methyl-1H-indol-2-yl)-1H-1,2,4-triazol-3-yl) (3-hydroxypyrrolidin-1-yl) methanone;
(R)-(3-(6-chloro-7-fluoro-3-(1H-imidazol-1-yl)-5-methoxy-1-methyl-1H-indol-2-yl)-1H-1,2,4-triazol-5-yl) (3-hydroxypyrrolidin-1-yl) methanone;
(S)-(5-(6-chloro-7-fluoro-3-(1H-imidazol-1-yl)-5-methoxy-1-methyl-1H-indol-2-yl)-4H-1,2,4-triazol-3-yl) (3-hydroxypiperidin-1-yl) methanone;
(S)-(5-(6-chloro-7-fluoro-3-(1H-imidazol-1-yl)-5-methoxy-1-methyl-1H-indol-2-yl)-1H-1,2,4-triazol-3-yl) (3-hydroxypiperidin-1-yl) methanone;
(S)-(3-(6-chloro-7-fluoro-3-(1H-imidazol-1-yl)-5-methoxy-1-methyl-1H-indol-2-yl)-1H-1,2,4-triazol-5-yl) (3-hydroxypiperidin-1-yl) methanone;
(R)-(5-(6-chloro-7-fluoro-3-(1H-imidazol-1-yl)-5-methoxy-1-methyl-1H-indol-2-yl)-4H-1,2,4-triazol-3-yl) (3-hydroxypiperidin-1-yl) methanone;
(R)-(5-(6-chloro-7-fluoro-3-(1H-imidazol-1-yl)-5-methoxy-1-methyl-1H-indol-2-yl)-1H-1,2,4-triazol-3-yl) (3-hydroxypiperidin-1-yl) methanone;
(R)-(3-(6-chloro-7-fluoro-3-(1H-imidazol-1-yl)-5-methoxy-1-methyl-1H-indol-2-yl)-1H-1,2,4-triazol-5-yl) (3-hydroxypiperidin-1-yl) methanone;
(S)-6-chloro-2-(5-(1-hydroxy-2-methoxyethyl)-4H-1,2,4-triazol-3-yl)-3-(1H-imidazol-1-yl)-5-methoxy-1-methyl-1H-indole-7-carbonitrile;
(S)-6-chloro-2-(3-(1-hydroxy-2-methoxyethyl)-1H-1,2,4-triazol-5-yl)-3-(1H-imidazol-1-yl)-5-methoxy-1-methyl-1H-indole-7-carbonitrile;
(S)-6-chloro-2-(5-(1-hydroxy-2-methoxyethyl)-1H-1,2,4-triazol-3-yl)-3-(1H-imidazol-1-yl)-5-methoxy-1-methyl-1H-indole-7-carbonitrile;
(R)-6-chloro-2-(5-(1-hydroxy-2-methoxyethyl)-4H-1,2,4-triazol-3-yl)-3-(1H-imidazol-1-yl)-5-methoxy-1-methyl-1H-indole-7-carbonitrile;
(R)-6-chloro-2-(3-(1-hydroxy-2-methoxyethyl)-1H-1,2,4-triazol-5-yl)-3-(1H-imidazol-1-yl)-5-methoxy-1-methyl-1H-indole-7-carbonitrile;
(R)-6-chloro-2-(5-(1-hydroxy-2-methoxyethyl)-1H-1,2,4-triazol-3-yl)-3-(1H-imidazol-1-yl)-5-methoxy-1-methyl-1H-indole-7-carbonitrile;
(R)-1-(5-(6-chloro-7-fluoro-5-methoxy-1-methyl-3-(1H-pyrazol-4-yl)-1H-indol-2-yl)-4H-1,2,4-triazol-3-yl)-2-methoxyethan-1-ol;

(R)-1-(5-(6-chloro-7-fluoro-5-methoxy-1-methyl-3-(1H-pyrazol-4-yl)-1H-indol-2-yl)-1H-1,2,4-triazol-3-yl)-2-methoxyethan-1-ol;
(R)-1-(3-(6-chloro-7-fluoro-5-methoxy-1-methyl-3-(1H-pyrazol-4-yl)-1H-indol-2-yl)-1H-1,2,4-triazol-5-yl)-2-methoxyethan-1-ol;
(S)-1-(5-(6-chloro-7-fluoro-5-methoxy-1-methyl-3-(1H-pyrazol-4-yl)-1H-indol-2-yl)-4H-1,2,4-triazol-3-yl)-2-methoxyethan-1-ol;
(S)-1-(5-(6-chloro-7-fluoro-5-methoxy-1-methyl-3-(1H-pyrazol-4-yl)-1H-indol-2-yl)-1H-1,2,4-triazol-3-yl)-2-methoxyethan-1-ol;
(S)-1-(3-(6-chloro-7-fluoro-5-methoxy-1-methyl-3-(1H-pyrazol-4-yl)-1H-indol-2-yl)-1H-1,2,4-triazol-5-yl)-2-methoxyethan-1-ol;
(S)-6-chloro-7-fluoro-2-(5-(1-fluoro-2-methoxyethyl)-4H-1,2,4-triazol-3-yl)-5-methoxy-1-methyl-3-(1H-pyrazol-4-yl)-1H-indole;
(S)-6-chloro-7-fluoro-2-(3-(1-fluoro-2-methoxyethyl)-1H-1,2,4-triazol-5-yl)-5-methoxy-1-methyl-3-(1H-pyrazol-4-yl)-1H-indole;
(S)-6-chloro-7-fluoro-2-(5-(1-fluoro-2-methoxyethyl)-1H-1,2,4-triazol-3-yl)-5-methoxy-1-methyl-3-(1H-pyrazol-4-yl)-1H-indole;
(R)-6-chloro-7-fluoro-2-(5-(1-fluoro-2-methoxyethyl)-4H-1,2,4-triazol-3-yl)-5-methoxy-1-methyl-3-(1H-pyrazol-4-yl)-1H-indole;
(R)-6-chloro-7-fluoro-2-(3-(1-fluoro-2-methoxyethyl)-1H-1,2,4-triazol-5-yl)-5-methoxy-1-methyl-3-(1H-pyrazol-4-yl)-1H-indole;
(R)-6-chloro-7-fluoro-2-(5-(1-fluoro-2-methoxyethyl)-1H-1,2,4-triazol-3-yl)-5-methoxy-1-methyl-3-(1H-pyrazol-4-yl)-1H-indole;
(R)-6-chloro-7-fluoro-2-(5-(1-fluoroethyl)-4H-1,2,4-triazol-3-yl)-5-methoxy-3-(1H-pyrazol-4-yl)-1H-indole;
(R)-6-chloro-7-fluoro-2-(3-(1-fluoroethyl)-1H-1,2,4-triazol-5-yl)-5-methoxy-3-(1H-pyrazol-4-yl)-1H-indole;
(R)-6-chloro-7-fluoro-2-(5-(1-fluoroethyl)-1H-1,2,4-triazol-3-yl)-5-methoxy-3-(1H-pyrazol-4-yl)-1H-indole;
(S)-6-chloro-7-fluoro-2-(5-(1-fluoroethyl)-4H-1,2,4-triazol-3-yl)-5-methoxy-3-(1H-pyrazol-4-yl)-1H-indole;
(S)-6-chloro-7-fluoro-2-(3-(1-fluoroethyl)-1H-1,2,4-triazol-5-yl)-5-methoxy-3-(1H-pyrazol-4-yl)-1H-indole;
(S)-6-chloro-7-fluoro-2-(5-(1-fluoroethyl)-1H-1,2,4-triazol-3-yl)-5-methoxy-3-(1H-pyrazol-4-yl)-1H-indole;
(R)-6-chloro-7-fluoro-2-(5-(1-fluoroethyl)-4H-1,2,4-triazol-3-yl)-5-methoxy-1-methyl-3-(1H-pyrazol-4-yl)-1H-indole;
(R)-6-chloro-7-fluoro-2-(3-(1-fluoroethyl)-1H-1,2,4-triazol-5-yl)-5-methoxy-1-methyl-3-(1H-pyrazol-4-yl)-1H-indole;
(R)-6-chloro-7-fluoro-2-(5-(1-fluoroethyl)-1H-1,2,4-triazol-3-yl)-5-methoxy-1-methyl-3-(1H-pyrazol-4-yl)-1H-indole;
(S)-6-chloro-7-fluoro-2-(5-(1-fluoroethyl)-4H-1,2,4-triazol-3-yl)-5-methoxy-1-methyl-3-(1H-pyrazol-4-yl)-1H-indole;
(S)-6-chloro-7-fluoro-2-(3-(1-fluoroethyl)-1H-1,2,4-triazol-5-yl)-5-methoxy-1-methyl-3-(1H-pyrazol-4-yl)-1H-indole;
(S)-6-chloro-7-fluoro-2-(5-(1-fluoroethyl)-1H-1,2,4-triazol-3-yl)-5-methoxy-1-methyl-3-(1H-pyrazol-4-yl)-1H-indole;
(R)-2-(5-(6-chloro-7-fluoro-5-methoxy-1-methyl-3-(1H-pyrazol-4-yl)-1H-indol-2-yl)-4H-1,2,4-triazol-3-yl)-2-methoxy-N,N-dimethylethan-1-amine;
(R)-2-(5-(6-chloro-7-fluoro-5-methoxy-1-methyl-3-(1H-pyrazol-4-yl)-1H-indol-2-yl)-1H-1,2,4-triazol-3-yl)-2-methoxy-N,N-dimethylethan-1-amine;
(R)-2-(3-(6-chloro-7-fluoro-5-methoxy-1-methyl-3-(1H-pyrazol-4-yl)-1H-indol-2-yl)-1H-1,2,4-triazol-5-yl)-2-methoxy-N,N-dimethylethan-1-amine;
(S)-2-(5-(6-chloro-7-fluoro-5-methoxy-1-methyl-3-(1H-pyrazol-4-yl)-1H-indol-2-yl)-4H-1,2,4-triazol-3-yl)-2-methoxy-N,N-dimethylethan-1-amine;
(S)-2-(5-(6-chloro-7-fluoro-5-methoxy-1-methyl-3-(1H-pyrazol-4-yl)-1H-indol-2-yl)-1H-1,2,4-triazol-3-yl)-2-methoxy-N,N-dimethylethan-1-amine;
(S)-2-(3-(6-chloro-7-fluoro-5-methoxy-1-methyl-3-(1H-pyrazol-4-yl)-1H-indol-2-yl)-1H-1,2,4-triazol-5-yl)-2-methoxy-N,N-dimethylethan-1-amine;
(S)-1-(5-(6-chloro-7-fluoro-5-methoxy-3-(1H-pyrazol-4-yl)-1H-indol-2-yl)-4H-1,2,4-triazol-3-yl)-N,N-dimethylethan-1-amine;
(S)-1-(5-(6-chloro-7-fluoro-5-methoxy-3-(1H-pyrazol-4-yl)-1H-indol-2-yl)-1H-1,2,4-triazol-3-yl)-N,N-dimethylethan-1-amine;
(S)-1-(3-(6-chloro-7-fluoro-5-methoxy-3-(1H-pyrazol-4-yl)-1H-indol-2-yl)-1H-1,2,4-triazol-5-yl)-N,N-dimethylethan-1-amine;
(R)-1-(5-(6-chloro-7-fluoro-5-methoxy-3-(1H-pyrazol-4-yl)-1H-indol-2-yl)-4H-1,2,4-triazol-3-yl)-N,N-dimethylethan-1-amine;
(R)-1-(5-(6-chloro-7-fluoro-5-methoxy-3-(1H-pyrazol-4-yl)-1H-indol-2-yl)-1H-1,2,4-triazol-3-yl)-N,N-dimethylethan-1-amine;
(R)-1-(3-(6-chloro-7-fluoro-5-methoxy-3-(1H-pyrazol-4-yl)-1H-indol-2-yl)-1H-1,2,4-triazol-5-yl)-N,N-dimethylethan-1-amine;
(S)-1-(5-(6-chloro-7-fluoro-5-methoxy-1-methyl-3-(1H-pyrazol-4-yl)-1H-indol-2-yl)-4H-1,2,4-triazol-3-yl)-N,N-dimethylethan-1-amine;
(S)-1-(5-(6-chloro-7-fluoro-5-methoxy-1-methyl-3-(1H-pyrazol-4-yl)-1H-indol-2-yl)-1H-1,2,4-triazol-3-yl)-N,N-dimethylethan-1-amine;
(S)-1-(3-(6-chloro-7-fluoro-5-methoxy-1-methyl-3-(1H-pyrazol-4-yl)-1H-indol-2-yl)-1H-1,2,4-triazol-5-yl)-N,N-dimethylethan-1-amine;
(R)-1-(5-(6-chloro-7-fluoro-5-methoxy-1-methyl-3-(1H-pyrazol-4-yl)-1H-indol-2-yl)-4H-1,2,4-triazol-3-yl)-N,N-dimethylethan-1-amine;
(R)-1-(5-(6-chloro-7-fluoro-5-methoxy-1-methyl-3-(1H-pyrazol-4-yl)-1H-indol-2-yl)-1H-1,2,4-triazol-3-yl)-N,N-dimethylethan-1-amine;
(R)-1-(3-(6-chloro-7-fluoro-5-methoxy-1-methyl-3-(1H-pyrazol-4-yl)-1H-indol-2-yl)-1H-1,2,4-triazol-5-yl)-N,N-dimethylethan-1-amine;
(R)-1-(5-(6-chloro-7-fluoro-5-methoxy-1-methyl-3-(1H-pyrazol-4-yl)-1H-indol-2-yl)-4H-1,2,4-triazol-3-yl)-2-methoxy-N,N-dimethylethan-1-amine;
(R)-1-(5-(6-chloro-7-fluoro-5-methoxy-1-methyl-3-(1H-pyrazol-4-yl)-1H-indol-2-yl)-1H-1,2,4-triazol-3-yl)-2-methoxy-N,N-dimethylethan-1-amine;
(R)-1-(3-(6-chloro-7-fluoro-5-methoxy-1-methyl-3-(1H-pyrazol-4-yl)-1H-indol-2-yl)-1H-1,2,4-triazol-5-yl)-2-methoxy-N,N-dimethylethan-1-amine;
(S)-1-(5-(6-chloro-7-fluoro-5-methoxy-1-methyl-3-(1H-pyrazol-4-yl)-1H-indol-2-yl)-4H-1,2,4-triazol-3-yl)-2-methoxy-N,N-dimethylethan-1-amine;
(S)-1-(5-(6-chloro-7-fluoro-5-methoxy-1-methyl-3-(1H-pyrazol-4-yl)-1H-indol-2-yl)-1H-1,2,4-triazol-3-yl)-2-methoxy-N,N-dimethylethan-1-amine;

(S)-1-(3-(6-chloro-7-fluoro-5-methoxy-1-methyl-3-(1H-pyrazol-4-yl)-1H-indol-2-yl)-1H-1,2,4-triazol-5-yl)-2-methoxy-N,N-dimethylethan-1-amine;
(R)-2-(5-(6-chloro-7-fluoro-5-methoxy-1-methyl-3-(1H-pyrazol-4-yl)-1H-indol-2-yl)-4H-1,2,4-triazol-3-yl) propanenitrile;
(R)-2-(5-(6-chloro-7-fluoro-5-methoxy-1-methyl-3-(1H-pyrazol-4-yl)-1H-indol-2-yl)-1H-1,2,4-triazol-3-yl) propanenitrile;
(R)-2-(3-(6-chloro-7-fluoro-5-methoxy-1-methyl-3-(1H-pyrazol-4-yl)-1H-indol-2-yl)-1H-1,2,4-triazol-5-yl) propanenitrile;
(S)-2-(5-(6-chloro-7-fluoro-5-methoxy-1-methyl-3-(1H-pyrazol-4-yl)-1H-indol-2-yl)-4H-1,2,4-triazol-3-yl) propanenitrile;
(S)-2-(5-(6-chloro-7-fluoro-5-methoxy-1-methyl-3-(1H-pyrazol-4-yl)-1H-indol-2-yl)-1H-1,2,4-triazol-3-yl) propanenitrile;
(S)-2-(3-(6-chloro-7-fluoro-5-methoxy-1-methyl-3-(1H-pyrazol-4-yl)-1H-indol-2-yl)-1H-1,2,4-triazol-5-yl) propanenitrile;
(S)-1-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-ol;
(S)-1-(5-(6-chloro-7-fluoro-3-(1H-imidazol-1-yl)-5-methoxy-1-methyl-1H-indol-2-yl)-1H-1,2,4-triazol-3-yl)-2-methoxyethan-1-ol;
(S)-1-(3-(6-chloro-7-fluoro-3-(1H-imidazol-1-yl)-5-methoxy-1-methyl-1H-indol-2-yl)-1H-1,2,4-triazol-5-yl)-2-methoxyethan-1-ol;
(R)-1-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-ol;
(R)-1-(5-(6-chloro-7-fluoro-3-(1H-imidazol-1-yl)-5-methoxy-1-methyl-1H-indol-2-yl)-1H-1,2,4-triazol-3-yl)-2-methoxyethan-1-ol;
(R)-1-(3-(6-chloro-7-fluoro-3-(1H-imidazol-1-yl)-5-methoxy-1-methyl-1H-indol-2-yl)-1H-1,2,4-triazol-5-yl)-2-methoxyethan-1-ol;
(R)-1-(5-(6-chloro-7-fluoro-3-(1H-imidazol-1-yl)-5-methoxy-1-methyl-1H-indol-2-yl)-4H-1,2,4-triazol-3-yl) pyrrolidin-3-ol;
(R)-1-(5-(6-chloro-7-fluoro-3-(1H-imidazol-1-yl)-5-methoxy-1-methyl-1H-indol-2-yl)-1H-1,2,4-triazol-3-yl) pyrrolidin-3-ol;
(R)-1-(3-(6-chloro-7-fluoro-3-(1H-imidazol-1-yl)-5-methoxy-1-methyl-1H-indol-2-yl)-1H-1,2,4-triazol-5-yl) pyrrolidin-3-ol;
(S)-1-(5-(6-chloro-7-fluoro-3-(1H-imidazol-1-yl)-5-methoxy-1-methyl-1H-indol-2-yl)-4H-1,2,4-triazol-3-yl) pyrrolidin-3-ol;
(S)-1-(5-(6-chloro-7-fluoro-3-(1H-imidazol-1-yl)-5-methoxy-1-methyl-1H-indol-2-yl)-1H-1,2,4-triazol-3-yl) pyrrolidin-3-ol;
(S)-1-(3-(6-chloro-7-fluoro-3-(1H-imidazol-1-yl)-5-methoxy-1-methyl-1H-indol-2-yl)-1H-1,2,4-triazol-5-yl) pyrrolidin-3-ol;
(S)-2-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-ol;
(S)-2-(5-(6-chloro-7-fluoro-3-(1H-imidazol-1-yl)-5-methoxy-1-methyl-1H-indol-2-yl)-1H-1,2,4-triazol-3-yl)-2-methoxyethan-1-ol;
(S)-2-(3-(6-chloro-7-fluoro-3-(1H-imidazol-1-yl)-5-methoxy-1-methyl-1H-indol-2-yl)-1H-1,2,4-triazol-5-yl)-2-methoxyethan-1-ol;
(R)-2-(5-(6-chloro-7-fluoro-3-(1H-imidazol-1-yl)-5-methoxy-1-methyl-1H-indol-2-yl)-4H-1,2,4-triazol-3-yl)-2-methoxyethan-1-ol;
(R)-2-(5-(6-chloro-7-fluoro-3-(1H-imidazol-1-yl)-5-methoxy-1-methyl-1H-indol-2-yl)-1H-1,2,4-triazol-3-yl)-2-methoxyethan-1-ol;
(R)-2-(3-(6-chloro-7-fluoro-3-(1H-imidazol-1-yl)-5-methoxy-1-methyl-1H-indol-2-yl)-1H-1,2,4-triazol-5-yl)-2-methoxyethan-1-ol;
(S)-1-(5-(6-chloro-7-fluoro-3-(1H-imidazol-1-yl)-5-methoxy-1-methyl-1H-indol-2-yl)-4H-1,2,4-triazol-3-yl)-2,2-difluoroethan-1-ol;
(S)-1-(5-(6-chloro-7-fluoro-3-(1H-imidazol-1-yl)-5-methoxy-1-methyl-1H-indol-2-yl)-1H-1,2,4-triazol-3-yl)-2,2-difluoroethan-1-ol;
(S)-1-(3-(6-chloro-7-fluoro-3-(1H-imidazol-1-yl)-5-methoxy-1-methyl-1H-indol-2-yl)-1H-1,2,4-triazol-5-yl)-2,2-difluoroethan-1-ol;
(R)-1-(5-(6-chloro-7-fluoro-3-(1H-imidazol-1-yl)-5-methoxy-1-methyl-1H-indol-2-yl)-4H-1,2,4-triazol-3-yl)-2,2-difluoroethan-1-ol;
(R)-1-(5-(6-chloro-7-fluoro-3-(1H-imidazol-1-yl)-5-methoxy-1-methyl-1H-indol-2-yl)-1H-1,2,4-triazol-3-yl)-2,2-difluoroethan-1-ol;
(R)-1-(3-(6-chloro-7-fluoro-3-(1H-imidazol-1-yl)-5-methoxy-1-methyl-1H-indol-2-yl)-1H-1,2,4-triazol-5-yl)-2,2-difluoroethan-1-ol;
(R)-2-(5-(6-chloro-7-fluoro-3-(1H-imidazol-1-yl)-5-methoxy-1-methyl-1H-indol-2-yl)-4H-1,2,4-triazol-3-yl)-2-methoxy-N,N-dimethylethan-1-amine;
(R)-2-(5-(6-chloro-7-fluoro-3-(1H-imidazol-1-yl)-5-methoxy-1-methyl-1H-indol-2-yl)-1H-1,2,4-triazol-3-yl)-2-methoxy-N,N-dimethylethan-1-amine;
(R)-2-(3-(6-chloro-7-fluoro-3-(1H-imidazol-1-yl)-5-methoxy-1-methyl-1H-indol-2-yl)-1H-1,2,4-triazol-5-yl)-2-methoxy-N,N-dimethylethan-1-amine;
(S)-2-(5-(6-chloro-7-fluoro-3-(1H-imidazol-1-yl)-5-methoxy-1-methyl-1H-indol-2-yl)-4H-1,2,4-triazol-3-yl)-2-methoxy-N,N-dimethylethan-1-amine;
(S)-2-(5-(6-chloro-7-fluoro-3-(1H-imidazol-1-yl)-5-methoxy-1-methyl-1H-indol-2-yl)-1H-1,2,4-triazol-3-yl)-2-methoxy-N,N-dimethylethan-1-amine;
(S)-2-(3-(6-chloro-7-fluoro-3-(1H-imidazol-1-yl)-5-methoxy-1-methyl-1H-indol-2-yl)-1H-1,2,4-triazol-5-yl)-2-methoxy-N,N-dimethylethan-1-amine;
(S)-1-(5-(6-chloro-7-fluoro-3-(1H-imidazol-1-yl)-5-methoxy-1-methyl-1H-indol-2-yl)-4H-1,2,4-triazol-3-yl)-2,2,2-trifluoroethan-1-ol;
(S)-1-(5-(6-chloro-7-fluoro-3-(1H-imidazol-1-yl)-5-methoxy-1-methyl-1H-indol-2-yl)-1H-1,2,4-triazol-3-yl)-2,2,2-trifluoroethan-1-ol;
(S)-1-(3-(6-chloro-7-fluoro-3-(1H-imidazol-1-yl)-5-methoxy-1-methyl-1H-indol-2-yl)-1H-1,2,4-triazol-5-yl)-2,2,2-trifluoroethan-1-ol;
(R)-1-(5-(6-chloro-7-fluoro-3-(1H-imidazol-1-yl)-5-methoxy-1-methyl-1H-indol-2-yl)-4H-1,2,4-triazol-3-yl)-2,2,2-trifluoroethan-1-ol;
(R)-1-(5-(6-chloro-7-fluoro-3-(1H-imidazol-1-yl)-5-methoxy-1-methyl-1H-indol-2-yl)-1H-1,2,4-triazol-3-yl)-2,2,2-trifluoroethan-1-ol;
(R)-1-(3-(6-chloro-7-fluoro-3-(1H-imidazol-1-yl)-5-methoxy-1-methyl-1H-indol-2-yl)-1H-1,2,4-triazol-5-yl)-2,2,2-trifluoroethan-1-ol;
(S)-6-chloro-2-(5-(2,2-difluoro-1-methoxyethyl)-4H-1,2,4-triazol-3-yl)-7-fluoro-3-(1H-imidazol-1-yl)-5-methoxy-1-methyl-1H-indole;

(S)-6-chloro-2-(3-(2,2-difluoro-1-methoxyethyl)-1H-1,2,4-triazol-5-yl)-7-fluoro-3-(1H-imidazol-1-yl)-5-methoxy-1-methyl-1H-indole;
(S)-6-chloro-2-(5-(2,2-difluoro-1-methoxyethyl)-1H-1,2,4-triazol-3-yl)-7-fluoro-3-(1H-imidazol-1-yl)-5-methoxy-1-methyl-1H-indole;
(R)-6-chloro-2-(5-(2,2-difluoro-1-methoxyethyl)-4H-1,2,4-triazol-3-yl)-7-fluoro-3-(1H-imidazol-1-yl)-5-methoxy-1-methyl-1H-indole;
(R)-6-chloro-2-(3-(2,2-difluoro-1-methoxyethyl)-1H-1,2,4-triazol-5-yl)-7-fluoro-3-(1H-imidazol-1-yl)-5-methoxy-1-methyl-1H-indole;
(R)-6-chloro-2-(5-(2,2-difluoro-1-methoxyethyl)-1H-1,2,4-triazol-3-yl)-7-fluoro-3-(1H-imidazol-1-yl)-5-methoxy-1-methyl-1H-indole;
(S)-2-(5-(1-(1H-imidazol-1-yl)-2-methoxyethyl)-4H-1,2,4-triazol-3-yl)-6-chloro-7-fluoro-3-(1H-imidazol-1-yl)-5-methoxy-1-methyl-1H-indole;
(S)-2-(3-(1-(1H-imidazol-1-yl)-2-methoxyethyl)-1H-1,2,4-triazol-5-yl)-6-chloro-7-fluoro-3-(1H-imidazol-1-yl)-5-methoxy-1-methyl-1H-indole;
(S)-2-(5-(1-(1H-imidazol-1-yl)-2-methoxyethyl)-1H-1,2,4-triazol-3-yl)-6-chloro-7-fluoro-3-(1H-imidazol-1-yl)-5-methoxy-1-methyl-1H-indole;
(R)-2-(5-(1-(1H-imidazol-1-yl)-2-methoxyethyl)-4H-1,2,4-triazol-3-yl)-6-chloro-7-fluoro-3-(1H-imidazol-1-yl)-5-methoxy-1-methyl-1H-indole;
(R)-2-(3-(1-(1H-imidazol-1-yl)-2-methoxyethyl)-1H-1,2,4-triazol-5-yl)-6-chloro-7-fluoro-3-(1H-imidazol-1-yl)-5-methoxy-1-methyl-1H-indole;
(R)-2-(5-(1-(1H-imidazol-1-yl)-2-methoxyethyl)-1H-1,2,4-triazol-3-yl)-6-chloro-7-fluoro-3-(1H-imidazol-1-yl)-5-methoxy-1-methyl-1H-indole;
(S)-4-(1-(5-(6-chloro-7-fluoro-3-(1H-imidazol-1-yl)-5-methoxy-1-methyl-1H-indol-2-yl)-4H-1,2,4-triazol-3-yl)ethyl) morpholine;
(S)-4-(1-(5-(6-chloro-7-fluoro-3-(1H-imidazol-1-yl)-5-methoxy-1-methyl-1H-indol-2-yl)-1H-1,2,4-triazol-3-yl)ethyl) morpholine;
(S)-4-(1-(3-(6-chloro-7-fluoro-3-(1H-imidazol-1-yl)-5-methoxy-1-methyl-1H-indol-2-yl)-1H-1,2,4-triazol-5-yl)ethyl) morpholine;
(R)-4-(1-(5-(6-chloro-7-fluoro-3-(1H-imidazol-1-yl)-5-methoxy-1-methyl-1H-indol-2-yl)-4H-1,2,4-triazol-3-yl)ethyl) morpholine;
(R)-4-(1-(5-(6-chloro-7-fluoro-3-(1H-imidazol-1-yl)-5-methoxy-1-methyl-1H-indol-2-yl)-1H-1,2,4-triazol-3-yl)ethyl) morpholine;
(R)-4-(1-(3-(6-chloro-7-fluoro-3-(1H-imidazol-1-yl)-5-methoxy-1-methyl-1H-indol-2-yl)-1H-1,2,4-triazol-5-yl)ethyl) morpholine;
(S)-1-(5-(6-chloro-7-fluoro-3-(1H-imidazol-1-yl)-5-methoxy-1-methyl-1H-indol-2-yl)-4H-1,2,4-triazol-3-yl)-N,N-dimethylethan-1-amine;
(S)-1-(5-(6-chloro-7-fluoro-3-(1H-imidazol-1-yl)-5-methoxy-1-methyl-1H-indol-2-yl)-1H-1,2,4-triazol-3-yl)-N,N-dimethylethan-1-amine;
(S)-1-(3-(6-chloro-7-fluoro-3-(1H-imidazol-1-yl)-5-methoxy-1-methyl-1H-indol-2-yl)-1H-1,2,4-triazol-5-yl)-N,N-dimethylethan-1-amine;
(R)-1-(5-(6-chloro-7-fluoro-3-(1H-imidazol-1-yl)-5-methoxy-1-methyl-1H-indol-2-yl)-4H-1,2,4-triazol-3-yl)-N,N-dimethylethan-1-amine;
(R)-1-(5-(6-chloro-7-fluoro-3-(1H-imidazol-1-yl)-5-methoxy-1-methyl-1H-indol-2-yl)-1H-1,2,4-triazol-3-yl)-N,N-dimethylethan-1-amine;
(R)-1-(3-(6-chloro-7-fluoro-3-(1H-imidazol-1-yl)-5-methoxy-1-methyl-1H-indol-2-yl)-1H-1,2,4-triazol-5-yl)-N,N-dimethylethan-1-amine;
(S)-1-(5-(6-chloro-7-fluoro-3-(1H-imidazol-1-yl)-5-methoxy-1-methyl-1H-indol-2-yl)-4H-1,2,4-triazol-3-yl)-N-methylethan-1-amine;
(S)-1-(5-(6-chloro-7-fluoro-3-(1H-imidazol-1-yl)-5-methoxy-1-methyl-1H-indol-2-yl)-1H-1,2,4-triazol-3-yl)-N-methylethan-1-amine;
(S)-1-(3-(6-chloro-7-fluoro-3-(1H-imidazol-1-yl)-5-methoxy-1-methyl-1H-indol-2-yl)-1H-1,2,4-triazol-5-yl)-N-methylethan-1-amine;
(R)-1-(5-(6-chloro-7-fluoro-3-(1H-imidazol-1-yl)-5-methoxy-1-methyl-1H-indol-2-yl)-1H-1,2,4-triazol-3-yl)-N-methylethan-1-amine;
(R)-1-(3-(6-chloro-7-fluoro-3-(1H-imidazol-1-yl)-5-methoxy-1-methyl-1H-indol-2-yl)-1H-1,2,4-triazol-5-yl)-N-methylethan-1-amine;
(R)-1-(5-(6-chloro-7-fluoro-3-(1H-imidazol-1-yl)-5-methoxy-1-methyl-1H-indol-2-yl)-4H-1,2,4-triazol-3-yl)-2-methoxy-N,N-dimethylethan-1-amine;
(R)-1-(5-(6-chloro-7-fluoro-3-(1H-imidazol-1-yl)-5-methoxy-1-methyl-1H-indol-2-yl)-1H-1,2,4-triazol-3-yl)-2-methoxy-N,N-dimethylethan-1-amine;
(R)-1-(3-(6-chloro-7-fluoro-3-(1H-imidazol-1-yl)-5-methoxy-1-methyl-1H-indol-2-yl)-1H-1,2,4-triazol-5-yl)-2-methoxy-N,N-dimethylethan-1-amine;
(S)-1-(5-(6-chloro-7-fluoro-3-(1H-imidazol-1-yl)-5-methoxy-1-methyl-1H-indol-2-yl)-4H-1,2,4-triazol-3-yl)-2-methoxy-N,N-dimethylethan-1-amine;
(S)-1-(5-(6-chloro-7-fluoro-3-(1H-imidazol-1-yl)-5-methoxy-1-methyl-1H-indol-2-yl)-1H-1,2,4-triazol-3-yl)-2-methoxy-N,N-dimethylethan-1-amine;
(S)-1-(3-(6-chloro-7-fluoro-3-(1H-imidazol-1-yl)-5-methoxy-1-methyl-1H-indol-2-yl)-1H-1,2,4-triazol-5-yl)-2-methoxy-N,N-dimethylethan-1-amine;
(R)-1-(5-(6-chloro-7-fluoro-3-(1H-imidazol-1-yl)-5-methoxy-1-methyl-1H-indol-2-yl)-4H-1,2,4-triazol-3-yl)-2-methoxy-N-methylethan-1-amine;
(R)-1-(5-(6-chloro-7-fluoro-3-(1H-imidazol-1-yl)-5-methoxy-1-methyl-1H-indol-2-yl)-1H-1,2,4-triazol-3-yl)-2-methoxy-N-methylethan-1-amine;
(R)-1-(3-(6-chloro-7-fluoro-3-(1H-imidazol-1-yl)-5-methoxy-1-methyl-1H-indol-2-yl)-1H-1,2,4-triazol-5-yl)-2-methoxy-N-methylethan-1-amine;
(S)-1-(5-(6-chloro-7-fluoro-3-(1H-imidazol-1-yl)-5-methoxy-1-methyl-1H-indol-2-yl)-4H-1,2,4-triazol-3-yl)-2-methoxy-N-methylethan-1-amine;
(S)-1-(5-(6-chloro-7-fluoro-3-(1H-imidazol-1-yl)-5-methoxy-1-methyl-1H-indol-2-yl)-1H-1,2,4-triazol-3-yl)-2-methoxy-N-methylethan-1-amine;
(S)-1-(3-(6-chloro-7-fluoro-3-(1H-imidazol-1-yl)-5-methoxy-1-methyl-1H-indol-2-yl)-1H-1,2,4-triazol-5-yl)-2-methoxy-N-methylethan-1-amine;
(R)-4-(1-(5-(6-chloro-7-fluoro-3-(1H-imidazol-1-yl)-5-methoxy-1-methyl-1H-indol-2-yl)-4H-1,2,4-triazol-3-yl)-2-methoxyethyl) morpholine;
(R)-4-(1-(5-(6-chloro-7-fluoro-3-(1H-imidazol-1-yl)-5-methoxy-1-methyl-1H-indol-2-yl)-1H-1,2,4-triazol-3-yl)-2-methoxyethyl) morpholine;
(R)-4-(1-(3-(6-chloro-7-fluoro-3-(1H-imidazol-1-yl)-5-methoxy-1-methyl-1H-indol-2-yl)-1H-1,2,4-triazol-5-yl)-2-methoxyethyl) morpholine;

(S)-4-(1-(5-(6-chloro-7-fluoro-3-(1H-imidazol-1-yl)-5-methoxy-1-methyl-1H-indol-2-yl)-4H-1,2,4-triazol-3-yl)-2-methoxyethyl) morpholine;
(S)-4-(1-(5-(6-chloro-7-fluoro-3-(1H-imidazol-1-yl)-5-methoxy-1-methyl-1H-indol-2-yl)-1H-1,2,4-triazol-3-yl)-2-methoxyethyl) morpholine;
(S)-4-(1-(3-(6-chloro-7-fluoro-3-(1H-imidazol-1-yl)-5-methoxy-1-methyl-1H-indol-2-yl)-1H-1,2,4-triazol-5-yl)-2-methoxyethyl) morpholine;
(R)-2-(5-(1-(azetidin-1-yl)-2-methoxyethyl)-4H-1,2,4-triazol-3-yl)-6-chloro-7-fluoro-3-(1H-imidazol-1-yl)-5-methoxy-1-methyl-1H-indole;
(R)-2-(3-(1-(azetidin-1-yl)-2-methoxyethyl)-1H-1,2,4-triazol-5-yl)-6-chloro-7-fluoro-3-(1H-imidazol-1-yl)-5-methoxy-1-methyl-1H-indole;
(R)-2-(5-(1-(azetidin-1-yl)-2-methoxyethyl)-1H-1,2,4-triazol-3-yl)-6-chloro-7-fluoro-3-(1H-imidazol-1-yl)-5-methoxy-1-methyl-1H-indole;
(S)-2-(5-(1-(azetidin-1-yl)-2-methoxyethyl)-4H-1,2,4-triazol-3-yl)-6-chloro-7-fluoro-3-(1H-imidazol-1-yl)-5-methoxy-1-methyl-1H-indole;
(S)-2-(3-(1-(azetidin-1-yl)-2-methoxyethyl)-1H-1,2,4-triazol-5-yl)-6-chloro-7-fluoro-3-(1H-imidazol-1-yl)-5-methoxy-1-methyl-1H-indole;
(S)-2-(5-(1-(azetidin-1-yl)-2-methoxyethyl)-1H-1,2,4-triazol-3-yl)-6-chloro-7-fluoro-3-(1H-imidazol-1-yl)-5-methoxy-1-methyl-1H-indole;
(S)-1-(5-(6-chloro-7-fluoro-3-(1H-imidazol-1-yl)-5-methoxy-1-methyl-1H-indol-2-yl)-4H-1,2,4-triazol-3-yl)-N-(2-methoxyethyl)-N-methylethan-1-amine;
(S)-1-(5-(6-chloro-7-fluoro-3-(1H-imidazol-1-yl)-5-methoxy-1-methyl-1H-indol-2-yl)-1H-1,2,4-triazol-3-yl)-N-(2-methoxyethyl)-N-methylethan-1-amine;
(S)-1-(3-(6-chloro-7-fluoro-3-(1H-imidazol-1-yl)-5-methoxy-1-methyl-1H-indol-2-yl)-1H-1,2,4-triazol-5-yl)-N-(2-methoxyethyl)-N-methylethan-1-amine;
(R)-1-(5-(6-chloro-7-fluoro-3-(1H-imidazol-1-yl)-5-methoxy-1-methyl-1H-indol-2-yl)-4H-1,2,4-triazol-3-yl)-N-(2-methoxyethyl)-N-methylethan-1-amine;
(R)-1-(5-(6-chloro-7-fluoro-3-(1H-imidazol-1-yl)-5-methoxy-1-methyl-1H-indol-2-yl)-1H-1,2,4-triazol-3-yl)-N-(2-methoxyethyl)-N-methylethan-1-amine;
(R)-1-(3-(6-chloro-7-fluoro-3-(1H-imidazol-1-yl)-5-methoxy-1-methyl-1H-indol-2-yl)-1H-1,2,4-triazol-5-yl)-N-(2-methoxyethyl)-N-methylethan-1-amine;
(S)-1-(5-(6-chloro-7-fluoro-3-(1H-imidazol-1-yl)-5-methoxy-1-methyl-1H-indol-2-yl)-4H-1,2,4-triazol-3-yl)-N-(2-methoxyethyl) ethan-1-amine;
(S)-1-(5-(6-chloro-7-fluoro-3-(1H-imidazol-1-yl)-5-methoxy-1-methyl-1H-indol-2-yl)-1H-1,2,4-triazol-3-yl)-N-(2-methoxyethyl) ethan-1-amine;
(S)-1-(3-(6-chloro-7-fluoro-3-(1H-imidazol-1-yl)-5-methoxy-1-methyl-1H-indol-2-yl)-1H-1,2,4-triazol-5-yl)-N-(2-methoxyethyl) ethan-1-amine;
(R)-1-(5-(6-chloro-7-fluoro-3-(1H-imidazol-1-yl)-5-methoxy-1-methyl-1H-indol-2-yl)-4H-1,2,4-triazol-3-yl)-N-(2-methoxyethyl) ethan-1-amine;
(R)-1-(5-(6-chloro-7-fluoro-3-(1H-imidazol-1-yl)-5-methoxy-1-methyl-1H-indol-2-yl)-1H-1,2,4-triazol-3-yl)-N-(2-methoxyethyl) ethan-1-amine;
(R)-1-(3-(6-chloro-7-fluoro-3-(1H-imidazol-1-yl)-5-methoxy-1-methyl-1H-indol-2-yl)-1H-1,2,4-triazol-5-yl)-N-(2-methoxyethyl) ethan-1-amine;
(S)-6-(1-(5-(6-chloro-7-fluoro-3-(1H-imidazol-1-yl)-5-methoxy-1-methyl-1H-indol-2-yl)-4H-1,2,4-triazol-3-yl)ethyl)-2-oxa-6-azaspiro[3.3]heptane;
(S)-6-(1-(5-(6-chloro-7-fluoro-3-(1H-imidazol-1-yl)-5-methoxy-1-methyl-1H-indol-2-yl)-1H-1,2,4-triazol-3-yl)ethyl)-2-oxa-6-azaspiro[3.3]heptane;
(S)-6-(1-(3-(6-chloro-7-fluoro-3-(1H-imidazol-1-yl)-5-methoxy-1-methyl-1H-indol-2-yl)-1H-1,2,4-triazol-5-yl)ethyl)-2-oxa-6-azaspiro[3.3]heptane;
(R)-6-(1-(5-(6-chloro-7-fluoro-3-(1H-imidazol-1-yl)-5-methoxy-1-methyl-1H-indol-2-yl)-4H-1,2,4-triazol-3-yl)ethyl)-2-oxa-6-azaspiro[3.3]heptane;
(R)-6-(1-(5-(6-chloro-7-fluoro-3-(1H-imidazol-1-yl)-5-methoxy-1-methyl-1H-indol-2-yl)-1H-1,2,4-triazol-3-yl)ethyl)-2-oxa-6-azaspiro[3.3]heptane; and
(R)-6-(1-(3-(6-chloro-7-fluoro-3-(1H-imidazol-1-yl)-5-methoxy-1-methyl-1H-indol-2-yl)-1H-1,2,4-triazol-5-yl)ethyl)-2-oxa-6-azaspiro[3.3]heptane, or a pharmaceutically acceptable salt thereof.

4. A pharmaceutical composition comprising a compound according to claim 3, or a pharmaceutically acceptable salt thereof, and a pharmaceutically acceptable carrier or excipient.

* * * * *